US011192950B2

(12) United States Patent
Hotzel et al.

(10) Patent No.: US 11,192,950 B2
(45) Date of Patent: Dec. 7, 2021

(54) HUMANIZED AND AFFINITY MATURED ANTIBODIES TO FCRH5 AND METHODS OF USE

(71) Applicant: Genentech, Inc., South San Francisco, CA (US)

(72) Inventors: Isidro Hotzel, Brisbane, CA (US); Teemu T. Junttila, San Mateo, CA (US); Ji Li, South San Francisco, CA (US); Justin Scheer, South San Francisco, CA (US); Danielle Dicara, South San Francisco, CA (US); Diego Ellerman, San Francisco, CA (US); Christoph Spiess, Mountain View, CA (US); Paul J. Carter, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 316 days.

(21) Appl. No.: 16/395,009

(22) Filed: Apr. 25, 2019

(65) Prior Publication Data
US 2019/0315860 A1 Oct. 17, 2019

Related U.S. Application Data

(62) Division of application No. 15/184,690, filed on Jun. 16, 2016, now Pat. No. 10,323,094.

(60) Provisional application No. 62/180,459, filed on Jun. 16, 2015.

(51) Int. Cl.
| | | |
|---|---|---|
| C07H 21/02 | (2006.01) | |
| C07H 21/04 | (2006.01) | |
| C12P 21/06 | (2006.01) | |
| C12P 21/04 | (2006.01) | |
| C12N 5/00 | (2006.01) | |
| C12N 5/16 | (2006.01) | |
| C12N 1/20 | (2006.01) | |
| C07K 16/28 | (2006.01) | |
| A61K 47/68 | (2017.01) | |
| A61K 39/395 | (2006.01) | |
| A61K 45/06 | (2006.01) | |
| C07K 16/30 | (2006.01) | |
| G01N 33/574 | (2006.01) | |
| C07K 16/00 | (2006.01) | |
| A61K 39/00 | (2006.01) | |

(52) U.S. Cl.
CPC ...... C07K 16/283 (2013.01); A61K 39/39558 (2013.01); A61K 45/06 (2013.01); A61K 47/6849 (2017.08); A61K 47/6851 (2017.08); C07K 16/2809 (2013.01); C07K 16/2827 (2013.01); C07K 16/30 (2013.01); G01N 33/57492 (2013.01); A61K 2039/505 (2013.01); A61K 2039/507 (2013.01); C07K 2317/24 (2013.01); C07K 2317/31 (2013.01); C07K 2317/33 (2013.01); C07K 2317/52 (2013.01); C07K 2317/55 (2013.01); C07K 2317/56 (2013.01); C07K 2317/565 (2013.01); C07K 2317/567 (2013.01); C07K 2317/62 (2013.01); C07K 2317/73 (2013.01); C07K 2317/76 (2013.01); C07K 2317/92 (2013.01); C07K 2317/94 (2013.01); G01N 2333/70535 (2013.01)

(58) Field of Classification Search
None
See application file for complete search history.

(56) References Cited

U.S. PATENT DOCUMENTS

| | | |
|---|---|---|
| 4,975,278 A | 12/1990 | Senter et al. |
| 5,500,362 A | 3/1996 | Robinson et al. |
| 5,624,821 A | 4/1997 | Winter et al. |
| 5,648,260 A | 7/1997 | Winter et al. |
| 5,677,171 A | 10/1997 | Hudziak et al. |
| 5,731,168 A | 3/1998 | Carter et al. |
| 5,767,237 A | 6/1998 | Sakakibara et al. |
| 5,821,337 A | 10/1998 | Carter et al. |
| 5,869,046 A | 2/1999 | Presta et al. |
| 6,124,431 A | 9/2000 | Sakakibara et al. |
| 6,194,551 B1 | 2/2001 | Idusogie et al. |
| 6,248,516 B1 | 6/2001 | Winter et al. |
| 6,248,564 B1 | 6/2001 | Walter et al. |
| 6,455,043 B1 | 9/2002 | Grillo-Lopez |
| 6,602,684 B1 | 8/2003 | Umana et al. |
| 6,737,056 B1 | 5/2004 | Presta |
| 7,105,149 B1 | 9/2006 | Dalla-Favera |
| 7,332,581 B2 | 2/2008 | Presta |

(Continued)

FOREIGN PATENT DOCUMENTS

| | | |
|---|---|---|
| CN | 102973947 A | 3/2013 |
| CN | 101675077 B | 9/2013 |

(Continued)

OTHER PUBLICATIONS

Lee et al., "Current concepts in the diagnosis and management of cytokine release syndrome," retrieved from <www.ncbi.nlm.nih.gov/pmc/articles/PMC4093680/?report=printable> on Feb. 19, 2020, Blood 124(2):188-95 (2014) (18 pages).

Nishimoto et al., "Toxicity, pharmacokinetics, and dose-finding study of repetitive treatment with the humanized anti-interleukin 6 receptor antibody MRA in rheumatoid arthritis. Phase I/II clinical study," J Rheumatol. 30(7):1426-35 (2003).

(Continued)

*Primary Examiner* — Chun W Dahle
(74) *Attorney, Agent, or Firm* — Clark & Elbing LLP; Thomas J. Takara

(57) ABSTRACT

The present invention relates to anti-FcRH5 antibodies, including anti-FcRH5 antibodies comprising an FcRH5 binding domain and a CD3 binding domain (e.g., FcRH5 T cell-dependent bispecific (TDB) antibodies), and methods of using the same.

38 Claims, 83 Drawing Sheets
Specification includes a Sequence Listing.

(56) References Cited

U.S. PATENT DOCUMENTS

| | | |
|---|---|---|
| 7,371,826 B2 | 5/2008 | Presta |
| 7,375,078 B2 | 5/2008 | Feng |
| 7,491,529 B2 | 2/2009 | Goddard et al. |
| 7,498,298 B2 | 3/2009 | Doronina et al. |
| 7,682,612 B1 | 3/2010 | White et al. |
| 7,695,936 B2 | 4/2010 | Carter et al. |
| 7,745,394 B2 | 6/2010 | Doronina et al. |
| 7,799,900 B2 | 9/2010 | Adams et al. |
| 7,858,330 B2 | 12/2010 | Hongo et al. |
| 7,863,424 B2 | 1/2011 | Dalla-Favera |
| 7,888,478 B2 | 2/2011 | Chang et al. |
| 7,947,839 B2 | 5/2011 | Gazzard et al. |
| 7,964,566 B2 | 6/2011 | Doronina et al. |
| 7,964,567 B2 | 6/2011 | Doronina et al. |
| 7,994,135 B2 | 8/2011 | Doronina et al. |
| 7,999,077 B2 | 8/2011 | Pastan et al. |
| 8,142,784 B2 | 3/2012 | Ebens, Jr. et al. |
| 8,219,149 B2 | 7/2012 | Lafata et al. |
| 8,362,213 B2 | 1/2013 | Elkins et al. |
| 8,388,973 B2 | 3/2013 | Chang et al. |
| 8,466,260 B2 | 6/2013 | Elkins et al. |
| 8,562,992 B2 | 10/2013 | Adams et al. |
| 8,617,559 B2 | 12/2013 | Elkins et al. |
| 8,709,421 B2 | 4/2014 | Heiss et al. |
| 8,969,526 B2 | 3/2015 | Baehner et al. |
| 9,011,864 B2 | 4/2015 | Schulz et al. |
| 9,017,676 B2 | 4/2015 | Lindhofer |
| 9,017,951 B2 | 4/2015 | Elkins et al. |
| 9,308,257 B2 | 4/2016 | Sharma, Sr. et al. |
| 9,315,567 B2 | 4/2016 | Chang et al. |
| 9,360,484 B2 | 6/2016 | Elkins et al. |
| 9,587,021 B2 | 3/2017 | Huang et al. |
| 9,657,102 B2 | 5/2017 | Smith et al. |
| 9,714,294 B2 | 7/2017 | De Goeij et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2003/0165496 A1 | 9/2003 | Basi et al. |
| 2004/0018194 A1 | 1/2004 | Francisco et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2004/0253233 A1 | 12/2004 | Del Rio et al. |
| 2005/0014934 A1 | 1/2005 | Hinton et al. |
| 2005/0095243 A1 | 5/2005 | Chan et al. |
| 2005/0123546 A1 | 6/2005 | Umana et al. |
| 2005/0226869 A1 | 10/2005 | Chang et al. |
| 2005/0238649 A1 | 10/2005 | Doronina et al. |
| 2006/0182751 A1 | 8/2006 | Gazzard et al. |
| 2006/0216232 A1 | 9/2006 | Chang et al. |
| 2006/0251662 A1 | 11/2006 | Chang et al. |
| 2007/0092940 A1 | 4/2007 | Eigenbrot et al. |
| 2007/0134243 A1 | 6/2007 | Gazzard et al. |
| 2007/0148176 A1 | 6/2007 | Dalla-Favera |
| 2008/0226657 A1 | 9/2008 | Doronina et al. |
| 2008/0247944 A1 | 10/2008 | Graziano et al. |
| 2008/0248051 A1 | 10/2008 | Doronina et al. |
| 2008/0248053 A1 | 10/2008 | Doronina et al. |
| 2008/0292632 A1 | 11/2008 | Pastan et al. |
| 2009/0047296 A1 | 2/2009 | Doronina et al. |
| 2009/0202536 A1 | 8/2009 | Ebens, Jr. et al. |
| 2009/0252683 A1 | 10/2009 | Kischel et al. |
| 2010/0015133 A1 | 1/2010 | Igawa et al. |
| 2010/0150918 A1 | 6/2010 | Kufer et al. |
| 2010/0260748 A1 | 10/2010 | Elkins et al. |
| 2011/0076287 A1 | 3/2011 | Cohen et al. |
| 2011/0110951 A1 | 5/2011 | Dalla-Favera |
| 2011/0123532 A1 | 5/2011 | Gurney et al. |
| 2011/0256157 A1 | 10/2011 | Howard et al. |
| 2011/0268657 A1 | 11/2011 | Chang et al. |
| 2012/0003247 A1 | 1/2012 | Doronina et al. |
| 2012/0003248 A1 | 1/2012 | Doronina et al. |
| 2012/0027783 A1 | 2/2012 | Doronina et al. |
| 2012/0027784 A1 | 2/2012 | Doronina et al. |
| 2012/0034246 A1 | 2/2012 | Doronina et al. |
| 2012/0034247 A1 | 2/2012 | Doronina et al. |
| 2012/0141508 A1 | 6/2012 | Doronina et al. |
| 2012/0141509 A1 | 6/2012 | Doronina et al. |
| 2012/0141510 A1 | 6/2012 | Doronina et al. |
| 2012/0148608 A1 | 6/2012 | Doronina et al. |
| 2012/0148610 A1 | 6/2012 | Doronina et al. |
| 2012/0251531 A1 | 10/2012 | Baehner et al. |
| 2013/0089555 A1 | 4/2013 | Elkins et al. |
| 2013/0129723 A1 | 5/2013 | Blankenship et al. |
| 2013/0171095 A1 | 7/2013 | Bernett et al. |
| 2013/0287774 A1 | 10/2013 | Zugmaier et al. |
| 2014/0079689 A1 | 3/2014 | Elliott et al. |
| 2014/0088295 A1 | 3/2014 | Smith et al. |
| 2014/0112914 A1 | 4/2014 | Nezu et al. |
| 2014/0170149 A1 | 6/2014 | Neijssen et al. |
| 2014/0187753 A1 | 7/2014 | Blein et al. |
| 2014/0302064 A1 | 10/2014 | Moore |
| 2014/0377270 A1 | 12/2014 | Moore et al. |
| 2015/0079093 A1 | 3/2015 | Stuhler |
| 2015/0098900 A1 | 4/2015 | Ebens et al. |
| 2015/0133640 A1 | 5/2015 | Blein et al. |
| 2015/0166661 A1 | 6/2015 | Chen et al. |
| 2015/0266966 A1 | 9/2015 | Smith et al. |
| 2016/0017058 A1 | 1/2016 | Kim et al. |
| 2016/0075785 A1 | 3/2016 | Ast et al. |
| 2016/0090416 A1 | 3/2016 | Gunde et al. |
| 2016/0159906 A1 | 6/2016 | Sun et al. |
| 2016/0368985 A1 | 12/2016 | Hotzel et al. |
| 2016/0368994 A1 | 12/2016 | Kelley et al. |
| 2017/0008971 A1 | 1/2017 | Dennis et al. |
| 2017/0158773 A1 | 6/2017 | Adams et al. |
| 2017/0204194 A1 | 7/2017 | Chen et al. |
| 2017/0224818 A1 | 8/2017 | Lindhofer et al. |
| 2017/0267783 A1 | 9/2017 | Nezu et al. |
| 2018/0057593 A1 | 3/2018 | Dennis |

FOREIGN PATENT DOCUMENTS

| | | |
|---|---|---|
| EP | 1391213 A1 | 2/2004 |
| EP | 1870459 A1 | 12/2007 |
| EP | 1870459 A4 | 9/2010 |
| EP | 2578230 A1 | 4/2013 |
| EP | 2647707 A1 | 10/2013 |
| EP | 2647707 A4 | 4/2014 |
| EP | 1870459 B1 | 6/2016 |
| JP | 2005-536439 A | 12/2005 |
| JP | 2008/291036 A | 12/2008 |
| JP | 2009-539413 A | 11/2009 |
| JP | 2011-528360 A | 11/2011 |
| JP | 2012-522513 A | 9/2012 |
| JP | 2013-515509 A | 5/2013 |
| JP | 2013-523895 A | 6/2013 |
| JP | 2013-529084 A | 7/2013 |
| RU | 2539112 C2 | 1/2015 |
| TW | 201039846 A | 11/2010 |
| TW | 201508008 A | 3/2015 |
| WO | WO-92/22653 A1 | 12/1992 |
| WO | WO-94/29351 A2 | 12/1994 |
| WO | WO-96/01126 A1 | 1/1996 |
| WO | WO-96/27011 A1 | 9/1996 |
| WO | WO-97/30087 A1 | 8/1997 |
| WO | WO-98/50431 A2 | 11/1998 |
| WO | WO-98/58964 A1 | 12/1998 |
| WO | WO-98/50431 A3 | 1/1999 |
| WO | WO-99/22764 A1 | 5/1999 |
| WO | WO-99/51642 A1 | 10/1999 |
| WO | WO-00/61739 A1 | 10/2000 |
| WO | WO-01/29246 A1 | 4/2001 |
| WO | WO-01/38490 A2 | 5/2001 |
| WO | WO-02/31140 A1 | 4/2002 |
| WO | WO-02/088172 A2 | 11/2002 |
| WO | WO-02/102972 A2 | 12/2002 |
| WO | WO-03/011878 A2 | 2/2003 |
| WO | WO-03/024392 A2 | 3/2003 |
| WO | WO-03/043583 A2 | 5/2003 |
| WO | WO-03/077836 A2 | 9/2003 |
| WO | WO-03/084570 A1 | 10/2003 |

(56) References Cited

FOREIGN PATENT DOCUMENTS

| WO | WO-03/085107 A1 | 10/2003 |
|---|---|---|
| WO | WO-03/085119 A1 | 10/2003 |
| WO | WO-2004/032828 A2 | 4/2004 |
| WO | WO-2004/056312 A1 | 7/2004 |
| WO | WO-2005/035586 A1 | 4/2005 |
| WO | WO-2005/035778 A1 | 4/2005 |
| WO | WO-2005/053742 A1 | 6/2005 |
| WO | WO-2005/063299 A2 | 7/2005 |
| WO | WO-2005/081711 A2 | 9/2005 |
| WO | WO-2005/100402 A1 | 10/2005 |
| WO | WO-2005/117986 A2 | 12/2005 |
| WO | WO-2006/029879 A2 | 3/2006 |
| WO | WO-2006/034488 A2 | 3/2006 |
| WO | WO-2006/039238 A2 | 4/2006 |
| WO | WO-2006/076691 A2 | 7/2006 |
| WO | WO-2007/001851 A2 | 1/2007 |
| WO | WO-2007/042261 A2 | 4/2007 |
| WO | WO-2007/110205 A2 | 10/2007 |
| WO | WO-2007/146968 A2 | 12/2007 |
| WO | WO-2008/077546 A1 | 7/2008 |
| WO | WO-2008/109533 A2 | 9/2008 |
| WO | WO-2008/119566 A2 | 10/2008 |
| WO | WO-2008/119567 A2 | 10/2008 |
| WO | WO-2009/070642 A1 | 6/2009 |
| WO | WO-2010/009124 A2 | 1/2010 |
| WO | WO-2010/114940 A1 | 10/2010 |
| WO | WO-2010/120561 A1 | 10/2010 |
| WO | WO-2011/028945 A1 | 3/2011 |
| WO | WO-2011/028952 A1 | 3/2011 |
| WO | WO-2011/090754 A1 | 7/2011 |
| WO | WO-2011/090762 A1 | 7/2011 |
| WO | WO-2011/130598 A1 | 10/2011 |
| WO | WO-2011/131746 A2 | 10/2011 |
| WO | WO-2011/143545 A1 | 11/2011 |
| WO | WO-2012/058768 A1 | 5/2012 |
| WO | WO-2012/058768 A8 | 6/2012 |
| WO | WO-2012/073985 A1 | 6/2012 |
| WO | WO-2012/143524 A2 | 10/2012 |
| WO | WO-2012/162067 A2 | 11/2012 |
| WO | WO-2012/158818 A2 | 11/2012 |
| WO | WO-2014/022540 A1 | 2/2014 |
| WO | WO-2014/028560 A2 | 2/2014 |
| WO | WO-2014/047231 A1 | 3/2014 |
| WO | WO-2014/028560 A3 | 5/2014 |
| WO | WO-2014/083178 A1 | 6/2014 |
| WO | WO-2014/122251 A2 | 8/2014 |
| WO | WO-2014/141152 A2 | 9/2014 |
| WO | WO-2014/153002 A1 | 9/2014 |
| WO | WO-2014/122251 A3 | 10/2014 |
| WO | WO-2014/141152 A3 | 12/2014 |
| WO | WO-2014/191113 A1 | 12/2014 |
| WO | WO-2014/191113 A8 | 12/2014 |
| WO | WO-2014/210064 A1 | 12/2014 |
| WO | WO-2015/006749 A2 | 1/2015 |
| WO | WO-2016/020065 A1 | 2/2016 |
| WO | WO-2016/036678 A1 | 3/2016 |
| WO | WO-2016/081490 A1 | 5/2016 |
| WO | WO-2016110576 A1 | 7/2016 |
| WO | WO-2016/179003 A1 | 11/2016 |
| WO | WO-2016/191750 A1 | 12/2016 |
| WO | WO-2016/201300 A1 | 12/2016 |
| WO | WO-2016/204966 A1 | 12/2016 |
| WO | WO-2016/205520 A1 | 12/2016 |
| WO | WO-2016/205531 A2 | 12/2016 |
| WO | WO-2017/132279 A1 | 8/2017 |

OTHER PUBLICATIONS

Saphire et al., "Crystal structure of a neutralizing human IgG against HIV-1: a template for vaccine design," Science. 293(5532):1155-9 (2001).

Communication pursuant to Article 94(3) EPC for European Patent Application No. 16733812.8, dated Jul. 16, 2019 (7 pages).

English Translation of Examination Report for Pakistan Patent Application No. 359/2016, received Jan. 7, 2020 (1 page).

Office Action for Russian Patent Application No. 2018100820, dated Dec. 6, 2019 (10 pages).

Anderson et al., "G19.4(alpha CD3) x B43(alpha CD19) monoclonal antibody heteroconjugate triggers CD19 antigen-specific lysis of t(4;11) acute lymphoblastic leukemia cells by activated CD3 antigen-positive cytotoxic T cells," Blood. 80(11):2826-34 (1992).

Atwell et al., "Stable heterodimers from remodeling the domain interface of a homodimer using a phage display library," J Mol Biol. 270(1):26-35 (1997).

Baeuerle et al., "Bispecific T-cell engaging antibodies for cancer therapy," Cancer Res. 69(12):4941-4 (2009).

Bargou et al., "Tumor regression in cancer patients by very low doses of a T cell-engaging antibody," Science. 321(5891):974-7 (2008) (5 pages).

Bendayan, "Possibilities of false immunocytochemical results generated by the use of monoclonal antibodies: the example of the anti-proinsulin antibody," J Histochem Cytochem. 43(9):881-6 (1995).

Bendig, "Humanization of rodent monoclonal antibodies by CDR grafting," Methods: A Companion to Methods in Enzymology. 8:83-93 (1995).

Bernhard et al., "Cysteine analogs of recombinant barley ribosome inactivating protein form antibody conjugates with enhanced stability and potency in vitro," Bioconjug Chem. 5(2):126-32 (1994).

Better et al., "Gelonin analogs with engineered cysteine residues form antibody immunoconjugates with unique properties," J Biol Chem. 269(13):9644-50 (1994).

Bhaskar et al., "E-selectin up-regulation allows for targeted drug delivery in prostate cancer," Cancer Res. 63(19):6387-94 (2003).

Boring et al., "Cancer statistics, 1993," CA Cancer J Clin. 43(1):7-26 (1993).

Bortoletto et al., "Optimizing anti-CD3 affinity for effective T cell targeting against tumor cells," Eur J Immunol. 32(11):3102-7 (2002).

Bost et al., "Antibodies against a peptide sequence within the HIV envelope protein crossreacts with human interleukin-2," Immunol Invest. 17(6-7):577-86 (1988).

Brekke et al., "Human IgG isotype-specific amino acid residues affecting complement-mediated cell lysis and phagocytosis," Eur J Immunol. 24(10):2542-7 (1994).

Brüggemann et al., "Comparison of the effector functions of human immunoglobulins using a matched set of chimeric antibodies," J Exp Med. 166(5):1351-61 (1987).

Carter et al., "Humanization of an anti-p185HER2 antibody for human cancer therapy," Proc Natl Acad Sci U S A. 89(10):4285-9 (1992).

Carter, "Bispecific human IgG by design," J Immunol Methods. 248(1-2):7-15 (2001).

Chen et al., "Generation and analysis of random point mutations in an antibody CDR2 sequence: many mutated antibodies lose their ability to bind antigen," J Exp Med. 176(3):855-66 (1992).

Chmura et al., "Antibodies with infinite affinity," Proc Natl Acad Sci U S A. 98(15):8480-4 (2001).

Clark et al., "Affinity enhancement of an in vivo matured therapeutic antibody using structure-based computational design," Protein Sci. 15(5):949-60 (2006).

Clynes et al., "Fc receptors are required in passive and active immunity to melanoma," Proc Natl Acad Sci U S A. 95(2):652-6 (1998).

Colman, "Effects of amino acid sequence changes on antibody-antigen interactions," Res Immunol. 145(1):33-6 (1994).

Cragg et al., "Antibody specificity controls in vivo effector mechanisms of anti-CD20 reagents," Blood. 103(7):2738-43 (2004).

Davis et al., "Identification of a family of Fc receptor homologs with preferential B cell expression," Proc Natl Acad Sci U S A. 98(17):9772-7 (2001).

Dement-Brown et al., "Fc receptor-like 5 promotes B cell proliferation and drives the development of cells displaying switched isotypes," J Leukoc Biol. 91(1):59-67 (2012) (10 pages).

Doronina et al., "Development of potent monoclonal antibody auristatin conjugates for cancer therapy," Nat Biotechnol. 21(7):778-84 (2003) (9 pages).

(56) References Cited

OTHER PUBLICATIONS

Dreier et al., "Extremely potent, rapid and costimulation-independent cytotoxic T-cell response against lymphoma cells catalyzed by a single-chain bispecific antibody," Int J Cancer. 100(6):690-7 (2002).
Duncan et al., "The binding site for C1q on IgG," Nature. 332(6166):738-40 (1988).
Edelman et al., "The covalent structure of an entire gammaG immunoglobulin molecule," Proc Natl Acad Sci U S A. 63(1):78-85 (1969).
Elkins et al., "FcRL5 as a target of antibody-drug conjugates for the treatment of multiple myeloma," Mol Cancer Ther. 11(10):2222-32 (2012).
Francisco et al., "cAC10-vcMMAE, an anti-CD30-monomethyl auristatin E conjugate with potent and selective antitumor activity," Blood. 102(4):1458-65 (2003).
Greenspan et al., "Defining epitopes: It's not as easy as it seems," Nat Biotechnol. 17(10):936-7 (1999).
Greenwood et al., "Engineering multiple-domain forms of the therapeutic antibody CAMPATH-1H: effects on complement lysis," Ther Immunol. 1(5):247-55 (1994).
Guyer et al., "Immunoglobulin binding by mouse intestinal epithelial cell receptors," J Immunol. 117(2):587-93(1976).
Güssow et al., "Humanization of monoclonal antibodies," Methods Enzymol. 203:99-121 (1991).
Hatzivassiliou et al., "IRTA1 and IRTA2, novel immunoglobulin superfamily receptors expressed in B cells and involved in chromosome 1q21 abnormalities in B cell malignancy," Immunity. 14(3):277-89 (2001).
Hellström et al., "Antitumor effects of L6, an IgG2a antibody that reacts with most human carcinomas," Proc Natl Acad Sci U S A. 83(18):7059-63 (1986).
Hellström et al., "Strong antitumor activities of IgG3 antibodies to a human melanoma-associated ganglioside," Proc Natl Acad Sci U S A. 82(5):1499-502 (1985).
Hinman et al., "Preparation and characterization of monoclonal antibody conjugates of the calicheamicins: a novel and potent family of antitumor antibiotics," Cancer Res. 53(14):3336-42 (1993).
Holliger et al., "'Diabodies': small bivalent and bispecific antibody fragments," Proc Natl Acad Sci U S A. 90(14):6444-8 (1993).
Holliger et al., "Specific killing of lymphoma cells by cytotoxic T-cells mediated by a bispecific diabody," Protein Eng. 9(3):299-305 (1996).
Holm et al., "Functional mapping and single chain construction of the anti-cytokeratin 8 monoclonal antibody TS1," Mol Immunol. 44(6):1075-84 (2007).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hudson et al., "Engineered antibodies," Nat Med. 9(1):129-34 (2003).
Idusogie et al., "Mapping of the C1q binding site on rituxan, a chimeric antibody with a human IgG1 Fc," J Immunol. 164(8):4178-84 (2000).
Igawa et al., "VH/VL interface engineering to promote selective expression and inhibit conformational isomerization of thrombopoietin receptor agonist single-chain diabody," Protein Eng Des Sel. 23(8):667-77 (2010) (11 pages).
Inoue et al., "Overexpression of PDZK1 within the 1q12-q22 amplicon is likely to be associated with drug-resistance phenotype in multiple myeloma," Am J Pathol. 165(1):71-81 (2004).
Ise et al., "Elevation of soluble CD307 (IRTA2/FcRH5) protein in the blood and expression on malignant cells of patients with multiple myeloma, chronic lymphocytic leukemia, and mantle cell lymphoma," Leukemia. 21 (1):169-74 (2007).
Ise et al., "Immunoglobulin superfamily receptor translocation associated 2 protein on lymphoma cell lines and hairy cell leukemia cells detected by novel monoclonal antibodies," Clin Cancer Res. 11(1):87-96 (2005).
Jager et al., "The trifunctional antibody ertumaxomab destroys tumor cells that express low levels of human epidermal growth factor receptor 2," Cancer Res. 69(10):4270-6 (2009).
Janeway et al., Chapter 3: Structure of the Antibody Molecule and Immunoglobulin Genes, *Immunobiology, Third Edition*. Penolope Austin, Eleanor Lawrence, and Miranda Robertson, Current Biology Ltd./Garland Publishing Inc., 3:1-3:11 (1997) (14 pages).
Junttila et al., "Antitumor efficacy of a bispecific antibody that targets HER2 and activates T cells," Cancer Res. 74(19):5561-71 (2014).
Junutula et al., "Rapid identification of reactive cysteine residues for site-specific labeling of antibody-Fabs," J Immunol Methods. 332(1-2):41-52 (2008).
Junutula et al., "Site-specific conjugation of a cytotoxic drug to an antibody improves the therapeutic index," Nat Biotechnol. 26(8):925-32 (2008).
Kanda et al., "Comparison of cell lines for stable production of fucose-negative antibodies with enhanced ADCC," Biotechnol Bioeng. 94(4):680-8 (2006).
Kanno et al., "Assembling of engineered IgG-binding protein on gold surface for highly oriented antibody immobilization," J Biotechnol. 76(2-3):207-14 (2000).
Kiewe et al., "Phase I trial of the trifunctional anti-HER2 x anti-CD3 antibody ertumaxomab in metastatic breast cancer," 2005 ASCO Annual Meeting Proceedings. J Clin Oncol. 23(16S):Abstract 2530 (2005).
Kiewe et al., "Phase I trial of the trifunctional anti-HER2 x anti-CD3 antibody ertumaxomab in metastatic breast cancer," Clin Cancer Res. 12(10):3085-91 (2006).
Kim et al., "Localization of the site of the murine IgG1 molecule that is involved in binding to the murine intestinal Fc receptor," Eur J Immunol. 24(10):2429-34 (1994).
Kipriyanov et al., "Bispecific tandem diabody for tumor therapy with improved antigen binding and pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," MAbs. 4(2):182-97 (2012).
Krishnan et al., "Role of antibody paratope conformational flexibility in the manifestation of molecular mimicry," Biophys J. 94(4):1367-76 (2008).
Lambert, "Drug-conjugated monoclonal antibodies for the treatment of cancer," Curr Opin Pharmacol. 5(5):543-9 (2005).
Law et al., "Expression and characterization of recombinant soluble human CD3 molecules: presentation of antigenic epitopes defined on the native TCR-CD3 complex," Int Immunol. 14(4): 389-400 (2002).
Leabman et al., "Effects of altered FcgammaR binding on antibody pharmacokinetics in cynomolgus monkeys," MAbs. 5(6):896-903 (2013).
Lippow et al., "Computational design of antibody affinity improvement beyond in vivo maturation," available in PMC Jan. 7, 2010, published in final edited form as: Nat Biotechnol. 25(10):1171-6 (2007) (14 pages).
Liu et al., "Eradication of large colon tumor xenografts by targeted delivery of maytansinoids," Proc Natl Acad Sci U S A. 93(16):8618-23 (1996).
Liu et al., "Heteroantibody duplexes target cells for lysis by cytotoxic T lymphocytes," Proc Natl Acad Sci U S A. 82(24):8648-52 (1985).
Lode et al., "Targeted therapy with a novel enediyene antibiotic calicheamicin theta(I)1 effectively suppresses growth and dissemination of liver metastases in a syngeneic model of murine neuroblastoma," Cancer Res. 58(14):2925-8 (1998).
Lum et al., "Targeting T cells with bispecific antibodies for cancer therapy," available in PMC Oct. 8, 2013, published in final edited form as: BioDrugs. 25(6):365-79 (2011) (24 pages).
MacCallum et al., "Antibody-antigen interactions: contact analysis and binding site topography," J Mol Biol. 262(5):732-45 (1996).

(56) References Cited

OTHER PUBLICATIONS

Mandler et al., "Immunoconjugates of geldanamycin and anti-HER2 monoclonal antibodies: antiproliferative activity on human breast carcinoma cell lines," J Natl Cancer Inst. 92(19):1573-81 (2000).
Mandler et al., "Modifications in synthesis strategy improve the yield and efficacy of geldanamycin-herceptin immunoconjugates," Bioconjug Chem. 13(4):786-91 (2002).
Mandler et al., "Synthesis and evaluation of antiproliferative activity of a geldanamycin-Herceptin(TM) immunoconjugate," Bioorg Med Chem Lett. 10(10):1025-8 (2000).
Mao et al., "EphB2 as a therapeutic antibody drug target for the treatment of colorectal cancer," Cancer Res. 64(3):781-8 (2004).
Mariuzza et al., "The structural basis of antigen-antibody recognition," Annu Rev Biophys Biophys Chem. 16:139-59 (1987).
Merchant et al., "An efficient route to human bispecific IgG," Nat Biotechnol. 16(7):677-81 (1998).
Metz et al., "Bispecific antibody derivatives with restricted binding functionalities that are activated by proteolytic processing," Protein Eng Des Sei. 25(10):571-80 (2012).
Miller et al., "IRTAs: a new family of immunoglobulinlike receptors differentially expressed in B cells," Blood. 99(8):2662-9 (2002) (9 pages).
Moore et al., "Application of dual affinity retargeting molecules to achieve optimal redirected T-cell killing of B-cell lymphoma," Blood. 117(17):4542-51 (2011) (11 pages).
Nagorsen et al., "Immunomodulatory therapy of cancer with T cell-engaging BiTE antibody blinatumomab," Exp Cell Res. 317(9):1255-60 (2011).
Nakayama et al., "Altered gene expression upon BCR cross-linking in Burkitt's lymphoma B cell line," Biochem Biophys Res Commun. 277(1):124-7 (2000).
Ohno et al., "Antigen-binding specificities of antibodies are primarily determined by seven residues of VH," Proc Natl Acad Sci U S A. 82(9):2945-9 (1985).
Okazaki et al., "Fucose depletion from human IgG1 oligosaccharide enhances binding enthalpy and association rate between IgG1 and FcgammaRIIIa," J Mol Biol. 336(5):1239-49 (2004).
Paul, Chapter 9: Structure and Function of Immunoglobulins. *Fundamental Immunology, Third Edition.* Raven Press Ltd., 292-295 (1993).
Payne, "Progress in immunoconjugate cancer therapeutics," Cancer Cell. 3(3):207-12 (2003).
Pessano et al., "The T3/T cell receptor complex: antigenic distinction between the two 20-kd T3 (T3-delta and T3-epsilon) subunits," EMBO J. 4(2):337-44 (1985).
Petkova et al., "Enhanced half-life of genetically engineered human IgG1 antibodies in a humanized FcRn mouse model: potential application in humorally mediated autoimmune disease," Int Immunol. 18(12):1759-69 (2006).
Polson et al., "Expression pattern of the human FcRH/IRTA receptors in normal tissue and in B-chronic lymphocytic leukemia," Int Immunol. 18(9):1363-73 (2006).
Ravetch et al., "Fc receptors," Annu Rev Immunol. 9:457-92 (1991).
Ridgway et al., "'Knobs-into-holes' engineering of antibody CH3 domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Ripka et al., "Two Chinese hamster ovary glycosylation mutants affected in the conversion of GDP-mannose to GDP-fucose," Arch Biochem Biophys. 249(2):533-45 (1986).
Rowland et al., "Drug localisation and growth inhibition studies of vindesine-monoclonal anti-CEA conjugates in a human tumour xenograft," Cancer Immunol Immunother. 21(3):183-7 (1986).
Rudikoff et al., "Single amino acid substitution altering antigen-binding specificity," Proc Natl Acad Sci U S A. 79(6):1979-83 (1982).

Seimetz et al., "Development and approval of the trifunctional antibody catumaxomab (anti-EpCAM x anti-CD3) as a targeted cancer immunotherapy," Cancer Treat Rev. 36(6):458-67 (2010).
Senter et al., "Immunoconjugates comprised of drugs with impaired cellular permeability: A new approach to targeted therapy," Proc Amer Assoc Cancer Res. 45:144 Abstract 623 (2004) (1 page).
Shalaby et al., "Bispecific HER2 x CD3 antibodies enhance T-cell cytotoxicity in vitro and localize to HER2-overexpressing xenografts in nude mice," Clin Immunol Immunopathol. 74(2):185-92 (1995).
Shalaby et al., "Development of humanized bispecific antibodies reactive with cytotoxic lymphocytes and tumor cells overexpressing the HER2 protooncogene," J Exp Med. 175(1):217-25 (1992).
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem. 276(9):6591-604 (2001).
Sondermann et al., "The 3.2-A crystal structure of the human IgG1 Fc fragment-Fc gammaRIII complex," Nature. 406(6793):267-73 (2000).
Spiess et al., "Bispecific antibodies with natural architecture produced by co-culture of bacteria expressing two distinct half-antibodies," Nat Biotechnol. 31(8):753-8 (2013) (7 pages).
Springer et al., "Antibody-directed enzyme prodrug therapy (ADEPT): a review," Adv Drug Deliv Rev. 26(2-3):151-172 (1997).
Stanglmaier et al., "Bi20 (FBTA05), a novel trifunctional bispecific antibody (anti-CD20 x anti-CD3), mediates efficient killing of B-cell lymphoma cells even with very low CD20 expression levels," Int J Cancer. 123(5):1181-9 (2008).
Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Syrigos et al., "Antibody directed enzyme prodrug therapy (ADEPT): a review of the experimental and clinical considerations," Anticancer Res. 19(1A):605-13 (1999).
Tu et al., "Protein footprinting at cysteines: probing ATP-modulated contacts in cysteine-substitution mutants of yeast DNA topoisomerase II," Proc Natl Acad Sci U S A. 96(9):4862-7 (1999).
Vajdos et al., "Comprehensive functional maps of the antigen-binding site of an anti-ErbB2 antibody obtained with shotgun scanning mutagenesis," J Mol Biol. 320(2):415-28 (2002).
Westin et al., "Safety and activity of PD1 blockade by pidilizumab in combination with rituximab in patients with relapsed follicular lymphoma: a single group, open-label, phase 2 trial," Lancet Oncol. 15(1):69-77 (2014).
Wright et al., "Effect of glycosylation on antibody function: implications for genetic engineering," Trends Biotechnol. 15(1):26-32 (1997).
Wu et al., "Arming antibodies: prospects and challenges for immunoconjugates," Nat Biotechnol. 23(9):1137-46 (2005).
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotechnol Bioeng. 87(5):614-22 (2004).
Zhang et al., "Complete disulfide bond assignment of a recombinant immunoglobulin G4 monoclonal antibody," Anal Biochem. 311(1):1-9 (2002).
Zhu et al., "Engineering high affinity humanized anti-p185HER2/anti-CD3 bispecific F(ab')2 for efficient lysis of p185HER2 overexpressing tumor cells," Int J Cancer. 62(3):319-24 (1995).
Zhu et al., "Identification of heavy chain residues in a humanized anti-CD3 antibody important for efficient antigen binding and T cell activation," J Immunol. 155(4):1903-10 (1995).
Communication pursuant to Article 94(3) dated Apr. 10, 2017, for Chen et al., "Anti-CD3 Antibodies and Methods of Use," European Patent Application No. 14828608.1, filed Dec. 17, 2014 (7 pages).
Communication pursuant to Article 94(3) dated Nov. 8, 2017, for Chen et al., "Anti-CD3 Antibodies and Methods of Use," European Patent Application No. 14828608.1, filed Dec. 17, 2014 (11 pages).
Communication pursuant to Article 94(3) EPC for European Patent Application No. 16733812.8, dated Nov. 9, 2018 (7 pages).

(56) References Cited

OTHER PUBLICATIONS

Extended European Search Report dated May 29, 2017, for Chen et al., "Anti-CD3 Antibodies and Methods of Use," European Patent Application No. 17156352.1, filed Dec. 17, 2014 (10 pages).
International Preliminary Report on Patentability dated Dec. 19, 2017, for Hotzel et al., "Humanized and Affinity Matured Antibodies to FCRH5 and Methods of Use," International Patent Application No. PCT/US2016/037879, filed Jun. 16, 2016 (12 pages).
International Preliminary Report on Patentability dated Jun. 21, 2016, for Chen et al., "Anti-CD3 Antibodies and Methods of Use," International Patent Application No. PCT/US2014/070951, filed Dec. 17, 2014 (19 pages).
International Search Report and Written Opinion for International Patent Application No. PCT/US2010/029516, dated Aug. 23, 2010 (18 pages).
International Search Report and Written Opinion for International Patent Application No. PCT/US2010/029521, dated Jul. 20, 2010 (16 pages).
International Search Report and Written Opinion for International Patent Application No. PCT/US2014/043952, dated Oct. 7, 2014 (13 pages).
International Search Report and Written Opinion dated May 28, 2015, for Chen et al., "Anti-CD3 Antibodies and Methods of Use," International Patent Application No. PCT/US2014/070951, filed Dec. 17, 2014 (33 pages).
International Search Report and Written Opinion dated Nov. 4, 2016, for Hotzel et al., "Humanized and Affinity Matured Antibodies To FCRH5 and Methods of Use," International Patent Application No. PCT/US2016/037879, filed Jun. 16, 2016 (20 pages).
Invitation to Pay Additional Fees mailed Apr. 9, 2015, for Chen et al., "Anti-CD3 Antibodies and Methods of Use," International Patent Application No. PCT/US2014/070951, filed Dec. 17, 2014 (12 pages).
Invitation to Pay Additional Fees mailed Sep. 12, 2016, for Hotzel et al., "Humanized and Affinity Matured Antibodies to FCRH5 and Methods of Use," International Patent Application No. PCT/US2016/037879, filed Jun. 16, 2016 (8 pages).
Notice of Preliminary Rejection for Korean Patent Application No. 10-2011-7025864, dated Nov. 21, 2016 (19 pages).
Notice of Reasons for Rejection dated Dec. 19, 2017, for Chen et al., "Anti-CD3 Antibodies and Methods of Use," Japanese Patent Application No. 2016-539276, filed Dec. 17, 2014 (6 pages).
Notice of Reasons for Rejection for Japanese Patent Application No. 2016-521907, dated Jun. 12, 2018 (16 pages).
Objection filed by Asociación Industrial de Laboratorios Farmacéuticos AG against Chilean Patent Application No. 2417-2011, dated Mar. 30, 2012 (6 pages).
Office Action for Russian Patent Application No. 2016101965, dated Dec. 4, 2017 (6 pages).
Office Action for Thai Patent Application No. 1701007500, dated Feb. 12, 2019 (10 pages).
Search Report dated Aug. 8, 2017, for Chen et al., "Anti-CD3 Antibodies and Methods of Use," Singaporean Patent Application No. 11201604990P, filed Dec. 17, 2014 (6 pages).
Search Report for Singaporean Patent Application No. 11201510653Y, dated Nov. 9, 2016 (3 pages).
Written Opinion dated Aug. 8, 2017, for Chen et al., "Anti-CD3 Antibodies and Methods of Use," Singaporean Patent Application No. 11201604990P, filed Dec. 17, 2014 (7 pages).
Written Opinion for Singaporean Patent Application No. 11201510653Y, dated Dec. 12, 2016 (7 pages).
Philips et al., "Therapeutic uses of anti-PD-1 and anti-PD-L1 antibodies," Int Immunol (1):39-26 (2015).
Notice of Reasons for Rejection for Japanese Patent Application No. 2017-565794, dated Jun. 30, 2020 (16 pages).
Office Action for Argentine Patent Application No. P160101805, dated Jun. 4, 2020 (10 pages).
Office Action for Colombian Patent Application No. 2018/0000244, dated Jul. 24, 2020 (11 pages).
Office Action for Russian Patent Application No. 2018100820, dated Apr. 30, 2020 (11 pages).
Office Action for Taiwan Patent Application No. 105118965, dated Jun. 30, 2020 (17 pages).
Second Written Opinion for Singaporean Patent Application No. 11201710377X, dated Jun. 10, 2020 (6 pages).

FIG. 3

| | | | v1 | v1.3 | v1.4 | v1.5 | v1.6 | v1.7 |
|---|---|---|---|---|---|---|---|---|
| | | v1 | 27.0 | | | | | |
| W52 mutated | | W52F | 253.5 | 177.0 | 119.0 | 47.5 | 81.4 | 76.6 |
| | | W52Y | 146.0 | 641.0 | 131.0 | 177.0 | 529.0 | 136.0 |
| | | W52L | 103.0 | 239.0 | 92.0 | 125.0 | 250.0 | 129.0 |
| | | W52H | 120.0 | 65.5 | 60.4 | 67.3 | 109.0 | 89.8 |
| M64 mutated | | M64I | 29.8 | 2.1 | 2.5 | 2.7 | 2.7 | 2.6 |
| | | M64V | 27.4 | 2.5 | 2.5* | 2.5 | 2.7 | 2.5 |
| | | M64L | 26.5 | 2.4 | 2.5 | 2.3 | 2.6 | 2.0 |
| | | M64F | 25.9 | 2.2 | 2.5 | 1.4 | 2.6 | 2.4 |

Heavy chain variable domain

| Kabat number | 1 2 3 4 5 6 7 8 9 10 11 12 13 14 15 16 17 18 19 20 21 22 23 24 25 | 26 27 28 29 30 31 32 33 34 35 | 36 37 38 39 40 41 42 43 44 |
|---|---|---|---|
| | | HVR-H1 | |
| hIGHV4-59*01 | Q V Q L Q E S G P G L V K P S E T L S L T C T V S | G G S I S S Y Y W S | W I R Q P P G K G |
| huIG7.v93 | E V Q L V E S G P G L V K P S E T L S L T C T V S | G F S T T R F G V H | W V R Q P P G K G |
| huIG7.v85 | E V Q L V E S G P G L V K P S E T L S L T C T V S | G F S L T R F G V H | W V R Q P P G K G |

| Kabat number | 45 46 47 48 49 | 50 51 52 | 53 54 55 56 57 58 59 60 61 62 63 64 65 | 66 67 68 69 70 71 72 73 74 75 76 77 78 79 80 81 82 a b c 83 84 |
|---|---|---|---|---|
| | | | HVR-H2 | |
| hIGHV4-59*01 | L E W I G | Y I Y | Y S G S T N Y N P S L K S | R V T I S V D T S K N Q F S L K L S S V T A |
| huIG7.v93 | L E W L G | V I W | . . R G G S T D Y N A F W S | R L T I S K D N S K N Q V S L K L S S V T A |
| huIG7.v85 | L E W L G | V I W | . . R G G S T D Y N A F V S | R L T I S K D N S K N Q V S L K L S S V T A |

| Kabat number | 85 86 87 88 89 90 91 92 93 | 94 95 96 97 98 99 100 a b c | 101 102 103 104 105 106 107 108 109 110 111 112 113 | |
|---|---|---|---|---|
| | | HVR-H3 | | |
| hIGHV4-59*01 | A D T A V Y Y C A R | . . . . . . . . . . | F D Y W G Q G T L V T V S S | |
| huIG7.v93 | A D T A V Y Y C S N | H Y Y G S P D Y A . | L D N W G Q G T L V T V S S | (SEQ ID NO: 106) |
| huIG7.v85 | A D T A V Y Y C S N | H Y Y G S D Y A . . | L D N W G Q G T L V T V S S | (SEQ ID NO: 104) |

FIG. 5A

Light chain variable domain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | HVR-L1 | | | | | | | | |
| hIGKV1-16*01 | D | I | Q | M | T | Q | S | P | S | S | L | S | A | S | V | G | D | R | V | T | I | T | C | R | A | S | Q | . | . | G | I | S | N | Y | L | A |
| huIG7.v93 | D | I | Q | M | T | Q | S | P | S | S | L | S | A | S | V | G | D | R | V | T | I | T | C | K | A | S | Q | . | . | D | V | S | N | L | V | W |
| huIG7.v85 | D | I | Q | M | T | Q | S | P | S | S | L | S | A | S | V | G | D | R | V | T | I | T | C | K | A | S | Q | . | . | D | V | R | N | L | V | W |

| Kabat number | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|---|---|---|---|---|---|---|---|---|---|---|---|---|---|---|---|---|
| | | | | | | | | | | | | | | HVR-L2 | | | | | | | | | | | | | | | | | | | | |
| hIGKV1-16*01 | Q | Q | K | P | G | K | A | P | K | S | L | I | Y | A | A | S | S | L | Q | S | G | V | P | S | R | F | S | G | S | G | S | G | T | D | F |
| huIG7.v93 | Q | Q | K | P | G | K | A | P | K | L | L | I | Y | S | G | S | Y | R | Y | S | G | V | P | S | R | F | S | G | S | G | S | G | T | D | F |
| huIG7.v85 | Q | Q | K | P | G | K | A | P | K | L | L | I | Y | S | G | S | K | R | X | S | G | V | P | S | R | F | S | G | S | G | S | G | T | D | F |

| Kabat number | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | |
|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | HVR-L3 | | | | | | | | | | | | | | |
| hIGKV1-16*01 | T | L | T | I | S | S | L | Q | P | E | D | F | A | T | Y | Y | C | Q | Q | Y | N | S | Y | P | . | Y | T | F | G | Q | G | T | K | L | E | I | K |
| huIG7.v93 | T | L | T | I | S | S | L | Q | P | E | D | F | A | T | Y | Y | C | Q | Q | H | T | S | P | P | . | Y | T | F | G | Q | G | T | K | V | W | I | K | (SEQ ID NO: 107) |
| huIG7.v85 | T | L | T | I | S | S | L | Q | P | E | D | F | A | T | Y | Y | C | Q | Q | H | Y | S | R | P | . | Y | T | F | G | Q | G | T | K | V | W | I | K | (SEQ ID NO: 105) |

Heavy chain variable domain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| hu1G7.v93 | E | V | Q | L | V | E | S | G | P | G | L | V | K | P | S | E | T | L | S | L | T | C | T | V | S | G | F | S | T | T | R | F | G | V | H | W | V | R | Q | P | P | G |

HVR-H1 Contact: 30–35; HVR-H1 Kabat: 31–35

| Kabat number | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82a | 82b | 82c |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| hu1G7.v93 | K | G | L | E | W | L | G | V | I | W | R | G | G | S | T | D | Y | N | A | A | F | V | S | R | L | T | I | S | K | D | N | S | K | N | Q | V | S | L | K | L | S | S | S |

HVR-H2 Contact: 47–58; HVR-H2 Kabat: 50–65

| Kabat number | 82c | 83 | 84 | 85 | 86 | 87 | 88 | 89 | 90 | 91 | 92 | 93 | 94 | 95 | 96 | 97 | 98 | 99 | 100 | 100a | 100b | 100c | 100d | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|---|
| hu1G7.v93 | V | T | A | A | D | T | A | V | Y | Y | C | S | N | H | Y | Y | G | S | P | D | Y | A | L | D | N | W | G | Q | G | T | L | V | T | V | S | S |

HVR-H3 Contact: 93–101; HVR-H3 Kabat: 95–102

(SEQ ID NO: 106)

*FIG. 7A*

Light chain variable domain

Kabat number:         1   2   3   4   5   6   7   8   9  10  11  12  13  14  15  16  17  18  19  20  21  22  23  24  25  26  27  27a 27b 28  29  30  31  32  33  34  35  36  37  38  39  40
Hu7D8L1H2:            D   A   Q   L   T   Q   S   P   S   S   L   S   A   S   V   G   D   R   V   T   I   T   C   Q   S   S   Q   S   V   F   N   N   A   Q   L   S   W   Y   Q   Q   K   P HVR-L1 Contact: 24–34
HVR-L1 Kabat: 24–34

Kabat number:        41  42  43  44  45  46  47  48  49  50  51  52  53  54  55  56  57  58  59  60  61  62  63  64  65  66  67  68  69  70  71  72  73  74  75  76  77  78  79  80  81  82
Hu7D8L1H2:            G   K   P   P   K   L   L   I   Y   D   T   S   N   L   A   S   G   V   P   S   R   F   S   G   S   G   S   G   T   D   F   T   L   T   I   S   S   L   Q   P   E   D HVR-L2 Contact
HVR-L2 Kabat Kabat number:        83  84  85  86  87  88  89  90  91  92  93  94  95  95a 95b 96  97  98  99  100 101 102 103 104 105 106 107
Hu7D8L1H2:            F   A   T   Y   Y   C   L   G   A   Y   T   D   D   A   D   N   A   F   G   Q   G   T   K   V   E   I   K HVR-L3 Contact
HVR-L3 Kabat (SEQ ID NO: 109)

FIG. 11B

Light chain variable domain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 17B1 | E | N | V | L | T | Q | S | P | A | I | M | S | A | S | P | G | E | K | V | T | M | T | C | S | A | D | S | S | V | D | Y | I | H | W | Y | Q | Q | K | S | N | T | S |

HVR-L1 – Contact: positions 24–34; HVR-L1 Kabat: positions 24–34

| Kabat number | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 17B1 | P | K | L | W | I | Y | D | T | S | K | L | A | S | G | V | P | G | R | F | S | G | S | G | S | G | N | S | Y | S | L | T | I | S | S | M | E | A | E | D | F | A | T |

HVR-L2 – Contact: positions 47–53; HVR-L2 Kabat: positions 50–56

| Kabat number | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|
| 17B1 | Y | Y | C | F | Q | G | S | G | Y | P | L | T | F | G | S | G | T | K | L | E | L | K |

HVR-L3 – Contact: positions 89–96; HVR-L3 Kabat: positions 89–97

(SEQ ID NO: 111)

Light chain variable domain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 15G8 | Q | I | V | L | T | Q | S | P | A | I | M | S | A | S | P | G | E | K | V | T | M | T | C | S | A | S | S | S | V | D | Y | M | H | W | Y | Q | Q | K | S | G | T | S |  |

HVR-L1 – Contact (residues 24–34); HVR-L1 – Kabat (residues 24–34)

| Kabat number | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 15G8 | P | K | K | W | I | Y | D | T | S | K | L | A | S | G | V | P | A | R | F | S | G | S | G | S | G | T | S | Y | S | L | T | I | G | S | M | E | A | E | D | A | A | T |

HVR-L2 – Contact (residues 47–53); HVR-L2 – Kabat (residues 50–56)

| Kabat number | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|
| 15G8 | Y | Y | C | Q | Q | W | S | S | N | P | P | T | F | G | G | G | T | K | L | E | I | K |

HVR-L3 – Contact (residues 89–96); HVR-L3 – Kabat (residues 89–97)

(SEQ ID NO: 113)

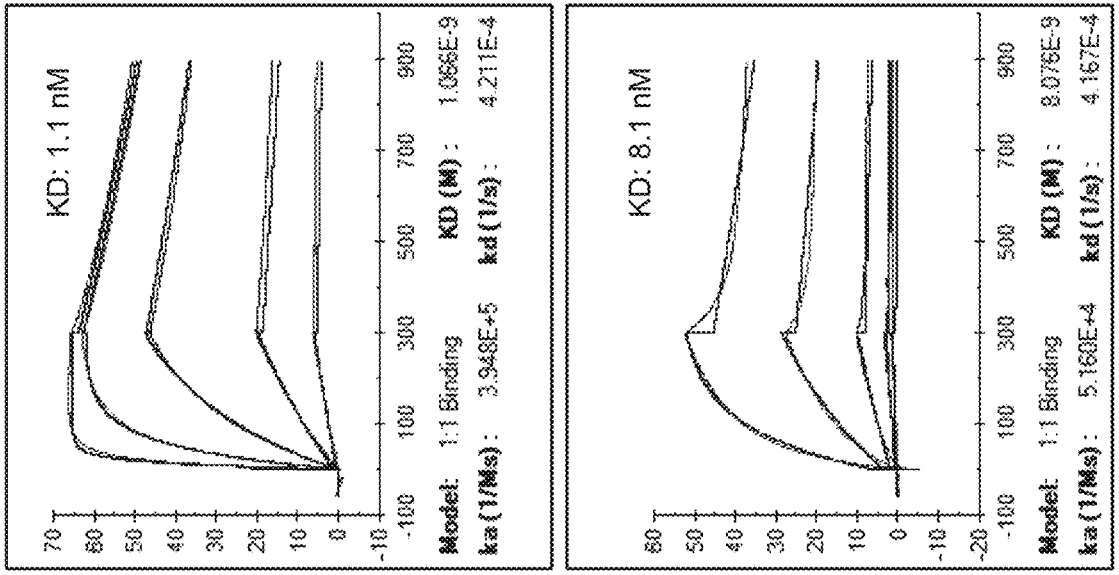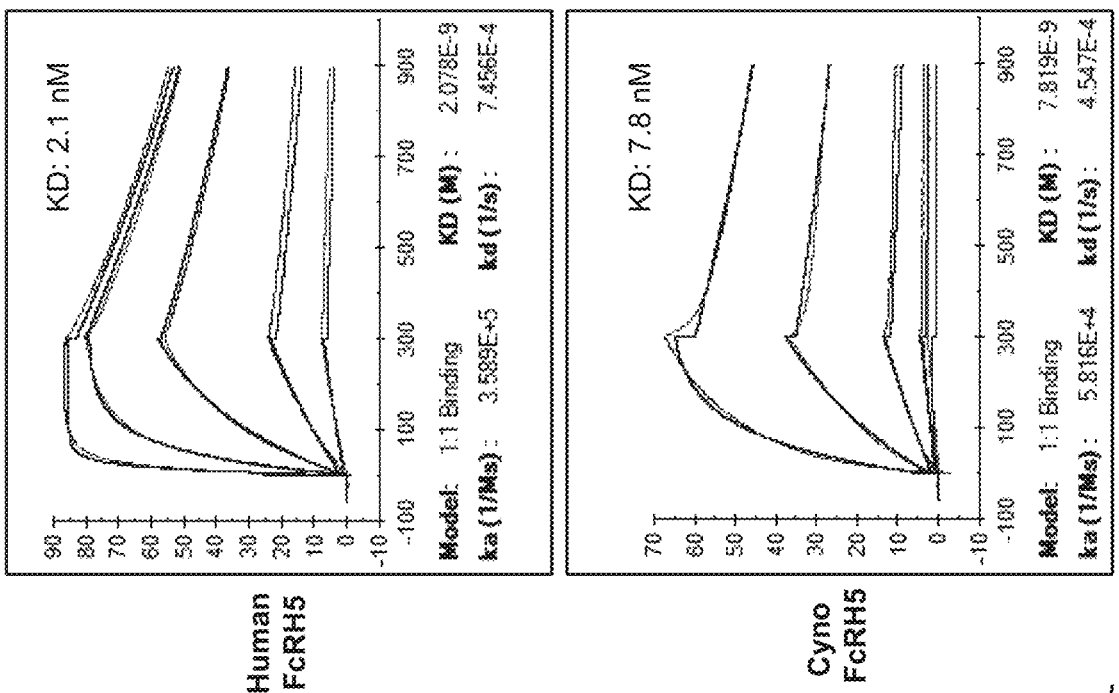
FIG. 15

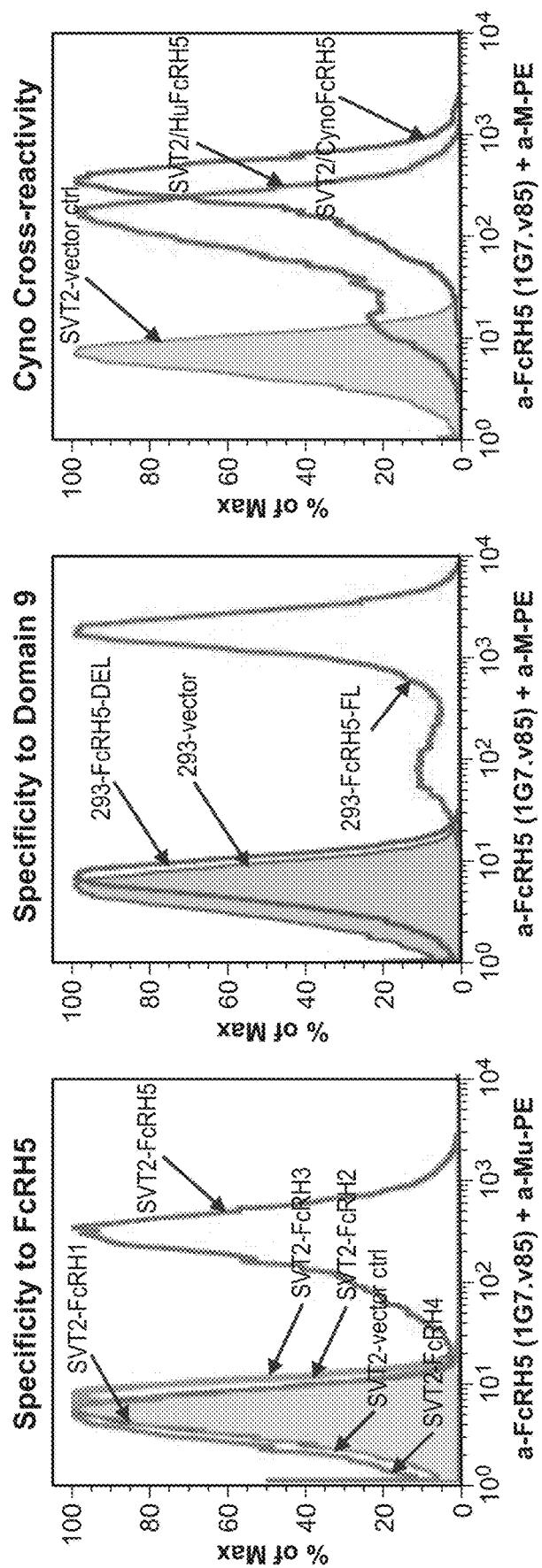

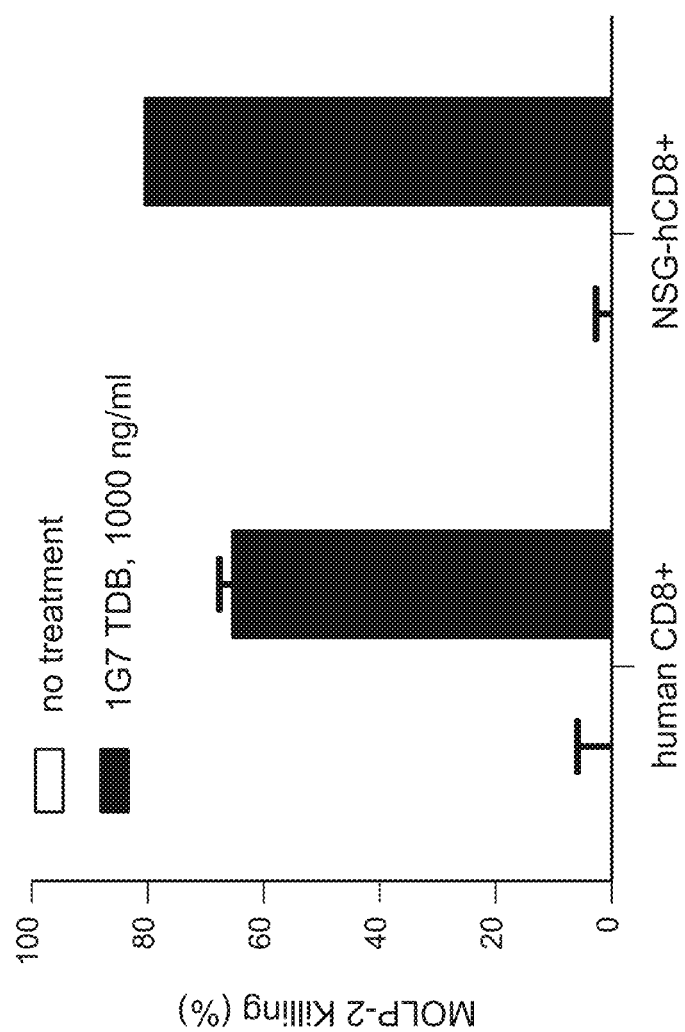

FIG. 42

| Expt. | Clone | Screening K_D (nM) | Fold improvement of screening K_D compared to hu1G7.v1 control(s) | HVR-L1 (24-34) K A S Q D V S N I V V | HVR-L2 (50-56) S A S Y R Y T | HVR-L3 (89-97) Q Q H Y S S P Y T |
|---|---|---|---|---|---|---|
| 1 | LC.01 | 5 | 5.2 | K A S Q D V S N L V V | S A S Y R Y S | Q Q H Y S P P Y T |
| 1 | LC.02 | 5 | 5.0 | K A S Q D V S N L V V | S G S Y R Y T | Q Q H Y Q S P Y T |
| 2 | LC.03 | 6 | 4.3 | K A S Q D V S N I V V | S G S Y R Y T | Q Q H Y S P P Y T |
| 2 | LC.04 | 6 | 4.2 | K A S Q D V S N L V V | S G S Y R Y T | Q Q H Y Q S P Y T |
| 1 | LC.05 | 6 | 4.0 | K A S Q D V S N I V V | S G S Y R Y T | Q Q H Y S P P Y T |
| 1 | LC.06 | 7 | 3.6 | K A S Q D V S N I V V | S G S Y R Y T | Q Q H Y S P P Y T |
| 1 | LC.07 | 8 | 3.1 | K A S H D V S N I V V | S G S Y R Y T | Q Q Q Y S S P Y T |
| 2 | LC.08 | 8 | 3.0 | K A S Q D V S N I V V | S A R Y R Y T | Q Q F S S P Y T (shifted) |
| 1 | LC.09 | 9 | 2.9 | K A S Q D V R N I V V | S A S N R Y T | Q Q G Y S S P Y T |
| 2 | LC.10 | 10 | 2.5 | K A S Q D V R N I V V | S A S Y R Y T | Q Q Q Y S S P Y T |
| 2 | LC.11 | 10 | 2.5 | K A S Q D V R N I V V | S A S N R Y T | Q Q Q Y S S P Y T |
| 1 | LC.12 | 10 | 2.4 | K A S Q D V S N L V V | S A S Y R Y T | Q Q H Y R S P Y T |
| 2 | LC.13 | 11 | 2.3 | K A S Q D V S N I V V | S G S Y R Y S | Q Q H Y S S P Y T |
| 2 | LC.14 | 11 | 2.3 | K A S Q D V K N I V V | S A S D R Y T | Q Q H Y S R P Y T |
| 1 | LC.15 | 11 | 2.3 | K A S Q D V S N L V V | S S S Y R Y T | Q Q H Y S S P Y T |
| 2 | LC.16 | 11 | 2.2 | K A S Q D V R N I V V | S A S Y R Y T | Q Q Q Y S S P Y T |
| 2 | LC.17 | 12 | 2.0 | K A S Q D V K N I V V | S A S D R Y T | Q Q H Y S P P Y T |
| 2 | LC.18 | 12 | 2.0 | K A S Q R V S N I V V | S S S Y R Y T | Q Q H Y S S P Y T |
| 2 | LC.19 | 12 | 2.0 | K A S Q D V S N I V V | S A S Y R Y T | Q Q G Y S S P Y T |
| 1 | LC.20 | 13 | 1.9 | K A S Q D V S N I V V | S G S Y R Y T | Q Q H Y S P P Y T |
| 2 | LC.21 | 13 | 1.8 | K A S Q D V S N I V V | S A X Y R Y S | Q Q H Y S S P Y T |
| 1 | LC.22 | 14 | 1.8 | K A S Q D V S N I V V | S G S Y R Y T | Q Q H Y S S P Y T |
| 2 | LC.23 | 14 | 1.7 | K A S Q D V K N I V V | S A A Y R Y T | Q Q H Y S S P Y T |
| 1 | LC.24 | 14 | 1.7 | K A S Q D V S N L V V | S A S Y R Y H | Q Q H Y A P Y T (shifted) |
| 2 | LC.25 | 15 | 1.7 | K A S R D V S N I V V | S A S Y R Y T | Q Q H Y S S P P T |
| 1 | LC.26 | 15 | 1.7 | K A S Q S V S N I V V | S A S Y R Y T | Q Q H Y S S P Y T |
| 1 | LC.27 | 15 | 1.6 | K A S Q D V S N L V V | S A S Y R Y T | Q Q H Y A S P Y T |
| 2 | LC.28 | 15 | 1.6 | K A S Q D V S N I V V | S G S N R Y T | Q Q H Y S S P Y T |
| 2 | LC.29 | 17 | 1.4 | K A S Q D V R N I V V | S A S Y R Y T | Q Q H Y S S P Y T |
| 2 | LC.30 | 17 | 1.4 | K A S Q D V S N A V V | S A S Y R Y T | Q Q H Y S S P Y T |
| 1 | LC.31 | 19 | 1.3 | K A S Q N V S N I V V | S S S Y R Y T | Q Q H Y S S P Y T |
| 2 | LC.32 | 20 | 1.2 | K A S Q E V S N I V V | S A S F R Y T | Q Q H Y S S P Y T |
| 2 | LC.33 | 20 | 1.2 | K A S Q D V S R I V V | S A S Y R Y S | Q Q H Y S S P Y T |
| 2 | LC.34 | 20 | 1.2 | K A S K D V S N I V V | S A R Y R Y T | Q Q H Y S S P Y T |
| 2 | LC.35 | 21 | 1.2 | K A S Q E V R N I V V | S A S Y R Y T | Q Q H Y S S P Y T |
| 2 | LC.36 | 21 | 1.2 | K A S K D V S N I V V | S A T Y R Y T | Q Q H Y S S P Y T |
| 1 | LC.37 | 22 | 1.1 | K A S Q D V S N I V V | S A S Y R Y T | Q Q H Y K S P Y T |
| 1 | LC.38 | 24 | 1.1 | K A S Q N V S N I V V | S A S Y R Y T | Q Q H Y S S P Y T |
| 2 | LC.39 | 43 | 0.6 | K A S H D V S N I V V | S A S D R Y T | Q Q H Y S S P Y T |

FIG. 43

| Expt. | Ref. | Screening $K_D$ (nM) | Fold improvement of screening $K_D$ compared to huIG7.v1 control(s) | HVR-H1 / HVR-H2 / HVR-H3 sequence |
|---|---|---|---|---|
| 1 | HC.01 | 15 | 1.7 | R L T R F G V H V I W R G G S T D Y N A A P M S H Y Y G S S D Y A L D N |
| 1 | HC.02 | 17 | 1.5 | S T T R F G V H V I W R G G T T D Y N A A P M S H Y Y G S S D Y A L D N |
| 1 | HC.03 | 20 | 1.3 | S T T R F G V H V I W R G G T T D Y N A A P M S H Y Y G S S D Y A L D N |
| 2 | HC.04 | 20 | 1.2 | R L T R F G V H V I W R G G R T D Y N A A P M S H Y Y G S S D Y A L D N |
| 2 | HC.05 | 22 | 1.1 | S L T R F G V H V I W R G G S T D Y N A A P M S H Y Y G S Q D Y A L D N |
| 1 | HC.06 | 23 | 1.1 | S T T R F G V H V I W R G G S T D Y N A A P M S H Y Y G S S D Y A L D N |
| 1 | HC.07 | 23 | 1.1 | S T T R F G V H V I W R G G K T D Y N A A P M S H Y Y G S S D Y A L D N |
| 2 | HC.08 | 25 | 1.0 | S K R F G V H V I W R G G T T D Y N A A P M S H Y Y G S S D Y A L D N |
| 1 | HC.09 | 26 | 1.0 | S L T R F G V H V I W R S G S T D Y N A A P M S H Y Y G S S D Y A L D N |
| 2 | HC.10 | 26 | 0.9 | S L R F G V H V I W R G G S T D Y N A A P M S H Y Y G S Q D Y A L D N |
| 1 | HC.11 | 26 | 0.9 | S T T R F G V H V I W R G G T T D Y N A A P M S H Y Y G S S D Y A L D N |
| 2 | HC.12 | 28 | 0.9 | S L T R F G V H V I W R G G S T D Y N A A P M S H Y Y G S S D Y A L D N |
| 1 | HC.13 | 30 | 0.8 | S Y T R F G V H V I W R G G S T D Y N A A P M S H Y Y G S S D Y A L D N |
| 2 | HC.14 | 30 | 0.8 | S K R F G V H V I W R G G H T D Y N A A P M S H Y Y G S S D Y A L D N |
| 1 | HC.15 | 32 | 0.8 | S T T R F G V H V I W R G G S T D Y N A A P M S H Y Y G S I D Y A L D N |
| 2 | HC.16 | 33 | 0.7 | S K R F G V H V I W R G G S T D Y N A A P M S H Y Y G S S D Y A L D N |
| 1 | HC.17 | 45 | 0.6 | S K R F G V H V I W R G G T T D Y N A A P M S H Y Y G S S D Y A L D N |
| 2 | HC.18 | 46 | 0.5 | L L T R F G V H V I W R N G S T D Y N A A P M S H Y Y G S Q D Y A L D N |
| 2 | HC.19 | 48 | 0.5 | S L T R F G L H V I W R D G S T D Y N A A P M S H Y Y G S S D Y A L D N |
| 2 | HC.20 | 50 | 0.5 | S L K R F G V H V I W R G G S T E Y N A A P M S H Y Y G S S D Y A L D N |
| 1 | HC.21 | 67 | 0.4 | S L T R F G V H V I W R G G R T D Y N A A P M S H Y Y G S S D Y A L D N |

FIG. 44

| Sample name | $KD_{Control}/KD_{Sample}$ *Mean, n=2 | HVR-L1 #30 | #32 | #43 | HVR-L2 #51 | #56 | HVR-L3 #91 | #94 |
|---|---|---|---|---|---|---|---|---|
| LC.H91Q.S94P | 4.1 | S | I | A | A | T | Q | P |
| LC.A51G.S94P | 3.6 | S | I | A | G | T | H | P |
| LC.I32L.A51G | 2.8 | S | L | A | G | T | H | S |
| LC.I32L.S94P | 2.7 | S | L | A | A | T | H | P |
| LC.S30R.I32L | 2.2 | R | L | A | A | T | H | S |
| LC.T56S.S94P | 2.1 | S | I | A | A | S | H | P |
| LC.S30R.S94P | 2.1 | R | I | A | A | T | H | P |
| LC.A51G.H91Q | 2.1 | S | I | A | G | T | Q | S |
| LC.S30R.H91Q | 1.7 | R | I | A | A | T | Q | S |
| LC.S30R.A51G | 1.6 | R | I | A | G | T | H | S |
| LC.A51G.T56S | 1.5 | S | I | A | G | S | H | S |
| LC.T56S.H91Q | 1.3 | S | I | A | A | S | Q | S |
| LC.I32L.T56S | 1.3 | S | L | A | A | S | H | S |
| hu1G7.v1 (Control) | 1.0 | S | I | S | A | T | H | S |
| hu1G7.v1 (Control) | 1.0 | S | I | S | A | T | H | S |
| LC.I32L.H91Q | 0.7 | S | L | A | A | T | Q | S |

| Region | Position | A | C | D | E | F | G | H | I | K | L | M | N | P | Q | R | S | T | V | W | Y |
|---|---|---|---|---|---|---|---|---|---|---|---|---|---|---|---|---|---|---|---|---|---|
| FW1 | E1 | | | | | 1.1 | | 1.0 | 0.8 | | 0.6 | | 0.8 | | | | 1.0 | 0.7 | | | 0.7 |
| | V2 | | | | | | | | | | | | | | | | | | | | |
| | V34 | | | | | | | | | | | | | | | | | | | | |
| | S25 | | | | | | | | | | | | | | | | | | | | |
| CDR 1 | S26 | | | | | | | | | | | | | | | | | | | | |
| | P27 | | | | | | | | | | | | | | | | | | | | |
| | S28 | | | | | | | | | | | | | 0.5 | | | | | | | |
| | L29 | | | | | | | | 0.5 | | | | | | | | | 1.3 | | | |
| | T30 | | | | | | | | | | | | | | | | | | | | |
| | R31 | | | | | | | | | | | | | | | | | | | | |
| | P32 | | | | | | | | | | | | | | | | | | | | |
| | G33 | | | | | | | | | | | | | | | | | | | | |
| | V34 | | | | | | | | | | | | | | | | | | | | |
| | H35 | | | | | | | | | | | | | | | | | | | | |
| FW2 | V37 | | | | | | | | | | | | | | | | | | | | 1.4 |
| | R38 | | | | | | | | | | | | | | | | | | | | |
| | Q39 | | | | | | | | | | | | | | | | | | | | |
| | P40 | | | | | | | | | | | | | | | | | | | | |
| | K43 | | | | | | | | | | | | | | | | | | | | |
| | L45 | | | | | | | | | | | | | | | | | | | | |
| | E46 | | | | | | | | | | | | | | | | | | | | |
| | W47 | | | | | | | | | | | | | | | | | | | | |
| | L48 | | | | | | | | | | | | | | | | | | | | |
| | G49 | | | | | | | | | | | | | | | | | | | | |
| CDR 2 | V50 | | | | | | | | | | | | | | | | | | | | |
| | I51 | | | | | | | | | | | | | | | | | | | | |
| | W52 | | | | | | | | | | | | | | | | | | | | |
| | R53 | | | | | | | | | | | | | | | | | | | | |
| | G54 | | | | | | | | | | | | 0.6 | | | | | | | | |
| | G55 | | | | | | | | | | | | | | | | | | | | |
| | S56 | | | | | | | | | | | | | | | | | | | | |
| | T57 | | | | | | | | | | | | | | | | | | | | |
| | D58 | | | | | | | | | | | | | | | | | | | | |
| | Y59 | | | | | | | | | | | | | | | | | | | | |
| | N60 | | | | | | | | | | | | | | | | | | | | |
| | A61 | | | | | | | | | | | | | 1.3 | | | | | | | |
| | A62 | | | | | | | | | | | | | | | | | | | | |
| | F63 | | | | | | | | | | | | | | | | | | | | |
| | M64 | | | | | | | 0.8 | | | | | | | | | | | | | |
| | S65 | | | 0.7 | | | | | | | | | | | | | 0.6 | | | | |
| FW3 | R66 | | | | | | | | | | | | | | | | | | | | |
| | L67 | | | | | | | | | | | | | | | | | | | | |
| | T68 | | | | | | | | | | | | | | | | | | | | |
| | I69 | | | | | | | | | | | | | | | | | | | | |
| | S70 | | | | | | | | | | | | | | | | | | | | |
| | K71 | | | | | | | | | | | | | | | | | | | | |
| | D72 | | | | | | | | | | | | | | | | | | | | |
| | N73 | | | | | | | | | | | | | | | | | | | | |
| | S74 | | | | | | | | | | | | | | | | | | | | |
| | K75 | | | | | | | | | | | | | | | | | | | | |
| | N76 | | | | | | | | | | | | | | | | | | | | |
| | Q77 | | | | | | | | | | | | | | | | | | | | |
| | V78 | | | | | | | | | | | | | | | | | | | | |
| | L80 | | | | | | | | | | | | | | | | | | | | |
| | K81 | | | | | | | | | | | | 0.5 | | | | | | | | |
| | S82a | | | | | | | | | | | | | | | | | | | | |
| | S82b | | | 0.9 | | | | | | | | | | | | | | | | | |
| | T83 | | | | | | | | | | | | | | | | | | | | |
| | A85 | | | | | | | | | | | | | | | | | | | | |
| | D86 | | | | | | | | | | | | | | | | | | | | |
| | Y91 | | | | | | | | | | | | | | | | | | | | |
| | S93 | | | | | | | | | | | | | | | | | | | | |
| | N94 | | | | | | | | | | | | | | | | | | | | |
| CDR 3 | H95 | | | | | | | | | | | | | | | | | | | | |
| | Y96 | | | | | | | | | | | | | | | | | | | | |
| | Y97 | | | | | | | | | | | | | | | | | | | | |
| | G98 | | | | | | | | | | | | | | | | | | | | |
| | S99 | | | | | | | | | | | | | | | | | | | | |
| | S100 | | | | | | | | | | | | | 0.5 | | | | | | | |
| | D100a | | | | | | | | | | | | | | | | | | | | |
| | Y100b | | | | | | | | | | | | | | | | | | | | |
| | A100c | | | | | | | | | | | | | | | | | | | | |
| | L100d | | | | | | | | | | | | | | | | | | | | |
| | D101 | | | | | | | | | | | | | | | | | | | | |
| | N102 | | | | | | | | | | | | | | | | | | | | |

HUMANIZED AND AFFINITY MATURED ANTIBODIES TO FCRH5 AND METHODS OF USE

FIELD OF THE INVENTION

The present invention relates to anti-FcRH5 antibodies and methods of using the same.

BACKGROUND OF THE INVENTION

Cell proliferative disorders, such as cancer, are characterized by the uncontrolled growth of cell subpopulations. They are the leading cause of death in the developed world and the second leading cause of death in developing countries, with over 14 million new cancer cases diagnosed and over eight million cancer deaths occurring each year. The National Cancer Institute has estimated that greater than half a million Americans will die of cancer in 2016, accounting for nearly one out of every four deaths in the country. As the elderly population has grown, the incidence of cancer has concurrently risen, as the probability of developing cancer is more than two-fold higher after the age of seventy. Cancer care thus represents a significant and ever-increasing societal burden.

The Fc receptor-like 5 (FcRH5, also known as FcRL5 or IRTA2) gene belongs to a family of six recently identified genes of the immunoglobulin superfamily (IgSF). This family of genes is closely related to the Fc receptors with the conserved genomic structure, extracellular Ig domain composition, and immunoreceptor tyrosine-based inhibitory (ITIM) and immunoreceptor tyrosine-based activation (ITAM) like signaling motifs (Davis et al. *Eur. J. Immunol.* 35:674-80, 2005). Six members of the FcRH/IRTA receptor family have been described: FcRH1/IRTA5, FcRH2/IRTA4, FcRH3/IRTA3, FcRH4/IRTA1, FcRH5/IRTA2, and FcRH6 (Polson et al. *Int. Immunol.* 18(9):1363-1373, 2006. The FcRH cDNAs encode type I transmembrane glycoproteins with multiple Ig-like extracellular domains and cytoplasmic domains containing consensus immunoreceptor tyrosine-based activating and/or inhibitory signaling motifs. The FcRH genes are structurally related, and their protein products share 28-60% extracellular identity with each other. They also share 15-31% identity with their closest FcR relatives. There is a high degree of homology between the different FcRHs.

The ligand(s) for FcRH5 are unknown, but FcRH5 has been implicated in enhanced proliferation and downstream isotype expression during the development of antigen-primed B-cells (Dement-Brown et al. *J. Leukoc. Biol.* 91:59-67, 2012). The FcRH5 locus has three major mRNA isoforms (FcRH5a, FcRH5b, and FcRH5c). The major FcRH5 protein isoforms encoded by these transcripts share a common amino acid sequence until residue 560, featuring a common signal peptide and six extracellular Ig-like domains. FcRH5a represents a 759-amino acid secreted glycoprotein with eight Ig-like domains followed by 13 unique, predominantly polar amino acids at its C-terminus. FcRH5b diverges from FcRH5a at amino acid residue 560 and extends for a short stretch of 32 additional residues, whose hydrophobicity is compatible with its docking to the plasma membrane via a GPI anchor. FcRH5c is the longest isoform whose sequence deviates from FcRH5a at amino acid 746. FcRH5c encodes a 977-amino acid type I transmembrane glycoprotein with nine extracellular Ig-type domains harboring eight potential N-linked glycosylation sites, a 23-amino acid transmembrane domain, and a 104-amino acid cytoplasmic domain with three consensus SH2 binding motifs having an ITIM consensus.

The FcRH genes are clustered together in the midst of the classical FcR genes (FcγRI, FcγRII, FcγRIII, and FcRI) in the 1q21-23 region of chromosome 1. This region contains one of the most frequent secondary chromosomal abnormalities associated with malignant phenotype in hematopoietic tumors, especially in multiple myeloma (Hatzivassiliou et al. *Immunity.* 14:277-89, 2001). FcRH5 is expressed only in the B-cell lineage, starting as early as pre-B-cells, but does not attain full expression until the mature B-cell stage. Unlike most known other B-cell-specific surface proteins (e.g., CD20, CD19, and CD22), FcRH5 continues to be expressed in plasma cells, whereas other B-cell-specific markers are downregulated (Polson et al. *Int. Immunol.* 18:1363-73, 2006). In addition, FcRH5 mRNA is overexpressed in multiple myeloma cell lines with 1q21 abnormalities as detected by oligonucleotide arrays (Inoue *Am. J. Pathol.* 165:71-81, 2004). The expression pattern indicates that FcRH5 could be a target for antibody-based therapies for the treatment of multiple myeloma. Multiple myeloma is a malignancy of plasma cells characterized by skeletal lesions, renal failure, anemia, and hypercalcemia, and it is essentially incurable by current therapies. Current drug treatments for multiple myeloma include combinations of the proteosome inhibitor bortezomib (VELCADE®), the immunomodulator lenalidomide (REVLIMID®), and the steroid dexamethasone.

Monoclonal antibody (mAb)-based therapy has become an important treatment modality for cancer. FcRH5c-specific antibody-based therapies and detection methods may be particularly efficacious as they specifically recognize target cell, membrane-associated FcRH5 rather than antibodies which recognize both soluble and membrane isoforms of FcRH5. However, only the last Ig-like domain of FcRH5 (Ig-like domain 9) is a unique extracellular region that differentiates between the three major isoforms of FcRH5 (e.g., FcRH5a, FcRH5b, and FcRH5c), and there is significant homology between the Ig-like domains within FcRH5. Further, the last Ig-like domain is highly conserved between FcRH1, FcRH2, FcRH3, and FcRH5. Any antibody-based therapy that specifically targeted FcRH5 should have minimal cross-reactivity with other FcRHs to avoid adverse off-target effects (e.g., FcRH3 is expressed on normal NK cells).

In view of the above, there is an unmet need in the field for safe and effective agents for use in the treatment of cell proliferative disorders (e.g., cancers, e.g., FcRH5-positive cancers, e.g., multiple myeloma).

SUMMARY OF THE INVENTION

The present invention provides anti-FcRH5 antibodies (e.g., bispecific antibodies, e.g., FcRH5 T cell-dependant bispecific (TDB) antibodies), compositions, and methods of using the same for the treatment of cell proliferative disorders (e.g., cancers, e.g., FcRH5-positive cancers, e.g., multiple myeloma).

In a first aspect, the invention features an anti-Fc Receptor-like 5 (FcRH5) antibody, including a binding domain comprising the following six hypervariable regions (HVRs): (a) an HVR-H1 comprising the amino acid sequence of SEQ ID NO: 1, (b) an HVR-H2 comprising the amino acid sequence of SEQ ID NO: 2, (c) an HVR-H3 comprising the amino acid sequence of SEQ ID NO: 3, (d) an HVR-L1 comprising the amino acid sequence of SEQ ID NO: 4, (e)

an HVR-L2 comprising the amino acid sequence of SEQ ID NO: 5, and (f) an HVR-L3 comprising the amino acid sequence of SEQ ID NO: 6.

In some embodiments, the anti-FcRH5 antibody comprises a binding domain comprising the following six HVRs: (a) an HVR-H1 comprising the amino acid sequence of SEQ ID NO: 1, (b) an HVR-H2 comprising the amino acid sequence of SEQ ID NO: 8, (c) an HVR-H3 comprising the amino acid sequence of SEQ ID NO: 9, (d) an HVR-L1 comprising the amino acid sequence of SEQ ID NO: 12, (e) an HVR-L2 comprising the amino acid sequence of SEQ ID NO: 16, and (f) an HVR-L3 comprising the amino acid sequence of SEQ ID NO: 23. In some embodiments, the binding domain comprises (a) a heavy chain variable (VH) domain comprising an amino acid sequence having at least 95% sequence identity to the amino acid sequence of SEQ ID NO: 104, (b) a light chain variable (VL) domain comprising an amino acid sequence having at least 95% sequence identity to the amino acid sequence of SEQ ID NO: 105, or (c) a VH domain as in (a) and a VL domain as in (b). In some embodiments, the antibody further comprises the following heavy chain variable region framework regions (FRs): (a) an FR-H1 comprising the amino acid sequence of SEQ ID NO: 52, (b) an FR-H2 comprising the amino acid sequence of SEQ ID NO: 54, (c) an FR-H3 comprising the amino acid sequence of SEQ ID NO: 46, and (d) an FR-H4 comprising the amino acid sequence of SEQ ID NO: 47. In some embodiments, the VH domain comprises the amino acid sequence of SEQ ID NO: 104. In some embodiments, the antibody further comprises the following light chain variable region FRs: (a) an FR-L1 comprising the amino acid sequence of SEQ ID NO: 48, (b) an FR-L2 comprising the amino acid sequence of SEQ ID NO: 57, (c) an FR-L3 comprising the amino acid sequence of SEQ ID NO: 50, and (d) an FR-L4 comprising the amino acid sequence of SEQ ID NO: 51. In some embodiments, the VL domain comprises the amino acid sequence of SEQ ID NO: 105. In some embodiments, the anti-FcRH5 antibody comprises a binding domain comprising (a) a VH domain comprising an amino acid sequence of SEQ ID NO: 104 and (b) a VL domain comprising an amino acid sequence of SEQ ID NO: 105.

In other embodiments, the anti-FcRH5 antibody comprises a binding domain comprising the following six HVRs: (a) an HVR-H1 comprising the amino acid sequence of SEQ ID NO: 1, (b) an HVR-H2 comprising the amino acid sequence of SEQ ID NO: 8, (c) an HVR-H3 comprising the amino acid sequence of SEQ ID NO: 10, (d) an HVR-L1 comprising the amino acid sequence of SEQ ID NO: 14, (e) an HVR-L2 comprising the amino acid sequence of SEQ ID NO: 16, and (f) an HVR-L3 comprising the amino acid sequence of SEQ ID NO: 23. In some embodiments, the binding domain comprises (a) a VH domain comprising an amino acid sequence having at least 95% sequence identity to the amino acid sequence of SEQ ID NO: 106, (b) a VL domain comprising an amino acid sequence having at least 95% sequence identity to the amino acid sequence of SEQ ID NO: 107, or (c) a VH domain as in (a) and a VL domain as in (b). In some embodiments, the antibody further comprises the following heavy chain variable region FRs: (a) an FR-H1 comprising the amino acid sequence of SEQ ID NO: 53, (b) an FR-H2 comprising the amino acid sequence of SEQ ID NO: 54, (c) an FR-H3 comprising the amino acid sequence of SEQ ID NO: 46, and (d) an FR-H4 comprising the amino acid sequence of SEQ ID NO: 47. In some embodiments, the VH domain comprises the amino acid sequence of SEQ ID NO: 106. In some embodiments, the antibody further comprises the following light chain variable region FRs: (a) an FR-L1 comprising the amino acid sequence of SEQ ID NO: 48, (b) an FR-L2 comprising the amino acid sequence of SEQ ID NO: 57, (c) an FR-L3 comprising the amino acid sequence of SEQ ID NO: 50, and (d) an FR-L4 comprising the amino acid sequence of SEQ ID NO: 51. In some embodiments, the VL domain comprises the amino acid sequence of SEQ ID NO: 107. In some embodiments, the anti-FcRH5 antibody comprises a binding domain comprising (a) a VH domain comprising an amino acid sequence of SEQ ID NO: 106 and (b) a VL domain comprising an amino acid sequence of SEQ ID NO: 107.

In other embodiments, the anti-FcRH5 antibody comprises a binding domain comprising the following six HVRs: (a) an HVR-H1 comprising the amino acid sequence of SEQ ID NO: 1, (b) an HVR-H2 comprising the amino acid sequence of SEQ ID NO: 7, (c) an HVR-H3 comprising the amino acid sequence of SEQ ID NO: 9, (d) an HVR-L1 comprising the amino acid sequence of SEQ ID NO: 11, (e) an HVR-L2 comprising the amino acid sequence of SEQ ID NO: 15, and (f) an HVR-L3 comprising the amino acid sequence of SEQ ID NO: 20. In some embodiments, the binding domain comprises (a) a VH domain comprising an amino acid sequence having at least 95% sequence identity to the amino acid sequence of SEQ ID NO: 82, (b) a VL domain comprising an amino acid sequence having at least 95% sequence identity to the amino acid sequence of SEQ ID NO: 83, or (c) a VH domain as in (a) and a VL domain as in (b). In some embodiments, the antibody further comprises the following heavy chain variable region FRs: (a) an FR-H1 comprising the amino acid sequence of SEQ ID NO: 52, (b) an FR-H2 comprising the amino acid sequence of SEQ ID NO: 54, (c) an FR-H3 comprising the amino acid sequence of SEQ ID NO: 46, and (d) an FR-H4 comprising the amino acid sequence of SEQ ID NO: 47. In some embodiments, the VH domain comprises the amino acid sequence of SEQ ID NO: 82. In some embodiments, the antibody further comprises the following light chain variable region FRs: (a) an FR-L1 comprising the amino acid sequence of SEQ ID NO: 48, (b) an FR-L2 comprising the amino acid sequence of SEQ ID NO: 56, (c) an FR-L3 comprising the amino acid sequence of SEQ ID NO: 50, and (d) an FR-L4 comprising the amino acid sequence of SEQ ID NO: 51. In some embodiments, the VL domain comprises the amino acid sequence of SEQ ID NO: 83. In some embodiments, the anti-FcRH5 antibody comprises a binding domain comprising (a) a VH domain comprising an amino acid sequence of SEQ ID NO: 82 and (b) a VL domain comprising an amino acid sequence of SEQ ID NO: 83.

In other embodiments, the anti-FcRH5 antibody comprises a binding domain comprising the following six HVRs: (a) an HVR-H1 comprising the amino acid sequence of SEQ ID NO: 1, (b) an HVR-H2 comprising the amino acid sequence of SEQ ID NO: 7, (c) an HVR-H3 comprising the amino acid sequence of SEQ ID NO: 9, (d) an HVR-L1 comprising the amino acid sequence of SEQ ID NO: 12, (e) an HVR-L2 comprising the amino acid sequence of SEQ ID NO: 16, and (f) an HVR-L3 comprising the amino acid sequence of SEQ ID NO: 21. In some embodiments, the binding domain comprises (a) a VH domain comprising an amino acid sequence having at least 95% sequence identity to the amino acid sequence of SEQ ID NO: 84, (b) a VL domain comprising an amino acid sequence having at least 95% sequence identity to the amino acid sequence of SEQ ID NO: 85, or (c) a VH domain as in (a) and a VL domain as in (b). In some embodiments, the antibody further comprises the following heavy chain variable region FRs: (a) an FR-H1 comprising the amino acid sequence of SEQ ID NO: 52, (b) an FR-H2 comprising the amino acid sequence of SEQ ID NO: 54, (c) an FR-H3 comprising the amino acid sequence of SEQ ID NO: 46, and (d) an FR-H4 comprising the amino acid sequence of SEQ ID NO: 47. In some embodiments, the VH domain comprises the amino acid sequence of SEQ ID NO: 84. In some embodiments, the antibody further comprises the following light chain variable region FRs: (a) an FR-L1 comprising the amino acid sequence of SEQ ID NO: 48, (b) an FR-L2 comprising the amino acid sequence of SEQ ID NO: 57, (c) an FR-L3 comprising the amino acid sequence of SEQ ID NO: 50, and (d) an FR-L4 comprising the amino acid sequence of SEQ ID NO: 51. In some embodiments, the VL domain comprises the amino acid sequence of SEQ ID NO: 85. In some embodiments, the anti-FcRH5 antibody comprises a binding domain comprising (a) a VH domain comprising an amino acid sequence of SEQ ID NO: 84 and (b) a VL domain comprising an amino acid sequence of SEQ ID NO: 85.

In other embodiments, the anti-FcRH5 antibody comprises a binding domain comprising the following six HVRs: (a) an HVR-H1 comprising the amino acid sequence of SEQ ID NO: 1, (b) an HVR-H2 comprising the amino acid sequence of SEQ ID NO: 7, (c) an HVR-H3 comprising the amino acid sequence of SEQ ID NO: 9, (d) an HVR-L1 comprising the amino acid sequence of SEQ ID NO: 12, (e) an HVR-L2 comprising the amino acid sequence of SEQ ID NO: 17, and (f) an HVR-L3 comprising the amino acid sequence of SEQ ID NO: 22. In some embodiments, the binding domain comprises (a) a VH domain comprising an amino acid sequence having at least 95% sequence identity to the amino acid sequence of SEQ ID NO: 86, (b) a VL domain comprising an amino acid sequence having at least 95% sequence identity to the amino acid sequence of SEQ ID NO: 87, or (c) a VH domain as in (a) and a VL domain as in (b). In some embodiments, the antibody further comprises the following heavy chain variable region FRs: (a) an FR-H1 comprising the amino acid sequence of SEQ ID NO: 52, (b) an FR-H2 comprising the amino acid sequence of SEQ ID NO: 54, (c) an FR-H3 comprising the amino acid sequence of SEQ ID NO: 46, and (d) an FR-H4 comprising the amino acid sequence of SEQ ID NO: 47. In some embodiments, the VH domain comprises the amino acid sequence of SEQ ID NO: 86. In some embodiments, the antibody further comprises the following light chain variable region FRs: (a) an FR-L1 comprising the amino acid sequence of SEQ ID NO: 48, (b) an FR-L2 comprising the amino acid sequence of SEQ ID NO: 57, (c) an FR-L3 comprising the amino acid sequence of SEQ ID NO: 50, and (d) an FR-L4 comprising the amino acid sequence of SEQ ID NO: 51. In some embodiments, the VL domain comprises the amino acid sequence of SEQ ID NO: 87. In some embodiments, the anti-FcRH5 antibody comprises a binding domain comprising (a) a VH domain comprising an amino acid sequence of SEQ ID NO: 86 and (b) a VL domain comprising an amino acid sequence of SEQ ID NO: 87.

In other embodiments, the anti-FcRH5 antibody comprises a binding domain comprising the following six HVRs: (a) an HVR-H1 comprising the amino acid sequence of SEQ ID NO: 1, (b) an HVR-H2 comprising the amino acid sequence of SEQ ID NO: 7, (c) an HVR-H3 comprising the amino acid sequence of SEQ ID NO: 9, (d) an HVR-L1 comprising the amino acid sequence of SEQ ID NO: 13, (e) an HVR-L2 comprising the amino acid sequence of SEQ ID NO: 16, and (f) an HVR-L3 comprising the amino acid sequence of SEQ ID NO: 21. In some embodiments, the binding domain comprises (a) a VH domain comprising an amino acid sequence having at least 95% sequence identity to the amino acid sequence of SEQ ID NO: 88, (b) a VL domain comprising an amino acid sequence having at least 95% sequence identity to the amino acid sequence of SEQ ID NO: 89, or (c) a VH domain as in (a) and a VL domain as in (b). In some embodiments, the antibody further comprises the following heavy chain variable region FRs: (a) an FR-H1 comprising the amino acid sequence of SEQ ID NO: 52, (b) an FR-H2 comprising the amino acid sequence of SEQ ID NO: 54, (c) an FR-H3 comprising the amino acid sequence of SEQ ID NO: 46, and (d) an FR-H4 comprising the amino acid sequence of SEQ ID NO: 47. In some embodiments, the VH domain comprises the amino acid sequence of SEQ ID NO: 88. In some embodiments, the antibody further comprises the following light chain variable region FRs: (a) an FR-L1 comprising the amino acid sequence of SEQ ID NO: 48, (b) an FR-L2 comprising the amino acid sequence of SEQ ID NO: 57, (c) an FR-L3 comprising the amino acid sequence of SEQ ID NO: 50, and (d) an FR-L4 comprising the amino acid sequence of SEQ ID NO: 51. In some embodiments, the VL domain comprises the amino acid sequence of SEQ ID NO: 89. In some embodiments, the anti-FcRH5 antibody comprises a binding domain comprising (a) a VH domain comprising an amino acid sequence of SEQ ID NO: 88 and (b) a VL domain comprising an amino acid sequence of SEQ ID NO: 89.

In other embodiments, the anti-FcRH5 antibody comprises a binding domain comprising the following six HVRs: (a) an HVR-H1 comprising the amino acid sequence of SEQ ID NO: 1, (b) an HVR-H2 comprising the amino acid sequence of SEQ ID NO: 7, (c) an HVR-H3 comprising the amino acid sequence of SEQ ID NO: 9, (d) an HVR-L1 comprising the amino acid sequence of SEQ ID NO: 12, (e) an HVR-L2 comprising the amino acid sequence of SEQ ID NO: 16, and (f) an HVR-L3 comprising the amino acid sequence of SEQ ID NO: 23. In some embodiments, the binding domain comprises (a) a VH domain comprising an amino acid sequence having at least 95% sequence identity to the amino acid sequence of SEQ ID NO: 90, (b) a VL domain comprising an amino acid sequence having at least 95% sequence identity to the amino acid sequence of SEQ ID NO: 91, or (c) a VH domain as in (a) and a VL domain as in (b). In some embodiments, the antibody further comprises the following heavy chain variable region FRs: (a) an FR-H1 comprising the amino acid sequence of SEQ ID NO: 52, (b) an FR-H2 comprising the amino acid sequence of SEQ ID NO: 54, (c) an FR-H3 comprising the amino acid sequence of SEQ ID NO: 46, and (d) an FR-H4 comprising the amino acid sequence of SEQ ID NO: 47. In some embodiments, the VH domain comprises the amino acid sequence of SEQ ID NO: 90. In some embodiments, the antibody further comprises the following light chain variable region FRs: (a) an FR-L1 comprising the amino acid sequence of SEQ ID NO: 48, (b) an FR-L2 comprising the amino acid sequence of SEQ ID NO: 57, (c) an FR-L3 comprising the amino acid sequence of SEQ ID NO: 50, and (d) an FR-L4 comprising the amino acid sequence of SEQ ID NO: 51. In some embodiments, the VL domain comprises the amino acid sequence of SEQ ID NO: 91. In some embodiments, the anti-FcRH5 antibody comprises a binding domain comprising (a) a VH domain comprising an amino acid sequence of SEQ ID NO: 90 and (b) a VL domain comprising an amino acid sequence of SEQ ID NO: 91.

In other embodiments, the anti-FcRH5 antibody comprises a binding domain comprising the following six HVRs: (a) an HVR-H1 comprising the amino acid sequence of SEQ ID NO: 1, (b) an HVR-H2 comprising the amino acid sequence of SEQ ID NO: 7, (c) an HVR-H3 comprising the amino acid sequence of SEQ ID NO: 9, (d) an HVR-L1 comprising the amino acid sequence of SEQ ID NO: 11, (e) an HVR-L2 comprising the amino acid sequence of SEQ ID NO: 18, and (f) an HVR-L3 comprising the amino acid sequence of SEQ ID NO: 22. In some embodiments, the binding domain comprises (a) a VH domain comprising an amino acid sequence having at least 95% sequence identity to the amino acid sequence of SEQ ID NO: 92, (b) a VL domain comprising an amino acid sequence having at least 95% sequence identity to the amino acid sequence of SEQ ID NO: 93, or (c) a VH domain as in (a) and a VL domain as in (b). In some embodiments, the antibody further comprises the following heavy chain variable region FRs: (a) an FR-H1 comprising the amino acid sequence of SEQ ID NO: 52, (b) an FR-H2 comprising the amino acid sequence of SEQ ID NO: 54, (c) an FR-H3 comprising the amino acid sequence of SEQ ID NO: 46, and (d) an FR-H4 comprising the amino acid sequence of SEQ ID NO: 47. In some embodiments, the VH domain comprises the amino acid sequence of SEQ ID NO: 92. In some embodiments, the antibody further comprises the following light chain variable region FRs: (a) an FR-L1 comprising the amino acid sequence of SEQ ID NO: 48, (b) an FR-L2 comprising the amino acid sequence of SEQ ID NO: 56, (c) an FR-L3 comprising the amino acid sequence of SEQ ID NO: 50, and (d) an FR-L4 comprising the amino acid sequence of SEQ ID NO: 51. In some embodiments, the VL domain comprises the amino acid sequence of SEQ ID NO: 93. In some embodiments, the anti-FcRH5 antibody comprises a binding domain comprising (a) a VH domain comprising an amino acid sequence of SEQ ID NO: 92 and (b) a VL domain comprising an amino acid sequence of SEQ ID NO: 93.

In other embodiments, the anti-FcRH5 antibody comprises a binding domain comprising the following six HVRs: (a) an HVR-H1 comprising the amino acid sequence of SEQ ID NO: 1, (b) an HVR-H2 comprising the amino acid sequence of SEQ ID NO: 7, (c) an HVR-H3 comprising the amino acid sequence of SEQ ID NO: 9, (d) an HVR-L1 comprising the amino acid sequence of SEQ ID NO: 11, (e) an HVR-L2 comprising the amino acid sequence of SEQ ID NO: 19, and (f) an HVR-L3 comprising the amino acid sequence of SEQ ID NO: 24. In some embodiments, the binding domain comprises (a) a VH domain comprising an amino acid sequence having at least 95% sequence identity to the amino acid sequence of SEQ ID NO: 94, (b) a VL domain comprising an amino acid sequence having at least 95% sequence identity to the amino acid sequence of SEQ ID NO: 95, or (c) a VH domain as in (a) and a VL domain as in (b). In some embodiments, the antibody further comprises the following heavy chain variable region FRs: (a) an FR-H1 comprising the amino acid sequence of SEQ ID NO: 52, (b) an FR-H2 comprising the amino acid sequence of SEQ ID NO: 54, (c) an FR-H3 comprising the amino acid sequence of SEQ ID NO: 46, and (d) an FR-H4 comprising the amino acid sequence of SEQ ID NO: 47. In some embodiments, the VH domain comprises the amino acid sequence of SEQ ID NO: 94. In some embodiments, the antibody further comprises the following light chain variable region FRs: (a) an FR-L1 comprising the amino acid sequence of SEQ ID NO: 48, (b) an FR-L2 comprising the amino acid sequence of SEQ ID NO: 57, (c) an FR-L3 comprising the amino acid sequence of SEQ ID NO: 50, and (d) an FR-L4 comprising the amino acid sequence of SEQ ID NO: 51. In some embodiments, the VL domain comprises the amino acid sequence of SEQ ID NO: 95. In some embodiments, the anti-FcRH5 antibody comprises a binding domain comprising (a) a VH domain comprising an amino acid sequence of SEQ ID NO: 94 and (b) a VL domain comprising an amino acid sequence of SEQ ID NO: 95.

In other embodiments, the anti-FcRH5 antibody comprises a binding domain comprising the following six HVRs: (a) an HVR-H1 comprising the amino acid sequence of SEQ ID NO: 1, (b) an HVR-H2 comprising the amino acid sequence of SEQ ID NO: 7, (c) an HVR-H3 comprising the amino acid sequence of SEQ ID NO: 9, (d) an HVR-L1 comprising the amino acid sequence of SEQ ID NO: 12, (e) an HVR-L2 comprising the amino acid sequence of SEQ ID NO: 18, and (f) an HVR-L3 comprising the amino acid sequence of SEQ ID NO: 25. In some embodiments, the binding domain comprises (a) a VH domain comprising an amino acid sequence having at least 95% sequence identity to the amino acid sequence of SEQ ID NO: 96, (b) a VL domain comprising an amino acid sequence having at least 95% sequence identity to the amino acid sequence of SEQ ID NO: 97, or (c) a VH domain as in (a) and a VL domain as in (b). In some embodiments, the antibody further comprises the following heavy chain variable region FRs: (a) an FR-H1 comprising the amino acid sequence of SEQ ID NO: 53, (b) an FR-H2 comprising the amino acid sequence of SEQ ID NO: 54, (c) an FR-H3 comprising the amino acid sequence of SEQ ID NO: 46, and (d) an FR-H4 comprising the amino acid sequence of SEQ ID NO: 47. In some embodiments, the VH domain comprises the amino acid sequence of SEQ ID NO: 96. In some embodiments, the antibody further comprises the following light chain variable region FRs: (a) an FR-L1 comprising the amino acid sequence of SEQ ID NO: 48, (b) an FR-L2 comprising the amino acid sequence of SEQ ID NO: 57, (c) an FR-L3 comprising the amino acid sequence of SEQ ID NO: 50, and (d) an FR-L4 comprising the amino acid sequence of SEQ ID NO: 51. In some embodiments, the VL domain comprises the amino acid sequence of SEQ ID NO: 97. In some embodiments, the anti-FcRH5 antibody comprises a binding domain comprising (a) a VH domain comprising an amino acid sequence of SEQ ID NO: 96 and (b) a VL domain comprising an amino acid sequence of SEQ ID NO: 97.

In other embodiments, the anti-FcRH5 antibody comprises a binding domain comprising the following six HVRs: (a) an HVR-H1 comprising the amino acid sequence of SEQ ID NO: 1, (b) an HVR-H2 comprising the amino acid sequence of SEQ ID NO: 7, (c) an HVR-H3 comprising the amino acid sequence of SEQ ID NO: 9, (d) an HVR-L1 comprising the amino acid sequence of SEQ ID NO: 12, (e) an HVR-L2 comprising the amino acid sequence of SEQ ID NO: 18, and (f) an HVR-L3 comprising the amino acid sequence of SEQ ID NO: 25. In some embodiments, the binding domain comprises (a) a VH domain comprising an amino acid sequence having at least 95% sequence identity to the amino acid sequence of SEQ ID NO: 98, (b) a VL domain comprising an amino acid sequence having at least 95% sequence identity to the amino acid sequence of SEQ ID NO: 99, or (c) a VH domain as in (a) and a VL domain as in (b). In some embodiments, the antibody further comprises the following heavy chain variable region FRs: (a) an FR-H1 comprising the amino acid sequence of SEQ ID NO: 52, (b) an FR-H2 comprising the amino acid sequence of SEQ ID NO: 55, (c) an FR-H3 comprising the amino acid sequence of SEQ ID NO: 46, and (d) an FR-H4 comprising the amino acid sequence of SEQ ID NO: 47. In some embodiments, the VH domain comprises the amino acid sequence of SEQ ID NO: 98. In some embodiments, the antibody further comprises the following light chain variable region FRs: (a) an FR-L1 comprising the amino acid sequence of SEQ ID NO: 48, (b) an FR-L2 comprising the amino acid sequence of SEQ ID NO: 57, (c) an FR-L3 comprising the amino acid sequence of SEQ ID NO: 50, and (d) an FR-L4 comprising the amino acid sequence of SEQ ID NO: 51. In some embodiments, the VL domain comprises the amino acid sequence of SEQ ID NO: 99. In some embodiments, the anti-FcRH5 antibody comprises a binding domain comprising (a) a VH domain comprising an amino acid sequence of SEQ ID NO: 98 and (b) a VL domain comprising an amino acid sequence of SEQ ID NO: 99.

In other embodiments, the anti-FcRH5 antibody comprises a binding domain comprising the following six HVRs: (a) an HVR-H1 comprising the amino acid sequence of SEQ ID NO: 1, (b) an HVR-H2 comprising the amino acid sequence of SEQ ID NO: 7, (c) an HVR-H3 comprising the amino acid sequence of SEQ ID NO: 9, (d) an HVR-L1 comprising the amino acid sequence of SEQ ID NO: 12, (e) an HVR-L2 comprising the amino acid sequence of SEQ ID NO: 18, and (f) an HVR-L3 comprising the amino acid sequence of SEQ ID NO: 25. In some embodiments, the binding domain comprises (a) a VH domain comprising an amino acid sequence having at least 95% sequence identity to the amino acid sequence of SEQ ID NO: 100, (b) a VL domain comprising an amino acid sequence having at least 95% sequence identity to the amino acid sequence of SEQ ID NO: 101, or (c) a VH domain as in (a) and a VL domain as in (b). In some embodiments, the antibody further comprises the following heavy chain variable region FRs: (a) an FR-H1 comprising the amino acid sequence of SEQ ID NO: 52, (b) an FR-H2 comprising the amino acid sequence of SEQ ID NO: 54, (c) an FR-H3 comprising the amino acid sequence of SEQ ID NO: 46, and (d) an FR-H4 comprising the amino acid sequence of SEQ ID NO: 47. In some embodiments, the VH domain comprises the amino acid sequence of SEQ ID NO: 100. In some embodiments, the antibody further comprises the following light chain variable region FRs: (a) an FR-L1 comprising the amino acid sequence of SEQ ID NO: 48, (b) an FR-L2 comprising the amino acid sequence of SEQ ID NO: 57, (c) an FR-L3 comprising the amino acid sequence of SEQ ID NO: 50, and (d) an FR-L4 comprising the amino acid sequence of SEQ ID NO: 51. In some embodiments, the VL domain comprises the amino acid sequence of SEQ ID NO: 101. In some embodiments, the anti-FcRH5 antibody comprises a binding domain comprising (a) a VH domain comprising an amino acid sequence of SEQ ID NO: 100 and (b) a VL domain comprising an amino acid sequence of SEQ ID NO: 101.

In other embodiments, the anti-FcRH5 antibody comprises a binding domain comprising the following six HVRs: (a) an HVR-H1 comprising the amino acid sequence of SEQ ID NO: 1, (b) an HVR-H2 comprising the amino acid sequence of SEQ ID NO: 8, (c) an HVR-H3 comprising the amino acid sequence of SEQ ID NO: 9, (d) an HVR-L1 comprising the amino acid sequence of SEQ ID NO: 11, (e) an HVR-L2 comprising the amino acid sequence of SEQ ID NO: 15, and (f) an HVR-L3 comprising the amino acid sequence of SEQ ID NO: 20. In some embodiments, the binding domain comprises (a) a VH domain comprising an amino acid sequence having at least 95% sequence identity to the amino acid sequence of SEQ ID NO: 102, (b) a VL domain comprising an amino acid sequence having at least 95% sequence identity to the amino acid sequence of SEQ ID NO: 103, or (c) a VH domain as in (a) and a VL domain as in (b). In some embodiments, the antibody further comprises the following heavy chain variable region FRs: (a) an FR-H1 comprising the amino acid sequence of SEQ ID NO: 52, (b) an FR-H2 comprising the amino acid sequence of SEQ ID NO: 54, (c) an FR-H3 comprising the amino acid sequence of SEQ ID NO: 46, and (d) an FR-H4 comprising the amino acid sequence of SEQ ID NO: 47. In some embodiments, the VH domain comprises the amino acid sequence of SEQ ID NO: 102. In some embodiments, the antibody further comprises the following light chain variable region FRs: (a) an FR-L1 comprising the amino acid sequence of SEQ ID NO: 48, (b) an FR-L2 comprising the amino acid sequence of SEQ ID NO: 56, (c) an FR-L3 comprising the amino acid sequence of SEQ ID NO: 50, and (d) an FR-L4 comprising the amino acid sequence of SEQ ID NO: 51. In some embodiments, the VL domain comprises the amino acid sequence of SEQ ID NO: 103. In some embodiments, the anti-FcRH5 antibody comprises a binding domain comprising (a) a VH domain comprising an amino acid sequence of SEQ ID NO: 102 and (b) a VL domain comprising an amino acid sequence of SEQ ID NO: 103.

In another aspect, the invention features an anti-FcRH5 antibody including a binding domain comprising the following six HVRs: (a) an HVR-H1 comprising the amino acid sequence of SEQ ID NO: 32, (b) an HVR-H2 comprising the amino acid sequence of SEQ ID NO: 33, (c) an HVR-H3 comprising the amino acid sequence of SEQ ID NO: 34, (d) an HVR-L1 comprising the amino acid sequence of SEQ ID NO: 35, (e) an HVR-L2 comprising the amino acid sequence of SEQ ID NO: 36, and (f) an HVR-L3 comprising the amino acid sequence of SEQ ID NO: 37. In some embodiments, the binding domain comprises (a) a VH domain comprising an amino acid sequence having at least 95% sequence identity to the amino acid sequence of SEQ ID NO: 110, (b) a VL domain comprising an amino acid sequence having at least 95% sequence identity to the amino acid sequence of SEQ ID NO: 111, or (c) a VH domain as in (a) and a VL domain as in (b). In some embodiments, the antibody further comprises the following heavy chain variable region FRs: (a) an FR-H1 comprising the amino acid sequence of SEQ ID NO: 66, (b) an FR-H2 comprising the amino acid sequence of SEQ ID NO: 67, (c) an FR-H3 comprising the amino acid sequence of SEQ ID NO: 68, and (d) an FR-H4 comprising the amino acid sequence of SEQ ID NO: 69. In some embodiments, the VH domain comprises the amino acid sequence of SEQ ID NO: 110. In some embodiments, the antibody further comprises the following light chain variable region FRs: (a) an FR-L1 comprising the amino acid sequence of SEQ ID NO: 70, (b) an FR-L2 comprising the amino acid sequence of SEQ ID NO: 71, (c) an FR-L3 comprising the amino acid sequence of SEQ ID NO: 72, and (d) an FR-L4 comprising the amino acid sequence of SEQ ID NO: 73. In some embodiments, the VL domain comprises the amino acid sequence of SEQ ID NO: 111. In some embodiments, the anti-FcRH5 antibody comprises a binding domain comprising (a) a VH domain comprising an amino acid sequence of SEQ ID NO: 110 and (b) a VL domain comprising an amino acid sequence of SEQ ID NO: 111.

In another aspect, the invention features an anti-FcRH5 antibody including a binding domain comprising the following six HVRs: (a) an HVR-H1 comprising the amino acid sequence of SEQ ID NO: 38, (b) an HVR-H2 comprising the amino acid sequence of SEQ ID NO: 39, (c) an HVR-H3 comprising the amino acid sequence of SEQ ID NO: 40, (d) an HVR-L1 comprising the amino acid sequence of SEQ ID NO: 41, (e) an HVR-L2 comprising the amino acid sequence of SEQ ID NO: 42, and (f) an HVR-L3 comprising the amino acid sequence of SEQ ID NO: 43. In other embodiments, the binding domain comprises (a) a VH domain comprising an amino acid sequence having at least 95% sequence identity to the amino acid sequence of SEQ ID NO: 112, (b) a VL domain comprising an amino acid sequence having at least 95% sequence identity to the amino acid sequence of SEQ ID NO: 113, or (c) a VH domain as in (a) and a VL domain as in (b). In other embodiments, the antibody further comprises the following heavy chain variable region FRs: (a) an FR-H1 comprising the amino acid sequence of SEQ ID NO: 74, (b) an FR-H2 comprising the amino acid sequence of SEQ ID NO: 75, (c) an FR-H3 comprising the amino acid sequence of SEQ ID NO: 76, and (d) an FR-H4 comprising the amino acid sequence of SEQ ID NO: 77. In other embodiments, the VH domain comprises the amino acid sequence of SEQ ID NO: 112. In other embodiments, the antibody further comprises the following light chain variable region FRs: (a) an FR-L1 comprising the amino acid sequence of SEQ ID NO: 78, (b) an FR-L2 comprising the amino acid sequence of SEQ ID NO: 79, (c) an FR-L3 comprising the amino acid sequence of SEQ ID NO: 80, and (d) an FR-L4 comprising the amino acid sequence of SEQ ID NO: 81. In other embodiments, the VL domain comprises the amino acid sequence of SEQ ID NO: 113. In other embodiments, the anti-FcRH5 antibody comprises a binding domain comprising (a) a VH domain comprising an amino acid sequence of SEQ ID NO: 112 and (b) a VL domain comprising an amino acid sequence of SEQ ID NO: 113.

In another aspect, the invention features an anti-FcRH5 antibody including a binding domain comprising the following six HVRs: (a) an HVR-H1 comprising the amino acid sequence of SEQ ID NO: 26, (b) an HVR-H2 comprising the amino acid sequence of SEQ ID NO: 27, (c) an HVR-H3 comprising the amino acid sequence of SEQ ID NO: 28, (d) an HVR-L1 comprising the amino acid sequence of SEQ ID NO: 29, (e) an HVR-L2 comprising the amino acid sequence of SEQ ID NO: 30, and (f) an HVR-L3 comprising the amino acid sequence of SEQ ID NO: 31. In some embodiments, the binding domain comprises (a) a VH domain comprising an amino acid sequence having at least 95% sequence identity to the amino acid sequence of SEQ ID NO: 108, (b) a VL domain comprising an amino acid sequence having at least 95% sequence identity to the amino acid sequence of SEQ ID NO: 109, or (c) a VH domain as in (a) and a VL domain as in (b). In some embodiments, the antibody further comprises the following heavy chain variable region FRs: (a) an FR-H1 comprising the amino acid sequence of SEQ ID NO: 58, (b) an FR-H2 comprising the amino acid sequence of SEQ ID NO: 59, (c) an FR-H3 comprising the amino acid sequence of SEQ ID NO: 60, and (d) an FR-H4 comprising the amino acid sequence of SEQ ID NO: 61. In some embodiments, the VH domain comprises the amino acid sequence of SEQ ID NO: 108. In some embodiments, the antibody further comprises the following light chain variable region FRs: (a) an FR-L1 comprising the amino acid sequence of SEQ ID NO: 62, (b) an FR-L2 comprising the amino acid sequence of SEQ ID NO: 63, (c) an FR-L3 comprising the amino acid sequence of SEQ ID NO: 64, and (d) an FR-L4 comprising the amino acid sequence of SEQ ID NO: 65. In some embodiments, the VL domain comprises the amino acid sequence of SEQ ID NO: 109. In some embodiments, the anti-FcRH5 antibody comprises a binding domain comprising (a) a VH domain comprising an amino acid sequence of SEQ ID NO: 108 and (b) a VL domain comprising an amino acid sequence of SEQ ID NO: 109.

In some embodiments of any one of the preceding aspects, the anti-FcRH5 antibody binds to an epitope in the Ig-like domain 9 of FcRH5. In some embodiments, the epitope comprises a portion of amino acids 743-850 of SEQ ID NO: 114. In some embodiments, the binding domain binds to human FcRH5, cynomolgus monkey (cyno) FcRH5, or both. In some embodiments, the binding domain does not specifically bind to FcRH1, FcRH2, FcRH3, and/or FcRH4. In some embodiments, the anti-FcRH5 antibody binds human FcRH5 with a $K_D$ of about 100 nM or lower. In some embodiments, the anti-FcRH5 antibody binds human FcRH5 with a $K_D$ of between about 10 pM and about 100 nM. In some embodiments, the anti-FcRH5 antibody binds human FcRH5 with a $K_D$ of between about 100 pM and about 100 nM. In some embodiments, the anti-FcRH5 antibody binds human FcRH5 with a $K_D$ of between about 1 nM and about 20 nM. In some embodiments, the anti-FcRH5 antibody binds human FcRH5 with a $K_D$ of between about 1 nM and about 10 nM. In some embodiments, the anti-FcRH5 antibody binds cyno FcRH5 with a $K_D$ of about 100 nM or lower. In some embodiments, the anti-FcRH5 antibody binds cyno FcRH5 with a $K_D$ of between about 10 pM and about 100 nM. In some embodiments, the anti-FcRH5 antibody binds cyno FcRH5 with a $K_D$ of between about 100 pM and about 100 nM. In some embodiments, the anti-FcRH5 antibody binds cyno FcRH5 with a $K_D$ of between about 1 nM and about 50 nM.

In other embodiments, the anti-FcRH5 antibody comprises an aglycosylation site mutation. In some embodiments, the aglycosylation site mutation is a substitution mutation. In some embodiments, the aglycosylation site mutation reduces effector function of the anti-FcRH5 antibody. In some embodiments, the substitution mutation is at amino acid residue N297, L234, L235, D265, and/or P329 (EU numbering). In some embodiments, the substitution mutation is selected from the group consisting of N297G, N297A, L234A, L235A, D265A, and P329G. In some embodiments, the substitution mutation is an N297G mutation.

In other embodiments, the anti-FcRH5 antibody is an IgG antibody.

In some embodiments, the anti-FcRH5 antibody is an antibody fragment that binds FcRH5. In some embodiments, the antibody fragment is selected from the group consisting of bis-Fab, Fab, Fab'-SH, Fv, scFv, and (Fab')$_2$ fragments. In some embodiments, the antibody fragment is a bis-Fab fragment.

In other embodiments, the anti-FcRH5 antibody is a full-length antibody.

In some embodiments, the anti-FcRH5 antibody is a monospecific antibody.

In some embodiments, the anti-FcRH5 antibody is a multispecific antibody. In some embodiments, the multispecific antibody is a bispecific antibody. In some embodiments, the bispecific antibody comprises a second binding domain that binds cluster of differentiation 3 (CD3). In some embodiments, the second binding domain binds to an epitope on CD3 comprising amino acid residue Glu6 of CD3. In some embodiments, the epitope further comprises one or more additional amino acid residues selected from the group consisting of Gln1, Asp2, and Met7 of CD3. In some embodiments, the epitope comprises amino acid residues Gln1, Asp2, and Glu6 of CD3. In some embodiments, the epitope comprises amino acid residues Gln1, Asp2, Glu6, and Met7 of CD3. In some embodiments, the epitope does not comprise amino acid residue Glu5 of CD3. In some embodiments, the epitope does not comprise amino acid residues Gly3 and Glu5 of CD3. In some embodiments, the epitope consists of amino acid residues Gln1, Asp2, Glu6, and Met7 of CD3. In some embodiments, the second binding domain is capable of binding to a human CD3 polypeptide or a cyno CD3 polypeptide. In some embodiments, the human CD3 polypeptide or the cyno CD3 polypeptide is a human CD3ε polypeptide or a cyno CD3ε polypeptide, respectively. In some embodiments, the human CD3 polypeptide or the cyno CD3 polypeptide is a human CD3γ polypeptide or a cyno CD3γ polypeptide, respectively. In some embodiments, the second binding domain binds the human CD3ε polypeptide with a $K_D$ of about 100 nM or lower. In some embodiments, the second binding domain binds the human CD3ε polypeptide with a $K_D$ of between about 10 pM to about 100 nM. In some embodiments, the second binding domain binds the human CD3ε polypeptide with a $K_D$ of between about 100 pM to about 50 nM. In some embodiments, the second binding domain binds the human CD3ε polypeptide with a $K_D$ of between about 1 nM to about 10 nM.

In some embodiments, the second binding domain comprises the following six HVRs: (a) an HVR-H1 comprising the amino acid sequence of SEQ ID NO: 115, (b) an HVR-H2 comprising the amino acid sequence of SEQ ID NO: 116, (c) an HVR-H3 comprising the amino acid sequence of SEQ ID NO: 117, (d) an HVR-L1 comprising the amino acid sequence of SEQ ID NO: 118, (e) an HVR-L2 comprising the amino acid sequence of SEQ ID NO: 119, and (f) an HVR-L3 comprising the amino acid sequence of SEQ ID NO: 120. In some embodiments, the second binding domain comprises the following six HVRs: (a) an HVR-H1 comprising the amino acid sequence of SEQ ID NO: 115, (b) an HVR-H2 comprising the amino acid sequence of SEQ ID NO: 116, (c) an HVR-H3 comprising the amino acid sequence of SEQ ID NO: 121, (d) an HVR-L1 comprising the amino acid sequence of SEQ ID NO: 118, (e) an HVR-L2 comprising the amino acid sequence of SEQ ID NO: 119, and (f) an HVR-L3 comprising the amino acid sequence of SEQ ID NO: 123. In some embodiments, the second binding domain comprises (a) a VH domain comprising an amino acid sequence having at least 95% sequence identity to the amino acid sequence of SEQ ID NO: 133, (b) a VL domain comprising an amino acid sequence having at least 95% sequence identity to the amino acid sequence of SEQ ID NO: 134, or (c) a VH domain as in (a) and a VL domain as in (b). In some embodiments, the second binding domain comprises the following heavy chain variable region FRs: (a) an FR-H1 comprising the amino acid sequence of SEQ ID NO: 125, (b) an FR-H2 comprising the amino acid sequence of SEQ ID NO: 126, (c) an FR-H3 comprising the amino acid sequence of SEQ ID NO: 127, and (d) an FR-H4 comprising the amino acid sequence of SEQ ID NO: 128. In some embodiments, the second binding domain comprises a VH domain comprising the amino acid sequence of SEQ ID NO: 133. In some embodiments, the second binding domain further comprises the following light chain variable region FRs: (a) an FR-L1 comprising the amino acid sequence of SEQ ID NO: 129, (b) an FR-L2 comprising the amino acid sequence of SEQ ID NO: 130, (c) an FR-L3 comprising the amino acid sequence of SEQ ID NO: 131, and (d) an FR-L4 comprising the amino acid sequence of SEQ ID NO: 132. In some embodiments, the second binding domain comprises a VL domain comprising the amino acid sequence of SEQ ID NO: 134. In some embodiments, the second binding domain comprises (a) a VH domain comprising an amino acid sequence of SEQ ID NO: 133 and (b) a VL domain comprising an amino acid sequence of SEQ ID NO: 134.

In other embodiments, the second binding domain comprises the following six HVRs: (a) an HVR-H1 comprising the amino acid sequence of SEQ ID NO: 115, (b) an HVR-H2 comprising the amino acid sequence of SEQ ID NO: 116, (c) an HVR-H3 comprising the amino acid sequence of SEQ ID NO: 121, (d) an HVR-L1 comprising the amino acid sequence of SEQ ID NO: 118, (e) an HVR-L2 comprising the amino acid sequence of SEQ ID NO: 119, and (f) an HVR-L3 comprising the amino acid sequence of SEQ ID NO: 124. In some embodiments, the second binding domain comprises (a) a VH domain comprising an amino acid sequence having at least 95% sequence identity to the amino acid sequence of SEQ ID NO: 137, (b) a VL domain comprising an amino acid sequence having at least 95% sequence identity to the amino acid sequence of SEQ ID NO: 138, or (c) a VH domain as in (a) and a VL domain as in (b). In some embodiments, the second binding domain comprises the following heavy chain variable region FRs: (a) an FR-H1 comprising the amino acid sequence of SEQ ID NO: 125, (b) an FR-H2 comprising the amino acid sequence of SEQ ID NO: 126, (c) an FR-H3 comprising the amino acid sequence of SEQ ID NO: 127, and (d) an FR-H4 comprising the amino acid sequence of SEQ ID NO: 128. In some embodiments, the second binding domain comprises a VH domain comprising the amino acid sequence of SEQ ID NO: 137. In some embodiments, the second binding domain further comprises the following light chain variable region FRs: (a) an FR-L1 comprising the amino acid sequence of SEQ ID NO: 129, (b) an FR-L2 comprising the amino acid sequence of SEQ ID NO: 130, (c) an FR-L3 comprising the amino acid sequence of SEQ ID NO: 131, and (d) an FR-L4 comprising the amino acid sequence of SEQ ID NO: 132. In some embodiments, the second binding domain comprises a VL domain comprising the amino acid sequence of SEQ ID NO: 138. In some embodiments, the second binding domain comprises (a) a VH domain comprising an amino acid sequence of SEQ ID NO: 137 and (b) a VL domain comprising an amino acid sequence of SEQ ID NO: 138.

In other embodiments, the second binding domain comprises the following six HVRs: (a) an HVR-H1 comprising the amino acid sequence of SEQ ID NO: 139, (b) an HVR-H2 comprising the amino acid sequence of SEQ ID NO: 140, (c) an HVR-H3 comprising the amino acid sequence of SEQ ID NO: 141, (d) an HVR-L1 comprising the amino acid sequence of SEQ ID NO: 142, (e) an HVR-L2 comprising the amino acid sequence of SEQ ID NO: 143, and (f) an HVR-L3 comprising the amino acid sequence of SEQ ID NO: 144. In some embodiments, the second binding domain comprises (a) a VH domain comprising an amino acid sequence having at least 95% sequence identity to the amino acid sequence of SEQ ID NO: 153, (b) a VL domain comprising an amino acid sequence having at least 95% sequence identity to the amino acid sequence of SEQ ID NO: 154, or (c) a VH domain as in (a) and a VL domain as in (b). In some embodiments, the second binding domain comprises the following heavy chain variable region FRs: (a) an FR-H1 comprising the amino acid sequence of SEQ ID NO: 145, (b) an FR-H2 comprising the amino acid sequence of SEQ ID NO: 146, (c) an FR-H3 comprising the amino acid sequence of SEQ ID NO: 147, and (d) an FR-H4 comprising the amino acid sequence of SEQ ID NO: 148. In some embodiments, the second binding domain comprises a VH domain comprising the amino acid sequence of SEQ ID NO: 153. In some embodiments, the second binding domain further comprises the following light chain variable region FRs: (a) an FR-L1 comprising the amino acid sequence of SEQ ID NO: 149, (b) an FR-L2 comprising the amino acid sequence of SEQ ID NO: 150, (c)

an FR-L3 comprising the amino acid sequence of SEQ ID NO: 151, and (d) an FR-L4 comprising the amino acid sequence of SEQ ID NO: 152. In some embodiments, the second binding domain comprises a VL domain comprising the amino acid sequence of SEQ ID NO: 154. In some embodiments, the second binding domain comprises (a) a VH domain comprising an amino acid sequence of SEQ ID NO: 153 and (b) a VL domain comprising an amino acid sequence of SEQ ID NO: 154.

In other embodiments, the second binding domain comprises the following six HVRs: (a) an HVR-H1 comprising the amino acid sequence of SEQ ID NO: 155, (b) an HVR-H2 comprising the amino acid sequence of SEQ ID NO: 156, (c) an HVR-H3 comprising the amino acid sequence of SEQ ID NO: 157, (d) an HVR-L1 comprising the amino acid sequence of SEQ ID NO: 158, (e) an HVR-L2 comprising the amino acid sequence of SEQ ID NO: 159, and (f) an HVR-L3 comprising the amino acid sequence of SEQ ID NO: 160.

In some embodiments, the second binding domain comprises the following six HVRs: (a) an HVR-H1 comprising the amino acid sequence of SEQ ID NO: 155, (b) an HVR-H2 comprising the amino acid sequence of SEQ ID NO: 162, (c) an HVR-H3 comprising the amino acid sequence of SEQ ID NO: 157, (d) an HVR-L1 comprising the amino acid sequence of SEQ ID NO: 158, (e) an HVR-L2 comprising the amino acid sequence of SEQ ID NO: 159, and (f) an HVR-L3 comprising the amino acid sequence of SEQ ID NO: 160. In some embodiments, the second binding domain comprises (a) a VH domain comprising an amino acid sequence having at least 95% sequence identity to the amino acid sequence of SEQ ID NO: 172, (b) a VL domain comprising an amino acid sequence having at least 95% sequence identity to the amino acid sequence of SEQ ID NO: 173, or (c) a VH domain as in (a) and a VL domain as in (b). In some embodiments, the second binding domain comprises the following heavy chain variable region FRs: (a) an FR-H1 comprising the amino acid sequence of SEQ ID NO: 164, (b) an FR-H2 comprising the amino acid sequence of SEQ ID NO: 165, (c) an FR-H3 comprising the amino acid sequence of SEQ ID NO: 166, and (d) an FR-H4 comprising the amino acid sequence of SEQ ID NO: 167. In some embodiments, the second binding domain comprises a VH domain comprising the amino acid sequence of SEQ ID NO: 172. In some embodiments, the second binding domain further comprises the following light chain variable region FRs: (a) an FR-L1 comprising the amino acid sequence of SEQ ID NO: 168, (b) an FR-L2 comprising the amino acid sequence of SEQ ID NO: 169, (c) an FR-L3 comprising the amino acid sequence of SEQ ID NO: 170, and (d) an FR-L4 comprising the amino acid sequence of SEQ ID NO: 171. In some embodiments, the second binding domain comprises a VL domain comprising the amino acid sequence of SEQ ID NO: 173. In some embodiments, the second binding domain comprises (a) a VH domain comprising an amino acid sequence of SEQ ID NO: 172 and (b) a VL domain comprising an amino acid sequence of SEQ ID NO: 173.

In other embodiments, the binding domain that binds FcRH5 comprises a VH domain ($VH_1$) comprising a charged region ($CR_1$) and a VL domain ($VL_1$) comprising a charged region ($CR_2$), wherein the $CR_1$ in the $VH_1$ forms a charge pair with the $CR_2$ in the $VL_1$. In some embodiments, the $CR_1$ comprises a basic amino acid residue and the $CR_2$ comprises an acidic amino acid residue. In some embodiments, the $CR_1$ comprises a Q39K substitution mutation (EU numbering). In some embodiments, the $CR_1$ consists of the Q39K substitution mutation. In some embodiments, the $CR_2$ comprises a Q38E substitution mutation (EU numbering). In some embodiments, the $CR_2$ consists of the Q38E substitution mutation. In some embodiments, the second binding domain that binds CD3 comprises a VH domain ($VH_2$) comprising a charged region ($CR_3$) and a VL domain ($VL_2$) comprising a charged region ($CR_4$), wherein the $CR_4$ in the $VL_2$ forms a charge pair with the $CR_3$ in the $VH_2$. In some embodiments, the $CR_4$ comprises a basic amino acid residue and the $CR_3$ comprises an acidic amino acid residue. In some embodiments, the $CR_4$ comprises a Q38K substitution mutation (EU numbering). In some embodiments, the $CR_4$ consists of the Q38K substitution mutation. In some embodiments, the $CR_3$ comprises a Q39E substitution mutation (EU numbering). In some embodiments, the $CR_3$ consists of the Q39E substitution mutation. In some embodiments, the $VL_1$ domain is linked to a light chain constant (CL) domain ($CL_1$) and the $VH_1$ is linked to a first heavy chain constant (CH1) domain ($CH1_1$), wherein the $CL_1$ comprises a charged region ($CR_5$) and the $CH1_1$ comprises a charged region ($CR_6$), and wherein the $CR_5$ in the $CL_1$ forms a charge pair with the $CR_6$ in the $CH1_1$. In some embodiments, the $CR_5$ comprises a basic amino acid residue and the $CR_6$ comprises an acidic amino acid residue. In some embodiments, the $CR_5$ comprises a V133K substitution mutation (EU numbering). In some embodiments, the $CR_5$ consists of the V133K substitution mutation. In some embodiments, the $CR_6$ comprises a S183E substitution mutation (EU numbering). In some embodiments, the $CR_6$ consists of the S183E substitution mutation.

In other embodiments, the $VL_2$ domain is linked to a CL domain ($CL_2$) and the $VH_2$ is linked to a CH1 domain ($CH1_2$), wherein the $CL_2$ comprises a charged region ($CR_7$) and the $CH1_2$ comprise a charged region ($CR_8$), and wherein the $CR_8$ in the $CH1_2$ forms a charge pair with the $CR_7$ in the $CL_2$. In some embodiments, the $CR_8$ comprises a basic amino acid residue and the $CR_7$ comprises an acidic amino acid residue. In some embodiments, the $CR_8$ comprises a S183K substitution mutation (EU numbering). In some embodiments, the $CR_8$ consists of the S183K substitution mutation. In some embodiments, the $CR_7$ comprises a V133E substitution mutation (EU numbering). In some embodiments, the $CR_7$ consists of the V133E substitution mutation.

In other embodiments, the $VL_2$ domain is linked to a CL domain ($CL_2$) and the $VH_2$ is linked to a CH1 domain ($CH1_2$), wherein (a) the $CL_2$ comprises one or more mutations at amino acid residues F116, L135, S174, S176, and/or T178 (EU numbering) and (b) the $CH1_2$ comprises one or more mutations at amino acid residues A141, F170, S181, S183, and/or V185 (EU numbering). In some embodiments, the $CL_2$ comprises one or more of the following substitution mutations: F116A, L135V, S174A, S176F, and/or T178V. In some embodiments, the $CL_2$ comprises the following substitution mutations: F116A, L135V, S174A, S176F, and T178V. In some embodiments, the $CH1_2$ comprises one or more of the following substitution mutations: A141I, F170S, S181M, S183A, and/or V185A. In some embodiments, the $CH1_2$ comprises the following substitution mutations: A141I, F170S, S181M, S183A, and V185A.

In other embodiments, the binding domain that binds FcRH5 comprises a VH domain ($VH_1$) comprising a charged region ($CR_1$) and a VL domain ($VL_1$) comprising a charged region ($CR_2$), wherein the $CR_2$ in the $VL_1$ forms a charge pair with the $CR_1$ in the $VH_1$. In some embodiments, the $CR_2$ comprises a basic amino acid residue and the $CR_1$ comprises an acidic amino acid residue. In some embodiments, the $CR_2$ comprises a Q38K substitution mutation (EU numbering). In some embodiments, the $CR_2$ consists of the Q38K substitution mutation. In some embodiments, the $CR_1$ comprises a Q39E substitution mutation (EU numbering). In some embodiments, the $CR_1$ consists of the Q39E substitution mutation. In some embodiments, the second binding domain that binds CD3 comprises a VH domain ($VH_2$) comprising a charged region ($CR_3$) and a VL domain ($VL_2$) comprising a charged region ($CR_4$), wherein the $CR_3$ in the $VH_2$ forms a charge pair with the $CR_4$ in the $VL_2$. In some embodiments, the $CR_3$ comprises a basic amino acid residue and the $CR_4$ comprises an acidic amino acid residue. In some embodiments, the $CR_3$ comprises a Q39K substitution mutation (EU numbering). In some embodiments, the $CR_3$ consists of the Q39K substitution mutation. In some embodiments, the $CR_4$ comprises a Q38E substitution mutation (EU numbering). In some embodiments, the $CR_4$ consists of the Q38E substitution mutation. In some embodiments, the $VL_1$ domain is linked to a light chain constant (CL) domain ($CL_1$) and the $VH_1$ is linked to a first heavy chain constant (CH1) domain ($CH1_1$), wherein the $CL_1$ comprises a charged region ($CR_5$) and the $CH1_1$ comprises a charged region ($CR_6$), and wherein the $CR_6$ in the $CH1_1$ forms a charge pair with the $CR_5$ in the $CL_1$. In some embodiments, the $CR_6$ comprises a basic amino acid residue and the $CR_5$ comprises an acidic amino acid residue. In some embodiments, the $CR_6$ comprises a S183K substitution mutation (EU numbering). In some embodiments, the $CR_6$ consists of the S183K substitution mutation. In some embodiments, the $CR_5$ comprises a V133E substitution mutation (EU numbering). In some embodiments, the $CR_5$ consists of the V133E substitution mutation.

In other embodiments, the $VL_2$ domain is linked to a CL domain ($CL_2$) and the $VH_2$ is linked to a CH1 domain ($CH1_2$), wherein the $CL_2$ comprises a charged region ($CR_7$) and the $CH1_2$ comprises a charged region ($CR_8$), and wherein the $CR_7$ in the $CL_2$ forms a charged pair with the $CR_8$ in the $CH1_2$. In some embodiments, the $CR_7$ comprises a basic amino acid residue and the $CR_8$ comprises an acidic residue. In some embodiments, the $CR_7$ comprises a V133K substitution mutation (EU numbering). In some embodiments, the $CR_7$ consists of the V133K substitution mutation. In some embodiments, the $CR_8$ comprises a S183E substitution mutation (EU numbering). In some embodiments, the $CR_8$ consists of the S183E substitution mutation.

In other embodiments, the $VL_2$ domain is linked to a CL domain ($CL_2$) and the $VH_2$ is linked to a CH1 domain ($CH1_2$), wherein (a) the $CL_2$ comprises one or more mutations at amino acid residues F116, L135, S174, S176, and/or T178 (EU numbering) and (b) the $CH1_2$ comprises one or more mutations at amino acid residues A141, F170, S181, S183, and/or V185 (EU numbering). In some embodiments, the $CL_2$ comprises one or more of the following substitution mutations: F116A, L135V, S174A, S176F, and/or T178V. In some embodiments, the $CL_2$ comprises the following substitution mutations: F116A, L135V, S174A, S176F, and T178V. In some embodiments, the $CH1_2$ comprises one or more of the following substitution mutations: A141I, F170S, S181M, S183A, and/or V185A. In some embodiments, the $CH1_2$ comprises the following substitution mutations: A141I, F170S, S181M, S183A, and V185A. In some embodiments, the anti-FcRH5 antibody comprises one or more heavy chain constant domains, wherein the one or more heavy chain constant domains are selected from a first CH2 domain ($CH2_1$), a first CH3 domain ($CH3_1$), a second CH2 domain ($CH2_2$), and a second CH3 domain ($CH3_2$). In some embodiments, at least one of the one or more heavy chain constant domains is paired with another heavy chain constant domain. In some embodiments, the $CH3_1$ and the $CH3_2$ each comprise a protuberance ($P_1$) or a cavity ($C_1$), and wherein the $P_1$ or the $C_1$ in the $CH3_1$ is positionable in the $C_1$ or the $P_1$, respectively, in the $CH3_2$. In some embodiments, the $CH3_1$ and the $CH3_2$ meet at an interface between the $P_1$ and the $C_1$. In some embodiments, the $CH2_1$ and the $CH2_2$ each comprise ($P_2$) or a cavity ($C_2$), and wherein the $P_2$ or the $C_2$ in the $CH2_1$ is positionable in the $C_2$ or the $P_2$, respectively, in the $CH2_2$. In some embodiments, the $CH2_1$ and the $CH2_2$ meet at an interface between the $P_2$ and the $C_2$.

In another aspect, the invention features an anti-FcRH5 antibody that binds to FcRH5 and CD3, wherein the anti-FcRH5 antibody comprises an anti-FcRH5 arm comprising a first binding domain comprising the following six HVRs: (a) an HVR-H1 comprising the amino acid sequence of SEQ ID NO: 1, (b) an HVR-H2 comprising the amino acid sequence of SEQ ID NO: 8, (c) an HVR-H3 comprising the amino acid sequence of SEQ ID NO: 9, (d) an HVR-L1 comprising the amino acid sequence of SEQ ID NO: 12, (e) an HVR-L2 comprising the amino acid sequence of SEQ ID NO: 16, and (f) an HVR-L3 comprising the amino acid sequence of SEQ ID NO: 23, and an anti-CD3 arm comprising a second binding domain comprising the following six HVRs: (a) an HVR-H1 comprising the amino acid sequence of SEQ ID NO: 115, (b) an HVR-H2 comprising the amino acid sequence of SEQ ID NO: 116, (c) an HVR-H3 comprising the amino acid sequence of SEQ ID NO: 121, (d) an HVR-L1 comprising the amino acid sequence of SEQ ID NO: 118, (e) an HVR-L2 comprising the amino acid sequence of SEQ ID NO: 119, and (f) an HVR-L3 comprising the amino acid sequence of SEQ ID NO: 123, and wherein the anti-FcRH5 arm and the anti-CD3 arm each comprise an N297G substitution mutation (EU numbering), and wherein the anti-FcRH5 arm comprises a T366W substitution mutation and the anti-CD3 arm comprises T366S, L368A, and Y407V substitution mutations.

In another aspect, the invention features an anti-FcRH5 antibody that binds to FcRH5 and CD3, wherein the anti-FcRH5 antibody comprises an anti-FcRH5 arm comprising a first binding domain comprising the following six HVRs: (a) an HVR-H1 comprising the amino acid sequence of SEQ ID NO: 1, (b) an HVR-H2 comprising the amino acid sequence of SEQ ID NO: 8, (c) an HVR-H3 comprising the amino acid sequence of SEQ ID NO: 9, (d) an HVR-L1 comprising the amino acid sequence of SEQ ID NO: 12, (e) an HVR-L2 comprising the amino acid sequence of SEQ ID NO: 16, and (f) an HVR-L3 comprising the amino acid sequence of SEQ ID NO: 23, and an anti-CD3 arm comprising a second binding domain comprising the following six HVRs: (a) an HVR-H1 comprising the amino acid sequence of SEQ ID NO: 115, (b) an HVR-H2 comprising the amino acid sequence of SEQ ID NO: 116, (c) an HVR-H3 comprising the amino acid sequence of SEQ ID NO: 121, (d) an HVR-L1 comprising the amino acid sequence of SEQ ID NO: 118, (e) an HVR-L2 comprising the amino acid sequence of SEQ ID NO: 119, and (f) an HVR-L3 comprising the amino acid sequence of SEQ ID NO: 123, and wherein the anti-FcRH5 arm comprises a light chain comprising Q38E and V133K substitution mutations and a heavy chain comprising Q39K, S183E, and N297G substitution mutations, and wherein the anti-CD3 arm comprises a light chain comprising Q38K and V133E substitution mutations and a heavy chain comprising Q39E, S183K, and N297G substitution mutations (EU numbering).

In another aspect, the invention features an anti-FcRH5 antibody that binds to FcRH5 and CD3, wherein the anti- FcRH5 antibody comprises: (a) an anti-FcRH5 arm comprising a first binding domain comprising a VH domain comprising an amino acid sequence of SEQ ID NO: 104 and a VL domain comprising an amino acid sequence of SEQ ID NO: 105, wherein the anti-FcRH5 arm comprises a light chain comprising Q38E and V133K substitution mutations and a heavy chain comprising Q39K, S183E, and N297G substitution mutations, and (b) an anti-CD3 arm comprising a second binding domain comprising a VH domain comprising an amino acid sequence of SEQ ID NO: 133 and a VL domain comprising an amino acid sequence of SEQ ID NO: 134, wherein the anti-CD3 arm comprises a light chain comprising Q38K and V133E substitution mutations and a heavy chain comprising Q39E, S183K, and N297G substitution mutations (EU numbering).

In another aspect, the invention features an anti-FcRH5 antibody that binds to FcRH5 and CD3, wherein the anti-FcRH5 antibody comprises an anti-FcRH5 arm comprising a first binding domain comprising the following six HVRs: (a) an HVR-H1 comprising the amino acid sequence of SEQ ID NO: 1, (b) an HVR-H2 comprising the amino acid sequence of SEQ ID NO: 8, (c) an HVR-H3 comprising the amino acid sequence of SEQ ID NO: 9, (d) an HVR-L1 comprising the amino acid sequence of SEQ ID NO: 12, (e) an HVR-L2 comprising the amino acid sequence of SEQ ID NO: 16, and (f) an HVR-L3 comprising the amino acid sequence of SEQ ID NO: 23, and an anti-CD3 arm comprising a second binding domain comprising the following six HVRs: (a) an HVR-H1 comprising the amino acid sequence of SEQ ID NO: 115, (b) an HVR-H2 comprising the amino acid sequence of SEQ ID NO: 116, (c) an HVR-H3 comprising the amino acid sequence of SEQ ID NO: 121, (d) an HVR-L1 comprising the amino acid sequence of SEQ ID NO: 118, (e) an HVR-L2 comprising the amino acid sequence of SEQ ID NO: 119, and (f) an HVR-L3 comprising the amino acid sequence of SEQ ID NO: 123, and wherein the anti-FcRH5 arm comprises a light chain comprising Q38K and V133E substitution mutations and a heavy chain comprising Q39E, S183K, and N297G substitution mutations, and wherein the anti-CD3 arm comprises a light chain comprising Q38E and V133K substitution mutations and a heavy chain comprising Q39K, S183E, and N297G substitution mutations (EU numbering).

In another aspect, the invention features an anti-FcRH5 antibody that binds to FcRH5 and CD3, wherein the anti-FcRH5 antibody comprises: (a) an anti-FcRH5 arm comprising a first binding domain comprising a VH domain comprising an amino acid sequence of SEQ ID NO: 104 and a VL domain comprising an amino acid sequence of SEQ ID NO: 105, wherein the anti-FcRH5 arm comprises a light chain comprising Q38K and V133E substitution mutations and a heavy chain comprising Q39E, S183K, and N297G substitution mutations, and (b) an anti-CD3 arm comprising a second binding domain comprising a VH domain comprising an amino acid sequence of SEQ ID NO: 133 and a VL domain comprising an amino acid sequence of SEQ ID NO: 134, wherein the anti-CD3 arm comprises a light chain comprising Q38E and V133K substitution mutations and a heavy chain comprising Q39K, S183E, and N297G substitution mutations (EU numbering).

In another aspect, the invention features an anti-FcRH5 antibody that binds to FcRH5 and CD3, wherein the anti-FcRH5 antibody comprises an anti-FcRH5 arm comprising a first binding domain comprising the following six HVRs: (a) an HVR-H1 comprising the amino acid sequence of SEQ ID NO: 1, (b) an HVR-H2 comprising the amino acid sequence of SEQ ID NO: 8, (c) an HVR-H3 comprising the amino acid sequence of SEQ ID NO: 9, (d) an HVR-L1 comprising the amino acid sequence of SEQ ID NO: 12, (e) an HVR-L2 comprising the amino acid sequence of SEQ ID NO: 16, and (f) an HVR-L3 comprising the amino acid sequence of SEQ ID NO: 23, and an anti-CD3 arm comprising a second binding domain comprising the following six HVRs: (a) an HVR-H1 comprising the amino acid sequence of SEQ ID NO: 115, (b) an HVR-H2 comprising the amino acid sequence of SEQ ID NO: 116, (c) an HVR-H3 comprising the amino acid sequence of SEQ ID NO: 121, (d) an HVR-L1 comprising the amino acid sequence of SEQ ID NO: 118, (e) an HVR-L2 comprising the amino acid sequence of SEQ ID NO: 119, and (f) an HVR-L3 comprising the amino acid sequence of SEQ ID NO: 123, and wherein the anti-FcRH5 arm comprises a light chain comprising Q38E and V133K substitution mutations and a heavy chain comprising Q39K, S183E, and N297G substitution mutations, and wherein the anti-CD3 arm comprises a light chain comprising Q38K, F116A, L135V, S174A, S176F, and T178V substitution mutations and a heavy chain comprising Q39E, A141I, F170S, S181M, S183A, V185A, and N297G substitution mutations (EU numbering).

In another aspect, the invention features an anti-FcRH5 antibody that binds to FcRH5 and CD3, wherein the anti-FcRH5 antibody comprises: (a) an anti-FcRH5 arm comprising a first binding domain comprising a VH domain comprising an amino acid sequence of SEQ ID NO: 104 and a VL domain comprising an amino acid sequence of SEQ ID NO: 105, wherein the anti-FcRH5 arm comprises a light chain comprising Q38E and V133K substitution mutations and a heavy chain comprising Q39K, S183E, and N297G substitution mutations, and (b) an anti-CD3 arm comprising a second binding domain comprising a VH domain comprising an amino acid sequence of SEQ ID NO: 133 and a VL domain comprising an amino acid sequence of SEQ ID NO: 134, wherein the anti-CD3 arm comprises a light chain comprising Q38K, F116A, L135V, S174A, S176F, and T178V substitution mutations and a heavy chain comprising Q39E, A141I, F170S, S181M, S183A, V185A, and N297G substitution mutations (EU numbering).

In another aspect, the invention features an anti-FcRH5 antibody that binds to FcRH5 and CD3, wherein the anti-FcRH5 antibody comprises an anti-FcRH5 arm comprising a first binding domain comprising the following six HVRs: (a) an HVR-H1 comprising the amino acid sequence of SEQ ID NO: 1, (b) an HVR-H2 comprising the amino acid sequence of SEQ ID NO: 8, (c) an HVR-H3 comprising the amino acid sequence of SEQ ID NO: 9, (d) an HVR-L1 comprising the amino acid sequence of SEQ ID NO: 12, (e) an HVR-L2 comprising the amino acid sequence of SEQ ID NO: 16, and (f) an HVR-L3 comprising the amino acid sequence of SEQ ID NO: 23, and an anti-CD3 arm comprising a second binding domain comprising the following six HVRs: (a) an HVR-H1 comprising the amino acid sequence of SEQ ID NO: 115, (b) an HVR-H2 comprising the amino acid sequence of SEQ ID NO: 116, (c) an HVR-H3 comprising the amino acid sequence of SEQ ID NO: 121, (d) an HVR-L1 comprising the amino acid sequence of SEQ ID NO: 118, (e) an HVR-L2 comprising the amino acid sequence of SEQ ID NO: 119, and (f) an HVR-L3 comprising the amino acid sequence of SEQ ID NO: 123, and wherein the anti-FcRH5 arm comprises a light chain comprising Q38K and V133E substitution mutations and a heavy chain comprising Q39E, S183K, and N297G substitution mutations, and wherein the anti-CD3 arm comprises a light chain comprising Q38E, F116A, L135V, S174A, S176F, and T178V substitution mutations and a heavy chain comprising Q39K, A141I, F170S, S181M, S183A, V185A, and N297G substitution mutations (EU numbering).

In another aspect, the invention features an anti-FcRH5 antibody that binds to FcRH5 and CD3, wherein the anti-FcRH5 antibody comprises: (a) an anti-FcRH5 arm comprising a first binding domain comprising a VH domain comprising an amino acid sequence of SEQ ID NO: 104 and a VL domain comprising an amino acid sequence of SEQ ID NO: 105, wherein the anti-FcRH5 arm comprises a light chain comprising Q38K and V133E substitution mutations and a heavy chain comprising Q39E, S183K, and N297G substitution mutations, and (b) an anti-CD3 arm comprising a second binding domain comprising a VH domain comprising an amino acid sequence of SEQ ID NO: 133 and a VL domain comprising an amino acid sequence of SEQ ID NO: 134, wherein the anti-CD3 arm comprises a light chain comprising Q38E, F116A, L135V, S174A, S176F, and T178V substitution mutations and a heavy chain comprising Q39K, A141I, F170S, S181M, S183A, V185A, and N297G substitution mutations (EU numbering).

In some embodiments of any one of the aspects of the invention, the anti-FcRH5 antibody has a clearance following intravenous injection of between about 10 ml/kg/day to about 35 ml/kg/day. In some embodiments, the anti-FcRH5 antibody has a clearance following intravenous injection of about 10 ml/kg/day to about 20 ml/kg/day in a mouse. In some embodiments, the anti-FcRH5 antibody has a clearance following intravenous injection of about 12 ml/kg/day to about 16 ml/kg/day in a mouse. In some embodiments, the anti-FcRH5 antibody has a clearance following intravenous injection of about 20 ml/kg/day to about 40 ml/kg/day in a cyno. In some embodiments, the anti-FcRH5 antibody has a clearance following intravenous injection of about 25 ml/kg/day to about 35 ml/kg/day in a cyno. In some embodiments, the anti-FcRH5 antibody has a clearance following intravenous injection of about 30 ml/kg/day to about 35 ml/kg/day in a cyno.

In another aspect, the invention features an isolated nucleic acid encoding an anti-FcRH5 antibody of any one of the preceding aspects, or a portion thereof comprising a binding domain thereof that binds to FcRH5.

In another aspect, the invention features a vector comprising an isolated nucleic acid of the previous aspect.

In another aspect, the invention features a host cell comprising a vector of the previous aspect. In some embodiments, the host cell is a mammalian cell. In some embodiments, the mammalian cell is a Chinese hamster ovary (CHO) cell. In some embodiments, the host cell is a prokaryotic cell. In some embodiments, the prokaryotic cell is an *E. coli* cell.

In another aspect, the invention features a method of producing an anti-FcRH5 antibody of any one of the preceding aspects of the invention, the method comprises culturing the host cell of the previous aspect in a culture medium. In some embodiments, the method further comprises recovering the anti-FcRH5 antibody from the host cell or the culture medium. In some embodiments, the method further comprising culturing a second host cell comprising a second nucleic acid encoding an anti-CD3 antibody that comprises a binding domain that binds CD3. In some embodiments, the host cells are co-cultured. In some embodiments, the method further comprises recovering the bispecific anti-FcRH5 antibody from the host cells or the culture medium.

In another aspect, the invention features an immunoconjugate comprising an anti-FcRH5 antibody of any one of the previous aspects and a cytotoxic agent.

In another aspect, the invention features a composition comprising an anti-FcRH5 antibody of any one of the aspects of the invention. In some embodiments, the composition further comprising a pharmaceutically acceptable excipient or diluent. In some embodiments, the pharmaceutically acceptable excipient is a buffer, carrier, stabilizer, or preservative. In some embodiments, the composition is a pharmaceutical composition. In some embodiments, the composition further comprises a PD-1 axis binding antagonist or an additional therapeutic agent.

In another aspect, the invention features an anti-FcRH5 antibody of any one of the preceding aspects of the invention for use as a medicament.

In another aspect, the invention features an anti-FcRH5 antibody of any one of the preceding aspects of the invention for use in treating or delaying progression of an FcRH5-positive cancer in a subject in need thereof.

In another aspect, the invention features an anti-FcRH5 antibody of any one of the preceding aspects of the invention for use in enhancing immune function in a subject having an FcRH5-positive cancer. In some embodiments, the FcRH5-positive cancer is a B cell cancer. In another aspect, the B cell cancer is selected from the group consisting of multiple myeloma (MM), chronic lymphoid leukemia (CLL), mantle cell lymphoma (MCL), diffuse large B-cell lymphoma (DLBCL), and follicular lymphoma (FL). In another embodiment, the B cell cancer is MM.

In another aspect, the invention features the use of an anti-FcRH5 antibody or a composition of any one of the previous aspects in the manufacture of a medicament for treating or delaying progression of an FcRH5-positive cancer in a subject. In another aspect, the invention features the use of an anti-FcRH5 antibody or a composition of any one of the previous aspects in the manufacture of a medicament for enhancing immune function in a subject having an FcRH5-positive cancer. In some embodiments, the FcRH5-positive cancer is a B cell cancer. In some embodiments, the B cell cancer is selected from the group consisting of MM, CLL, MCL, DLBCL, and FL. In some embodiments, the B cell cancer is MM.

In another aspect, the invention features a method of treating or delaying the progression of an FcRH5-positive cancer in a subject in need thereof, the method comprising administering to the subject an anti-FcRH5 antibody of any one of the preceding aspects of the invention. In another aspect, the invention features a method of enhancing immune function in a subject having an FcRH5-positive cancer, the method comprising administering to the subject an effective amount of an anti-FcRH5 antibody of any one of the preceding aspects of the invention. In some embodiments, the FcRH5-positive cancer is a B cell cancer. In some embodiments, the B cell cancer is selected from the group consisting of MM, CLL, MCL, DLBCL, and FL. In some embodiments, the B cell cancer is MM. In some embodiments, the anti-FcRH5 antibody binds to (a) an FcRH5 molecule located on a target cell and (b) a CD3 molecule located on an immune effector cell. In some embodiments, the anti-FcRH5 antibody activates the immune effector cell following binding to the FcRH5 molecule and the CD3 molecule. In some embodiments, the activated immune effector cell is capable of exerting a cytotoxic effect and/or an apoptotic effect on the target cell. In some embodiments, the target cell is a plasma cell. In some embodiments, the plasma cell is a short-lived plasma cell. In some embodiments, the plasma cell is a long-lived plasma cell. In some embodiments, the plasma cell is a myeloma cell. In some embodiments, the method comprises administering to the subject the anti-FcRH5 antibody at a dosage of about 0.01 mg/kg/wk to about 50 mg/kg/wk. In some embodiments, the method comprises administering to the subject the anti-FcRH5 antibody at a dosage of about 0.1 mg/kg/wk to about 10 mg/kg/wk. In some embodiments, the method comprises administering to the subject the anti-FcRH5 antibody at a dosage of about 1 mg/kg/wk.

In other embodiments, the method further comprising administering to the subject a PD-1 axis binding antagonist and/or an additional therapeutic agent. In some embodiments, the PD-1 axis binding antagonist or additional therapeutic agent is administered prior to or subsequent to the administration of the anti-FcRH5 antibody. In some embodiments, the PD-1 axis binding antagonist or additional therapeutic agent is administered concurrently with the anti-FcRH5 antibody. In some embodiments, the PD-1 axis binding antagonist is selected from the group consisting of a PD-L1 binding antagonist, a PD-1 binding antagonist, and a PD-L2 binding antagonist. In some embodiments, the PD-1 axis binding antagonist is a PD-L1 binding antagonist. In some embodiments, the PD-L1 binding antagonist is selected from the group consisting of MPDL3280A (atezolizumab), YW243.55.S70, MDX-1105, MED14736 (durvalumab), and MSB0010718C (avelumab). In some embodiments, the PD-L1 binding antagonist is MPDL3280A (atezolizumab). In some embodiments, the PD-1 axis binding antagonist is a PD-1 binding antagonist. In some embodiments, the PD-1 binding antagonist is selected from the group consisting of MDX 1106 (nivolumab), MK-3475 (pembrolizumab), CT-011 (pidilizumab), MEDI-0680 (AMP-514), PDR001, REGN2810, and BGB-108. In some embodiments, the PD-1 axis binding antagonist is a PD-L2 binding antagonist. In some embodiments, the PD-L2 binding antagonist is an antibody or an immunoadhesin. In some embodiments, the subject a steroid, an immunomodulator (IMiD), a proteosome inhibitor (PI), or a combination thereof. In some embodiments, the steroid is a glucocorticoid. In some embodiments, the glucocorticoid is dexamethasone. In some embodiments, the IMiD is lenalidomide. In some embodiments, the PI is bortezomib.

In other embodiments, the method comprises administering the anti-FcRH5 antibody, PD-1 axis binding antagonist, steroid, IMiD, PI, or combination thereof, of any one of the preceding aspects, intravenously, subcutaneously, intramuscularly, topically, orally, transdermally, intraperitoneally, intraorbitally, by implantation, by inhalation, intrathecally, intraventricularly, or intranasally. In some embodiments, the method comprises administering the anti-FcRH5 antibody, PD-1 axis binding antagonist, steroid, IMiD, PI, or combination thereof, intravenously. In some embodiments, the method comprises administering the anti-FcRH5 antibody, PD-1 axis binding antagonist, steroid, IMiD, PI, or combination thereof, subcutaneously. In some embodiments of any one of the preceding aspects, the subject is a human.

In another aspect, the invention features a method for detecting FcRH5 in a biological sample from a subject, wherein the method comprises: (a) contacting the biological sample with an anti-FcRH5 antibody of any one of the aspects of the invention under conditions permissive for binding of the anti-FcRH5 antibody to a naturally occurring FcRH5 in the biological sample, and (b) detecting whether a complex is formed between the anti-FcRH5 antibody and a naturally occurring FcRH5 in the biological sample. In some embodiments, the biological sample is a blood sample. In some embodiments of this aspect, the subject is a human.

In another aspect, the invention features a kit comprising an anti-FcRH5 antibody of any one of the preceding aspects of the invention and a package insert comprising instructions for using the anti-FcRH5 antibody for treating or delaying progression of an FcRH5-positive cancer in a subject. In another aspect, the invention features a kit comprising an anti-FcRH5 antibody of any one of the preceding aspects of the invention and a package insert comprising instructions for using the anti-FcRH5 antibody for enhancing immune function in a subject having an FcRH5-positive cancer. In some embodiments of these aspects, the subject is a human.

BRIEF DESCRIPTION OF THE DRAWINGS

FIG. 3 is an alignment of the heavy chain variable (VH) domain sequences of select anti-FcRH5 antibodies. Changes from clone 1G7 (see U.S. Pub. No. 2015-0098900) are shown in dark boxes. Hypervariable regions (HVRs) are indicated by lines above and/or below the alignments. These VH domain sequences are also disclosed as SEQ ID NOs: 82, 84, 86, 88, 90, 92, 94, 96, 98, and 100.

FIG. 4 is a table showing the impact on binding affinity of amino acid substitutions at position 52 of the indicated anti-FcRH5 antibodies.

FIG. 5A is an alignment of the heavy chain variable (VH) domain sequences of hu1G7.v85 and hu1G7.v93. Changes from the human germline sequence hIGHV4-59*01 are shown in shaded boxes. Hypervariable regions (HVRs) are indicated by labels above the alignments. These VH domain sequences are also disclosed as SEQ ID NOs: 104 (hu1G7.v85) and 106 (hu1G7.v93).

FIG. 5B is an alignment of the light chain variable (VL) domain sequences of hu1G7.v85 and hu1G7.v93. Changes from the human germline sequence hIGKV1-16*01 are shown in shaded boxes. Hypervariable regions (HVRs) are indicated by labels above the alignments. These VL domain sequences are also disclosed as SEQ ID NOs: 105 (hu1G7.v85) and 107 (hu1G7.v93).

Figure 6B:
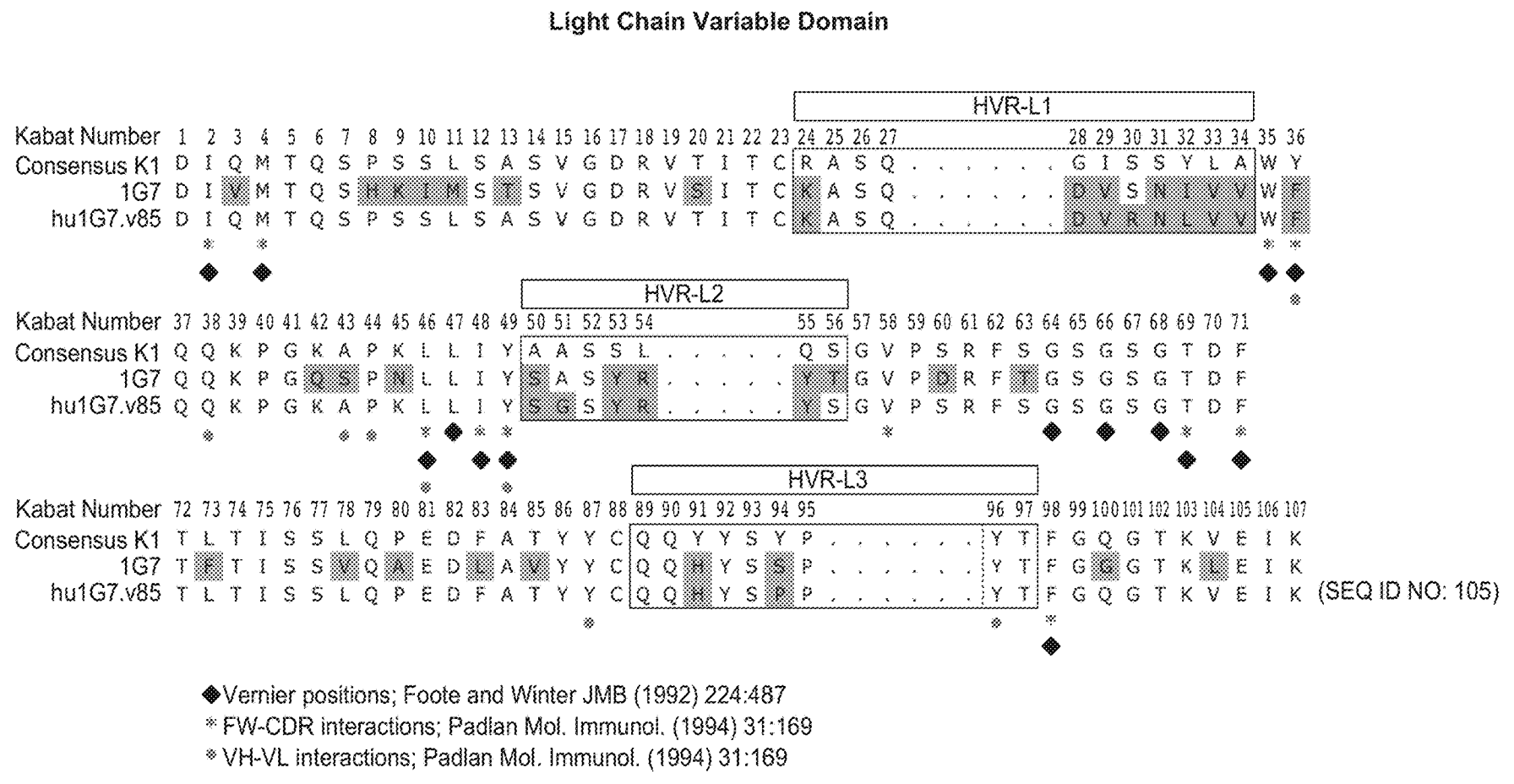

FIG. 6B is an alignment of the light chain variable (VL) domain sequences of hu1G7.v85, 1G7, and consensus KI. Changes from the humanized, affinity matured, and polished clone 1G7 are shown in shaded boxes. The VL domain sequence of hu1G7.v85 is disclosed as SEQ ID NO: 105.

FIG. 7A shows the heavy chain variable (VH) domain sequence of anti-FcRH5 antibody hu1G7.v93 (SEQ ID NO: 106).

FIG. 11B shows the sequence of the light chain variable (VL) domain sequence of humanized, rabbit-derived anti-FcRH5 antibody hu7D8.L1H2. The VL domain sequence of hu7D8.L1H2 is disclosed as SEQ ID NO: 109.

FIG. 12B shows the sequence of the light chain variable (VL) domain sequence of mouse-derived anti-FcRH5 antibody 17B1. The VL domain sequences of 17B1 is disclosed as SEQ ID NO: 111.

FIG. 13B shows the sequence of the light chain variable (VL) domain sequence of mouse-derived anti-FcRH5 antibody 15G8. The VL domain sequence of 15G8 is disclosed as SEQ ID NO: 113.

FIG. 15 is a series of graphs showing that the FcRH5 TDBs 1G7.v85 TDB and hu1G7.v93/38E4.v1 ("1G7.v93 TDB") bind with comparable affinity to both human FcRH5 and cyno FcRH5.

In FIG. 17A, the 1G7 TDB, hu1G7.v1.1/38E4.v1 ("1G7.v1.1 TDB"), hu1G7.v1.2/38E4.v1 ("1G7.v1.2 TDB"), hu1G7.v1.3/38E4.v1 ("1G7.v1.3 TDB"), and 1G7.v1.4 TDB were evaluated. In FIG. 17B, the 1G7.v1.4 TDB, hu1G7.v1.5/38E4.v1 ("1G7.v1.5" TDB), hu1G7.v1.13/38E4.v1 ("1G7.v1.13 TDB"), hu1G7.v1.7/38E4.v1 ("1G7.v1.7 TDB"), and hu1G7.v1.13.1/38E4.v1 ("1G7.v1.13.1") were evaluated. The 1G7.v.1.4 TDB improved target cell killing (EC50) 5- to 13-fold over murine 1G7 TDB (n=10).

FIG. 25A is an overlay histogram of six cell lines (SVT2-vector, SVT2-FcRH1, SVT2-FCRH2, SVT2-FcRH3, SVT2-FcRH4, and SVT2-FcRH5), showing that the 1G7.v85 TDB binds to FcRH5, but not to other family members.

FIG. 25B is a histogram overlay of three cell lines (293 parental, 293-FcRH5 full-length, and 293-FcRH5-D9-deletion), showing that the 1G7.v85 TDB binds to the membrane proximal domain of FcRH5.

FIG. 25C is an overlay histogram of three cell lines (SVT2-vector, SVT2-huFcRH5, and SVT2-cyno FcRH5), showing that the 1G7.v85 TDB binds to cyno FcRH5 and human FcRH5.

FIG. 30A is a graph showing that splenic human T cells isolated from spleens of humanized NOD/SCID gamma mice (NSG) have comparable activity to peripheral human T cells from heathy donors.

FIGS. 31F-31H are plotted with group mean and standard error of mean (SEM).

FIG. 42 is a table showing the corresponding HVR-L1, HVR-L2, and HVR-L3 sequences of each antibody clone examined by surface plasmon resonance along with K$_D$ (nM) and fold improvement of the particular clones as compared to hu1G7.v1 controls.

FIG. 43 is a table showing the corresponding HVR-H1, HVR-H2, and HVR-H3 sequences of each antibody clone examined by surface plasmon resonance along with K$_D$ (nM) and fold improvement of the particular clones as compared to hu1G7.v1 controls.

FIG. 44 is a table showing combinatorial analysis of mutations identified by antibody phage display.

Figure 45:
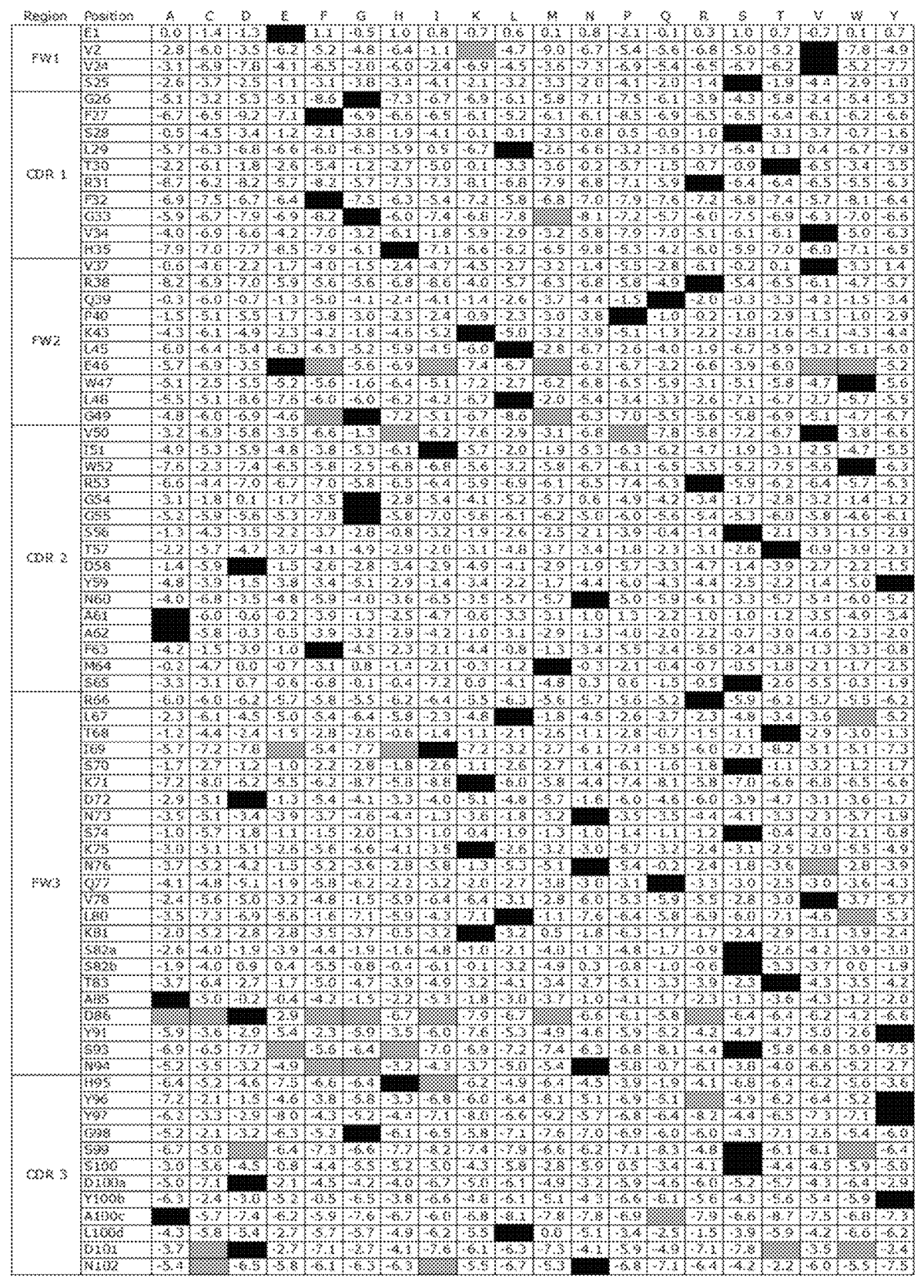

FIG. 45 is a table showing enrichment scores of mutations in hu1G7.v1 selected with human FcRH5.

Figure 46:
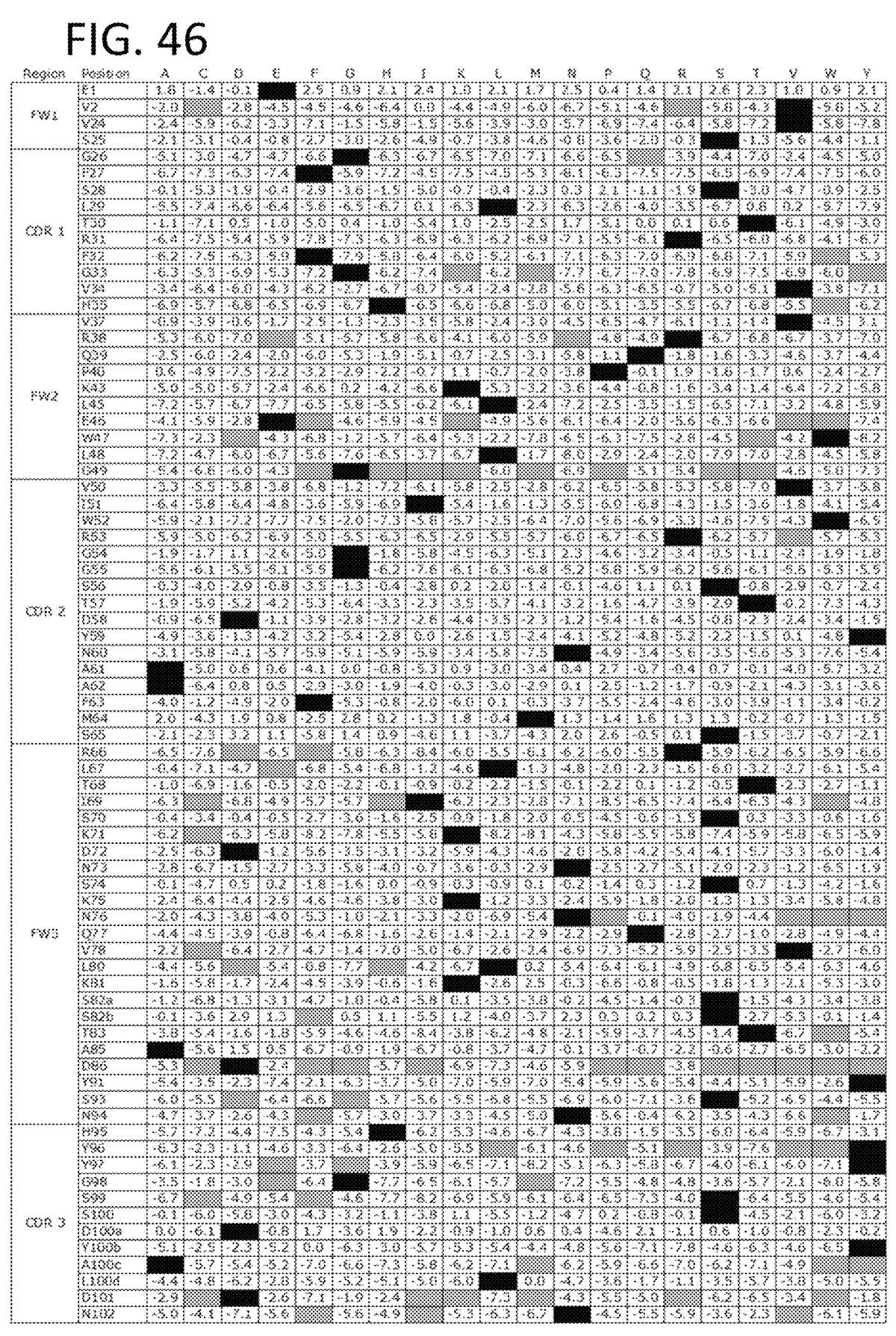

FIG. 46 is a table showing enrichment scores of mutations in hu1G7.v1 selected with cynomolgous FcRH5.

FIG. 47 is a table showing mutations with enrichment scores of at least 0.5 in selections with human FcRH5 and enrichment scores of at least 0 in selections with cynomolgous FcRH5. The mutations selected for further analysis are highlighted in black or gray, and the L29T mutation identified by Sanger sequencing is highlighted in gray.

DETAILED DESCRIPTION OF THE INVENTION

I. Definitions

Figure 1A:
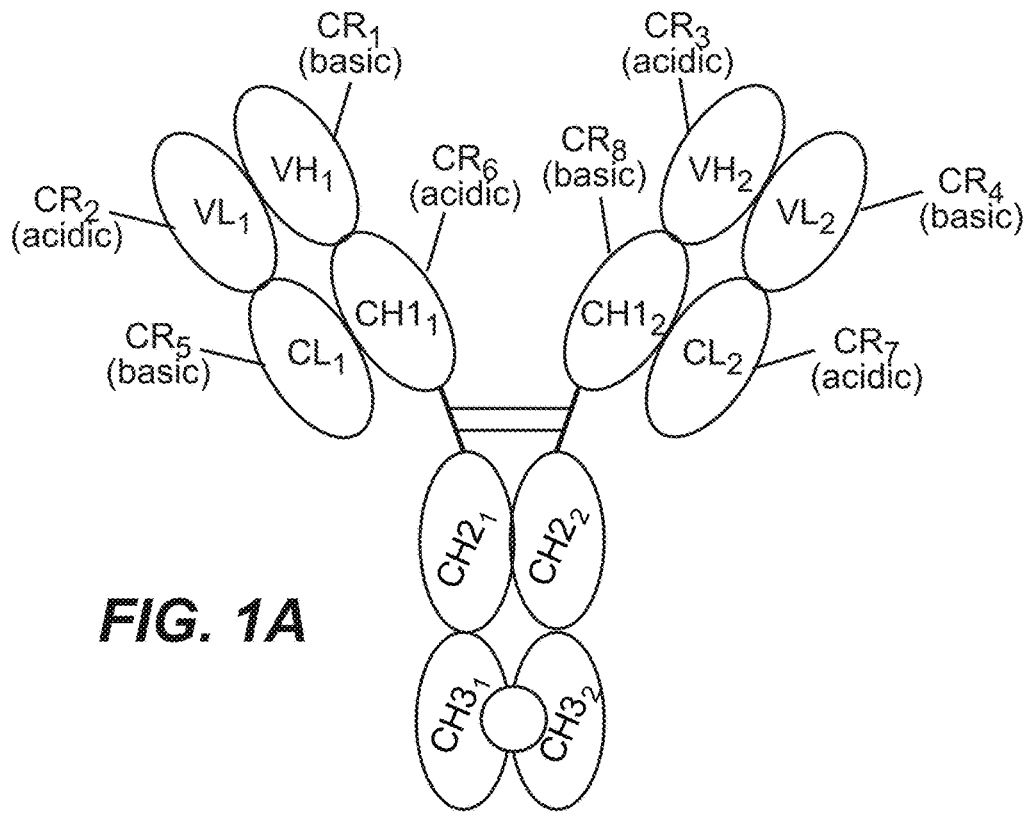
FIG. 1A is a schematic diagram showing an exemplary Rational Design configuration (Configuration 1) of an FcRH5 TDB having VL, VH, CL, and CH1 domains including one or more charged regions. For Configuration 1, the $VH_1$, $CL_1$, $VL_2$, and $CH1_2$ domains contain basic charged regions, and the $VL_1$, $CH1_1$, $VH_2$, and $CL_2$ domains contain acidic charged regions.

The term "about" as used herein refers to the usual error range for the respective value readily known to the skilled person in this technical field. Reference to "about" a value or parameter herein includes (and describes) embodiments that are directed to that value or parameter per se.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or fewer, 9 or fewer, 8 or fewer, 7 or fewer, 6 or fewer, 5 or fewer, 4 or fewer, 3 or fewer, or 2 or fewer. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (K$_D$). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "anti-FcRH5 antibody" or "an antibody that binds to FcRH5" refers to an antibody that is capable of binding FcRH5 with sufficient affinity such that the antibody is useful as a diagnostic and/or therapeutic agent in targeting FcRH5. In one embodiment, the extent of binding of an anti-FcRH5 antibody to an unrelated, non-FcRH5 protein is less than about 10% of the binding of the antibody to FcRH5 as measured, e.g., by a radioimmunoassay (RIA). In certain embodiments, an antibody that binds to FcRH5 has a dissociation constant (K$_D$) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In certain embodiments, an anti-FcRH5 antibody binds to an epitope of FcRH5 that is conserved among FcRH5 from different species.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one embodiment, the extent of binding of an anti-CD3 antibody to an unrelated, non-CD3 protein is less than about 10% of the binding of the antibody to CD3 as measured, e.g., by a radioimmunoassay (RIA). In certain embodiments, an antibody that binds to CD3 has a dissociation constant (K$_D$) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In certain embodiments, an anti-CD3 antibody binds to an epitope of CD3 that is conserved among CD3 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments (e.g., bis-Fabs) so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to bis-Fabs; Fv; Fab; Fab, Fab'-SH; F(ab')$_2$; diabodies; linear antibodies; single-chain antibody molecules (e.g., scFv); and multispecific antibodies formed from antibody fragments.

By "binding domain" is meant a part of a compound or a molecule that specifically binds to a target epitope, antigen, ligand, or receptor. Binding domains include but are not limited to antibodies (e.g., monoclonal, polyclonal, recombinant, humanized, and chimeric antibodies), antibody fragments or portions thereof (e.g., bis-Fab fragments, Fab fragments, F(ab')$_2$, scFv antibodies, SMIP, domain antibodies, diabodies, minibodies, scFv-Fc, affibodies, nanobodies, and VH and/or VL domains of antibodies), receptors, ligands, aptamers, and other molecules having an identified binding partner.

As used herein the term "charged region" refers to a location of a polypeptide (e.g., an antibody) that includes one or more (e.g., 1, 2, 3, 4, 5, 6, 7, 8, 9, or 10) basic or acidic amino acids that are capable of forming a charge pair with a cognate charged region having one or more (e.g., 1, 2, 3, 4, 5, 6, 7, 8, 9, or 10) basic or acidic amino acids, when the charged region and its cognate charged region have opposite overall relative charge.

As used herein the term "charge pair" refers to the bond that is formed between two charged regions of opposite overall charge.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII (see, e.g., Nicolaou et al. *Angew. Chem Intl. Ed. Engl.* 33: 183-186, 1994); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); combretastatin; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®, Bristol-Myers Squibb Oncology, Princeton, N.J.), albumin-engineered nanoparticle formulation of paclitaxel (ABRAXANE™), and docetaxel (TAXOTERE®, Rhome-Poulene Rorer, Antony, France); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R) (e.g., erlotinib (Tarceva™)); and VEGF-A that reduce cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors; tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin, and pharmaceutically acceptable salts, acids or derivatives of any of the above; as well as combinations of two or more of the above.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON.cndot.toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above; as well as combinations of two or more of the above.

The term "immunomodulatory drug" or "IMiD" refers to a class of drugs that modifies the immune system response or the functioning of the immune system, such as by the stimulation of antibody formation and/or the inhibition of peripheral blood cell activity, and include, but are not limited to, thalidomide ($\alpha$-N-phthalimido-glutarimide) and its analogues, REVLIMID® (lenalidomide), ACTI-MID™ (pomalidomide), OTEZLA® (apremilast), and pharmaceutically acceptable salts or acids thereof.

The term "chimeric" antibody refers to an antibody in which a portion of the heavy and/or light chain is derived from a particular source or species, while the remainder of the heavy and/or light chain is derived from a different source or species.

The term "FcRH5," as used herein, refers to any native FcRH5 which results from the production of a FcRH5 protein in a cell. The term includes FcRH5 from any vertebrate source, including mammals such as primates (e.g., humans and cynomolgus monkeys) and rodents (e.g., mice and rats), unless otherwise indicated. The term also includes naturally occurring variants of FcRH5, e.g., splice variants or allelic variants. The amino acid sequence of an exemplary human FcRH5 protein sequence is shown in SEQ ID NO: 114. The amino acid sequence of an exemplary cynomolgus monkey FcRH5 protein is shown in SEQ ID NO: 215.

The term "cluster of differentiation 3" or "CD3," as used herein, refers to any native CD3 from any vertebrate source, including mammals such as primates (e.g., humans) and rodents (e.g., mice and rats), unless otherwise indicated, including, for example, CD3$\varepsilon$, CD3$\gamma$, CD3$\alpha$, and CD3$\beta$ chains. The term encompasses "full-length," unprocessed CD3 (e.g., unprocessed or unmodified CD3$\varepsilon$ or CD3$\gamma$), as well as any form of CD3 that results from processing in the cell. The term also encompasses naturally occurring variants of CD3, including, for example, splice variants or allelic variants. CD3 includes, for example, human CD3$\varepsilon$ protein (NCBI RefSeq No. NP_000724), which is 207 amino acids in length, and human CD3$\gamma$ protein (NCBI RefSeq No. NP_000064), which is 182 amino acids in length.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called $\alpha$, $\delta$, $\varepsilon$, $\gamma$, and $\mu$, respectively.

It is understood that aspects and embodiments of the invention described herein include "comprising," "consisting," and "consisting essentially of" aspects and embodiments.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is a tumor.

The terms "cancer" and "cancerous" refer to or describe the physiological condition in mammals that is typically characterized by unregulated cell growth/proliferation. Examples of cancer include, but are not limited to, myeloma, carcinoma, lymphoma (e.g., Hodgkin's and non-Hodgkin's lymphoma), blastoma, sarcoma, and leukemia. In some embodiments, the cancer is an FcRH5-positive cancer. More particular examples of such cancers include multiple myeloma (MM), chronic lymphoid leukemia (CLL), mantle cell lymphoma (MCL), diffuse large B-cell lymphoma (DLBCL), follicular lymphoma (FL), acute myeloid leukemia (AML), myelodysplastic syndrome (MDS), chronic myelogenous leukemia (CML), chronic myelomonocytic leukemia, acute promyelocytic leukemia (APL), chronic myeloproliferative disorder, thrombocytic leukemia, precursor B-cell acute lymphoblastic leukemia (pre-B-ALL), precursor T cell acute lymphoblastic leukemia (pre-T-ALL), mast cell disease, mast cell leukemia, mast cell sarcoma, myeloid sarcomas, lymphoid leukemia, and undifferentiated leukemia. In some embodiments, the cancer is a B cell cancer. In particular, cancer can include conditions involving the production of excess antibodies, such as monoclonal gammopathy, light chain amyloidosis, monoclonal gammopathy of undetermined significance and solitary plasmacytomas, isolated plasmacytoma and extramedullary plasmacytoma.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

An "effective amount" of a compound, for example, an anti-FcRH5 antibody of the invention or a composition (e.g., pharmaceutical composition) thereof, is at least the minimum amount required to achieve the desired therapeutic or prophylactic result, such as a measurable improvement or prevention of a particular disorder (e.g., a cell proliferative disorder, e.g., cancer). An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications, and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al. *Sequences of Proteins of Immunological Interest,* 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "FcRH5-positive cell" refers to a cell that expresses FcRH5 on its surface. In some embodiments, FcRH5 is one or more of FcRH5a, FcRH5b, FcRH5c, UniProt Identifier Q96RD9-2, and/or FcRH5d. In some embodiments, the FcRH5 is FcRH5c.

The term "FcRH5-positive cancer" refers to a cancer comprising cells that express FcRH5 on their surface. For the purposes of determining whether a cell expresses FcRH5 on the surface, FcRH5 mRNA expression is considered to correlate to FcRH5 expression on the cell surface. In some embodiments, expression of FcRH5 mRNA is determined by a method selected from in situ hybridization and RT-PCR (including quantitative RT-PCR). Alternatively, expression of FcRH5 on the cell surface can be determined, for example, using antibodies to FcRH5 in a method such as immunohistochemistry, FACS, etc. In some embodiments, FcRH5 is one or more of FcRH5a, FcRH5b, FcRH5c, UniProt Identifier Q96RD9-2, and/or FcRH5d. In some embodiments, the FcRH5 is FcRH5c.

The terms "full-length antibody," "intact antibody," and "whole antibody" are used herein interchangeably to refer to an antibody having a structure substantially similar to a native antibody structure or having heavy chains that contain an Fc region as defined herein.

The term "glycosylated forms of FcRH5" refers to naturally occurring forms of FcRH5 that are post-translationally modified by the addition of carbohydrate residues.

A "growth inhibitory agent" when used herein refers to a compound or composition which inhibits growth of a cell either in vitro or in vivo. In one embodiment, growth inhibitory agent is growth inhibitory antibody that prevents or reduces proliferation of a cell expressing an antigen to which the antibody binds.

In another embodiment, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies can be produced using various techniques known in the art, including phage-display libraries. Hoogenboom and Winter. *J. Mol. Biol.* 227:381, 1991; Marks et al. *J. Mol. Biol.* 222:581, 1991. Also available for the preparation of human monoclonal antibodies are methods described in Cole et al. *Monoclonal Antibodies and Cancer Therapy*, Alan R. Liss, p. 77 (1985); Boerner et al. *J. Immunol.*, 147(1):86-95, 1991. See also van Dijk and van de Winkel. *Curr. Opin. Pharmacol.* 5:368-74, 2001. Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al. *Proc. Natl. Acad. Sci. USA*. 103:3557-3562, 2006 regarding human antibodies generated via a human B-cell hybridoma technology.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al. supra. In one embodiment, for the VH, the subgroup is subgroup III as in Kabat et al. supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917, 1987);

(b) CDRs occurring at amino acid residues 24-34 (L1), 50-56 (L2), 89-97 (L3), 31-35b (H1), 50-65 (H2), and 95-102 (H3) (Kabat et al. *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262:732-745, 1996); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al. supra.

An "immunoconjugate" is an antibody conjugated to one or more heterologous molecule(s), including but not limited to a cytotoxic agent.

A "subject" or an "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the subject or individual is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al. *J. Chromatogr. B* 848:79-87, 2007.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-FcRH5 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

"Isolated nucleic acid encoding an anti-CD3 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

The term "PD-1 axis binding antagonist" refers to a molecule that inhibits the interaction of a PD-1 axis binding partner with either one or more of its binding partner, so as to remove T cell dysfunction resulting from signaling on the PD-1 signaling axis—with a result being to restore or enhance T cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific embodiment, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T cell less dysfunctional (e.g., enhancing effector responses to antigen recognition). In some embodiments, the PD-1 binding antagonist is an anti-PD-1 antibody. In a specific embodiment, a PD-1 binding antagonist is MDX-1106 (nivolumab). In another specific embodiment, a PD-1 binding antagonist is MK-3475 (pembrolizumab). In another specific embodiment, a PD-1 binding antagonist is CT-011 (pidilizumab). In another specific embodiment, a PD-1 binding antagonist is AMP-224. In another specific embodiment, a PD-1 binding antagonist is MED1-0680. In another specific embodiment, a PD-1 binding antagonist is PDR001. In another specific embodiment, a PD-1 binding antagonist is REGN2810. In another specific embodiment, a PD-1 binding antagonist is BGB-108.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific embodiment, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T cell less dysfunctional (e.g., enhancing effector responses to antigen recognition). In some embodiments, a PD-L1 binding antagonist is an anti-PD-L1 antibody. In still another specific embodiment, an anti-PD-L1 antibody is MPDL3280A (atezolizumab, marketed as TECENTRIQ™ with a WHO Drug Information (International Nonproprietary Names for Pharmaceutical Substances), Recommended INN: List 74, Vol. 29, No. 3, 2015 (see page 387)). In a specific embodiment, an anti-PD-L1 antibody is YW243.55.S70. In another specific embodiment, an anti-PD-L1 antibody is MDX-1105. In another specific embodiment, an anti PD-L1 antibody is MSB0015718C. In still another specific embodiment, an anti-PD-L1 antibody is MED14736.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific embodiment, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T cell less dysfunctional (e.g., enhancing effector responses to antigen recognition). In some embodiments, a PD-L2 binding antagonist is an immunoadhesin.

The term "protein," as used herein, refers to any native protein from any vertebrate source, including mammals such as primates (e.g., humans) and rodents (e.g., mice and rats), unless otherwise indicated. The term encompasses "full-length," unprocessed protein as well as any form of the protein that results from processing in the cell. The term also encompasses naturally occurring variants of the protein, e.g., splice variants or allelic variants.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full-length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

As used herein, "delaying progression" of a disorder or disease means to defer, hinder, slow, retard, stabilize, and/or postpone development of the disease or disorder (e.g., a cell proliferative disorder, e.g., cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

The term "epitope" refers to the particular site on an antigen molecule to which an antibody binds. In some embodiments, the particular site on an antigen molecule to which an antibody binds is determined by hydroxyl radical footprinting (e.g., FcRH5 binding domain). In some embodiments, the particular site on an antigen molecule to which an antibody binds is determined by crystallography.

By "reduce" or "inhibit" is meant the ability to cause an overall decrease, for example, of 20% or greater, of 50% or greater, or of 75%, 85%, 90%, 95%, or greater. In certain embodiments, reduce or inhibit can refer to the effector function of an antibody that is mediated by the antibody Fc region, such effector functions specifically including complement-dependent cytotoxicity (CDC), antibody-dependent cellular cytotoxicity (ADCC), and antibody-dependent cellular phagocytosis (ADCP).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6*th* ed. W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al. *J. Immunol.* 150:880-887, 1993; Clarkson et al. *Nature* 352:624-628, 1991.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

As used herein, "administering" is meant a method of giving a dosage of a compound (e.g., an anti-FcRH5 antibody of the invention or a nucleic acid encoding an anti-FcRH5 antibody of the invention) or a composition (e.g., a pharmaceutical composition, e.g., a pharmaceutical composition including an anti-FcRH5 antibody of the invention) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The method of administration can vary depending on various factors (e.g., the compound or composition being administered and the severity of the condition, disease, or disorder being treated).

II. Compositions and Methods

In one aspect, the invention is based in part on anti-FcRH5 antibodies. In certain embodiments, the anti-FcRH5 antibodies are multispecific (e.g., bispecific) and bind, in addition to FcRH5 or a fragment thereof, a second biological molecule (e.g., a cell surface antigen, e.g., a T cell marker, e.g., CD3 (e.g., CD3ε and/or CD3γ)). Antibodies of the invention are useful, for example, for diagnosing and/or treating or delaying the progression of a cell proliferative disorder (e.g., cancer, e.g., an FcRH5-positive cancer, e.g., multiple myeloma) in a subject.

A. Exemplary Anti-FcRH5 Antibodies

In one aspect, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 2; (c) an HVR-H3 comprising the amino acid sequence of SEQ ID NO: 3; (d) an HVR-L1 comprising the amino acid sequence of SEQ ID NO: 4; (e) an HVR-L2 comprising the amino acid sequence of SEQ ID NO: 5; and (f) an HVR-L3 comprising the amino acid sequence of SEQ ID NO: 6.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 16; and (f) an HVR-L3 comprising the amino acid sequence of SEQ ID NO: 23. In some instances, the anti-FcRH5 antibody may have a heavy chain variable (VH) domain including an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 104 and/or a light chain variable (VL) domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 105. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NOs: 52, 54, 46, and 47, respectively. In some instances, the anti-FcRH5 antibody may have a heavy chain variable (VH) domain including the amino acid sequence of SEQ ID NO: 104. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 57, 50, and 51, respectively. In some instances, the anti-FcRH5 antibody may have a VL domain comprising the amino acid sequence of SEQ ID NO: 105. In a particular instance, the anti-FcRH5 antibody can be 1G7.v85, or a derivative or clonal relative thereof. In some instances, for example, the invention provides an anti-FcRH5 antibody having a binding domain comprising (a) a VH domain comprising an amino acid sequence of SEQ ID NO: 104 and (b) a VL domain comprising an amino acid sequence of SEQ ID NO: 105.

In some instances, the invention provides an anti-FcRH5 antibody having a binding domain comprising at least one, two, three, four, five, or six hypervariable regions (HVRs) selected from SEQ ID NO: 1; (b) an HVR-H2 comprising the amino acid sequence of SEQ ID NO: 8; (c) an HVR-H3 comprising the amino acid sequence of SEQ ID NO: 10; (d) an HVR-L1 comprising the amino acid sequence of SEQ ID NO: 14; (e) an HVR-L2 comprising the amino acid sequence of SEQ ID NO: 16; and (f) an HVR-L3 comprising the amino acid sequence of SEQ ID NO: 23. In some instances, the anti-FcRH5 antibody may have a VH domain including an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 106 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 107. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 53, 54, 46, and 47, respectively. In some instances, the anti-FcRH5 antibody may have a VH domain comprising the amino acid sequence of SEQ ID NO: 106. In some instances, the anti-FcRH5 further includes at least one (e.g., 1, 2, 3, or 4) of the light chain framework regions FR-L1, FR-L2, FR-L3, and FR-L4 comprising the sequences of SEQ ID NOs: 48, 57, 50, and 51, respectively. In some instances, the anti-FcRH5 antibody may have a VL domain comprising the amino acid sequence of SEQ ID NO: 107. In a particular instance, the anti-FcRH5 antibody can be 1G7.v93, or a derivative or clonal relative thereof. In some instances, for example, the invention provides an anti-FcRH5 antibody having a binding domain comprising (a) a VH domain comprising an amino acid sequence of SEQ ID NO: 106 and (b) a VL domain comprising an amino acid sequence of SEQ ID NO: 107.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 11; (e) an HVR-L2 comprising the amino acid sequence of SEQ ID NO: 15; and (f) an HVR-L3 comprising the amino acid sequence of SEQ ID NO: 20. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 82 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 83. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 52, 54, 46, and 47. In some instances, the anti-FcRH5 antibody may have a VH domain comprising the amino acid sequence of SEQ ID NO: 82. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 83. In a particular instance, the anti-FcRH5 antibody can be 1G7.v1, or a derivative or clonal relative thereof. In some instances, for example, the invention provides an anti-FcRH5 antibody having a binding domain comprising (a) a VH domain comprising an amino acid sequence of SEQ ID NO: 82 and (b) a VL domain comprising an amino acid sequence of SEQ ID NO: 83.

In some instances, the anti-FcRH5 antibody includes a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 16; and (f) an HVR-L3 comprising the amino acid sequence of SEQ ID NO: 21. In some instances, the anti-FcRH5 antibody includes a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 84 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 85. In some instances, the anti-FcRH5 antibody further includes the heavy chain framework regions FR-H1, FR-H2, FR-H3, and FR-H4 of SEQ ID NO: 52, 54, 46, and 47, respectively. In some instances, the anti-FcRH5 antibody may have a VH domain comprising the amino acid sequence of SEQ ID NO: 84. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 57, 50, and 51, respectively. In some instances, the anti-FcRH5 antibody may have a VL domain comprising the amino acid sequence of SEQ ID NO: 85. In a particular instance, the anti-FcRH5 antibody can be 1G7.v1.1, or a derivative or clonal relative thereof. In some instances, for example, the invention provides an anti-FcRH5 antibody having a binding domain comprising (a) a VH domain comprising an amino acid sequence of SEQ ID NO: 84 and (b) a VL domain comprising an amino acid sequence of SEQ ID NO: 85.

In some instances, the anti-FcRH5 antibody has a binding domain comprising six hypervariable regions (HVRs) (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 17; and (f) an HVR-L3 comprising the amino acid sequence of SEQ ID NO: 22. In some instances, the anti-FcRH5 antibody includes a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 86 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 87. In some instances, the anti-FcRH5 antibody further comprises further includes the heavy chain framework regions FR-H1, FR-H2, FR-H3, and FR-H4 comprising the amino acid sequences of SEQ ID NO: 52, 54, 46, and 47. In some instances, the anti-FcRH5 antibody may have a VH domain comprising the amino acid sequence of SEQ ID NO: 86. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 57, 50, and 51, respectively. In some instances, the anti-FcRH5 antibody of claim may have a VL domain comprising the amino acid sequence of SEQ ID NO: 87. In a particular instance, the anti-FcRH5 antibody can be 1G7.v1.2, or a derivative or clonal relative thereof. In some instances, for example, the invention provides an anti-FcRH5 antibody having a binding domain comprising (a) a VH domain comprising an amino acid sequence of SEQ ID NO: 86 and (b) a VL domain comprising an amino acid sequence of SEQ ID NO: 87.

In some instances, the anti-FcRH5 antibody having a binding domain comprising six hypervariable regions (HVRs) (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 13; (e) an HVR-L2 comprising the amino acid sequence of SEQ ID NO: 16; and (f) an HVR-L3 comprising the amino acid sequence of SEQ ID NO: 21. In some instances, the anti-FcRH5 antibody comprises a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 88 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 89. In some instances, the anti-FcRH5 antibody further includes the heavy chain framework regions FR-H1, FR-H2, FR-H3, and FR-H4 comprising the amino acid sequences of SEQ ID NOs: 52, 54, 46, and 47, respectively. In some instances, the anti-FcRH5 antibody may have a VH domain comprising the amino acid sequence of SEQ ID NO: 88. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 57, 50, and 51, respectively. In some instances, the anti-FcRH5 antibody may have a VL domain comprising the amino acid sequence of SEQ ID NO: 89. In a particular instance, the anti-FcRH5 antibody can be 1G7.v1.3, or a derivative or clonal relative thereof. In some instances, for example, the invention provides an anti-FcRH5 antibody comprising a binding domain comprising (a) a VH domain comprising an amino acid sequence of SEQ ID NO: 88 and (b) a VL domain comprising an amino acid sequence of SEQ ID NO: 89.

In some instances, the anti-FcRH5 antibody includes a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 16; and (f) an HVR-L3 comprising the amino acid sequence of SEQ ID NO: 23. In some instances, the anti-FcRH5 antibody may have a binding domain including a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 90 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 91. In some instances, the anti-FcRH5 antibody further includes the heavy chain framework regions FR-H1, FR-H2, FR-H3, and FR-H4 SEQ ID NO: 52, 54, 46, and 47. In some instances, the anti-FcRH5 antibody may have a VH domain comprising the amino acid sequence of SEQ ID NO: 90. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 57, 50, and 51, respectively. In some instances, the anti-FcRH5 antibody may have a VL domain comprising the amino acid sequence of SEQ ID NO: 91. In a particular instance, the anti-FcRH5 antibody can be 1G7.v1.4, or a derivative or clonal relative thereof. In some instances, for example, the invention provides an anti-FcRH5 antibody having a binding domain comprising (a) a VH domain comprising an amino acid sequence of SEQ ID NO: 90 and (b) a VL domain comprising an amino acid sequence of SEQ ID NO: 91.

In some instances, the anti-FcRH5 antibody includes a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 11; (e) an HVR-L2 comprising the amino acid sequence of SEQ ID NO: 18; and (f) an HVR-L3 comprising the amino acid sequence of SEQ ID NO: 22. In some instances, the anti-FcRH5 antibody includes a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 92 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 93. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NOs: 52, 54, 46, and 47, respectively. In some instances, the anti-FcRH5 antibody may have a VH domain comprising the amino acid sequence of SEQ ID NO: 92. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51, respectively. In some instances, the anti-FcRH5 antibody may have a VL domain comprising the amino acid sequence of SEQ ID NO: 93. In a particular instance, the anti-FcRH5 antibody can be 1G7.v1.5, or a derivative or clonal relative thereof. In some instances, for example, the invention provides an anti-FcRH5 antibody having a binding domain comprising (a) a VH domain comprising an amino acid sequence of SEQ ID NO: 92 and (b) a VL domain comprising an amino acid sequence of SEQ ID NO: 93.

In some instances, the anti-FcRH5 antibody includes a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 11; (e) an HVR-L2 comprising the amino acid sequence of SEQ ID NO: 19; and (f) an HVR-L3 comprising the amino acid sequence of SEQ ID NO: 24. In some instances. The anti-FcRH5 antibody includes a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 94 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 95. In some instances, the anti-FcRH5 antibody includes the heavy chain framework regions FR-H1, FR-H2, FR-H3, and FR-H4 comprising the amino acid sequences of SEQ ID NOs: 52, 54, 46, and 47, respectively. In some instances, the anti-FcRH5 antibody may have a VH domain comprising the amino acid sequence of SEQ ID NO: 94. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 57, 50, and 51, respectively. In some instances, the anti-FcRH5 antibody includes a VL domain comprising the amino acid sequence of SEQ ID NO: 95. In a particular instance, the anti-FcRH5 antibody can be 1G7.v1.6, or a derivative or clonal relative thereof. In some instances, for example, the invention provides an anti-FcRH5 antibody having a binding domain including (a) a VH domain comprising an amino acid sequence of SEQ ID NO: 94 and (b) a VL domain comprising an amino acid sequence of SEQ ID NO: 95.

In some instances, the anti-FcRH5 antibody includes a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 18; and (f) an HVR-L3 comprising the amino acid sequence of SEQ ID NO: 25. In some instances, the anti-FcRH5 antibody includes a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 96 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 97. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NOs: 53, 54, 46, and 47. In some instances, the anti-FcRH5 antibody includes a VH domain comprising the amino acid sequence of SEQ ID NO: 96. In some instances, the anti-FcRH5 includes at least one (e.g., 1, 2, 3, or 4) of the light chain framework regions FR-L1, FR-L2, FR-L3, and FR-L4 comprising the sequences of SEQ ID NOs: 48, 57, 50, and 51. In some instances, the anti-FcRH5 antibody includes a VL domain comprising the amino acid sequence of SEQ ID NO: 97. In a particular instance, the anti-FcRH5 antibody can be 1G7.v1.7, or a derivative or clonal relative thereof. In some instances, for example, the invention provides an anti-FcRH5 antibody, having a binding domain including (a) a VH domain comprising an amino acid sequence of SEQ ID NO: 96 and (b) a VL domain comprising an amino acid sequence of SEQ ID NO: 97.

In some instances, the anti-FcRH5 antibody includes a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 18; and (f) an HVR-L3 comprising the amino acid sequence of SEQ ID NO: 25. In some instances, the anti-FcRH5 antibody includes a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 98, and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 99. In some instances, the anti-FcRH5 comprises at least one (e.g., 1, 2, 3, or 4) of heavy chain framework regions FR-H1, FR-H2, FR-H3, and FR-H4 comprising the sequences of SEQ ID NOs: 52, 55, 46, and 47, respectively. In some instances, the anti-FcRH5 antibody includes a VH domain comprising the amino acid sequence of SEQ ID NO: 98. In some instances, the anti-FcRH5 antibody includes at least one (e.g., 1, 2, 3, or 4) of the light chain framework regions FR-L1, FR-L2, FR-L3, and FR-L4 comprising the sequences of SEQ ID NOs: 48, 57, 50, and 51. In some instances, the anti-FcRH5 antibody may have a VL domain comprising the amino acid sequence of SEQ ID NO: 99. In a particular instance, the anti-FcRH5 antibody can be 1G7.v1.13, or a derivative or clonal relative thereof. In some instances, for example, an anti-FcRH5 antibody may include a VH domain comprising an amino acid sequence of SEQ ID NO: 98 and (b) a VL domain comprising an amino acid sequence of SEQ ID NO: 99.

In some instances, the anti-FcRH5 antibody includes a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 18; and (f) an HVR-L3 comprising the amino acid sequence of SEQ ID NO: 25. In some instances, the anti-FcRH5 antibody includes (a) a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 100 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 101. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NOs: 52, 54, 46, and 47. In some instances, the anti-FcRH5 may have a VH domain comprising the amino acid sequence of SEQ ID NO: 100. In some instances, The anti-FcRH5 antibody of any one of claims 79-82, wherein the antibody further includes at least one (e.g., 1, 2, 3, or 4) of the light chain framework regions FR-L1, FR-L2, FR-L3, and FR-L4 comprising the sequences of SEQ ID NOs: 48, 57, 50, and 51. In some instances, the anti-FcRH5 antibody may have a VL domain comprising the amino acid sequence of SEQ ID NO: 101. In a particular instance, the anti-FcRH5 antibody can be 1G7.v1.13.1, or a derivative or clonal relative thereof. In some instances, for example, the invention provides an anti-FcRH5 antibody including (a) a VH domain comprising an amino acid sequence of SEQ ID NO: 100 and (b) a VL domain comprising an amino acid sequence of SEQ ID NO: 101.

In some instances, the anti-FcRH5 antibody includes a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 11; (e) an HVR-L2 comprising the amino acid sequence of SEQ ID NO: 15; and (f) an HVR-L3 comprising the amino acid sequence of SEQ ID NO: 20. In some instances, the anti-FcRH5 antibody includes (a) a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 102 and/or (b) a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 103. In some instances, the anti-FcRH5 antibody further comprises at least one (e.g., 1, 2, 3, or 4) of heavy chain framework regions FR-H1, FR-H2, FR-H3, and FR-H4 comprising the sequences of SEQ ID NOs: 52, 54, 46, and 47, respectively. In some instances, the anti-FcRH5 antibody may have a VH domain comprising the amino acid sequence of SEQ ID NO: 102. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 103. In a particular instance, the anti-FcRH5 antibody can be 1G7.v87, or a derivative or clonal relative thereof. In some instances, for example, the invention provides an anti-FcRH5 antibody comprising (a) a VH domain comprising an amino acid sequence of SEQ ID NO: 102 and (b) a VL domain comprising an amino acid sequence of SEQ ID NO: 103.

In some instances, an anti-FcRH5 antibody may have a binding domain comprising at least one, two, three, four, five, or six hypervariable regions (HVRs) selected from (a) an HVR-H1 comprising the amino acid sequence of SEQ ID NO: 32; (b) an HVR-H2 comprising the amino acid sequence of SEQ ID NO: 33; (c) an HVR-H3 comprising the amino acid sequence of SEQ ID NO: 34; (d) an HVR-L1 comprising the amino acid sequence of SEQ ID NO: 35; (e) an HVR-L2 comprising the amino acid sequence of SEQ ID NO: 36; and (f) an HVR-L3 comprising the amino acid sequence of SEQ ID NO: 37. In some instances, the anti-FcRH5 comprises a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 110 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 111. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NOs: 66, 67, 68, and 69, respectively. In some instances, the anti-FcRH5 antibody of claim 95, wherein the VH domain comprising the amino acid sequence of SEQ ID NO: 110. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 70, 71, 72, and 73. In some instances, the anti-FcRH5 antibody may have a VL domain comprising the amino acid sequence of SEQ ID NO: 111. In a particular instance, the anti-FcRH5 antibody can be 17B1, or a derivative or clonal relative thereof. In some instances, for example, the invention provides an anti-FcRH5 antibody comprising (a) a VH domain comprising an amino acid sequence of SEQ ID NO: 110 and (b) a VL domain comprising an amino acid sequence of SEQ ID NO: 111.

In some instances, an anti-FcRH5 antibody having a binding domain comprising at least one, two, three, four, five, or six hypervariable regions (HVRs) selected from (a) an HVR-H1 comprising the amino acid sequence of SEQ ID NO: 38; (b) an HVR-H2 comprising the amino acid sequence of SEQ ID NO: 39; (c) an HVR-H3 comprising the amino acid sequence of SEQ ID NO: 40; (d) an HVR-L1 comprising the amino acid sequence of SEQ ID NO: 41; (e) an HVR-L2 comprising the amino acid sequence of SEQ ID NO: 42; and (f) an HVR-L3 comprising the amino acid sequence of SEQ ID NO: 43. In some instances, the anti-FcRH5 antibody includes a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 112 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 113. In some instances, the anti-FcRH5 comprises at least one (e.g., 1, 2, 3, or 4) of heavy chain framework regions FR-H1, FR-H2, FR-H3, and FR-H4 comprising the sequences of SEQ ID NO: 74, 75, 76, and 77, respectively. In some instances, the anti-FcRH5 antibody may have a VH domain comprising the amino acid sequence of SEQ ID NO: 112. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 78, 79, 80, and 81. In some instances, the anti-FcRH5 antibody may have a VL domain comprising the amino acid sequence of SEQ ID NO: 113. In a particular instance, the anti-FcRH5 antibody can be 15G8, or a derivative or clonal relative thereof. In some instances, for example, the invention provides an anti-FcRH5 antibody comprising (a) a VH domain comprising an amino acid sequence of SEQ ID NO: 112 and (b) a VL domain comprising an amino acid sequence of SEQ ID NO: 113.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 26; (b) an HVR-H2 comprising the amino acid sequence of SEQ ID NO: 27; (c) an HVR-H3 comprising the amino acid sequence of SEQ ID NO: 28; (d) an HVR-L1 comprising the amino acid sequence of SEQ ID NO: 29; (e) an HVR-L2 comprising the amino acid sequence of SEQ ID NO: 30; and (f) an HVR-L3 comprising the amino acid sequence of SEQ ID NO: 31. In some instances, the anti-FcRH5 antibody includes a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 108 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 109. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NOs: 58, 59, 60, and 61, respectively. In some instances, the anti-FcRH5 antibody may have a VH domain comprising the amino acid sequence of SEQ ID NO: 108. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 62, 63, 64, and 65. In some instances, the anti-FcRH5 antibody may have a VL domain comprising the amino acid sequence of SEQ ID NO: 109. In a particular instance, the anti-FcRH5 antibody can be 7D8, or a derivative or clonal relative thereof. In some instances, for example, the invention provides an anti-FcRH5 antibody comprising (a) a VH domain comprising an amino acid sequence of SEQ ID NO: 108 and (b) a VL domain comprising an amino acid sequence of SEQ ID NO: 109.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 11; (e) an HVR-L2 comprising the amino acid sequence of SEQ ID NO: 15; and (f) an HVR-L3 comprising the amino acid sequence of SEQ ID NO: 20. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 185 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 186. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 179, 54, 46, and 47. In some instances, the anti-FcRH5 antibody may have a VH domain comprising the amino acid sequence of SEQ ID NO: 185. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 186. In a particular instance, the anti-FcRH5 antibody can be 1G7.v1A, or a derivative or clonal relative thereof. In some instances, for example, the invention provides an anti-FcRH5 antibody having a binding domain comprising (a) a VH domain comprising an amino acid sequence of SEQ ID NO: 185 and (b) a VL domain comprising an amino acid sequence of SEQ ID NO: 186.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 11; (e) an HVR-L2 comprising the amino acid sequence of SEQ ID NO: 15; and (f) an HVR-L3 comprising the amino acid sequence of SEQ ID NO: 20. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 187 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 188. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 180, 54, 46, and 47. In some instances, the anti-FcRH5 antibody may have a VH domain comprising the amino acid sequence of SEQ ID NO: 187. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 188. In a particular instance, the anti-FcRH5 antibody can be 1G7.v1B, or a derivative or clonal relative thereof. In some instances, for example, the invention provides an anti-FcRH5 antibody having a binding domain comprising (a) a VH domain comprising an amino acid sequence of SEQ ID NO: 187 and (b) a VL domain comprising an amino acid sequence of SEQ ID NO: 188.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 11; (e) an HVR-L2 comprising the amino acid sequence of SEQ ID NO: 15; and (f) an HVR-L3 comprising the amino acid sequence of SEQ ID NO: 20. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 189 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 190. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 181, 54, 46, and 47. In some instances, the anti-FcRH5 antibody may have a VH domain comprising the amino acid sequence of SEQ ID NO: 189. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 190. In a particular instance, the anti-FcRH5 antibody can be 1G7.v1C, or a derivative or clonal relative thereof. In some instances, for example, the invention provides an anti-FcRH5 antibody having a binding domain comprising (a) a VH domain comprising an amino acid sequence of SEQ ID NO: 189 and (b) a VL domain comprising an amino acid sequence of SEQ ID NO: 190.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 11; (e) an HVR-L2 comprising the amino acid sequence of SEQ ID NO: 15; and (f) an HVR-L3 comprising the amino acid sequence of SEQ ID NO: 20. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 191 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 192. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 23, 54, 46, and 47. In some instances, the anti-FcRH5 antibody may have a VH domain comprising the amino acid sequence of SEQ ID NO: 191. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 192. In a particular instance, the anti-FcRH5 antibody can be 1G7.v1 D, or a derivative or clonal relative thereof. In some instances, for example, the invention provides an anti-FcRH5 antibody having a binding domain comprising (a) a VH domain comprising an amino acid sequence of SEQ ID NO: 191 and (b) a VL domain comprising an amino acid sequence of SEQ ID NO: 192.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 11; (e) an HVR-L2 comprising the amino acid sequence of SEQ ID NO: 15; and (f) an HVR-L3 comprising the amino acid sequence of SEQ ID NO: 20. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 193 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 194. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 52, 182, 46, and 47. In some instances, the anti-FcRH5 antibody may have a VH domain comprising the amino acid sequence of SEQ ID NO: 193. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 194. In a particular instance, the anti-FcRH5 antibody can be 1G7.v1E, or a derivative or clonal relative thereof. In some instances, for example, the invention provides an anti-FcRH5 antibody having a binding domain comprising (a) a VH domain comprising an amino acid sequence of SEQ ID NO: 193 and (b) a VL domain comprising an amino acid sequence of SEQ ID NO: 194.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 175; (c) an HVR-H3 comprising the amino acid sequence of SEQ ID NO: 9; (d) an HVR-L1 comprising the amino acid sequence of SEQ ID NO: 11; (e) an HVR-L2 comprising the amino acid sequence of SEQ ID NO: 15; and (f) an HVR-L3 comprising the amino acid sequence of SEQ ID NO: 20. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 195 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 196. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 52, 54, 46, and 47. In some instances, the anti-FcRH5 antibody may have a VH domain comprising the amino acid sequence of SEQ ID NO: 195. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 196. In a particular instance, the anti-FcRH5 antibody can be 1G7.v1F, or a derivative or clonal relative thereof. In some instances, for example, the invention provides an anti-FcRH5 antibody having a binding domain comprising (a) a VH domain comprising an amino acid sequence of SEQ ID NO: 195 and (b) a VL domain comprising an amino acid sequence of SEQ ID NO: 196.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 176; (c) an HVR-H3 comprising the amino acid sequence of SEQ ID NO: 9; (d) an HVR-L1 comprising the amino acid sequence of SEQ ID NO: 11; (e) an HVR-L2 comprising the amino acid sequence of SEQ ID NO: 15; and (f) an HVR-L3 comprising the amino acid sequence of SEQ ID NO: 20. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 197 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 198. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 52, 54, 46, and 47. In some instances, the anti-FcRH5 antibody may have a VH domain comprising the amino acid sequence of SEQ ID NO: 197. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 198. In a particular instance, the anti-FcRH5 antibody can be 1G7.v1 G, or a derivative or clonal relative thereof. In some instances, for example, the invention provides an anti-FcRH5 antibody having a binding domain comprising (a) a VH domain comprising an amino acid sequence of SEQ ID NO: 197 and (b) a VL domain comprising an amino acid sequence of SEQ ID NO: 198.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 177; (c) an HVR-H3 comprising the amino acid sequence of SEQ ID NO: 9; (d) an HVR-L1 comprising the amino acid sequence of SEQ ID NO: 11; (e) an HVR-L2 comprising the amino acid sequence of SEQ ID NO: 15; and (f) an HVR-L3 comprising the amino acid sequence of SEQ ID NO: 20. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 199 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 200. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 52, 54, 46, and 47. In some instances, the anti-FcRH5 antibody may have a VH domain comprising the amino acid sequence of SEQ ID NO: 199. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 200. In a particular instance, the anti-FcRH5 antibody can be 1G7.v1H, or a derivative or clonal relative thereof. In some instances, for example, the invention provides an anti-FcRH5 antibody having a binding domain comprising (a) a VH domain comprising an amino acid sequence of SEQ ID NO: 199 and (b) a VL domain comprising an amino acid sequence of SEQ ID NO: 200.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 178; (c) an HVR-H3 comprising the amino acid sequence of SEQ ID NO: 9; (d) an HVR-L1 comprising the amino acid sequence of SEQ ID NO: 11; (e) an HVR-L2 comprising the amino acid sequence of SEQ ID NO: 15; and (f) an HVR-L3 comprising the amino acid sequence of SEQ ID NO: 20. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 201 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 202. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 52, 54, 46, and 47. In some instances, the anti-FcRH5 antibody may have a VH domain comprising the amino acid sequence of SEQ ID NO: 201. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 202. In a particular instance, the anti-FcRH5 antibody can be 1G7.v1I, or a derivative or clonal relative thereof. In some instances, for example, the invention provides an anti-FcRH5 antibody having a binding domain comprising (a) a VH domain comprising an amino acid sequence of SEQ ID NO: 201 and (b) a VL domain comprising an amino acid sequence of SEQ ID NO: 202.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 11; (e) an HVR-L2 comprising the amino acid sequence of SEQ ID NO: 15; and (f) an HVR-L3 comprising the amino acid sequence of SEQ ID NO: 20. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 203 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 204. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 52, 54, 183, and 47. In some instances, the anti-FcRH5 antibody may have a VH domain comprising the amino acid sequence of SEQ ID NO: 203. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 204. In a particular instance, the anti-FcRH5 antibody can be 1G7.v1J, or a derivative or clonal relative thereof. In some instances, for example, the invention provides an anti-FcRH5 antibody having a binding domain comprising (a) a VH domain comprising an amino acid sequence of SEQ ID NO: 203 and (b) a VL domain comprising an amino acid sequence of SEQ ID NO: 204.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 11; (e) an HVR-L2 comprising the amino acid sequence of SEQ ID NO: 15; and (f) an HVR-L3 comprising the amino acid sequence of SEQ ID NO: 20. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 205 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 206. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 52, 54, 184, and 47. In some instances, the anti-FcRH5 antibody may have a VH domain comprising the amino acid sequence of SEQ ID NO: 205. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 206. In a particular instance, the anti-FcRH5 antibody can be 1G7.v1K, or a derivative or clonal relative thereof. In some instances, for example, the invention provides an anti-FcRH5 antibody having a binding domain comprising (a) a VH domain comprising an amino acid sequence of SEQ ID NO: 205 and (b) a VL domain comprising an amino acid sequence of SEQ ID NO: 206.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 7; (c) an HVR-H3 comprising the amino acid sequence of SEQ ID NO: 10; (d) an HVR-L1 comprising the amino acid sequence of SEQ ID NO: 11; (e) an HVR-L2 comprising the amino acid sequence of SEQ ID NO: 15; and (f) an HVR-L3 comprising the amino acid sequence of SEQ ID NO: 20. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 207 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 208. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 52, 54, 46, and 47. In some instances, the anti-FcRH5 antibody may have a VH domain comprising the amino acid sequence of SEQ ID NO: 207. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 208. In a particular instance, the anti-FcRH5 antibody can be 1G7.v1 L, or a derivative or clonal relative thereof. In some instances, for example, the invention provides an anti-FcRH5 antibody having a binding domain comprising (a) a VH domain comprising an amino acid sequence of SEQ ID NO: 207 and (b) a VL domain comprising an amino acid sequence of SEQ ID NO: 208.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 14; (e) an HVR-L2 comprising the amino acid sequence of SEQ ID NO: 16; and (f) an HVR-L3 comprising the amino acid sequence of SEQ ID NO: 23. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 209 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 210. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 52, 54, 46, and 47. In some instances, the anti-FcRH5 antibody may have a VH domain comprising the amino acid sequence of SEQ ID NO: 209. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 210. In a particular instance, the anti-FcRH5 antibody can be 1G7.v86, or a derivative or clonal relative thereof. In some instances, for example, the invention provides an anti-FcRH5 antibody having a binding domain comprising (a) a VH domain comprising an amino acid sequence of SEQ ID NO: 209 and (b) a VL domain comprising an amino acid sequence of SEQ ID NO: 210.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 14; (e) an HVR-L2 comprising the amino acid sequence of SEQ ID NO: 16; and (f) an HVR-L3 comprising the amino acid sequence of SEQ ID NO: 23. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 211 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 212. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 53, 54, 46, and 47. In some instances, the anti-FcRH5 antibody may have a VH domain comprising the amino acid sequence of SEQ ID NO: 211. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 212. In a particular instance, the anti-FcRH5 antibody can be 1G7.v191, or a derivative or clonal relative thereof. In some instances, for example, the invention provides an anti-FcRH5 antibody having a binding domain comprising (a) a VH domain comprising an amino acid sequence of SEQ ID NO: 211 and (b) a VL domain comprising an amino acid sequence of SEQ ID NO: 212.

In some instances, the invention provides an anti-FcRH5 antibody having a binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 8; (c) an HVR-H3 comprising the amino acid sequence of SEQ ID NO: 10; (d) an HVR-L1 comprising the amino acid sequence of SEQ ID NO: 14; (e) an HVR-L2 comprising the amino acid sequence of SEQ ID NO: 16; and (f) an HVR-L3 comprising the amino acid sequence of SEQ ID NO: 23. In some instances, the anti-FcRH5 antibody of claim may have a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 213 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 214. In some instances, the anti-FcRH5 antibody comprises at least one (e.g., 1, 2, 3, or 4) of heavy chain framework regions FR-H1, FR-H2, FR-H3, and FR-H4 comprising the sequences of SEQ ID NO: 52, 54, 46, and 47. In some instances, the anti-FcRH5 antibody may have a VH domain comprising the amino acid sequence of SEQ ID NO: 213. In some instances, the anti-FcRH5 antibody further includes at least one (e.g., 1, 2, 3, or 4) of the light chain framework regions FR-L1, FR-L2, FR-L3, and FR-L4 comprising the sequences of SEQ ID NOs: 48, 56, 50, and 51. In some instances, the anti-FcRH5 antibody may have a VL domain comprising the amino acid sequence of SEQ ID NO: 214. In a particular instance, the anti-FcRH5 antibody can be 1G7.v92, or a derivative or clonal relative thereof. In some instances, for example, the invention provides an anti-FcRH5 antibody having a binding domain comprising (a) a VH domain comprising an amino acid sequence of SEQ ID NO: 213 and (b) a VL domain comprising an amino acid sequence of SEQ ID NO: 214.

In certain embodiments, an antibody provided herein is a monoclonal, human, humanized, or chimeric antibody. In some instances, the anti-FcRH5 antibody is an IgG antibody. The anti-FcRH5 may be a full-length antibody and/or a monospecific antibody. In certain embodiments, the anti-FcRH5 antibody may bind to an epitope in the Ig-like domain 9 of FcRH5. For example, the epitope may comprises a portion of amino acids 743-850 of SEQ ID NO: 114. In some instances, the anti-FcRH5 antibody binds to human FcRH5 or cynomolgus monkey (cyno) FcRH5, or both. In other instances, the binding domain does not specifically bind to FcRH1, FcRH2, FcRH3, and/or FcRH4.

In some instances, the anti-FcRH5 antibody has a clearance following intravenous injection of between about 10 ml/kg/day to about 45 ml/kg/day (e.g., about 1 ml/kg/day, 5 ml/kg/day, 10 ml/kg/day, 11 ml/kg/day, 12 ml/kg/day, 13 ml/kg/day, 14 ml/kg/day, 15 ml/kg/day, 16 ml/kg/day, 17 ml/kg/day, 18 ml/kg/day, 19 ml/kg/day, 20 ml/kg/day, 21 ml/kg/day, 22 ml/kg/day, 23 ml/kg/day, 24 ml/kg/day, 25 ml/kg/day, 26 ml/kg/day, 27 ml/kg/day, 28 ml/kg/day, 29 ml/kg/day, 30 ml/kg/day, 31 ml/kg/day, 32 ml/kg/day, 33 ml/kg/day, 34 ml/kg/day, 35 ml/kg/day, 36 ml/kg/day, 37 ml/kg/day, 38 ml/kg/day, 39 ml/kg/day, 40 ml/kg/day, 41 ml/kg/day, 42 ml/kg/day, 43 ml/kg/day, or 44 ml/kg/day).

In some instances, the anti-FcRH5 antibody has a clearance following intravenous injection of about 1 ml/kg/day to about 5 ml/kg/day, about 6 ml/kg/day to about 10 ml/kg/day, about 11 ml/kg/day to about 15 ml/kg/day, about 16 ml/kg/day to about 20 ml/kg/day, about 21 ml/kg/day to about 25 ml/kg/day, about 26 ml/kg/day to about 30 ml/kg/day, about 31 ml/kg/day to about 35 ml/kg/day, about 36 ml/kg/day to about 40 ml/kg/day, about 41 ml/kg/day to about 45 ml/kg/day in a mouse. In some instances, the anti-FcRH5 antibody has a clearance following intravenous injection of about 10 ml/kg/day to about 35 ml/kg/day in a mouse. In some instances, the anti-FcRH5 antibody has a clearance following intravenous injection of about 10 ml/kg/day to about 20 ml/kg/day in a mouse. In some instances, the anti-FcRH5 antibody has a clearance following intravenous injection of about 12 ml/kg/day to about 16 ml/kg/day in a mouse.

In some instances, the anti-FcRH5 antibody has a clearance following intravenous injection of about 1 ml/kg/day to about 5 ml/kg/day, about 6 ml/kg/day to about 10 ml/kg/day, about 11 ml/kg/day to about 15 ml/kg/day, about 16 ml/kg/day to about 20 ml/kg/day, about 21 ml/kg/day to about 25 ml/kg/day, about 26 ml/kg/day to about 30 ml/kg/day, about 31 ml/kg/day to about 35 ml/kg/day, about 36 ml/kg/day to about 40 ml/kg/day, about 41 ml/kg/day to about 45 ml/kg/day in cyno. In some instances, the anti-FcRH5 antibody has a clearance following intravenous injection of about 20 ml/kg/day to about 40 ml/kg/day in a cyno. In some instances, the anti-FcRH5 antibody has a clearance following intravenous injection of about 25 ml/kg/day to about 35 ml/kg/day in a cyno. In some instances, the anti-FcRH5 antibody has a clearance following intravenous injection of about 30 ml/kg/day to about 35 ml/kg/day in a cyno.

In a further aspect, an anti-FcRH5 antibody according to any of the above embodiments may incorporate any of the features, singly or in combination, as described in Sections 1-7 below.

1. Antibody Affinity

In particular instances, the anti-FcRH5 antibody binds to human and/or cyno FcRH5 with a dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M, e.g., from $10^{-10}$ to $10^{-13}$ M, e.g., from $10^{-11}$ to $10^{-13}$ M, e.g., from $10^{-12}$ to $10^{-13}$ M). For example, in some instances the anti-FcRH5 antibody binds to human FcRH5 with a $K_D$ of ≤100 nM (e.g, ≤90 nM, ≤80 nM, ≤70 nM, ≤60 nM, ≤50 nM, ≤40 nM, 530 nM, ≤20 nM, ≤10 nM, ≤5 nM, ≤1 nM, ≤750 pM, ≤500 pM, ≤250 pM, ≤100 pM, ≤50 pM, 525 pM, ≤10 pM, 55 pM, or ≤1 pM) or lower.

In some instances, the anti-FcRH5 antibody binds to human FcRH5 with a $K_D$ of about 1 pM to about 500 nM (e.g., about 1 pM to 200 pM, 100 pM to 300 pM, 200 pM to 400 pM, 300 pM to 500 pM, 400 pM to 600 pM, 500 pM to 700 pM, 600 pM to 800 pM, 700 pM to 900 pM, 800 pM to 1 nM, 900 pM to 100 nM, 1 nM to 200 nM, 100 nM to 300 nM, 200 nM to 400 nM, or 300 nM to 500 nM). In some instances, the anti-FcRH5 antibody binds to human FcRH5 with a $K_D$ of about 1 pM to about 1 nM (e.g., about 1 pM to 100 pM, 50 pM to 150 pM, 100 pM to 200 pM, 150 pM to 250 pM, 200 pM to 300 pM, 250 pM to 350 pM, 300 pM to 400 pM, 350 pM to 450 pM, 400 pM to 500 pM, 450 pM to 550 pM, 500 pM to 600 pM, 550 pM to 650 pM, 600 pM to 700 pM, 650 pM to 750 pM, 700 pM to 800 pM, 750 pM to 850 pM, 800 pM to 900 pM, 850 pM to 950 pM, or 900 pM to 1 nM). In some instances, the anti-FcRH5 antibody binds to human FcRH5 with a $K_D$ of about 100 pM to about 500 pM (e.g., about 100 pM, 125 pM, 150 pM, 175 pM, 200 pM, 225 pM, 250 pM, 275 pM, 300 pM, 325 pM, 350 pM, 375 pM, 400 pM, 425 pM, 450 pM, 475 pM, or 500 pM). In some instances, the anti-FcRH5 antibody binds to human FcRH5 with a $K_D$ of about 100 pM to about 160 pM (e.g., about 100 pM, 105 pM, 110 pM, 115 pM, 120 pM, 125 pM, 130 pM, 135 pM, 140 pM, 145 pM, 150 pM, 155 pM, or 160 pM). In some instances, the anti-FcRH5 antibody binds to human FcRH5 with a $K_D$ of about 1 nM to about 150 nM (e.g., about 1 nM, 2 nM, 3 nM, 4 nM, 5 nM, 6 nM, 7 nM, 8 nM, 9 nM, 10 nM, 11 nM, 12, nM, 13 nM, 14 nM, 15 nM, 16 nM, 17 nM, 18 nM, 19 nM, 20 nM, 21 nM, 22 nM, 23 nM, 24 nM, 25 nM, 26 nM, 27 nM, 28 nM, 29 nM, 30 nM, 31 nM, 32 nM, 33 nM, 34 nM, 35 nM, 36 nM, 37 nM, 38 nM, 39 nM, 40 nM, 41 nM, 42 nM, 43 nM, 44 nM, 45 nM, 46 nM, 47 nM, 48 nM, 49 nM, 50 nM, 55 nM, 60 nM, 65 nM, 70 nM, 75 nM, 80 nM, 85 nM, 90 nM, 95 nM, 100 nM, 105 nM, 110 nM, 115 nM, 120 nM, 125 nM, 130 nM, 135 nM, 140 nM, 145 nM, or 150 nM).

In some instances the anti-FcRH5 antibody binds to cyno FcRH5 with a $K_D$ of ≤100 nM (e.g, ≤90 nM, ≤80 nM, ≤70 nM, ≤60 nM, ≤50 nM, ≤40 nM, ≤30 nM, ≤20 nM, ≤10 nM, ≤5 nM, ≤1 nM, ≤750 pM, ≤500 pM, ≤250 pM, ≤100 pM, ≤50 pM, ≤25 pM, ≤10 pM, ≤5 pM, or ≤1 pM, e.g., from $10^{-8}$M to $10^{-13}$ M, e.g., from $10^{-9}$ M to $10^{-13}$ M, e.g., from $10^{-10}$ to $10^{-13}$ M, e.g., from $10^{-11}$ to $10^{-13}$M, e.g., from $10^{-12}$ to $10^{-13}$M) or lower. In some instances, the anti-FcRH5 antibody binds to cyno FcRH5 with a $K_D$ of about 1 pM to about 500 nM (e.g., about 1 pM to 200 pM, 100 pM to 300 pM, 200 pM to 400 pM, 300 pM to 500 pM, 400 pM to 600 pM, 500 pM to 700 pM, 600 pM to 800 pM, 700 pM to 900 pM, 800 pM to 1 nM, 900 pM to 100 nM, 1 nM to 200 nM, 100 nM to 300 nM, 200 nM to 400 nM, or 300 nM to 500 nM). In some instances, the anti-FcRH5 antibody binds to cyno FcRH5 with a $K_D$ of about 1 pM to about 1 nM (e.g., about 1 pM to 100 pM, 50 pM to 150 pM, 100 pM to 200 pM, 150 pM to 250 pM, 200 pM to 300 pM, 250 pM to 350 pM, 300 pM to 400 pM, 350 pM to 450 pM, 400 pM to 500 pM, 450 pM to 550 pM, 500 pM to 600 pM, 550 pM to 650 pM, 600 pM to 700 pM, 650 pM to 750 pM, 700 pM to 800 pM, 750 pM to 850 pM, 800 pM to 900 pM, 850 pM to 950 pM, or 900 pM to 1 nM). In some instances, the anti-FcRH5 antibody binds to cyno FcRH5 with a $K_D$ of about 100 pM to about 500 pM (e.g., about 100 pM, 125 pM, 150 pM, 175 pM, 200 pM, 225 pM, 250 pM, 275 pM, 300 pM, 325 pM, 350 pM, 375 pM, 400 pM, 425 pM, 450 pM, 475 pM, or 500 pM). In some instances, the anti-FcRH5 antibody binds to cyno FcRH5 with a $K_D$ of about 100 pM to about 160 pM (e.g., about 100 pM, 105 pM, 110 pM, 115 pM, 120 pM, 125 pM, 130 pM, 135 pM, 140 pM, 145 pM, 150 pM, 155 pM, or 160 pM). In some instances, the anti-FcRH5 antibody binds to cyno FcRH5 with a $K_D$ of about 1 nM to about 150 nM (e.g., about 1 nM, 2 nM, 3 nM, 4 nM, 5 nM, 6 nM, 7 nM, 8 nM, 9 nM, 10 nM, 11 nM, 12, nM, 13 nM, 14 nM, 15 nM, 16 nM, 17 nM, 18 nM, 19 nM, 20 nM, 21 nM, 22 nM, 23 nM, 24 nM, 25 nM, 26 nM, 27 nM, 28 nM, 29 nM, 30 nM, 31 nM, 32 nM, 33 nM, 34 nM, 35 nM, 36 nM, 37 nM, 38 nM, 39 nM, 40 nM, 41 nM, 42 nM, 43 nM, 44 nM, 45 nM, 46 nM, 47 nM, 48 nM, 49 nM, 50 nM, 55 nM, 60 nM, 65 nM, 70 nM, 75 nM, 80 nM, 85 nM, 90 nM, 95 nM, 100 nM, 105 nM, 110 nM, 115 nM, 120 nM, 125 nM, 130 nM, 135 nM, 140 nM, 145 nM, or 150 nM).

In one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen. et al. *J. Mol. Biol.* 293:865-881, 1999). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al. *Cancer Res.* 57:4593-4599, 1997). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, $K_D$ is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at 10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{on}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, for example, Chen et al. *J. Mol. Biol.* 293:865-881, 1999. If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, bis-Fabs, Fab, Fab', Fab'-SH, F(ab')$_2$, Fv, and scFv fragments, and other fragments described below. For a review of certain antibody fragments, see Hudson et al. *Nat. Med.* 9:129-134, 2003. For a review of scFv fragments, see, e.g., Plückthün, in *The Pharmacology of Monoclonal Antibodies*, vol. 113, Rosenburg and Moore eds., (Springer-Verlag, New York), pp. 269-315, 1994; see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Antibody fragments in which the two Fabs are linked through bis-maleimide are referred to herein as bismaleimido-(thio-Fab)$_2$ or bis-Fabs.

Diabodies are antibody fragments with two antigen-binding sites that may be bivalent or bispecific. See, for example, EP 404,097; WO 1993/01161; Hudson et al. *Nat. Med.* 9:129-134, 2003; and Hollinger et al. *Proc. Natl. Acad. Sci. USA* 90:6444-6448, 1993. Triabodies and tetrabodies are also described in Hudson et al. *Nat. Med.* 9:129-134, 2003.

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al. *Proc. Natl. Acad. Sci. USA*, 81:6851-6855, 1984. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro et al. *Front. Biosci.* 13:1619-1633, 2008, and are further described, e.g., in Riechmann et al. *Nature* 332:323-329, 1988; Queen et al. *Proc. Natl Acad. Sci. USA* 86:10029-10033, 1989; U.S. Pat. Nos. 5,821,337, 7,527,791, 6,982,321, and 7,087,409; Kashmiri et al. *Methods* 36:25-34, 2005 (describing specificity determining region (SDR) grafting); Padlan *Mol. Immunol.* 28:489-498, 1991 (describing "resurfacing"); Dall'Acqua et al. *Methods* 36:43-60, 2005 (describing "FR shuffling"); and Osbourn et al. *Methods* 36:61-68, 2005; and Klimka et al. *Br. J. Cancer,* 83:252-260, 2000 (describing the "guided selection" approach to FR shuffling).

Human framework regions that may be used for humanization include, but are not limited to, framework regions selected using the "best-fit" method (see, e.g., Sims et al. *J. Immunol.* 151:2296, 1993); framework regions derived from the consensus sequence of human antibodies of a particular subgroup of light or heavy chain variable regions (see, e.g., Carter et al. *Proc. Natl. Acad. Sci. USA,* 89:4285, 1992; and Presta et al. *J. Immunol.* 151:2623, 1993); human mature (somatically mutated) framework regions or human germline framework regions (see, e.g., Almagro et al. *Front. Biosci.* 13:1619-1633, 2008); and framework regions derived from screening FR libraries (see, e.g., Baca et al. *J. Biol. Chem.* 272:10678-10684, 1997 and Rosok et al. *J. Biol. Chem.* 271:22611-22618, 1996).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74, 2001 and Lonberg, *Curr. Opin. Immunol.* 20:450-459, 2008.

Human antibodies may be prepared by administering an immunogen to a transgenic animal that has been modified to produce intact human antibodies or intact human antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125, 2005. See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described (see, e.g., Kozbor *J. Immunol.*, 133: 3001, 1984; Brodeur et al. *Monoclonal Antibody Production Techniques and Applications*, pp. 51-63 (Marcel Dekker, Inc., New York, 1987); and Boerner et al. *J. Immunol.*, 147: 86, 1991). Human antibodies generated via human B-cell hybridoma technology are also described in Li et al. *Proc. Natl. Acad. Sci. USA*, 103:3557-3562, 2006. Additional methods include those described, for example, in U.S. Pat. No. 7,189,826 (describing production of monoclonal human IgM antibodies from hybridoma cell lines) and Ni, *Xiandai Mianyixue*, 26(4):265-268, 2006 (describing human-human hybridomas). Human hybridoma technology (Trioma technology) is also described in Vollmers and Brandlein, *Histology and Histopathology*, 20(3):927-937, 2005 and Vollmers and Brandlein, *Methods and Findings in Experimental and Clinical Pharmacology*, 27(3):185-91, 2005.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al. ed., Human Press, Totowa, N.J., 2001) and further described, e.g., in the McCafferty et al. *Nature* 348:552-554; Clackson et al. *Nature* 352: 624-628, 1991; Marks et al. *J. Mol. Biol.* 222: 581-597, 1992; Marks and Bradbury, in *Methods in Molecular Biology* 248:161-175 (Lo, ed., Human Press, Totowa, N.J., 2003); Sidhu et al. *J. Mol. Biol.* 338(2): 299-310, 2004; Lee et al. *J. Mol. Biol.* 340(5):1073-1093, 2004; Fellouse, *Proc. Natl. Acad. Sci. USA* 101(34): 12467-12472, 2004; and Lee et al. *J. Immunol. Methods* 284(1-2):119-132, 2004.

In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.*, 12: 433-455, 1994. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al. *EMBO J*, 12: 725-734, 1993. Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388, 1992. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360. Antibodies or antibody fragments isolated from human antibody libraries are considered human antibodies or human antibody fragments herein.

6. Multispecific Antibodies, Including FcRH5 T Cell-Dependent Bispecific (TDB) Antibodies In any one of the above aspects, the anti-FcRH5 antibody provided herein is a multispecific antibody, for example, a bispecific antibody. Multispecific antibodies are monoclonal antibodies that have binding specificities for at least two different sites. In certain embodiments, bispecific antibodies may bind to two different epitopes of FcRH5.

In certain embodiments, one of the binding specificities is for FcRH5 and the other is for CD3 (e.g., CD3ε or CD3γ). Such bispecific anti-FcRH5 antibodies are also referred to as FcRH5 T cell-dependent bispecific (TDB) antibodies or FcRH5 TDBs. In some instances, the second binding domain binds to an epitope on CD3 comprising amino acid residue Glu6 of CD3. In some instances, the epitope further comprises one or more additional amino acid residues selected from the group consisting of Gln1, Asp2, and Met7 of CD3. In some instances, the epitope comprises amino acid residues Gln1, Asp2, and Glu6 of CD3. In some instances, the epitope comprises amino acid residues Gln1, Asp2, Glu6, and Met7 of CD3. In some instances, the epitope does not comprise amino acid residue Glu5 of CD3. In some instances, the epitope does not comprise amino acid residues Gly3 and Glu5 of CD3. In some instances, the epitope consists of amino acid residues Gln1, Asp2, Glu6, and Met7 of CD3.

In other some instances, the second binding domain is capable of binding to a human CD3 polypeptide or a cyno CD3 polypeptide. In some instances, the human CD3 polypeptide or the cyno CD3 polypeptide is a human CD3ε polypeptide or a cyno CD3ε polypeptide, respectively. In some instances, the human CD3 polypeptide or the cyno CD3 polypeptide is a human CD3γ polypeptide or a cyno CD3γ polypeptide, respectively.

In particular instances, the second binding domain binds the human CD3ε polypeptide with dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). For example, in some instances the the second binding domain binds the human CD3ε polypeptide with a $K_D$ of ≤100 nM (e.g, ≤90 nM, 580 nM, ≤70 nM, ≤60 nM, ≤50 nM, ≤40 nM, ≤30 nM, ≤20 nM, ≤10 nM, ≤5 nM, ≤1 nM, ≤750 µM, ≤500 µM, ≤250 µM, ≤100 µM, ≤50 µM, ≤25 µM, ≤10 µM, ≤5 µM, or ≤1 µM) or lower.

In some instances, for example, the invention provides an anti-FcRH5 antibody, wherein the second binding domain comprises at least one, two, three, four, five, or six hypervariable regions (HVRs) selected from (a) an HVR-H1 comprising the amino acid sequence of SEQ ID NO: 115; (b) an HVR-H2 comprising the amino acid sequence of SEQ ID NO: 116; (c) an HVR-H3 comprising the amino acid sequence of SEQ ID NO: 117; (d) an HVR-L1 comprising the amino acid sequence of SEQ ID NO: 118; (e) an HVR-L2 comprising the amino acid sequence of SEQ ID NO: 119; and (f) an HVR-L3 comprising the amino acid sequence of SEQ ID NO: 120.

In some instances, the invention provides an anti-FcRH5 antibody, wherein the second binding domain comprises at least one, two, three, four, five, or six hypervariable regions (HVRs) selected from (a) an HVR-H1 comprising the amino acid sequence of SEQ ID NO: 115; (b) an HVR-H2 comprising the amino acid sequence of SEQ ID NO: 116; (c) an HVR-H3 comprising the amino acid sequence of SEQ ID NO: 121; (d) an HVR-L1 comprising the amino acid sequence of SEQ ID NO: 118; (e) an HVR-L2 comprising the amino acid sequence of SEQ ID NO: 119; and (f) an HVR-L3 comprising the amino acid sequence of SEQ ID NO: 123. In some instances, the invention provides an anti-FcRH5 antibody, wherein the second binding domain includes a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 133 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 134. In some instances, the anti-FcRH5 antibody includes a second binding domain comprising at least one (e.g., 1, 2, 3, or 4) of heavy chain framework regions FR-H1, FR-H2, FR-H3, and FR-H4 comprising the sequences of SEQ ID NOs: 125, 126, 127, and 128, respectively. In some instances, the second binding domain comprises a VH domain comprising the amino acid sequence of SEQ ID NO: 133. In some instances, the second binding domain further includes at least one (e.g., 1, 2, 3, or 4) of the light chain framework regions FR-L1, FR-L2, FR-L3, and FR-L4 comprising the sequences of SEQ ID NOs: 129, 130, 131, and 132, respectively. In some instances, the second binding domain comprises a VL domain comprising the amino acid sequence of SEQ ID NO: 134. In some instances, the second binding domain includes a VH domain comprising an amino acid sequence of SEQ ID NO: 133 and (b) a VL domain comprising an amino acid sequence of SEQ ID NO: 134. Accordingly, in some instances, a half-antibody variant of an anti-FcRH5 antibody of the invention may be paired with a half-antibody variant of anti-CD3 antibody 38E4.v1 to form an FcRH5 TDB (i.e., an anti-FcRH5/38E4.v1 TDB).

In some instances, the invention provides an anti-FcRH5 antibody, wherein the second binding domain comprises at least one, two, three, four, five, or six hypervariable regions (HVRs) selected from (a) an HVR-H1 comprising the amino acid sequence of SEQ ID NO: 115; (b) an HVR-H2 comprising the amino acid sequence of SEQ ID NO: 116; (c) an HVR-H3 comprising the amino acid sequence of SEQ ID NO: 122; (d) an HVR-L1 comprising the amino acid sequence of SEQ ID NO: 118; (e) an HVR-L2 comprising the amino acid sequence of SEQ ID NO: 119; and (f) an HVR-L3 comprising the amino acid sequence of SEQ ID NO: 123. In some instances, the invention provides an anti-FcRH5 antibody, wherein the second binding domain includes a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 135 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 136. In some instances, the anti-FcRH5 antibody includes a second binding domain comprising at least one (e.g., 1, 2, 3, or 4) of heavy chain framework regions FR-H1, FR-H2, FR-H3, and FR-H4 comprising the sequences of SEQ ID NOs: 125, 126, 127, and 128, respectively. In some instances, the second binding domain comprises a VH domain comprising the amino acid sequence of SEQ ID NO: 135. In some instances, the second binding domain further includes at least one (e.g., 1, 2, 3, or 4) of the light chain framework regions FR-L1, FR-L2, FR-L3, and FR-L4 comprising the sequences of SEQ ID NOs: 129, 130, 131, and 132, respectively. In some instances, the second binding domain comprises a VL domain comprising the amino acid sequence of SEQ ID NO: 136. In some instances, the second binding domain includes a VH domain comprising an amino acid sequence of SEQ ID NO: 135 and (b) a VL domain comprising an amino acid sequence of SEQ ID NO: 136. Accordingly, in some instances, a half-antibody variant of an anti-FcRH5 antibody of the invention may be paired with a half-antibody variant of anti-CD3 antibody 38E4.v1 to form an FcRH5 TDB (i.e., an anti-FcRH5/38E4.v1 TDB).

In some instances, the invention provides an anti-FcRH5 antibody, wherein the second binding domain comprises at least one, two, three, four, five, or six hypervariable regions (HVRs) selected from (a) an HVR-H1 comprising the amino acid sequence of SEQ ID NO: 115; (b) an HVR-H2 comprising the amino acid sequence of SEQ ID NO: 116; (c) an HVR-H3 comprising the amino acid sequence of SEQ ID NO: 121; (d) an HVR-L1 comprising the amino acid sequence of SEQ ID NO: 118; (e) an HVR-L2 comprising the amino acid sequence of SEQ ID NO: 119; and (f) an HVR-L3 comprising the amino acid sequence of SEQ ID NO: 124. In some instances, the invention provides an anti-FcRH5 antibody, wherein the second binding domain includes a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 137 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 138. In some instances, the anti-FcRH5 antibody includes a second binding domain comprising at least one (e.g., 1, 2, 3, or 4) of heavy chain framework regions FR-H1, FR-H2, FR-H3, and FR-H4 comprising the sequences of SEQ ID NOs: 125, 126, 127, and 128, respectively. In some instances, the second binding domain comprises a VH domain comprising the amino acid sequence of SEQ ID NO: 137. In some instances, the second binding domain further includes at least one (e.g., 1, 2, 3, or 4) of the light chain framework regions FR-L1, FR-L2, FR-L3, and FR-L4 comprising the sequences of SEQ ID NOs: 129, 130, 131, and 132, respectively. In some instances, the second binding domain comprises a VL domain comprising the amino acid sequence of SEQ ID NO: 138. In some instances, the second binding domain includes a VH domain comprising an amino acid sequence of SEQ ID NOs: 137 and (b) a VL domain comprising an amino acid sequence of SEQ ID NO: 138. Accordingly, in some instances, a half-antibody variant of an anti-FcRH5 antibody of the invention may be paired with a half-antibody variant of anti-CD3 antibody 38E4.v11 to form an FcRH5 TDB (i.e., an anti-FcRH5/38E4.v11 TDB).

In some instances, the invention provides an anti-FcRH5 antibody, wherein the second binding domain comprises at least one, two, three, four, five, or six hypervariable regions (HVRs) selected from (a) an HVR-H1 comprising the amino acid sequence of SEQ ID NO: 139; (b) an HVR-H2 comprising the amino acid sequence of SEQ ID NO: 140; (c) an HVR-H3 comprising the amino acid sequence of SEQ ID NO: 141; (d) an HVR-L1 comprising the amino acid sequence of SEQ ID NO: 142; (e) an HVR-L2 comprising the amino acid sequence of SEQ ID NO: 143; and (f) an HVR-L3 comprising the amino acid sequence of SEQ ID NO: 144. In some instances, the invention provides an anti-FcRH5 antibody, wherein the second binding domain includes a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 153 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 154. In some instances, the anti-FcRH5 antibody includes a second binding domain comprising at least one (e.g., 1, 2, 3, or 4) of heavy chain framework regions FR-H1, FR-H2, FR-H3, and FR-H4 comprising the sequences of SEQ ID NOs: 145, 146, 147, and 148, respectively. In some instances, the second binding domain comprises a VH domain comprising the amino acid sequence of SEQ ID NO: 153. In some instances, the second binding domain further includes at least one (e.g., 1, 2, 3, or 4) of the light chain framework regions FR-L1, FR-L2, FR-L3, and FR-L4 comprising the sequences of SEQ ID NOs: 149, 150, 151, and 152, respectively. In some instances, the second binding domain comprises a VL domain comprising the amino acid sequence of SEQ ID NO: 154. In some instances, the second binding domain includes a VH domain comprising an amino acid sequence of SEQ ID NOs: 153 and (b) a VL domain comprising an amino acid sequence of SEQ ID NO: 154. Accordingly, in some instances, a half-antibody variant of an anti-FcRH5 antibody of the invention may be paired with a half-antibody variant of anti-CD3 antibody hu40G5c to form an FcRH5 TDB (i.e., an anti-FcRH5/hu40G5c TDB).

In some instances, for example, the invention provides an anti-FcRH5 antibody, wherein the second binding domain comprises at least one, two, three, four, five, or six hypervariable regions (HVRs) selected from (a) an HVR-H1 comprising the amino acid sequence of SEQ ID NO: 155; (b) an HVR-H2 comprising the amino acid sequence of SEQ ID NO: 156; (c) an HVR-H3 comprising the amino acid sequence of SEQ ID NO: 157; (d) an HVR-L1 comprising the amino acid sequence of SEQ ID NO: 158; (e) an HVR-L2 comprising the amino acid sequence of SEQ ID NO: 159; and (f) an HVR-L3 comprising the amino acid sequence of SEQ ID NO: 160.

In some instances, the invention provides an anti-FcRH5 antibody, wherein the second binding domain comprises at least one, two, three, four, five, or six hypervariable regions (HVRs) selected from (a) an HVR-H1 comprising the amino acid sequence of SEQ ID NO: 155; (b) an HVR-H2 comprising the amino acid sequence of SEQ ID NO: 162; (c) an HVR-H3 comprising the amino acid sequence of SEQ ID NO: 157; (d) an HVR-L1 comprising the amino acid sequence of SEQ ID NO: 158; (e) an HVR-L2 comprising the amino acid sequence of SEQ ID NO: 159; and (f) an HVR-L3 comprising the amino acid sequence of SEQ ID NO: 160. In some instances, for example, the second binding domain includes a VH domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 172 and/or a VL domain comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) sequence identity to, or the sequence of, SEQ ID NO: 173. In some instances, for example, the anti-FcRH5 antibody includes a second binding domain comprising at least one (e.g., 1, 2, 3, or 4) of heavy chain framework regions FR-H1, FR-H2, FR-H3, and FR-H4 comprising the sequences of SEQ ID NOs: 164, 165, 166, and 167, respectively. In some instances, the second binding domain comprises a VH domain comprising the amino acid sequence of SEQ ID NO: 172. In some instances, the second binding domain further includes at least one (e.g., 1, 2, 3, or 4) of the light chain framework regions FR-L1, FR-L2, FR-L3, and FR-L4 comprising the sequences of SEQ ID NOs: 168, 169, 170, and 171, respectively. In some instances, the second binding domain comprises a VL domain comprising the amino acid sequence of SEQ ID NO: 173. In some instances, the second binding domain includes a VH domain comprising an amino acid sequence of SEQ ID NOs: 172 and (b) a VL domain comprising an amino acid sequence of SEQ ID NO: 173. Accordingly, in some instances, a half-antibody variant of an anti-FcRH5 antibody of the invention may be paired with a half-antibody variant of anti-CD3 antibody huUCHT1.v9 to form an FcRH5 TDB (i.e., an anti-FcRH5/huUCHT1.v9 TDB).

In some instances, for example, the invention provides an anti-FcRH5 antibody, wherein the binding domain that binds FcRH5 comprises a VH domain ($VH_1$) comprising a charged region ($CR_1$) and a VL domain ($VL_1$) comprising a charged region ($CR_2$), wherein the $CR_1$ in the $VH_1$ forms a charge pair with the $CR_2$ in the $VL_1$. In some instances, the $CR_1$ comprises a basic amino acid residue and the $CR_2$ comprises an acidic amino acid residue. In some instances, the $CR_1$ comprises a Q39K substitution mutation (EU numbering). In some instances, the $CR_1$ consists of the Q39K substitution mutation. In some instances, the $CR_2$ comprises a Q38E substitution mutation (EU numbering). In some instances, the $CR_2$ consists of the Q38E substitution mutation. In some instances, the second binding domain that binds CD3 comprises a VH domain ($VH_2$) comprising a charged region ($CR_3$) and a VL domain ($VL_2$) comprising a charged region ($CR_4$), wherein the $CR_4$ in the $VL_2$ forms a charge pair with the $CR_3$ in the $VH_2$. In some instances, the $CR_4$ comprises a basic amino acid residue and the $CR_3$ comprises an acidic amino acid residue. In some instances, the $CR_4$ comprises a Q38K substitution mutation (EU numbering). In some instances, the $CR_4$ consists of the Q38K substitution mutation. In some instances, the $CR_3$ comprises a Q39E substitution mutation (EU numbering). In some instances, the $CR_3$ consists of the Q39E substitution mutation. In some instances, the $VL_1$ domain is linked to a light chain constant (CL) domain ($CL_1$) and the $VH_1$ is linked to a first heavy chain constant (CH1) domain ($CH1_1$), wherein the $CL_1$ comprises a charged region ($CR_5$) and the $CH1_1$ comprises a charged region ($CR_6$), and wherein the $CR_5$ in the $CL_1$ forms a charge pair with the $CR_6$ in the $CH1_1$. In some instances, the $CR_5$ comprises a basic amino acid residue and the $CR_6$ comprises an acidic residue. In some instances, the $CR_5$ comprises a V133K substitution mutation (EU numbering). In some instances, the $CR_5$ consists of the V133K substitution mutation. In some instances, the $CR_6$ comprises a S183E substitution mutation (EU numbering). In some instances, the $CR_6$ consists of the S183E substitution mutation.

In some instances, the invention provides an anti-FcRH5 antibody, wherein the $VL_2$ domain is linked to a CL domain ($CL_2$) and the $VH_2$ is linked to a CH1 domain ($CH1_2$), wherein the $CL_2$ comprises a charged region ($CR_7$) and the $CH1_2$ comprises a charged region ($CR_8$), and wherein the $CR_8$ in the $CH1_2$ forms a charge pair with the $CR_7$ in the $CL_2$. In some instances, the $CR_8$ comprises a basic amino acid residue and the $CR_7$ comprises an acidic amino acid residue. In some instances, the $CR_8$ comprises a S183K substitution mutation (EU numbering). In some instances, the $CR_8$ consists of the S183K substitution mutation. In some instances, the $CR_7$ comprises a V133E substitution mutation (EU numbering). In some instances, the $CR_7$ consists of the V133E substitution mutation.

In some instances, for example, the invention provides an anti-FcRH5 antibody, wherein the $VL_2$ domain is linked to a CL domain ($CL_2$) and the $VH_2$ is linked to a CH1 domain ($CH1_2$), wherein the $CL_2$ comprises one or more mutations at amino acid residues F116, L135, S174, S176, and/or T178 (EU numbering) and the $CH1_2$ comprises one or more mutations at amino acid residues A141, F170, S181, S183, and/or V185 (EU numbering). In some instances, the $CL_2$ comprises one or more of the following substitution mutations: F116A, L135V, S174A, S176F, and/or T178V. In some instances, the $CL_2$ comprises the following substitution mutations: F116A, L135V, S174A, S176F, and T178V. In some instances, the $CH1_2$ comprises one or more of the following substitution mutations: A141I, F170S, S181M, S183A, and/or V185A. In some instances, the $CH1_2$ comprises the following substitution mutations: A141I, F170S, S181M, S183A, and V185A.

In some instances, the invention provides an anti-FcRH5 antibody, wherein the binding domain that binds FcRH5 comprises a VH domain ($VH_1$) comprising a charged region ($CR_1$) and a VL domain ($VL_1$) comprising a charged region ($CR_2$), wherein the $CR_2$ in the $VL_1$ forms a charge pair with the $CR_1$ in the $VH_1$. In some instances, the $CR_2$ comprises a basic amino acid residue and the $CR_1$ comprises an acidic amino acid residue. In some instances, the $CR_2$ comprises a Q38K substitution mutation (EU numbering). In some instances, the $CR_2$ consists of the Q38K substitution mutation. In some instances, the $CR_1$ comprises a Q39E substitution mutation (EU numbering). In some instances, the $CR_1$ consists of the Q39E substitution mutation. In some instances, the second binding domain that binds CD3 comprises a VH domain ($VH_2$) comprising a charged region ($CR_3$) and a VL domain ($VL_2$) comprising a charged region ($CR_4$), wherein the $CR_3$ in the $VH_2$ forms a charge pair with the $CR_4$ in the $VL_2$. In some instances, the $CR_3$ comprises a basic amino acid residue and the $CR_4$ comprises an acidic amino acid residue. In some instances, the $CR_3$ comprises a Q39K substitution mutation (EU numbering). In some instances, the $CR_3$ consists of the Q39K substitution mutation. In some instances, the $CR_4$ comprises a Q38E substitution mutation (EU numbering). In some instances, the $CR_4$ consists of the Q38E substitution mutation. In some instances, the $VL_1$ domain is linked to a light chain constant (CL) domain ($CL_1$) and the $VH_1$ is linked to a first heavy chain constant (CH1) domain ($CH1_1$), wherein the $CL_1$ comprises a charged region ($CR_5$) and the $CH1_1$ comprises a charged region ($CR_6$), and wherein the $CR_6$ in the CH1 forms a charge pair with the $CR_5$ in the $CL_1$. In some instances, the $CR_6$ comprises a basic amino acid residue and the $CR_5$ comprises an acidic amino acid residue. In some instances, the $CR_6$ comprises a S183K substitution mutation (EU numbering). In some instances, the $CR_6$ consists of the S183K substitution mutation. In some instances, the $CR_5$ comprises a V133E substitution mutation (EU numbering). In some instances, the $CR_5$ consists of the V133E substitution mutation.

In some instances, for example, the invention provides an anti-FcRH5 antibody, wherein the $VL_2$ domain is linked to a CL domain ($CL_2$) and the $VH_2$ is linked to a CH1 domain ($CH1_2$), wherein the $CL_2$ comprises a charged region ($CR_7$) and the $CH1_2$ comprises a charged region ($CR_8$), and wherein the $CR_7$ in the $CL_2$ forms a charged pair with the $CR_8$ in the $CH1_2$. In some instances, the $CR_7$ comprises a basic amino acid residue and the $CR_8$ comprises an acidic residue. In some instances, the $CR_7$ comprises a V133K substitution mutation (EU numbering). In some instances, the $CR_7$ consists of the V133K substitution mutation. In some instances, the $CR_8$ comprises a S183E substitution mutation (EU numbering). In some instances, the $CR_8$ consists of the S183E substitution mutation.

In some instances, for example, the invention provides an anti-FcRH5 antibody, wherein the $VL_2$ domain is linked to a CL domain ($CL_2$) and the $VH_2$ is linked to a CH1 domain ($CH1_2$), wherein the $CL_2$ comprises one or more mutations at amino acid residues F116, L135, S174, S176, and/or T178 (EU numbering) and the $CH1_2$ comprises one or more mutations at amino acid residues A141, F170, S181, S183, and/or V185 (EU numbering). In some instances, the $CL_2$ comprises one or more of the following substitution mutations: F116A, L135V, S174A, S176F, and/or T178V. In some instances, the $CL_2$ comprises the following substitution mutations: F116A, L135V, S174A, S176F, and T178V. In some instances, the $CH1_2$ comprises one or more of the following substitution mutations: A141I, F170S, S181M, S183A, and/or V185A. In some instances, the $CH1_2$ comprises the following substitution mutations: A141I, F170S, S181M, S183A, and V185A. In some instances, the anti-FcRH5 antibody comprises one or more heavy chain constant domains, wherein the one or more heavy chain constant domains are selected from a first CH2 domain ($CH2_1$), a first CH3 domain ($CH3_1$), a second CH2 domain ($CH2_2$), and a second CH3 domain ($CH3_2$). In some instances, at least one of the one or more heavy chain constant domains is paired with another heavy chain constant domain. In some instances, the $CH3_1$ and the $CH3_2$ each comprise a protuberance ($P_1$) or a cavity ($C_1$), and the $P_1$ or the $C_1$ in the $CH3_1$ is positionable in the $C_1$ or the $P_1$, respectively, in the $CH3_2$. In some instances, the $CH3_1$ and the $CH3_2$ meet at an interface between the $P_1$ and the $C_1$. In some instances, the $CH2_1$ and the $CH2_2$ each comprise ($P_2$) or a cavity ($C_2$), and the $P_2$ or the $C_2$ in the $CH2_1$ is positionable in the $C_2$ or the $P_2$, respectively, in the $CH2_2$. In some instances, the $CH2_1$ and the $CH2_2$ meet at an interface between the $P_2$ and the $C_2$.

In another aspect, the invention provides an anti-FcRH5 antibody that binds to FcRH5 and CD3, wherein the anti-FcRH5 antibody comprises an anti-FcRH5 arm comprising a first binding domain at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 16; and (f) an HVR-L3 comprising the amino acid sequence of SEQ ID NO: 23; and an anti-CD3 arm comprising a second binding domain comprising at least one, two, three, four, five, or six hypervariable regions (HVRs) selected from: (a) an HVR-H1 comprising the amino acid sequence of SEQ ID NO: 115; (b) an HVR-H2 comprising the amino acid sequence of SEQ ID NO: 116; (c) an HVR-H3 comprising the amino acid sequence of SEQ ID NO:121; (d) an HVR-L1 comprising the amino acid sequence of SEQ ID NO: 118; (e) an HVR-L2 comprising the amino acid sequence of SEQ ID NO: 119; and (f) an HVR-L3 comprising the amino acid sequence of SEQ ID NO: 123; and wherein the anti-FcRH5 arm and the anti-CD3 arm each comprise an N297G substitution mutation (EU numbering); and wherein the anti-FcRH5 arm comprises a T366W substitution mutation and the anti-CD3 arm comprises a T366S, L368A, and Y407V substitution mutation. In some instances, the anti-FcRH5 antibody comprises an anti-FcRH5 arm comprising a first binding domain comprising the six hypervariable regions (HVRs): (a) an HVR-H1 comprising the amino acid sequence of SEQ ID NO: 1; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 16; and (f) an HVR-L3 comprising the amino acid sequence of SEQ ID NO: 23; and an anti-CD3 arm comprising a second binding domain comprising the six hypervariable regions (HVRs): (a) an HVR-H1 comprising the amino acid sequence of SEQ ID NO: 115; (b) an HVR-H2 comprising the amino acid sequence of SEQ ID NO: 116; (c) an HVR-H3 comprising the amino acid sequence of SEQ ID NO: 121; (d) an HVR-L1 comprising the amino acid sequence of SEQ ID NO: 118; (e) an HVR-L2 comprising the amino acid sequence of SEQ ID NO: 119; and (f) an HVR-L3 comprising the amino acid sequence of SEQ ID NO: 123; and wherein the anti-FcRH5 arm and the anti-CD3 arm each comprise an N297G substitution mutation (EU numbering); and wherein the anti-FcRH5 arm comprises a T366W substitution mutation and the anti-CD3 arm comprises a T366S, L368A, and Y407V substitution mutation.

In another aspect, the invention provides an anti-FcRH5 antibody that binds to FcRH5 and CD3, wherein the anti-FcRH5 antibody comprises an anti-FcRH5 arm comprising a first binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 16; and (f) an HVR-L3 comprising the amino acid sequence of SEQ ID NO: 23; and an anti-CD3 arm comprising a second binding domain comprising at least one, two, three, four, five, or six hypervariable regions (HVRs) selected from: (a) an HVR-H1 comprising the amino acid sequence of SEQ ID NO: 115; (b) an HVR-H2 comprising the amino acid sequence of SEQ ID NO: 116; (c) an HVR-H3 comprising the amino acid sequence of SEQ ID NO: 121; (d) an HVR-L1 comprising the amino acid sequence of SEQ ID NO: 118; (e) an HVR-L2 comprising the amino acid sequence of SEQ ID NO: 119; and (f) an HVR-L3 comprising the amino acid sequence of SEQ ID NO: 123; and wherein the anti-FcRH5 arm comprises a light chain comprising Q38E and V133K substitution mutations and a heavy chain comprising Q39K, S183E, and N297G substitution mutations; and wherein the anti-CD3 arm comprises a light chain comprising Q38K and V133E substitution mutations and a heavy chain comprising Q39E, S183K, and N297G substitution mutations (EU numbering). In some instances, the anti-FcRH5 antibody comprises an anti-FcRH5 arm comprising a first binding domain comprising the six hypervariable regions (HVRs): (a) an HVR-H1 comprising the amino acid sequence of SEQ ID NO: 1; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 16; and (f) an HVR-L3 comprising the amino acid sequence of SEQ ID NO: 23; and an anti-CD3 arm comprising a second binding domain comprising the six hypervariable regions (HVRs): (a) an HVR-H1 comprising the amino acid sequence of SEQ ID NO: 115; (b) an HVR-H2 comprising the amino acid sequence of SEQ ID NO: 116; (c) an HVR-H3 comprising the amino acid sequence of SEQ ID NO: 121; (d) an HVR-L1 comprising the amino acid sequence of SEQ ID NO: 118; (e) an HVR-L2 comprising the amino acid sequence of SEQ ID NO: 119; and (f) an HVR-L3 comprising the amino acid sequence of SEQ ID NO: 123; and wherein the anti-FcRH5 arm comprises a light chain comprising Q38E and V133K substitution mutations and a heavy chain comprising Q39K, S183E, and N297G substitution mutations; and wherein the anti-CD3 arm comprises a light chain comprising Q38K and V133E substitution mutations and a heavy chain comprising Q39E, S183K, and N297G substitution mutations (EU numbering).

In another aspect, the invention provides an anti-FcRH5 antibody that binds to FcRH5 and CD3, wherein the anti-FcRH5 antibody comprises: (a) an anti-FcRH5 arm comprising a first binding domain comprising a VH domain comprising an amino acid sequence having at least 90% (e.g., 90%, 91%, 92%, 93%, 94%, 95%, 96%, 97%, 98%, or 99%) sequence identity to, or the sequence of, SEQ ID NO: 104 and a VL domain comprising an amino acid sequence having at least 90% (e.g., 90%, 91%, 92%, 93%, 94%, 95%, 96%, 97%, 98%, or 99%) sequence identity to, or the sequence of, SEQ ID NO: 105, wherein the anti-FcRH5 arm comprises a light chain comprising Q38E and V133K substitution mutations and a heavy chain comprising Q39K, S183E, and N297G substitution mutations; and (b) an anti-CD3 arm comprising a second binding domain comprising a VH domain comprising an amino acid sequence having at least 90% (e.g., 90%, 91%, 92%, 93%, 94%, 95%, 96%, 97%, 98%, or 99%) sequence identity to, or the sequence of, SEQ ID NO: 133 and a VL domain comprising an amino acid sequence having at least 90% (e.g., 90%, 91%, 92%, 93%, 94%, 95%, 96%, 97%, 98%, or 99%) sequence identity to, or the sequence of, SEQ ID NO: 134, wherein the anti-CD3 arm comprises a light chain comprising Q38K and V133E substitution mutations and a heavy chain comprising Q39E, S183K, and N297G substitution mutations (EU numbering). In some instances, the invention provides an anti-FcRH5 antibody that binds to FcRH5 and CD3, wherein the anti-FcRH5 antibody comprises: (a) an anti-FcRH5 arm comprising a first binding domain comprising a VH domain comprising an amino acid sequence of SEQ ID NO: 104 and a VL domain comprising an amino acid sequence of SEQ ID NO: 105, wherein the anti-FcRH5 arm comprises a light chain comprising Q38E and V133K substitution mutations and a heavy chain comprising Q39K, S183E, and N297G substitution mutations; and (b) an anti-CD3 arm comprising a second binding domain comprising a VH domain comprising an amino acid sequence of SEQ ID NO: 133 and a VL domain comprising an amino acid sequence of SEQ ID NO: 134, wherein the anti-CD3 arm comprises a light chain comprising Q38K and V133E substitution mutations and a heavy chain comprising Q39E, S183K, and N297G substitution mutations (EU numbering).

In another aspect, the invention provides an anti-FcRH5 antibody that binds to FcRH5 and CD3, wherein the anti-FcRH5 antibody comprises an anti-FcRH5 arm comprising a first binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 16; and (f) an HVR-L3 comprising the amino acid sequence of SEQ ID NO: 23; and an anti-CD3 arm comprising a second binding domain comprising at least one, two, three, four, five, or six hypervariable regions (HVRs) selected from (a) an HVR-H1 comprising the amino acid sequence of SEQ ID NO: 115; (b) an HVR-H2 comprising the amino acid sequence of SEQ ID NO: 116; (c) an HVR-H3 comprising the amino acid sequence of SEQ ID NO: 121; (d) an HVR-L1 comprising the amino acid sequence of SEQ ID NO: 118; (e) an HVR-L2 comprising the amino acid sequence of SEQ ID NO: 119; and (f) an HVR-L3 comprising the amino acid sequence of SEQ ID NO: 123; and wherein the anti-FcRH5 arm comprises a light chain comprising Q38K and V133E substitution mutations and a heavy chain comprising Q39E, S183K, and N297G substitution mutations (EU numbering). In some instances, the anti-FcRH5 antibody comprises an anti-FcRH5 arm comprising a first binding domain comprising the six hypervariable regions (HVRs): (a) an HVR-H1 comprising the amino acid sequence of SEQ ID NO: 1; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 16; and (f) an HVR-L3 comprising the amino acid sequence of SEQ ID NO: 23; and an anti-CD3 arm comprising a second binding domain comprising the six hypervariable regions (HVRs): (a) an HVR-H1 comprising the amino acid sequence of SEQ ID NO: 115; (b) an HVR-H2 comprising the amino acid sequence of SEQ ID NO: 116; (c) an HVR-H3 comprising the amino acid sequence of SEQ ID NO: 121; (d) an HVR-L1 comprising the amino acid sequence of SEQ ID NO: 118; (e) an HVR-L2 comprising the amino acid sequence of SEQ ID NO: 119; and (f) an HVR-L3 comprising the amino acid sequence of SEQ ID NO: 123; and wherein the anti-FcRH5 arm comprises a light chain comprising Q38K and V133E substitution mutations and a heavy chain comprising Q39E, S183K, and N297G substitution mutations; and wherein the anti-CD3 arm comprises a light chain comprising Q38E and V133K substitution mutations and a heavy chain comprising Q39K, S183E, and N297G substitution mutations (EU numbering).

In another aspect, the invention provides the invention provides an anti-FcRH5 antibody that binds to FcRH5 and CD3, wherein the anti-FcRH5 antibody comprises: (a) an anti-FcRH5 arm comprising a first binding domain comprising a VH domain comprising an amino acid sequence having at least 90% (e.g., 90%, 91%, 92%, 93%, 94%, 95%, 96%, 97%, 98%, or 99%) sequence identity to, or the sequence of, SEQ ID NO: 104 and a VL domain comprising an amino acid sequence having at least 90% (e.g., 90%, 91%, 92%, 93%, 94%, 95%, 96%, 97%, 98%, or 99%) sequence identity to, or the sequence of, SEQ ID NO: 105, wherein the anti-FcRH5 arm comprises a light chain comprising Q38K and V133E substitution mutations and a heavy chain comprising Q39E, S183K, and N297G substitution mutations; and (b) an anti-CD3 arm comprising a second binding domain comprising a VH domain comprising an amino acid sequence of SEQ ID NO: 133 and a VL domain comprising an amino acid sequence of SEQ ID NO: 134, wherein the anti-CD3 arm comprises a light chain comprising Q38E and V133K substitution mutations and a heavy chain comprising Q39K, S183E, and N297G substitution mutations (EU numbering). In some instances, the invention provides an anti-FcRH5 antibody that binds to FcRH5 and CD3, wherein the anti-FcRH5 antibody comprises: (a) an anti-FcRH5 arm comprising a first binding domain comprising a VH domain comprising an amino acid sequence of SEQ ID NO: 104 and a VL domain comprising an amino acid sequence of SEQ ID NO: 105, wherein the anti-FcRH5 arm comprises a light chain comprising Q38K and V133E substitution mutations and a heavy chain comprising Q39E, S183K, and N297G substitution mutations; and (b) an anti-CD3 arm comprising a second binding domain comprising a VH domain comprising an amino acid sequence of SEQ ID NO: 133 and a VL domain comprising an amino acid sequence of SEQ ID NO: 104, wherein the anti-CD3 arm comprises a light chain comprising Q38E and V133K substitution mutations and a heavy chain comprising Q39K, S183E, and N297G substitution mutations (EU numbering).

In another aspect, the invention provides an anti-FcRH5 antibody that binds to FcRH5 and CD3, wherein the anti-FcRH5 antibody comprises an anti-FcRH5 arm comprising a first binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 16; and (f) an HVR-L3 comprising the amino acid sequence of SEQ ID NO: 23; and an anti-CD3 arm comprising a second binding domain comprising at least one, two, three, four, five, or six hypervariable regions (HVRs) selected from (a) an HVR-H1 comprising the amino acid sequence of SEQ ID NO: 115; (b) an HVR-H2 comprising the amino acid sequence of SEQ ID NO: 116; (c) an HVR-H3 comprising the amino acid sequence of SEQ ID NO: 121; (d) an HVR-L1 comprising the amino acid sequence of SEQ ID NO: 118; (e) an HVR-L2 comprising the amino acid sequence of SEQ ID NO: 119; and (f) an HVR-L3 comprising the amino acid sequence of SEQ ID NO: 123; and wherein the anti-FcRH5 arm comprises a light chain comprising Q38E and V133K substitution mutations and a heavy chain comprising Q39K, S183E, and N297G substitution mutations; and wherein the anti-CD3 arm comprises a light chain comprising Q38K, F116A, L135V, S174A, S176F, and T178V substitution mutations and a heavy chain comprising Q39E, A141I, F170S, S181M, S183A, V185A, and N297G substitution mutations (EU numbering). In some instances, the anti-FcRH5 antibody comprises an anti-FcRH5 arm comprising a first binding domain comprising the six hypervariable regions (HVRs): (a) an HVR-H1 comprising the amino acid sequence of SEQ ID NO: 1; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 16; and (f) an HVR-L3 comprising the amino acid sequence of SEQ ID NO: 23; and an anti-CD3 arm comprising a second binding domain comprising the six hypervariable regions (HVRs): (a) an HVR-H1 comprising the amino acid sequence of SEQ ID NO: 115; (b) an HVR-H2 comprising the amino acid sequence of SEQ ID NO: 116; (c) an HVR-H3 comprising the amino acid sequence of SEQ ID NO: 121; (d) an HVR-L1 comprising the amino acid sequence of SEQ ID NO: 118; (e) an HVR-L2 comprising the amino acid sequence of SEQ ID NO: 119; and (f) an HVR-L3 comprising the amino acid sequence of SEQ ID NO: 123; and wherein the anti-FcRH5 arm comprises a light chain comprising Q38E and V133K substitution mutations and a heavy chain comprising Q39K, S183E, and N297G substitution mutations; and wherein the anti-CD3 arm comprises a light chain comprising Q38K, F116A, L135V, S174A, S176F, and T178V substitution mutations and a heavy chain comprising Q39E, A141I, F170S, S181M, S183A, V185A, and N297G substitution mutations (EU numbering).

In another aspect, the invention provides the invention provides an anti-FcRH5 antibody that binds to FcRH5 and CD3, wherein the anti-FcRH5 antibody comprises: (a) an anti-FcRH5 arm comprising a first binding domain comprising a VH domain comprising an amino acid sequence having at least 90% (e.g., 90%, 91%, 92%, 93%, 94%, 95%, 96%, 97%, 98%, or 99%) sequence identity to, or the sequence of, SEQ ID NO: 104 and a VL domain comprising an amino acid sequence having at least 90% (e.g., 90%, 91%, 92%, 93%, 94%, 95%, 96%, 97%, 98%, or 99%) sequence identity to, or the sequence of, SEQ ID NO: 105, wherein the anti-CD3 arm comprises a light chain comprising Q38K, F116A, L135V, S174A, S176F, and T178V substitution mutations and a heavy chain comprising Q39E, A141I, F170S, 5181M, S183A, V185A, and N297G substitution mutations (EU numbering). In some instances, the invention provides an anti-FcRH5 antibody that binds to FcRH5 and CD3, wherein the anti-FcRH5 antibody comprises: (a) an anti-FcRH5 arm comprising a first binding domain comprising a VH domain comprising an amino acid sequence of SEQ ID NO: 104 and a VL domain comprising an amino acid sequence of SEQ ID NO: 105, wherein the anti-FcRH5 arm comprises a light chain comprising Q38E and V133K substitution mutations and a heavy chain comprising Q39K, S183E, and N297G substitution mutations; and (b) an anti-CD3 arm comprising a second binding domain comprising a VH domain comprising an amino acid sequence of SEQ ID NO: 133 and a VL domain comprising an amino acid sequence of SEQ ID NO: 134, wherein the anti-CD3 arm comprises a light chain comprising Q38K, F116A, L135V, S174A, S176F, and T178V substitution mutations and a heavy chain comprising Q39E, A141I, F170S, 5181M, S183A, V185A, and N297G substitution mutations (EU numbering).

In another aspect, the invention provides an anti-FcRH5 antibody that binds to FcRH5 and CD3, wherein the anti-FcRH5 antibody comprises an anti-FcRH5 arm comprising a first binding domain comprising at least one, two, three, four, five, or six hypervariable regions (HVRs) selected from (a) an HVR-H1 comprising the amino acid sequence of SEQ ID NO: 1; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 16; and (f) an HVR-L3 comprising the amino acid sequence of SEQ ID NO: 23; and an anti-CD3 arm comprising a second binding domain comprising at least one, two, three, four, five, or six hypervariable regions (HVRs) selected from (a) an HVR-H1 comprising the amino acid sequence of SEQ ID NO: 115; (b) an HVR-H2 comprising the amino acid sequence of SEQ ID NO: 116; (c) an HVR-H3 comprising the amino acid sequence of SEQ ID NO: 121; (d) an HVR-L1 comprising the amino acid sequence of SEQ ID NO: 118; (e) an HVR-L2 comprising the amino acid sequence of SEQ ID NO: 119; and (f) an HVR-L3 comprising the amino acid sequence of SEQ ID NO: 123; and wherein the anti-FcRH5 arm comprises a light chain comprising Q38K and V133E substitution mutations and a heavy chain comprising Q39E, S183K, and N297G substitution mutations; and wherein the anti-CD3 arm comprises a light chain comprising Q38E, F116A, L135V, S174A, S176F, and T178V substitution mutations and a heavy chain comprising Q39K, A141I, F170S, S181M, S183A, V185A, and N297G substitution mutations (EU numbering). In some instances, the anti-FcRH5 antibody comprises an anti-FcRH5 arm comprising a first binding domain comprising the six hypervariable regions (HVRs): (a) an HVR-H1 comprising the amino acid sequence of SEQ ID NO: 1; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 12; (e) an HVR-L2 comprising the amino acid sequence of SEQ ID NO: 16; and (f) an HVR-L3 comprising the amino acid sequence of SEQ ID NO: 23; and an anti-CD3 arm comprising a second binding domain comprising the six hypervariable regions (HVRs): (a) an HVR-H1 comprising the amino acid sequence of SEQ ID NO: 115; (b) an HVR-H2 comprising the amino acid sequence of SEQ ID NO: 116; (c) an HVR-H3 comprising the amino acid sequence of SEQ ID NO: 121; (d) an HVR-L1 comprising the amino acid sequence of SEQ ID NO: 118; (e) an HVR-L2 comprising the amino acid sequence of SEQ ID NO: 119; and (f) an HVR-L3 comprising the amino acid sequence of SEQ ID NO: 123; and wherein the anti-FcRH5 arm comprises a light chain comprising Q38K and V133E substitution mutations and a heavy chain comprising Q39E, S183K, and N297G substitution mutations; and wherein the anti-CD3 arm comprises a light chain comprising Q38E, F116A, L135V, S174A, S176F, and T178V substitution mutations and a heavy chain comprising Q39K, A141I, F170S, 5181M, S183A, V185A, and N297G substitution mutations (EU numbering).

In another aspect, the invention provides an anti-FcRH5 antibody that binds to FcRH5 and CD3, wherein the anti-FcRH5 antibody comprises: (a) an anti-FcRH5 arm comprising a first binding domain comprising a VH domain comprising an amino acid sequence having at least 90% (e.g., 90%, 91%, 92%, 93%, 94%, 95%, 96%, 97%, 98%, or 99%) sequence identity to, or the sequence of, SEQ ID NO:

104 and a VL domain comprising an amino acid sequence having at least 90% (e.g., 90%, 91%, 92%, 93%, 94%, 95%, 96%, 97%, 98%, or 99%) sequence identity to, or the sequence of, SEQ ID NO: 105, wherein the anti-FcRH5 arm comprises a light chain comprising Q38K and V133E substitution mutations and a heavy chain comprising Q39E, S183K, and N297G substitution mutations; and (b) an anti-CD3 arm comprising a second binding domain comprising a VH domain comprising an amino acid sequence of SEQ ID NO: 133 and a VL domain comprising an amino acid sequence of SEQ ID NO: 134, wherein the anti-CD3 arm comprises a light chain comprising Q38E, F116A, L135V, S174A, S176F, and T178V substitution mutations and a heavy chain comprising Q39K, A141I, F170S, S181M, S183A, V185A, and N297G substitution mutations (EU numbering). In some instances, the invention provides an anti-FcRH5 antibody that binds to FcRH5 and CD3, wherein the anti-FcRH5 antibody comprises: (a) an anti-FcRH5 arm comprising a first binding domain comprising a VH domain comprising an amino acid sequence of SEQ ID NO: 104 and a VL domain comprising an amino acid sequence of SEQ ID NO: 105, wherein the anti-FcRH5 arm comprises a light chain comprising Q38K and V133E substitution mutations and a heavy chain comprising Q39E, S183K, and N297G substitution mutations; and (b) an anti-CD3 arm comprising a second binding domain comprising a VH domain comprising an amino acid sequence of SEQ ID NO:133 and a VL domain comprising an amino acid sequence of SEQ ID NO: 134, wherein the anti-CD3 arm comprises a light chain comprising Q38E, F116A, L135V, S174A, S176F, and T178V substitution mutations and a heavy chain comprising Q39K, A141I, F170S, S181M, S183A, V185A, and N297G substitution mutations (EU numbering).

7. Antibody Variants

In certain embodiments, amino acid sequence variants of the anti-FcRH5 antibodies of the invention (e.g., bispecific anti-FcRH5 antibodies of the invention that bind to FcRH5 and a second biological molecule, e.g., CD3, such as FcRH5 TDB antibodies of the invention or variants thereof) are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

a. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 1

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196, 2008), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al. ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two, or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b. Glycosylation Variants

In certain embodiments, anti-FcRH5 antibodies of the invention can be altered to increase or decrease the extent to which the antibody is glycosylated. Addition or deletion of glycosylation sites to anti-FcRH5 antibody of the invention may be conveniently accomplished by altering the amino acid sequence such that one or more glycosylation sites is created or removed. Addition or removal of a glycosylation site may alter the effector function of an antibody, such as an anti-FcRH5 antibody (e.g., an FcRH5 TDB). In some embodiments, the anti-FcRH5 antibody (e.g., an FcRH5 TDB) may contain an aglycosylation site mutation. In some embodiments, the aglycosylation site mutation is a substitution mutation. In some embodiments, the aglycosylation site mutation reduces the effector function of the anti-FcRH5 antibody by at least 1% or more (e.g., 2%, 3%, 4%, 5%, 6%, 7%, 8%, 9%, 10%, 20%, 30%, 40%, 50%, 60%, 70%, 80%, or 90% or more). In some embodiments, the substitution mutation is at amino acid residue N297, L234, L235, D265, and/or P329 (EU numbering). In some embodiments, the substitution mutation is selected from the group consisting of N297G, N297A, L234A, L235A, D265A, and P329G. In some embodiments, the substitution mutation is an N297G mutation.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, anti-FcRH5 antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249, 2004; Yamane-Ohnuki et al. Biotech. Bioeng. 87: 614, 2004. Examples of cell lines capable of producing defucosylated antibodies include Lec13 CHO cells deficient in protein fucosylation (Ripka et al. Arch. Biochem. Biophys. 249:533-545, 1986; US Pat Appl No US 2003/0157108 A1, Presta, L; and WO 2004/056312 A1, Adams et al. especially at Example 11), and knockout cell lines, such as alpha-1,6-fucosyltransferase gene, FUT8, knockout CHO cells (see, e.g., Yamane-Ohnuki et al. Biotech. Bioeng. 87:614, 2004; Kanda, Y. et al. Biotechnol. Bioeng., 94(4):680-688, 2006; and WO2003/085107).

Anti-FcRH5 antibodies variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c. VH, VL, CH1, and CL Domain Variants

In certain embodiments, one or more amino acid modifications may be introduced into the heavy chain variable (VH, e.g., $VH_1$ and/or $VH_2$) domain, light chain variable (VL, e.g., $VL_1$ and/or $VL_2$) domain, heavy chain constant (CH1, e.g., $CH1_1$ and/or $CH1_2$) domain, and/or the light chain constant (CL, e.g., $CL_1$ and/or $CL_2$) domain of an anti-FcRH5 antibody of the invention (e.g., a bispecific anti-FcRH5 antibody of the invention that binds to FcRH5 and a second biological molecule, e.g., an FcRH5 TDB antibody of the invention or variant thereof). The VH, VL, CH1, and/or CL domains may have amino acid modifications (e.g., substitutions) at one or more (e.g., 1, 2, 3, 4, 5, 6, 7, 8, 9, or 10) amino acid positions. In particular embodiments, the amino acid substitutions comprise acidic and/or basic amino acid residues. Amino acid modifications, may form charged regions within the VH, VL, CH1, and/or CL domains (e.g., regions comprising acidic and/or basic amino acid residues). Charged regions within the VH, VL, CH1, and/or CL domains may interact with a second charged regions of opposite overall charge to form a charge pair. For example, amino acid modifications may mediate the formation of a charge pair between charged regions present within the $VL_1$ and $VH_1$ domains of the FcRH5 arm of a TDB. In some instances, amino acid modifications may mediate the formation of a charge pair between charged regions present within the $CL_1$ and $CH1_1$ domains of the FcRH5 arm of a TDB. In some instances, amino acid modifications may mediate the formation of a charge pair between charged regions present within the $VL_2$ and $VH_2$ domains of the second arm of a TDB (e.g., the CD3 arm of the TDB). In some instances, amino acid modifications may mediate the formation of a charge pair between charged regions present within the $CL_2$ and $CH1_2$ domains of the second arm of a TDB (e.g., the CD3 arm of the TDB). Exemplary configurations of FcRH5 TDBs containing VH, VL, CH1, and/or CL domain variants are presented in FIGS. 1A-1S.

In certain embodiments, an anti-FcRH5 antibody (e.g., a bispecific anti-FcRH5 antibody of the invention that binds to FcRH5 and a second biological molecule, e.g., CD3, such as an FcRH5 TDB antibody of the invention) comprises one or more asymmetrical modifications in the VH, VL, CH1, and/or CL regions to facilitate correct heavy/light chain pairing. In other embodiments, the anti-FcRH5 antibody further comprises one or more modifications in the Fc region to facilitate heterodimerization of the two arms (e.g., an anti-FcRH5 arm and an anti-CD3 arm) of the anti-FcRH5 antibody (e.g., FcRH5 TDB).

In some embodiments, the $CH1_1$ domain comprises an amino acid substitution at S183 (EU numbering) and the $CL_1$ domain comprises an amino acid substitution at V133 (EU numbering). In other embodiments, the light chain of the first arm (e.g., an FcRH5 binding arm) of the anti-FcRH5 antibody is a kappa chain. In some embodiments, the light chain of the second arm (e.g., an anti-CD3 binding arm) of the anti-FcRH5 antibody is a kappa chain. In certain embodiments, the light chains in both arms of the anti-FcRH5 antibody (e.g, the FcRH5 binding arm and the CD3 binding arm) are kappa chains.

In some embodiments, the CH1 domain comprises an S183E mutation and the $CL_1$ domain comprises a V133K mutation. In other embodiments, the CH1 domain comprises an S183K mutation and the $CL_1$ domain comprises a V133E mutation.

In some embodiments, the $CH1_1$ domain comprises an S183K mutation, the $CL_1$ domain comprises a V133E mutation, the $CH1_2$ domain comprises an S183E mutation, and the $CL_2$ domain comprises a V133K mutation.

In some embodiments, the anti-FcRH5 antibody further comprises a Q39E mutation in the $VH_1$ domain, a Q38K mutation in the $VL_1$ domain, a Q39K mutation in the $VH_2$ domain, and a Q38E mutation in the $VL_2$ domain.

In some embodiments, the anti-FcRH5 antibody further comprises a knob (e.g., protuberance) mutation in the $CH3_1$ domain and a hole (e.g., cavity) mutation in the $CH3_2$ domain. In certain embodiments, the knob mutation comprises a T366W mutation (EU numbering). In certain embodiments, the hole mutation comprises at least one, at least two, or all three of T366S, L368A, and Y407V mutations (EU numbering). In certain embodiments, the anti-FcRH5 antibody further comprises a T366W mutation in the first heavy chain and T366S, L368A, and Y407V mutations in the second heavy chain.

In some embodiments, the $CH1_1$ domain comprises A141I, F170S, S181M, S183A, and V185A mutations and the $CL_1$ domain comprises F116A, L135V, S174A, S176F, and T178V mutations. In certain other embodiments, the $CH1_1$ domain comprises A141I, F170S, S181M, S183A, and V185A mutations; the $CL_1$ domain comprises F116A, L135V, S174A, S176F, and T178V mutations; the $CH1_2$ domain comprises an S183E mutation; and the $CL_2$ domain comprises a V133K mutation.

d. Fc Region Variants

In certain embodiments, one or more amino acid modifications may be introduced into the Fc region of an anti-FcRH5 antibody of the invention (e.g., a bispecific anti-FcRH5 antibody of the invention that binds to FcRH5 and a second biological molecule, e.g., CD3, such as a TDB antibody of the invention or variant thereof), thereby generating an Fc region variant (see e.g., U.S. Pub. No. 2012/0251531, which is incorporated herein by reference in its entirety). In certain other embodiments, an anti-FcRH5 antibody comprises one or more modifications in the Fc region to facilitate heterodimerization of the two arms (e.g., an anti-FcRH5 arm and an anti-CD3 arm) of the anti-FcRH5 antibody (e.g., FcRH5 TDB). In certain embodiments, the anti-FcRH5 antibody (e.g., FcRH5 TDB) having one or more Fc modifications may also have one or more modifications in the VH, VL, CH1, and/or CL domains, as described above. In some embodiments, the FcRH5 antibody (e.g., FcRH5 TDB) containing Fc, VH, VL, CH1, and/or CL modifications may be produced by a one-cell antibody production approach, as described herein. The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an anti-FcRH5 antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc RII only, whereas monocytes express Fc RI, Fc RII, and Fc RIII. FcR expression on hematopoietic cells is summarized in Table 3 on page 464 of Ravetch et al. *Annu. Rev. Immunol.* 9:457-492, 1991. Non-limiting examples of in vitro assays to assess ADCC activity of a molecule of interest is described in U.S. Pat. No. 5,500,362 (see, e.g., Hellstrom et al. *Proc. NatlAcad. Sci. USA* 83:7059-7063, 1986) and Hellstrom et al. *Proc. NatlAcad. Sci. USA* 82:1499-1502, 1985; 5,821,337 (see Bruggemann, et al. *J. Exp. Med.* 166:1351-1361, 1987). Alternatively, non-radioactive assays methods may be employed (see, for example, ACTI™ non-radioactive cytotoxicity assay for flow cytometry (CellTechnology, Inc. Mountain View, Calif.; and CYTOTOX 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. NatlAcad. Sci. USA* 95:652-656, 1998. Clq binding assays may also be carried out to confirm that the antibody is unable to bind Clq and hence lacks CDC activity. See, e.g., Clq and C3c binding ELISA in WO 2006/029879 and WO 2005/100402. To assess complement activation, a CDC assay may be performed (see, for example, Gazzano-Santoro et al. *J. Immunol. Methods* 202: 163, 1996; Cragg, M. S. et al. *Blood.* 101:1045-1052, 2003; and Cragg, M. S. and M. J. Glennie *Blood.* 103:2738-2743, 2004). FcRn binding and in vivo clearance/half life determinations can also be performed using methods known in the art (see, e.g., Petkova, S. B. et al. *Int'l. Immunol.* 18(12):1759-1769, 2006).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

In certain embodiments, the proline at position 329 of a wild-type human Fc region in the antibody is substituted with glycine or arginine or an amino acid residue large enough to destroy the proline sandwich within the Fc/Fc.gamma. receptor interface that is formed between the proline 329 of the Fc and tryptophan residues Trp87 and Trp110 of FcgRIII (Sondermann et al. *Nature.* 406:267-273, 2000). In certain embodiments, the antibody comprises at least one further amino acid substitution. In one embodiment, the further amino acid substitution is S228P, E233P, L234A, L235A, L235E, N297A, N297D, or P331S, and still in another embodiment the at least one further amino acid substitution is L234A and L235A of the human IgG1 Fc region or S228P and L235E of the human IgG4 Fc region (see e.g., US 2012/0251531), and still in another embodiment the at least one further amino acid substitution is L234A and L235A and P329G of the human IgG1 Fc region.

Certain antibody variants with improved or diminished binding to FcRs are described (see, e.g., U.S. Pat. No. 6,737,056; WO 2004/056312, and Shields et al. *J. Biol. Chem.* 9(2):6591-6604, 2001).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) Clq binding and/or Complement Dependent Cytotoxicity (CDC), e.g., as described in U.S. Pat. No. 6,194,551, WO 99/51642, and Idusogie et al. *J. Immunol.* 164: 4178-4184, 2000.

Antibodies with increased half-lives and improved binding to the neonatal Fc receptor (FcRn), which is responsible for the transfer of maternal IgGs to the fetus (Guyer et al. *J. Immunol.* 117:587, 1976; Kim et al. *J. Immunol.* 24:249, 1994), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan et al. *Nature* 322:738-40, 1988; U.S. Pat. Nos. 5,648,260; 5,624,821; and WO 94/29351 concerning other examples of Fc region variants.

In certain embodiments, the anti-FcRH5 antibody comprises an aglycosylation site mutation. The aglycosylation site mutation may be a substitution mutation. The aglycosylation site mutation may reduce effector function of the anti-FcRH5 antibody, as compared to an unmutated version, by at least 1% (e.g., 2%, 3%, 4%, 5%, 6%, 7%, 8%, 9%, 10%, 20%, 30%, 40%, 50%, 60%, 70%, 80%, or 90%) or more. In some instances, the substitution mutation is at amino acid residue N297, L234, L235, D265, and/or P329 (EU numbering). Additionally, the substitution mutation may be selected from the group consisting of N297G, N297A, L234A, L235A, D265A, and P329G. In particular instances, the substitution mutation is an N297G mutation.

e. Knob and Hole Variants

Knob and hole variants of antibodies may also be produced in which an amino acid modification (e.g., a substitution) of one or more (e.g., 1, 2, 3, 4, 5, 6, 7, 8, 9, or 10) amino acid residues creates a protuberance (knob) or a cavity (hole). In some instances, the protuberance located on one polypeptide of the antibody is positionable within the cavity located on a second polypeptide of the antibody such that the two constituent polypeptides of the antibody can meet at an interface between the protuberance and the cavity. A knob may be formed by the substitution of one or more amino acid residues with one or more amino acid residues of larger size. A cavity may be formed by the substitution of a one or more amino acid residues with one or more amino acid residues of smaller size. The protuberance or cavity can be introduced into either arm of an anti-FcRH5 antibody (e.g., an FcRH5 TDB (e.g., either the anti-FcRH5 arm or the anti-CD3 arm)). Knob and hole modifications (e.g., of the Fc domain) are particularly useful in increasing overall yield, homogeneity, and stability of bispecific antibodies (e.g., TDBs). In some instances (e.g., when the protuberance-cavity pair are located on the LC/HC interfaces (e.g., VH and VL or CL and CH1)), amino acid modifications that introduce knob and hole modifications can reduce light chain swapping. In some embodiments, the protuberance is formed by introducing a T366W mutation into one arm of an anti-FcRH5 antibody (e.g., either the anti-FcRH5 arm or the anti-CD3 arm). In some embodiments, the T366W mutation is in the anti-FcRH5 arm. In some embodiments the T366W mutation is in the anti-CD3 arm. In some embodiments, a cavity is formed by introducing a T366W, L368A, and/or a Y407V mutation into one arm of an anti-FcRH5 antibody (e.g., either the anti-FcRH5 arm or the anti-CD3 arm). In some embodiments, a T366W, L368A, and/or a Y407V mutation is in the anti-FcRH5 arm. In some embodiments, a T366W, L368A, and/or a Y407V mutation is in the anti-CD3 arm.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). "Knob-in-hole" engineering of multispecific antibodies may be utilized to generate a first arm containing a knob and a second arm containing the hole into which the knob of the first arm may bind. For example, the TDB antibodies of the invention may contain a knob located on its anti-CD3 arm and a hole located on its tumor-targeting arm. Alternatively, the TDB antibodies of the invention may contain a knob located on its tumor-targeting arm and a hole located on its anti-CD3 arm. Multispecific antibodies may also be engineered using immunoglobulin crossover (also known as Fab domain exchange or CrossMab format) technology (see eg., WO2009/080253; Schaefer et al., *Proc. Natl. Acad. Sci. USA*, 108:11187-11192 (2011)). Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

f. Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, for example, in U.S. Pat. No. 7,521,541, which is incorporated herein by reference in its entirety.

g. Other Antibody Derivatives

In certain embodiments, an anti-FcRH5 antibody of the invention (e.g., bispecific anti-FcRH5 antibody of the invention that binds to FcRH5 and a second biological molecule, e.g., CD3, such as a TDB antibody of the invention or variant thereof) provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al. *Proc. Natl. Acad. Sci. USA* 102:11600-11605, 2005). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Anti-FcRH5 antibodies of the invention (e.g., bispecific anti-FcRH5 antibodies of the invention that bind to FcRH5 and a second biological molecule, e.g., CD3, such as TDB antibodies of the invention or variants thereof) may be produced using recombinant methods and compositions, for example, as described in U.S. Pat. No. 4,816,567. In one embodiment, isolated nucleic acid encoding an anti-FcRH5 antibody described herein is provided. In one embodiment, the host cell is eukaryotic, e.g., a Chinese Hamster Ovary (CHO) cell. In one embodiment, the host cell is prokaryotic, e.g., an *E. coli* cell. In one embodiment, a method of making an anti-FcRH5 antibody is provided, wherein the method comprises culturing a host cell comprising a nucleic acid encoding the antibody, as provided above, under conditions suitable for expression of the antibody, and optionally recovering the antibody from the host cell (or host cell culture medium). In another embodiment, the method further comprises culturing a second host cell comprising a second nucleic acid encoding an anti-CD3 antibody that comprises a binding domain that binds CD3. In some embodiments, the host cells are co-cultured. A further embodiment, comprises recovering the bispecific anti-FcRH5 antibody from the host cell or the culture medium. In some embodiments, the anti-FcRH5 and anti-CD3 antibodies are produced in the same host cell (e.g., a one-cell approach). In some embodiments, the anti-FcRH5 and anti-CD3 antibodies are produced in separate host cells (e.g., a two-cell approach).

In the one-cell and two-cell approaches, one or more plasmids encoding the FcRH5 TDB (e.g, an FcRH5 half-antibody and a CD3 half-antibody) are introduced into one or more host cells for culture and expression of the TDB. In one instance, a single plasmid may encode both the FcRH5 half-antibody and the CD3 half-antibody. Alternatively, the half-antibodies can be encoded by separate plasmids. In another instance, the heavy chain of each half-antibody is encoded on a first plasmid, while the light chain of each half-antibody is encoded on a second plasmid. In the one-cell approach, the FcRH5 TDB is produced in a single host. In the two-cell approach, the FcRH5 TDB is produced by expressing the half-antibodies in separate hosts (e.g., separate cultures of the same host cells, or separate cultures of different host cells). In the two-cell approach, the two hosts can be cultured in the same vessel or in different vessels. The two host cultures can be combined prior to lysis and purification of the FcRH5 TDB or the two half-antibodies can be purified separately.

In some embodiments, an anti-FcRH5 antibody of the invention (e.g., a bispecific anti-FcRH5 antibody of the invention that binds to FcRH5 and a second biological molecule, e.g., CD3, such as an FcRH5 TDB antibody of the invention) that has been modified to include asymmetrical modifications (e.g., mutations of the VH, VL, CH1, CL and/or Fc domains described above) is produced using a one-cell approach, which results in improved correct heavy chain/light chain pairing and/or improved yield of the anti-FcRH5 antibody as compared to an anti-FcRH5 antibody that has not been modified to include the asymmetrical modifications.

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523 (see, e.g., Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414, 2004, and Li et al. *Nat. Biotech.* 24:210-215, 2006.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. *J. Gen Virol.* 36:59, 1977); baby hamster kidney cells (BHK); mouse sertoli cells (TM4 cells as described, e.g., in Mather *Biol. Reprod.* 23:243-251, 1980); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al. *Annals N.Y. Acad. Sci.* 383:44-68, 1982; MRC-5 cells; and FS4 cells. Other useful mammalian host cell lines include Chinese hamster ovary (CHO) cells, including DHFR-CHO cells (Urlaub et al. *Proc. Natl. Acad. Sci. USA* 77:4216, 1980); and myeloma cell lines such as Y0, NS0 and Sp2/0. For a review of certain mammalian host cell lines suitable for antibody production, see, e.g., Yazaki et al. *Methods in Molecular Biology,* 248:255-268, 2003.

C. Assays

Anti-FcRH5 antibodies of the invention (e.g., bispecific anti-FcRH5 antibodies of the invention that bind to FcRH5 and a second biological molecule, e.g., CD3, such as TDB antibodies of the invention or variants thereof) provided herein may be identified, screened for, or characterized for their physical/chemical properties and/or biological activities by various assays known in the art.

1. Binding Assays and Other Assays

In one aspect, an anti-FcRH5 antibody of the invention is tested for its antigen binding activity, for example, by known methods such as ELISA, Western blot, etc.

In another aspect, competition assays may be used to identify an antibody that competes with an anti-FcRH5 antibody of the invention for binding to FcRH5.

In an exemplary competition assay, immobilized FcRH5 is incubated in a solution comprising a first labeled antibody that binds to FcRH5 and a second unlabeled antibody that is being tested for its ability to compete with the first antibody for binding to FcRH5. The second antibody may be present in a hybridoma supernatant. As a control, immobilized FcRH5 is incubated in a solution comprising the first labeled antibody but not the second unlabeled antibody. After incubation under conditions permissive for binding of the first antibody to FcRH5, excess unbound antibody is removed, and the amount of label associated with immobilized FcRH5 is measured. If the amount of label associated with immobilized FcRH5 is substantially reduced in the test sample relative to the control sample, then that indicates that the second antibody is competing with the first antibody for binding to FcRH5. See, e.g., Harlow and Lane (1988) *Antibodies: A Laboratory Manual.* Ch.14 (Cold Spring Harbor Laboratory, Cold Spring Harbor, N.Y.).

2. Activity Assays

In one aspect, assays are provided for identifying anti-FcRH5 antibodies thereof having biological activity. Biological activity may include, for example, binding to FcRH5, or a peptide fragment thereof, either in vivo, in vitro, or ex vivo. In the case of a multispecific (e.g., bispecific) anti-FcRH5 antibody of the invention (e.g., a TDB antibody having one anti-FcRH5 arm and one arm that recognizes a second biological molecule, e.g., CD3), biological activity may also include, for example, effector cell activation (e.g., T cell (e.g., CD8+ and/or CD4+ T cell) activation), effector cell population expansion (i.e., an increase in T cell count), target cell population reduction (i.e., a decrease in the population of cells expressing the second biological molecule on their cell surfaces), and/or target cell killing. Antibodies having such biological activity in vivo and/or in vitro are provided. In certain embodiments, an antibody of the invention is tested for such biological activity, as described in detail in the Examples herein below.

In some embodiments, the anti-FcRH5 antibody (e.g., FcRH5 TDB) activity comprises ability to support B cell killing and/or the activation of the cytotoxic T cells. In certain embodiments, an FcRH5 TDB antibody of the invention is tested for such B cell killing and/or the activation of the cytotoxic effect of T cells biological activity by any of the methods described herein, in particular the Examples. In some embodiments of any of these activity assays, PBMCs may be isolated from whole blood of healthy donors by Ficoll separation. In particular, human blood may be collected in heparinized syringes, and PBMCs isolated using Leucosep and Ficoll Paque Plus. If needed CD4+T and CD8+ T cells may be separated with Miltenyi kits according to manufacturer's instructions.

Further, cells may be washed in RPMI medium containing 10% FBS, supplemented with GlutaMax, penicillin & streptomycin, and 0.2 million suspended cells added to a 96-well U-bottom plate. Cells may be cultured in RPMI1640 supplemented with 10% FBS at 37° C. in a humidified standard cell culture incubator. For BJAB cell killing assays, 20,000 BJAB cells may be incubated with effector cells, either as huPBMCs or purified T cells, as indicated ratios per assay, in the presence of various concentrations of TDB antibodies for 24 hours. For endogenous B cell killing assays, 200,000 huPBMCs may be incubated with various concentrations of TDB antibodies for 24 hours.

After culturing, cells may be washed with FACS buffer (0.5% BSA, 0.05% Na Azide in PBS). Cells may then be stained in FACS buffer, washed with FACS buffer and suspended in 100 μl of FACS buffer containing 1 μg/ml Propidium Iodide. Data may be collected on a FACSCalibur flow cytometer and analyzed using FlowJo. Live B cells may be gated out as PI-negative CD19+ or PI-negative CD20+ B cells by FACS, and absolute cell count may be obtained with FITC beads added to reaction mix as an internal counting control. The percent (%) of cell killing may be calculated based on non-TDB treated controls. Activated T cells may be detected by CD69 and CD25 surface expression using anti-CD69-FITC and anti-CD25-PE.

D. Immunoconjugates

The invention also provides immunoconjugates comprising an anti-FcRH5 antibody, for example an anti-FcRH5 multispecific antibody, for example an FcRH5 TDB described herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al. *Cancer Res.* 53:3336-3342, 1993; and Lode et al. *Cancer Res.* 58:2925-2928, 1998); an anthracycline such as daunomycin or doxorubicin (see Kratz et al. *Current Med. Chem.* 13:477-523, 2006; Jeffrey et al. *Bioorganic & Med. Chem. Letters* 16:358-362, 2006; Torgov et al. *Bioconj. Chem.* 16:717-721, 2005; Nagy et al. *Proc. Natl. Acad. Sci. USA* 97:829-834, 2000; Dubowchik et al. *Bioorg. & Med. Chem. Letters* 12:1529-1532, 2002; King et al. *J. Med. Chem.* 45:4336-4343, 2002; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an anti-FcRH5 antibody (for example, an anti-FcRH5 multispecific antibody, for example an FcRH5 TDB) described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an anti-FcRH5 antibody (for example, an anti-FcRH5 multispecific antibody, for example an FcRH5 TDB) described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 µgain, iodine-131, indium-111, fluorine-19, carbon-13, nitrogen-15, oxygen-111, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al. *Science* 238:1098, 1987. Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al. *Cancer Res.* 52:127-131, 1992; U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Pharmaceutical Formulations

Pharmaceutical formulations of an anti-FcRH5 antibody of the invention (e.g., a bispecific anti-FcRH5 antibody of the invention that binds to FcRH5 and a second biological molecule, e.g., CD3, e.g., an FcRH5 TDB) are prepared by mixing such antibody having the desired degree of purity with one or more optional pharmaceutically acceptable carriers, buffers, stabilizers, and/or preservatives (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an additional therapeutic agent (e.g., a chemotherapeutic agent, a cytotoxic agent, a growth inhibitory agent, and/or an anti-hormonal agent, such as those recited herein above). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some instances, the composition may comprise a PD-1 axis binding antagonist and/or an additional therapeutic agent. For example, the PD-1 axis binding antagonist may be selected from the consisiting of MPDL3280A (atezolizumab), YW243.55.S70, MDX-1105, MEDI473 (durvalumab), and MSB0010718C (avelumab), MDX 1106 (nivolumab), MK-3475 (pembrolizumab), CT-011 (pidilizumab), MEDI-0680 (AMP-514), PDR001, REGN2810, and BGB-108. Additionally, a composition comprising an anti-FcRH5 antibody of the invention (e.g., an FcRH5 TDB) may comprise a steroid, an immunomodulator (IMiD), a proteosome inhibitor (PI), or a combination thereof.

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes.

F. Therapeutic Methods and Compositions

Any of the anti-FcRH5 antibodies of the invention (e.g., bispecific anti-FcRH5 antibodies of the invention that bind to FcRH5 and a second biological molecule, e.g., CD3, e.g., an FcRH5 TDB) may be used in therapeutic methods.

In one aspect, an anti-FcRH5 antibody for use as a medicament is provided. In further aspects, an anti-FcRH5 antibody for use in treating or delaying progression of a cell proliferative disorder (e.g., cancer, e.g., an FcRH5-positive cancer, e.g., multiple myeloma (MM)) and/or enhancing an immune function in an individual is provided. In certain embodiments, an anti-FcRH5 antibody for use in a method of treatment is provided. In certain embodiments, the invention provides an anti-FcRH5 antibody for use in a method of treating an individual having a cell proliferative disorder (e.g., cancer, e.g., an FcRH5-positive cancer, e.g., MM)) comprising administering to the individual an effective amount of the anti-FcRH5 antibody. In one such embodiment, the method further comprises administering to the individual an effective amount of at least one additional therapeutic agent, for example, as described below.

In further embodiments, the invention provides an anti-FcRH5 antibody for use in enhancing immune function in an individual having a cell proliferative disorder, such as an FcRH5-positive cancer (e.g., MM). In certain embodiments, the invention provides an anti-FcRH5 antibody for use in a method of enhancing immune function in an individual having a cell proliferative disorder comprising administering to the individual an effective of the anti-FcRH5 antibody to activate effector cells (e.g., T cells, e.g., CD8+ and/or CD4+ T cells) capable of exerting a cytotoxic and/or an apoptotic effect on target cells (e.g., a cell expressing a second biological molecule recognized by an anti-FcRH5 antibody of the invention, such as a FcRH5 TDB antibody of the invention) in an individual. The anti-FcRH5 antibody may bind to both an FcRH5 molecule located on a target cell and a CD3 molecule located on an immune effector cell. The target cell may be plasma cell, such as a long or short lived plasma cell. Additionally, the target cell may be a myeloma cell. An "individual" according to any of the above embodiments may be a human.

In a further aspect, the invention provides for the use of an anti-FcRH5 antibody in the manufacture or preparation of a medicament. In one embodiment, the medicament is for treatment of a cell proliferative disorder (e.g., cancer, e.g., an FcRH5-positive cancer, e.g., MM)). In a further embodiment, the medicament is for use in a method of treating a cell proliferative disorder comprising administering to an individual having a cell proliferative disorder or an effective amount of the medicament. In one such embodiment, the method further comprises administering to the individual an effective amount of at least one additional therapeutic agent, for example, as described below.

In a further embodiment, the medicament is for activating effector cells activate effector cells (e.g., T cells, e.g., CD8+ and/or CD4+ T cells) capable of exerting a cytotoxic and/or an apoptotic effect on target cells (e.g., a cell expressing a second biological molecule recognized by an anti-FcRH5 antibody of the invention, such as a FcRH5 TDB antibody of the invention) in an individual. In a further embodiment, the medicament is for use in a method of enhancing immune function in an individual having a cell proliferative disorder comprising administering to the individual an amount effective of the medicament to activate effector cells (e.g., T cells, e.g., CD8+ and/or CD4+ T cells), expand (increase) an effector cell population, reduce a target cell (e.g., a cell expressing a second biological molecule recognized by an anti-FcRH5 antibody of the invention, such as a FcRH5 TDB antibody of the invention) population, and/or kill a target cell (e.g., target tumor cell). An "individual" according to any of the above embodiments may be a human.

In a further aspect, the invention provides a method for treating a cell proliferative disorder (e.g., cancer). The FcRH5-positive cancer may be a B cell cancer. In some instances, the B-cell cancer may be multiple myeloma (MM), chronic lymphoid leukemia (CLL), mantle cell lymphoma (MCL), diffuse large B-cell lymphoma (DLBCL), and/or follicular lymphoma (FL). In particular instances, the B cell cancer is MM. In other instances, the FcRH5-positive cancer is a B cell cancer. In one embodiment, the method comprises administering to an individual having such a cell proliferative disorder (e.g., cancer, e.g., FcRH5-positive cancer, e.g., multiple myeloma (MM)) an effective amount of an anti-FcRH5 antibody. In one such embodiment, the method further comprises administering to the individual an effective amount of at least one additional therapeutic agent, for example, as described below. An "individual" according to any of the above embodiments may be a human.

Antibodies of the invention can be used either alone or in combination with other agents in a therapy. For instance, an antibody of the invention may be co-administered with at least one additional therapeutic agent. In certain embodiments, an additional therapeutic agent is a PD-1 axis binding antagonist such as MPDL3280A (atezolizumab), YW243.55.S70, MDX-1105, MED1473 (durvalumab), and MSB0010718C (avelumab), MDX 1106 (nivolumab), MK-3475 (pembrolizumab), CT-011 (pidilizumab), MEDI-0680 (AMP-514), PDR001, REGN2810, and/or BGB-108. Additionally, a steroid, an immunomodulator (IMiD), a proteosome inhibitor (PI), or a combination thereof may also be administered to a subject. In one embodiment, the glucocorticoid is dexamethasone. In some embodiments, the IMiD is lenalidomide. In some embodiments, the PI is bortezomib.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-FcRH5 antibody and administration of an additional therapeutic agent occur within about one month, or within about one, two or three weeks, or within about one, two, three, four, five, or six days, of each other.

An antibody of the invention (and/or any additional therapeutic agent) can be administered by any suitable means, including intravenously, subcutaneously, intramuscularly, topically, orally, transdermally, intraperitoneally, intraorbitally, by implantation, by inhalation, intrathecally, intraventricularly, or intranasally. Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question.

The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease (e.g., a proliferative cell disorder, e.g., cancer, e.g., a FcRH5-positive cancer, e.g., MM)), the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

As a general proposition, the therapeutically effective amount of the anti-FcRH5 antibody administered to a human will be in the range of about 0.01 to about 100 mg/kg of patient body weight whether by one or more administrations. In some embodiments, the antibody used is about 0.01 to about 0.01 to about 55 mg/kg, 50 mg/kg, 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In one embodiment, an anti-FcRH5 antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. In some embodiments, the anti-FcRH5 antibody is administered at a dosage of about 0.01 mg/kg/wk to about 10 mg/kg/wk. In other embodiments, the anti-FcRH5 antibody is administered at a dosage of 0.1 mg/kg/wk to about 10 mg/kg/wk. In other embodiments, anti-FcRH5 antibody is administered at a dosage of about 1 mg/kg/wk.

Such doses may be administered intermittently, for example, every week or every three weeks (e.g., such that the patient receives from about two to about twenty, or, for example, about six doses of the anti-FcRH5 antibody). An initial higher loading dose, followed by one or more lower doses may be administered. The progress of this therapy is easily monitored by conventional techniques and assays.

In some embodiments, the methods may further comprise an additional therapy. The additional therapy may be radiation therapy, surgery, chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy may be a separate administration of one or more of the therapeutic agents described above.

G. Methods and Compositions for Diagnostics and Detection

In certain embodiments, any of the anti-FcRH5 antibodies of the invention is useful for detecting the presence of FcRH5 in a biological sample. The term "detecting" as used herein encompasses quantitative or qualitative detection. In certain embodiments, a biological sample comprises a cell or tissue.

In one embodiment, an anti-FcRH5 antibody for use in a method of diagnosis or detection is provided. In a further aspect, a method of detecting the presence of naturally occurring FcRH5 in a biological sample is provided. In certain embodiments, the method comprises contacting the biological sample with an anti-FcRH5 antibody as described herein under conditions permissive for binding of the anti-FcRH5 antibody to the naturally occurring FcRH5, and detecting whether a complex is formed between the anti-FcRH5 antibody and naturally occurring FcRH5. Such method may be an in vitro or in vivo method. In some instances, the biological sample is a blood sample. In some instances, the subject is a human.

In certain embodiments, labeled anti-FcRH5 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, ß-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

H. Articles of Manufacture

In another aspect, the invention features an article of manufacture containing materials useful for the treatment, prevention, and/or diagnosis of proliferative cell disorders (e.g., cancer, e.g., an FcRH5-positive cancer, e.g., multiple myeloma (MM)) in a subject (e.g., a human). The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing, and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution, and dextrose solution. It may further include other materials desirable from a commercial and user standpoint, including other buffers, diluents, filters, needles, and syringes. In some instances, the kit includes a package insert comprising instructions for using the antibody for treating or delaying progression of an FcRH5-positive cancer (e.g., MM) in a subject. In other instances, the kit includes a package insert comprising instructions for using the antibody for enhancing immune function in a subject having an FcRH5-positive cancer (e.g., MM).

III. Examples

The following are examples of methods and compositions of the invention. It is understood that various other embodiments may be practiced, given the general description provided above.

Example 1. Generation of Anti-FcRH5 Antibodies

Immunizations and Screening

BALB/c mice (Charles River, Hollister, Calif.) were immunized with 2 µg, 10 µg, or 100 µg/injection per mouse. Antigens were suspended in monophosphoryl lipid A (MPL)/trehalose dicorynomycolate (TDM) (Ribi) adjuvant or Freund's adjuvant and injected into the footpad, peritoneum, or the base of the tail of each immunized animal. Mice received a total of 9 to 18 doses and 1 to 2 prefusion boosts in PBS alone via footpad, intraperitoneally (IP), and/or hock routes 2 to 4 days prior to fusion. Immunization Campaign A, described in U.S. Pub. No. 2015/0098900, produced the parental anti-FcRH5 antibody 1G7, which is optimized and further characterized herein.

A. Immunization Campaign B

To produce isoform-specific antibodies for the membrane-proximal Ig-domain of FcRH5, mice were immunized with E11 protein (amino acids 745-850 of SEQ ID NO: 114) with an N-terminal His-expression tag that was expressed in CHO cells. Five mice were immunized with 10 µg of His-tagged E11 protein in Ribi adjuvant via the IP route. Mice received 18 doses followed by two prefusion boosts in PBS alone via the IP route seven and four days prior to fusion. After 18 doses of the recombinant E11 protein, serum was analyzed for FcRH5-binding antibodies using FACS and by titration in ELISA using E11 as the antigen. Significant reactivity was detected to SVT2 cells that expressed full-length human FcRH5, full-length cyno FcRH5, or E11 protein, but not vector transfected SVT2 cells, indicating that FcRH5 binding antibodies were present in the sera of all five immunized mice. After 20 doses, lymphocytes from the immunized mice were electrofused with P3X63Ag8U.1.22 mouse myeloma cells.

Clones were tested for binding to recombinant human and cyno E11 proteins by ELISA. Eight clones that were cross-reactive to both human and cyno FcRH5 in ELISA were tested for binding to SVT2 cells that expressed full-length human FcRH5, full-length cyno FcRH5, or E11 protein by FACS. All eight clones bound SVT2 cells expressing the human E11 domain, transmembrane domain, and cytoplasmic domains.

To test binding to cancer cells which endogenously express FcRH5 or which were transfected with FcRH5, the cells were lifted using EDTA/PBS, and $1 \times 10^5$ cells were suspended in 100 µl and incubated with primary antibodies (1 volume of non-IgG quantitated subclone supernatant, 4 µg/ml IgG quantified subclone supernatant or 2 µg/ul purified monoclonal antibodies). Cells were washed twice with FACS buffer (PBS, 1% BSA, 2 mM EDTA) and incubated with 1:1000 dilution of goat anti-mouse secondary labeled with PE or 1:100 of goat anti-mouse APC. Cells were washed twice with FACS buffer and flow cytometry analysis was done on a FACSCalibur. Direct Xenon-labeling of antibodies was carried out according to manufacturer's protocol (Invitrogen), when indicated. However, only three of the clones bound to cells that expressed full-length human FcRH5 and none bound to cells that expressed full-length cyno FcRH5 (Table 2).

TABLE 2

Binding of mAbs from Immunization Campaign B in FACS to cells overexpressing human FcRH1, 2, 3, 4, and 5, human E11 domain, and cynomolgus FcRH5

| | Binding to FACS to SVT2 cells expressing: | | | | | | |
|---|---|---|---|---|---|---|---|
| mAb | Human FcRH1 | Human FcRH2 | Human FcRH3 | Human FcRH4 | Human FcRH5 | Human E11-TM-ICD* | Cynomolgus FcRH5 |
| 1E6 | − | − | − | − | + | + | − |
| 3D8 | − | − | − | − | − | + | − |
| 8G8 | − | − | − | − | − | + | − |
| 11A11 | − | − | − | − | − | + | − |
| 10D9 | − | − | − | − | + | + | − |
| 11H6 | − | − | − | − | − | + | − |
| 13D2 | − | − | − | − | + | + | − |
| 14E9 | − | − | − | − | − | + | − |

*E11 domain, transmembrane domain, and cytoplasmic domains of human FcRH5

B. Immunization and mAb Characterization Campaign C

For Immunization Campaign C, N-terminally His-tagged E11 protein was produced in CHO cells.

Mice were immunized with an initial injection of 100 µg of E11 protein in complete Freund's adjuvant in the base of the tail. Mice received a total of 17 doses, followed by one prefusion boost in PBS alone via the IP and hock routes two days prior to fusion (Table 3).

TABLE 3

Immunization schedule for the Immunization Campaign C

| Injection number | Adjuvant | Route | Volume per site | Volume per animal | Protein amount | Antigen |
|---|---|---|---|---|---|---|
| 1 | CFA | Base of tail | 100 µl | 100 µl | 100 µg | human E11 |
| 2 | IFA | Intraperitoneal | 100 µl | 100 µl | 50 µg | human E11 |
|  | IFA | Hock | 50 µl | 100 µl | 50 µg | human E11 |
| 3 | IFA | Base of tail | 100 µl | 100 µl | 50 µg | human E11 |
|  | IFA | Subcutaneous | 100 µl | 100 µl | 50 µg | human E11 |
|  | IFA | Intraperitoneal | 100 µl | 100 µl | 50 µg | human E11 |
| 4 | IFA | Hock | 100 µl | 100 µl | 50 µg | human E11 |
|  | IFA | Intraperitoneal | 100 µl | 100 µl | 50 µg | human E11 |
| 5 | IFA | Intraperitoneal | 100 µl | 100 µl | 50 µg | human E11 |
|  | IFA | Subcutaneous | 100 µl | 100 µl | 50 µg | human E11 |
|  | IFA | Base of tail | 100 µl | 100 µl | 50 µg | human E11 |
| 6 | IFA | Intraperitoneal | 100 µl | 100 µl | 50 µg | human E11 |
|  | IFA | Hock | 100 µl | 100 µl | 50 µg | human E11 |
| 7 | IFA | Base of tail | 100 µl | 100 µl | 50 µg | human E11 |
|  | IFA | Subcutaneous | 100 µl | 100 µl | 50 µg | human E11 |
|  | IFA | Intraperitoneal | 100 µl | 100 µl | 50 µg | human E11 |
| 8 | Sterile PBS | Intraperitoneal | 100 µl | 100 µl | 50 µg | human E11 |

TABLE 3-continued

Immunization schedule for the Immunization Campaign C

| Injection number | Adjuvant | Route | Volume per site | Volume per animal | Protein amount | Antigen |
|---|---|---|---|---|---|---|
| 9 | Sterile PBS | Intraperitoneal | 100 μl | 100 μl | 50 μg | human E11 |
| 10 | Ribi | Intraperitoneal | 100 μl | 100 μl | 10 μg | human E11 |
| 11 | Ribi | Intraperitoneal | 100 μl | 100 μl | 10 μg | human E11 |
| 12 | Ribi | Intraperitoneal | 100 μl | 100 μl | 10 μg | cynomolgus E11 and human E11 |
| 13 | Ribi | Intraperitoneal | 100 μl | 100 μl | 10 μg | cynomolgus E11 and human E11 |
| 14 | Ribi | Intraperitoneal | 100 μl | 100 μl | 3.3 μg | cynomolgus E11 and human E11 |
|  | Ribi | Hock | 100 μl | 100 μl | 3.3 μg | cynomolgus E11 and human E11 |
| 15 | Ribi | Base of tail | 100 μl | 100 μl | 3.3 μg | cynomolgus E11 and human E11 |
|  | Ribi | Subcutaneous | 100 μl | 100 μl | 3.3 μg | cynomolgus E11 and human E11 |
|  | Ribi | Intraperitoneal | 100 μl | 100 μl | 3.3 μg | cynomolgus E11 and human E11 |
| 16 | Ribi | Intraperitoneal | 100 μl | 100 μl | 3.3 μg | cynomolgus E11 and human E11 |
|  | Ribi | Hock | 100 μl | 200 μl | 6.6 μg | cynomolgus E11 and human E11 |
| 17 | Ribi | Base of tail | 100 μl | 100 μl | 3.3 μg | cynomolgus E11 and human E11 |
|  | Ribi | Subcutaneous | 100 μl | 100 μl | 3.3 μg | cynomolgus E11 and human E11 |
|  | Ribi | Intraperitoneal | 100 μl | 100 μl | 3.3 μg | cynomolgus E11 and human E11 |
| Pre-fusion boost | Sterile PBS | Intraperitoneal | 100 μl | 100 μl | 3.3 μg | cynomolgus E11 and human E11 |
|  | Sterile PBS | Hock | 100 μl | 200 μl | 6.6 μg | cynomolgus E11 and human E11 |

After 15 doses of the recombinant E11 protein followed by co-injections of the recombinant human and cyno E11 proteins, serum was analyzed for FcRH5-binding antibodies using FACS and by titration in ELISA using E11 protein as the antigen. Significant reactivity was detected to SVT2 cells that expressed full-length human FcRH5, full-length cyno FcRH5, or the human E11 domain, transmembrane domain, and cytoplasmic domains, but not vector transfected SVT2 cells, indicating that FcRH5 binding antibodies were present in the sera of all five immunized mice. After the final boost in PBS, lymphocytes from the immunized mice were electrofused with P3X63Ag8U.1.22 mouse myeloma cells.

Clones were tested for binding to recombinant human and cyno E11 proteins and binding to SVT2 cells that expressed full-length human FcRH5; full-length cyno FcRH5; full-length human FcRH1, FcRH2, FcRH3, or FcRH4; or human E11 domain, transmembrane domain, and cytoplasmic domains of FcRH5 by FACS. There were 44 human E11 protein-positive clones and 32 cyno E11 protein-positive clones in ELISA. Out of those, a total of 16 clones were identified that bound to cells that expressed human FcRH5 and cells that expressed cyno FcRH5, but not cells that expressed FcRH1, FcRH2, FcRH3, or FcRH4, indicative of specific FcRH5 cross-species reactivity (Table 4).

TABLE 4

Binding properties of monoclonal antibodies obtained from Immunization Campaign C

| mAb | Binding in FACS to SVT2 cells expressing: | | | | | | | MOLP-2 FACS binding | KD human E11 domain§ | KD cynomolgus E11 domain§ |
| | Human FcRH1 | Human FcRH2 | Human FcRH3 | Human FcRH4 | Human FcRH5 | Human E11-TM-ICD* | Cynomolgus FcRH5 | | | |
|---|---|---|---|---|---|---|---|---|---|---|
| 15G8 | − | − | − | − | + | + | +/− | +/− | 0.5 nM | 9.1 nM |
| 24H5 | − | − | − | − | + | + | + | + | 3.2 nM | 255 nM |
| 16H10 | − | − | − | − | + | + | + | + | 4.6 nM | 338 nM |
| 10A7 | − | − | − | − | + | + | + | + | 4.9 nM | 229 nM |
| 3C5 | − | − | − | − | + | + | + | + | 45 nM | 81 nM |
| 17B1 | − | − | − | − | + | + | + | + | 68 nM | 27 nM |
| 23E2 | − | − | − | − | + | + | + | + | Not done¶ | Not done¶ |
| 9B3 | − | − | − | − | + | + | + | − | Not done | Not done |
| 23B8 | − | − | − | − | + | + | + | − | Not done | Not done |
| 23G3 | − | − | − | − | + | + | + | − | Not done | Not done |
| 24F5 | − | − | − | − | + | + | + | − | Not done | Not done |
| 24G6 | − | − | − | − | + | + | + | − | Not done | Not done |
| 24C4 | − | − | − | − | +/− | + | +/− | − | Not done | Not done |
| 3C2 | − | − | − | − | + | + | +/− | − | Not done | Not done |
| 6H3 | − | − | − | − | +/− | + | +/− | − | Not done | Not done |
| 1D10 | − | − | + | − | + | + | + | Not done | Not done | Not done |
| 12B6 | + | + | + | − | + | + | + | Not done | Not done | Not done |
| 16A6 | + | + | + | − | + | + | + | Not done | Not done | Not done |
| 11C9 | − | − | − | − | + | + | − | Not done | Not done | Not done |
| 11H10 | − | − | − | − | + | + | − | Not done | Not done | Not done |
| 12E10 | − | − | − | − | + | + | − | Not done | Not done | Not done |
| 16BS | − | − | − | − | + | + | − | Not done | Not done | Not done |
| 16H1 | − | − | − | − | + | + | − | Not done | Not done | Not done |
| 17A6 | − | − | − | − | + | + | − | Not done | Not done | Not done |
| 2A10 | − | − | − | − | + | + | − | Not done | Not done | Not done |
| 2F9 | − | − | − | − | + | + | − | Not done | Not done | Not done |
| 3E3 | − | − | − | − | + | + | − | Not done | Not done | Not done |
| 5G9 | − | − | − | − | + | + | − | Not done | Not done | Not done |
| 6G4 | − | − | − | − | + | − | − | Not done | Not done | Not done |
| 7E2 | − | − | − | − | +/− | + | − | Not done | Not done | Not done |

TABLE 4-continued

Binding properties of monoclonal antibodies obtained from Immunization Campaign C

| | Binding in FACS to SVT2 cells expressing: | | | | | | | MOLP-2 | | |
|---|---|---|---|---|---|---|---|---|---|---|
| mAb | Human FcRH1 | Human FcRH2 | Human FcRH3 | Human FcRH4 | Human FcRH5 | Human E11-TM-ICD* | Cynomolgus FcRH5 | FACS binding | KD human E11 domain§ | KD cynomolgus E11 domain§ |
| 8E2 | − | − | − | − | + | + | − | Not done | Not done | Not done |
| 9A6 | − | − | − | − | + | + | − | Not done | Not done | Not done |
| 13C8 | − | − | − | − | − | + | − | Not done | Not done | Not done |
| 16E5 | − | − | − | − | − | + | − | Not done | Not done | Not done |
| 22C9 | − | − | − | − | − | + | − | Not done | Not done | Not done |
| 23B9 | − | − | − | − | − | + | − | Not done | Not done | Not done |
| 4H3 | − | − | − | − | − | + | − | Not done | Not done | Not done |
| 5B1 | − | − | − | − | − | + | − | Not done | Not done | Not done |
| 1B9 | − | − | − | − | − | +/− | − | Not done | Not done | Not done |
| 2C3 | − | − | − | − | − | +/− | − | Not done | Not done | Not done |
| 3G2 | − | − | − | − | − | +/− | − | Not done | Not done | Not done |
| 2G4 | − | − | − | − | − | − | − | Not done | Not done | Not done |

*E11 domain; transmembrane domain, and cytoplasmic domains of human FcRH5.
§Surface plasmon resonance BIACORE ® KD, monovalent affinity. Human E11 domain experiments were performed 1 to 3 times and averaged. Cynomolgus E11 domain experiments were performed once for each antibody.
¶No recombinant clones were obtained for antibody 23E2.

Purified IgG from the 16 selected monoclonal antibody (mAb) clones were further characterized for binding to cells that express human FcRH5 endogenously (MOLP-2 cells). A total of eight mAb clones were shown to bind MOLP-2 myeloma cells. Two of these eight mAb clones were found to be redundant based on sequence analysis and one was not molecularly cloned. The six molecularly cloned MOLP-2-positive mAb clones were expressed recombinantly as murine IgG2a and tested for affinity by surface plasmon resonance in a BIACORE® T200 apparatus in an IgG capture format.

Briefly, test antibodies were captured on flow cells 2, 3 or 4 with flow cell 1 as a reference on a protein A Series S CM5 chip (GE Life Sciences, Piscataway, N.J.). An FcRH5 protein fragment was used as analyte, with a flow rate of 30 µl/minute. Between injections the capture surface was regenerated by a 30 second injection of 10 mM glycine, pH 1.5 at a flow rate of 10 µl/minute. Interactions were assessed at 25° C. in 10 mM HEPES pH 7.4, 150 mM NaCl, 0.05% Tween 20 (HBSP). Reference data from the reference flow cell and from injection of buffer alone was subtracted prior to kinetic analysis. Kinetic information was calculated by fitting data to a 1:1 binding model. Reference subtraction and data fitting were performed using BIAevaluation software (GE Life Sciences, Piscataway, N.J.).

The monovalent affinities of these antibodies for the human E11 domain ranged from 0.5 nM to 68 nM while the affinities for cynomolgus E11 domain ranged from 9.1 nM to 338 nM (Table 4). Only one clone had an affinity for human E11 domain that was higher than antibody 1G7, mAb 15G8. However, the $K_D$ difference between human and cynomolgus E11 domains was about 20-fold, which rendered this clone unsuitable for further clinical development. In addition, despite the high affinity of this antibody clone for the isolated human domain E11, the binding of this antibody clone to MOLP-2 cells was very weak; it was weaker than the clones with lower affinities for isolated human E11 domain, indicating that this clone did not bind well to the native human FcRH5 protein.

Figure 2:
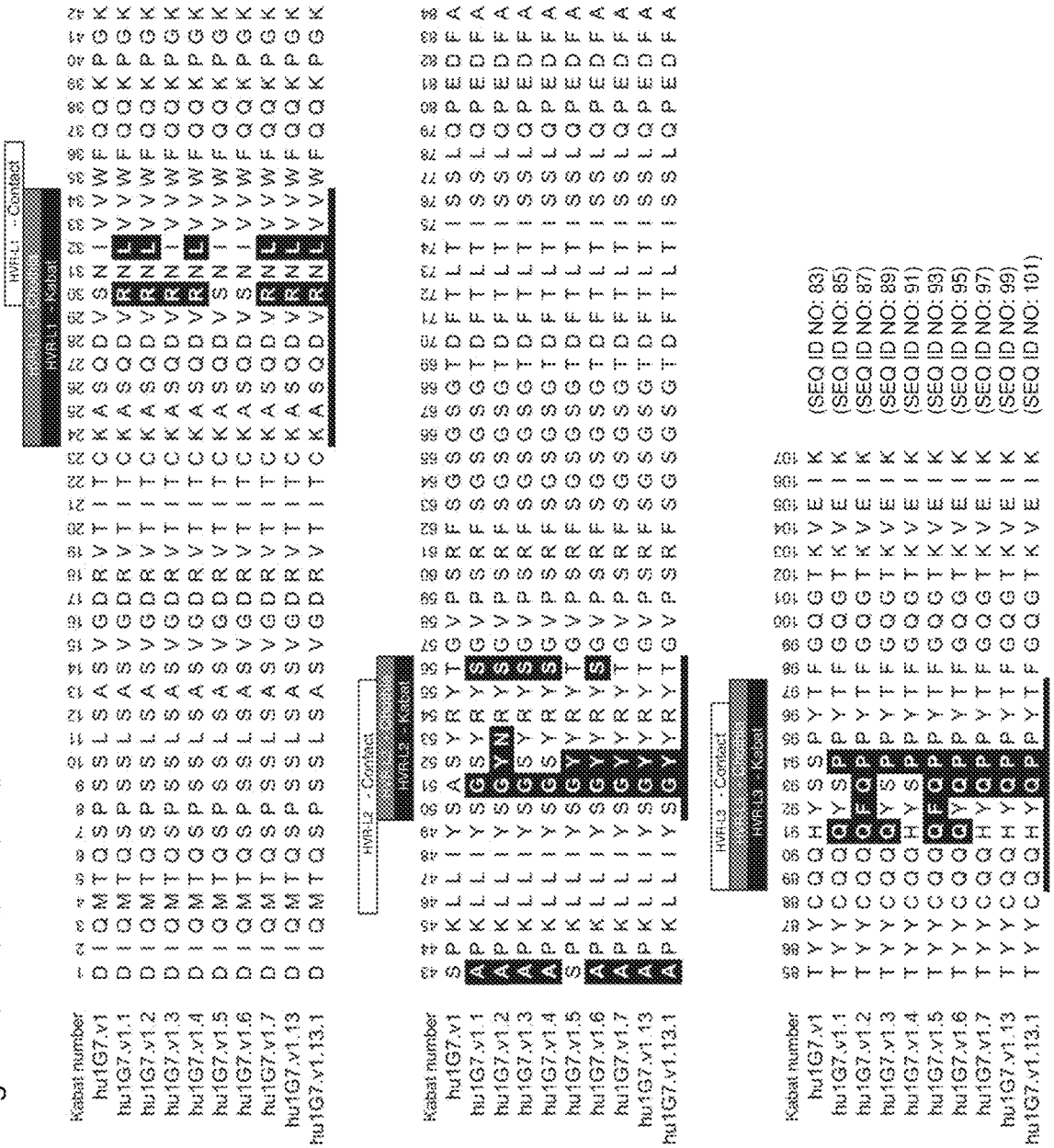
FIG. 2 is an alignment of the light chain variable (VL) domain sequences of select anti-FcRH5 antibodies. Changes from 1G7 (see U.S. Pub. No 2015-0098900, which is incorporated by reference herein in its entirety) are shown in dark boxes. Hypervariable regions (HVRs) are indicated by lines above and/or below the alignments. These VL domain sequences are also disclosed as SEQ ID NOs: 83, 85, 87, 89, 91, 93, 95, 97, 99, and 101.
Figure 3:
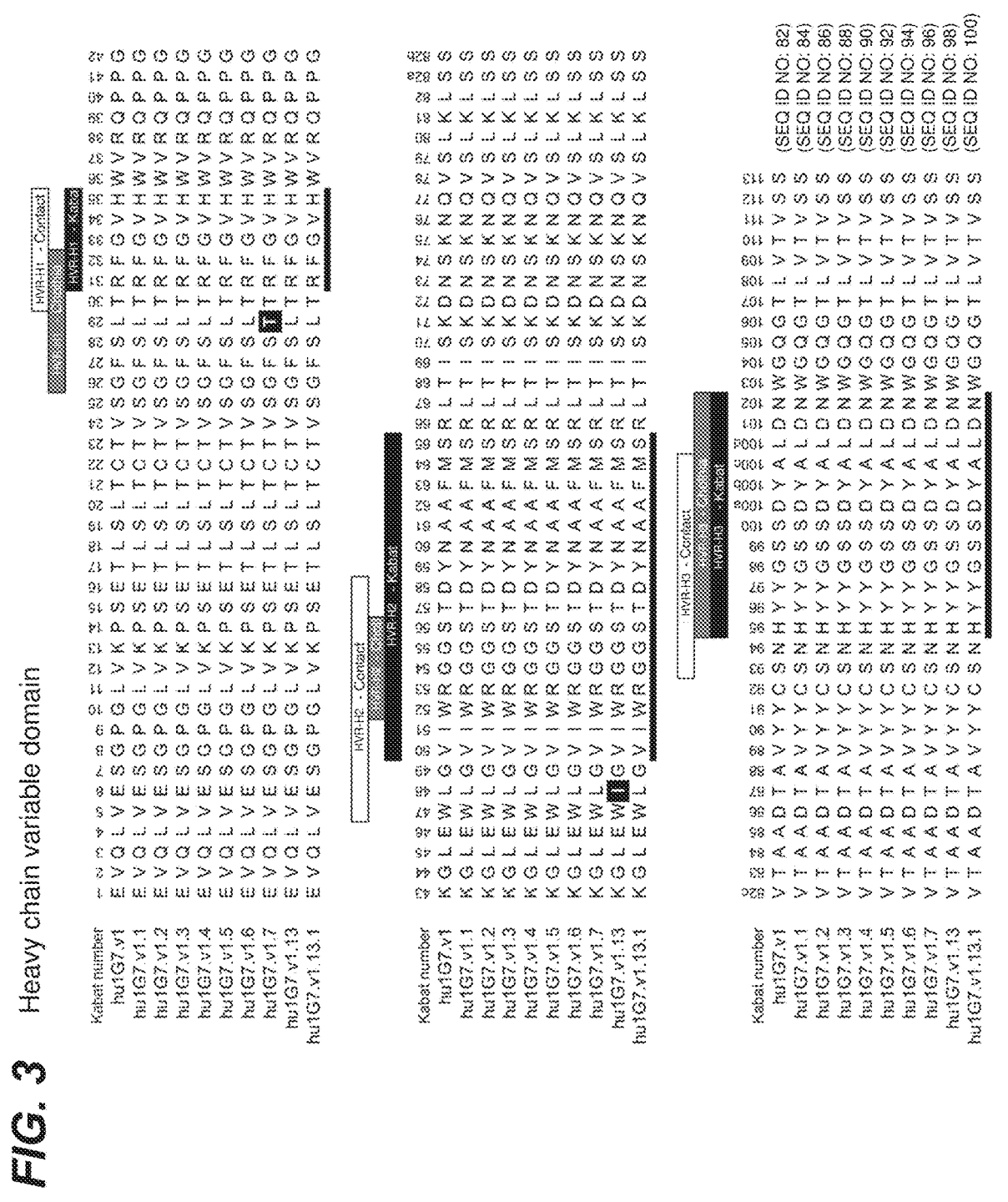
Figure 6A:
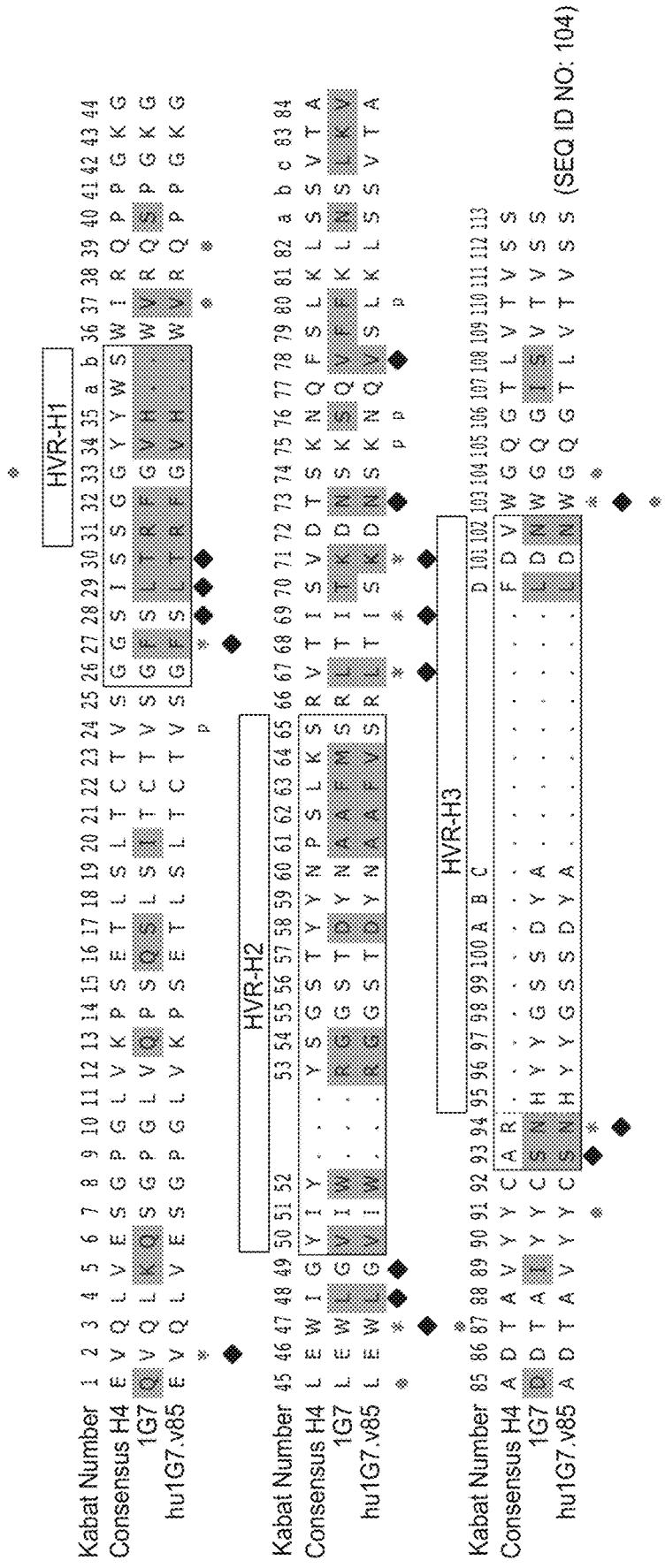
FIG. 6A is an alignment of the heavy chain variable (VH) domain sequences of hu1G7.v85. 1G7, and consensus H4. Changes from the humanized, affinity matured, and polished clone 1G7 (see U.S. Pub. No. 2015-0098900, which is incorporated by reference herein in its entirety) are shown in shaded boxes. Hypervariable regions (HVRs) are indicated by labels above the alignments. The VH domain sequence of hu1G7.v85 is disclosed as SEQ ID NO: 104.

Example 2. Generation and Characterization of Anti-FcRH5 Antibody Variants from Immunization Campaigns A and C A. Humanization of Anti-FcRH5 Monoclonal Antibodies from Immunization Campaign A Anti-FcRH5 antibody 1G7 from Immunization Campaign A, described in U.S. Pub. No. 2015/0098900, was humanized by the HVR graft method as previously described (Presta et al. *Cancer Res.* 57:4593-4599, 1997), except that consensus VH4 and VκI frameworks (Dennis, *Current Trends in Monoclonal Ant. Develop. and Manufac.* 9-28, 2010) were used as acceptor frameworks. The heavy chain graft also included murine residues at framework Kabat positions 37, 48, 67, 71, 73, 78, 93, and 94, and the light chain graft also included murine residues at framework positions 36 and 43 for proper HVR presentation and VH/VL domain contact. Residue numbers are according to Kabat et al. (*Sequences of proteins of immunological interest*, 5th Ed., Public Health Service, National Institutes of Health, Bethesda, Md., 1991). The sequence of humanized 1G7, herein referred to as hu1G7.v1 or 1G7.v1, is shown in FIGS. 2 and 3.

B. Affinity Maturation and Characterization of Hu 1G7.v1 Variants

To enhance potency, humanized antibody hu1G7.v1 was affinity matured using phage display. Briefly, randomized libraries of the Fab antibody fragment on the surface of M13 bacteriophage were displayed and panned for binders to biotinylated FcRH5 protein fragment. Favored mutations were identified by DNA sequencing of individual clones. These favored mutations were postulated to lead to variants with improved affinity (Li et al. *MAbs.* 6:437-445, 2014). Antibody clones with selected mutations were tested for affinity by surface plasmon resonance (FIGS. 42 and 43).

Briefly, a human IgG capture surface was generated on a Series S CM5 chip using amine coupling and the human IgG capture kit (GE Life Sciences, Piscataway, N.J.). Test antibodies were then captured on flow cells 2, 3, or 4, with flow cell 1 used as a reference. An FcRH5 protein fragment was used as the analyte, with a flow rate of >30 µl/minute. Between injections the capture surface was regenerated by a 30-second injection of 3M magnesium chloride or 10 mM glycine, pH 1.5. Interactions were assessed at 25° C. in 10 mM HEPES pH7.4, 150 mM NaCl, and 0.05% Tween 20 (HBSP). Reference data from the reference flow cell and from injection of buffer alone were subtracted prior to kinetic analysis. Kinetic information was calculated by fitting data to a 1:1 binding model. Reference subtraction and data fitting were performed using BIAevaluation software (GE Life Sciences, Piscataway, N.J.).

For initial affinity screening experiments, antibodies were captured directly from clarified culture media collected following transient transfection of Expi293 cells (Invitrogen) (FIGS. 42 and 43). The ability of each antibody to bind an FcRH5 protein fragment was assessed at 100 nM and 500 nM (Expt. 1, FIGS. 42 and 43) or 0 nM, 20 nM, 100 nM, and 500 nM (Expt. 2, FIGS. 42 and 43). Association and dissociation were monitored at a flow rate of 30 µl/min, for 180 s and 600 s, respectively. All sequences present within FIG. 42 are disclosed within SEQ ID NOs: 4-6 (i.e., the FcRH5 L1, L2, L3 broad consensus). All sequences present within FIG. 43 are disclosed within SEQ ID NOs: 1-3 (i.e., the FcRH5 H1, H2, H3 broad consensus). Affinity improvements of up to 5.2-fold were observed (FIG. 42). As each individual mutation did not provide the improvements sought, it was decided to combine various mutations with a focus on VL mutations S30R, I32L, A51G, S52Y, Y53N, T56S, H91Q, Y92F, S93Q, and S94P and VH mutations S28K, L29T, and S56T.

Antibody phage display libraries were designed using both hard and soft site-directed mutagenesis. Libraries L188 and L189 used soft mutagenesis to mutate VL residues 27-34, 50-56, 91-94, and 96 (L188) or VH residues 28-35, 50-58, and 95-100d (L189). At mutagenesis positions, soft mutagenesis oligonucleotides utilized 91% parent-encoding nucleotide and 3% of each other nucleotide. Libraries L190 and L191 used hard mutagenesis (NNKcodons) to mutate VL residues 27-34, 50-56, and 89-96 (L190) or VH residues 28-35, 50-58 and 95-100d (L191), one codon at a time, with up to three HVRs mutated simultaneously (Li et al. *MAbs*. 6:437-445, 2014).

Up to four rounds of selection for binding to FcRH5 protein fragment were performed. Selections were performed in both solid phase (target protein adsorbed directly onto microplates) and in solution. For solution selections, biotinylated target protein was used to enable capture of phage-antibody-target complexes. Clones with selected mutations were expressed in Expi293 cells (Thermo Fisher Scientific, Waltham, Mass.), and the supernatants screened by surface plasmon resonance.

Antibody phage display libraries were generated by Kunkel mutagenesis (Kunkel et al. Methods in Enzymology, 154:367-382, 1987) using as template single-stranded DNA produced in CJ236 bacteria and purified using the Qiagen QIAprep Spin M13 Kit (QIAGEN, Inc., Valencia, Calif.). Template DNA for initial affinity maturation libraries contained stop codons in those HVRs selected for mutagenesis; template DNA for the subsequent "focused" phage library described below did not utilize template HVR stop codons. Unless stated otherwise, residues in antibody variable regions are numbered according to the Kabat system. Enzymes were purchased from New England Biolabs (Ipswich, Mass.). Kunkel mutagenesis reactions were cleaned up using QIAprep mini spin columns (QIAGEN, Inc., Valencia, Calif.) and transformed into XLI Blue *E. coli* (Agilent Technologies, Santa Clara, Calif.) by electroporation. Following recovery in SOC medium at 37° C., cultures were infected with helper phage and incubated at 37° C. for an additional 0.5-2 hours before addition of antibiotics carbenicillin and kanamycin. Cultures were then incubated at 37° C. for an additional 4-5 hours followed by further incubation overnight at 30° C. Bacteriophage were purified from clarified culture medium by precipitation with approximately 1/6 volume of precipitation reagent (20% PEG, 2.5M sodium chloride). Precipitated phage were pelleted by centrifugation and solubilized in phosphate buffered saline (PBS). The solution was further clarified by centrifugation at 14,000 g.

Purified phage were stored in 50% glycerol in a −20° C. freezer and re-solubilized in PBS before use.

In a rational design approach, six VL mutations identified from the phage experiments (S30R, I32L, A51G, T56S, H91Q, and S94P) were combined with additional VL humanization mutation S43A and evaluated in pairs in order to assess compatibility (FIG. 44). For compatibility assessment of selected VL mutations (FIG. 44), antibodies were captured directly from clarified culture media collected following transient transfection of Expi293 cells. Binding of FcRH5 protein fragment was assessed at 6 nM, 19 nM, 56 nM, 167 nM, and 500 nM at a flow rate of 30 µl/min. Association and dissociation were monitored for 300 s and 600 s, respectively. The sequences disclosed in FIG. 44 are individual amino acids (i.e., the number at the top of the column is the amino acid number within the antibody sequence). The results indicated that the VL mutations I32L and H91Q, while individually improving affinity, did not benefit affinity when combined. However, the other sequences tested gave incremental affinity improvements of up to four-fold compared to the hu1G7.v1 control. Based on these results, antibodies hu1G7.v1.1, hu1G7.v1.2, hu1G7.v1.3 and hu1G7.v1.4 (FIGS. 2 and 3) were designed. Antibody hu1G7.v1.1 was designed to incorporate the six VL mutations S30R, I32L, A51G, T56S, H91Q, and S94P. Antibody hu1G7.v1.2 was designed to incorporate the ten VL mutations S30R, I32L, A51G, S52Y, Y53N, T56S, H91Q, Y92F, S93Q, and S94P. Antibodies hu1G7.v1.3 and hu1G7.v1.4 were based on hu1G7.v1.1 and designed to omit either I32L (hu1G7.v1.3) or H91Q (hu1G7.v1.4).

A focused phage library to investigate mutations of interest (VL mutations S30R, I32L, A51G, S52Y, Y53N, T56S, H91Q, Y92F, S93Q, S94P; VH mutations S28K, L29T, S56T) in many different combinations was also designed. In an effort to further increase similarity to human antibody sequences, the focused phage library also allowed limited variation at framework positions as follows: S43A in the LC, L48I in the HC, and/or N73T in the HC. Approximately $10^8$ transformants were obtained. Selections were performed using FcRH5 protein fragment as "bait". The selections were performed initially with solid phase immobilized target protein, with solution phase selections used in later rounds. Antibodies hu1G7.v1.5, hu1G7.v1.7, hu1G7.v1.13, and hu1G7.v1.13.1 (FIGS. 2 and 3) were derived from this library.

Sequencing data from experiments with the focused phage library also supported the concept (FIGS. 42 and 43) of negative interaction between the I32L and H91Q VL mutations. Following five rounds of selection on phage and subsequent analysis of 163 VL sequences, the frequency of glutamine at VL position 91 was found to be much higher in the presence of Ile32 (49/70 clones) than in the presence of Leu32 (5/93 clones). This effect was not observed in the unselected library, in which Gln91 was observed in 50% (9/18) of the analyzed clones that contained leucine at position 32. These results suggested negative selection of clones that contained both I32L and H91Q, despite positive enrichment of each of these mutations in other contexts.

Susceptibility to oxidation was investigated by incubating the antibody with 1 mM 2,2'-azobis(2-methylpropionamidine)dihydrochloride (AAPH) for 16 hours, followed by digestion with trypsin to create peptides that could be analyzed using liquid chromatography (LC)-mass spectrometry (MS) analysis. For each peptide in the sample, retention time from the LC, and high-resolution, accurate mass and peptide ion fragmentation information (amino acid sequence information) were acquired in the MS. Extracted ion chromatograms (XIC) were taken for peptides of interest (native and modified peptide ions) from the data sets at a window of ±10 ppm, and the peaks were integrated to determine area. Relative percentages of modification were calculated for each sample as follows: (area of the modified peptide)/(area of the modified peptide plus the area of the native peptide)× 100. These relative percentages were then compared between the control and the AAPH-treated samples.

Following a 16-hour incubation at 40° C. in the presence of 1 mM AAPH, an increase in oxidation of HVR-H2 Trp52 and Met64 (44.5% and 52.7%, respectively) was observed. Additionally, the Trp52 oxidation increased from 2% to 62% after light stress, and mutation of Trp-52HC resulted in an affinity loss for 1G7.v1.4 variants, as measured by BIACORE® (FIG. 4). Replacements of Trp52 with phenylalanine, tyrosine, leucine, or histidine and replacements of Met64 with phenylalanine, isoleucine, valine, or leucine were investigated in the context of the light chains from antibodies hu1G7.v1, hu1G7.v1.3, hu1G7.v1.4, hu1G7.v1.5, hu1G7.v1.6, and hu1G7.v1.7 (FIGS. 2 and 3). In particular, mutation of W52 to F, Y, L, or H resulted in $K_D$ values of 119 nM, 131 nM, 92 nM, and 60.4 nM, respectively. While mutation of M64 to V in 1G7.v85 resulted in a $K_D$ of 2.5 nM. For affinity screening of HVR-H2 Trp52 and Met64 variants (Table 5), antibodies were expressed by transient transfection of Expi293 cells and purified using tip columns that were custom packed with affinity resin MabSelect SuRe (Glygen Corp., Columbia, Md. & GE Life Sciences, Piscataway, N.J.). Control antibodies hu1G7.v1 and hu1G7.v1.5 were expressed by transient transfection of 293T cells and purified with MabSelect SuRe. Binding of FcRH5 protein fragment to captured antibodies was monitored at 100 nM and 500 nM. Association and dissociation were monitored at a flow rate of 40 μl/min, for 180 s and 300 s, respectively. The results, shown in Table 5, demonstrated that HVR-H2 Met64 can be mutated to valine while maintaining high affinity for FcRH5.

Antibody hu1G7.v1.4 was selected based on affinity and selectivity for FcRH5 over other FcRH family members. To improve the resistance of this antibody to oxidation, the M64V mutation described in Table 5 was also incorporated into the VH region. The resulting antibody hu1G7.v1.4.M64V was designated hu1G7.v85 (FIGS. 5A-5B) and was produced as a bivalent IgG and as a T cell-dependent bispecific antibody (TDB). The sequence of hu1G7.v85 is presented in FIGS. 6A-6B and FIG. 5A-5B. Kinetic analysis of hu1G7.v85 is shown in Table 6. Analysis of hu1G7.v1.4 is shown for comparison. Differences observed in $K_D$ of hu1G7.v1.4 (Tables 5 and 6) are within the experimental variation expected for these molecules.

A non-affinity matured version of hu1G7.v.1, hu1G7.v87, was also produced, which possesses the mouse 1G7 HVRs in the humanized framework described above, with an M64V mutation to improve oxidation resistance.

TABLE 5

Affinity screening of HVR-H2 position 52 and 54 variants of hu1G7.v1

| | | Light chain from antibody: | | | | | |
|---|---|---|---|---|---|---|---|
| Screening $K_D$ (M) | | hu1G7.v1 | hu1G7.v1.3 | hu1G7.v1.4 | hu1G7.v1.5 | hu1G7.v1.6 | hu1G7.v1.7 |
| Heavy chain mutation | None | $2.7 \times 10^{-8}$ | — | — | $2.0 \times 10^{-9}$ | — | — |
| | W52F | $2.5 \times 10^{-7}$ | $1.8 \times 10^{-7}$ | $1.2 \times 10^{-7}$ | $4.8 \times 10^{-8}$ | $8.1 \times 10^{-8}$ | $7.7 \times 10^{-8}$ |
| | W52Y | $1.5 \times 10^{-7}$ | $6.4 \times 10^{-7}$ | $1.3 \times 10^{-7}$ | $1.8 \times 10^{-7}$ | $5.3 \times 10^{-7}$ | $1.4 \times 10^{-7}$ |
| | W52L | $1.0 \times 10^{-7}$ | $2.4 \times 10^{-7}$ | $9.2 \times 10^{-8}$ | $1.3 \times 10^{-7}$ | $2.5 \times 10^{-7}$ | $1.3 \times 10^{-7}$ |
| | W52H | $1.2 \times 10^{-7}$ | $6.6 \times 10^{-8}$ | $6.0 \times 10^{-8}$ | $6.7 \times 10^{-8}$ | $1.1 \times 10^{-7}$ | $9.0 \times 10^{-8}$ |
| | M64I | $3.0 \times 10^{-8}$ | $2.1 \times 10^{-9}$ | $2.5 \times 10^{-9}$ | $2.7 \times 10^{-9}$ | $2.7 \times 10^{-9}$ | $2.6 \times 10^{-9}$ |
| | M64V | $2.7 \times 10^{-8}$ | $2.5 \times 10^{-9}$ | $2.5 \times 10^{-9}$ | $2.5 \times 10^{-9}$ | $2.7 \times 10^{-9}$ | $2.5 \times 10^{-9}$ |
| | M64L | $2.7 \times 10^{-8}$ | $2.4 \times 10^{-9}$ | $2.5 \times 10^{-9}$ | $2.3 \times 10^{-9}$ | $2.6 \times 10^{-9}$ | $2.0 \times 10^{-9}$ |
| | M64F | $2.6 \times 10^{-8}$ | $2.2 \times 10^{-9}$ | $2.5 \times 10^{-9}$ | $1.4 \times 10^{-9}$ | $2.6 \times 10^{-9}$ | $2.4 \times 10^{-9}$ |

TABLE 6

Kinetic analysis of hu1G7.v1.4 and hu1G7.v85 in hIgG1 and TDB formats

| | | Human FcRH5 | | | Cyno FcRH5 | | |
|---|---|---|---|---|---|---|---|
| Antibody | Format | $K_D$ (nM) | Ka (1/Ms) | Kd (1/s) | $K_D$ (nM) | Ka (1/Ms) | Kd (1/s) |
| 1G7.V1.4 | hIgG1 | 2.6 | $7 \times 10^5$ | $2 \times 10^{-3}$ | 7.7 | $1 \times 10^5$ | $1 \times 10^{-3}$ |
| | TDB | 2.4 | $5 \times 10^5$ | $1 \times 10^{-3}$ | 6.3 | $1 \times 10^5$ | $8 \times 10^{-4}$ |
| 1G7.V85 | hIgG1 | 2.5 | $6 \times 10^5$ | $2 \times 10^{-3}$ | 7.2 | $1 \times 10^5$ | $1 \times 10^{-3}$ |
| | TDB | 2.4 | $4 \times 10^5$ | $1 \times 10^{-3}$ | 6.8 | $1 \times 10^5$ | $8 \times 10^{-4}$ |

An additional affinity maturation method utilized Sanger sequencing to randomize the heavy chain HVR positions; however, no desirable mutations were identified by this method. Therefore, the number of positions tested for variants and the depth of screening using next-generation sequencing (Illumina sequencing) were expanded. A library was designed in which selected positions in the heavy chain variable region were randomized with an NNKcodon, which encodes any amino acid or an amber stop codon. The design allows only one amino acid change in the antibody variable regions per clone. The positions were selected from HVRs and framework positions in direct contact or proximal to HVRs. Kabat positions 1, 2, 24 to 40, 43, 45 to 78, 80 to 83, 85, 86, 91, and 93 to 102 were randomized. The library was created by DNA synthesis (GeneWiz), producing 75 independent linear DNA fragments with one position in each fragment randomized with the NNKcodon. The linear DNA fragments were pooled and cloned into a monovalent Fab fragment phage display vector (Lee et al. J. Immunol. Methods 284:119-132, 2004) containing the light chain variable region without affinity maturation mutations. Ligation products were electroporated into E. coli XL-1, superinfected with M13 KO7 helper phage (New England Biolabs) and grown as described. Binders were selected in three rounds of sorting with human or cynomolgus FcRH5 in parallel tracks. For these selections, ELISA plates coated with neutravidin (Pierce) were used to capture biotinylated human or cynomolgus FcRH5 domain 8 at 50 ng/ml in PBS. Phage (1 OD268/ml) was incubated with immobilized FcRH5 for two hours at room temperature and unbound phage removed by washing 10 times with PBS. Library and selected phage were used to infect E. coli XL-1, plasmid DNA was extracted and inserts were amplified by an 15-cycle PCR amplification using Phusion DNA polymerase (New England Biolabs) followed by agarose gel purification of amplicons. DNA from phage from the original library (2 OD2$_{68}$) was extracted with a M13 DNA purification kit (Qiagen) and 200 ng of DNA were used as template to amplify inserts using the same conditions as above. Amplicons were sequenced by Illumina sequencing as previously described (Koenig et al. J. Biol. Chem. 290:21773-21786, 2015). Sequences were filtered and analyzed as previously described (Koenig et al. J. Biol. Chem. 290:21773-21786, 2015), removing all sequences with more than one mutation in the variable region, sequences with mutations not conforming to the NNK degenerate codon usage and sequences with stop codons. Enrichment was calculated by dividing the frequency of a given mutation at a given position in the sorted sample by the frequency of the very same mutation in the unsorted (initial library) sample, as described previously (Fowler et al. Nat. Methods 7:741-746, 2010), using the following formula: $Ev=\log_2((Rv, s/\Sigma Rx, s)/(Rv, i/\Sigma Rx, i))$, where Ev is the enrichment of a mutant, Rv,s is the number of reads with mutation v in position s in the sorted population, Rx,s is number of reads in the sorted population with mutations in the same position as variant Rv,s, Rv,i is the number of reads of the same mutant as Rv,s in the input, unsorted population and Rx,i is the sum of all variants in the input, unsorted population with mutations in the same position as variant Rv,i. The Ev scores for selections with human and cyno FcRH5 are shown in FIGS. 45 and 46, respectively, and the gray boxes represent mutations that were not identified in the selected sample or in the library.

Figure 7B:
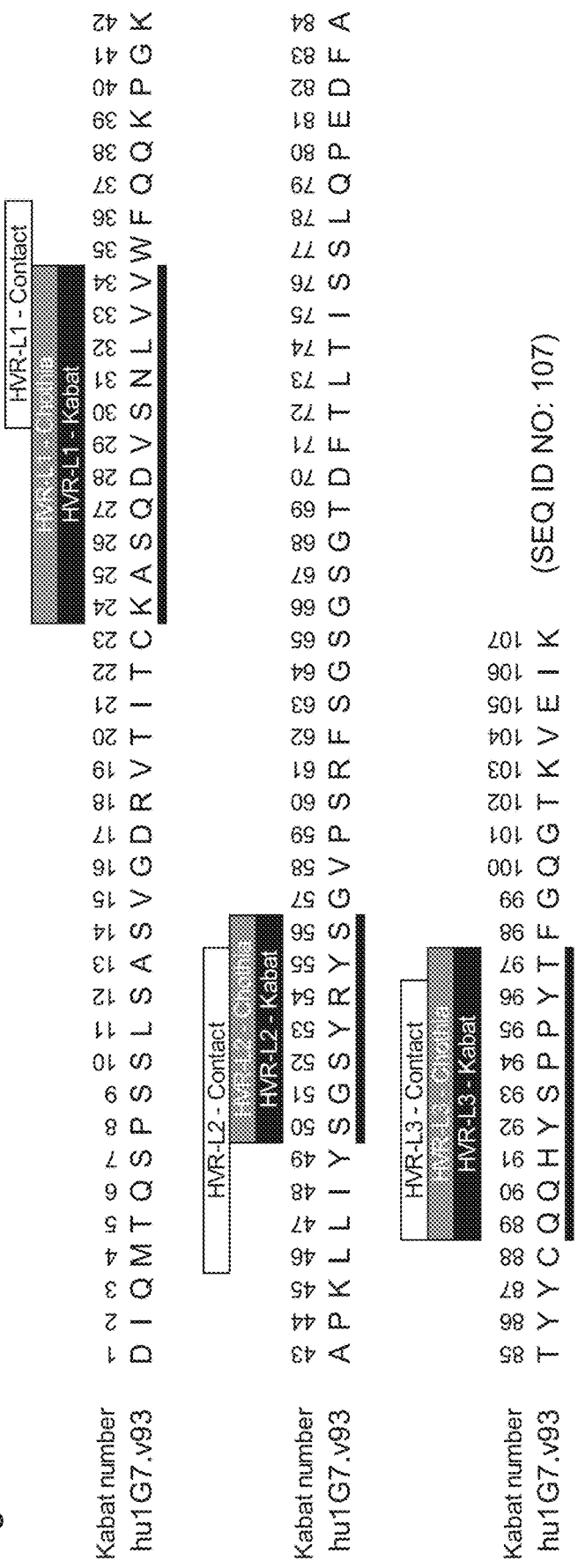
FIG. 7B shows the light chain variable (VL) domain sequence of anti-FcRH5 antibody hu1G7.v93 (SEQ ID NO: 107).

FIG. 47 shows the mutations with scores of at least 0.5 in selections with human FcRH5 and at least 0 in selections with cynomolgus FcRH5. In FIG. 47, the mutations selected for further analysis (i.e., mutations that are at least mildly favored for binding to human FcRH5 and that are neutral of better for cynomolgus FcRH5 binding) are highlighted in black or gray, and the L29T mutation identified by Sanger sequencing is highlighted in gray. A total of 11 positions had mutations meeting these criteria, with multiple variants in some positions. One position had a mutation that introduced a glycosylation site (G54N) and was not selected for further characterization. Another variant, L29T, had been identified by screening with Sanger sequencing but was only identified in clones with the S56T mutation. That variant showed an average improvement in affinity of 1.2-fold only. The S56T mutant had a strong negative enrichment score of -2.1 (FIG. 45), suggesting that the L29T mutation may have a beneficial effect that was obscured by the presence of the second S56T mutation in the double mutant. Of the other nine positions, the mutation with the highest score was selected except for positions 1 and 65, where two mutations were selected. These variants were made by DNA synthesis (GenWiz) and expressed as human IgG1 in combination with the light chain of hu1G7.v1 (without affinity maturation mutations) in Expi293 cells in 1-ml cultures. Human IgG1 variants were purified by protein A chromatography and tested in BIACORE® for affinity. Of the two mutations tested, only two, L29T and S100P, had a significant impact on affinity when tested in BIACORE® with soluble human FcRH5. The L29T mutation alone improved affinity in that context by 2.2-fold, whereas the S100P mutation improved affinity by 3-fold. These mutations were tested in isolation and in combination in the context of an affinity-matured light chain with the I32L, A51G, T56S, and S94P mutations present in hu1G7.v86. The heavy chain L29T improved the affinity of hu1G7.v86 by about 2-fold, similar to the effect in the context of a light chain without mutations. In contrast, the S100P, which in the context of a light chain without mutations improved the affinity by 3-fold, improved the affinity of hu1G7.v86 by 1.5-fold. Combined, the L29T and S100P mutations improved the affinity of hu1G7.v86 by 2.5-fold. Therefore, even using deep mining with next-generation sequencing and testing many framework positions in addition to the CDR positions for favored mutations in the heavy chain, only a 2.5-fold improvement in affinity could be achieved. The results indicated that mutations that significantly contributed to affinity when tested individually had much less of an impact in molecules which already had other mutations. This was particularly true of the S100P mutation in the heavy chain which, individually, improved affinity of hu1G7.v1 by about 3-fold but in the context of a molecule with the light chain mutations I32L, A51G, T56S, and S94P and heavy chain mutation L29T had little additional impact on affinity (Table 7, compare hu1G7.v91 and hu1G7.v93; hu1G7.v93 sequence presented in FIGS. 7A-7B). Thus, while significant affinity improvements could be achieved by adding several mutations to the light chain, relatively little improvement could be achieved by introducing mutations into the heavy chain.

TABLE 7

Affinities of hu1G7 variants with mutations identified by deep sequencing of phage display libraries selected with FcRH5

| | Mutations (Kabat position) | | | Fold improvement over: | |
|---|---|---|---|---|---|
| Variant | Heavy Chain | Light Chain | $K_D$ (nM) | hu1G7.v1 | hu1G7.v86 |
| hu1G7.v1 | — | — | 14.6 | — | |
| A | E1S | — | 14.6 | 1.0 | |
| B | E1F | — | 19.1 | 0.8 | |
| C | S28P | — | 13.3 | 1.1 | |
| D | L29T | — | 6.7 | 2.2 | |
| E | V37Y | — | 11.0 | 1.3 | |
| F | A61P | — | 11.7 | 1.2 | |
| G | M64G | — | 14.4 | 1.0 | |

TABLE 7-continued

Affinities of hu1G7 variants with mutations identified by deep sequencing of phage display libraries selected with FcRH5

| Variant | Mutations (Kabat position) | | $K_D$ (nM) | Fold improvement over: | |
|---|---|---|---|---|---|
| | Heavy Chain | Light Chain | | hu1G7.v1 | hu1G7.v86 |
| H | S65D | — | 15.0 | 1.0 | |
| I | S65P | — | 16.2 | 0.9 | |
| J | K81M | — | 15.3 | 1.0 | |
| K | S82bD | — | 15.0 | 1.0 | |
| L | S100P | — | 4.8 | 3.0 | |
| hu1G7.v85 | M64V | S30R, I32L, A51G, T56S, S94P | 0.8 | 17.0 | |
| hu1G7.v86 | M64V | I32L, A51G, T56S, S94P | 1.4 | 10.3 | |
| hu1G7.v91 | M64V, L29T | I32L, A51G, T56S, S94P | 0.7 | 20.9 | 2.0 |
| hu1G7.v92 | M64V, S100P | I32L, A51G, T56S, S94P | 0.9 | 15.9 | 1.5 |
| hu1G7.v93 | M64V, L29T, S100P | I32L, A51G, T56S, S94P | 0.6 | 25.3 | 2.5 |

Example 3. Generation and In Vitro Characterization of Exemplary FcRH5 TDBs

Anti-FcRH5 antibodies described herein were used to generate T cell-dependent bispecific (TDB) antibodies comprising the binding determinants of the anti-human FcRH5 on one arm and an anti-human CD3ε on the other arm. The FcRH5 binding determinants included the humanized and affinity matured monoclonal antibody clones 1G7, 1G7.v85, and 1G7.v87. The humanized binding determinants for anti-CD3ε included the high-affinity antibody clone 38E4.v1, the high-affinity clone 38E4.v11, and the low-affinity clone 40G5 (EC50 for hCD3ε=1.0 nM, 50 pM, and 13 nM, respectively). The anti-CD3 clones 38E4.v1, 38E4.v11, and 40G5c bind a human CD3ε polypeptide (a fragment of the human CD3ε polypeptide consisting of amino acids 1-26 or 1-27 (SEQ ID NO: 174)) and the amino acid residue Glu5 of CD3ε is not required for binding (see also PCT Pub. No. WO 2015/095392 and U.S. Pub. No. 2015-0166661, each of which is incorporated herein by reference in its entirety).

Exemplary FcRH5 TDBs were characterized to evaluate their therapeutic potential. Humanized full-length FcRH5 TDB molecules were found to kill human plasma cells and patient-derived primary myeloma tumor cells at extremely low (pM) doses and to trigger a robust proliferation of T cells. FcRH5 TDBs were efficacious in suppressing the growth of myeloma xenografts in vivo and resulted in complete depletion of B cells and plasma cells in primates at well tolerated dose levels which were expected to saturate the target. Complete plasma cell depletion provided compelling evidence of efficacy in the bone marrow microenvironment. Activity of the FcRH5 TDBs correlated with target expression (e.g., FcRH5 expression) level suggesting that high risk myeloma patients with chromosome 1 q copy gain may be uniquely sensitive to this immunotherapy.

Materials and Methods
A. Antibodies
a. Production of TDBs

1. Rational Design Approach

Figure 1B:
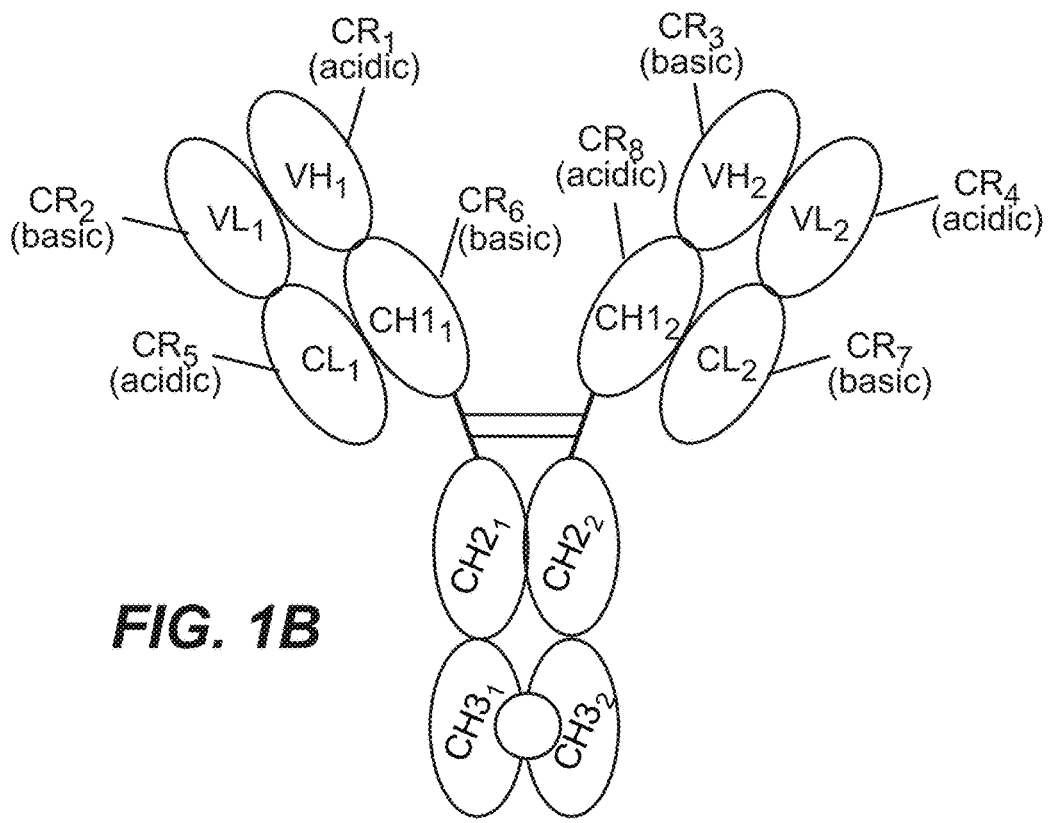
FIG. 1B is a schematic diagram showing an exemplary Rational Design configuration (Configuration 2) of an FcRH5 TDB having VL, VH, CL, and CH1 domains including one or more charged regions. For Configuration 2, the $VH_1$, $CL_1$, $VL_2$, and $CH1_2$ domains contain acidic charged regions, and the $VL_1$, $CH1_1$, $VH_2$, and $CL_2$ domains contain basic charged regions.
Figure 1C:
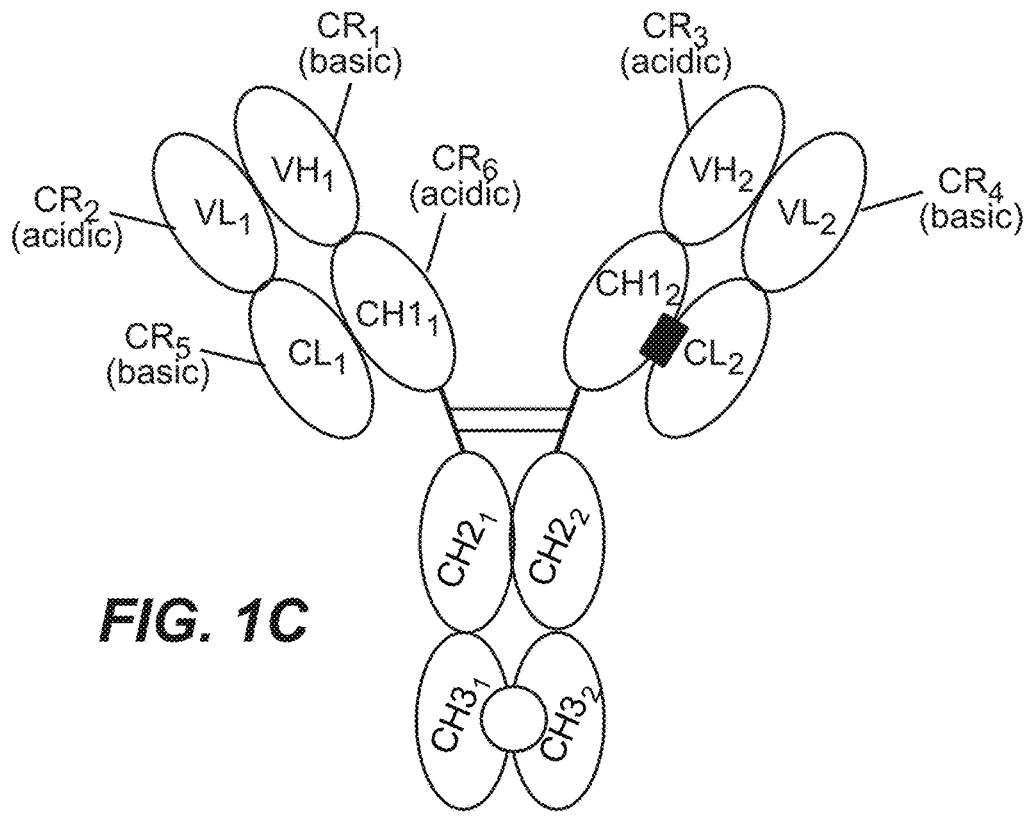
FIG. 1C is a schematic diagram showing an exemplary Rosetta Design configuration (Configuration 1) of an FcRH5 TDB having VL, VH, CL, and CH1 domains including one or more charged regions. For Configuration 1, the $VH_1$, $CL_1$, and $VL_2$ domains contain basic charged regions, and the $VL_1$, $CH1_1$, and $VH_2$ domains contain acidic charged regions. Additionally, the $CH1_2$ domain contains a cavity, and the $CL_2$ domain contains a protuberance. The cavity and protuberance are depicted as a black box at the $CH1_2/CL_2$ interface.
Figure 1D:
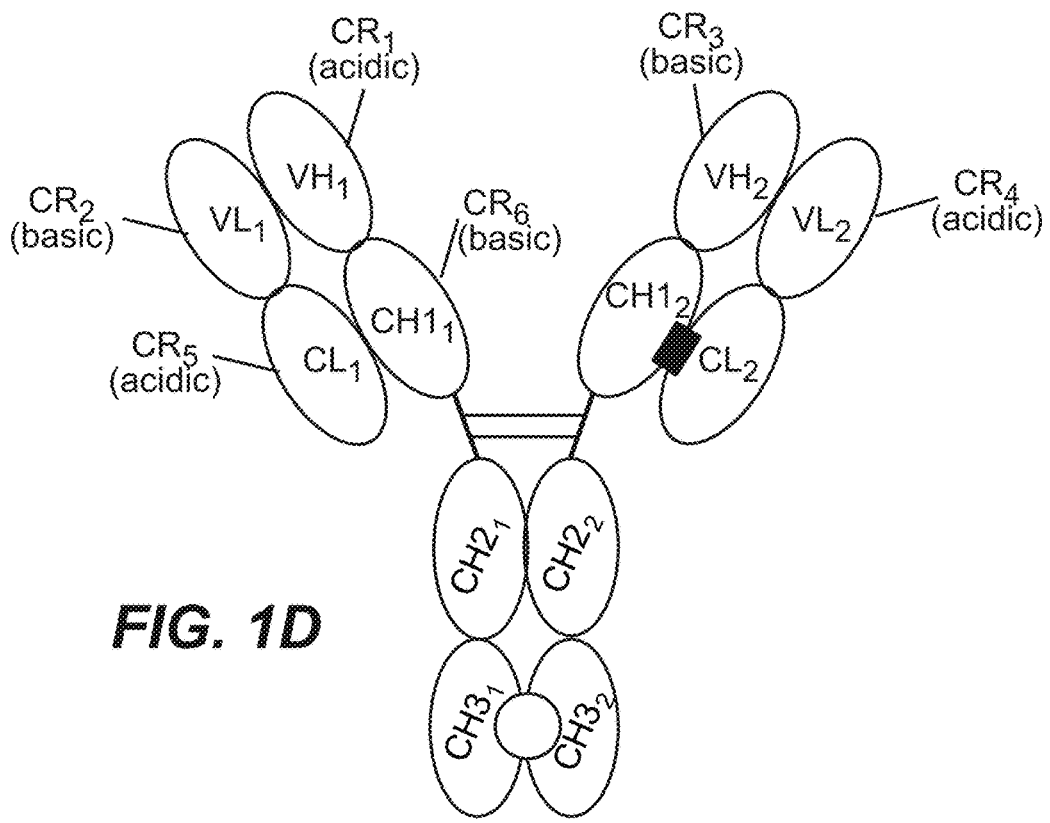
FIG. 1D is a schematic diagram showing an exemplary Rosetta Design configuration (Configuration 2) of an FcRH5 TDB having VL, VH, CL, and CH1 domains including one or more charged regions. For Configuration 2, the $VH_1$, $CL_1$, and $VL_2$ domains contain acidic charged regions, and the $VL_1$, $CH1_1$, and $VH_2$ domains contain basic charged regions. Additionally, the $CH1_2$ domain contains a cavity, and the $CL_2$ domain contains a protuberance. The cavity and protuberance are depicted as a black box at the $CH1_2/CL_2$ interface.
Figure 1E:
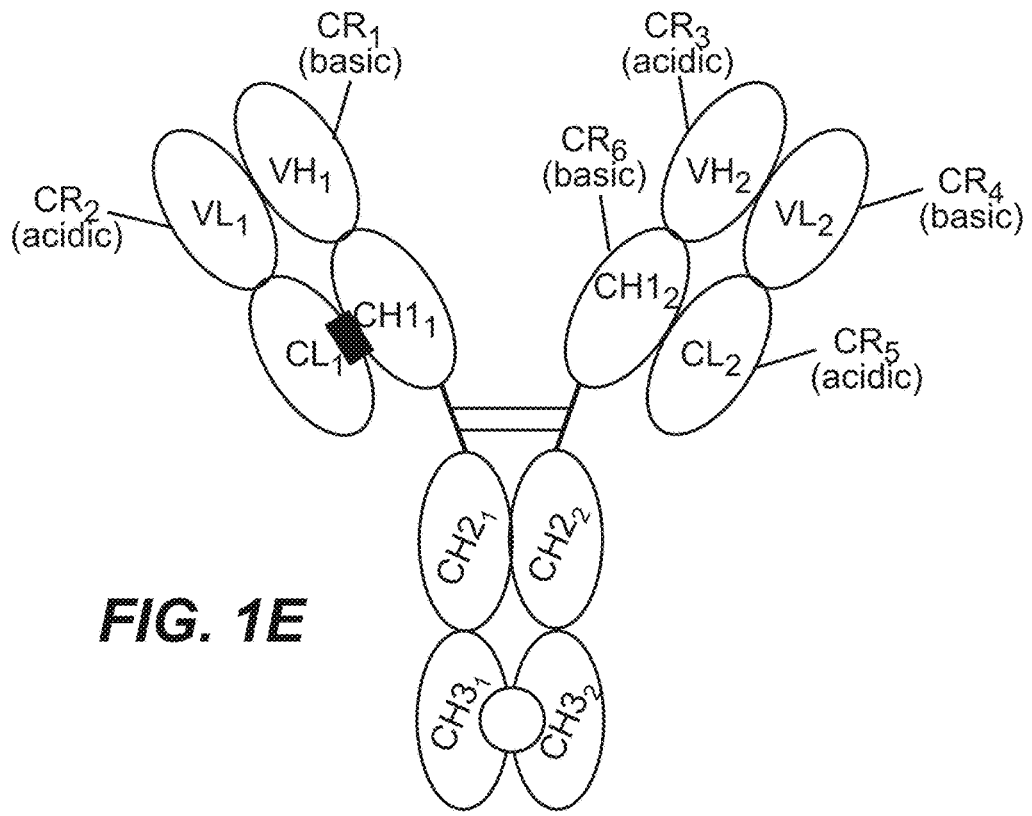
FIG. 1E is a schematic diagram showing an exemplary alternative Rosetta Design configuration (Alternative Configuration 1) of an FcRH5 TDB having VL, VH, CL, and CH1 domains including one or more charged regions. For Alternative Configuration 1, the $VL_1$, $VH_2$, and $CL_2$ domains contain acidic charged regions, and the $VH_1$, $CH1_2$, and $VL_2$ domains contain basic charged regions. Additionally, the $CH1_1$ domain contains a cavity, and the $CL_1$ domain contains a protuberance. The cavity and protuberance are depicted as a black box at the $CH1_1/CL_1$ interface.
Figure 1F:
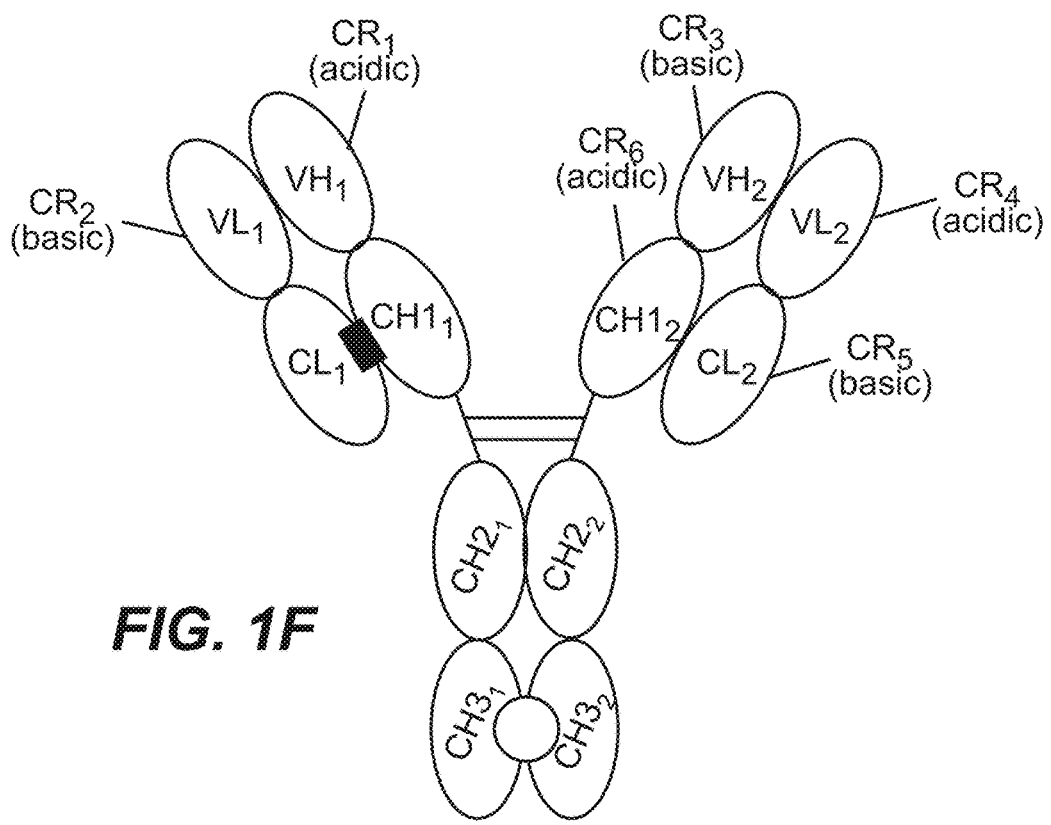
FIG. 1F is a schematic diagram showing an exemplary alternative Rosetta Design configuration (Alternative Configuration 2) of an FcRH5 TDB having VL, VH, CL, and CH1 domains including one or more charged regions. For Alternative Configuration 2, the $VL_1$, $VH_2$, and $CL_2$ domains contain basic charged regions, and the $VH_1$, $CH1_2$, and $VL_2$ domains contain acidic charged regions. Additionally, the CH1₁ domain contains a cavity, and the CL₁ domain contains a protuberance. The cavity and protuberance are depicted as a black box at the CH1₁/CL₁ interface.

To optimize expression and increase the yield of TDBs, mutations were engineered into the Fc, VH, VL, CH1, and CL domains of the anti-FcRH5 antibodies (e.g., FcRH5 TDBs) to drive appropriate antibody monomer formation. In particular, amino acid modifications that introduced charged regions into the VH, VL, CH1, and/or CL domains provided a mechanism to reduce heavy chain and light chain mispairing. Cognate charged regions having opposite overall charges are driven together and assist in appropriate heavy chain and light chain pairing, increasing the overall production yield of an anti-FcRH5 antibody (e.g., an FcRH5 TDB). Exemplary Rational Design configurations, including amino acid modifications of the Fc, VH, VL, CH1, and CL domains, are presented in FIGS. 1A-1B.

2. Rosetta Design Approach

In addition, or in the alternative, to optimize expression and increase the yield of TDBs, mutations were engineered into the Fc, VH, VL, CH1, and CL domains of the anti-FcRH5 antibodies (e.g., FcRH5 TDBs) to drive appropriate antibody monomer formation. The Rosetta Design approach provided an additional mechanism to drive appropriate heavy chain and light chain pairing, in addition to charged region mutations, in the form of knob and hole mutations in the CH1 and CL domains. Exemplary Rosetta Design configurations, including amino acid modifications of the Fc, VH, VL, CH1, and CL domains, are presented in FIGS. 1C-1F.

3. One-Cell Approach for FcRH5 TDB Production

In one approach, the FcRH5 TDBs can be produced by culturing host cells that have been co-transfected with two plasmids, each encoding one of the two arms of the FcRH5 TDB (e.g., a first plasmid encoding an anti-FcRH5 half-antibody and a second plasmid encoding an anti-CD3 half-antibody). Transfection of host cells (e.g., bacterial, mammalian, or insect cells) was performed in a 96-well plate format. To screen for FcRH5 TDB production, approximately 2,000 to 3,000 clones may be picked and assessed by ELISA and intact IgG homogeneous time resolved fluorescence (HTRF) for their ability to bind the target antigen, FcRH5. Clones producing FcRH5 TDBs capable of binding to FcRH5, or a fragment thereof, were selected for expansion and further screening (e.g., for binding to CD3). Top clones can then be selected for further analysis based on percent bispecific antibodies (bsAbs) produced, titer, and performance qualification (PQ).

An exemplary one-cell approach that can be used to produce FcRH5 TBDs of the invention is described in International Patent Application No. PCT/US16/28850, which is incorporated herein by reference in its entirety.

4. Two-Cell Approach for FcRH5 TDB Production

Alternatively, FcRH5 TDBs can be produced by culturing the antibody hemimers (e.g., half-antibodies) separately (i.e., in two different cell lines) using high-cell density fermentation and then isolating each half-antibody independently by Protein A chromatography. The purified half-antibodies can then be combined, for example, at a 1:1 molar ratio and incubated in 50 mM Tris, pH 8.5 in the presence of 2 mM DTT for 4 hours to allow annealing and the reduction of disulfides in the hinge region. Dialysis against the same buffer without DTT for 24-48 hours resulted in the formation of the inter-chain disulfide bonds.

TDBs may be alternatively produced by transfection of two plasmids, each encoding the distinct arms of the TDB, into separate host cells. The host cells may be co-cultured or cultured separately. Transfection of host cells may be performed in a 96-well plate format. To screen for TDB production, 2,000 to 3,000 clones are picked and assessed by ELISA and intact IgG homogeneous time resolved fluorescence (HTRF) for their ability to bind a selected antigen (e.g., FcRH5). Clones producing TDBs capable of binding to FcRH5, or a fragment thereof, are selected for expansion and further screening. Top clones are selected for further analysis based on percent bispecific antibodies (bsAbs) produced, titer, and PQ.

5. Exemplary Production Methods

In one example, using this strategy, FcRH5 TDBs were produced by a co-culture strategy using *E. coli* cells expressing one half-antibody (hole) and *E. coli* cells expressing the second half-antibody (knob) were grown together in shaker flasks at a predetermined ratio such that it produced similar amounts of each half-antibody (see, Spiess et al. *Nat. Biotechnol.* 31(8):753-8, 2013; PCT Pub. No. WO 2011/069104, which is incorporated herein by reference in its entirety). The co-cultured bacterial broth was then harvested, the cells disrupted in a microfluidizer and the antibodies purified by Protein A affinity. It has been observed that during microfluidizing and protein A capture the two arms annealed and formed the hinge inter-chain disulfide bridges.

In another example, full-length bispecific antibodies were produced as previously described (Junttila et al. *Cancer Res.* 74:5561-5571, 2014; Sun et al. *Science Trans. Med.* 7:287ra270, 2015). Briefly, the two half-antibodies (e.g., anti-FcRH5 (e.g., optimized variants of 1G7) and anti-CD3 (e.g., 38E4.v1)) containing "knob" or "hole" mutations in their CH3 domains were expressed by transient transfection of CHO cells and then affinity purified with Protein A. Equal amounts of the two half-antibodies were incubated with a 200 molar excess of reduced glutathione at pH 8.5 overnight at 32° C. to drive the formation of the knob-hole disulfide bonds. The assembled bispecific antibody (e.g., FcRH5 TDB) was purified from contaminants through hydrophobic interaction chromatography. The purified FcRH5 TDBs were characterized for purity by mass spectrometry, size exclusion chromatography (SEC), and gel electrophoresis.

b. Purification of FcRH5 TDBs

The FcRH5 TDBs were purified from contaminants by hydrophobic interaction chromatography (HIC). The resulting material was analyzed for endotoxin levels using an Endosafe portable test system, and, when needed, the endotoxin content was reduced by washing the protein with 0.1% Triton X-114. The molecular weights of the TDBs were analyzed by mass spectrometry (LC-ESI/TCF) as described before (Jackman et al. *The Journal of Biological Chemistry*. 285:20850-9, 2010). FcRH5 TDBs were also analyzed by analytical size exclusion chromatography on a Zenix SEC-300 column (Sepax Technologies USA) using an Agilent 1:100 HPLC system. The presence of residual antibody fragments were quantified by electrophoresis using a 2100 Bioanalyzer and a Protein 230 Chip.

c. Labelled Antibodies

All directly labeled antibodies for flow cytometry, except ones otherwise mentioned, were purchased from BD Bioscience. Anti-human PD-1 was purchased from Affymetrix. Goat anti-human IgG and goat anti-mouse IgG were purchased from Jackson Immunoresearch. Anti-PC-FITC (clone Vs38c) was purchased from DAKO. SLP-76 antibody for Western Blot was purchased from Cell Signaling Technology. The p-SLP76 (Ser376) was generated at Genentech, Inc.

For detection of FcRH5 from multiple myeloma (MM) samples and healthy donor plasma and B cells by FACS, anti-FcRH5 antibody 1G7 was labeled with PE by Southern Biotec. For microscopy, the TDBs were labeled with Alexa Fluor 647 using the appropriate protein labeling kit (ThermoFisher) according to the manufacturer's instructions. TDBs were dialyzed into PBS, pH 7.2 prior to labelling and a dye/protein ratio of 4 was routinely achieved.

B. Molecular Stability Assays

To assess molecular stability of the FcRH5 TDBs thermal stress tests were conducted at 30° C. to 40° C. over four weeks. The FcRH5 TDBs were incubated at 1 mg/mL in 20 mM his-acetate, 240 mM sucrose, pH 5.5, and evaluated after 2 weeks. The TDBs were evaluated for <5% change in N deamination/D isomerization, for <2.5% change in monomer loss by SEC, and for <16% in main peak loss by IEC at 2 weeks. The SEC buffer used was 0.25M KCl, 0.2M $K_3PO_4$, pH6.3. LC-MS was conducted in reduced conditions using TCEP at 60° C. for 10 minutes. LC-MS/MS analysis was conducted by RCM tryptic peptide mapping with DTT reduction, IAA capping, and pH 8.2 digestion.

An AAPH oxidation assay was conducted to evaluate <35% Trp oxidation and <1.1 Met Ox/Met256. The FcRH5 TDBs were incubated at a concentration of 1.0 mg/mL and stressed in 1 mM AAPH for 16 hours. A light oxidation assay was also conducted to evaluate Trp OX/TrpOX_ApoMabW53>0.5. For the light oxidation assay, the TDBs were incubated at a concentration of 1.0 mg/mL for 48 hours and exposed to light for 2.4 million lux hours. Oxidation was evaluated by LC-MS/MS analysis with RCM tryptic peptide mapping with DTT reduction, IAA capping, and pH 8.2 digestion.

C. Cell Culture and Stable Cell Line Generation

HEK-293T and HEK-T cells expressing the 1 G4 TCR complex and key TCR signaling components (James et al. *Nature* 487:64-69, 2012) were cultured in DMEM (Sigma Aldrich). All other cell lines were cultured in RPMI. All media was supplemented with 10% heat inactivated FBS (Life Technologies), 1 mM HEPES (Lonza), 2 mM glutamine, 100 U/ml penicillin and 100 µg/ml Streptomycin (Sigma Aldrich).

To evaluate the immunological synapse formation, SVT2 cells were infected with either retrovirus encoding full-length FcRH5 having an N-terminal gD tag or virus encoding a truncated FcRH5 (i.e., FcRH5 including a deletion of amino acids 1-744) having an N-terminal gD tag. To evaluate the target dependency of FcRH5 TDB killing, FOX-NY cells were infected with lentivirus encoding full-length FcRH5. Single cell derived clones with differential expression levels of FcRH5 were then selected with 2 µg/ml puromycin.

To evaluate the effect of PD-1/PD-L1 signaling on FcRH5 TDB activity, 293 cells were infected with lentivirus encoding FcRH5 followed by transfection of a plasmid encoding human PD-L1 using Lipofectamine (Invitrogen).

D. Radioligand Cell Binding Assay

The anti-FcRH5 1G7.v85 antibody was iodinated using the Iodogen method to a specific activity of 20 µCi/µg. Competition reaction mixtures containing a fixed concentration of iodinated antibody and decreasing concentrations of serially diluted, unlabeled antibody were placed into 96-well plates. The cell lines expressing endogenous human FcRH5 (e.g., MOLP-2, RI-1, KARPAS 620, and KMS21-BM) were washed with binding buffer, which consisted of Dulbecco's Modified Eagle Medium (DMEM) with 2% fetal bovine serum (FBS), 50 mM HEPES (pH 7.2), and 0.1% sodium azide and then added to the 96-well plates. The competition reactions with cells were assayed in triplicate for each concentration of unlabeled antibody and incubated for two hours at room temperature. After the two-hour incubation, the competition reactions were transferred to a Millipore Multiscreen filter plate (Billerica, Mass.) and washed four times with binding buffer to separate the free from the bound iodinated antibody. The air-dried filters were counted on a Wallac Wizard 2470 gamma counter (PerkinElmer Life and Analytical Sciences Inc.; Wellesley, Mass.) and the binding data were evaluated using NewLigand software (Genentech), which uses the fitting algorithm of Munson and Robard to determine the binding affinity of the antibody (Munson et al. *Anal. Biochem.* 107:22-39, 1980).

E. Vectors and Transient Transfection for Microscopy

FcRH5 having an N-terminal gD tag was fused to the fluorescent protein mRuby2 by first inserting FcRH5 into the pHR-SIN lentiviral vector, before ligating the mRuby2 DNA sequence into this vector, thereby creating pHR-FcRH5-mRuby2. The SFFV promoter in this vector was subsequently replaced with the mHSP promoter, creating pHRI-FcRH5-mRuby2, which utilizes a weaker promoter than pHR, allowing more physiological expression levels of FcRH5-Ruby. Vectors expressing LCK, ZAP70, CSK/CBP, and CD45 have been described previously (James et al. *Nature.* 487:64-69, 2012). The CD45 construct used was either the RO isoform or a construct containing the cytoplasmic domain of CD45 with the transmembrane and extracellular domains of CD43, which is known to mimic the function of CD45. Prior to transfecting constructs, HEK cells were seeded to approximately 60% confluency in 6-well plates. Vectors were then transiently transfected at appropriate ratios using GeneJuice (Novagen), following the manufacturer's instructions. Cells were used in experiments 24-48 hours after transfection.

F. Microscopy Imaging and Analysis

To image cell conjugates, $3 \times 10^5$ cells of each cell type to be imaged were harvested from culture and resuspended in 100 µl of 20 nM TDB in RPMI-1640 (without Phenol-red). After a 20-30 min incubation to allow cell conjugation, cells were washed with PBS, resuspended in DMEM$^{gfp2}$ imaging medium (Evrogen) and added to 35 mm imaging dishes (Mattek). An Andor spinning disc confocal microscope system was used to image the cells at 37° C. All images were analyzed and all presented images were manipulated in an equivalent manner using ImageJ. Presented images were background subtracted and then cropped to focus on the pair of cells and the contrast was optimized. The degree of protein clustering and segregation was determined by using the intensity of fluorescently labelled proteins in the plasma membrane. The plasma membrane was selected by manually drawing a line and the average fluorescence intensity of the plasma membrane within the cell-cell interface was divided by the average fluorescence intensity of the plasma membrane outside the cell-cell interface to calculate the degree of clustering or segregation. To generate an image of the interface of a pair of cells conjugated by TDBs from a z-stack, the image stack was first deconvolved and then cropped to highlight the interface region using Huygens software.

G. In Vitro Cytotoxicity and T Cell Activation Assays

Target cells were labeled with carboxyfluorescein succinimidyl ester (CFSE) according to manufacturer's protocol (Life Technology, #C34554). The CFSE-labeled target cells and purified CD8+ cells were mixed in 3:1 effector cell to target cell (E:T) ratio and incubated with TDB for 48 hours. At the end of the incubation, the cells were analyzed with flow cytometry on a FACSCalibur in automation format. The number of live target cells was counted by gating on CFSE+/PI-negative cells. The percentage of cytotoxicity was calculated as follows: % cytotoxicity (live target cell number w/o TDB–live target cell number w/TDB)/(live target cell number w/o TDB)×100.

a. In Vitro Cytotoxicity Assay Cell Lines

Peripheral blood mononuclear cells (PBMC) and CD8+ separation, Cell Titer Glo (Promega), and flow cytometry-based viability assays (48h) were conducted as previously described in Junttila et al. *Cancer Res.* 74:5561-5571, 2014. CD8+ cell were used as effectors in a 3:1 effector:target ratio.

b. Human Plasma Cells and Primary Multiple Myeloma Samples

Human bone marrow aspirate of healthy donors (ALL-CELLS) were diluted in PBS and bone marrow mononuclear cells (BMMCs) were isolated by conventional gradient separation (Lymphoprep, STEMCELL). A flow cytometry viability assay was used to test the effect of 72h FcRH5 TDB treatment on BMMC plasma cells. Frozen human BMMCs from MM patients were purchased from Conversant Bio. Myeloma BMMCs were mixed with freshly isolated healthy donor CD8+ T cells and the co-culture was treated with FcRH5 TDB for 72h. PI-negative CD38+CD138+ cells were counted by flow cytometry.

H. T Cell Activation and Proliferation Assays

The T cell activation assay has been previously described in Junttila et al. *Cancer Res.* 74:5561-5571, 2014. Freshly isolated CD8+ T cells were labeled with CFSE and mixed with target cells (e.g., MOLP-2 cells) *in* 1:1 ratio and co-cultured with 1 µg/ml TDB for 48 hours or five days. Cells were stained with anti-CD8-APC (BD Bioscience, #555634), anti-CD69-PE (BD Bioscience, #555531), and/or anti-CD25-APC (BD Bioscience, #555434) and the dilution of fluorescence intensity of CFSE was analyzed by flow cytometry.

I. Flow Cytometry Analysis for Cyno Plasma Cells

Cyno bone marrow aspirates were diluted (1:10) into ACK lysis buffer (Life Technology, #AI 0492) twice. Cyno bone marrow cells were stained with anti-CD45, anti-CD20, and anti-CD38. After wash, cells were fixed and permeabilized with IntraStain kit (DAKO). Cells then were stained with anti-PC (Clone Vs38c). The cyno plasma cells were classified by flow cytometry as CD45-CD20-CD38+PC+.

J. ELISA Analysis for Cyno IgG Level

Total cyno serum IgG was quantified using standard colorimetric based sandwiched ELISA. A goat anti-monkey IgG (Bethyl A140-202A) and a horseradish peroxidase (HRP) conjugated goat anti-monkey IgG (Bethyl A140-202P) were used as the capture and detection antibody, respectively. Cyno IgG (Cell Sciences CS120163A) was used as the protein quantification standard.

K. Western Blot Analysis

Freshly isolated human CD8+ T cells and 293T-FcRH5 cells (2:1 ratio) were treated with 1 μg/ml of 1G7.v85/38E4.v1 ("1G7.v85 TDB"), 10A8/38E4.v1 ("10A8 TDB"), or anti-gD/38E4.v1 ("anti-gD TDB") TDB and washed in phosphate-buffered saline (PBS) at 4° C. and lysed with RIPA lysis buffer (Cell Signaling Technology). pSLP76 (Ser376) and SLP76 were detected using standard Western blot methods and antibodies.

Results

A. Binding Affinity of FcRH5 TDBs

Figure 8:
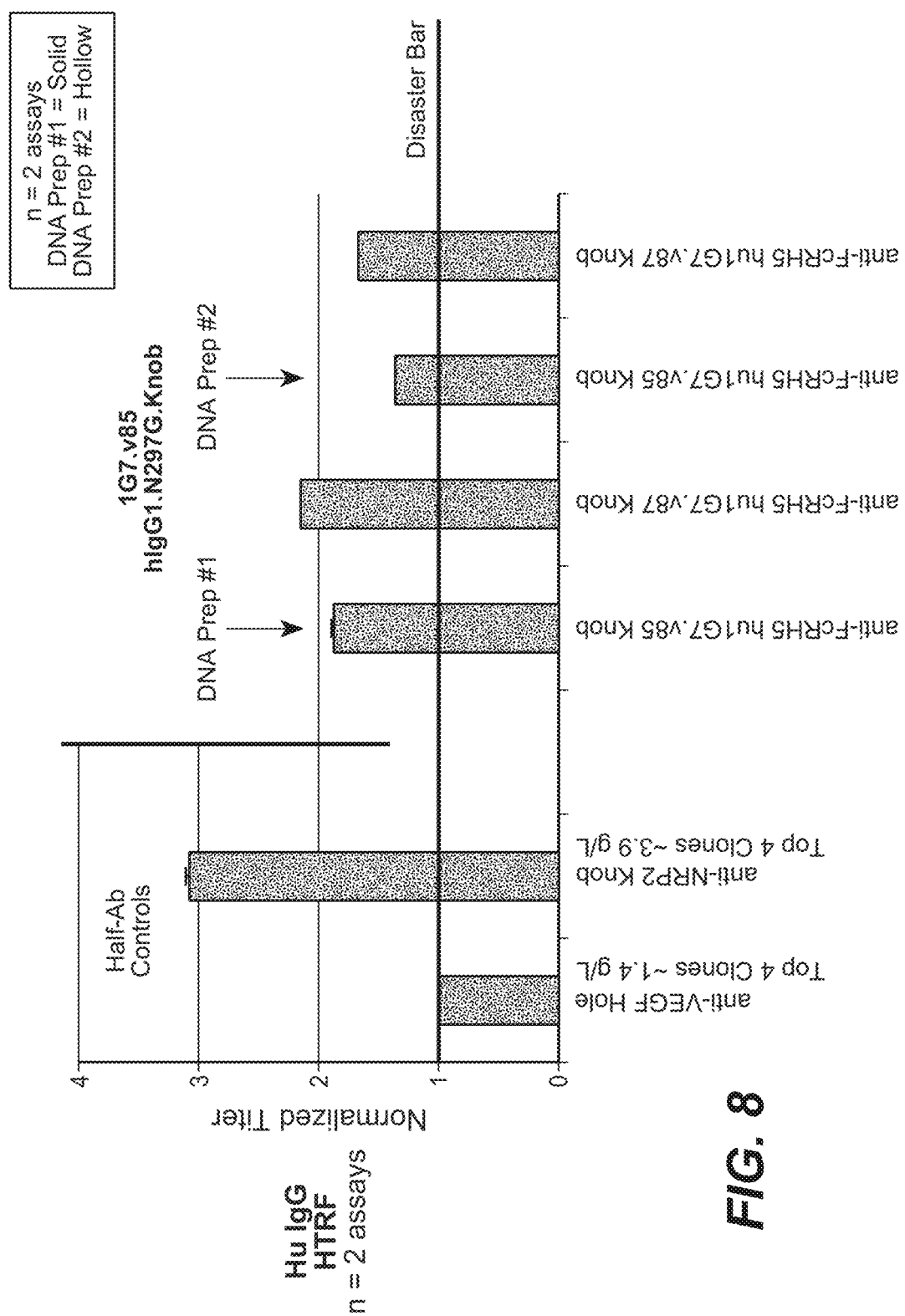
FIG. 8 is a graph showing the antibody titer of 1G7.v85 and 1G7.v87 antibodies.

Among the FcRH5 TDBs produced were molecules comprising clone 1G7 as the FcRH5-binding domain and selected clones as the CD3-binding domain, including 38E4.v1, 40G5c, and 38.E4.v11. Antibodies hu1G7.v1.1 ("1G7.v1.1 TDB"), hu1G7.v1.2 ("1G7.v1.2 TDB"), hu1G7.v1.3 ("1G7.v1.3 TDB"), hu1G7.v1.4 ("1G7.v1.4 TDB"), hu1G7.v1.5 ("1G7.v1.5 TDB"), hu1G7.v1.7 ("1G7.v1.7 TDB"), hu1G7.v1.13 ("1G7.v1.13 TDB"), and hu1G7.v1.13.1 ("1G7.v1.13.1 TDB") were generated as FcRH5 TDBs with an anti-CD3 38E4.v1 arm and determined by BIACORE®, generally as described herein, to have high affinity for soluble FcRH5 protein fragment (Table 8). Expression tests of 1G7.v85 and 1G7.v87 in half-antibody formats including "knob" mutants gave a titer above the disaster bar (FIG. 8).

TABLE 8

Affinity evaluation of eight selected affinity matured variants in TDB format

| Variable region category | Antibody | $K_D$ |
|---|---|---|
| Parental (murine variable region) | 1G7 TDB (mean, n = 3) | 5.4 nM |
| Site-directed mutagenesis of 1G7.v1 | 1G7.v1.1 TDB | 2.7 nM |
| | 1G7.v1.2 TDB | 2.6 nM |
| | 1G7.v1.3 TDB | 1.5 nM |
| | 1G7.v1.4 TDB | 1.4 nM |
| Focused phage antibody library (Library template = 1 G7.v1) | 1G7.v1.5 TDB | 1.1 nM |
| | 1G7.v1.7 TDB | 0.6 nM |
| | 1G7.v1.13 TDB | 1.2 nM |
| | 1G7.v1.13.1 TDB | 0.9 nM |

B. Binding and Cross Reactivity of FcRH5 TDBs

Human FcRH5, cyno FcRH5, human FcRH1, FcRH2, FcRH3, and FcRH4 transfected mouse SVT2 cells were used to test binding and cross-reactivity of FcRH5 TDBs. The method was carried out as follows. Cultured SVT2 cells were lifted using non-enzyme cell dissociation buffer (Sigma, #C5914). 1×10⁵ cells were suspended in 100 μL and incubated with FcRH5 TDBs at 3 μg/ml. Cells were then washed with FACS buffer (PBS, 1% BSA, 2 mM EDTA) and incubated with goat-anti-human Fc PE (Jackson Immunoresearch, #109-116-170) at a 1:100 dilution. Cells were washed twice with FACS buffer before flow cytometry analysis was carried out on a FACSCalibur.

Figures 9A, 9B:
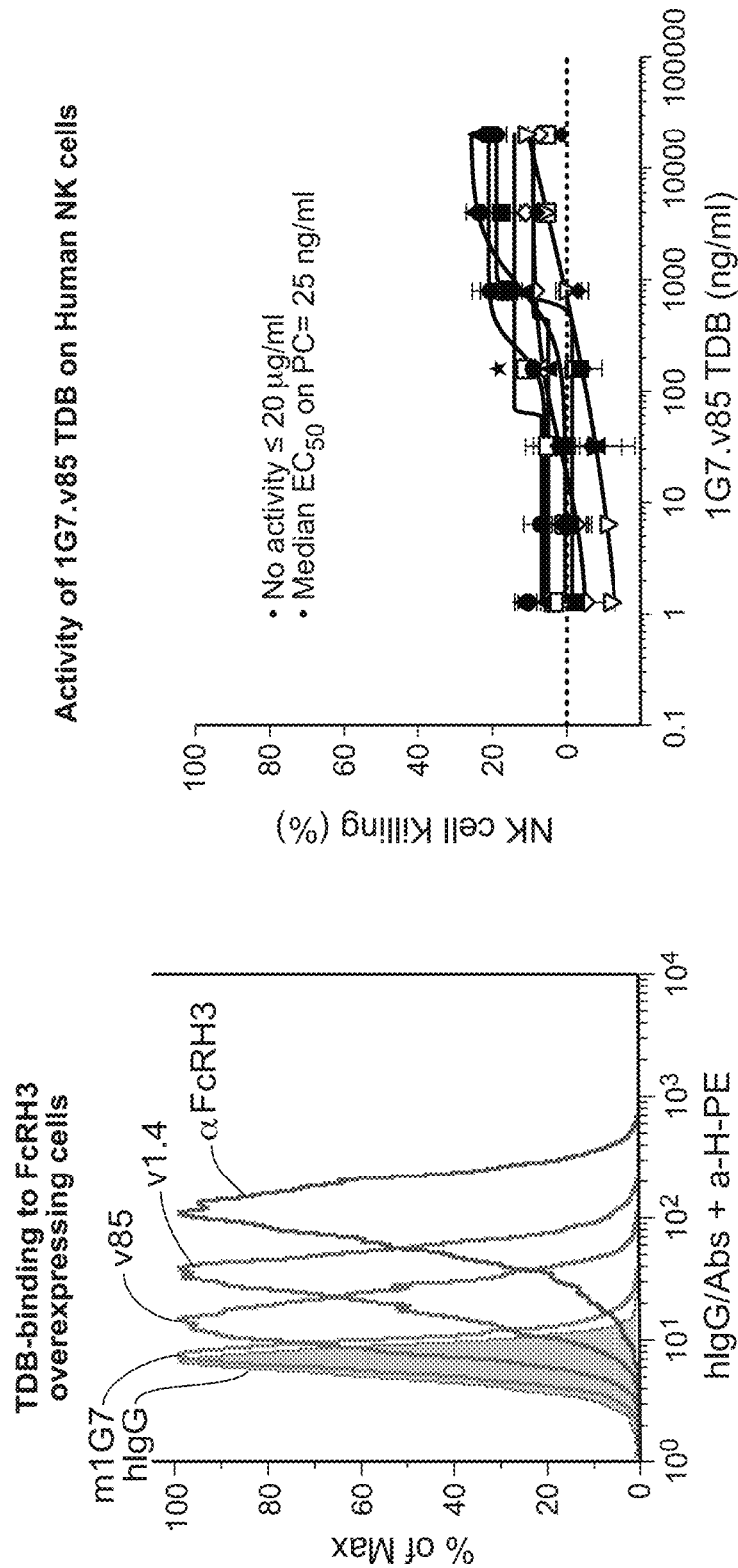
FIG. 9A is an overlay of histograms comparing the binding of FcRH5/38E4.v1 TDBs having different anti-FcRH5 arms (i.e., m1G7 ("1G7 TDB"), 1G7.v85 ("1G7.v85 TDB"), and 1G7.v1.4 ("1G7.v1.4 TDB")) to FcRH3-overexpressing cells.
FIG. 9B is a graph showing that the 1G7.v85 TDB does not deplete natural killer (NK) cells at concentrations of ≤20 μg/mL; 1G7.v85 TDB has a median EC50 of 25 ng/mL on plasma cells (PCs).
Figure 10A:
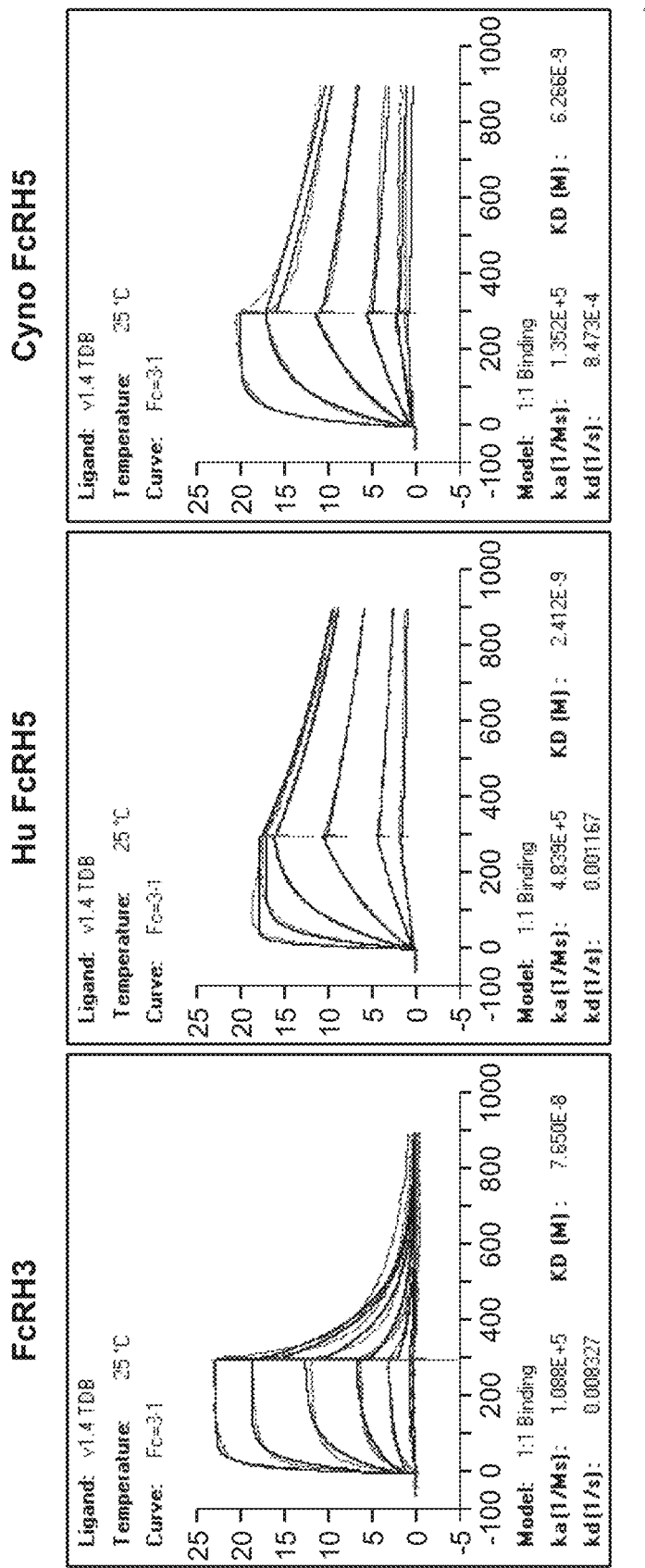
FIG. 10A is a series of graphs comparing the ability of the FcRH5 TDB 1G7.v1.4/38E4.v1 ("1G7.v1.4 TDB") to bind FcRH3, human FcRH5, and cyno FcRH5.
Figure 10B:
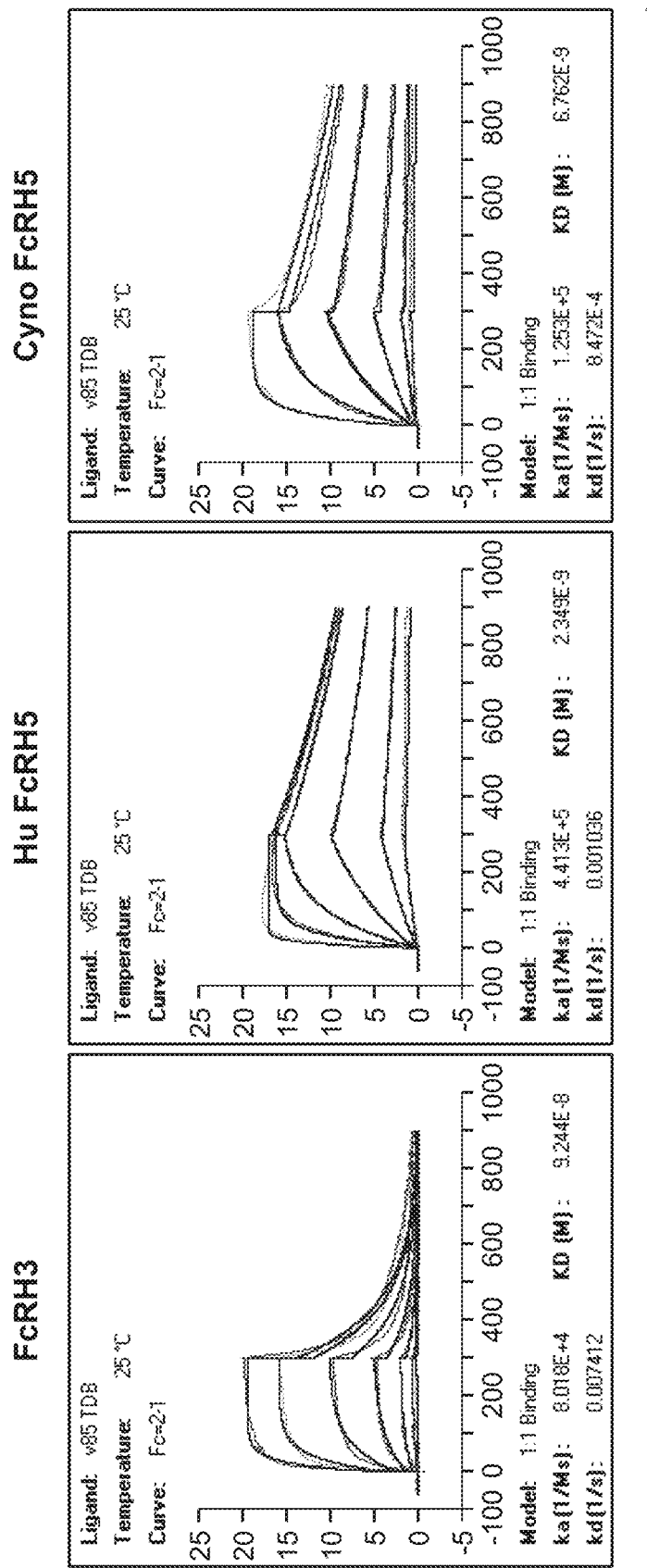
FIG. 10B is a series of graphs comparing the ability of the 1G7.v85 TDB to bind FcRH3, human FcRH5, and cyno FcRH5.
Figure 10C:
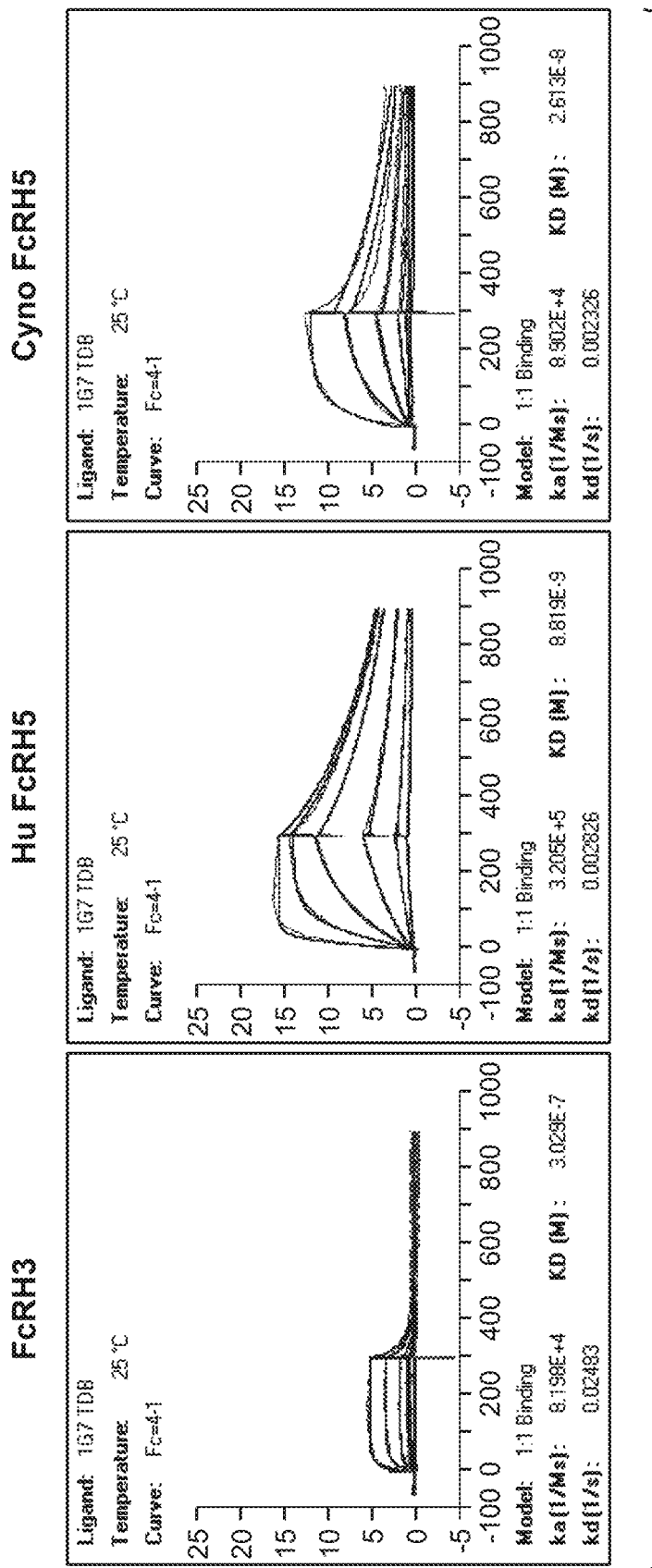
FIG. 10C is a series of graphs comparing the ability of the FcRH5 TDB 1G7/38E4.v1 ("1G7 TDB") to bind FcRH3, human FcRH5, and cyno FcRH5.
Figure 10D:
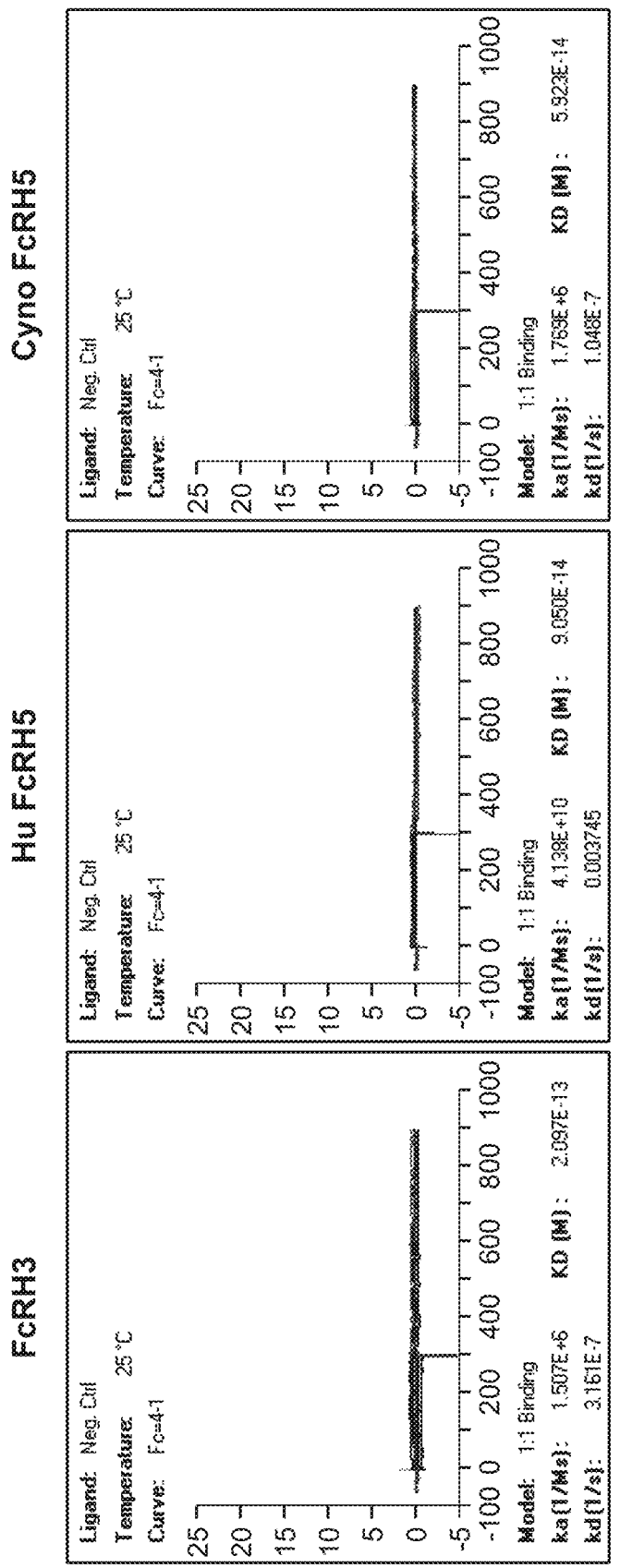
FIG. 10D is a series of graphs comparing the ability of a control antibody to bind FcRH3, human FcRH5, and cyno FcRH5.
Figure 11A:
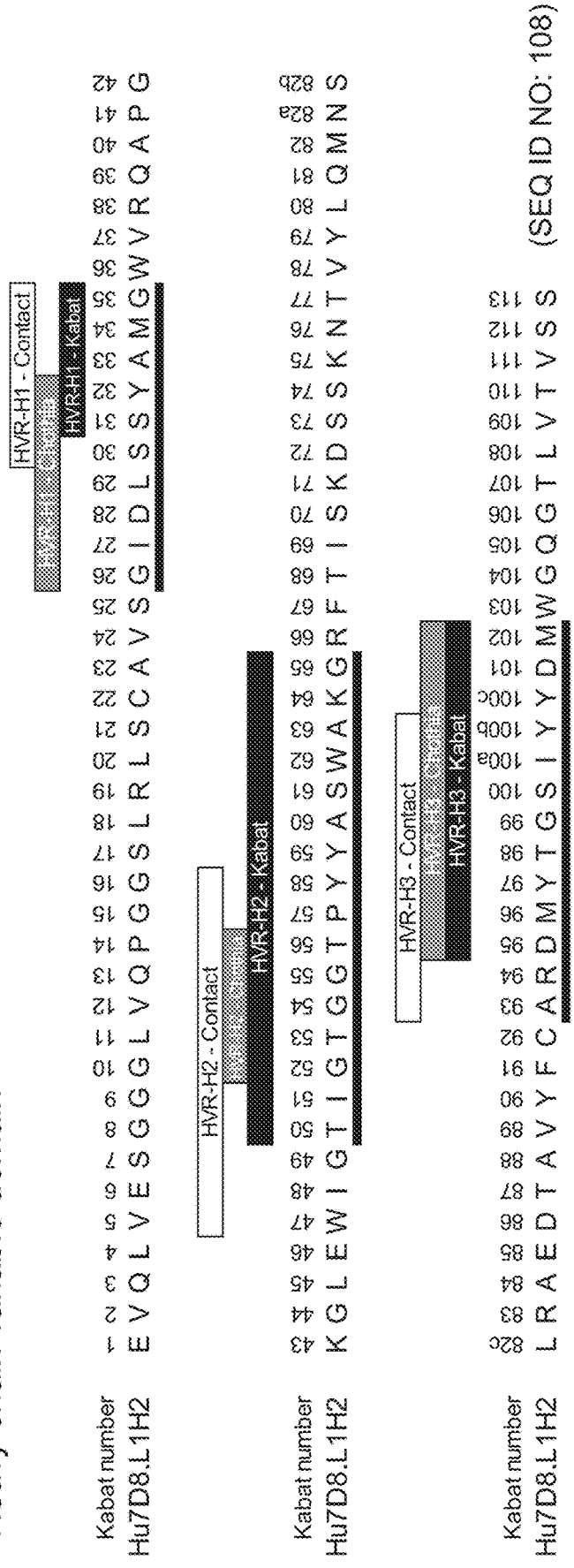
FIG. 11A shows the sequence of the heavy chain variable (VH) domain sequence of humanized, rabbit-derived anti-FcRH5 antibody hu7D8.L1H2. The VH domain sequence of hu7D8.L1H2 is disclosed as SEQ ID NO: 108.
Figure 12A:
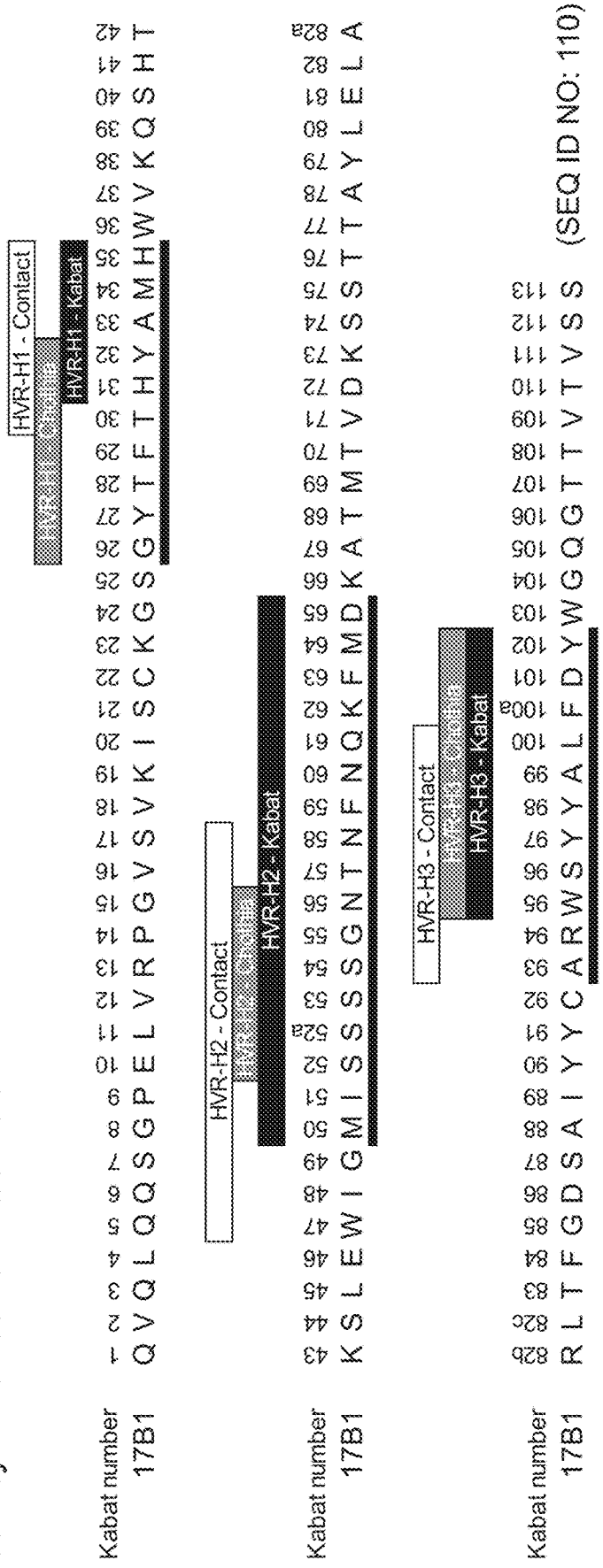
FIG. 12A shows the sequence of the heavy chain variable (VH) domain sequences of mouse-derived anti-FcRH5 antibody 17B1. The VH domain sequences of 17B1 is disclosed as SEQ ID NO: 110.
Figure 13A:
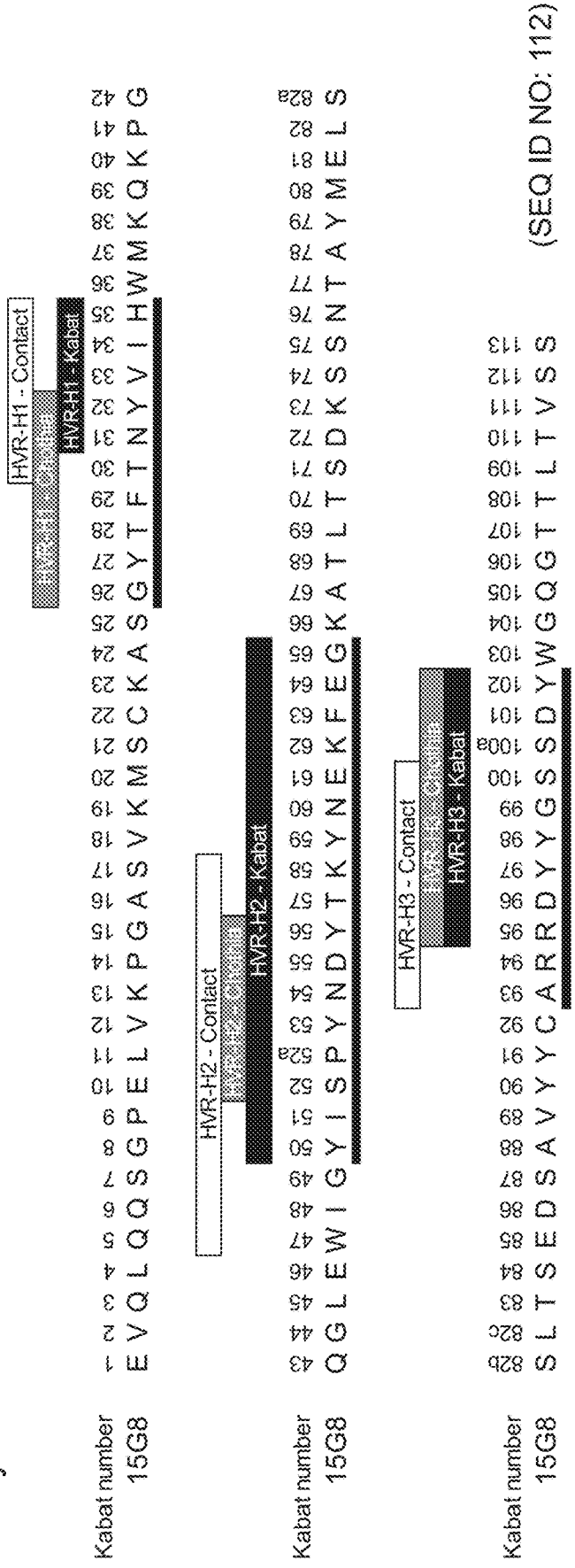
FIG. 13A shows the sequence of the heavy chain variable (VH) domain sequences of mouse-derived anti-FcRH5 antibody 15G8. The VH domain sequence of 15G8 is disclosed as SEQ ID NO: 112.

After humanization and affinity maturation of murine 1G7, eight affinity matured variants in TDB format were generated. The optimized 1G7 TDBs were generated in "knob-into-hole" format with 38E4.v1 as an anti-CD3 arm. All eight variants showed a 5- to 15-fold increased affinity over the murine 1G7 TDB by BIACORE® in the TDB format (Table 8). All variants demonstrated negative binding to FcRH1 or FcRH4, with different degrees of positive binding to FcRH2 or FcRH3. The 1G7.v1.4 TDB showed the least cross-reactivity to FcRH2 and FcRH3 (Table 9). Binding of FcRH5 TDBs containing different anti-FcRH5 arms (i.e., 1G7, 1G7.v85, or 1G7.v1.4) to FcRH3 was also evaluated by FACS (FIG. 9A).

TABLE 9

FcRH5 TDB Binding and Cross-reactivity

| TDB | SVT2-FcRH1 | SVT2-FcRH2 | SVT2-FcRH3 | SVT2-FcRH4 | SVT2-FcRH5 | SVT2-Cyno-FcRH5 |
|---|---|---|---|---|---|---|
| 1G7 | − | − | − | − | + | + |
| 1G7.v1.1 | − | + | + | − | ++ | ++ |
| 1G7.v1.2 | − | +/− | + | − | ++ | ++ |
| 1G7.v1.3 | − | + | + | − | ++ | ++ |
| 1G7.v1.4 | − | +/− | +/− | − | ++ | ++ |
| 1G7.v1.5 | − | + | + | − | ++ | ++ |
| 1G7.v1.13 | − | + | + | − | ++ | ++ |
| 1G7.v1.7 | − | + | + | − | ++ | ++ |
| 1G7.v1.13.1 | − | +/− | + | − | ++ | ++ |

Figure 14:
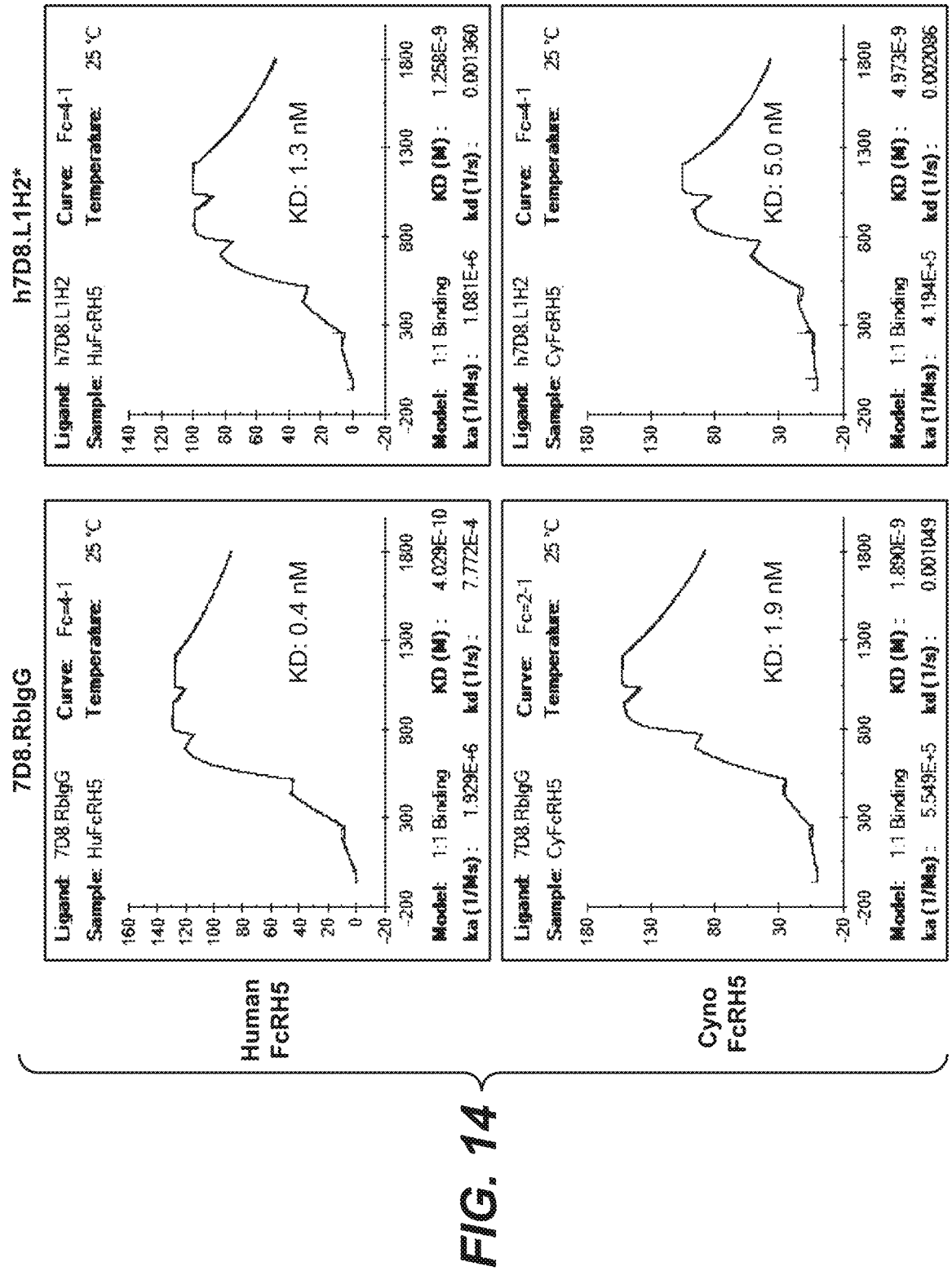
FIG. 14 is a series of graphs showing the binding affinity of humanized variant of rabbit-derived anti-FcRH5 antibodies 7D8.Rb and h7D8.L1H2 to human FcRH5 and cyno FcRH5.

The abilities of 1G7.v1.4, 1G7.v85, and 1G7 TDBs to bind huFcRH5 and huFcRH3 were evaluated by BIACORE® analysis (FIGS. 10A-10D). The affinities of 1G7.v85 TDB and 1G7.v1.4 TDB were comparable. 1G7.v1.4 TDB bound to human FcRH5 and human FcRH3 with a $K_D$ of 2.4 nM and 80 nM, respectively, and 1G7.v85 TDB bound to human FcRH5 and human FcRH3 with a $K_D$ of 2.4 nM and 90 nM, respectively (FIGS. 10A-10D). Additional anti-FcRH5 variants hu7D8.L1H2, 17B1-VH66, 17B1, and 15G8 (sequences presented in FIGS. 11A-13B) were also generated in the TDB format with the anti-CD3 arm 38E4.v1. The hu7D8.L1H2, 17B1, and 15G8 TDBs were tested for binding to human and cyno FcRH5. Results are presented in FIG. 14 and in Table 4.

Comparison of 1G7.v85 TDB and 1G7.v93 TDB binding to human FcRH5 and cyno FcRH5 was conducted by BIACORE® analysis (FIG. 15). 1G7.v85 TDB exhibited a $K_D$ of 2.1 nM for binding to human FcRH5 and a $K_D$ of 7.8 nm for binding to cyno FcRH5. 1G7.v93 TDB exhibited a $K_D$ of 1.1 nM for human FcRH5 and 8.1 nm for cyno FcRH5.

Figure 16A:
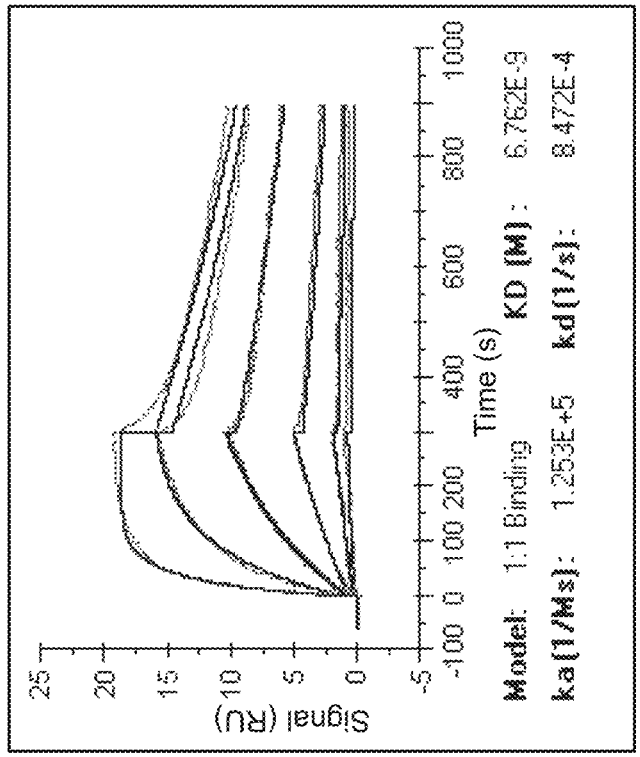
FIGS. 16A-16B are graphs showing the kinetic analysis of 1G7.v85 TDB binding to human FcRH5 and cyno FcRH5 with dissociation constants ($K_D$) of 2.35 nM and 6.76 nM, respectively, as measured by BIACORE® in an hIgG capture format using a 1:1 binding model of monovalent affinity.
Figure 16B:
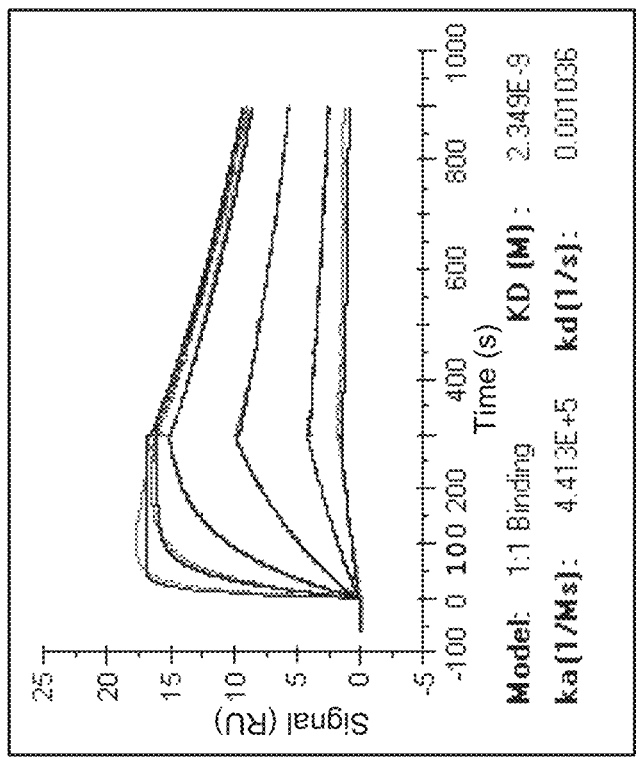

Kinetic characterization experiments were carried out (see Table 6). In these experiments, binding of soluble FcRH5 protein fragment to purified antibodies in human TDB antibody format was analyzed at six different non-zero concentrations (a 1:3 dilution series, one concentration injected twice as a replicate). Flow rate was set at 40 μl/min and association and dissociation monitored for 600 s. Kinetic analysis of monovalent 1G7.v85 TDB affinity using a hIgG capture format and 1:1 binding model produced a $K_D$ for human FcRH5 and cyno FcRH5 of 2.4 nM and 6.8 nM, respectively (FIGS. 16A-16B). Mutation of oxidation prone Met-64HC to Val in the 1G7.v85 TDB did not impact binding affinity.

C. In Vitro Cytotoxicity Assays

Figure 17A:
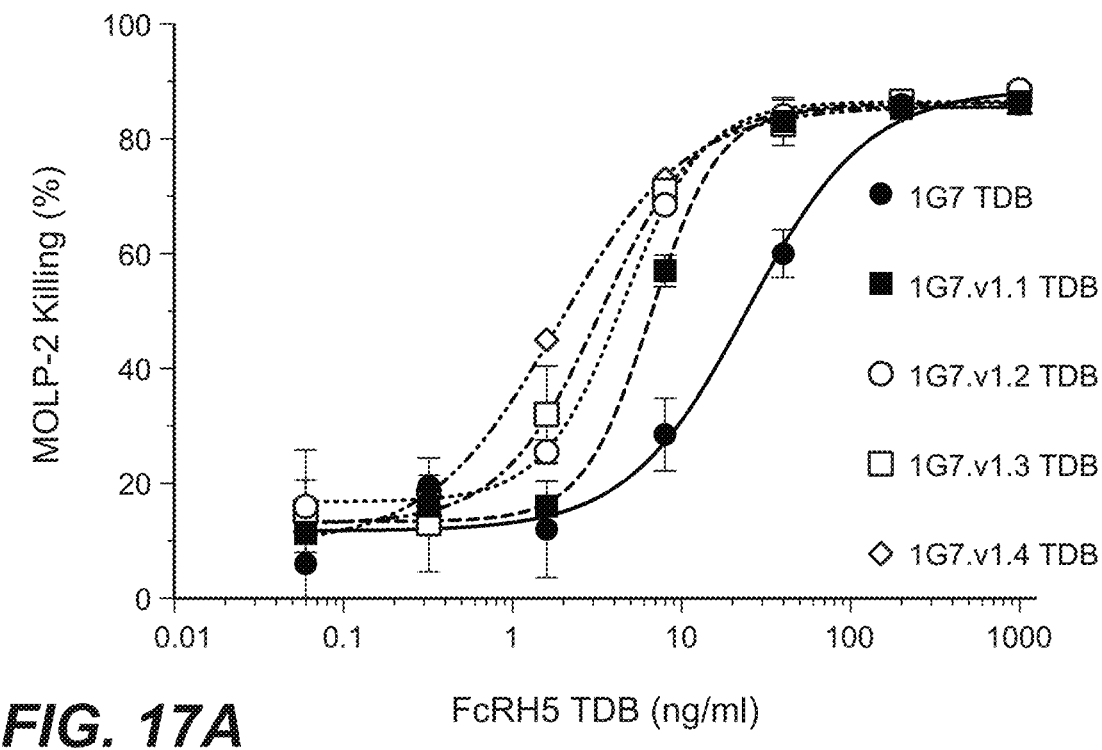
FIGS. 17A-17B are graphs demonstrating increased FcRH5-induced cell toxicity of MOLP-2 cells (i.e., human multiple myeloma cells that endogenously express FcRH5) using humanized and affinity matured variants of 1G7 formatted into T cell-dependent bispecific (TDB) antibodies having the CD3-binding arm of 38E4.v1 (see PCT Pub. No. WO 2015-095392 A1, which is incorporated by reference herein in its entirety).
Figure 17B:
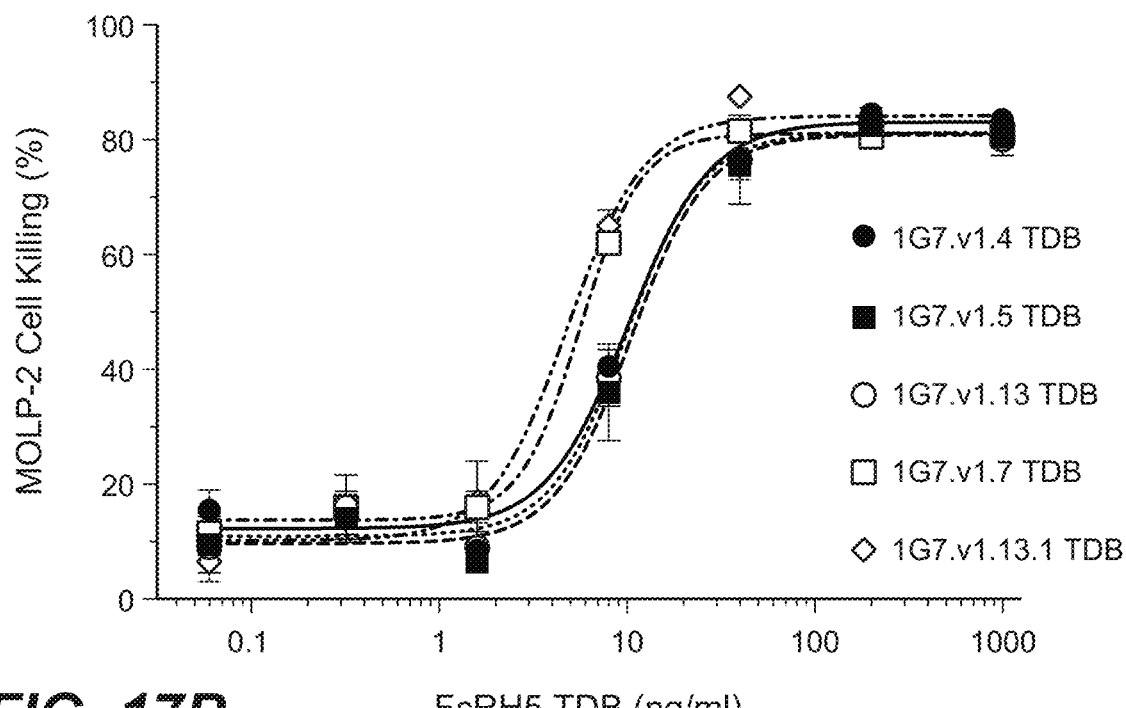

To evaluate the function of the humanized FcRH5 TDB variants, cell cytotoxicity on FcRH5 MOLP-2 cells that endogenously express FcRH5 was tested. All variants showed similar target cell killing activity but significantly increased activity compared to murine 1G7 (FIGS. 17A-17B). In the case of variant 1G7.v1.4 TDB, the EC50 improved 5- to 13-fold relative to murine 1G7 TDB (n=10).

Based on its high cytotoxic activity and low cross-reactivity to other family members, 1G7.v1.4 TDB was selected for further analysis. To increase the stability of the TDB molecule, the 1G7.v1.4 arm was mutated at potential oxidization sites, thereby generating a polished version, 1G7.v85. The two versions, 1G7.v1.4 and 1G7.v85, were evaluated in the TDB format in various assays, including T cell activation, MOLP-2 target cell killing activity, cyno B cell in vitro depletion, and cyno plasma cell depletion (FIGS. 18A-18D). In all tested assays, the 1G7.v85 TDB behaved indistinguishably from the 1G7.v1.4 TDB.

Figure 19A:
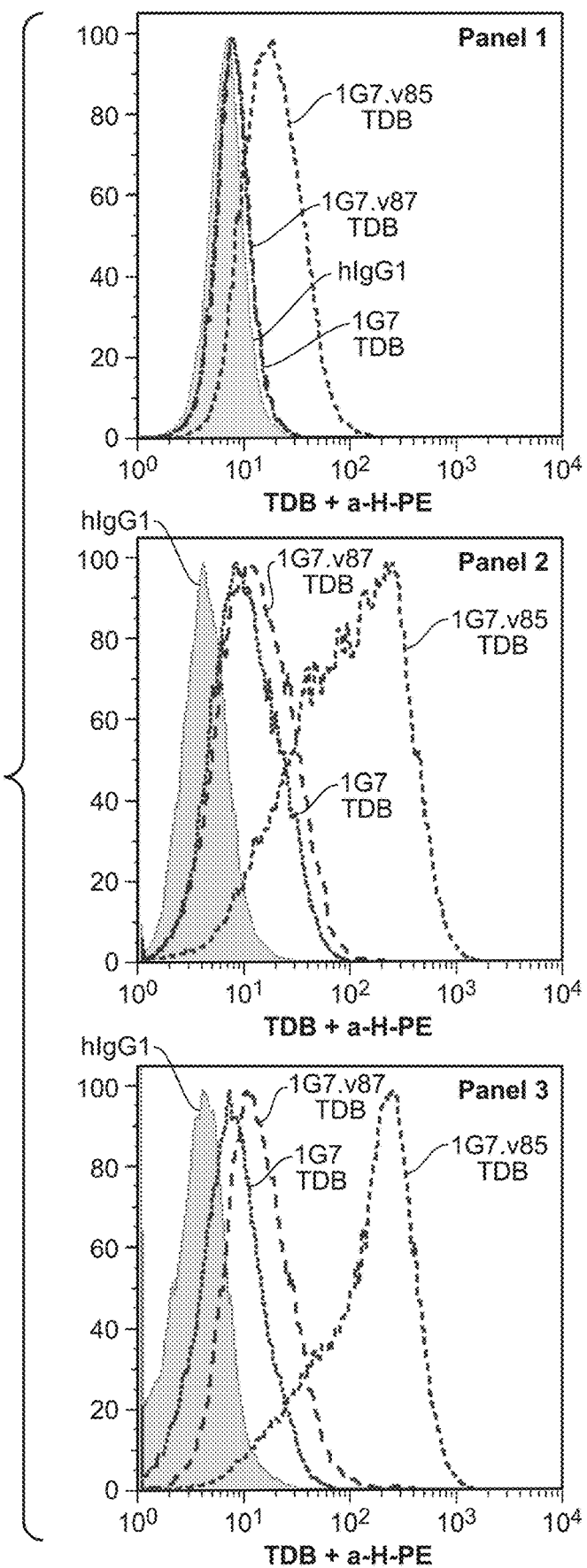
FIG. 19A is a series of histograms comparing the ability of the 1G7.v85 TDB and the hu1G7.v87/38E4.v1 TDB ("1G7.v87 TDB") to bind to and cross-react with mouse SVT2 cells expressing human FcRH5 (Panel 1), cyno FcRH5 (Panel 2), and human FcRH3 (Panel 3).

The humanized and polished 1G7.v87 TDB was also compared to the 1G7.v85 TDB. Consistent with its lower affinity, the 1G7.v87 TDB exhibited reduced binding to human FcRH5 relative to the 1G7.v85 TDB as indicated by flow cytometry analysis (FIG. 19A). 1G7.v87 also showed negative cross-reactivity to FcRH3.

Figure 19B:
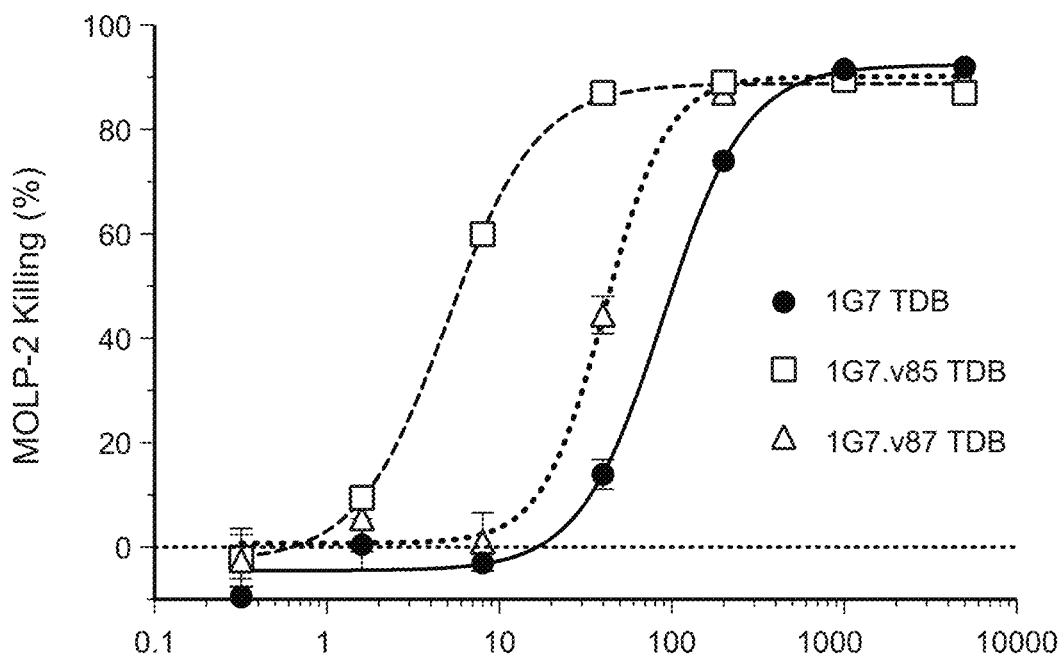
FIGS. 19B-19D are graphs comparing the ability of the 1G7.v85 TDB and the 1G7.v87 TDB to kill target MOLP-2 cells (FIG. 19B), human B cells (FIG. 19C), and cyno B cells (FIG. 19D).
Figure 19C:
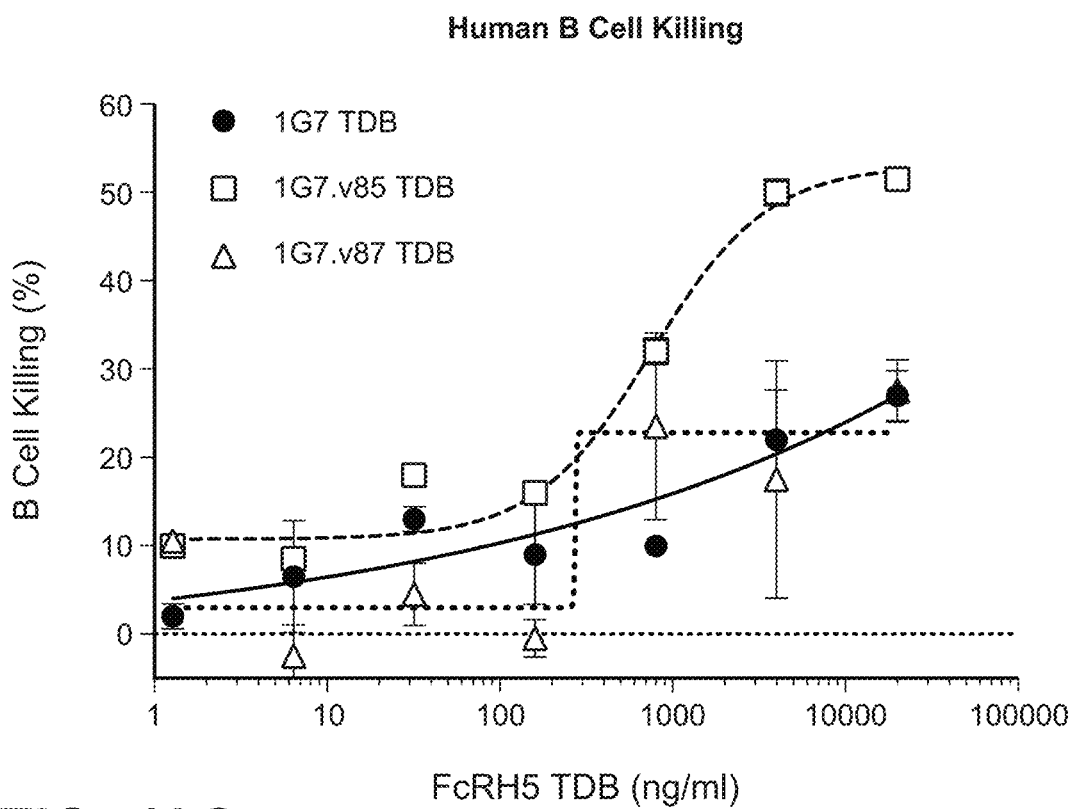
Figure 19D:
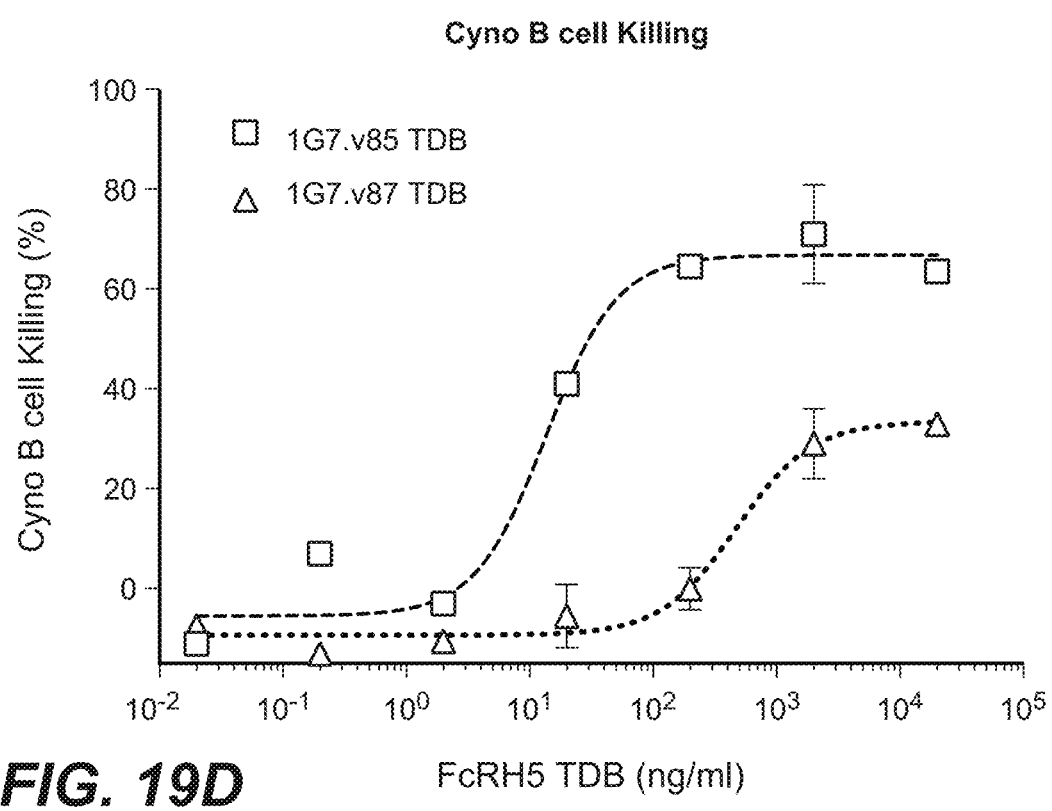
Figure 20A:
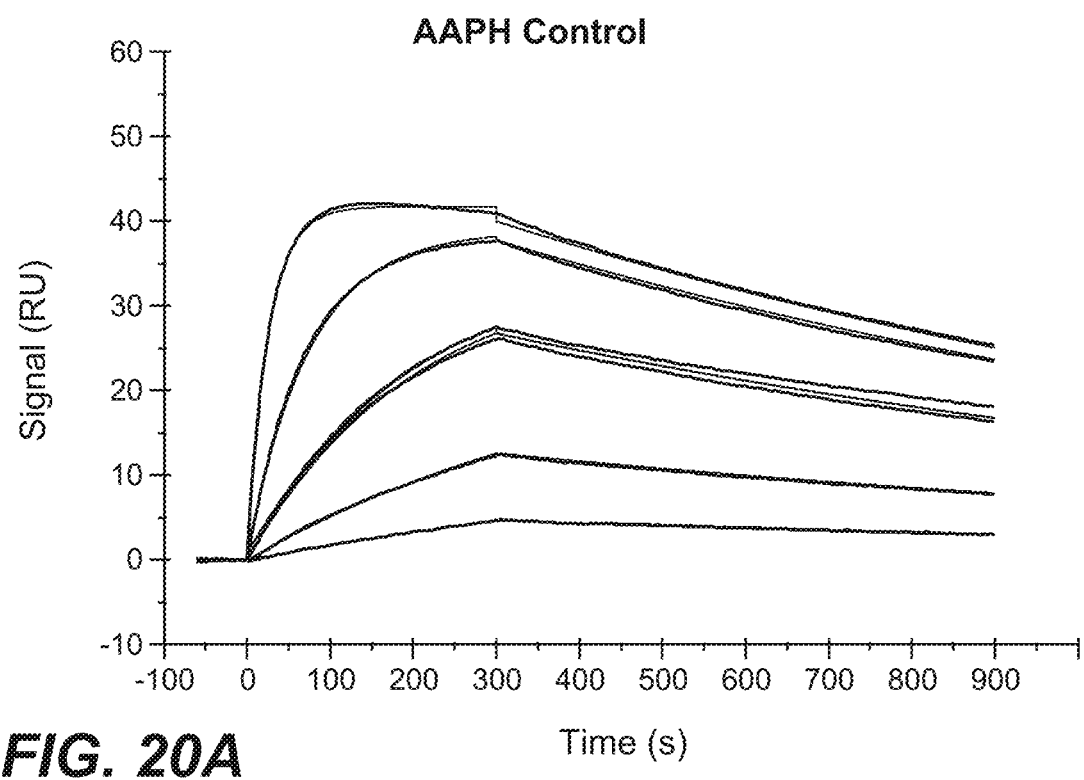
FIGS. 20A-20D are graphs showing a reduced ability of the 1G7.v85 TDB to bind FcRH5 after undergoing either a 2,2'-azobis(2-amidopropane)dihydrochloride (AAPH) stress test (FIG. 20B) or a light stress test (FIG. 20D), as compared to unstressed respective controls (FIGS. 20A and 20C).
Figure 20B:
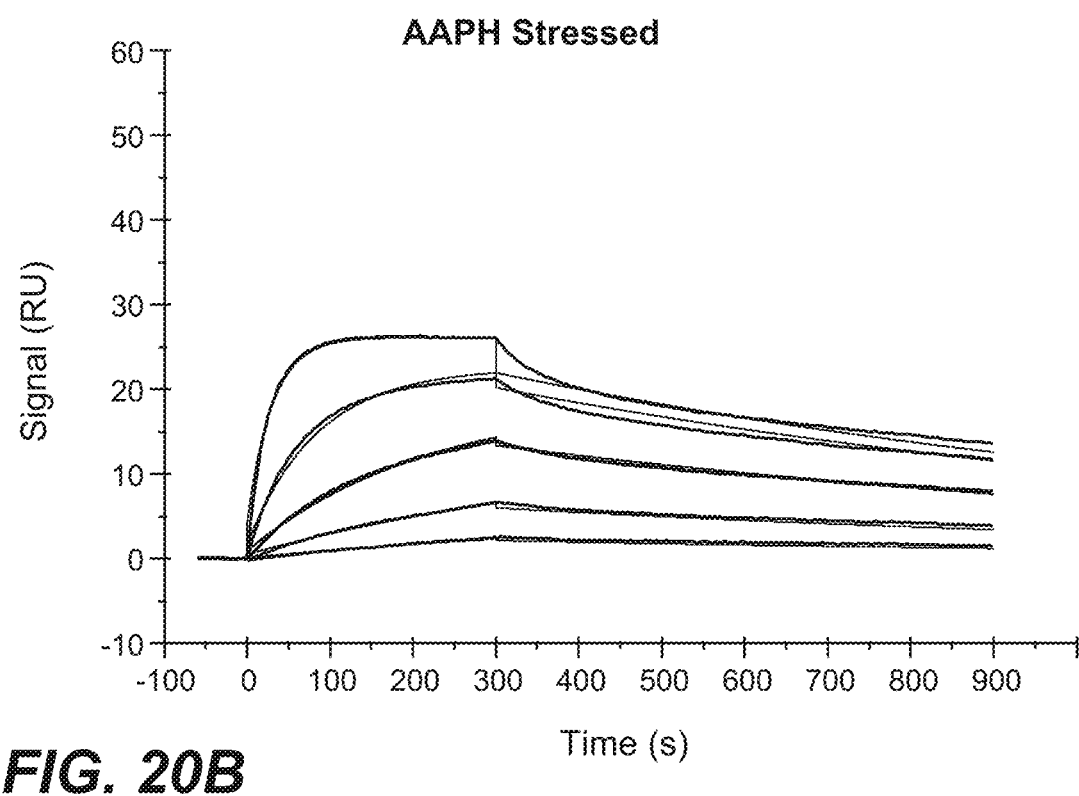
Figure 20C:
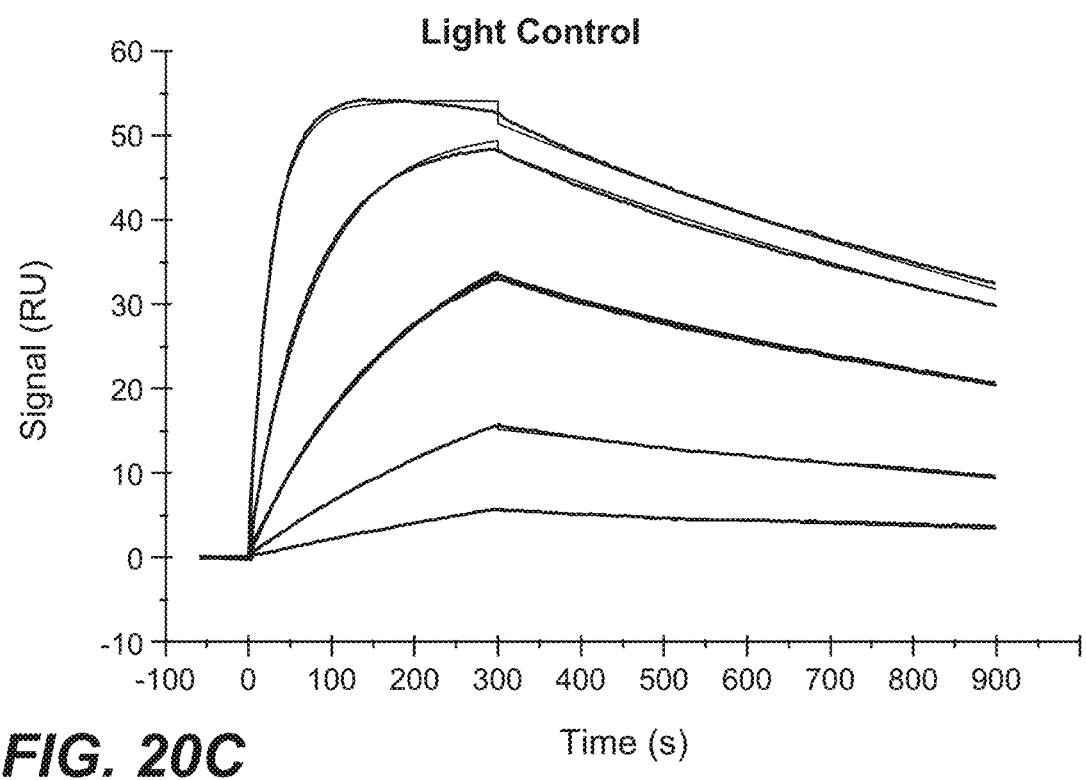
Figure 20D:
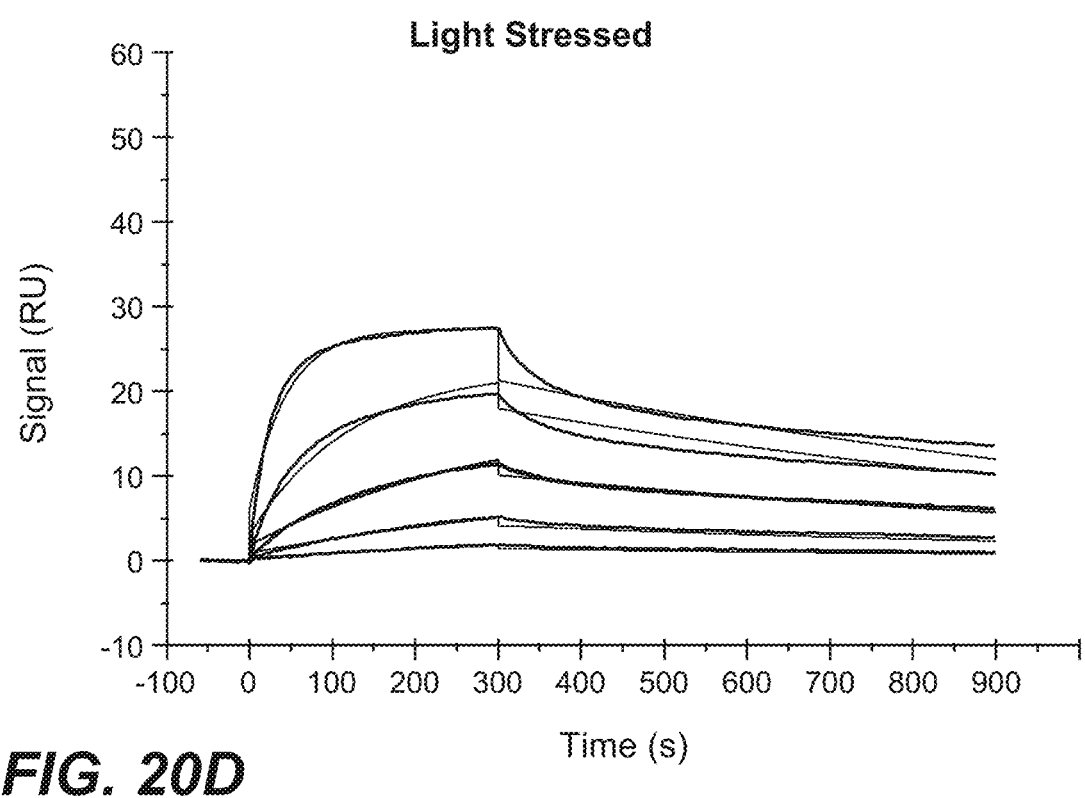

Target cell cytoxicity of the 1G7.v87 TDB and the 1G7.v85 TDB were evaluated on MOLP-2 CD8+ cells (FIG. 19B) and on PBMCs from four healthy donors (FIG. 19C). In all donors, the 1G7.v87 TDB was negative for human B cell killing, while the1 G7.v85 TDB showed some degree of positive killing activity. Cyno PBMCs from four healthy donors were also tested (FIG. 19D). The ranking of EC50's of three versions of 1G7 TDBs is consistent in all three donors. 1G7.v87 TDB is comparable to murine 1G7 TDB but has significantly less activity than the 1G7.v85 TDB. The 1G7.v87 TDB showed significantly weaker killing activity than the 1G7.v85 TDB on cyno B cells in vitro. The 1G7.v85 TDB was also evaluated for activity on human NK cells and found to have no killing activity ≤20 µg/mL (FIG. 9B). The EC50 of the 1G7.v85 TDB was 5- to 8-fold better than that of the 1G7.v87 TDB.

D. Molecular Assessment of Stability of FcRH5 TDBs

Figure 21A:
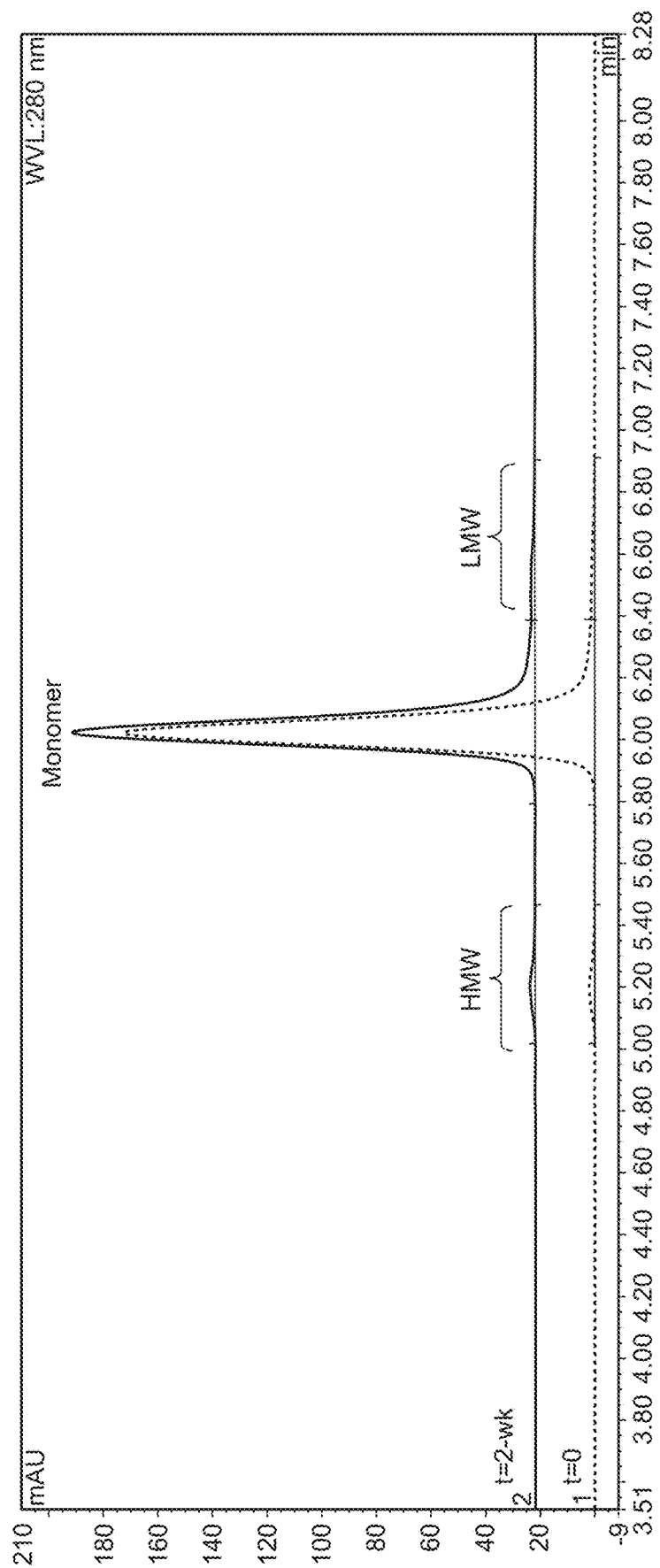
FIG. 21A is graph showing size distribution analysis of the 1G7.v85 TDB. The 1G7.v85 TDB lost 0.1% of the monomer peak after two weeks of stress in a his-acetate solution at pH 5.5.
Figure 21B:
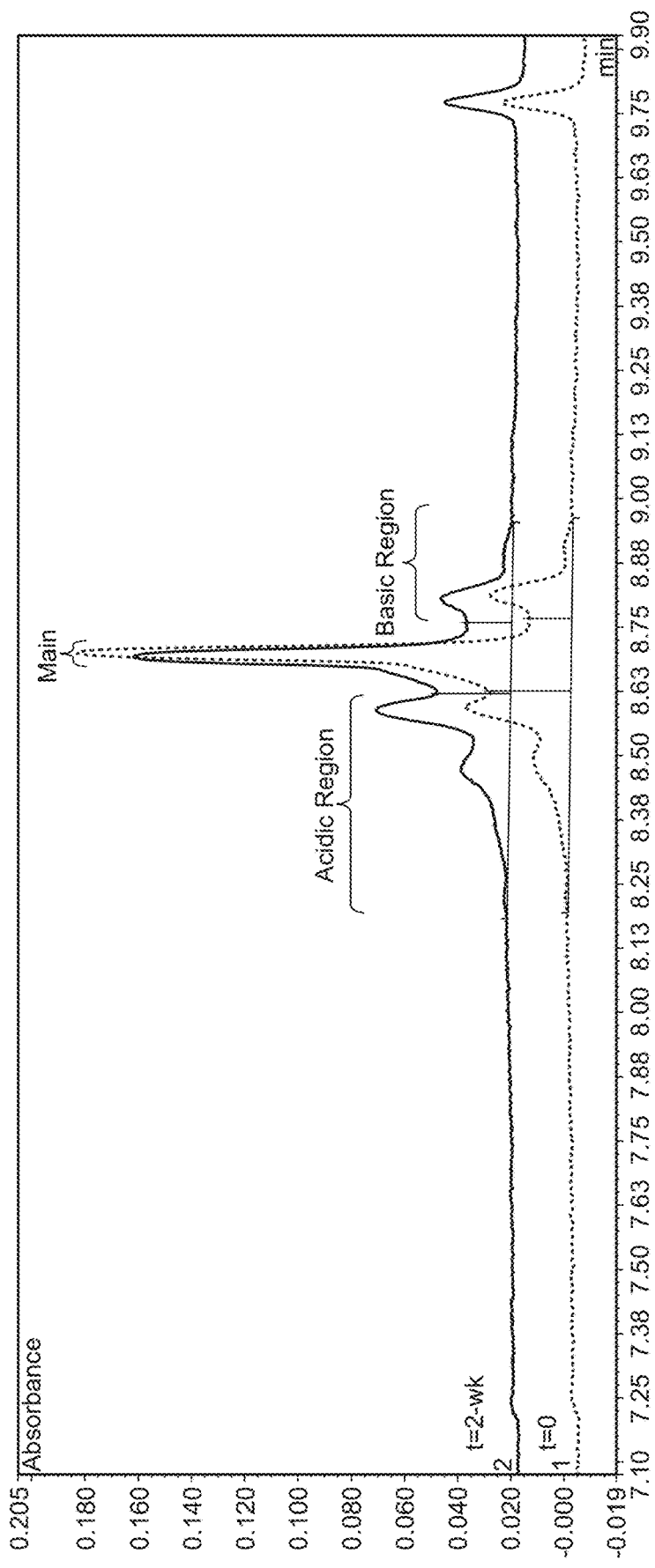
FIG. 21B is a graph showing the charge heterogeneity of the 1G7.v85 TDB. The 1G7.v85 TDB lost 7.7% of the monomer peak after two weeks of stress in a his-acetate solution at pH 5.5
Figure 22A:
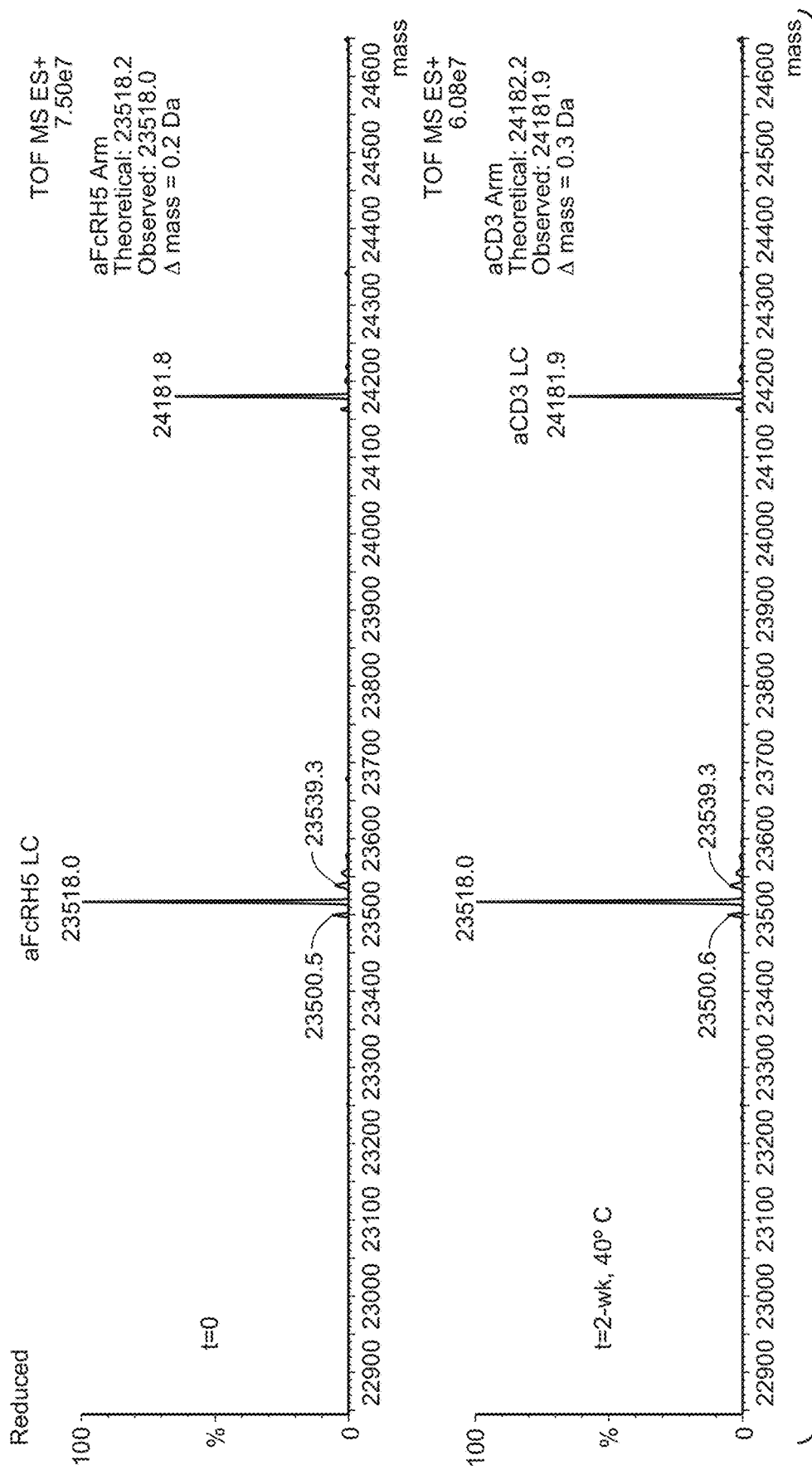
FIG. 22A is a graph showing that the 1G7.v85 TDB has no observable change in the reduced mass profile of the light chain mass after two weeks of stress in a his-acetate solution at pH 5.5.
Figure 22B:
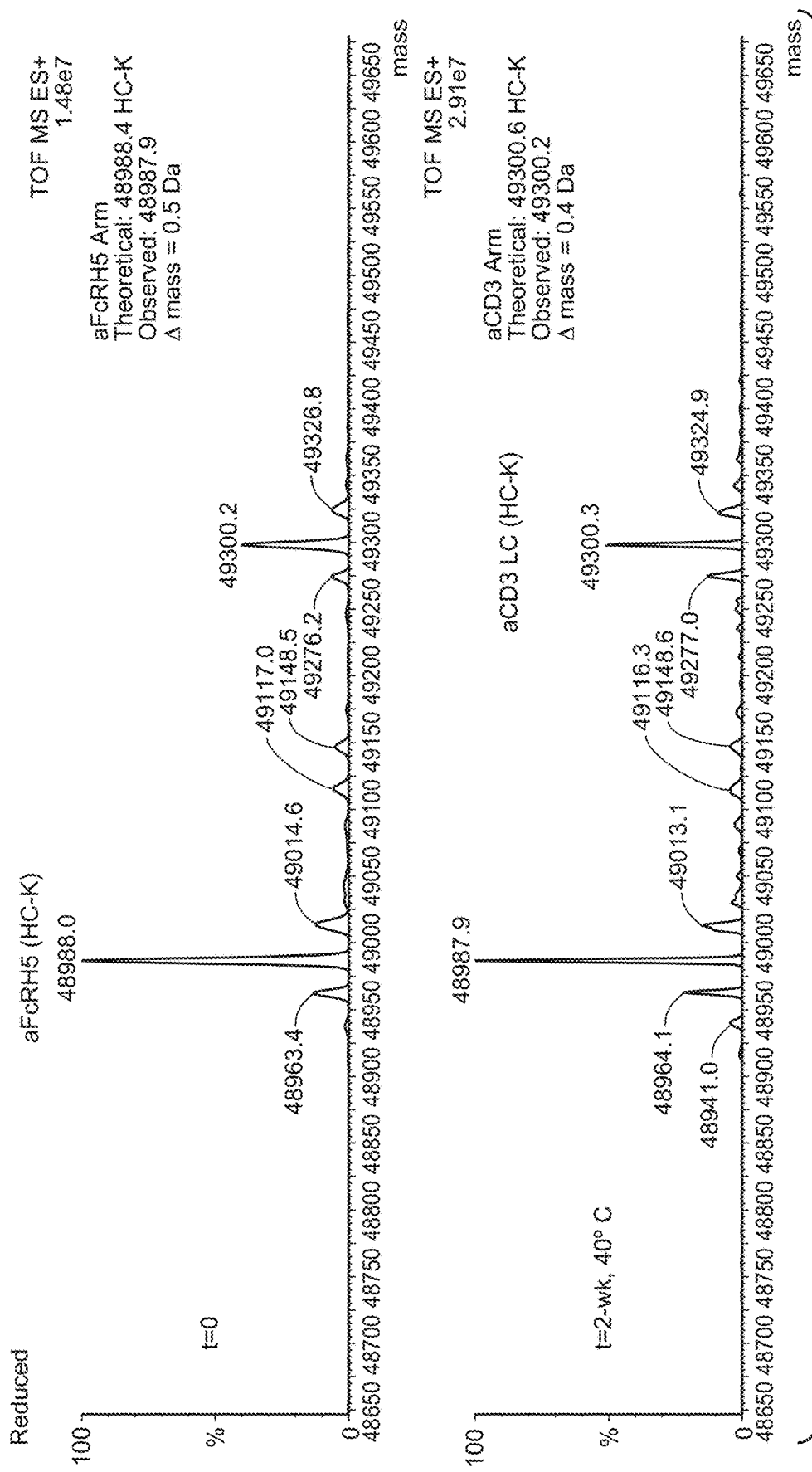
FIG. 22B is a graph showing that the 1G7.v85 TDB has no observable change in the reduced mass profile of the heavy chain mass after two weeks of stress in a his-acetate solution at pH 5.5.

Chemical stability of hu1G7.v1 prior to affinity maturation indicated oxidation susceptibility at Met-64HC and Trp-$52_{HC}$. 1G7.v85 TDB samples were stressed via AAPH and light stress tests and evaluated for FcRH5 binding by BIACORE®. The 1G7.v85 TDB demonstrated reduced binding for FcRH5 after both AAPH and light stress tests as compared to an unstressed control (FIGS. 20A-20D). Monomer stability and charge heterogeneity of the 1G7.v85 TDB was evaluated by size exclusion chromatography (SEC) and imaged capillary isoelectric focusing (icIEF), respectively, after being stressed in a low pH buffer (his-acetate, pH 5.5) for 2 weeks (FIGS. 21A-21B). The observable change in monomer peak loss was small for both monomer stability (0.1%) and charge heterogeneity (7.7%) (FIGS. 21A-21B). Furthermore, there was no observable change in the mass of either the light chain or heavy chains of 1G7.v85 TDB after two weeks of low pH stress (FIGS. 22A-22B). After thermal stress at 30° C. for 2 weeks, monomer peak loss was 0.1% by SEC and 8% by icIEF.

Figure 23A:
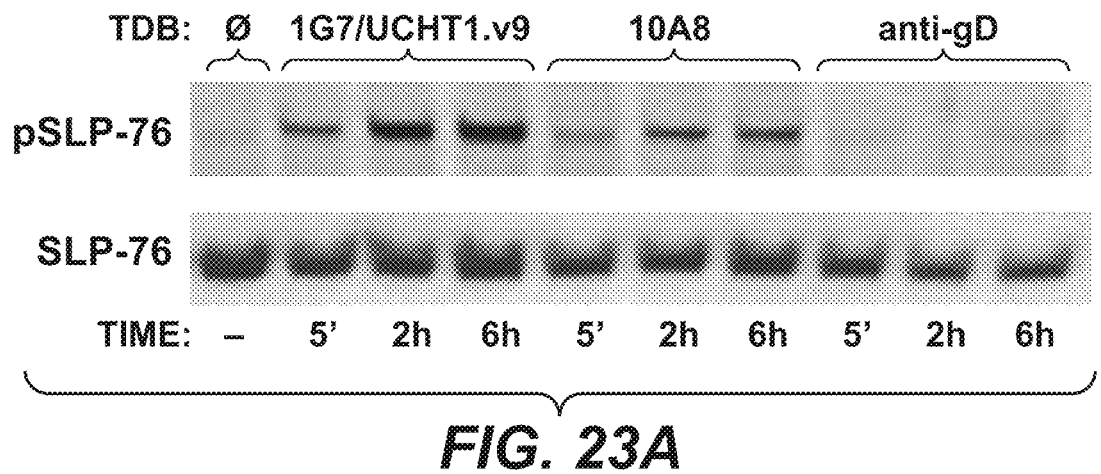
FIG. 23A is a phospho-SLP76 Western blot of a healthy donor peripheral CD8 cells stimulated with 1 μg/ml of the 1G7/UCHT1.v9 TDB, 10A8/UCHT1.v9 TDB ("10A8 TDB"), and anti-gD/UCHT1.v9 TDB ("anti-gD TDB"), and cells expressing human FcRH5 with N-terminal gD expression tag. Blotting for total SLP76, indicative of TCR signaling, was used to confirm equal sample loading.
Figure 23B:
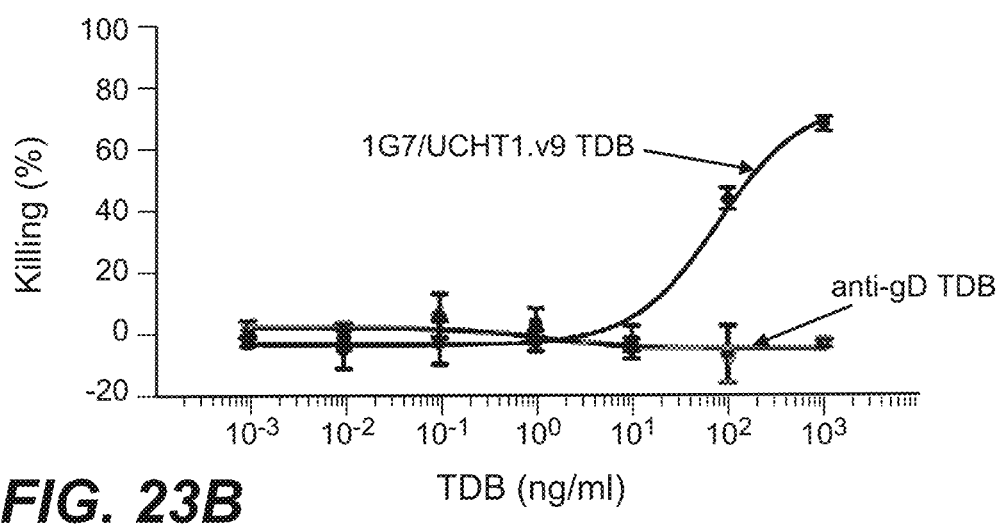
FIG. 23B is a graph showing FcRH5 target cell killing with either 1G7/UCHT1.v9 TDB or anti-gD TDB and CD8+ T cells.
Figure 23C:
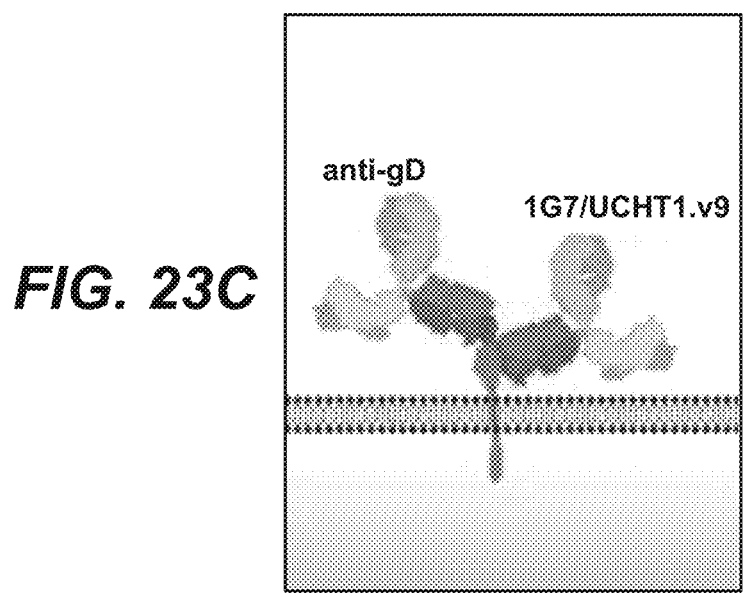
FIG. 23C is a schematic diagram of the truncated FcRH5 construct with the gD epitope now membrane-proximal.
Figure 23D:
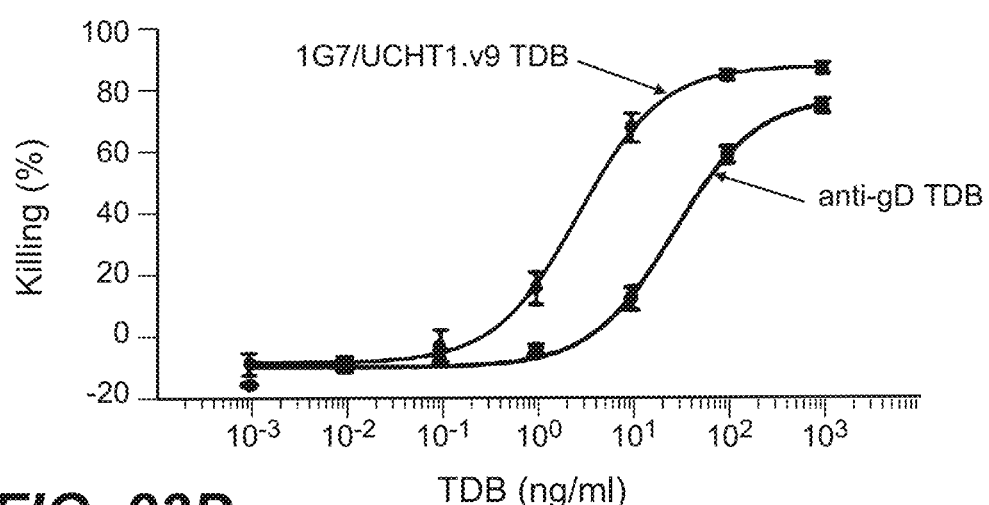
FIG. 23D is a graph showing target cell killing using the truncated FcRH5 construct with 1G7 TDB or anti-gD TDB. The activity of the proximal 1G7/UCHT1.v9 TDB increased by 25-fold (EC50=20 pM), and the anti-gD TDB was able to effectively mediate killing of cells (EC50=0.19 nM) when the interference caused by the ECD was removed. The truncated construct was expressed in 293 cells.
Figure 24A:
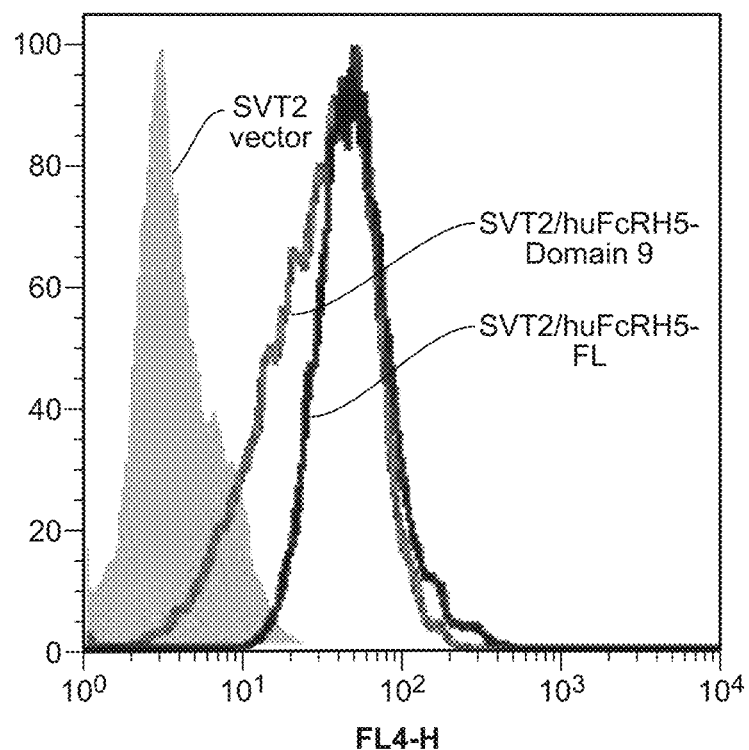
FIG. 24A is a histogram overlay of flow cytometry analysis of SVT2-parental, gD-FcRH5 full-length, and gD-FcRH5-domain 9 cells.

E. A Membrane Proximal Epitope is Required for Efficient TCR Signaling and Killing Activity of the FcRH5 TDB To characterize the molecular events that leads to triggering of the T cell receptor (TCR) upon stimulation by FcRH5 TDB, a reconstituted system was utilized (James et. al. *Nature.* 487:64-69, 2012) that allows initial events leading to receptor activation to be investigated in a controlled manner. Using healthy donor CD8 cells, the 1G7/UCHT1.v9 TDB resulted in a very robust SLP76 phosphorylation, indicative of TCR signaling, and mediated efficient killing of target cells (FIGS. 23A-23B; EC50=0.5 nM). In contrast, the anti-gD TDB, which targets a membrane-distal epitope, did not result in detectable TCR signaling and was unable to mediate T cell killing (FIGS. 23A-23B). It was also confirmed that the TDB activity was dictated by the location of the epitope and the size of the extracellular domain by targeting cells that expressed heavily truncated target that retained the 1G7 and gD epitopes (FIG. 23C). Activity of the proximal 1G7/UCHT1.v9 TDB increased by 25-fold (FIG. 23D; EC50=20 µM), and gD TDB and was able to effectively mediate killing of cells (EC50=0.19 nM) when the interference caused by the ECD was removed. Possibility of differential target expression level being the cause for the activity difference between cell lines was excluded by FACS analysis (FIG. 24A).

Figure 23E:
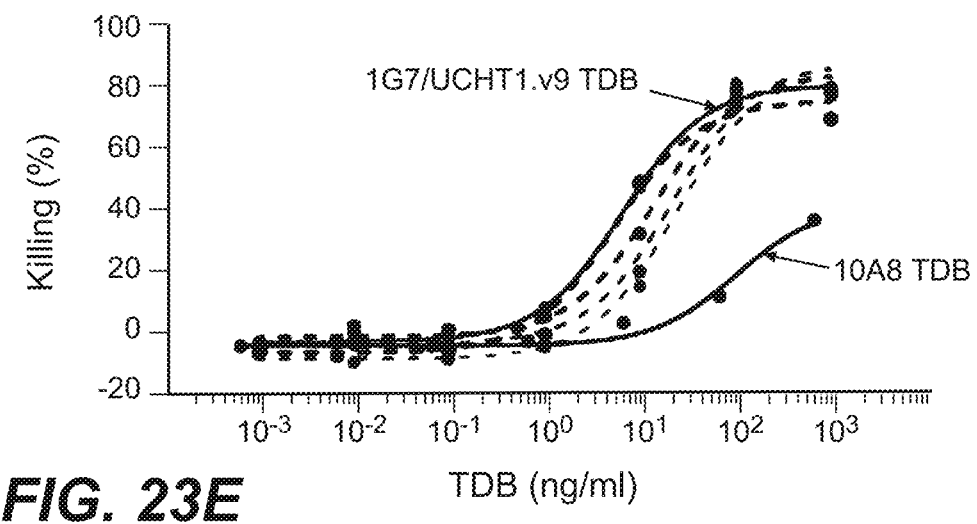
FIG. 23E is a graph showing that target cell killing for five alternate FcRH5 TDBs that recognize the membrane-proximal epitope (dashed lines) are equivalent to killing mediated by the 1G7/UCHT1.v9 TDB and significantly better than the 10A8 TDB.
Figure 24B:
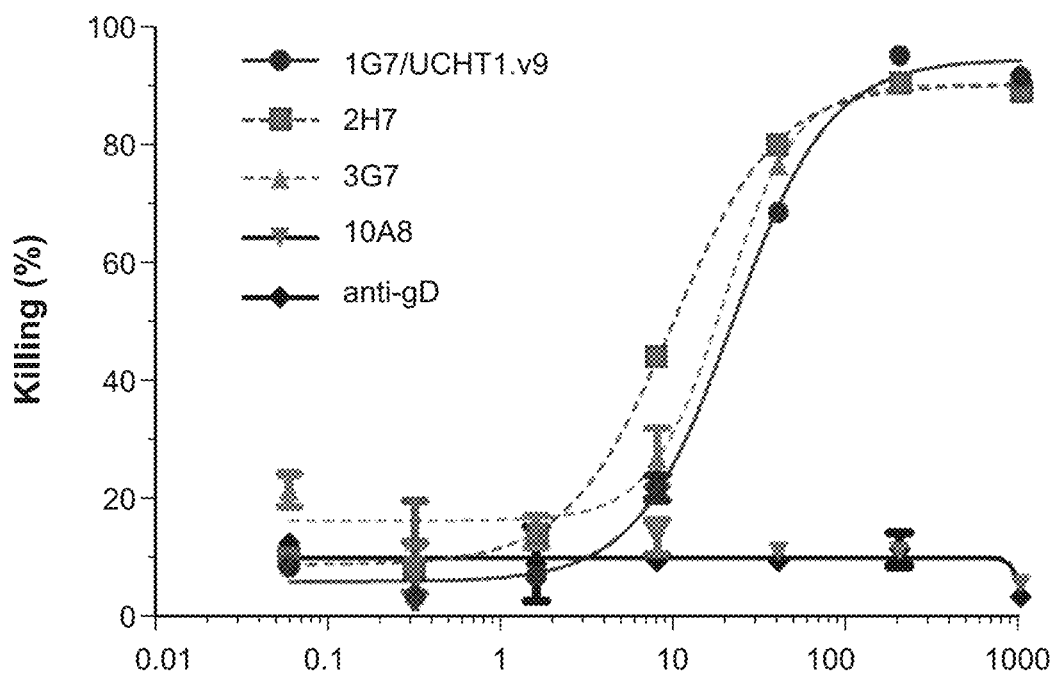
FIG. 24B is a graph showing percent target cell killing by 1G7/UCHT1.v9 TDB, 2H7/UCHT1.v9 TDB ("2H7 TDB"), 3G7/UCHT1.v9 TDB ("3G7 TDB"), 10A8 TDB, and anti-gD TDB.
Figure 26A:
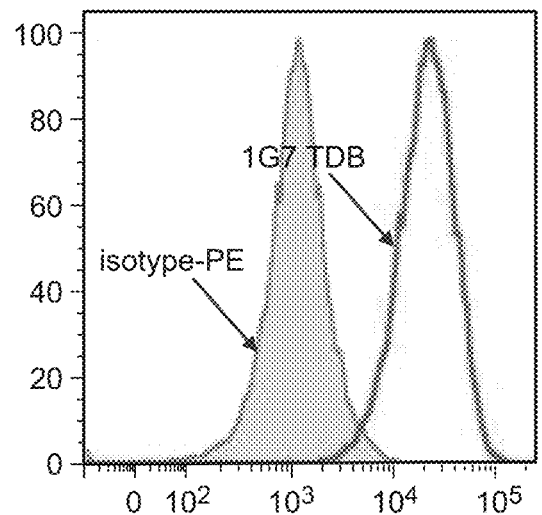
FIGS. 26A-26D are overlay histograms of three cell lines (SVT2-vector, SVT2-huFcRH5, and SVT2-cyno FcRH5), showing binding of the 1G7/38E4.v1 TDB ("1G7 TDB") to multiple myeloma (MM) cell line and primary cells. Overlay histograms are shown for isotype-PE and 1G7 TDB for MOLP-2 cells (FIG. 26A), human CD20+ B cells (FIG. 26B), human CD38+CD138+ plasma cells (FIG. 26C), and CD38+CD138+MM tumor cells from MM bone marrow aspirate (FIG. 26D).
Figure 26B:
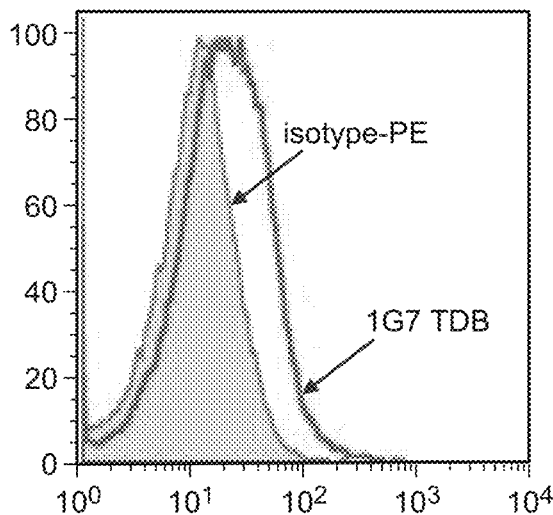
Figure 26C:
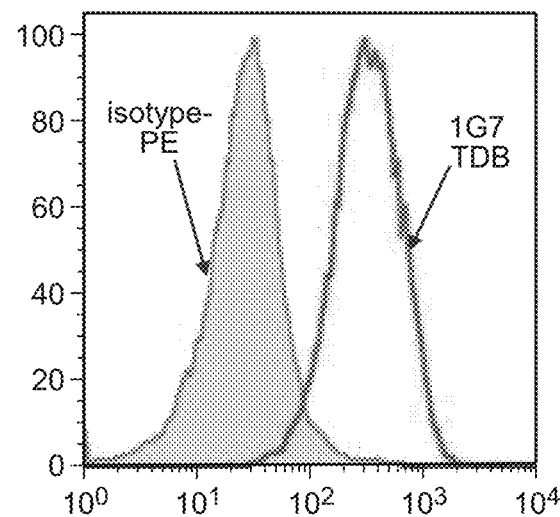
Figure 26D:
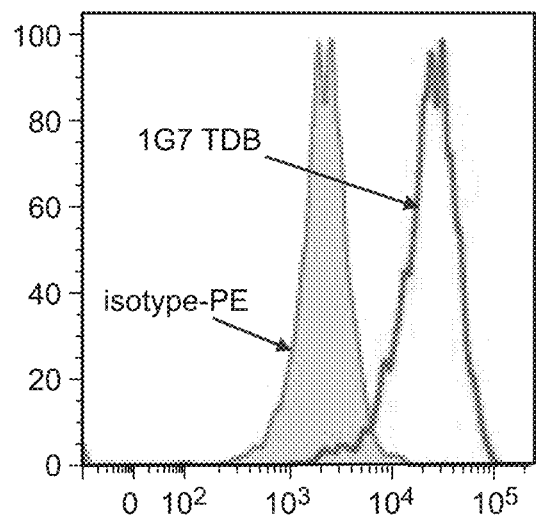

To demonstrate that the differences in the killing activity were related to the epitope rather than being properties of the specific antibody clones, a total of five unique antibody clones targeting the membrane proximal domain for the FcRH5 in TDB format were tested and demonstrated that the activity of each clone was 20-fold higher compared to 10A8 (FIG. 23E). Endogenous expression level of FcRH5 in multiple myeloma is low (e.g., ~100 to 2000 copies/cell) and comparable to the MOLP-2 myeloma cell line (e.g., 2200 copies/cell). When T cells were retargeted to kill MOLP-2 cells only membrane proximal TDBs induced killing of the MOLP-2 cells. Targeting the mid-region of FcRH5 using the 10A8 TDB did not lead to sufficiently high TCR triggering required for killing of myeloma cells (FIG. 24B).

F. FcRH5 TDB Induces Target-Dependent Cell Killing and T Cell Proliferation

Figure 18A:
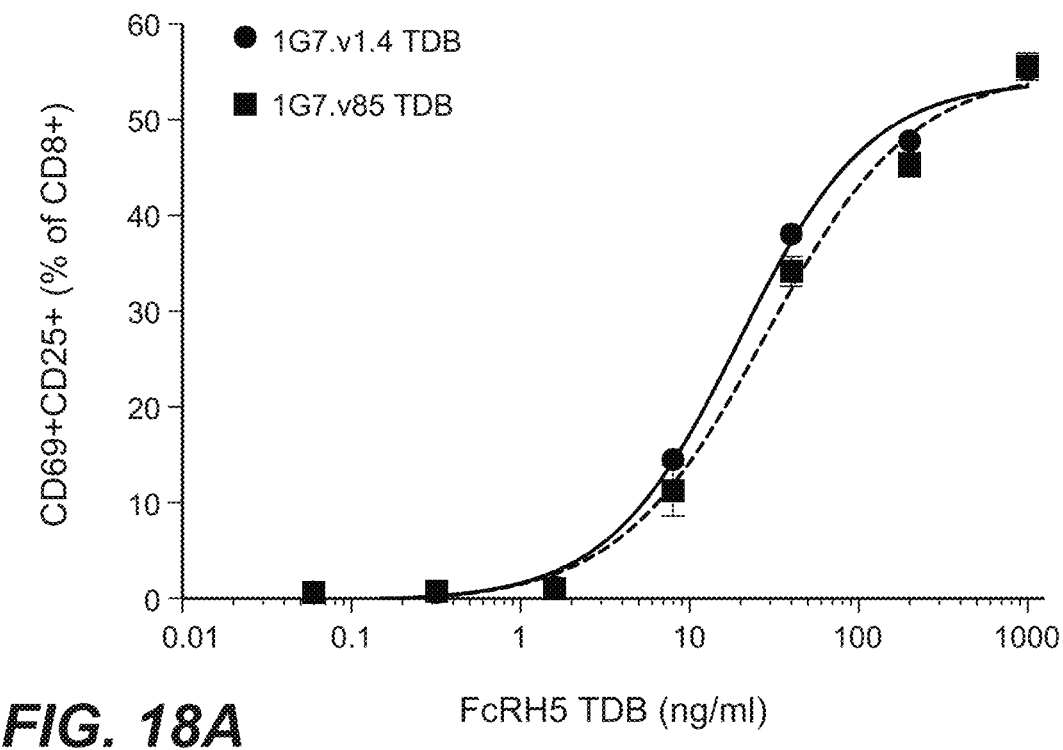
FIGS. 18A-18D are graphs comparing the ability of the 1G7.v1.4 TDB and the 1G7.v85 TDB to activate T cells (FIG. 18A), kill target MOLP-2 cells (FIG. 18B), kill target cyno plasma cells (FIG. 18C), and kill target cyno B cells (FIG. 18D).
Figure 18B:
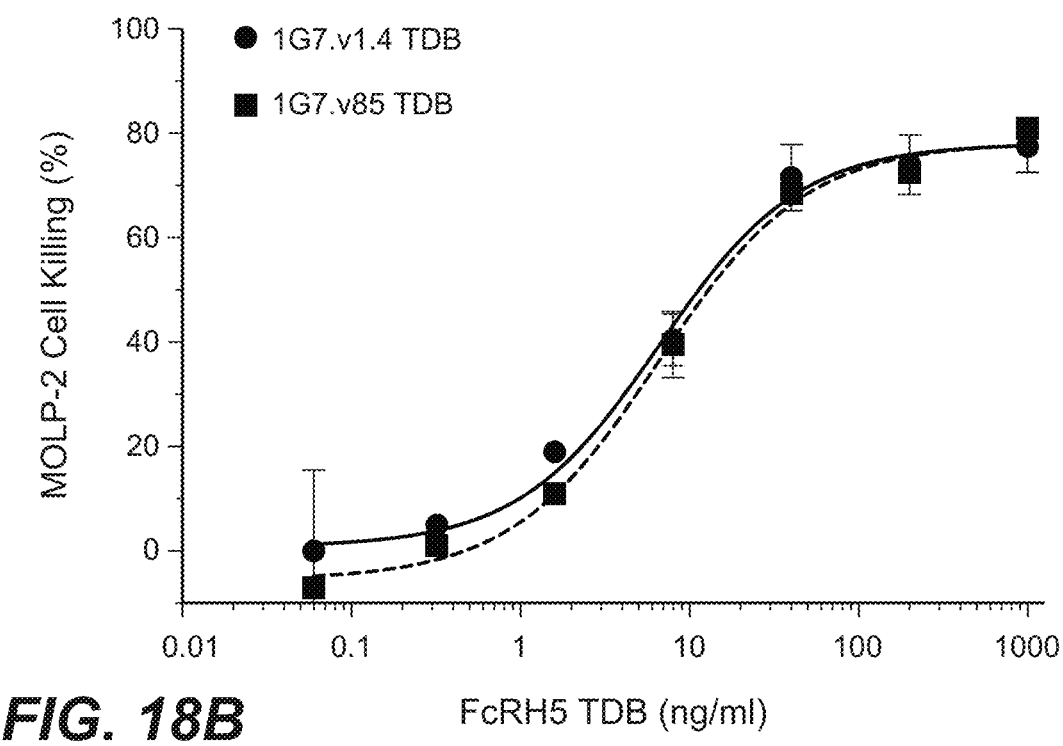
Figure 27A:
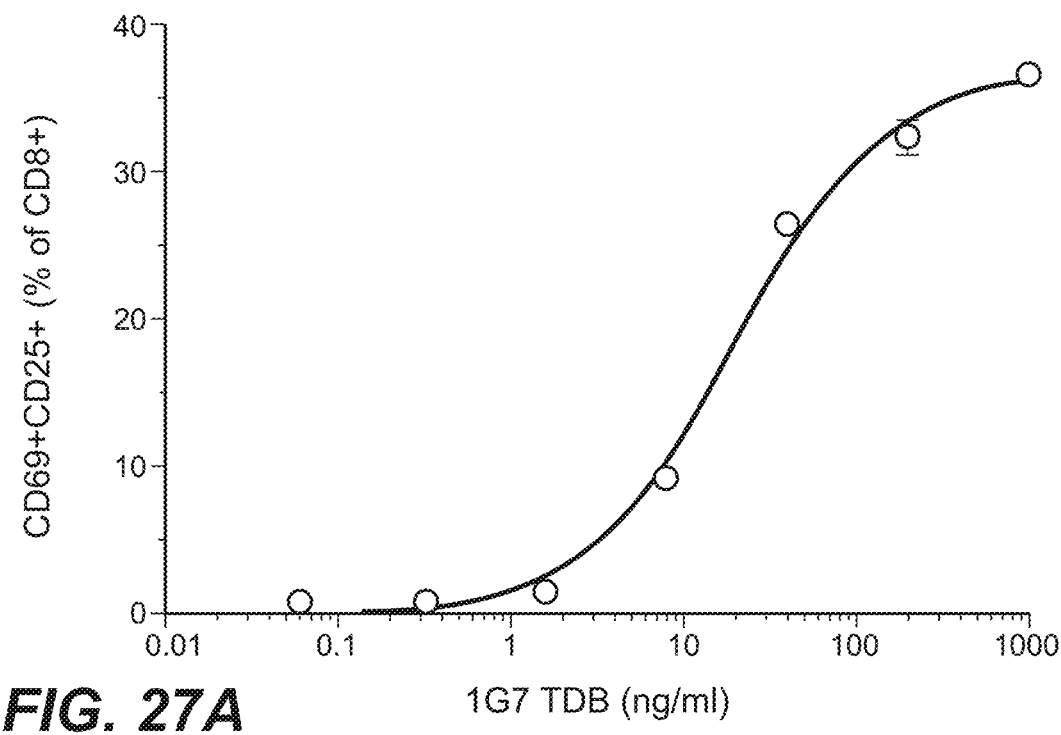
FIG. 27A is a graph showing dose-dependent activation of CD8+ cells upon stimulation with target cells (MOLP-2) and 1G7 TDB, detected by flow cytometry analysis.
Figure 27B:
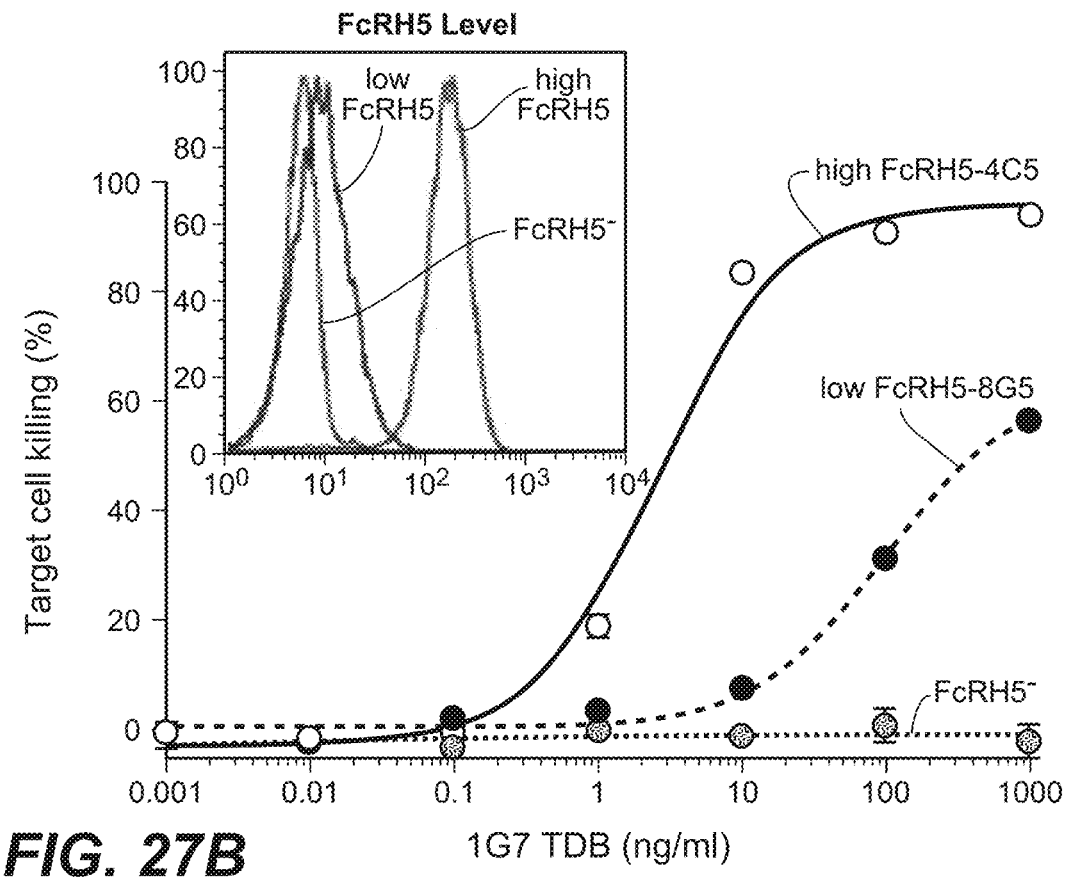
FIG. 27B is a graph showing target cell-dependent killing by 1G7 TDB. The insert shows a flow cytometry overlay of the parental Fox-NY cell line and clones transfected to express a low or a high level of human FcRH5. Error bars are standard deviation of triplicates.
Figure 27C:
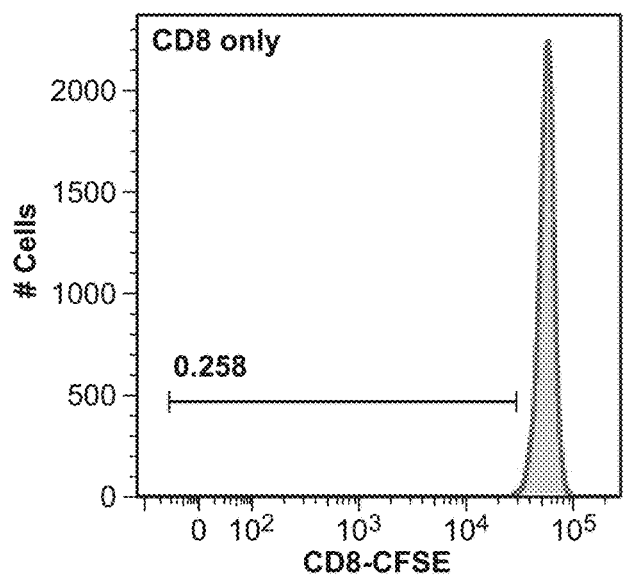
FIGS. 27C-27E are graphs showing that 1G7 TDB induced CD8 proliferation response (5 days), as detected by measuring CSFE fluorescence intensity dilution by flow cytometry. CFSE-labeled human CD8+ cells only (FIG. 27C), co-culture with MOLP-2 (FIG. 27D), or co-culture with MOLP-2 and 1000 ng/ml of the 1G7.v85 TDB (FIG. 27E).
Figure 27D:
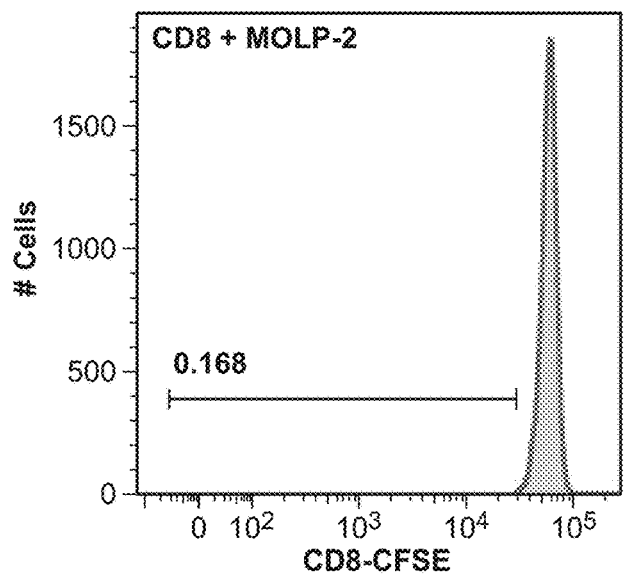
Figure 27E:
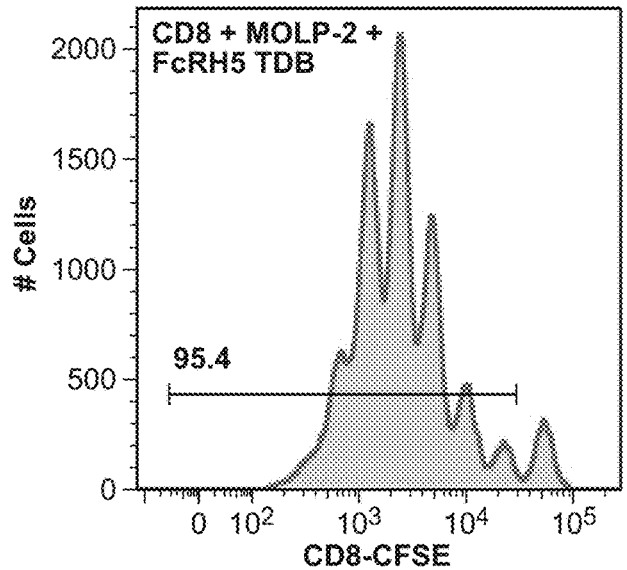
Figure 27F:
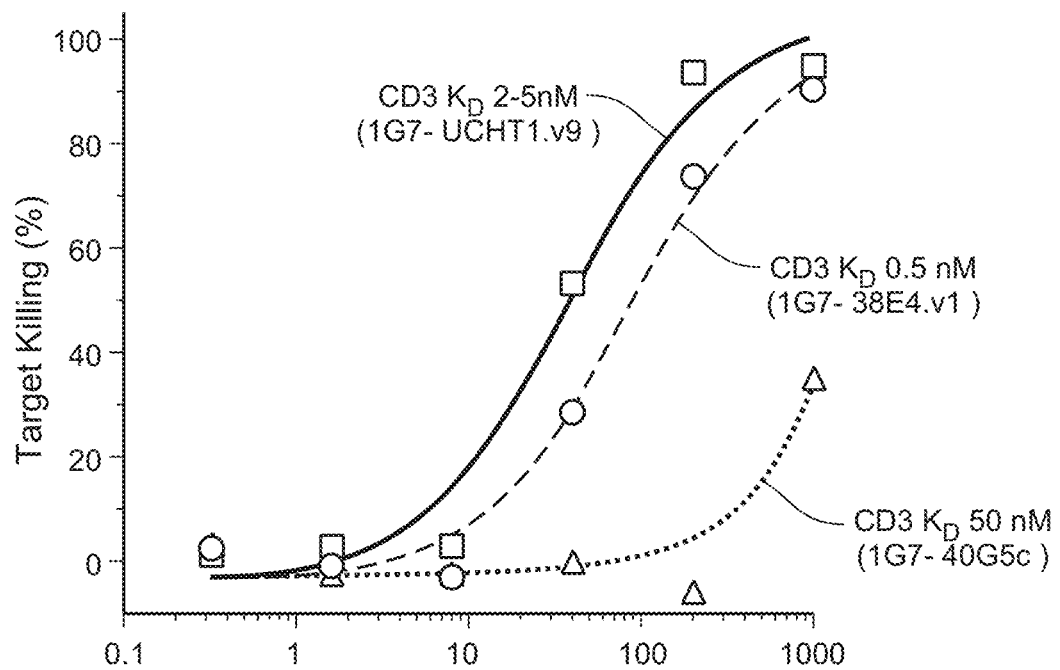
FIG. 27F is a graph showing target-dependent cell killing with FcRH5 TDBs containing different anti-CD3 arms (e.g., UCHT1.v9, 38E4.v1, and 40G5c) (see PCT Pub. No. WO 2015/095392 A1, which is incorporated by reference herein in its entirety). The anti-CD3 arms 38E4.v1 (monovalent $K_D$ 0.5 nM, BIACORE®), UCHT1.v9 (monovalent $K_D$=2.5 nM, BIACORE® and Scatchard), and 40G5c (monovalent $K_D$=51 nM, BIACORE®) were each paired with the anti-FcRH5 arm of ml G7 ($K_D$=11 nm, BIACORE®) and tested for binding to purified human CD8+ cells.
Figure 27G:
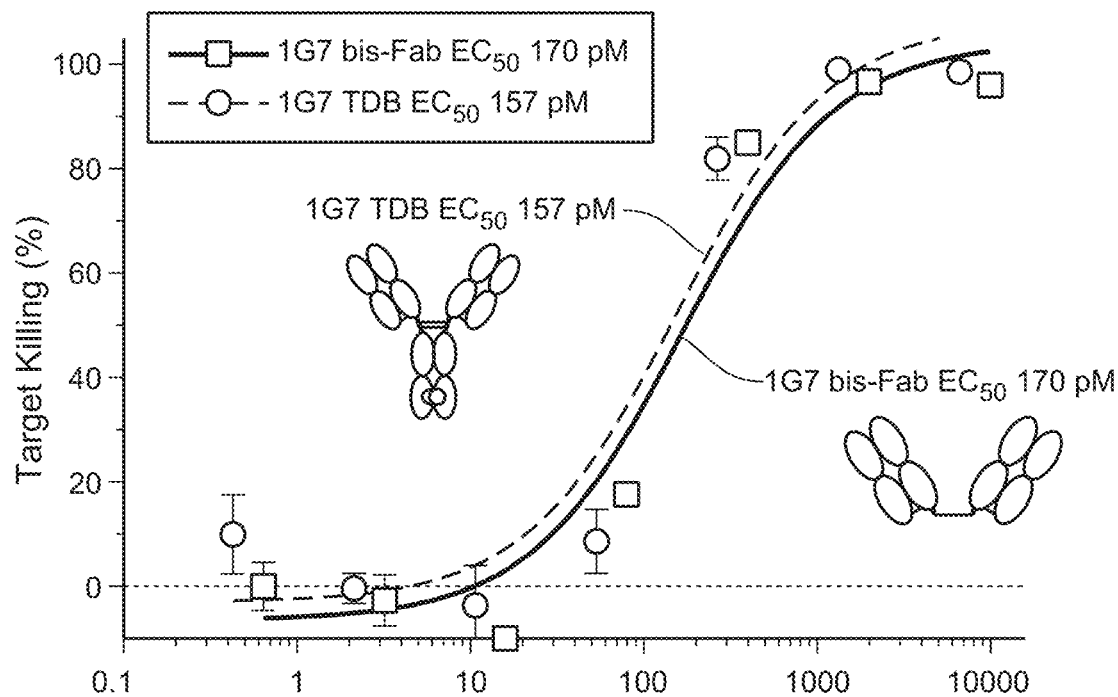
FIG. 27G is a graph showing target-dependent cell killing with the 1G7 TDB and 1G7/38E4.v1 bis-Fab ("1G7 bis-Fab").

In FIG. 18A, the 1G7.v1.4 TDB and the 1G7.v85 TDB were found to have indistinguishable T cell-activating abilities. The 1G7.v85 TDB was evaluated for 1G7 epitope specificity and cyno cross-reactivity (FIGS. 25A-25C). The 1G7/38E4.v1 TDB ("1G7 TDB") bound to MOLP-2 cells, healthy donor B cells, bone marrow plasma cells, and primary myeloma tumor cells as expected (FIGS. 26A-26D). Preclinical analysis of the 1G7 TDB activity was initiated by characterization of the mechanism of action using healthy donor CD8 cells. 1G7 TDB treatment of target expressing cells resulted in a dose dependent T cell activation (FIG. 27A). The cytotoxic activity of the 1G7 TDB was exclusive to target positive cells and correlated with FcRH5 expression level (FIG. 27B). T cell activation by stimulation with 1G7 TDB and target cell led to a robust proliferation of T cells. In five days 95% of the CD8 cells had undergone as many as six cell divisions as demonstrated by dilution of fluorescent dye CSFE (FIGS. 27C-27E). The contribution of the anti-CD3 arm and the Fc domain to the cytotoxic activity of the TDB was further evaluated, and it was found that a high-affinity anti-CD3 arm was required, while an Fc domain was not required, to achieve cytotoxic activity (FIGS. 27F-27G).

Figure 28A:
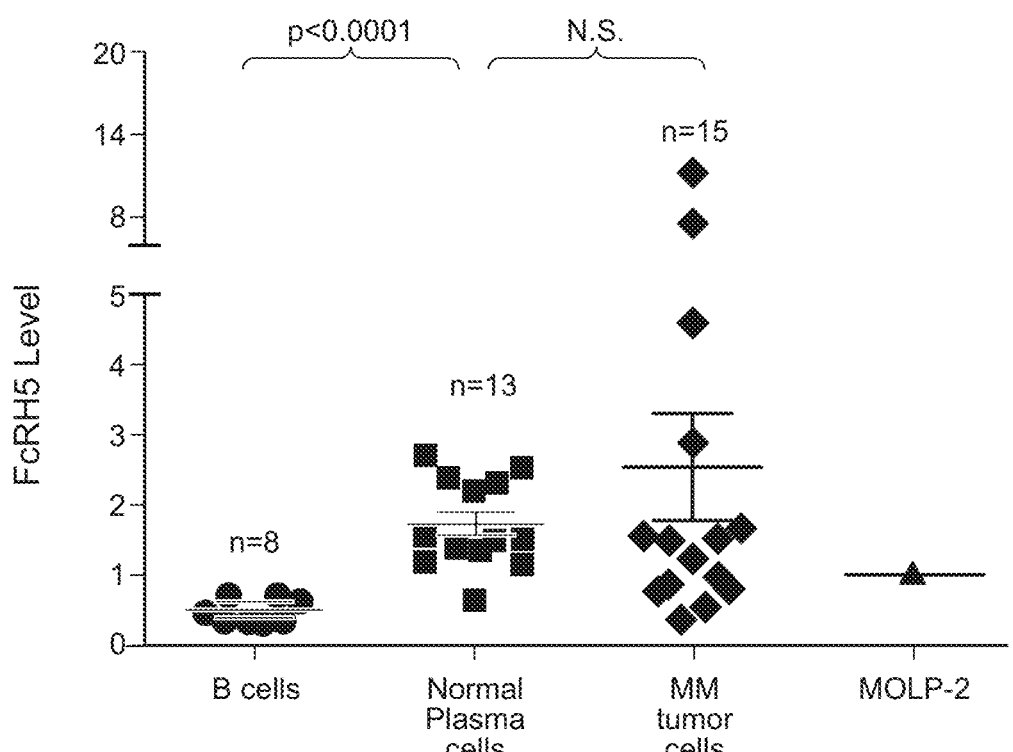
FIG. 28A is a graph showing FcRH5 expression in primary multiple myeloma tumor cells, healthy donor peripheral B cells, and bone marrow plasma cells. FcRH5 expression was analyzed by flow cytometry and normalized to expression in MOLP-2 internal and assay control. The relative level of FcRH5 was calculated as follows: (Geometric mean of FcRH5 of "X"/Geometric mean of isotype control of "X")/(Geometric mean of FcRH5 of MOLP-2/ Geometric mean of isotype control of MOLP-2).

G. FcRH5 TDB Mediates Potent Killing of Normal Plasma Cells and Patient Derived Primary Myeloma Cells Expression of FcRH5 in CD138+CD38+ multiple myeloma cells and normal bone marrow plasma cells was studied using the 1G7.v85 TDB and FACS. All patient-derived tumor cells and all normal plasma cells expressed FcRH5 in all samples suggesting, 100% prevalence in myeloma (FIG. 28A).

Considerable inter-patient variability in expression level was detected in myeloma. Generally, expression level in tumor cells was not significantly elevated compared to normal plasma cells, suggesting that developing a tumor cell-specific, normal plasma cell-sparing FcRH5 TDB was likely not feasible. Expression level in normal B cells is consistently and significantly lower compared to normal plasma cells and multiple myeloma tumor cells.

The FcRH5 gene is located in the chromosomal breakpoint in 1q21 (Hatzivassiliou et al. *Immunity.* 14:277-289, 2001). Analysis of 20 primary multiple myeloma biopsies demonstrated a significant association between FcRH5 RNA expression and 1q21 gain (FIG. 28E), demonstrating that the chromosomal translocation can lead to FcRH5 overexpression in high risk myeloma patients.

Figure 28B:
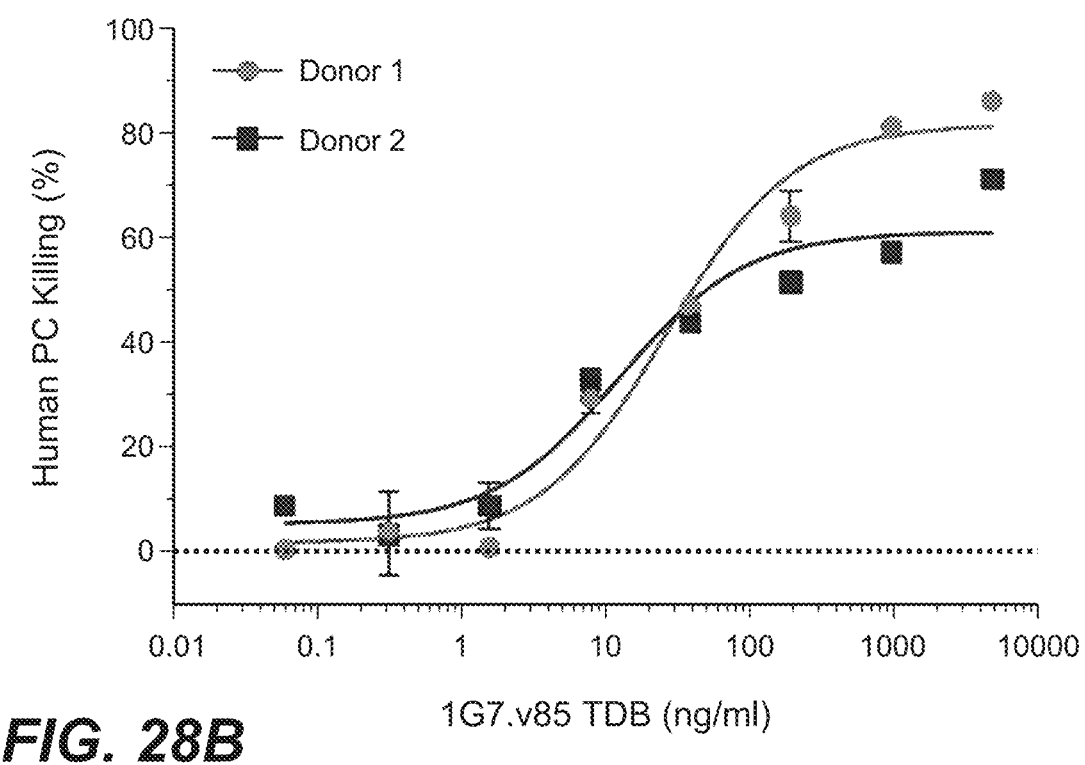
FIG. 28B is a graph showing cytotoxic activity of the 1G7.v85 TDB on human plasma cells. Human bone marrow mononuclear cells (BMMCs) were cultured with 1G7.v85 TDB and the cell number of live CD38+CD138+ was analyzed by flow cytometry.
Figure 28C:
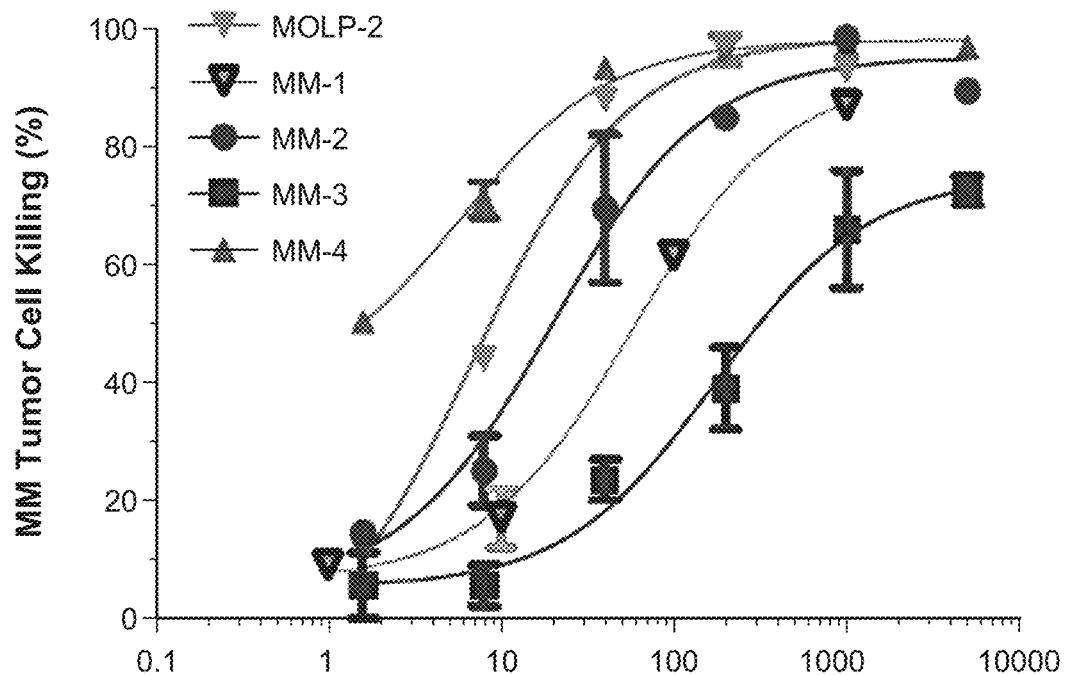
FIG. 28C is a graph showing the cytotoxic activity of the 1G7.v85 TDB on different patient-derived primary myeloma cells. Human myeloma BMMCs were co-cultured with CD8+ T cells isolated from healthy donor and 1G7.v85 TBD.

The ability of the 1G7.v85 TDB to kill plasma cells was analyzed by targeting bone marrow mononuclear cells (BMMC) isolated from bone marrow aspirates of healthy donors (FIG. 28B). The 1G7.v85 TDB induced dose-dependent, highly effective, and potent (EC50=85-180 μM) killing of plasma cells. Similar robust activity was detected when BMMC from multiple myeloma patients was subjected to 1G7.v85 TDB treatment (FIG. 28C). Near 100% killing of myeloma cells was detected with high potency (EC50=60-1200 μM) regardless of the in-life treatment history.

Figure 28D:
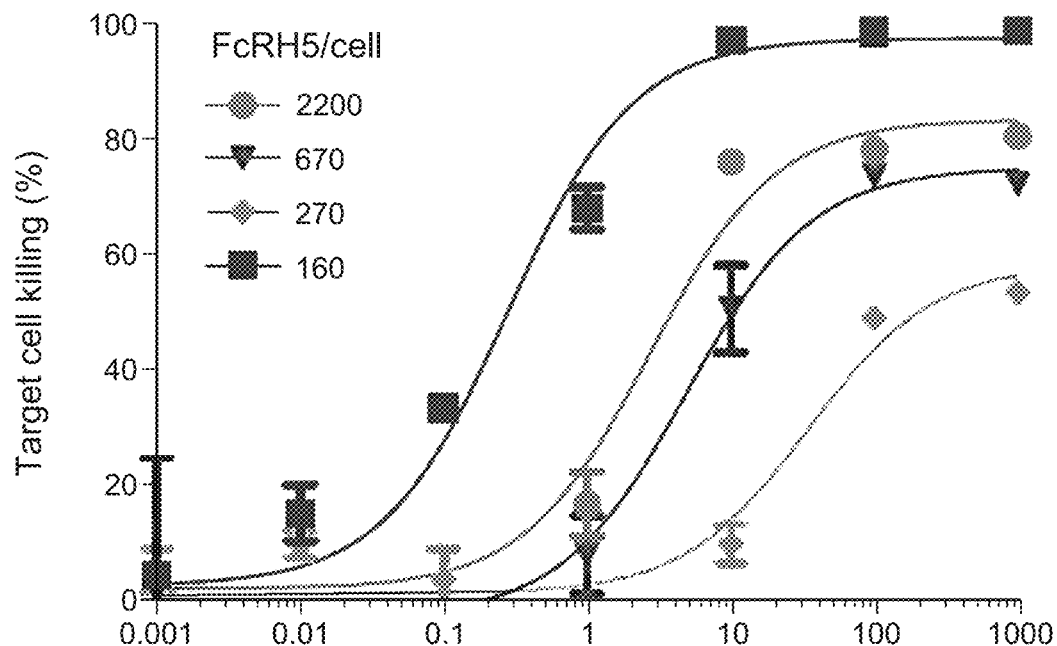
FIG. 28D is a graph showing that very low FcRH5 expression in target cells is sufficient for potent killing activity. FcRH5 copy number per cell was determined by Scatchard assay.
Figure 28E:
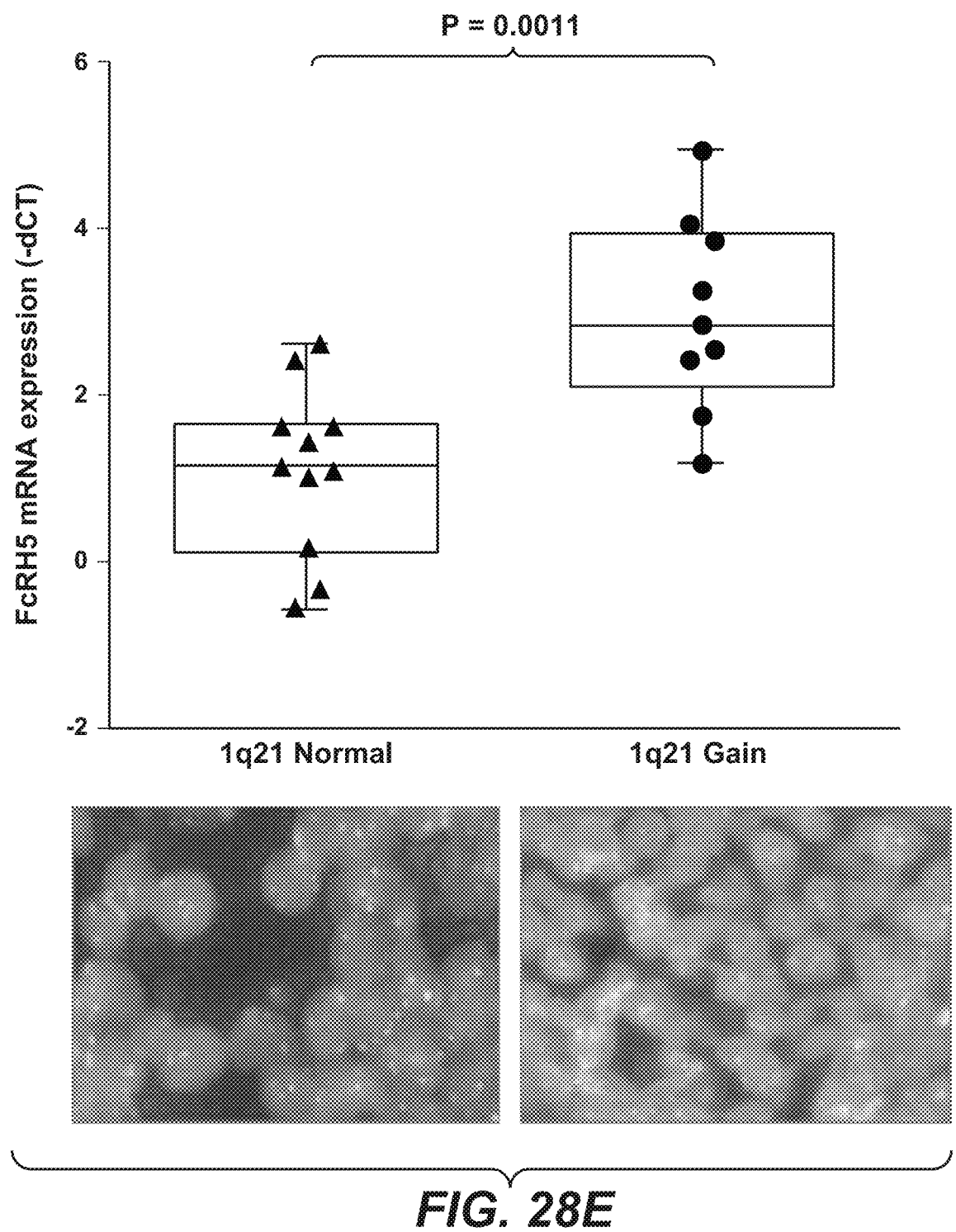
FIG. 28E (Top) is a graph showing qRT-PCR analysis of FcRH5 mRNA levels in bone marrow biopsies from high risk myeloma patients with 1q21 gain. mRNA expression level was calculated by the delta Ct (dCt) method. Statistical analysis was done using a Mann-Whitney U test. (Bottom) Are images of FISH analysis on primary multiple myeloma biopsies showing normal diploid of 1q21 (Left) and a mixture of approximately three to six copies of 1q21 (Right). A tumor sample was identified as 1q21 gain when >20% of the tumor cells scored had three or more copies of the 1q21.3 locus.

As FcRH5 expression is variable in myeloma (FIG. 28A) and 1G7.v85 TDB activity correlates with expression level (FIG. 28D), whether patients in the low end of the expression spectrum would be predicted to respond to FcRH5 TDBs was also investigated. MOLP-2 myeloma cell line was identified as a benchmark cell line which has an expression level of FcRH5 that is similar to average expression in plasma cells and primary MM cells (FIG. 28A). We also identified several cancer cell lines that express extremely low levels of the target and determined the number of FcRH5 per cell using Scatchard analysis. The range of FcRH5 binding sites in these cell lines varied from 2200 to as low as 160 per cell. Despite very low target copy number, the 1G7.v85 TDB induced robust killing of all tested cell lines (EC50=2-230 μM). Occupancy calculations indicated that as few as 50 TDB molecules (2% occupancy at MOLP-2; EC50=58 μM) were sufficient to induce T cell activation and target cell apoptosis.

In summary, FcRH5 is expressed in all myeloma patients. FcRH5 TDBs can kill human plasma cells and patient-derived primary myeloma tumor cells at pM doses. As very few TDBs are required to redirect T cell activity, the molecule potently kills cells with very low expression of the target. The results suggest that FcRH5 TDBs have the potential to be broadly active in myeloma patients and do not support excluding patients from the therapy based on FcRH5 expression level.

Figure 18C:
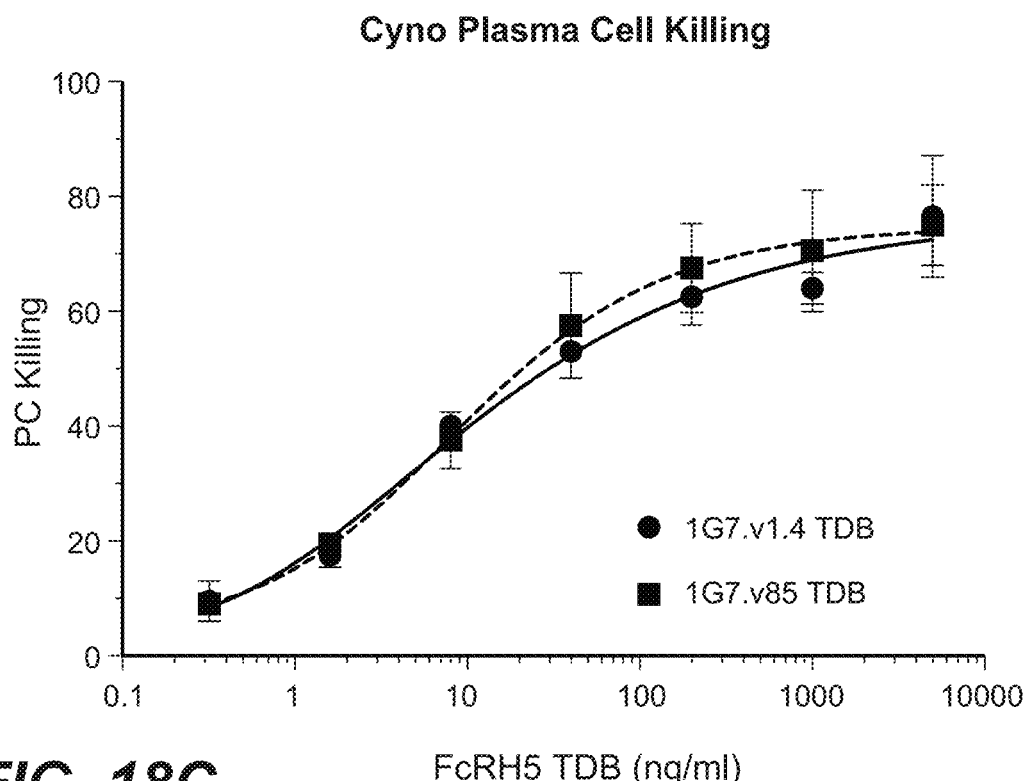
Figure 18D:
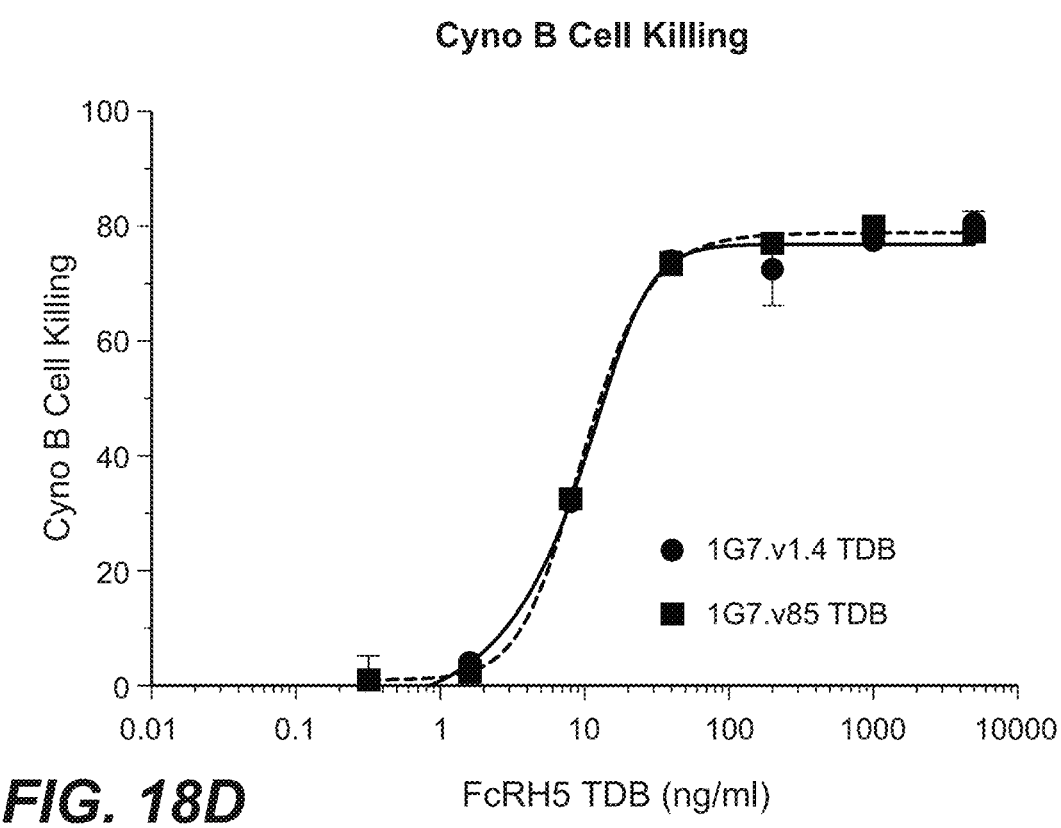
Figure 29A:
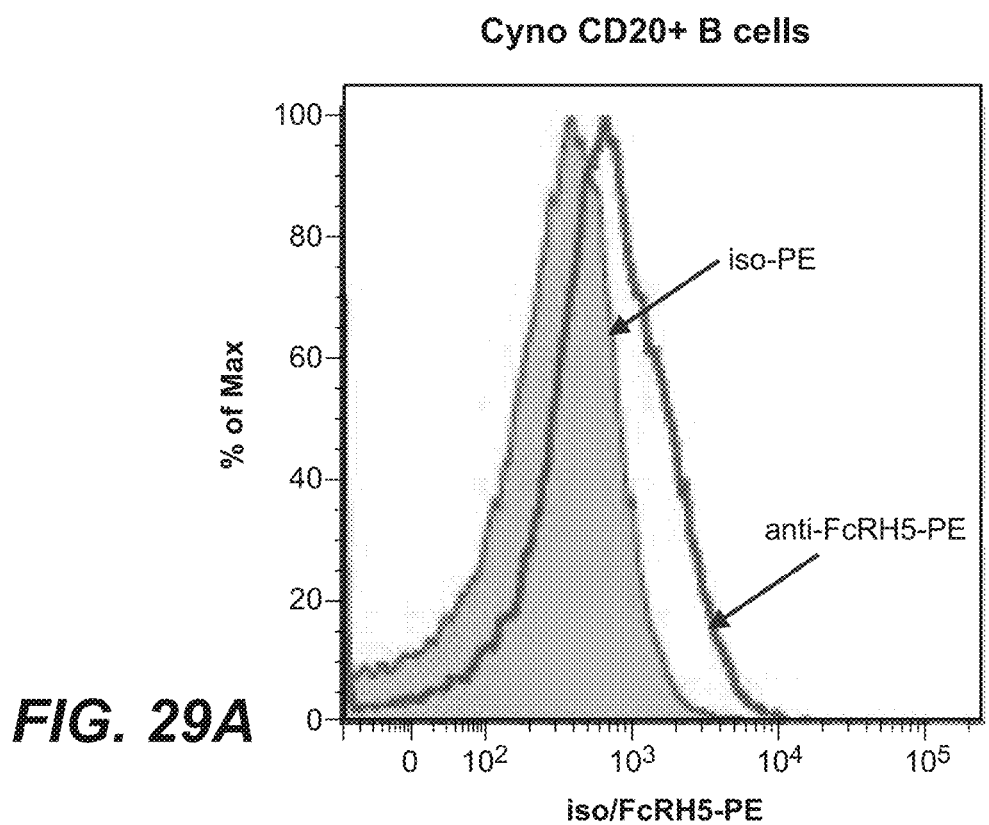
FIG. 29A is a histogram overlay of isotype-PE and anti-FcRH5 clone 1G7-PE, depicting the expression of FcRH5 on cyno CD20+ B cells.
Figure 29B:
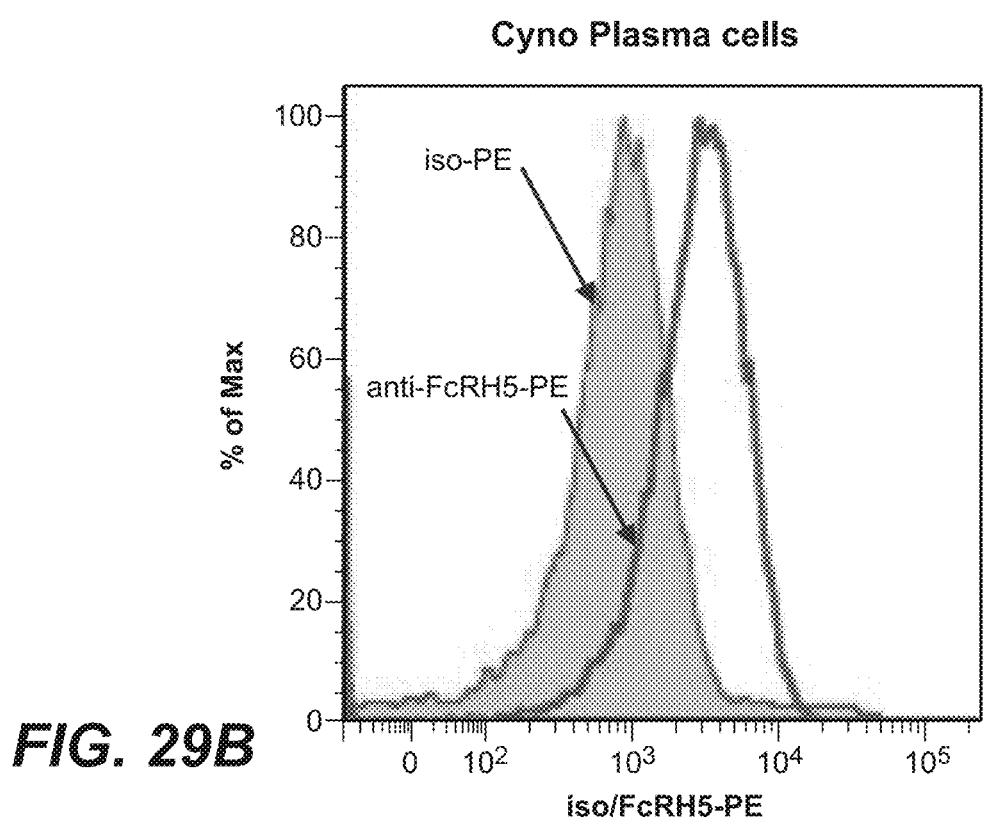
FIG. 29B is a histogram overlay of isotype-PE and anti-FcRH5 clone 1G7-PE, depicting the expression of FcRH5 on cyno on CD45-CD20-CD38+PC+ plasma cells.
Figure 29C:
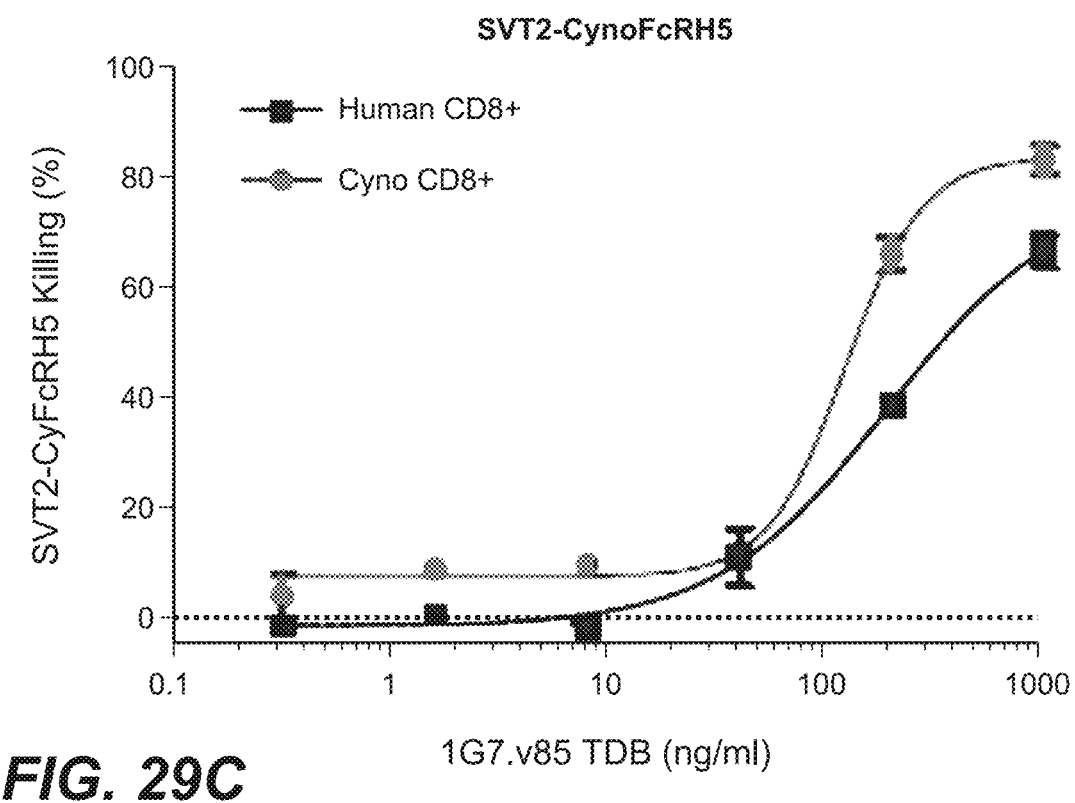
FIGS. 29C-29D are graphs showing comparable dose-dependent cytotoxic activity between cyno CD8+ T cells and human CD8+ T cells in an in vitro killing assay using SVT2-cyno-FcRH5 (FIG. 29C) and MOLP-2 (FIG. 29D) with human CD8+ T cells or cyno CD8+ T cells.
Figure 29D:
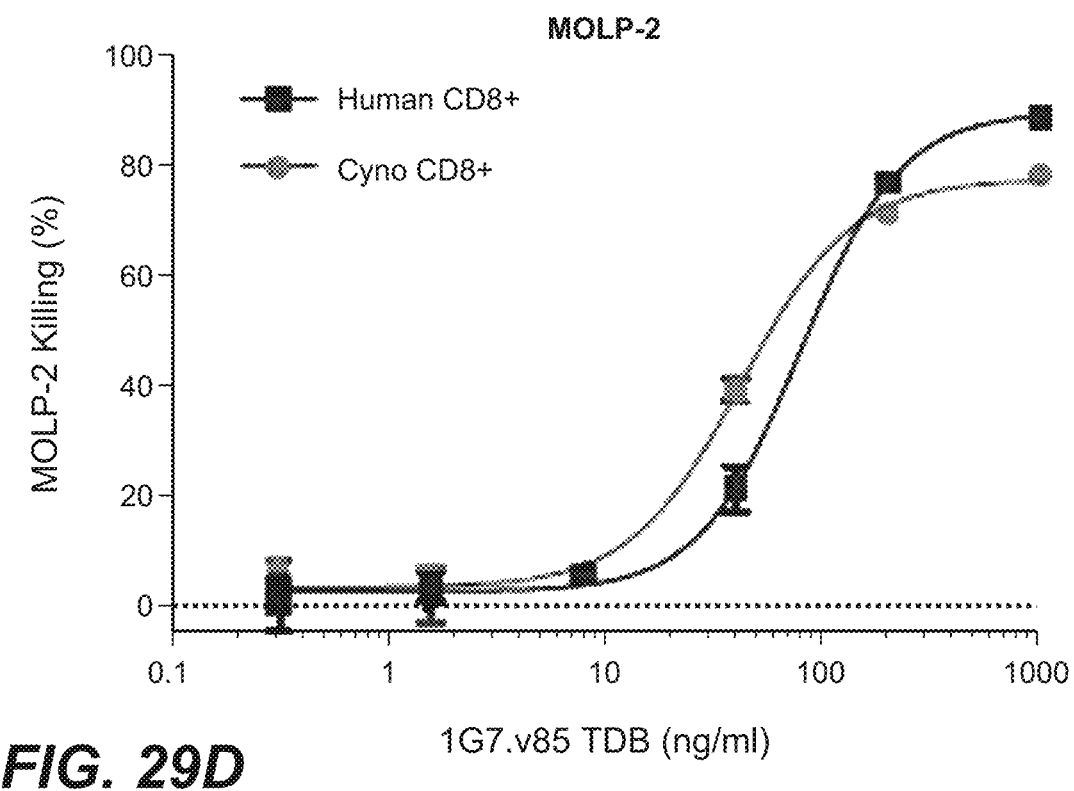
Figure 29E:
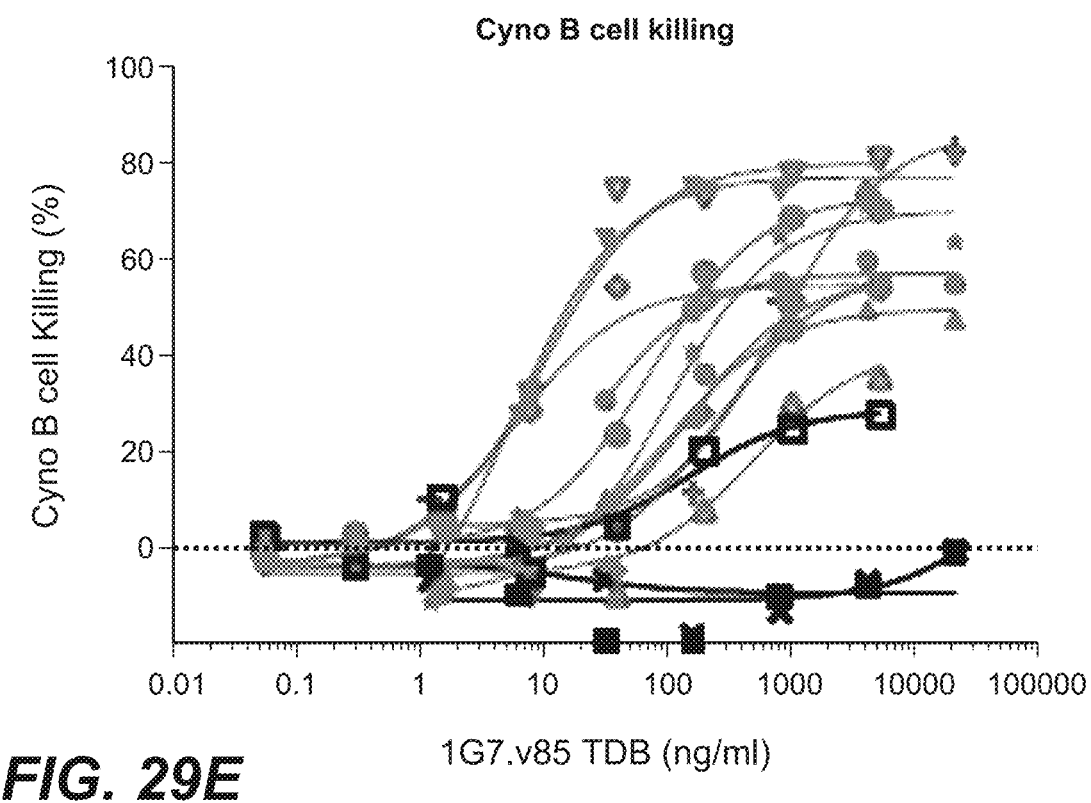
FIG. 29E is a graph showing in vitro killing activity of 1G7.v85 TDB on cyno CD20+ B cells (n=14).
Figure 29F:
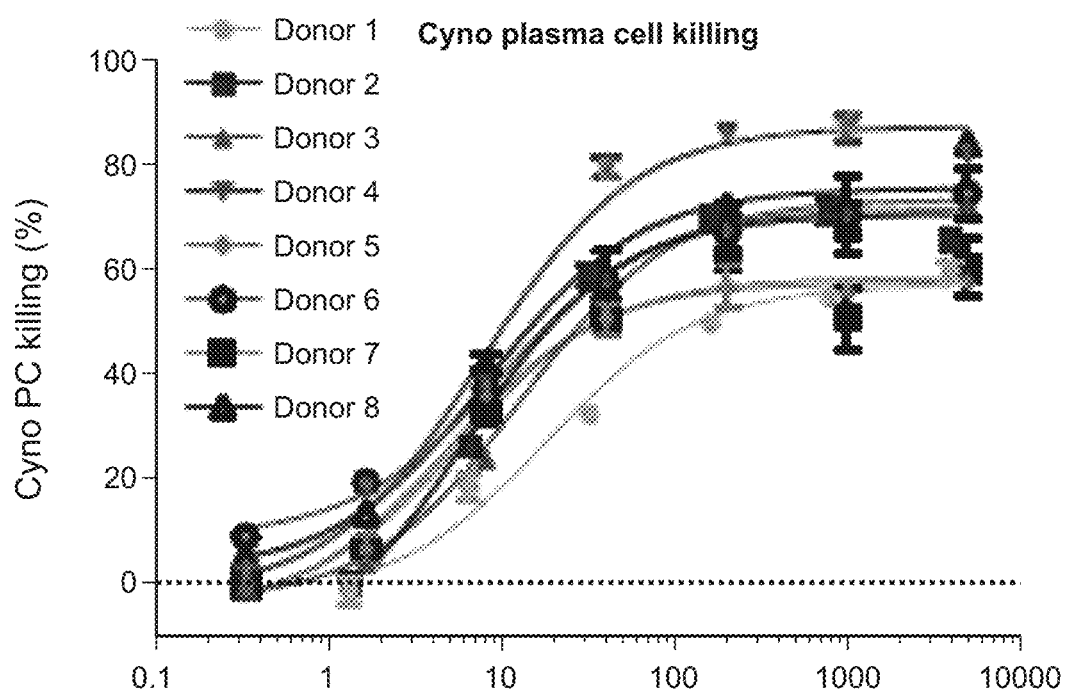
FIG. 29F is a graph showing in vitro killing activity of 1G7.v85 TDB on CD45-CD20-CD38+PC+ plasma cells from cyno bone marrow from eight different donors (n=8).

H. Cynomolgus Monkey (Cyno) is an Appropriate Safety and Efficacy Model for FcRH5 TDB FACS analysis of peripheral B cells and bone marrow plasma cells confirmed that FcRH5 is expressed throughout the B cell lineage in cyno similar to humans (FIGS. 29A-29B; Poison et al. *Int. Immunol.* 18:1363-1373, 2006). The amino acid sequences of human and cyno FcRH5 are 89% identical, and the 1G7.v85 TDB binds to cyno FcRH5 and CD3 with comparable affinity. In vitro treatment of target cells expressing cyno FcRH5 or MOLP-2 cells expressing human FcRH5 resulted in robust killing using peripheral T cells from either human or cyno with comparable efficiency (FIGS. 29C-29D). Adding the 1G7.v85 TDB to PBMC/BMMC samples from cyno resulted in a dose dependent and robust killing of cyno B cells (FIG. 29E) and bone marrow plasma cells (FIG. 29F). In FIG. 18C, the 1G7.v1.4 TDB and 1G7.v85 TDB were found to have indistinguishable cyno plasma cell killing abilities. These results validate cyno as an appropriate safety and efficacy model for anti-FcRH5/CD3.

Example 4. In Vivo Characterization of Exemplary FcRH5 TDBs

Materials and Methods
A. In Vivo Efficacy Studies in Murine Models
a. huNSG/MOLP-2 Mouse Xenograft Model Female humanized NOD.Cg-Prkdcscid Il2rgtm1Wjl/SzJ (NOD/scid gamma; NSG) mice were obtained from The Jackson Laboratory. On the day of cell inoculation, five animals were inoculated with 0.2 mL of MOLP-2 tumor cells at a concentration of 100 million cells/mL, in HBSS/matrigel, subcutaneously in the right flank. As soon as the tumor volumes reached a volume range of 100-250 mm$^3$, animals were randomized into two groups, a vehicle and treatment group, and the first treatments were administered at that time (Day 0). All treatments were administered once a week by intravenous (i.v.) tail vein injection for a total of four doses. The vehicle group was treated with 0.1 ml of 20 mM histidine acetate, pH 5.5, 240 mM sucrose, 0.02% TW-20 buffer. The treatment group was treated with 0.1 ml of 1G7.v85 TDB at a concentration of 0.5 mg/kg. Tumors were measured 1-2 times per week with calipers for the duration of the study, and animal body weights were taken at least once a week. For the duration of this study, clinical observations were performed twice per week to monitor the health of the animals.

B. Toxicology Study in Cynomolgus Monkeys

The tolerability, toxicity profile, pharmacokinetics (PK), and pharmacodynamics (PD) of anti-FcRH5 TDB were evaluated in naive, male cynomolgus monkeys (cynos) at Charles River Laboratories (CRL). Cynos were treated with a single dose, intravenous infusion (1 h) of vehicle, 1, 2, or 4 mg/kg 1G7.v85 TDB and were necropsied seven days after treatment. The animals were closely monitored for detailed clinical observations, respiratory rate, and body temperature during the first five hours and at termination. Cage-side clinical observations and body weights were collected daily. Blood samples were collected by venipuncture via the femoral vein pre-study and at selected time points throughout the study for analyses of hematology, serum chemistry, coagulation, and PK total antibody levels) and PD endpoints. PD consisted of measurements of cytokines (IL-1β, IL-1 RA, IL-2, IL-4, IL-5, IL-6, IL-12/23, IL-13, IL-17, G-CSF, GM-CSF, IFN-γ, TNF-α, and MCP-1), flow cytometry of T-lymphocytes, B-lymphocytes, NK cells, activated T-lymphocytes, PD-1, and circulating cyno IgG. Bone marrow was collected in anesthetized animals by aspiration from the humerus pre-study and prior to necropsy on Day 8 for evaluation of B-lymphocytes and plasma cells by flow cytometry. At necropsy, organ weights were measured and select organs and tissues were thoroughly examined by gross and microscopic examination. Spleen, mesenteric, and mandibular lymph nodes were evaluated for T-lymphocytes, B-lymphocytes, and NK cells. All procedures were performed in compliance with the Animal Welfare Act, the Guide for the Care and Use of Laboratory Animals, and the Office of Laboratory Animal welfare.

C. PKPD Study in Cynomolgus Monkeys and Mice

The concentrations of FcRH5 TDB in serum were determined by generic ELISA. Sheep anti-human IgG antibody was used as the capturing reagent, and sheep anti-human IgG conjugated to horseradish peroxidase (HRP) was used as the detection reagent. Analysis of serum concentration with time from available samples were analyzed by a non-compartmental with IV bolus input model (Phoenix™ WinNonlin®, Version 6.3; Pharsight Corporation; Mountain View, Calif.). Nominal sample collection time and nominal dose concentrations were used in the data analysis. All TK analysis was based on individual animal data.

Results

Figure 30B:
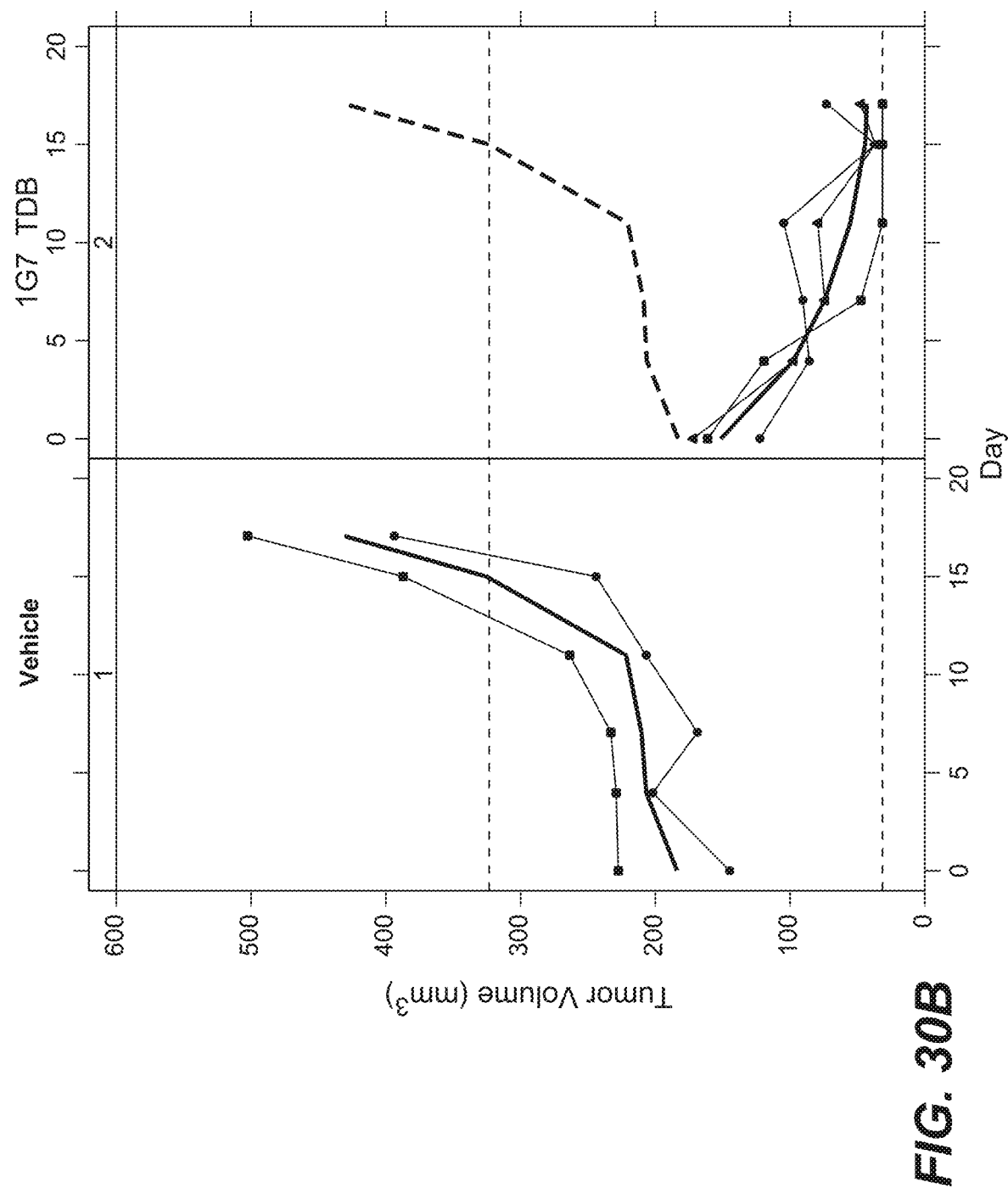
FIG. 30B is a graph showing that 1G7 TDB treatment induces regression of subcutaneous MOLP-2 xenograft tumors in humanized NSG mice. The mice were treated with a single intravenous dose of vehicle or 1G7.v85 TDB at 0.5 mg/kg. Mean tumor volume (black bold line), the individual tumor volumes (thin lines), and mean of control group (dashed line) are indicated.

A. FcRH5 TDB Suppresses Growth of Established MOLP-2 Tumors in Mice Reconstituted with Human Immune Cells Modeling anti-myeloma activity of the FcRH5 TDB in mice is challenging since anti-CD3 antibodies do not cross-react with mouse CD3 and an FcRH5 orthologue does not exist in mouse. Therefore, a mouse model with a reconstituted human immune system was established by transplanting CD34+ selected human hematopoietic stem cells into irradiated mice (huNSG mice). Human CD8+ cells harvested from spleens of huNSG mice were able to kill MOLP2 cells in vitro with comparable efficiency to human peripheral CD8+ cells from healthy donors (FIG. 30A). 20 weeks post-transplantation huNSG mice were inoculated with five million MOLP-2 cells subcutaneously. Mice with established 100-200 mm$^3$ tumors were treated with single IV dose of vehicle or 0.5 mg/kg of FcRH5 TDB. FcRH5 TDB treatment resulted in tumor regression in all animals (FIG. 30B), indicating that FcRH5 TDB treatment suppresses tumor growth in vivo.

B. FcRH5 TDB has Long Serum Half-Life

Figure 31A:
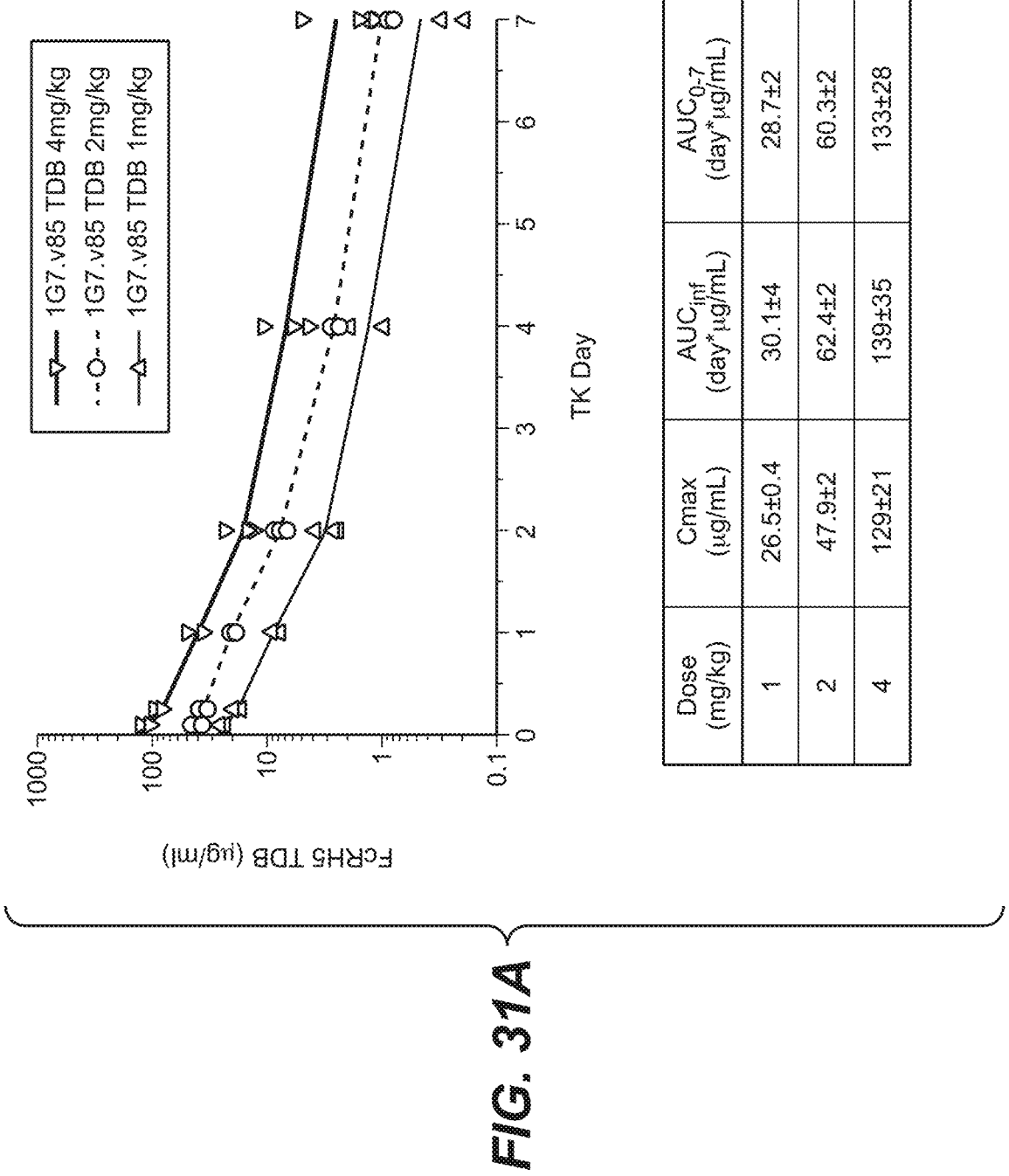
FIG. 31A is a graph showing the serum concentration of FcRH5 TDB plotted over the duration of the study after single-dose administration of 1G7.v85 TDB at 1 mg/kg, 2 mg/kg, or 4 mg/kg to three animals/group. A table showing pharmacodynamics parameters is shown below.
Figure 31B:
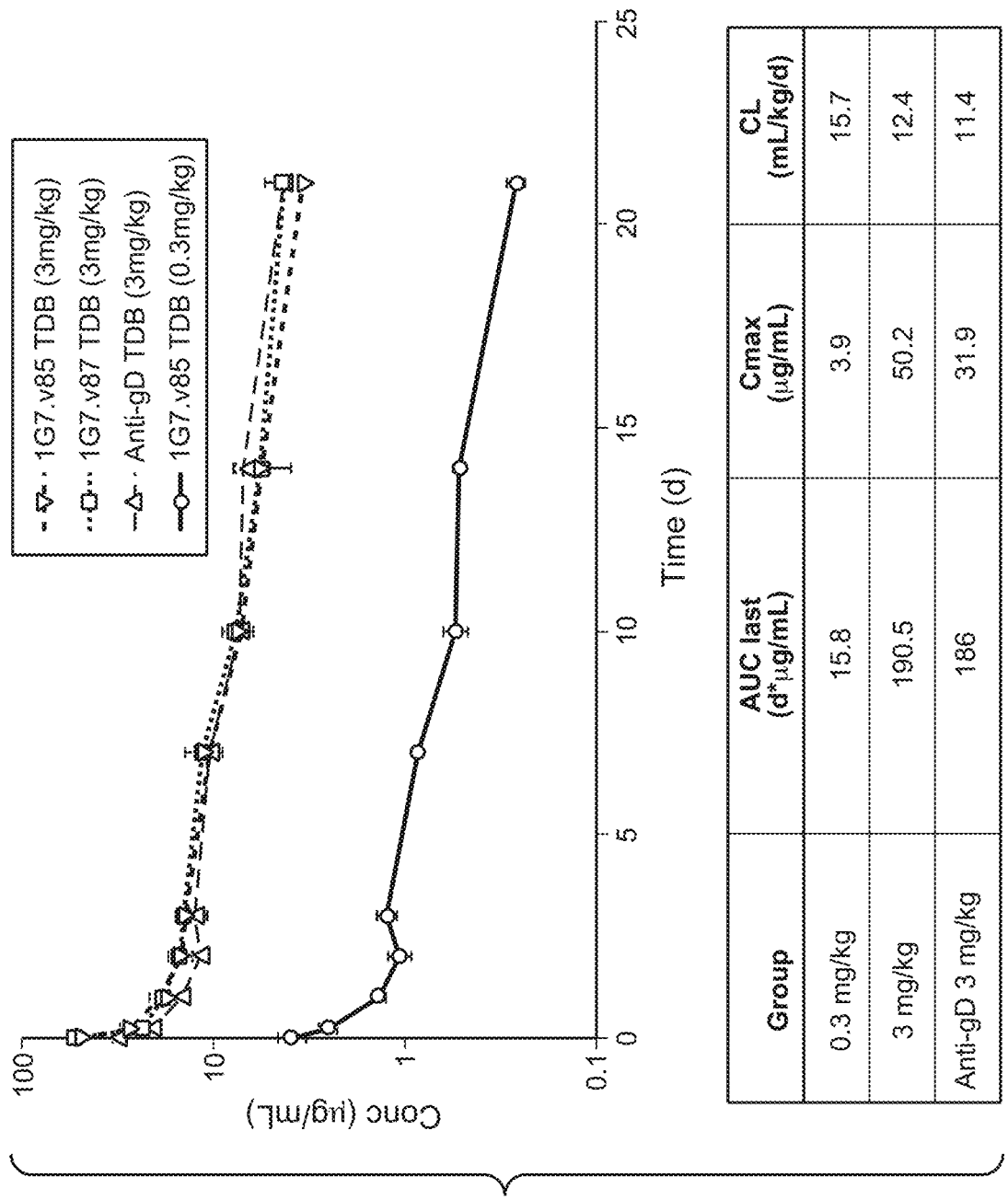
FIG. 31B is a graph showing the serum concentration of FcRH5 TDBs (1G7.v85 TDB and 1G7.v87/38E4.v1 TDB ("1G7.v87 TDB")) plotted over the duration of study after single dose administration of anti-gD TDB at 3 mg/kg or FcRH5 TDBs at 0.3 mg/kg or 3 mg/kg to three animals/group. A table showing pharmacodynamics parameters is shown below.
Figure 32A:
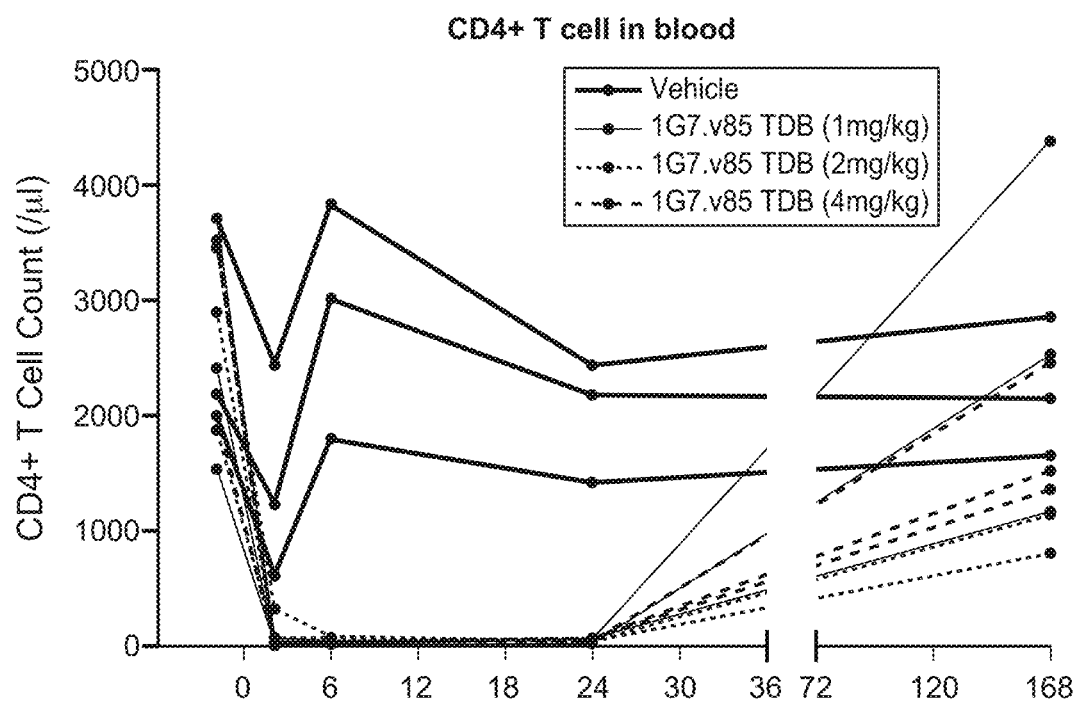
FIGS. 32A-32B are graphs showing the absolute count of CD4+ T cells in peripheral blood (FIG. 32A) and CD8+ T cells (FIG. 32B) in four groups of animals after single-dose intravenous administration of vehicle, 1G7.v85 TDB at 1 mg/kg, 1G7.v85 TDB at 2 mg/kg, or 1G7.v85 TDB at 4 mg/kg.
Figure 32B:
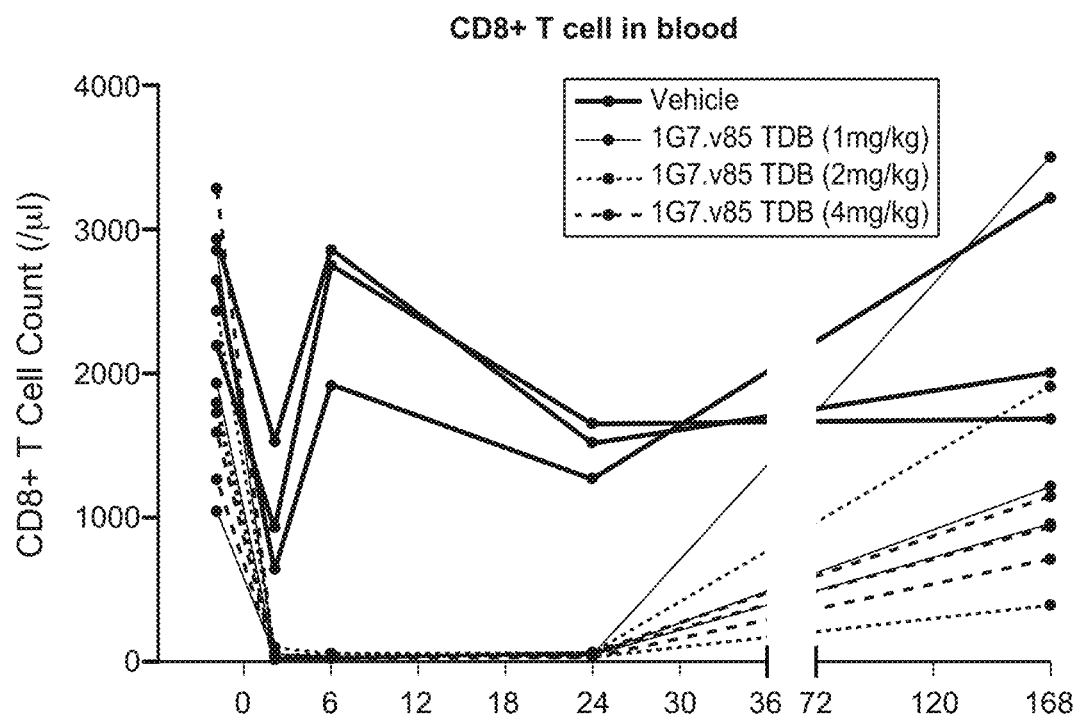
Figure 32C:
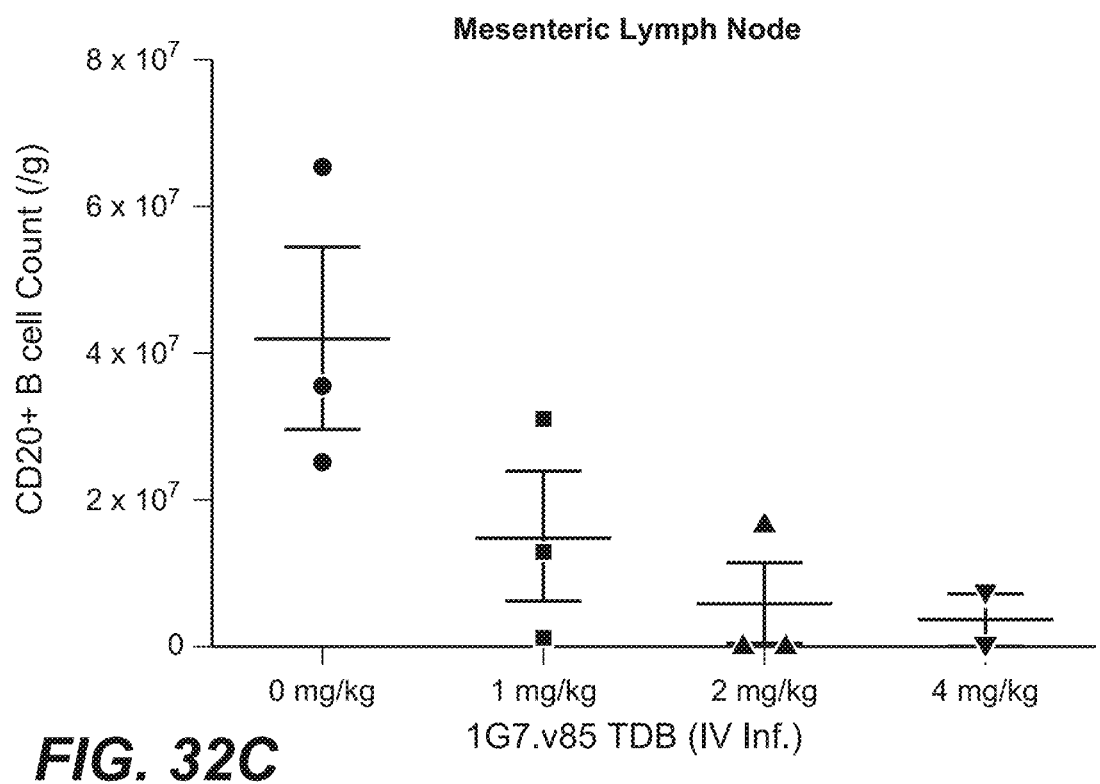
FIG. 32C is a graph showing the decrease in the absolute count of CD20+ B cells in mesenteric lymph nodes after 1G7.v85 TDB treatment. The plot is graphed as individual animals and mean group with SEM.
Figure 32D:
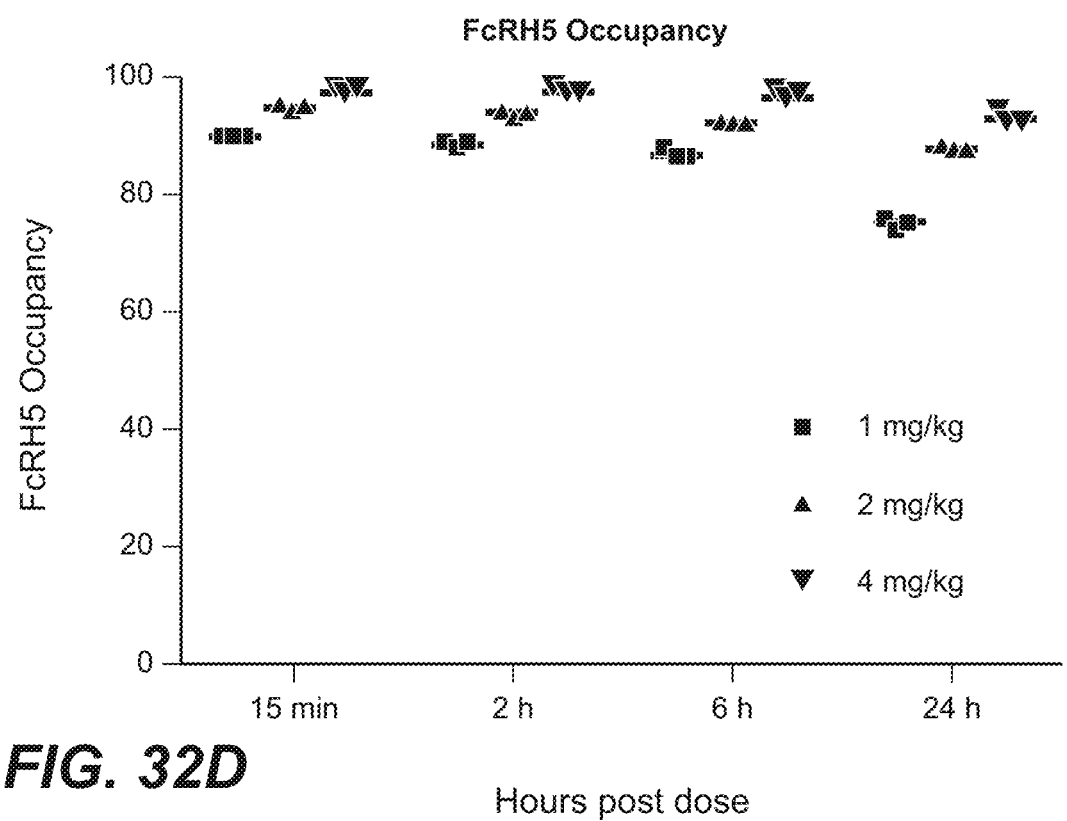
FIG. 32D is a graph showing FcRH5 occupancy after single-dose intravenous administration of 1G7.v85 TDB at 1 mg/kg, 2 mg/kg, or 4 mg/kg.
Figure 33A:
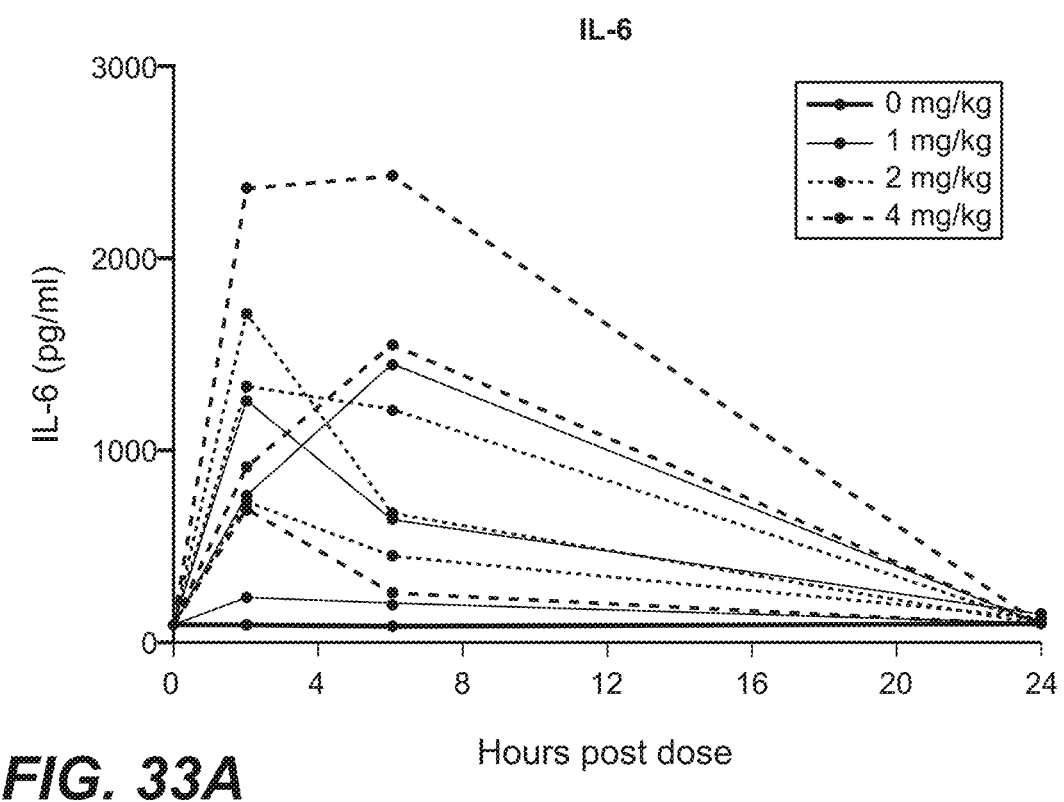
FIGS. 33A-33F are graphs showing the change in concentration of the cytokines IL-6 (FIG. 33A), IL-2 (FIG. 33B), IFN-γ (FIG. 33C), IL-1Rα (FIG. 33D), IL-5 (FIG. 33E), and MCP-1 (FIG. 33F) in four groups of animals after single-dose intravenous administration of vehicle, 1G7.v85 TDB at 1 mg/kg, 1G7.v85 TDB at 2 mg/kg, and 1G7.v85 TDB at 4 mg/kg.
Figure 33B:
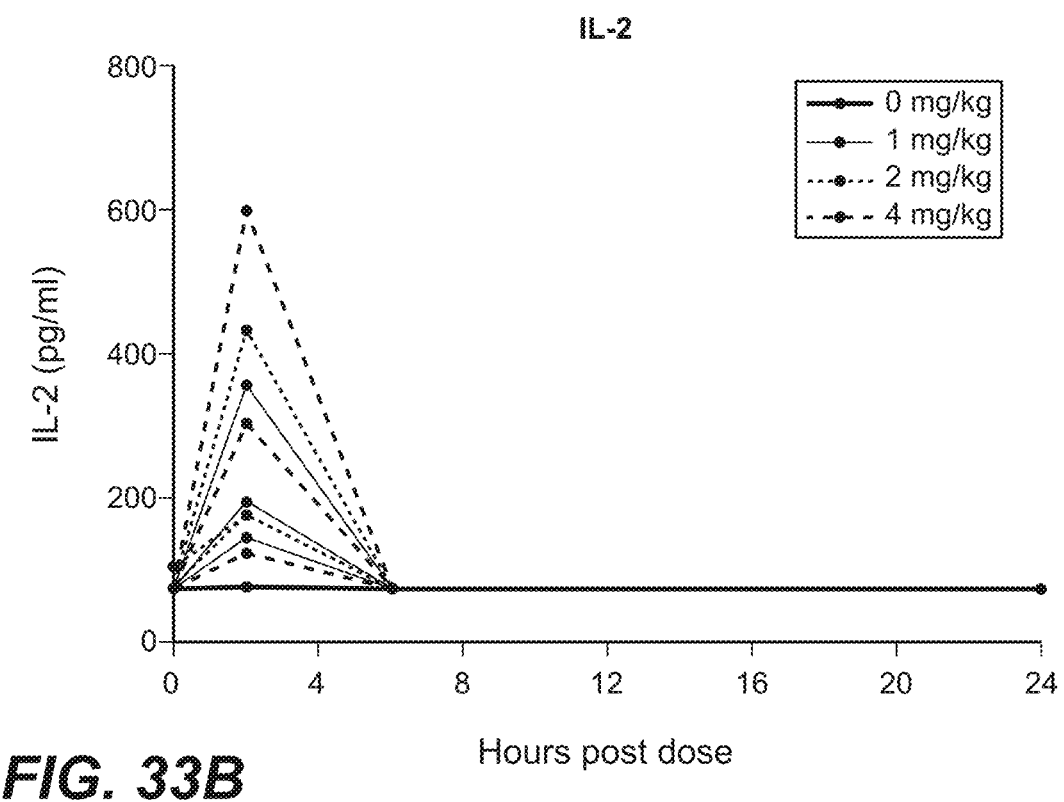
Figure 33C:
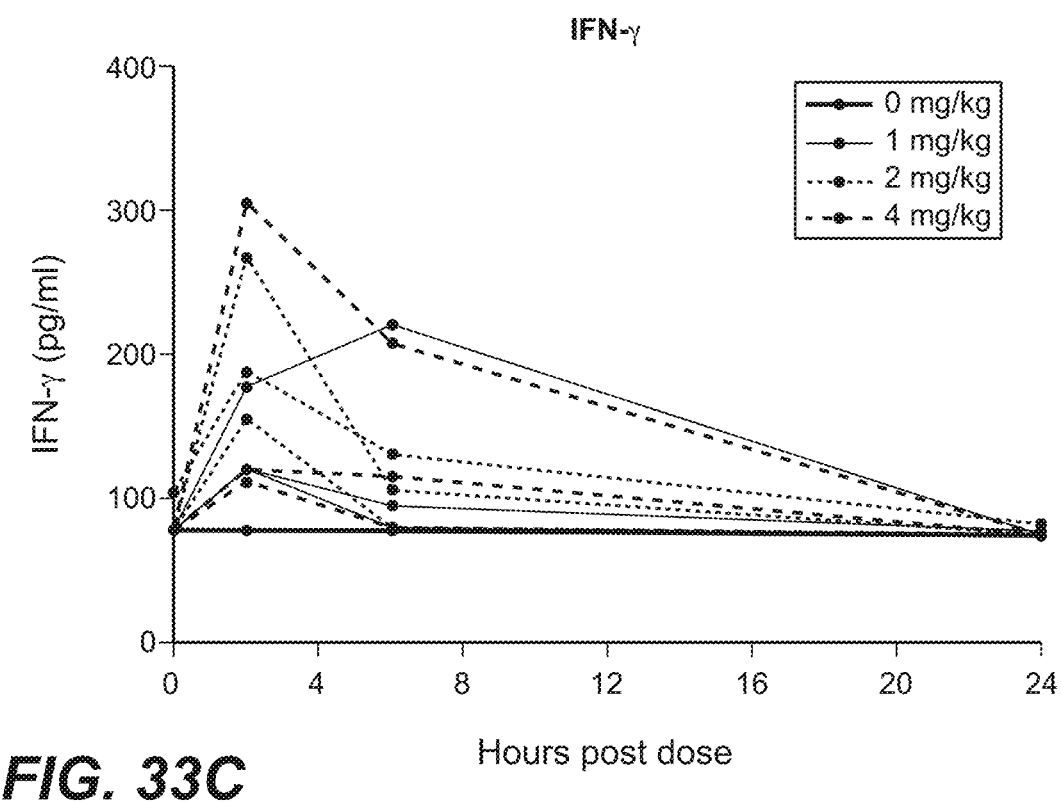
Figure 33D:
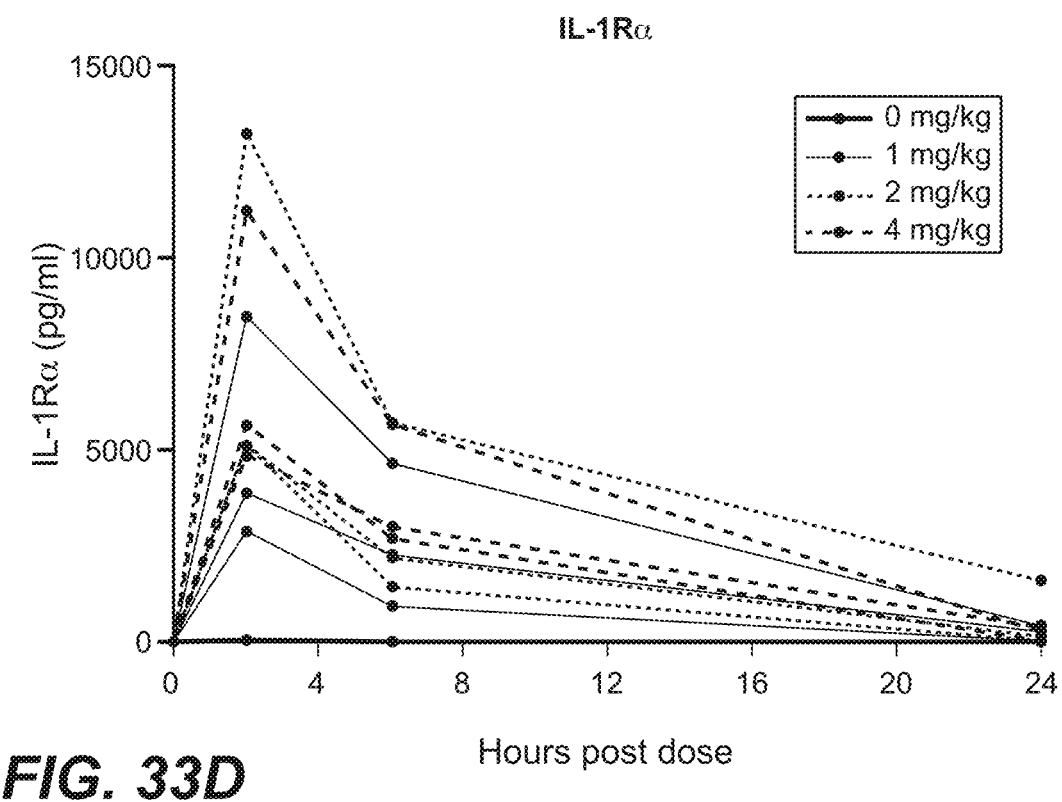
Figure 33E:
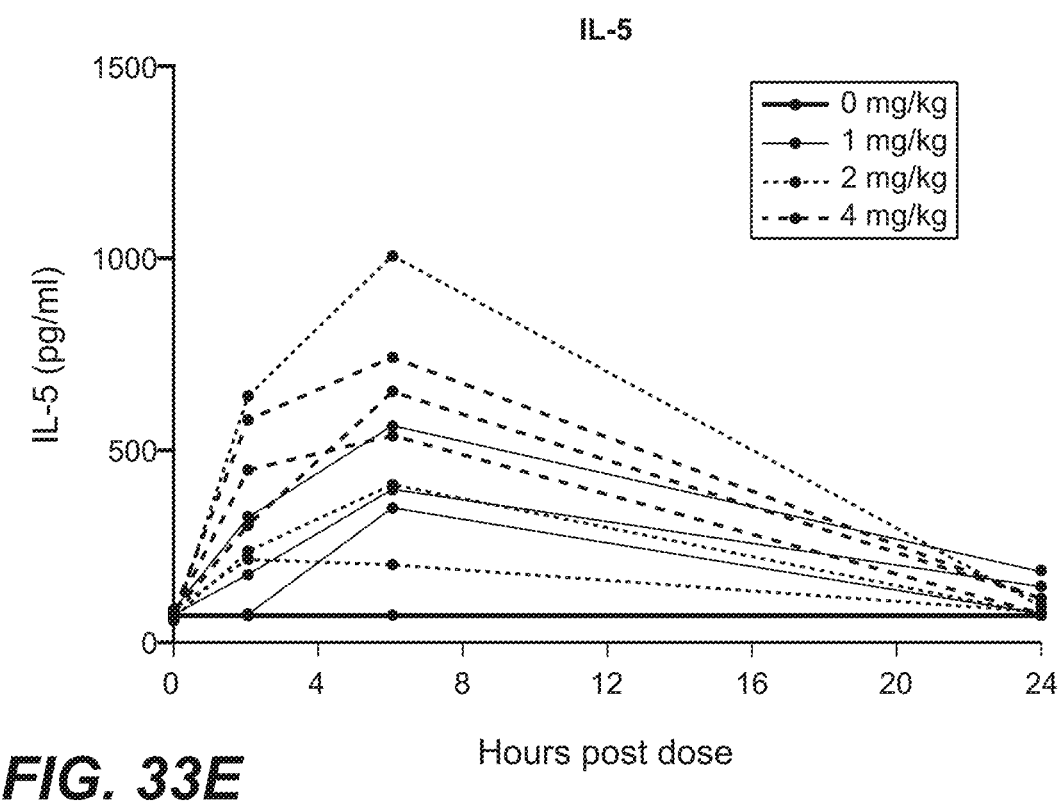
Figure 33F:
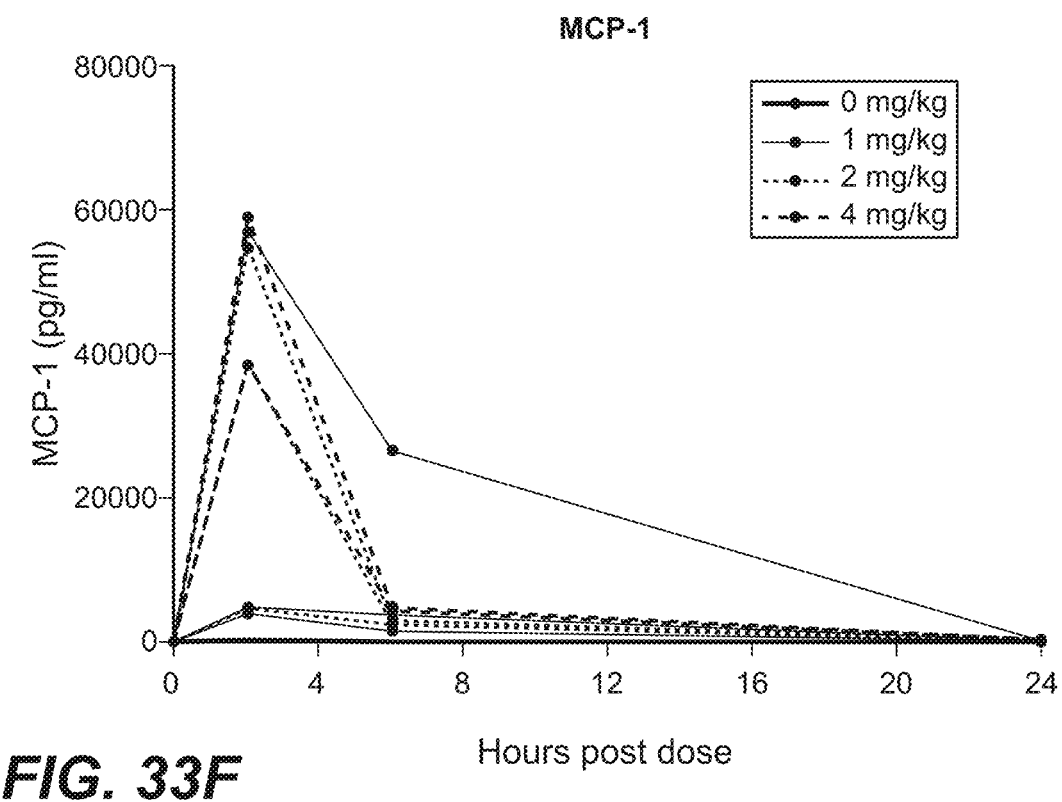

A single dose study was designed to evaluate safety, efficacy, pharmacokinetic (PK), and pharmacodynamic (PD) properties of the 1G7.v85 TDB in non-human primates. Cynos were treated with a single slow infusion intravenous dose of vehicle or 1-4 mg/kg 1G7.v85 TDB. The animals were closely monitored for adverse effects. Blood samples were collected at 0, 2, 6, and 24h for cytokine analysis, clinical pathology analysis, and PK/PD response. The study was terminated seven days after treatment was administered. The FcRH5 TDB demonstrated dose proportional exposure (Cmax and AUC) between 1-4 mg/kg and was cleared 29-33 ml/day/kg in all cohorts (FIG. 31A) and the Cmax at 4 mg/kg dose level was 129 μg/ml. This is 2000-fold higher than required to reach in vitro killing EC50 for human plasma cells and MOLP-2. A PK study was also conducted in SCID.bg mice, which are non-binding, and the 1G7.v85 TDB was found to be have comparable clearance rates as anti-gD TDB (FIG. 31B). Receptor occupancy calculations suggested near saturated FcRH5 engagement on peripheral blood B cells at Cmax at all dose levels (FIG. 32D). These results demonstrated that the 1G7.v85 TDB has a long in vivo half-life and support a weekly or less frequent dosing schedule.

C. FcRH5 TDB Depletes B Cells and Bone Marrow Plasma Cells in Cyno

Figure 31C:
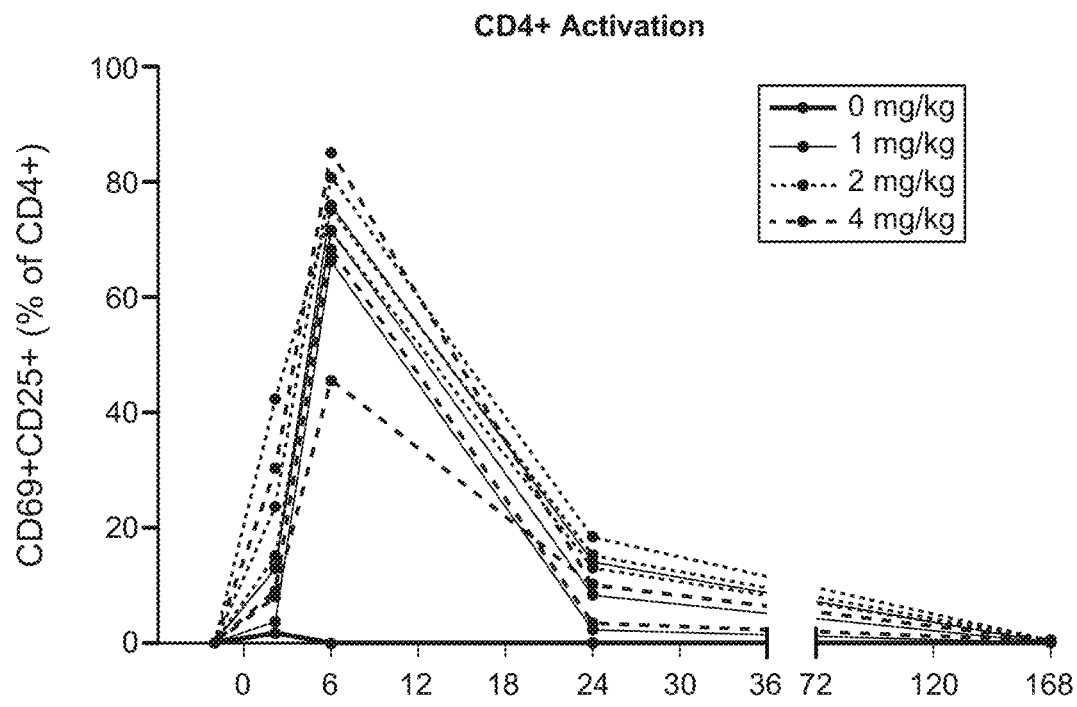
FIGS. 31C-31D are graphs showing 1G7.v85 TDB-induced transient T cell activation in cyno peripheral blood after single-dose intravenous administration of vehicle or 1G7.v85 TDB (1 mg/kg, 2 mg/kg, or 4 mg/kg) to three animals/group.
Figure 31D:
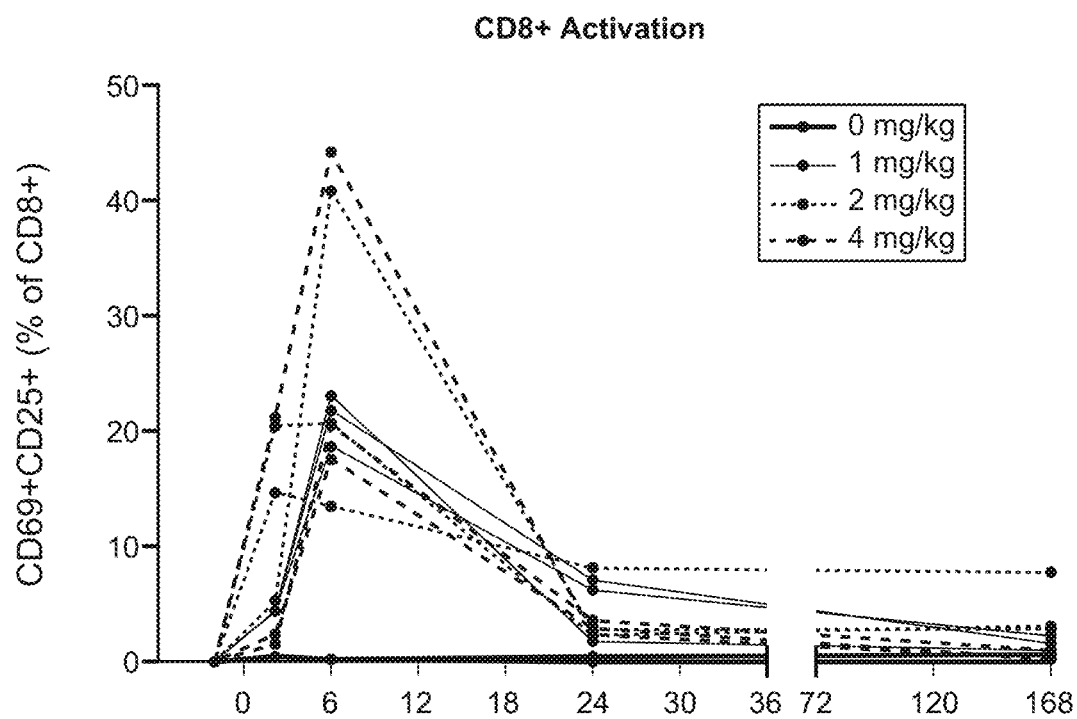
Figure 31E:
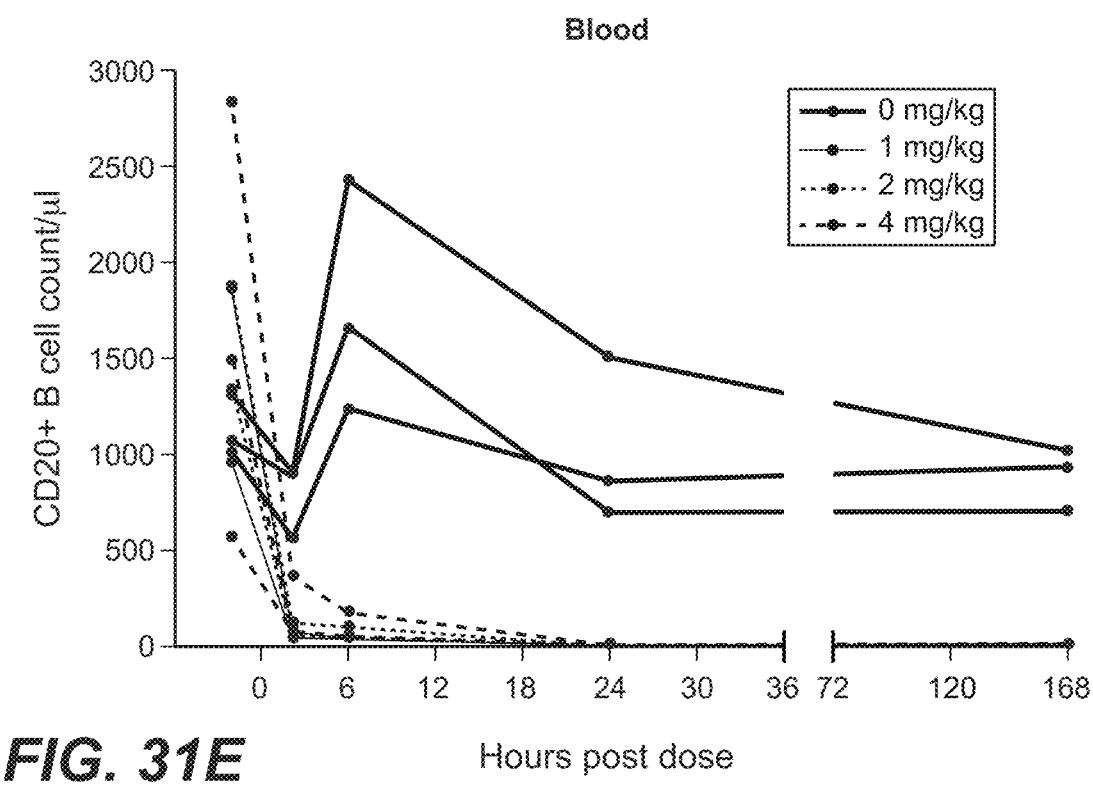
FIGS. 31E-31H are graphs showing the absolute count of CD20+ B cells in peripheral blood (FIG. 31E), spleen (FIG. 31F), mandibular lymph node (FIG. 31G), and bone marrow (FIG. 31H) in cyno after single-dose intravenous administration of vehicle or 1G7.v85 TDB (1 mg/kg, 2 mg/kg, or 4 mg/kg) to three animals/group.
Figure 31F:
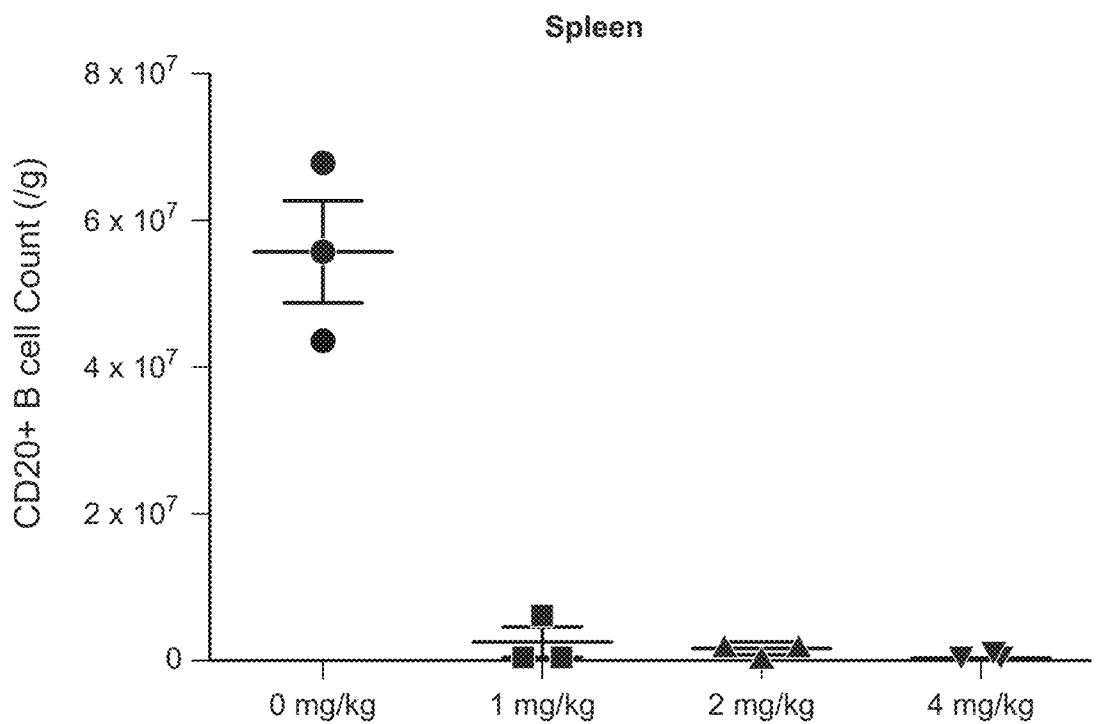
Figure 31G:
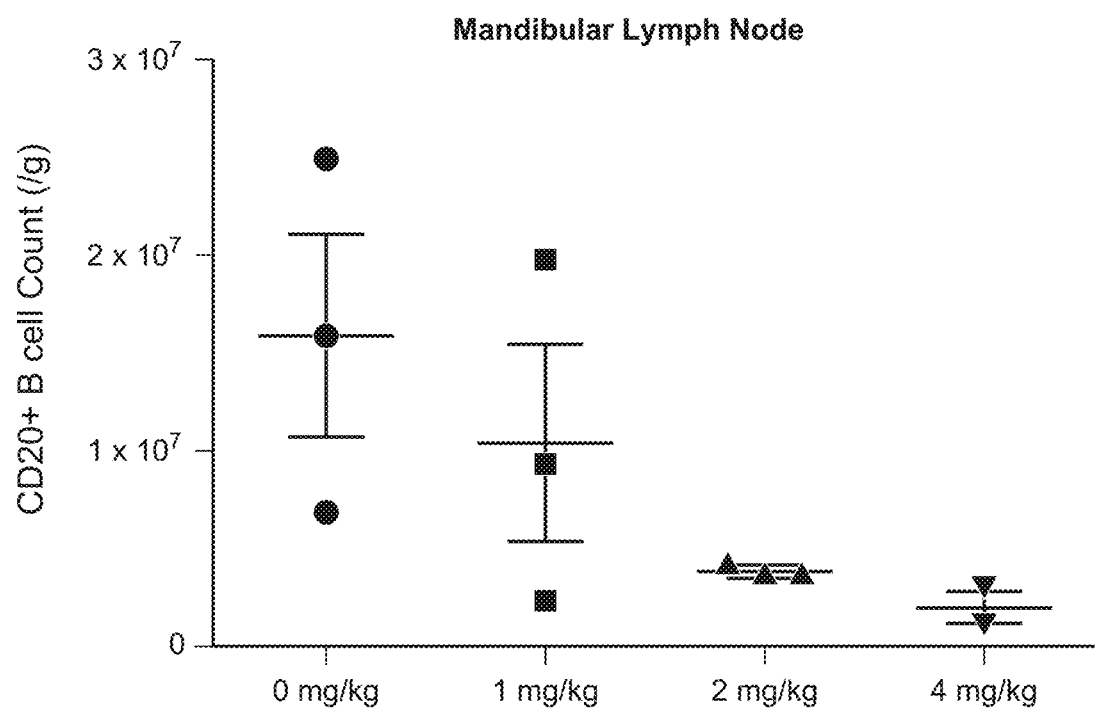
Figure 31H:
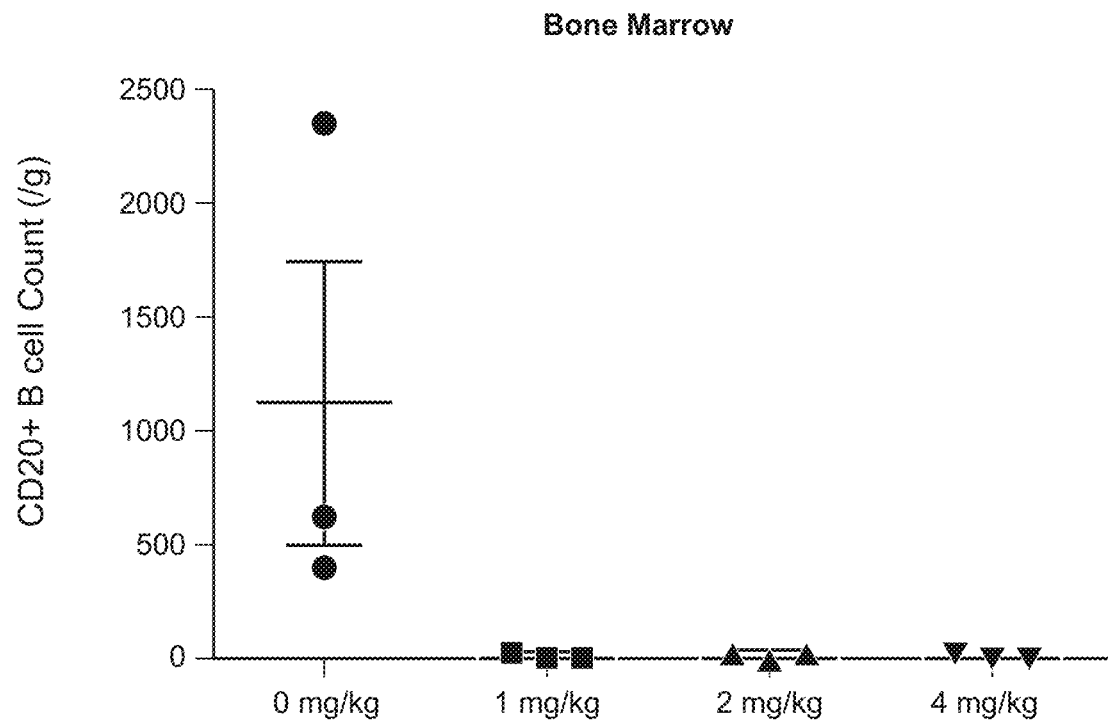

FACS analysis of peripheral blood demonstrated a robust pharmacologic effect on all dose levels. 1G7.v85 TDB treatment resulted in T cell activation and transient lymphopenia (margination response) within 24 hours (FIGS. 31C-31D). B cells remained undetectable in blood seven days after the dose, suggesting that they were depleted by the 1G7.v85 TDB (FIG. 31E). In contrast, CD4+ and CD8+ cells recovered by the end of the study (FIGS. 32A-32B). All dose levels resulted in complete depletion of B cells in spleen and bone marrow (FIGS. 31F and 31H). FcRH5 treatment induced a robust, dose-dependent depletion of B cells also from lymph nodes (FIGS. 31G and 32C).

Figure 31I:
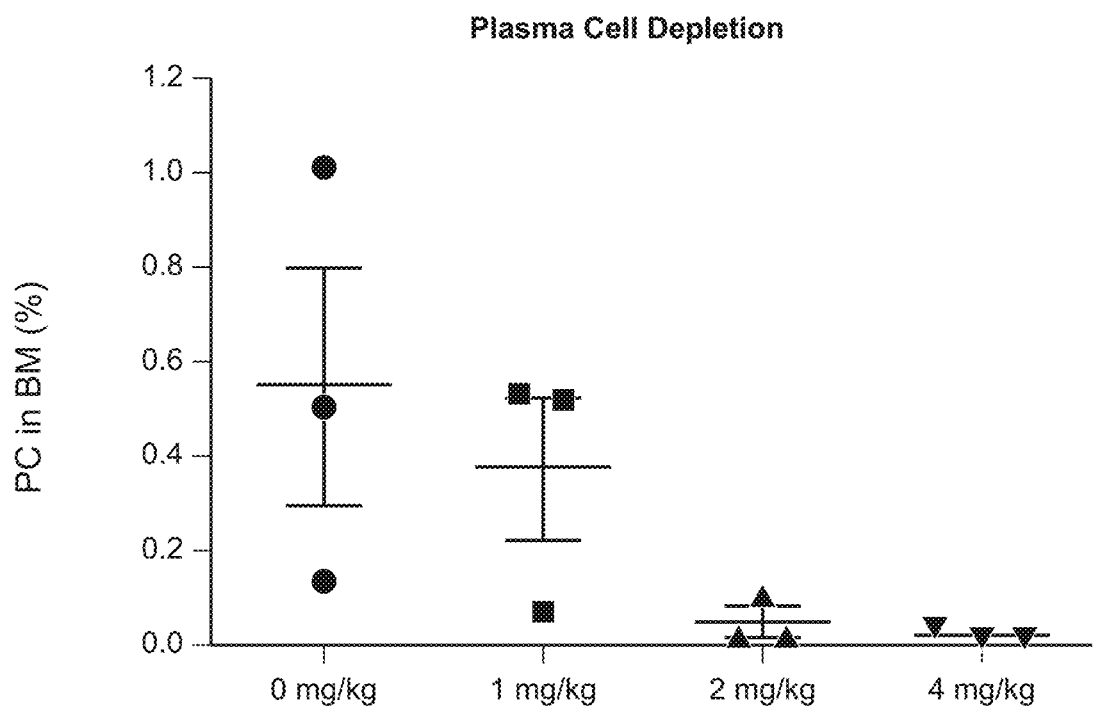
FIG. 31I is a graph showing that 1G7.v85 TDB depletes bone marrow plasma cells in cyno, with group measured SEM plotted.
Figure 31J:
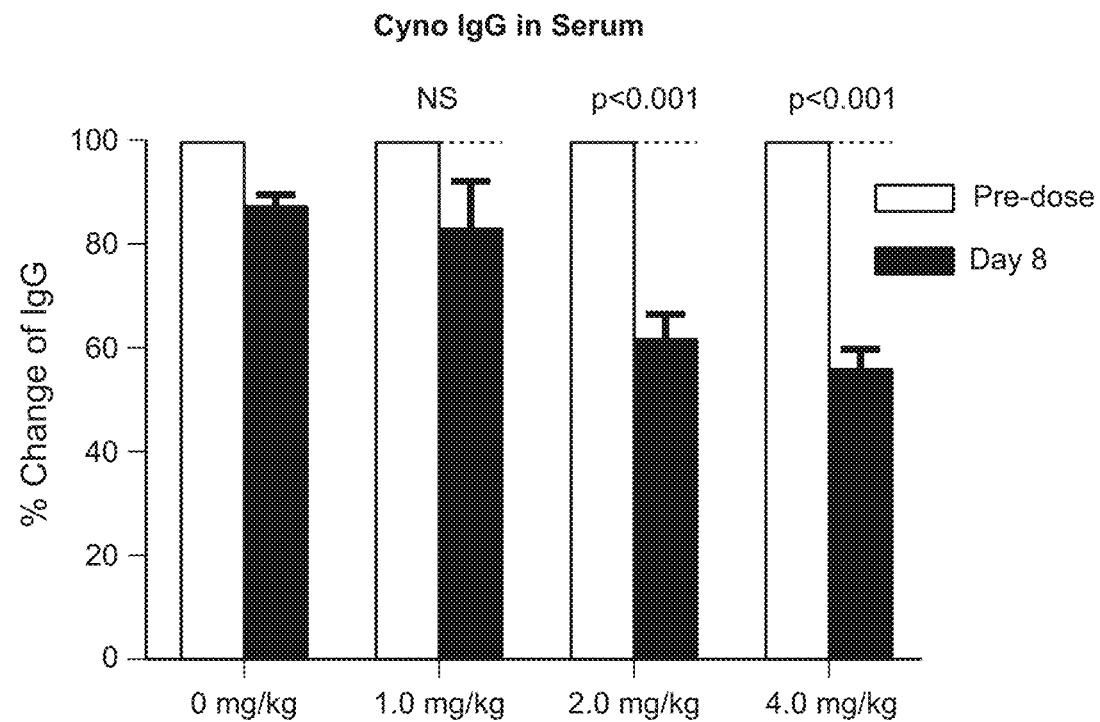
FIG. 31J is a graph showing the change of cyno IgG level response to treatment, calculated using formula {(IgG level pre-dose)−(IgG level end of study)}/(IgG level pre-dose)× 100. The difference between pre-dose and after treatment is analyzed by an unpaired t-test. The data are plotted with group mean and standard error of mean (SEM).

Depletion of cyno bone marrow plasma cells in vivo is a key efficacy endpoint in the preclinical development of the anti-FcRH5/CD3. Complete depletion of plasma cells was detected in the animals treated with 2-4 mg/kg doses (FIG. 31I). 1G7.v85 TDB treatment also resulted in dose-dependent reduction of cyno IgG, an expected secondary outcome resulting from plasma cell depletion. Theoretically, complete depletion of plasma cells should decrease IgG level ~30-40% by Day 7. The measured reduction in cyno IgG was 37% in 2 mg/kg group and 44% in 4 mg/kg group (FIG. 31J). In summary, 1G7.v85 TDBs induced a robust PD response in cyno, consistent with its mechanism of action. Complete plasma cell depletion provides compelling evidence of efficacy in the bone marrow microenvironment.

D. FcRH5 TDB is Well Tolerated in Cyno

The 1G7.v85 TDB was well tolerated in cyno at ≤4 mg/kg dose levels. The mild/moderate adverse effects that were detected were similar at all dose levels and we failed to see a clear dose response. Clinical observations were limited to reversible increases in body temperature ranging from 0.4-1.6° C. within four hours post-dose. Effects on hematology consisted of the expected acute and reversible lymphopenia attributed to margination. As expected, evidence of an acute and reversible pro-inflammatory state were detected (increased CRP, fibrinogen, prothrombin time, and activated partial thromboplastin time). Treatment caused a reversible increase of ALT, AST, and total bilirubin.

Consistent with the mechanism of action, the 1G7.v85 TDB induced a rapid, generally mild/moderate cytokine release (FIGS. 33A-33F). All dose levels induced a pro-inflammatory response (including IL-6, IL-5, IFN-g, IL-2, IL-13, G-CSF and MCP-1) and anti-inflammatory response to counter this (IL1R) peaking at 2-6 h. All cytokines were reversed to normal level within 24 hours. No signs of extensive or prolonged cytokine release were seen. Extensive histopathological analysis including detailed analysis of central nervous system (CNS) did not reveal significant organ toxicity. In summary, maximum tolerated dose was not reached in the study. The 1G7.v85 TDB was well tolerated at dose levels that are expected to saturate target and sufficient for complete depletion of B cells and plasma cells. No dose response was detected in adverse effects.

Example 5. FcRH5 Combination Therapies

To examine possible FcRH5 combination therapies, a FcRH5 TDB was tested in combination with each of two exemplary PD-1 axis binding antagonists. These experiments demonstrated that, while PD-1/PD-L1 feedback signaling could reduce FcRH5 TDB-mediated killing, PD-L1 blockade overcame this inhibition, resulting in improved therapeutic efficacy.

Materials and Methods

A. Antibodies

All labeled antibodies for flow cytometry, except ones otherwise mentioned, were purchased from BD Bioscience. The anti-PD-1 antibody used was KEYTRUDA® (pembrolizumab) and the anti-PD-L1 antibody was generated at Genentech, Inc. Goat anti-human IgG and goat anti-mouse IgG were purchased from Jackson Immunoresearch. Anti-PC-FITC (clone Vs38c) was purchased from DAKO.

B. PD-1 Induction and Cytotoxicity Assay with Anti-PD-L1

Fresh isolated human CD8+ T cells were mixed with MOLP-2 cells in a 1:1 ratio and co-cultured in the presence of 1000 ng/ml of 1G7.v85 TDB for 48 hours. The cells were stained with a fluorescein isothiocyanate (FITC)-labelled anti-CD8 antibody ("anti-CD8-FITC"), a phycoerythrin (PE)-conjugated anti-CD69 antibody ("anti-CD69-PE"), and an allophycocyanin (APC)-conjugated anti-PD-1 antibody ("anti-PD-1-APC"), and analyzed by flow cytometry. Cytotoxicity assay of HEK-293T cells expressing FcRH5 and PD-L1 ("293-FcRH5-PD-L1 cells") was set up, as generally described herein, with or without 10 mg/ml anti-PD-L1 or anti-PD-1 antibody and analyzed by flow cytometry.

C. Cell Culture and Stable Cell Line Generation

The effect of PD-1/PD-L1 signaling on 1G7.v85 TDB activity was evaluated by infecting HEK-293T cells with lentivirus encoding FcRH5 followed by transfection of a human PD-L1 encoding plasmid using lipofectamine (Invitrogen).

D. In Vitro Cytotoxicity and T Cell Activation Assays

Target cells were labeled with carboxyfluorescein succinimidyl ester (CFSE) according to manufacturer's protocol (Life Technology, #C34554). The CFSE-labeled target cells and purified CD8+ cells were mixed in 3:1 effector cell to target cell (E:T) ratio and incubated with 1G7.v85 TDB for 24 to 48 hours. At the end of the incubation, the cells were analyzed with flow cytometry on a FACSCalibur in automation format. The number of live target cells was counted by gating on CFSE+/PI-negative cells. The percentage of cytotoxicity was calculated as follows: % cytotoxicity (live target cell number w/o TDB-live target cell number w/TDB)/(live target cell number w/o TDB)×100.

Results

A. PD-1/PD-L1 Blockade Enhances Activity of the FcRH5 TDB

Figure 34:
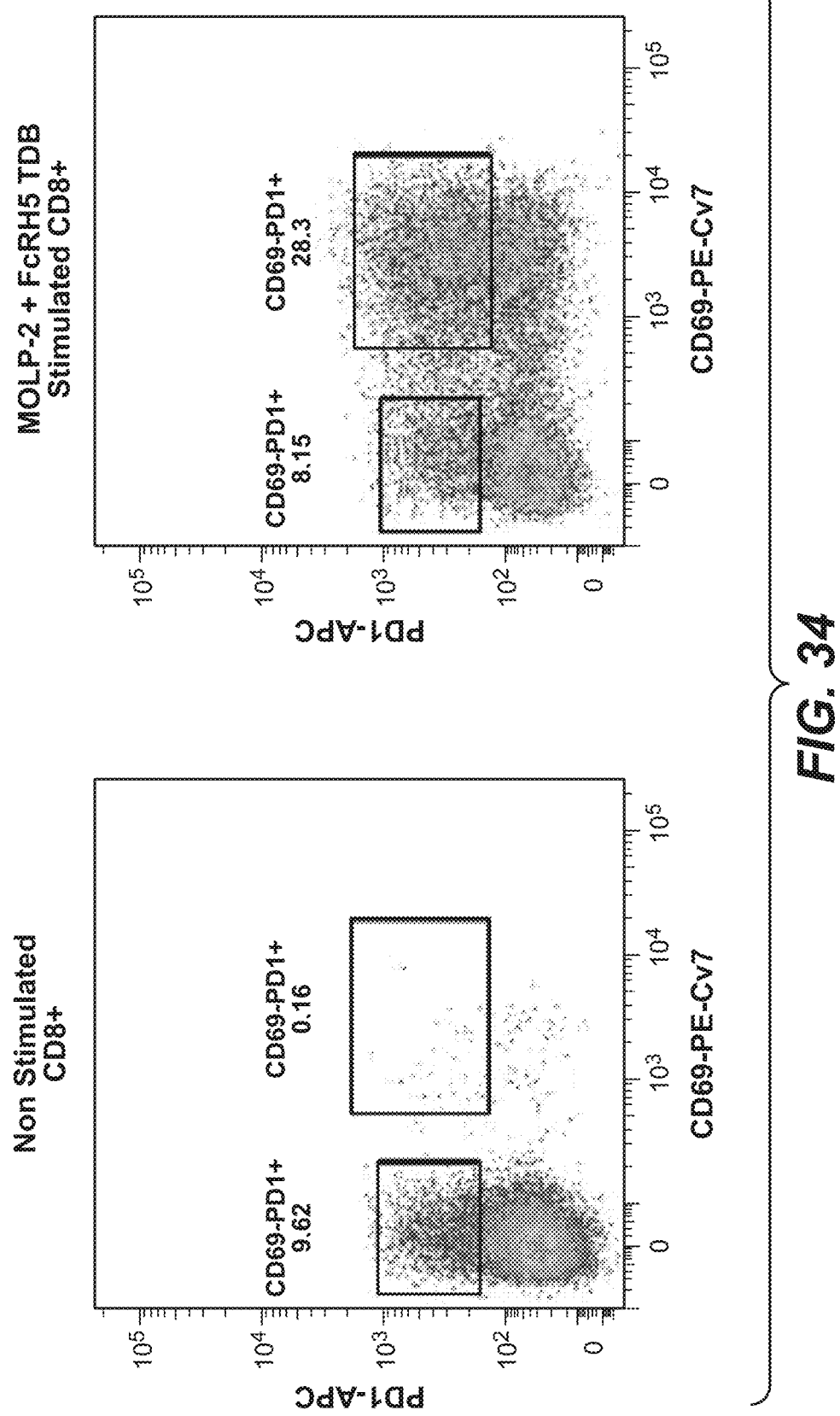
FIG. 34 is a series of plots showing that 1G7.v85 TDB treatment induces PD1 expression in human T cells. CD8+ T cells were stimulated for 48 hours with the 1G7.v85 TDB and MOLP-2 target cells and then analyzed by flow cytometry.
Figure 35A:
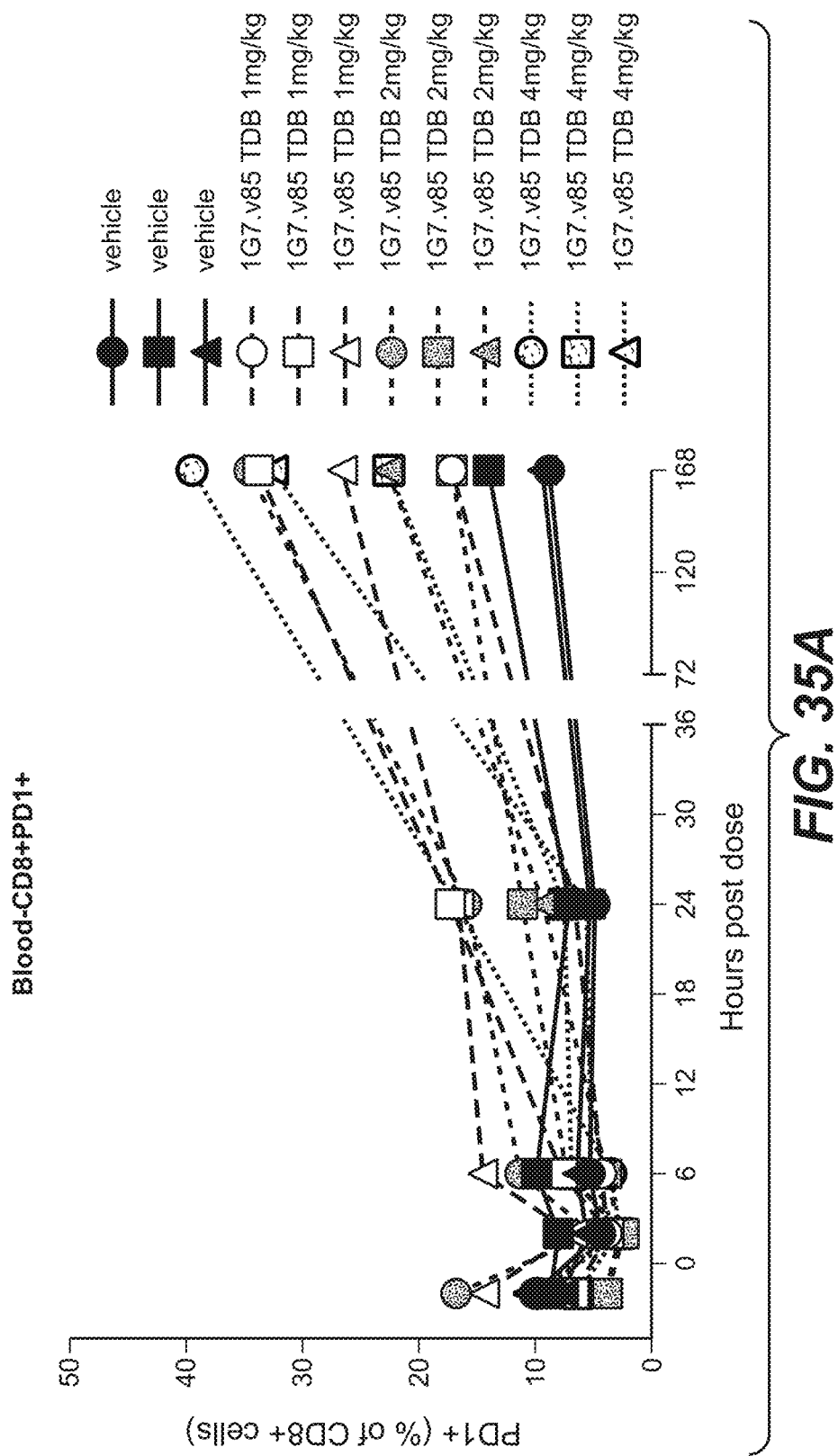
FIG. 35A is a graph showing the percentage of PD1+ in CD8+ T cells in cyno after a single-dose intravenous administration of vehicle, 1 mg/kg, 2 mg/kg, and 4 mg/kg of 1G7.v85 TDB. 1G7.v85 TDB treatment results in induction of PD1 in cyno T cells in vivo.
Figure 35B:
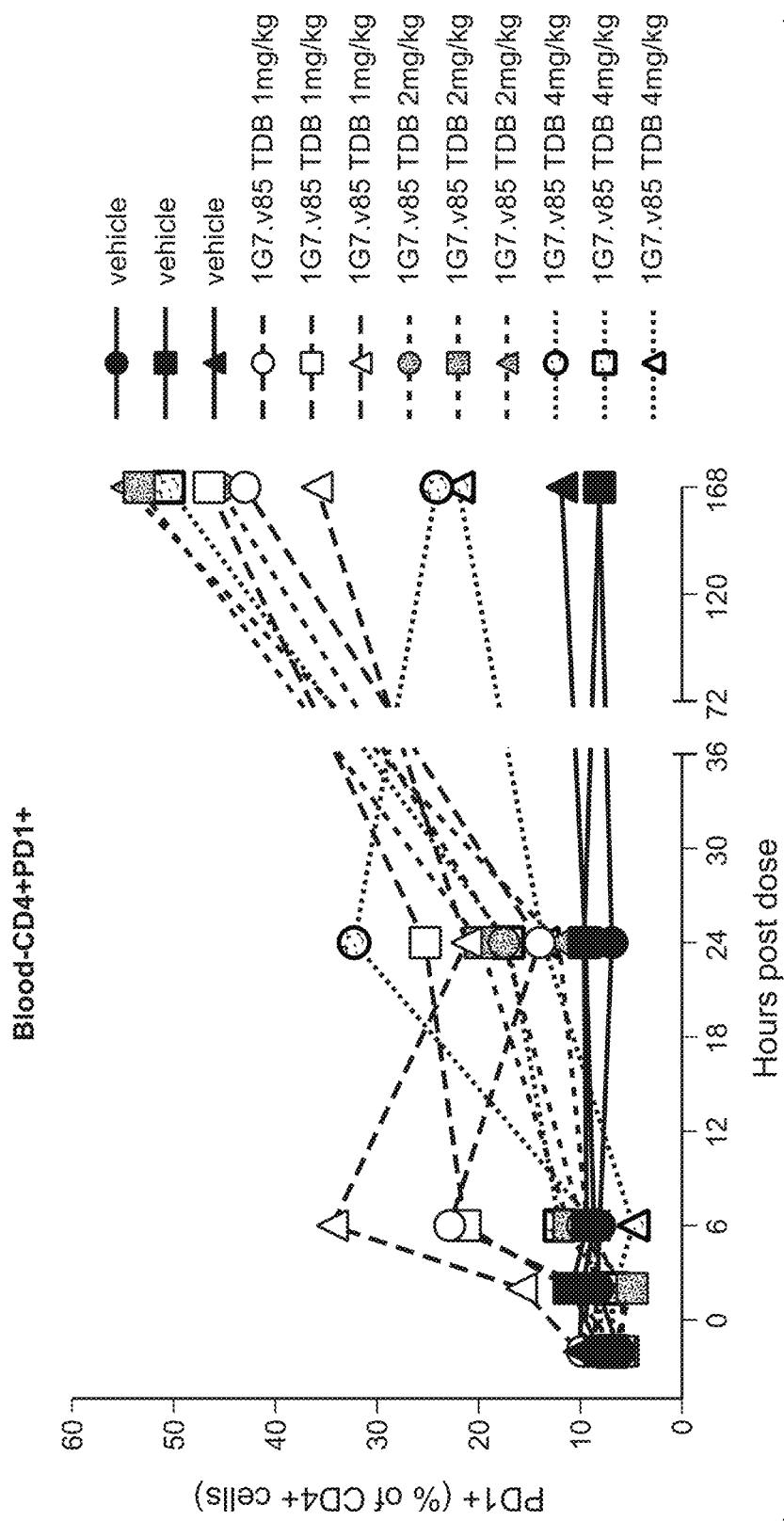
FIG. 35B is a graph showing the percentage of PD1+ in CD4+ T cells in cyno after single dose intravenous administration of vehicle, 1 mg/kg, 2 mg/kg, and 4 mg/kg of 1G7.v85 TDB.
Figure 36A:
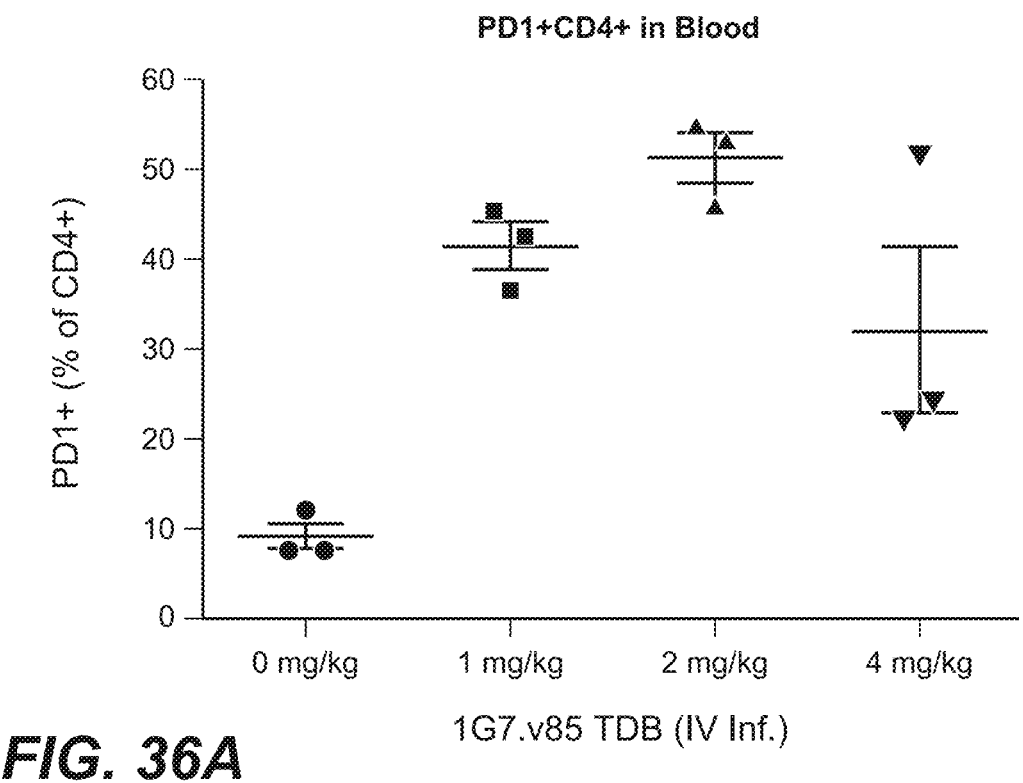
FIGS. 36A-36D are plots showing PD-1 expression in CD4+ T cells from blood (FIG. 36A), CD8+ T cells from spleen (FIG. 36B), CD8+ T cells from lymph node (FIG. 36C), and CD8+ T cells from bone marrow (FIG. 36D), as analyzed by FACS seven days after dosing with 1G7.v85 TDB or vehicle.
Figure 36B:
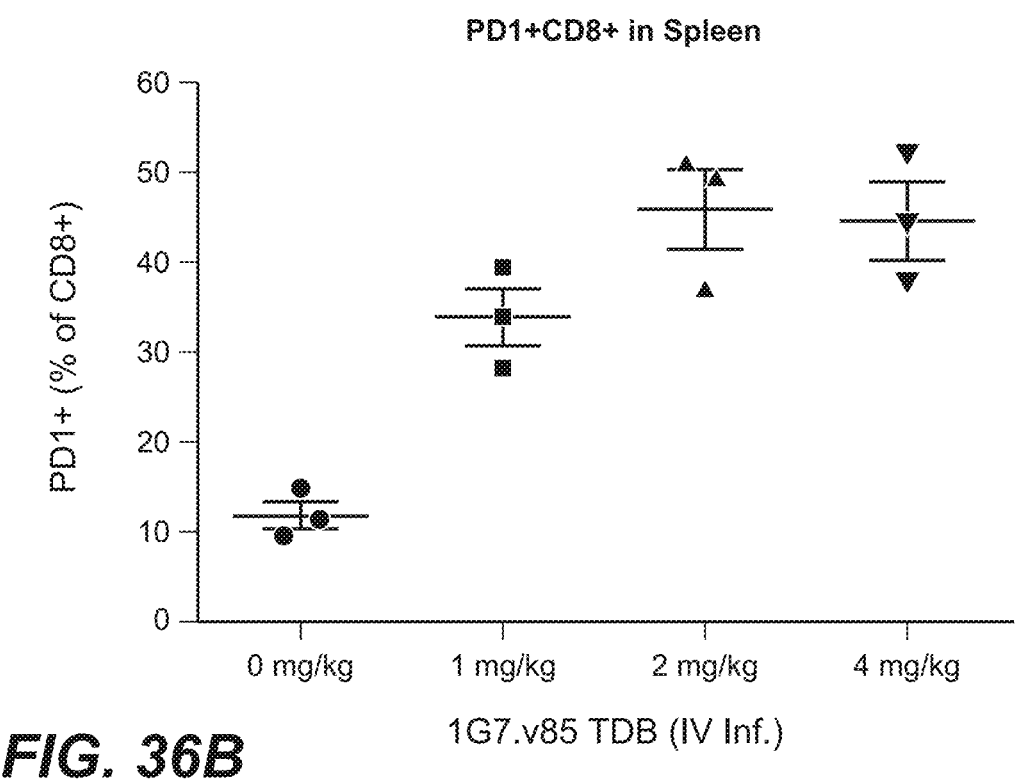
Figure 36C:
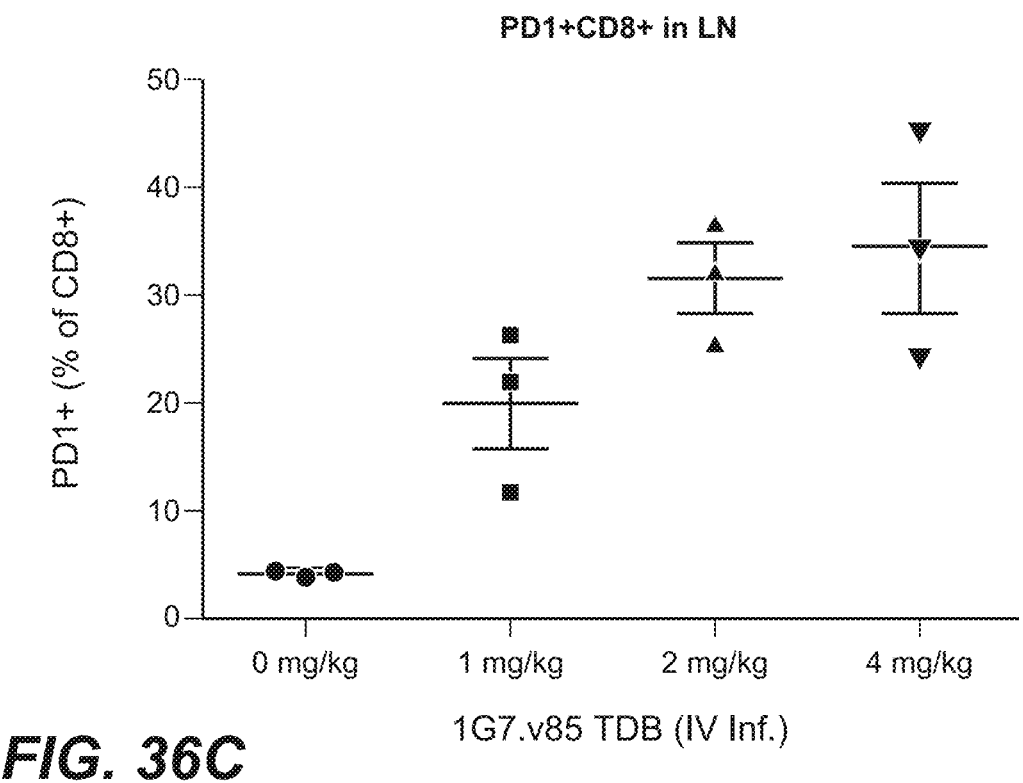
Figure 36D:
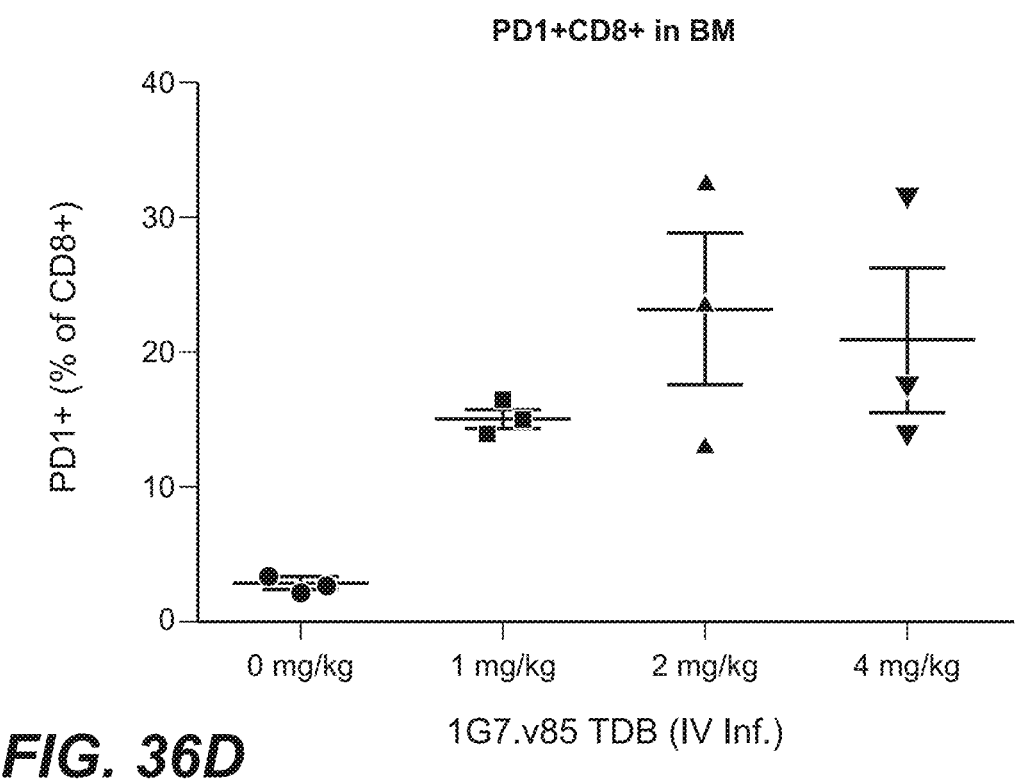

Strong TCR stimulation signal can lead to immunosuppressive feedback that restricts T cell activity. The PD-1/PD-L1 pathway is a critical component of this feedback and a therapeutically validated immune escape mechanism in several tumor indications. PD-L1 is frequently expressed by myeloma tumor cells (Gorgun et al. *Amer. Assoc. for Cancer Res.* 21:4607-4618, 2015), and its signaling may limit T cell activity in myeloma patients. PD-1 is absent in resting T cells, induced upon T cell activation and limits T cell activity in chronic infection (Zou et al. *Science Tran. Med.* 8:328rv324, 2016). 1G7.v85 TDB stimulation (48h) of human healthy donor CD8+ cells in the presence of FcRH5-expressing cells resulted in significant PD-1 induction in T cells (FIG. 34). The feedback signal is also activated in vivo. Significant increase in PD-1-positive T cells was seen in cyno T cells at all dose levels. PD-1 induction was detected in both CD8+ and CD4+ cells in blood, spleen, lymph nodes, and bone marrow (FIGS. 35A-35B and 36A-36D).

Figure 37A:
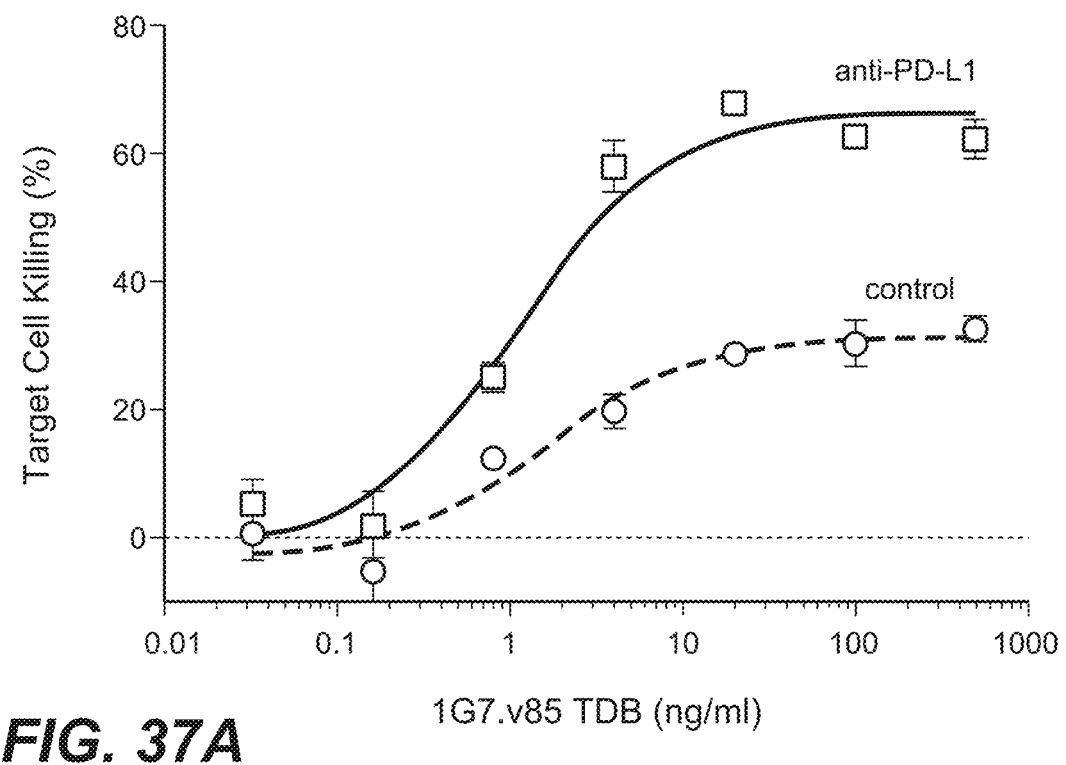
FIGS. 37A-37B are graphs showing the ability of the 1G7.v85 TDB to redirect activity of pre-stimulated CD8+ T cells to kill HEK-293T cells expressing FcRH5 and PD-1 ("293-FcRH5-PD-L1 cells") in the presence or absence of an anti-PD-L1 or anti-PD-1 antibody. The curve in FIG. 37A is graphed with mean and standard of error (SD) of triplicates.
Figure 37B:
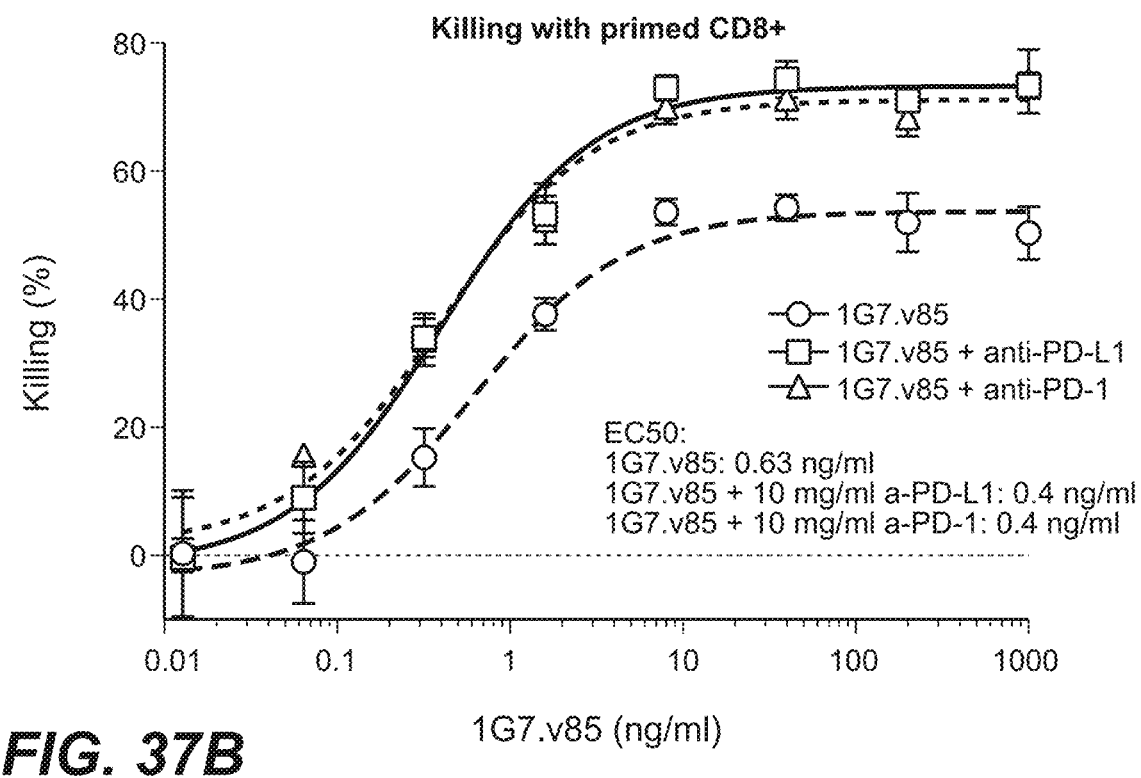

1G7.v85 TDB-mediated target cell killing with primed CD8+ cells was evaluated in the presence and absence of PD-1/PD-L1 antagonists. The efficiency of the 1G7.v85 TDB to prime CD8+ T cells to kill PD-L1 expressing target cells was modest (FIG. 37A). Blocking PD-1/PD-L1 signaling using anti-PD-L1 antibody significantly increased the efficiency of 1G7.v85 TDB-mediated killing (FIG. 37A). In a particular experiment, primed CD8+ cells were mixed with 293-FcRH5-PD-L1 cells and treated with the 1G7.v85 TDB alone, or in combination with an either an anti-PD-L1 antibody or the anti-PD-1 antibody (pembrolizumab) (FIG. 37B). Combined treatment with an anti-PD-L1 antibody or an anti-PD-1 antibody (pembrolizumab) significantly enhanced the efficacy of the 1G7.v85 TDB. The EC50 for both combined treatment methods was 0.4 ng/mL, while the EC50 for treatment with 1G7.v85 TDB alone was 0.63 ng/mL (FIG. 37B).

These results demonstrate that 1G7.v85 TDB-mediated activation of T cells leads to induction of PD-1 in T cells in vitro and in vivo. These results further demonstrate that PD-1/PD-L1 signaling can limit FcRH5 TDB-mediated killing and that PD-L1 blockage can overcome this inhibition and lead to improved efficacy. These data support the use of FcRH5 TDB in combination with a PD-1 axis binding antagonist, such as an anti-PD-1 antibody or an anti-PD-L1 antibody.

Figure 38A:
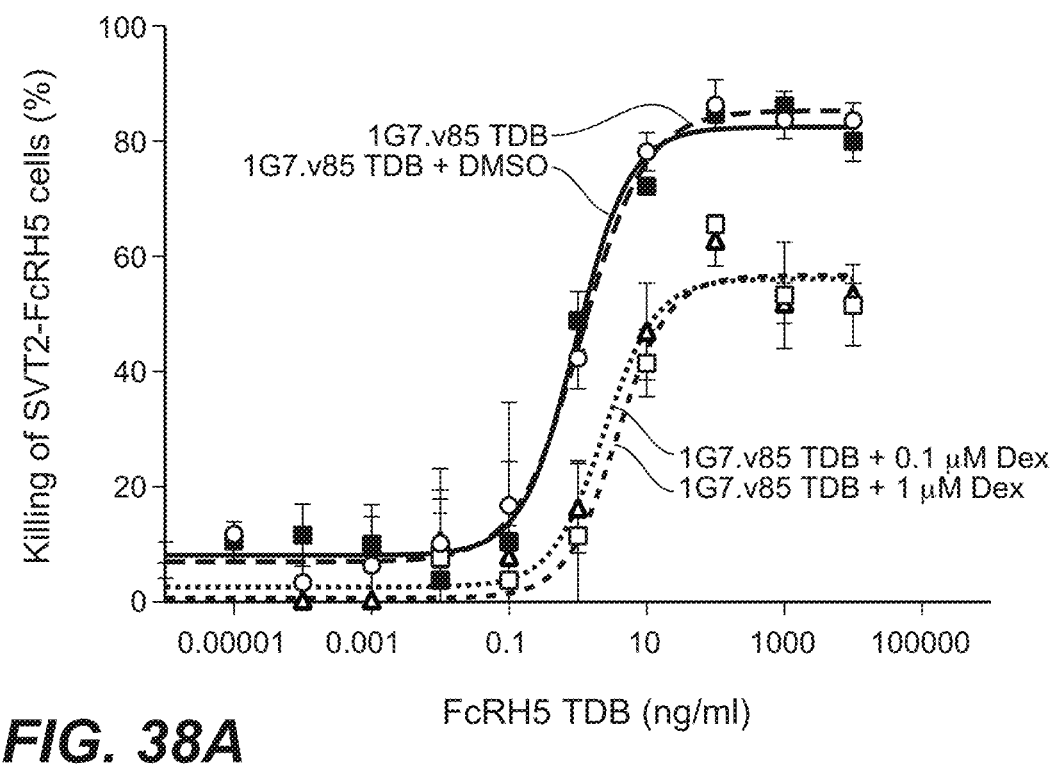
FIG. 38A is a graph showing target cell killing of SVT2-FcRH5 by 1G7.v85 TDB in the presence and absence of dexamethasone (Dex).
Figure 38B:
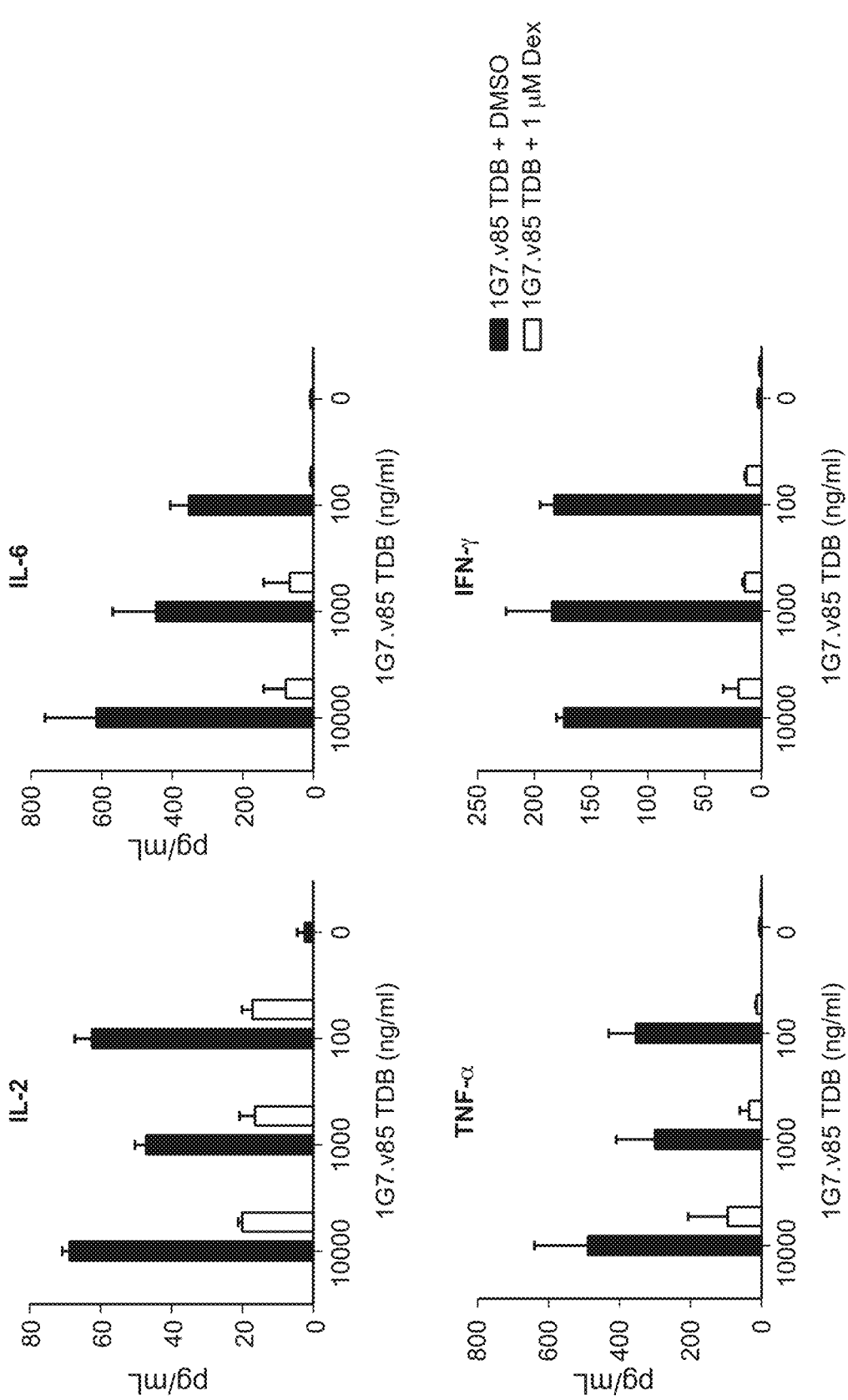
FIG. 38B is a series of graphs showing cytokine (i.e., IL-2, IL-6, TNF-α, and IFN-γ) release after treatment with 1G7.v85 TDB in the presence and absence of 1 pM Dex.

B. Dexamethasone Reduces the First-Dose Cytokine Response without Affecting FcRH5 TDB Activity Target cell killing was also evaluated in the presence and absence of dexamethasone (Dex), a component of standard of care in myeloma that has anti-inflammatory and immunosuppressant effects (FIG. 38A). The IC50 for the 1G7.v85 TDB in buffer or in DMSO was 7 µM and 6 µM, respectively. In the presence of 0.1 µM or 1 µM Dex, the IC50 for the 1G7.v85 TDB was 16 µM and 25 µM, respectively. Dex combination treatment had only a modest effect on 1G7.v85 TDB efficacy and significantly reduced IL-2, IL-6, TNF-α, and IFN-γ levels. These results demonstrate that dexamethasone may be used in combination with FcRH5 TDB therapy to mitigate a first-dose cytokine response in patients (FIG. 38B).

Example 6. Production and Testing of FcRH5 Bis-Fabs

A. Preparation of Thio-Fabs and Hinge-Cys-Fabs and Protein Production

To prepare antibody fragments with free sulfhydryl groups, cysteine (Cys) substitutions were introduced into antibody constructs at various positions in either the variable or the constant domains of light chains or heavy chains by site-directed mutagenesis to create thio-mAbs, as described previously in Junutula et al. *J. Immunol Methods* 332(1-2): 41-52, 2008. Thio-Fabs were generated enzymatically from thio-mAbs by diluting thio-mAbs to 1 mg/mL in 25 mM Tris, pH 8.0, followed by enzymatic digestion at 37° C. for 1 hour using Lys-C(Wako Chemicals USA, Inc., Richmond, Va.) at a 1:1000 (wt:wt) ratio of enzyme to antibody. The Lys-C digestion was stopped with 51aM of the protease inhibitor tosyl-L-lysine chloromethyl ketone (TLCK) (Bachem, Torrence, Calif.) and purified by cation ion exchange chromatography on a 5 mL Hi-Trap SP FF column (GE Healthcare, Piscataway, N.J.) using a 50-mM sodium acetate buffer and a 0-300-mM NaCl 10 column volume (CV) gradient. The thio-Fabs produced by this method are sometimes referred to as "enzymatic thio-Fabs" herein. In another approach, DNA constructs encoding Fabs having an engineered Cys residue or DNA constructs encoding heavy chain fragments containing one native Cys residue in the hinge region, were subcloned into plasmid expression vectors and expressed directly in CHO cells. The thio-Fabs produced by this method are sometimes referred to as "recombinant thio-Fabs" herein. A third approach was used for antibodies lacking an engineered Cys residue and relied upon the native Cys residue(s) present in the hinge region of IgG. This method is used to produce "hinge-cys-Fabs" and is described in further detail below.

Figure 39:
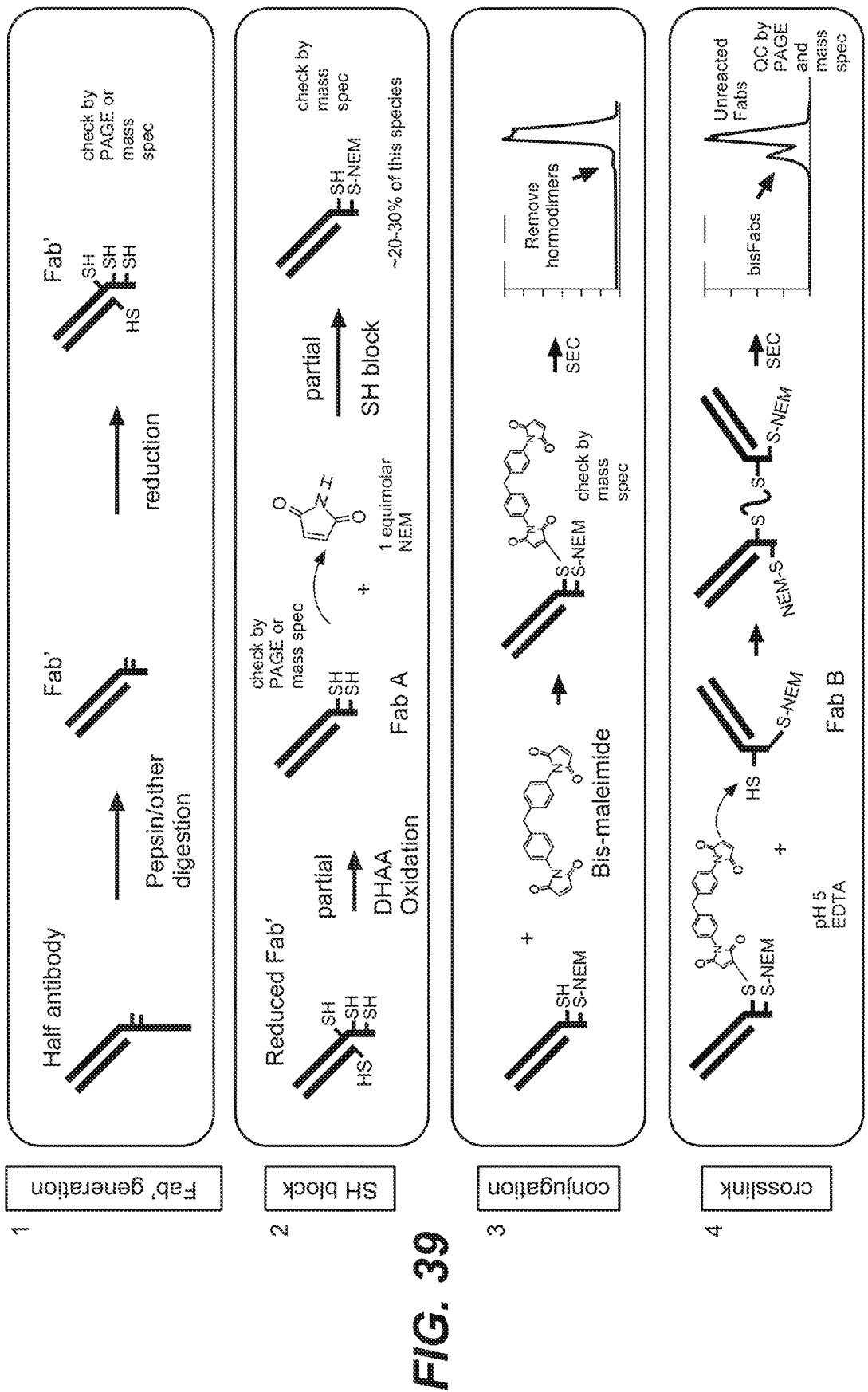
FIG. 39 is a schematic drawing showing the production of bis-Fabs from human IgG1.

For the preparation of hinge-cys-Fabs from native antibodies that do not contain an engineered cysteine for use in synthesis reactions, the following enzymatic procedure, as depicted in panel 1 of FIG. 39, was used. Both FcRH5 and CD3 parental antibodies were digested with pepsin (1% w/w) treatment in sodium acetate buffer at pH 4.5. After digestion for 1 hour, the F(ab')$_2$ was isolated from the digestion mixture by capture on an SP-HP cation exchange resin and purified by a 10 CV salt gradient of 0-1 M NaCl. The F(ab')$_2$ was then reduced in a buffer containing 25 mm MES, pH 5.8, 2 mM EDTA, and 300 mM NaCl. After reduction with 1 mM TCEP, the Fabs were oxidized, as depicted in panel 2 of FIG. 39, by the addition of 5 mM DHAA to reform the disulfide between the heavy chain and light chain. It was routinely observed that, under these reaction conditions, only the disulfide between the heavy chain and light chain was reformed; the two cysteine residues in the hinge region remained unoxidized.

The two free thiols (Cys residues) at the hinge, as depicted in panel 2 of FIG. 39, were then reacted with a 1M equivalent of N-ethylmaleimide (NEM) (Sigma Aldrich, St. Louis, Mo.). The resultant mixture containing singly-modified, doubly-modified, and unmodified Fabs was then reacted, as depicted in panel 3 of FIG. 39, with an excess of the bis-maleimide crosslinker.

These reaction conditions yielded three products: Fabs with one crosslinker and one NEM, Fabs with two NEM, and Fabs containing only one crosslinker. The Fabs containing only one crosslinker were found to have no free cysteine. Thus, under these reaction conditions, a single crosslinker reacted very efficiently with both cysteines resulting in a molecule in which the cysteines had been cyclized by the crosslinker. The material comprising the above three reaction products was purified from the reaction mixture (to remove unwanted reaction components) by gel filtration and used in coupling to other hinge-cys-Fabs, as depicted in panel 4 of FIG. 39, prepared in a similar manner or to thio-Fabs. Only hinge cys-Fabs or thio-Fabs prepared as described and containing one crosslinker, one free maleimide, and one free sulfhydryl were able to react in the bis-Fab synthesis reactions described in detail below.

B. Protein Expression and Purification

To facilitate purification, Fabs were expressed with either a Flag- or His-tag. Expression in CHO cells was carried out by standard procedures. Affinity purification following cell culturing was carried out using anti-Flag mAb resin or Nickel beads resin. Purified thio-Fabs were characterized by SDS-PAGE and mass spectrometry. These characterizations often showed mass increases of 275 Da and 306 Da. These mass increases were found to be disulfide adducts on the unpaired cysteine which were removed by reduction and oxidation to prepare the thio-Fabs for crosslinking with bis-maleimide. The reduction and oxidation of thio-Fabs was carried out as follows. First, thio-Fabs were reduced for 24 hrs by the addition of 2 mM tris(2-carboxyethyl) phosphine HCl (TCEP-HCl; also referred to as TCEP) (Pierce [Thermo Fisher Scientific], Rockford, Ill.) in a buffer containing 25 mM MES, pH 5.8, 300 mL NaCl, and 5 mM EDTA. After reduction, the protein was oxidized by the addition of 5 mM dehydroascorbic acid (DHAA) (Sigma-Aldrich, St. Louis, Mo.). The isolated thio-Fabs were analyzed by SDS-PAGE and mass spectrometry to ensure that the proteins are properly reduced and oxidized.

C. Bis-Fab Synthesis

Two different types of crosslinkers could be used to covalently link the two Fabs: bis-maleimide and the pair of adapters DBCO-PEG-malemide/bromoacetamide-PEG-Azide.

Conjugation Using Bis-Maleimide Crosslinkers

In the first stage of the bis-Fab synthesis, thio-Fabs or hinge-cys-Fabs with an unpaired cysteine were used. Generally, the thio-Fab or hinge-cys-Fab was in the same buffer in which the reduction (FIG. 39, panel 1) and oxidation (FIG. 39, panel 2) was carried out (MES, pH 5.8, 2 mM EDTA, and 300 mM NaCl) at a protein concentration of 1 mg/mL. There were two potential undesired reaction products at this stage: disulfide dimers and crosslinked dimers. Having a protein concentration of 1 mg/mL at this stage of the synthesis was an important feature of the reaction because dimerization was minimized at that protein concentration. In addition, controlling the reaction by using a low pH buffer with EDTA helped minimize dimerization.

A five-fold excess of bis-maleimide crosslinker (Quanta BioDesign, Powell, Ohio) was added to the reaction mixture, as depicted in panel 3 of FIG. 39. This five-fold excess of crosslinker was also helpful in minimizing undesirable dimerization. The reaction was incubated at room temperature (RT) or 37° C. for four hours until complete. The mixture was then concentrated to a volume suitable for gel filtration. A 22 mL S-200 Tricom column (GE Healthcare, Piscataway, N.J.) for ag to mg quantity synthesis was used. This first gel filtration step allowed for the removal of unused crosslinker yielding a purified thio-Fab or hinge-cys-Fab conjugated to the crosslinker. The conditions described above typically resulted in at least 90% or greater of the desired product. No thio-Fab or hinge-cys-Fab remained as free-thiol as all were conjugated to either a crosslinker or bound by disulfide to another thio-Fab or hinge-cys-Fab through the unpaired cysteines. The isolated and purified thio-Fab (or hinge-cys-Fab) plus crosslinker species was then added to the second thio-Fab (or hinge-cys-Fab) and concentrated to 5 mg/mL or greater, generally to a volume suitable for gel filtration, as depicted in panel 4 of FIG. 39. A protein concentration of at least 5 mg/mL during this stage of the synthesis was important to drive the reaction to completion. Lower protein concentrations resulted in formation of only small quantities of crosslinked bis-Fab dimers. Without being bound by theory, it was hypothesized that a steric effect or viscosity-related variable that hindered formation of cross-linked bis-Fab dimers was overcome by increasing concentrations of reactants. In addition, a range of protein concentrations up to and including 65 mg/mL was tested. A correlation between protein concentration and reaction time was found such that the higher the protein concentration, the faster the reaction reached completion. After 2-24 hours at room temperature or 37° C., the reaction was complete as determined by mass spectrometry. Generally, one reagent was in excess and remained uncoupled in the final mixture.

Conjugation Using DBCO-PEG-Malemide/Bromoacetamide-PEG-Azide

One of the purified and deblocked Fabs was reacted in 5 molar excess of DBCO-PEG-malemide (#760676, Sigma) in 50 mM HEPES pH 8 while the other Fab was reacted with 5 molar excess of Azide-PEG-maleimide (#21097 BroadPharm) in 50 mM HEPES pH 8. After a one-hour incubation at 37° C., the reaction was checked by mass spectrometry to verify completion of the reaction. The conjugated Fabs were purified from the excess of crosslinker by SEC and subsequently mixed at a 1:1 ratio and adjusted to a concentration above 5 mg/ml and incubated overnight at room temperature.

Regardless of the crosslinker used, the completed reaction was again purified by gel filtration; this time the dimeric peak was collected, which contained the 100 kD bis-Fab irreversibly crosslinked through the free cysteine amino acid (in the case of thio-Fabs) or through the unpaired cysteine located in the hinge region (in the case of unengineered hinge-cys-Fabs). The reaction progress during both steps was often monitored by mass spectrometry which clearly showed the presence of both reactants and the formation of the bis-Fab product. The purity of the desired product after the second gel filtration was determined by mass spectrometry and SDS-PAGE. Upon reduction and SDS-PAGE analysis, irreversible crosslinking was observed by the presence of a 50-kD band representing non-reducible crosslinked chains. Using the process described above at small scale, microgram yields with microgram quantities of starting materials were typically achieved. In addition, at a larger scale, milligram yields from milligram quantities of starting materials were typically achieved.

D. Synthesis of Bis-Fabs Targeting CD3 and FcRH5

Bispecific bis-Fabs obtained from two different antibodies that target CD3 and FcRH5 were generated. The anti-CD3 parent antibody used could be any anti-CD3 antibody, such as 38E4v.1, 38E4.v11, or 40G5. In one embodiment, the bis-Fab utilizes 38E4.v1 as the anti-CD3 component, with a light chain sequence of SEQ ID NO: 134 and a heavy chain sequence of SEQ ID NO: 133. The anti-FcRH5 antibody parent antibody used can also be any anti-FcRH5, for example, those antibodies described herein such as hu1G7.v85 and hu1G7.v87. Specifically, one exemplified bis-Fab includes a variable light chain sequence of SEQ ID NO: 105 and a variable heavy chain sequence of SEQ ID NO:104.

For each of these antibodies, recombinant thio-Fabs were produced in CHO cells as described above. Then bis-Fabs were synthesized from the thio-Fabs in a combinatorial format using a synthesis matrix, starting with approximately 2 mg of each thio-Fab. The different thio-Fabs were combined to synthesize four unique bis-Fab molecules. Approximately one mg of each bis-Fab was recovered from the synthesis for the shown examples but yields were expected to vary depending on the different thio-Fabs. Each of the bis-Fabs was given a unique identifier. The purity of each bis-Fab was analyzed by SDS-PAGE and mass spectrometry using standard methods well known in the art.

Using the matrix recombination approach described above, a series of CD3- and FcRH5-derived bis-Fab structural variants was synthesized. Four different thio-attachment points were chosen to synthesize the bis-Fabs; one of the positions was in the heavy chain of the anti-CD3 thio-Fab arm (e.g., at position 76 ($Cys76_{HC}$)), one position was in the light chain of the anti-CD3 thio-Fab arm (e.g., at position 22 ($Cys22_{LC}$)), one of the positions was in the heavy chain of the anti-FcRH5 thio-Fab arm (e.g., at position 114 ($Cys114_{HC}$)), and one position was in the light chain of the anti-FcRH5 thio-Fab arm (e.g., at position 149 ($Cys149_{LC}$)). Other positions can be utilized for the insertion of the required cysteines. Fabs containing thio-attachment points were derived from three different sources; (1) thio-mAbs with cysteine substitutions that were digested with Lysine-C to liberate the thio-Fab from the antibody, (2) thio-Fabs with cysteine substitutions that were directly expressed in and purified from CHO cells, and (3) hinge-cys-Fabs generated by the enzymatic method described above for the attachment of a single crosslinker to the hinge region of a non-engineered antibody after digestion with pepsin. This approach resulted in different substitution points in thio-Fabs for recombination with other thio-Fabs, thus yielding structural variants (see Table 10).

TABLE 10

Position of the engineered Cys in each Fab and corresponding bis-Fab numbers

| | | FcRH5 Fab (1G7.v85) | | |
|---|---|---|---|---|
| | | HC A114C | LC A149C | Hinge Cys |
| CD3 Fab (38E4.v1) | HC S76C | bis-Fab A | bis-Fab C | |
| | LC N22C | bis-Fab B | bis-Fab D | |
| | Hinge Cys | | | F(ab')$_2$ A |

E. Biological Activity of FcRH5 Bis-Fabs

Figure 40A:
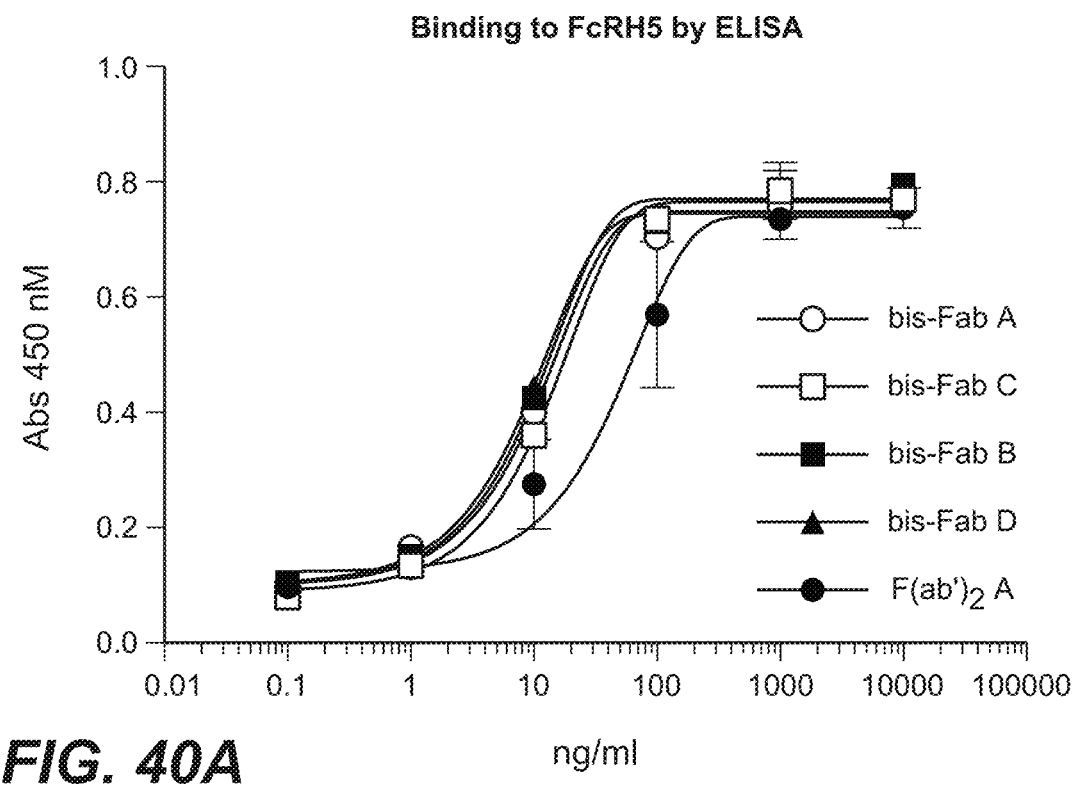
FIG. 40A is a graph showing the binding of FcRH5 by bis-Fabs A-D and F(ab')₂ A as determined by an ELISA assay.
Figure 40B:
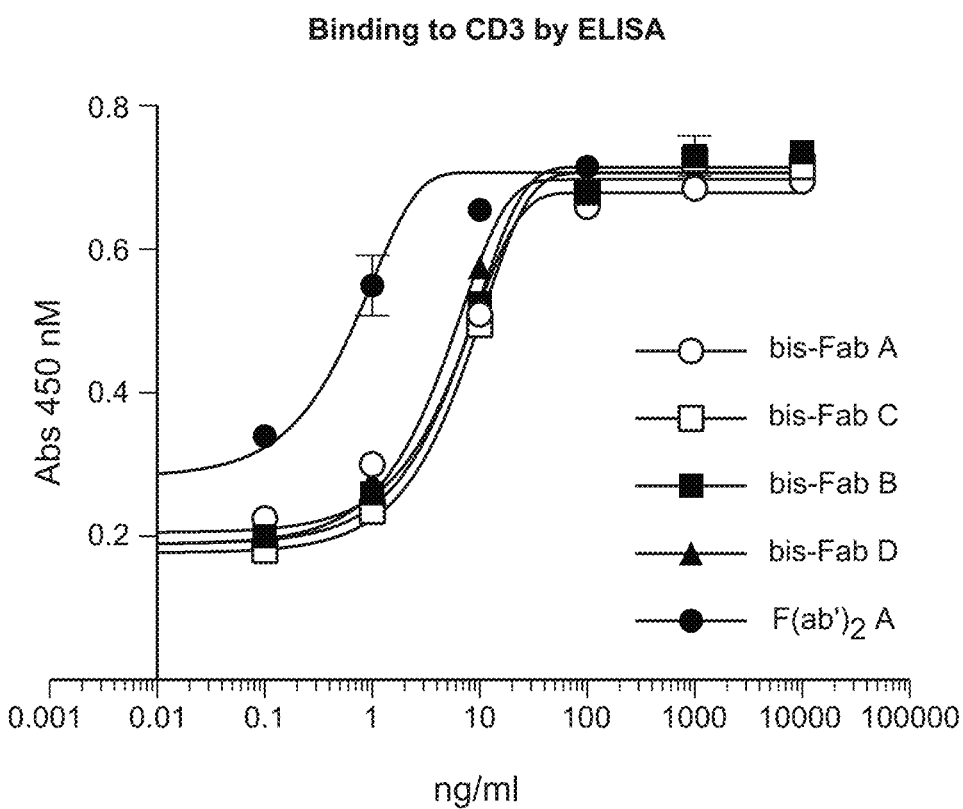
FIG. 40B is a graph showing the binding of CD3 by bis-Fabs A-D and F(ab')$_2$ A as determined by an ELISA assay.
Figure 41:
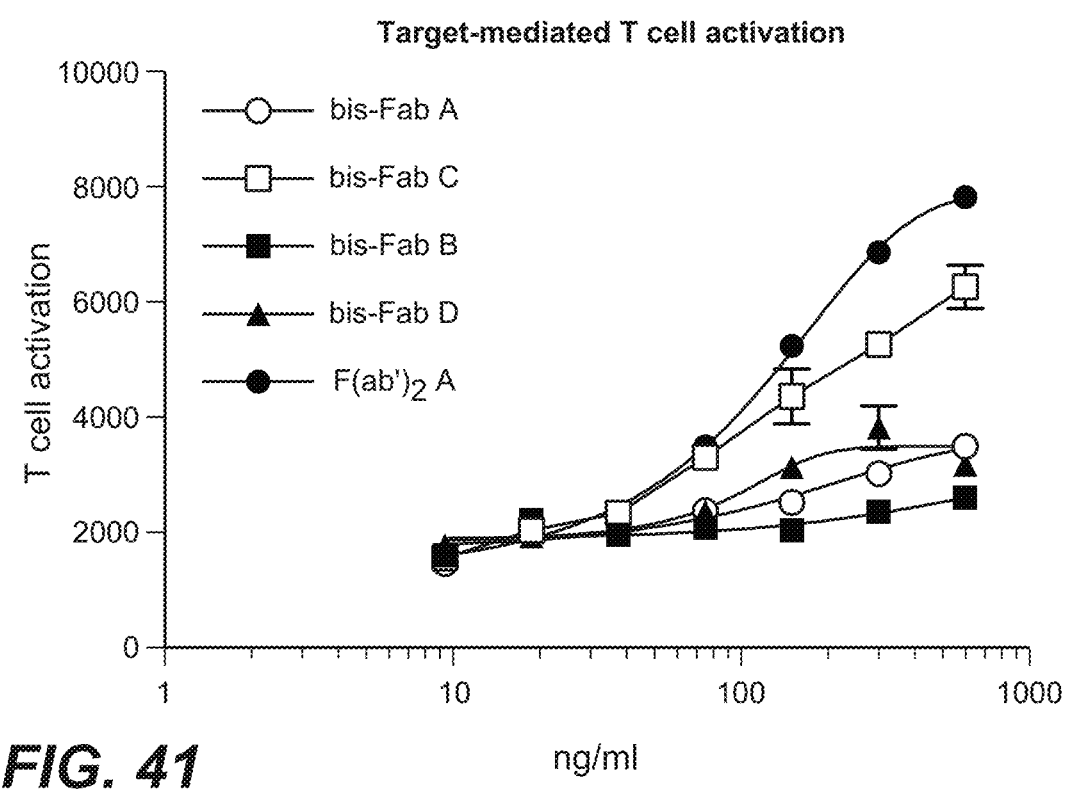
FIG. 41 is a graph showing the amount of target-mediated T cell activation by bis-Fabs A-D and F(ab')$_2$ A.

Next, each of the bis-Fab structural variants was tested for their binding ability to each of the antigens (i.e., CD3 and FcRH5) by ELISA. The bis-Fab generated by linking the Cys in the hinge region resembled the architecture of a natural antibody and served as a control. While all bis-Fab constructs had similar binding capability to FcRH5 (FIG. 40A), most of the bis-Fabs showed reduced binding to CD3 compared to the reference bis-Fab (FIG. 40B). The biological activity was evaluated in an in vitro T cell activation assay that served as a surrogate for T cell killing activity (FIG. 41). This assay used a Jurkat cell line (Jurkat-Dual, Invivogen) stably transfected with a luciferase reporter under the control of the transcription factor NF-kB, and the advantage of using this assay over a T cell killing assay was that the number of cells could be utilized was unlimited. In PBMC cell killing assays, the number of tests was limited by the number of cells that could be obtained from a single donor. The assay was carried out as follows. An appropriate cell line, such as MOLP-2, was chosen as the target cell and co-cultured with Jurkat cells. 10,000 cell line target cells and 50,000 effector cells (Jurkat) were added per well (10,000 target cells per well, 200 µL total volume, with ratio of target:effector=1:5), with or without the presence of bis-Fabs. After overnight incubation, 10 µl of the supernatant of the different wells was assayed for Luciferase activity using 50 µL of QUANTI-LUC (Invivogen), and luminescence was quantified in an Envision (Perkin Elmer) luminometer instrument.

Interestingly, although the HVR sequences of each bis-Fab variant generated for the anti-CD3 or the anti-FcRH5 were not altered in the generation of the bis-Fabs themselves, the maximum amount of T-cell stimulation observed for each bis-Fab showed variance, one bis-Fab from another, simply based upon the position of the cysteine engineered cross-linkage. Without being bound by theory, this may have implications for how toxicity and/or potency of a bis-Fab may be modulated to suit a particular therapeutic or diagnostic need. Another observation was that some bis-Fabs (e.g., bis-Fab C) had a significantly reduced affinity towards CD3, yet had a T cell activating activity comparable to that of the reference F(ab')$_2$ A (FIGS. 40B and 41, Table 10).

F. Biological Activity of FcRH5 Bis-Fabs Using Endogenous Human B Cells

Each bis-Fab variant was tested for its biological efficacy in a T cell dependent bis-Fab killing assay for peripheral endogenous B cell killing, as follows: 200,000 hPBMCs isolated from each of three healthy donors were added per well with or without bis-Fabs. After a 48-hr incubation, cells were stained with an appropriate cell surface antigen of the target cell line (B cells=CD20) (5 µl/well) and propidium iodide for cell viability assessment and then analyzed by FACS. The bis-Fab-dependent killing activities were calculated according to the following equation: % killing=(1−number of live cells with bis-Fabs/number of live cells without bis-Fabs)×100. As a positive control, an F(ab')$_2$ was used which was derived from a "knob into hole" FcRH5 TDB antibody wherein the anti-CD3 and anti-FcRH5 arms of each Fab had the same sequence as those used for the bis-Fabs tested (except without the cysteine-engineered point mutations) (see e.g., Ridgway et al. *Protein Eng.*, 9:617-621, 1996). Generally, results demonstrated reproducibility, despite using different donor cells.

The amounts of FcRH5 bis-Fabs tested herein required for half-maximal lysis of the peripheral endogenous human B cells, or EC50 potency value expressed in ng/ml, was calculated for each bis-Fab tested above. Overall, it was expected that trends in potency for each bis-Fab tested in the endogenous human B cell assay would track results determined in the ELISA assay described above (FIGS. 40A-40B).

What is claimed is:

1. One or more isolated nucleic acids encoding an anti-FcRH5 antibody, wherein the anti-FcRH5 antibody comprises a binding domain that binds to FcRH5, the binding domain comprising the following six HVRs:
   (a) an HVR-H1 comprising the amino acid sequence of SEQ ID NO: 1;
   (b) an HVR-H2 comprising the amino acid sequence of SEQ ID NO: 8;
   (c) an HVR-H3 comprising the amino acid sequence of SEQ ID NO: 9;
   (d) an HVR-L1 comprising the amino acid sequence of SEQ ID NO: 12;
   (e) an HVR-L2 comprising the amino acid sequence of SEQ ID NO: 16; and
   (f) an HVR-L3 comprising the amino acid sequence of SEQ ID NO: 23.

2. The one or more isolated nucleic acids of claim 1, wherein the binding domain comprises (a) a heavy chain variable (VH) domain comprising an amino acid sequence having at least 95% sequence identity to the amino acid sequence of SEQ ID NO: 104; (b) a light chain variable (VL) domain comprising an amino acid sequence having at least 95% sequence identity to the amino acid sequence of SEQ ID NO: 105; or (c) a VH domain as in (a) and a VL domain as in (b).

3. The one or more isolated nucleic acids of claim 1, wherein the anti-FcRH5 antibody further comprises the following heavy chain variable region framework regions (FRs):
   (a) an FR-H1 comprising the amino acid sequence of SEQ ID NO: 52;
   (b) an FR-H2 comprising the amino acid sequence of SEQ ID NO: 54;

(c) an FR-H3 comprising the amino acid sequence of SEQ ID NO: 46; and
(d) an FR-H4 comprising the amino acid sequence of SEQ ID NO: 47.

4. The one or more isolated nucleic acids of claim 3, wherein the VH domain comprises the amino acid sequence of SEQ ID NO: 104.

5. The one or more isolated nucleic acids of claim 1, wherein the anti-FcRH5 antibody further comprises the following light chain variable region FRs:
(a) an FR-L1 comprising the amino acid sequence of SEQ ID NO: 48;
(b) an FR-L2 comprising the amino acid sequence of SEQ ID NO: 57;
(c) an FR-L3 comprising the amino acid sequence of SEQ ID NO: 50; and
(d) an FR-L4 comprising the amino acid sequence of SEQ ID NO: 51.

6. The one or more isolated nucleic acids of claim 5, wherein the VL domain comprises the amino acid sequence of SEQ ID NO: 105.

7. One or more isolated nucleic acids encoding an anti-FcRH5 antibody, wherein the anti-FcRH5 antibody comprises a binding domain that binds to FcRH5, the binding domain comprising a binding domain comprising (a) a VH domain comprising the amino acid sequence of SEQ ID NO: 104 and (b) a VL domain comprising the amino acid sequence of SEQ ID NO: 105.

8. The one or more isolated nucleic acids of claim 1, wherein the anti-FcRH5 antibody comprises a substitution mutation reducing the effector function of the anti-FcRH5 antibody or FcRH5-binding antibody fragment thereof.

9. The one or more isolated nucleic acids of claim 8, wherein the substitution mutation is at amino acid residue N297, L234, L235, D265, and/or P329 (EU numbering).

10. The one or more isolated nucleic acids of claim 9, wherein the substitution mutation is selected from the group consisting of N297G, N297A, L234A, L235A, D265A, and P329G.

11. The one or more isolated nucleic acids of claim 10, wherein the substitution mutation is an N297G substitution mutation.

12. The one or more isolated nucleic acids of claim 1, wherein the anti-FcRH5 antibody is a monoclonal, humanized, or chimeric antibody.

13. The one or more isolated nucleic acids of claim 1, wherein the anti-FcRH5 antibody is an IgG antibody.

14. The one or more isolated nucleic acids of claim 1, wherein the anti-FcRH5 antibody is an antibody fragment that binds FcRH5.

15. The one or more isolated nucleic acids of claim 14, wherein the antibody fragment is selected from the group consisting of bis-Fab, Fab, Fab'-SH, Fv, scFv, and (Fab')$_2$ fragments.

16. The one or more isolated nucleic acids of claim 1, wherein the anti-FcRH5 antibody is a full-length antibody.

17. The one or more isolated nucleic acids of claim 1, wherein the anti-FcRH5 antibody is a multispecific antibody.

18. The one or more isolated nucleic acids of claim 17, wherein the multispecific antibody is a bispecific antibody.

19. The one or more isolated nucleic acids of claim 18, wherein the bispecific antibody comprises a second binding domain that binds cluster of differentiation 3 (CD3).

20. The one or more isolated nucleic acids of claim 19, wherein the second binding domain binds to an epitope on CD3 comprising amino acid residue Glu6 of CD3.

21. The one or more isolated nucleic acids of claim 20, wherein the second binding domain is capable of binding to a human CD3 polypeptide or a cyno CD3 polypeptide.

22. The one or more isolated nucleic acids of claim 19, wherein the second binding domain comprises the following six HVRs:
(a) an HVR-H1 comprising the amino acid sequence of SEQ ID NO: 115;
(b) an HVR-H2 comprising the amino acid sequence of SEQ ID NO: 116;
(c) an HVR-H3 comprising the amino acid sequence of SEQ ID NO: 117;
(d) an HVR-L1 comprising the amino acid sequence of SEQ ID NO: 118;
(e) an HVR-L2 comprising the amino acid sequence of SEQ ID NO: 119; and
(f) an HVR-L3 comprising the amino acid sequence of SEQ ID NO: 120.

23. The one or more isolated nucleic acids of claim 19, wherein the second binding domain comprises the following six HVRs:
(a) an HVR-H1 comprising the amino acid sequence of SEQ ID NO: 115;
(b) an HVR-H2 comprising the amino acid sequence of SEQ ID NO: 116;
(c) an HVR-H3 comprising the amino acid sequence of SEQ ID NO: 121;
(d) an HVR-L1 comprising the amino acid sequence of SEQ ID NO: 118;
(e) an HVR-L2 comprising the amino acid sequence of SEQ ID NO: 119; and
(f) an HVR-L3 comprising the amino acid sequence of SEQ ID NO: 123.

24. One or more isolated nucleic acids encoding an anti-FcRH5 antibody that binds to FcRH5 and CD3, wherein the anti-FcRH5 antibody comprises an anti-FcRH5 arm comprising a first binding domain comprising the following six HVRs:
(a) an HVR-H1 comprising the amino acid sequence of SEQ ID NO: 1;
(b) an HVR-H2 comprising the amino acid sequence of SEQ ID NO: 8;
(c) an HVR-H3 comprising the amino acid sequence of SEQ ID NO: 9;
(d) an HVR-L1 comprising the amino acid sequence of SEQ ID NO: 12;
(e) an HVR-L2 comprising the amino acid sequence of SEQ ID NO: 16; and
(f) an HVR-L3 comprising the amino acid sequence of SEQ ID NO: 23; and
an anti-CD3 arm comprising a second binding domain comprising the following six HVRs:
(a) an HVR-H1 comprising the amino acid sequence of SEQ ID NO: 115;
(b) an HVR-H2 comprising the amino acid sequence of SEQ ID NO: 116;
(c) an HVR-H3 comprising the amino acid sequence of SEQ ID NO: 121;
(d) an HVR-L1 comprising the amino acid sequence of SEQ ID NO: 118;
(e) an HVR-L2 comprising the amino acid sequence of SEQ ID NO: 119; and
(f) an HVR-L3 comprising the amino acid sequence of SEQ ID NO: 123.

25. The one or more isolated nucleic acids of claim 19, wherein the anti-FcRH5 antibody or FcRH5-binding antibody fragment thereof comprises one or more heavy chain constant domains, and wherein the one or more heavy chain constant domains are selected from a first CH2 domain (CH2$_1$), a first CH3 domain (CH3$_1$), a second CH2 domain (CH2$_2$), and a second CH3 domain (CH3$_2$).

26. The one or more isolated nucleic acids of claim 25, wherein at least one of the one or more heavy chain constant domains is paired with another heavy chain constant domain.

27. The one or more isolated nucleic acids of claim 26, wherein the CH3$_1$ and the CH3$_2$ each comprise a protuberance (P$_1$) or a cavity (C$_1$), and wherein the P$_1$ or the C$_1$ in the CH3$_1$ is positionable in the C$_1$ or the P$_1$, respectively, in the CH3$_2$.

28. The one or more isolated nucleic acids of claim 27, wherein the CH3$_1$ and the CH3$_2$ meet at an interface between the P$_1$ and the C$_1$.

29. The one or more isolated nucleic acids of claim 27 or 28, wherein:
   (a) the P$_1$ comprises a T366W substitution mutation (EU numbering); and/or
   (b) the C$_1$ comprises T366S, L368A, and Y407V substitution mutations (EU numbering).

30. One or more isolated nucleic acids encoding an anti-FcRH5 antibody that binds to FcRH5 and CD3, wherein the anti-FcRH5 antibody comprises an anti-FcRH5 arm comprising a first binding domain comprising the following six HVRs:
   (a) an HVR-H1 comprising the amino acid sequence of SEQ ID NO: 1;
   (b) an HVR-H2 comprising the amino acid sequence of SEQ ID NO: 8;
   (c) an HVR-H3 comprising the amino acid sequence of SEQ ID NO: 9;
   (d) an HVR-L1 comprising the amino acid sequence of SEQ ID NO: 12;
   (e) an HVR-L2 comprising the amino acid sequence of SEQ ID NO: 16; and
   (f) an HVR-L3 comprising the amino acid sequence of SEQ ID NO: 23; and
   an anti-CD3 arm comprising a second binding domain comprising the following six HVRs:
   (a) an HVR-H1 comprising the amino acid sequence of SEQ ID NO: 115;
   (b) an HVR-H2 comprising the amino acid sequence of SEQ ID NO: 116;
   (c) an HVR-H3 comprising the amino acid sequence of SEQ ID NO: 121;
   (d) an HVR-L1 comprising the amino acid sequence of SEQ ID NO: 118;
   (e) an HVR-L2 comprising the amino acid sequence of SEQ ID NO: 119; and
   (f) an HVR-L3 comprising the amino acid sequence of SEQ ID NO: 123; and
   wherein the anti-FcRH5 arm and the anti-CD3 arm each comprise an N297G substitution mutation (EU numbering); and
   wherein the anti-FcRH5 arm comprises a T366W substitution mutation (EU numbering) and the anti-CD3 arm comprises T366S, L368A, and Y407V substitution mutations (EU numbering).

31. One or more vectors comprising the one or more isolated nucleic acids of any one of claims 1, 24, and 30.

32. One or more host cells comprising the one or more vectors of claim 31.

33. The one or more host cells of claim 32, wherein the one or more host cells are one or more prokaryotic host cells.

34. The one or more host cells of claim 33, wherein the one or more prokaryotic host cells are one or more *E. coli* host cells.

35. The one or more host cells of claim 32, wherein the one or more host cells are one or more mammalian host cells.

36. The one or more host cells of claim 35, wherein the one or more mammalian host cells are one or more Chinese hamster ovary (CHO) host cells.

37. A method of producing an anti-FcRH5 antibody, the method comprising culturing the one or more host cells of claim 32 in a culture medium.

38. The method of claim 37, wherein the method further comprises recovering the anti-FcRH5 antibody from the one or more host cells or the culture medium.

* * * * *

SEQUENCE LISTING

<160> NUMBER OF SEQ ID NOS: 215

<210> SEQ ID NO 1
<211> LENGTH: 5
<212> TYPE: PRT
<213> ORGANISM: Artificial Sequence
<220> FEATURE:
<223> OTHER INFORMATION: Synthetic construct

<400> SEQUENCE: 1

Arg Phe Gly Val His
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (12)..(12)
<223> OTHER INFORMATION: Xaa is Ala or Pro
<220> FEATURE:
<221> NAME/KEY: MISC_FEATURE
<222> LOCATION: (15)..(15)
<223> OTHER INFORMATION: Xaa is Met, Gly, or Val
<220> FEATURE:
<221> NAME/KEY: MISC_FEATURE
<222> LOCATION: (16)..(16)
<223> OTHER INFORMATION: Xaa is Ser, Asp, or Pro

<400> SEQUENCE: 2

Val Ile Trp Arg Gly Gly Ser Thr Asp Tyr Asn Xaa Ala Phe Xaa Xaa
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa is Ser or Pro

<400> SEQUENCE: 3

His Tyr Tyr Gly Ser Xaa Asp Tyr Ala Leu Asp Asn
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: Xaa is Ser or Arg
<220> FEATURE:
<221> NAME/KEY: MISC_FEATURE
<222> LOCATION: (9)..(9)
<223> OTHER INFORMATION: Xaa is Ile or Leu

<400> SEQUENCE: 4

Lys Ala Ser Gln Asp Val Xaa Asn Xaa Val Val
1               5                   10

```
<210> SEQ ID NO 5
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ala or Gly
<220> FEATURE:
<221> NAME/KEY: MISC_FEATURE
<222> LOCATION: (3)..(3)
<223> OTHER INFORMATION: Xaa is Ser or Tyr
<220> FEATURE:
<221> NAME/KEY: MISC_FEATURE
<222> LOCATION: (4)..(4)
<223> OTHER INFORMATION: Xaa is Tyr or Asn
<220> FEATURE:
<221> NAME/KEY: MISC_FEATURE
<222> LOCATION: (7)..(7)
<223> OTHER INFORMATION: Xaa is Thr or Ser

<400> SEQUENCE: 5

Ser Xaa Xaa Xaa Arg Tyr Xaa
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is His or Gln
<220> FEATURE:
<221> NAME/KEY: MISC_FEATURE
<222> LOCATION: (4)..(4)
<223> OTHER INFORMATION: Xaa is Tyr or Phe
<220> FEATURE:
<221> NAME/KEY: MISC_FEATURE
<222> LOCATION: (5)..(5)
<223> OTHER INFORMATION: Xaa is Gln or Ser
<220> FEATURE:
<221> NAME/KEY: MISC_FEATURE
<222> LOCATION: (6)..(6)
<223> OTHER INFORMATION: Xaa is Ser or Pro

<400> SEQUENCE: 6

Gln Gln Xaa Xaa Xaa Xaa Pro Tyr Thr
1               5

<210> SEQ ID NO 7
<211> LENGTH: 16
<212> TYPE: PRT
<213> ORGANISM: Artificial Sequence
<220> FEATURE:
<223> OTHER INFORMATION: Synthetic construct

<400> SEQUENCE: 7

Val Ile Trp Arg Gly Gly Ser Thr Asp Tyr Asn Ala Ala Phe Met Ser
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic construct

<400> SEQUENCE: 8
```

```
Val Ile Trp Arg Gly Gly Ser Thr Asp Tyr Asn Ala Ala Phe Val Ser
1               5                   10                  15

<210> SEQ ID NO 9
<211> LENGTH: 12
<212> TYPE: PRT
<213> ORGANISM: Artificial Sequence
<220> FEATURE:
<223> OTHER INFORMATION: Synthetic construct

<400> SEQUENCE: 9

His Tyr Tyr Gly Ser Ser Asp Tyr Ala Leu Asp Asn
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic construct

<400> SEQUENCE: 10

His Tyr Tyr Gly Ser Pro Asp Tyr Ala Leu Asp Asn
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic construct

<400> SEQUENCE: 11

Lys Ala Ser Gln Asp Val Ser Asn Ile Val Val
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic construct

<400> SEQUENCE: 12

Lys Ala Ser Gln Asp Val Arg Asn Leu Val Val
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic construct

<400> SEQUENCE: 13

Lys Ala Ser Gln Asp Val Arg Asn Ile Val Val
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic construct

<400> SEQUENCE: 14
```

Lys Ala Ser Gln Asp Val Ser Asn Leu Val Val
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic construct

<400> SEQUENCE: 15

Ser Ala Ser Tyr Arg Tyr Thr
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic construct

<400> SEQUENCE: 16

Ser Gly Ser Tyr Arg Tyr Ser
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic construct

<400> SEQUENCE: 17

Ser Gly Tyr Asn Arg Tyr Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic construct

<400> SEQUENCE: 18

Ser Gly Tyr Tyr Arg Tyr Thr
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic construct

<400> SEQUENCE: 19

Ser Gly Tyr Tyr Arg Tyr Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic construct

<400> SEQUENCE: 20

Gln Gln His Tyr Ser Ser Pro Tyr Thr

```
1               5
```

<210> SEQ ID NO 21
<211> LENGTH: 9
<212> TYPE: PRT
<213> ORGANISM: Artificial Sequence
<220> FEATURE:
<223> OTHER INFORMATION: Synthetic construct

<400> SEQUENCE: 21

```
Gln Gln Gln Tyr Ser Pro Pro Tyr Thr
1               5
```

<210> SEQ ID NO 22
<211> LENGTH: 9
<212> TYPE: PRT
<213> ORGANISM: Artificial Sequence
<220> FEATURE:
<223> OTHER INFORMATION: Synthetic construct

<400> SEQUENCE: 22

```
Gln Gln Gln Phe Gln Pro Pro Tyr Thr
1               5
```

<210> SEQ ID NO 23
<211> LENGTH: 9
<212> TYPE: PRT
<213> ORGANISM: Artificial Sequence
<220> FEATURE:
<223> OTHER INFORMATION: Synthetic construct

<400> SEQUENCE: 23

```
Gln Gln His Tyr Ser Pro Pro Tyr Thr
1               5
```

<210> SEQ ID NO 24
<211> LENGTH: 9
<212> TYPE: PRT
<213> ORGANISM: Artificial Sequence
<220> FEATURE:
<223> OTHER INFORMATION: Synthetic construct

<400> SEQUENCE: 24

```
Gln Gln Gln Tyr Gln Pro Pro Tyr Thr
1               5
```

<210> SEQ ID NO 25
<211> LENGTH: 9
<212> TYPE: PRT
<213> ORGANISM: Artificial Sequence
<220> FEATURE:
<223> OTHER INFORMATION: Synthetic construct

<400> SEQUENCE: 25

```
Gln Gln His Tyr Gln Pro Pro Tyr Thr
1               5
```

<210> SEQ ID NO 26
<211> LENGTH: 10
<212> TYPE: PRT
<213> ORGANISM: Artificial Sequence
<220> FEATURE:
<223> OTHER INFORMATION: Synthetic construct

<400> SEQUENCE: 26

```
Gly Ile Asp Leu Ser Ser Tyr Ala Met Gly
1               5                   10
```

```
<210> SEQ ID NO 27
<211> LENGTH: 16
<212> TYPE: PRT
<213> ORGANISM: Artificial Sequence
<220> FEATURE:
<223> OTHER INFORMATION: Synthetic construct

<400> SEQUENCE: 27

Thr Ile Gly Thr Gly Gly Thr Pro Tyr Tyr Ala Ser Trp Ala Lys Gly
1               5                   10                  15

<210> SEQ ID NO 28
<211> LENGTH: 13
<212> TYPE: PRT
<213> ORGANISM: Artificial Sequence
<220> FEATURE:
<223> OTHER INFORMATION: Synthetic construct

<400> SEQUENCE: 28

Ala Arg Asp Met Tyr Thr Gly Ser Ile Tyr Tyr Asp Met
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic construct

<400> SEQUENCE: 29

Gln Ser Ser Gln Ser Val Phe Asn Asn Ala Gln Leu Ser
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Synthetic construct

<400> SEQUENCE: 30

Asp Thr Ser Asn Leu Ala Ser
1               5

<210> SEQ ID NO 31
<211> LENGTH: 11
<212> TYPE: PRT
<213> ORGANISM: Artificial Sequence
<220> FEATURE:
<223> OTHER INFORMATION: Synthetic construct

<400> SEQUENCE: 31

Leu Gly Ala Tyr Thr Asp Asp Ala Asp Asn Ala
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic construct

<400> SEQUENCE: 32

Gly Tyr Thr Phe Thr His Tyr Ala Met His
1               5                   10
```

```
<210> SEQ ID NO 33
<211> LENGTH: 17
<212> TYPE: PRT
<213> ORGANISM: Artificial Sequence
<220> FEATURE:
<223> OTHER INFORMATION: Synthetic construct

<400> SEQUENCE: 33

Met Ile Ser Ser Ser Ser Gly Asn Thr Asn Phe Asn Gln Lys Phe Met
1               5                   10                  15

Asp

<210> SEQ ID NO 34
<211> LENGTH: 11
<212> TYPE: PRT
<213> ORGANISM: Artificial Sequence
<220> FEATURE:
<223> OTHER INFORMATION: Synthetic construct

<400> SEQUENCE: 34

Ala Arg Trp Ser Tyr Tyr Ala Leu Phe Asp Tyr
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic construct

<400> SEQUENCE: 35

Ser Ala Asp Ser Ser Val Asp Tyr Ile His
1               5                   10

<210> SEQ ID NO 36
<211> LENGTH: 7
<212> TYPE: PRT
<213> ORGANISM: Artificial Sequence
<220> FEATURE:
<223> OTHER INFORMATION: Synthetic construct

<400> SEQUENCE: 36

Asp Thr Ser Lys Leu Ala Ser
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic construct

<400> SEQUENCE: 37

Phe Gln Gly Ser Gly Tyr Pro Leu Thr
1               5

<210> SEQ ID NO 38
<211> LENGTH: 10
<212> TYPE: PRT
<213> ORGANISM: Artificial Sequence
<220> FEATURE:
<223> OTHER INFORMATION: Synthetic construct

<400> SEQUENCE: 38

Gly Tyr Thr Phe Thr Asn Tyr Val Ile His
1               5                   10
```

<210> SEQ ID NO 39
<211> LENGTH: 17
<212> TYPE: PRT
<213> ORGANISM: Artificial Sequence
<220> FEATURE:
<223> OTHER INFORMATION: Synthetic construct

<400> SEQUENCE: 39

Tyr Ile Ser Pro Tyr Asn Asp Tyr Thr Lys Tyr Asn Glu Lys Phe Glu
1               5                   10                  15

Gly

<210> SEQ ID NO 40
<211> LENGTH: 11
<212> TYPE: PRT
<213> ORGANISM: Artificial Sequence
<220> FEATURE:
<223> OTHER INFORMATION: Synthetic construct

<400> SEQUENCE: 40

Ala Arg Arg Asp Tyr Tyr Gly Ser Ser Asp Tyr
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic construct

<400> SEQUENCE: 41

Ser Ala Ser Ser Ser Val Asp Tyr Met His
1               5                   10

<210> SEQ ID NO 42
<211> LENGTH: 7
<212> TYPE: PRT
<213> ORGANISM: Artificial Sequence
<220> FEATURE:
<223> OTHER INFORMATION: Synthetic construct

<400> SEQUENCE: 42

Asp Thr Ser Lys Leu Ala Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic construct

<400> SEQUENCE: 43

Gln Gln Trp Ser Ser Asn Pro Pro Thr
1               5

<210> SEQ ID NO 44
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Glu, Ser, or Phe

```
<220> FEATURE:
<221> NAME/KEY: MISC_FEATURE
<222> LOCATION: (28)..(28)
<223> OTHER INFORMATION: Xaa is Ser or Pro
<220> FEATURE:
<221> NAME/KEY: MISC_FEATURE
<222> LOCATION: (29)..(29)
<223> OTHER INFORMATION: Xaa is Leu or Thr

<400> SEQUENCE: 44

Xaa Val Gln Leu Val Glu Ser Gly Pro Gly Leu Val Lys Pro Ser Glu
1               5                   10                  15

Thr Leu Ser Leu Thr Cys Thr Val Ser Gly Phe Xaa Xaa Thr
            20                  25                  30

<210> SEQ ID NO 45
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Val or Tyr
<220> FEATURE:
<221> NAME/KEY: MISC_FEATURE
<222> LOCATION: (13)..(13)
<223> OTHER INFORMATION: Xaa is Leu or Ile

<400> SEQUENCE: 45

Trp Xaa Arg Gln Pro Pro Gly Lys Gly Leu Glu Trp Xaa Gly
1               5                   10

<210> SEQ ID NO 46
<211> LENGTH: 32
<212> TYPE: PRT
<213> ORGANISM: Artificial Sequence
<220> FEATURE:
<223> OTHER INFORMATION: Synthetic construct

<400> SEQUENCE: 46

Arg Leu Thr Ile Ser Lys Asp Asn Ser Lys Asn Gln Val Ser Leu Lys
1               5                   10                  15

Leu Ser Ser Val Thr Ala Ala Asp Thr Ala Val Tyr Tyr Cys Ser Asn
            20                  25                  30

<210> SEQ ID NO 47
<211> LENGTH: 11
<212> TYPE: PRT
<213> ORGANISM: Artificial Sequence
<220> FEATURE:
<223> OTHER INFORMATION: Synthetic construct

<400> SEQUENCE: 47

Trp Gly Gln Gly Thr Leu Val Thr Val Ser Ser
1               5                   10

<210> SEQ ID NO 48
<211> LENGTH: 23
<212> TYPE: PRT
<213> ORGANISM: Artificial Sequence
<220> FEATURE:
<223> OTHER INFORMATION: Synthetic construct

<400> SEQUENCE: 48

Asp Ile Gln Met Thr Gln Ser Pro Ser Ser Leu Ser Ala Ser Val Gly
1               5                   10                  15
```

```
Asp Arg Val Thr Ile Thr Cys
            20
```

```
<210> SEQ ID NO 49
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (9)..(9)
<223> OTHER INFORMATION: Xaa is Ala or Ser

<400> SEQUENCE: 49

Trp Phe Gln Gln Lys Pro Gly Lys Xaa Pro Lys Leu Leu Ile Tyr
1               5                   10                  15
```

```
<210> SEQ ID NO 50
<211> LENGTH: 32
<212> TYPE: PRT
<213> ORGANISM: Artificial Sequence
<220> FEATURE:
<223> OTHER INFORMATION: Synthetic construct

<400> SEQUENCE: 50

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

```
<210> SEQ ID NO 51
<211> LENGTH: 10
<212> TYPE: PRT
<213> ORGANISM: Artificial Sequence
<220> FEATURE:
<223> OTHER INFORMATION: Synthetic construct

<400> SEQUENCE: 51

Phe Gly Gln Gly Thr Lys Val Glu Ile Lys
1               5                   10
```

```
<210> SEQ ID NO 52
<211> LENGTH: 30
<212> TYPE: PRT
<213> ORGANISM: Artificial Sequence
<220> FEATURE:
<223> OTHER INFORMATION: Synthetic construct

<400> SEQUENCE: 52

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr
            20                  25                  30
```

```
<210> SEQ ID NO 53
<211> LENGTH: 30
<212> TYPE: PRT
<213> ORGANISM: Artificial Sequence
<220> FEATURE:
<223> OTHER INFORMATION: Synthetic construct

<400> SEQUENCE: 53

Glu Val Gln Leu Val Glu Ser Gly Pro Gly Leu Val Lys Pro Ser Glu
1               5                   10                  15
```

```
Thr Leu Ser Leu Thr Cys Thr Val Ser Gly Phe Ser Thr Thr
            20                  25                  30

<210> SEQ ID NO 54
<211> LENGTH: 14
<212> TYPE: PRT
<213> ORGANISM: Artificial Sequence
<220> FEATURE:
<223> OTHER INFORMATION: Synthetic construct

<400> SEQUENCE: 54

Trp Val Arg Gln Pro Pro Gly Lys Gly Leu Glu Trp Leu Gly
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Synthetic construct

<400> SEQUENCE: 55

Trp Val Arg Gln Pro Pro Gly Lys Gly Leu Glu Trp Ile Gly
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Synthetic construct

<400> SEQUENCE: 56

Trp Phe Gln Gln Lys Pro Gly Lys Ser Pro Lys Leu Leu Ile Tyr
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic construct

<400> SEQUENCE: 57

Trp Phe Gln Gln Lys Pro Gly Lys Ala Pro Lys Leu Leu Ile Tyr
1               5                   10                  15

<210> SEQ ID NO 58
<211> LENGTH: 25
<212> TYPE: PRT
<213> ORGANISM: Artificial Sequence
<220> FEATURE:
<223> OTHER INFORMATION: Synthetic construct

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Val Ser
            20                  25

<210> SEQ ID NO 59
<211> LENGTH: 14
<212> TYPE: PRT
<213> ORGANISM: Artificial Sequence
<220> FEATURE:
<223> OTHER INFORMATION: Synthetic construct
```

```
<400> SEQUENCE: 59

Trp Val Arg Gln Ala Pro Gly Lys Gly Leu Glu Trp Ile Gly
1               5                   10

<210> SEQ ID NO 60
<211> LENGTH: 30
<212> TYPE: PRT
<213> ORGANISM: Artificial Sequence
<220> FEATURE:
<223> OTHER INFORMATION: Synthetic construct

<400> SEQUENCE: 60

Arg Phe Thr Ile Ser Lys Asp Ser Ser Lys Asn Thr Val Tyr Leu Gln
1               5                   10                  15

Met Asn Ser Leu Arg Ala Glu Asp Thr Ala Val Tyr Phe Cys
            20                  25                  30

<210> SEQ ID NO 61
<211> LENGTH: 11
<212> TYPE: PRT
<213> ORGANISM: Artificial Sequence
<220> FEATURE:
<223> OTHER INFORMATION: Synthetic construct

<400> SEQUENCE: 61

Trp Gly Gln Gly Thr Leu Val Thr Val Ser Ser
1               5                   10

<210> SEQ ID NO 62
<211> LENGTH: 22
<212> TYPE: PRT
<213> ORGANISM: Artificial Sequence
<220> FEATURE:
<223> OTHER INFORMATION: Synthetic construct

<400> SEQUENCE: 62

Asp Ala Gln Leu Thr Gln Ser Pro Ser Ser Leu Ser Ala Ser Val Gly
1               5                   10                  15

Asp Arg Val Thr Ile Thr
            20

<210> SEQ ID NO 63
<211> LENGTH: 15
<212> TYPE: PRT
<213> ORGANISM: Artificial Sequence
<220> FEATURE:
<223> OTHER INFORMATION: Synthetic construct

<400> SEQUENCE: 63

Trp Tyr Gln Gln Lys Pro Gly Lys Pro Pro Lys Leu Leu Ile Tyr
1               5                   10                  15

<210> SEQ ID NO 64
<211> LENGTH: 32
<212> TYPE: PRT
<213> ORGANISM: Artificial Sequence
<220> FEATURE:
<223> OTHER INFORMATION: Synthetic construct

<400> SEQUENCE: 64

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 65
<211> LENGTH: 10
<212> TYPE: PRT
<213> ORGANISM: Artificial Sequence
<220> FEATURE:
<223> OTHER INFORMATION: Synthetic construct

<400> SEQUENCE: 65

Phe Gly Gln Gly Thr Lys Val Glu Ile Lys
1               5                   10

<210> SEQ ID NO 66
<211> LENGTH: 25
<212> TYPE: PRT
<213> ORGANISM: Artificial Sequence
<220> FEATURE:
<223> OTHER INFORMATION: Synthetic construct

<400> SEQUENCE: 66

Gln Val Gln Leu Gln Gln Ser Gly Pro Glu Leu Val Arg Pro Gly Val
1               5                   10                  15

Ser Val Lys Ile Ser Cys Lys Gly Ser
            20                  25

<210> SEQ ID NO 67
<211> LENGTH: 14
<212> TYPE: PRT
<213> ORGANISM: Artificial Sequence
<220> FEATURE:
<223> OTHER INFORMATION: Synthetic construct

<400> SEQUENCE: 67

Trp Val Lys Gln Ser His Thr Lys Ser Leu Glu Trp Ile Gly
1               5                   10

<210> SEQ ID NO 68
<211> LENGTH: 30
<212> TYPE: PRT
<213> ORGANISM: Artificial Sequence
<220> FEATURE:
<223> OTHER INFORMATION: Synthetic construct

<400> SEQUENCE: 68

Lys Ala Thr Met Thr Val Asp Lys Ser Ser Thr Thr Ala Tyr Leu Glu
1               5                   10                  15

Leu Ala Arg Leu Thr Phe Gly Asp Ser Ala Ile Tyr Tyr Cys
            20                  25                  30

<210> SEQ ID NO 69
<211> LENGTH: 11
<212> TYPE: PRT
<213> ORGANISM: Artificial Sequence
<220> FEATURE:
<223> OTHER INFORMATION: Synthetic construct

<400> SEQUENCE: 69

Trp Gly Gln Gly Thr Thr Val Thr Val Ser Ser
1               5                   10

<210> SEQ ID NO 70
<211> LENGTH: 23
<212> TYPE: PRT
<213> ORGANISM: Artificial Sequence
<220> FEATURE:
<223> OTHER INFORMATION: Synthetic construct -continued

```
<400> SEQUENCE: 70

Glu Asn Val Leu Thr Gln Ser Pro Ala Ile Met Ser Ala Ser Pro Gly
1               5                   10                  15

Glu Lys Val Thr Met Thr Cys
            20

<210> SEQ ID NO 71
<211> LENGTH: 15
<212> TYPE: PRT
<213> ORGANISM: Artificial Sequence
<220> FEATURE:
<223> OTHER INFORMATION: Synthetic construct

<400> SEQUENCE: 71

Trp Tyr Gln Gln Lys Ser Asn Thr Ser Pro Lys Leu Trp Ile Tyr
1               5                   10                  15

<210> SEQ ID NO 72
<211> LENGTH: 32
<212> TYPE: PRT
<213> ORGANISM: Artificial Sequence
<220> FEATURE:
<223> OTHER INFORMATION: Synthetic construct

<400> SEQUENCE: 72

Gly Val Pro Gly Arg Phe Ser Gly Ser Gly Ser Gly Asn Ser Tyr Ser
1               5                   10                  15

Leu Thr Ile Ser Ser Met Glu Ala Glu Asp Phe Ala Thr Tyr Tyr Cys
            20                  25                  30

<210> SEQ ID NO 73
<211> LENGTH: 10
<212> TYPE: PRT
<213> ORGANISM: Artificial Sequence
<220> FEATURE:
<223> OTHER INFORMATION: Synthetic construct

<400> SEQUENCE: 73

Phe Gly Ser Gly Thr Lys Leu Glu Leu Lys
1               5                   10

<210> SEQ ID NO 74
<211> LENGTH: 25
<212> TYPE: PRT
<213> ORGANISM: Artificial Sequence
<220> FEATURE:
<223> OTHER INFORMATION: Synthetic construct

<400> SEQUENCE: 74

Glu Val Gln Leu Gln Gln Ser Gly Pro Glu Leu Val Lys Pro Gly Ala
1               5                   10                  15

Ser Val Lys Met Ser Cys Lys Ala Ser
            20                  25

<210> SEQ ID NO 75
<211> LENGTH: 14
<212> TYPE: PRT
<213> ORGANISM: Artificial Sequence
<220> FEATURE:
<223> OTHER INFORMATION: Synthetic construct

<400> SEQUENCE: 75

Trp Met Lys Gln Lys Pro Gly Gln Gly Leu Glu Trp Ile Gly
1               5                   10
```

<210> SEQ ID NO 76
<211> LENGTH: 30
<212> TYPE: PRT
<213> ORGANISM: Artificial Sequence
<220> FEATURE:
<223> OTHER INFORMATION: Synthetic construct

<400> SEQUENCE: 76

Lys Ala Thr Leu Thr Ser Asp Lys Ser Ser Asn Thr Ala Tyr Met Glu
1               5                   10                  15

Leu Ser Ser Leu Thr Ser Glu Asp Ser Ala Val Tyr Tyr Cys
            20                  25                  30

<210> SEQ ID NO 77
<211> LENGTH: 11
<212> TYPE: PRT
<213> ORGANISM: Artificial Sequence
<220> FEATURE:
<223> OTHER INFORMATION: Synthetic construct

<400> SEQUENCE: 77

Trp Gly Gln Gly Thr Thr Leu Thr Val Ser Ser
1               5                   10

<210> SEQ ID NO 78
<211> LENGTH: 23
<212> TYPE: PRT
<213> ORGANISM: Artificial Sequence
<220> FEATURE:
<223> OTHER INFORMATION: Synthetic construct

<400> SEQUENCE: 78

Gln Ile Val Leu Thr Gln Ser Pro Ala Ile Met Ser Ala Ser Pro Gly
1               5                   10                  15

Glu Lys Val Thr Met Thr Cys
            20

<210> SEQ ID NO 79
<211> LENGTH: 15
<212> TYPE: PRT
<213> ORGANISM: Artificial Sequence
<220> FEATURE:
<223> OTHER INFORMATION: Synthetic construct

<400> SEQUENCE: 79

Trp Tyr Gln Gln Lys Ser Gly Thr Ser Pro Lys Lys Trp Ile Tyr
1               5                   10                  15

<210> SEQ ID NO 80
<211> LENGTH: 32
<212> TYPE: PRT
<213> ORGANISM: Artificial Sequence
<220> FEATURE:
<223> OTHER INFORMATION: Synthetic construct

<400> SEQUENCE: 80

Gly Val Pro Ala Arg Phe Ser Gly Ser Gly Ser Gly Thr Ser Tyr Ser
1               5                   10                  15

Leu Thr Ile Gly Ser Met Glu Ala Glu Asp Ala Ala Thr Tyr Tyr Cys
            20                  25                  30

<210> SEQ ID NO 81
<211> LENGTH: 10
<212> TYPE: PRT
<213> ORGANISM: Artificial Sequence

```
<220> FEATURE:
<223> OTHER INFORMATION: Synthetic construct

<400> SEQUENCE: 81

Phe Gly Gly Gly Thr Lys Leu Glu Ile Lys
1               5                   10

<210> SEQ ID NO 82
<211> LENGTH: 120
<212> TYPE: PRT
<213> ORGANISM: Artificial Sequence
<220> FEATURE:
<223> OTHER INFORMATION: Synthetic construct

<400> SEQUENCE: 82

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
            100                 105                 110

Gly Thr Leu Val Thr Val Ser Ser
        115                 120

<210> SEQ ID NO 83
<211> LENGTH: 107
<212> TYPE: PRT
<213> ORGANISM: Artificial Sequence
<220> FEATURE:
<223> OTHER INFORMATION: Synthetic construct

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Ile
            20                  25                  30

Val Val Trp Phe Gln Gln Lys Pro Gly Lys Ser Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ser Pro Tyr
                85                  90                  95

Thr Phe Gly Gln Gly Thr Lys Val Glu Ile Lys
            100                 105

<210> SEQ ID NO 84
<211> LENGTH: 120
<212> TYPE: PRT
<213> ORGANISM: Artificial Sequence
<220> FEATURE:
```

<223> OTHER INFORMATION: Synthetic construct

<400> SEQUENCE: 84

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
            100                 105                 110

Gly Thr Leu Val Thr Val Ser Ser
        115                 120

<210> SEQ ID NO 85
<211> LENGTH: 107
<212> TYPE: PRT
<213> ORGANISM: Artificial Sequence
<220> FEATURE:
<223> OTHER INFORMATION: Synthetic construct

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Asn Leu
            20                  25                  30

Val Val Trp Phe Gln Gln Lys Pro Gly Lys Ala Pro Lys Leu Leu Ile
        35                  40                  45

Tyr Ser Gly Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Pro Pro Tyr
                85                  90                  95

Thr Phe Gly Gln Gly Thr Lys Val Glu Ile Lys
            100                 105

<210> SEQ ID NO 86
<211> LENGTH: 120
<212> TYPE: PRT
<213> ORGANISM: Artificial Sequence
<220> FEATURE:
<223> OTHER INFORMATION: Synthetic construct

<400> SEQUENCE: 86

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Met

```
                    50                  55                  60

Ser Arg Leu Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ser
                     85                  90                  95

Asn His Tyr Tyr Gly Ser Ser Asp Tyr Ala Leu Asp Asn Trp Gly Gln
                    100                 105                 110

Gly Thr Leu Val Thr Val Ser Ser
            115                 120

<210> SEQ ID NO 87
<211> LENGTH: 107
<212> TYPE: PRT
<213> ORGANISM: Artificial Sequence
<220> FEATURE:
<223> OTHER INFORMATION: Synthetic construct

<400> SEQUENCE: 87

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Arg Asn Leu
                20                  25                  30

Val Val Trp Phe Gln Gln Lys Pro Gly Lys Ala Pro Lys Leu Leu Ile
            35                  40                  45

Tyr Ser Gly Tyr Asn Arg Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gln Phe Gln Pro Pro Tyr
                 85                  90                  95

Thr Phe Gly Gln Gly Thr Lys Val Glu Ile Lys
            100                 105

<210> SEQ ID NO 88
<211> LENGTH: 120
<212> TYPE: PRT
<213> ORGANISM: Artificial Sequence
<220> FEATURE:
<223> OTHER INFORMATION: Synthetic construct

<400> SEQUENCE: 88

Glu Val Gln Leu Val Glu Ser Gly Pro Gly Leu Val Lys Pro Ser Glu
 1               5                  10                  15

Thr Leu Ser Leu Thr Cys Thr Val Ser Gly Phe Ser Leu Thr Arg Phe
                20                  25                  30

Gly Val His Trp Val Arg Gln Pro Pro Gly Lys Gly Leu Glu Trp Leu
            35                  40                  45

Gly Val Ile Trp Arg Gly Gly Ser Thr Asp Tyr Asn Ala Ala Phe Met
 50                  55                  60

Ser Arg Leu Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ser
                 85                  90                  95

Asn His Tyr Tyr Gly Ser Ser Asp Tyr Ala Leu Asp Asn Trp Gly Gln
                100                 105                 110

Gly Thr Leu Val Thr Val Ser Ser
            115                 120
```

```
<210> SEQ ID NO 89
<211> LENGTH: 107
<212> TYPE: PRT
<213> ORGANISM: Artificial Sequence
<220> FEATURE:
<223> OTHER INFORMATION: Synthetic construct

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Asn Ile
            20                  25                  30

Val Val Trp Phe Gln Gln Lys Pro Gly Lys Ala Pro Lys Leu Leu Ile
        35                  40                  45

Tyr Ser Gly Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gln Tyr Ser Pro Pro Tyr
                85                  90                  95

Thr Phe Gly Gln Gly Thr Lys Val Glu Ile Lys
            100                 105

<210> SEQ ID NO 90
<211> LENGTH: 120
<212> TYPE: PRT
<213> ORGANISM: Artificial Sequence
<220> FEATURE:
<223> OTHER INFORMATION: Synthetic construct

<400> SEQUENCE: 90

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
            100                 105                 110

Gly Thr Leu Val Thr Val Ser Ser
        115                 120

<210> SEQ ID NO 91
<211> LENGTH: 107
<212> TYPE: PRT
<213> ORGANISM: Artificial Sequence
<220> FEATURE:
<223> OTHER INFORMATION: Synthetic construct

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Asn Leu
```

```
            20                  25                  30
Val Val Trp Phe Gln Gln Lys Pro Gly Lys Ala Pro Lys Leu Leu Ile
            35                  40                  45

Tyr Ser Gly Ser Tyr Arg Tyr Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Pro Pro Tyr
                85                  90                  95

Thr Phe Gly Gln Gly Thr Lys Val Glu Ile Lys
            100                 105
```

<210> SEQ ID NO 92
<211> LENGTH: 120
<212> TYPE: PRT
<213> ORGANISM: Artificial Sequence
<220> FEATURE:
<223> OTHER INFORMATION: Synthetic construct

<400> SEQUENCE: 92

```
Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
            35                  40                  45

Gly Val Ile Trp Arg Gly Gly Ser Thr Asp Tyr Asn Ala Ala Phe Met
            50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
            100                 105                 110

Gly Thr Leu Val Thr Val Ser Ser
            115                 120
```

<210> SEQ ID NO 93
<211> LENGTH: 107
<212> TYPE: PRT
<213> ORGANISM: Artificial Sequence
<220> FEATURE:
<223> OTHER INFORMATION: Synthetic construct

<400> SEQUENCE: 93

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Ile
            20                  25                  30

Val Val Trp Phe Gln Gln Lys Pro Gly Lys Ser Pro Lys Leu Leu Ile
            35                  40                  45

Tyr Ser Gly Tyr Tyr Arg Tyr Thr Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gln Phe Gln Pro Pro Tyr
                85                  90                  95
```

Thr Phe Gly Gln Gly Thr Lys Val Glu Ile Lys
            100                 105

<210> SEQ ID NO 94
<211> LENGTH: 120
<212> TYPE: PRT
<213> ORGANISM: Artificial Sequence
<220> FEATURE:
<223> OTHER INFORMATION: Synthetic construct

<400> SEQUENCE: 94

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
            100                 105                 110

Gly Thr Leu Val Thr Val Ser Ser
        115                 120

<210> SEQ ID NO 95
<211> LENGTH: 107
<212> TYPE: PRT
<213> ORGANISM: Artificial Sequence
<220> FEATURE:
<223> OTHER INFORMATION: Synthetic construct

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Ile
            20                  25                  30

Val Val Trp Phe Gln Gln Lys Pro Gly Lys Ala Pro Lys Leu Leu Ile
        35                  40                  45

Tyr Ser Gly Tyr Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gln Pro Pro Tyr
                85                  90                  95

Thr Phe Gly Gln Gly Thr Lys Val Glu Ile Lys
            100                 105

<210> SEQ ID NO 96
<211> LENGTH: 120
<212> TYPE: PRT
<213> ORGANISM: Artificial Sequence
<220> FEATURE:
<223> OTHER INFORMATION: Synthetic construct

<400> SEQUENCE: 96

Glu Val Gln Leu Val Glu Ser Gly Pro Gly Leu Val Lys Pro Ser Glu

```
            1               5                  10                 15
        Thr Leu Ser Leu Thr Cys Thr Val Ser Gly Phe Ser Thr Thr Arg Phe
                        20                  25                  30

Gly Val His Trp Val Arg Gln Pro Pro Gly Lys Gly Leu Glu Trp Leu
                        35                  40                  45

Gly Val Ile Trp Arg Gly Gly Ser Thr Asp Tyr Asn Ala Ala Phe Met
                        50                  55                  60

Ser Arg Leu Thr Ile Ser Lys Asp Asn Ser Lys Asn Gln Val Ser Leu
        65                  70                  75                  80

Lys Leu Ser Ser Val Thr Ala Ala Asp Thr Ala Val Tyr Tyr Cys Ser
                        85                  90                  95

Asn His Tyr Tyr Gly Ser Ser Asp Tyr Ala Leu Asp Asn Trp Gly Gln
                        100                 105                 110

Gly Thr Leu Val Thr Val Ser Ser
                        115                 120

<210> SEQ ID NO 97
<211> LENGTH: 107
<212> TYPE: PRT
<213> ORGANISM: Artificial Sequence
<220> FEATURE:
<223> OTHER INFORMATION: Synthetic construct

<400> SEQUENCE: 97

Asp Ile Gln Met Thr Gln Ser Pro Ser Ser Leu Ser Ala Ser Val Gly
        1               5                   10                  15

Asp Arg Val Thr Ile Thr Cys Lys Ala Ser Gln Asp Val Arg Asn Leu
                        20                  25                  30

Val Val Trp Phe Gln Gln Lys Pro Gly Lys Ala Pro Lys Leu Leu Ile
                        35                  40                  45

Tyr Ser Gly Tyr Arg Tyr Thr Gly Val Pro Ser Arg Phe Ser Gly
                        50                  55                  60

Ser Gly Ser Gly Thr Asp Phe Thr Leu Thr Ile Ser Ser Leu Gln Pro
        65                  70                  75                  80

Glu Asp Phe Ala Thr Tyr Tyr Cys Gln Gln His Tyr Gln Pro Pro Tyr
                        85                  90                  95

Thr Phe Gly Gln Gly Thr Lys Val Glu Ile Lys
                        100                 105

<210> SEQ ID NO 98
<211> LENGTH: 120
<212> TYPE: PRT
<213> ORGANISM: Artificial Sequence
<220> FEATURE:
<223> OTHER INFORMATION: Synthetic construct

<400> SEQUENCE: 98

Glu Val Gln Leu Val Glu Ser Gly Pro Gly Leu Val Lys Pro Ser Glu
        1               5                   10                  15

Thr Leu Ser Leu Thr Cys Thr Val Ser Gly Phe Ser Leu Thr Arg Phe
                        20                  25                  30

Gly Val His Trp Val Arg Gln Pro Pro Gly Lys Gly Leu Glu Trp Ile
                        35                  40                  45

Gly Val Ile Trp Arg Gly Gly Ser Thr Asp Tyr Asn Ala Ala Phe Met
                        50                  55                  60

Ser Arg Leu Thr Ile Ser Lys Asp Asn Ser Lys Asn Gln Val Ser Leu
        65                  70                  75                  80
```

```
Lys Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
            100                 105                 110

Gly Thr Leu Val Thr Val Ser Ser
        115                 120

<210> SEQ ID NO 99
<211> LENGTH: 107
<212> TYPE: PRT
<213> ORGANISM: Artificial Sequence
<220> FEATURE:
<223> OTHER INFORMATION: Synthetic construct

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Asn Leu
            20                  25                  30

Val Val Trp Phe Gln Gln Lys Pro Gly Lys Ala Pro Lys Leu Leu Ile
        35                  40                  45

Tyr Ser Gly Tyr Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gln Pro Pro Tyr
                85                  90                  95

Thr Phe Gly Gln Gly Thr Lys Val Glu Ile Lys
            100                 105

<210> SEQ ID NO 100
<211> LENGTH: 120
<212> TYPE: PRT
<213> ORGANISM: Artificial Sequence
<220> FEATURE:
<223> OTHER INFORMATION: Synthetic construct

<400> SEQUENCE: 100

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Met
50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
            100                 105                 110

Gly Thr Leu Val Thr Val Ser Ser
        115                 120

<210> SEQ ID NO 101
<211> LENGTH: 107
<212> TYPE: PRT
<213> ORGANISM: Artificial Sequence
```

```
<220> FEATURE:
<223> OTHER INFORMATION: Synthetic construct

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Asn Leu
            20                  25                  30

Val Val Trp Phe Gln Gln Lys Pro Gly Lys Ala Pro Lys Leu Leu Ile
        35                  40                  45

Tyr Ser Gly Tyr Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln His Tyr Gln Pro Pro Tyr
                85                  90                  95

Thr Phe Gly Gln Gly Thr Lys Val Glu Ile Lys
            100                 105

<210> SEQ ID NO 102
<211> LENGTH: 120
<212> TYPE: PRT
<213> ORGANISM: Artificial Sequence
<220> FEATURE:
<223> OTHER INFORMATION: Synthetic construct

<400> SEQUENCE: 102

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Val
    50                  55                  60

Ser Arg Leu Thr Ile Ser Lys Asp Asn Ser Lys Asn Gln Val Ser Leu
65              70                  75                  80

Lys Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
            100                 105                 110

Gly Thr Leu Val Thr Val Ser Ser
        115                 120

<210> SEQ ID NO 103
<211> LENGTH: 107
<212> TYPE: PRT
<213> ORGANISM: Artificial Sequence
<220> FEATURE:
<223> OTHER INFORMATION: Synthetic construct

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Ile
            20                  25                  30

Val Val Trp Phe Gln Gln Lys Pro Gly Lys Ser Pro Lys Leu Leu Ile
        35                  40                  45
```

```
Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ser Pro Tyr
                85                  90                  95

Thr Phe Gly Gln Gly Thr Lys Val Glu Ile Lys
                100                 105
```

<210> SEQ ID NO 104
<211> LENGTH: 120
<212> TYPE: PRT
<213> ORGANISM: Artificial Sequence
<220> FEATURE:
<223> OTHER INFORMATION: Synthetic construct

<400> SEQUENCE: 104

```
Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
                20                  25                  30

Gly Val His Trp Val Arg Gln Pro Pro Gly Lys Gly Leu Glu Trp Leu
            35                  40                  45

Gly Val Ile Trp Arg Gly Gly Ser Thr Asp Tyr Asn Ala Ala Phe Val
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
                100                 105                 110

Gly Thr Leu Val Thr Val Ser Ser
            115                 120
```

<210> SEQ ID NO 105
<211> LENGTH: 107
<212> TYPE: PRT
<213> ORGANISM: Artificial Sequence
<220> FEATURE:
<223> OTHER INFORMATION: Synthetic construct

<400> SEQUENCE: 105

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Asn Leu
                20                  25                  30

Val Val Trp Phe Gln Gln Lys Pro Gly Lys Ala Pro Lys Leu Leu Ile
            35                  40                  45

Tyr Ser Gly Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Pro Pro Tyr
                85                  90                  95

Thr Phe Gly Gln Gly Thr Lys Val Glu Ile Lys
                100                 105
```

<210> SEQ ID NO 106

<211> LENGTH: 120
<212> TYPE: PRT
<213> ORGANISM: Artificial Sequence
<220> FEATURE:
<223> OTHER INFORMATION: Synthetic construct

<400> SEQUENCE: 106

```
Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Thr Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Val
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                85                  90                  95

Asn His Tyr Tyr Gly Ser Pro Asp Tyr Ala Leu Asp Asn Trp Gly Gln
            100                 105                 110

Gly Thr Leu Val Thr Val Ser Ser
        115                 120
```

<210> SEQ ID NO 107
<211> LENGTH: 107
<212> TYPE: PRT
<213> ORGANISM: Artificial Sequence
<220> FEATURE:
<223> OTHER INFORMATION: Synthetic construct

<400> SEQUENCE: 107

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Leu
            20                  25                  30

Val Val Trp Phe Gln Gln Lys Pro Gly Lys Ala Pro Lys Leu Leu Ile
        35                  40                  45

Tyr Ser Gly Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Pro Pro Tyr
                85                  90                  95

Thr Phe Gly Gln Gly Thr Lys Val Glu Ile Lys
            100                 105
```

<210> SEQ ID NO 108
<211> LENGTH: 119
<212> TYPE: PRT
<213> ORGANISM: Artificial Sequence
<220> FEATURE:
<223> OTHER INFORMATION: Synthetic construct

<400> SEQUENCE: 108

```
Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Ser Tyr
            20                  25                  30
```

Ala Met Gly Trp Val Arg Gln Ala Pro Gly Lys Gly Leu Glu Trp Ile
            35                  40                  45

Gly Thr Ile Gly Thr Gly Gly Thr Pro Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Asp Met Tyr Thr Gly Ser Ile Tyr Tyr Asp Met Trp Gly Gln Gly
            100                 105                 110

Thr Leu Val Thr Val Ser Ser
        115

<210> SEQ ID NO 109
<211> LENGTH: 111
<212> TYPE: PRT
<213> ORGANISM: Artificial Sequence
<220> FEATURE:
<223> OTHER INFORMATION: Synthetic construct

<400> SEQUENCE: 109

Asp Ala Gln Leu Thr Gln Ser Pro Ser Ser Leu Ser Ala Ser Val Gly
1               5                   10                  15

Asp Arg Val Thr Ile Thr Cys Gln Ser Ser Gln Ser Val Phe Asn Asn
            20                  25                  30

Ala Gln Leu Ser Trp Tyr Gln Gln Lys Pro Gly Lys Pro Pro Lys Leu
        35                  40                  45

Leu Ile Tyr Asp Thr Ser Asn Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Ala Tyr Thr Asp
                85                  90                  95

Asp Ala Asp Asn Ala Phe Gly Gln Gly Thr Lys Val Glu Ile Lys
            100                 105                 110

<210> SEQ ID NO 110
<211> LENGTH: 118
<212> TYPE: PRT
<213> ORGANISM: Artificial Sequence
<220> FEATURE:
<223> OTHER INFORMATION: Synthetic construct

<400> SEQUENCE: 110

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr His Tyr
            20                  25                  30

Ala Met His Trp Val Lys Gln Ser His Thr Lys Ser Leu Glu Trp Ile
        35                  40                  45

Gly Met Ile Ser Ser Ser Gly Asn Thr Asn Phe Asn Gln Lys Phe
    50                  55                  60

Met Asp Lys Ala Thr Met Thr Val Asp Lys Ser Ser Thr Thr Ala Tyr
65                  70                  75                  80

Leu Glu Leu Ala Arg Leu Thr Phe Gly Asp Ser Ala Ile Tyr Tyr Cys
                85                  90                  95

Ala Arg Trp Ser Tyr Tyr Ala Leu Phe Asp Tyr Trp Gly Gln Gly Thr
            100                 105                 110

Thr Val Thr Val Ser Ser
          115

<210> SEQ ID NO 111
<211> LENGTH: 106
<212> TYPE: PRT
<213> ORGANISM: Artificial Sequence
<220> FEATURE:
<223> OTHER INFORMATION: Synthetic construct

<400> SEQUENCE: 111

Glu Asn Val Leu Thr Gln Ser Pro Ala Ile Met Ser Ala Ser Pro Gly
1               5                   10                  15

Glu Lys Val Thr Met Thr Cys Ser Ala Asp Ser Ser Val Asp Tyr Ile
            20                  25                  30

His Trp Tyr Gln Gln Lys Ser Asn Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Phe Ala Thr Tyr Tyr Cys Phe Gln Gly Ser Gly Tyr Pro Leu Thr
                85                  90                  95

Phe Gly Ser Gly Thr Lys Leu Glu Leu Lys
            100                 105

<210> SEQ ID NO 112
<211> LENGTH: 118
<212> TYPE: PRT
<213> ORGANISM: Artificial Sequence
<220> FEATURE:
<223> OTHER INFORMATION: Synthetic construct

<400> SEQUENCE: 112

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Met Lys Gln Lys Pro Gly Gln Gly Leu Glu Trp Ile
        35                  40                  45

Gly Tyr Ile Ser Pro Tyr Asn Asp Tyr Thr Lys Tyr Asn Glu Lys Phe
    50                  55                  60

Glu Gly Lys Ala Thr Leu Thr Ser Asp Lys Ser Ser Asn Thr Ala Tyr
65                  70                  75                  80

Met Glu Leu Ser Ser Leu Thr Ser Glu Asp Ser Ala Val Tyr Tyr Cys
                85                  90                  95

Ala Arg Arg Asp Tyr Tyr Gly Ser Ser Asp Tyr Trp Gly Gln Gly Thr
            100                 105                 110

Thr Leu Thr Val Ser Ser
          115

<210> SEQ ID NO 113
<211> LENGTH: 106
<212> TYPE: PRT
<213> ORGANISM: Artificial Sequence
<220> FEATURE:
<223> OTHER INFORMATION: Synthetic construct

<400> SEQUENCE: 113

-continued

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Asp Tyr Met
            20                  25                  30

His Trp Tyr Gln Gln Lys Ser Gly Thr Ser Pro Lys Lys Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Gly Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 114
<211> LENGTH: 977
<212> TYPE: PRT
<213> ORGANISM: Homo sapiens

<400> SEQUENCE: 114

Met Leu Leu Trp Val Ile Leu Val Leu Ala Pro Val Ser Gly Gln
1               5                   10                  15

Phe Ala Arg Thr Pro Arg Pro Ile Ile Phe Leu Gln Pro Pro Trp Thr
            20                  25                  30

Thr Val Phe Gln Gly Glu Arg Val Thr Leu Thr Cys Lys Gly Phe Arg
            35                  40                  45

Phe Tyr Ser Pro Gln Lys Thr Lys Trp Tyr His Arg Tyr Leu Gly Lys
        50                  55                  60

Glu Ile Leu Arg Glu Thr Pro Asp Asn Ile Leu Glu Val Gln Glu Ser
65                  70                  75                  80

Gly Glu Tyr Arg Cys Gln Ala Gln Gly Ser Pro Leu Ser Ser Pro Val
                85                  90                  95

His Leu Asp Phe Ser Ser Ala Ser Leu Ile Leu Gln Ala Pro Leu Ser
            100                 105                 110

Val Phe Glu Gly Asp Ser Val Val Leu Arg Cys Arg Ala Lys Ala Glu
        115                 120                 125

Val Thr Leu Asn Asn Thr Ile Tyr Lys Asn Asp Asn Val Leu Ala Phe
    130                 135                 140

Leu Asn Lys Arg Thr Asp Phe His Ile Pro His Ala Cys Leu Lys Asp
145                 150                 155                 160

Asn Gly Ala Tyr Arg Cys Thr Gly Tyr Lys Glu Ser Cys Cys Pro Val
                165                 170                 175

Ser Ser Asn Thr Val Lys Ile Gln Val Gln Glu Pro Phe Thr Arg Pro
            180                 185                 190

Val Leu Arg Ala Ser Ser Phe Gln Pro Ile Ser Gly Asn Pro Val Thr
        195                 200                 205

Leu Thr Cys Glu Thr Gln Leu Ser Leu Glu Arg Ser Asp Val Pro Leu
    210                 215                 220

Arg Phe Arg Phe Arg Asp Asp Gln Thr Leu Gly Leu Gly Trp Ser
225                 230                 235                 240

Leu Ser Pro Asn Phe Gln Ile Thr Ala Met Trp Ser Lys Asp Ser Gly
                245                 250                 255

Phe Tyr Trp Cys Lys Ala Ala Thr Met Pro Tyr Ser Val Ile Ser Asp
            260                 265                 270
```

```
Ser Pro Arg Ser Trp Ile Gln Val Gln Ile Pro Ala Ser His Pro Val
        275                 280                 285
Leu Thr Leu Ser Pro Glu Lys Ala Leu Asn Phe Glu Gly Thr Lys Val
        290                 295                 300
Thr Leu His Cys Glu Thr Gln Glu Asp Ser Leu Arg Thr Leu Tyr Arg
305                 310                 315                 320
Phe Tyr His Glu Gly Val Pro Leu Arg His Lys Ser Val Arg Cys Glu
                325                 330                 335
Arg Gly Ala Ser Ile Ser Phe Ser Leu Thr Thr Glu Asn Ser Gly Asn
            340                 345                 350
Tyr Tyr Cys Thr Ala Asp Asn Gly Leu Gly Ala Lys Pro Ser Lys Ala
        355                 360                 365
Val Ser Leu Ser Val Thr Val Pro Val Ser His Pro Val Leu Asn Leu
    370                 375                 380
Ser Ser Pro Glu Asp Leu Ile Phe Glu Gly Ala Lys Val Thr Leu His
385                 390                 395                 400
Cys Glu Ala Gln Arg Gly Ser Leu Pro Ile Leu Tyr Gln Phe His His
                405                 410                 415
Glu Gly Ala Ala Leu Glu Arg Arg Ser Ala Asn Ser Ala Gly Gly Val
            420                 425                 430
Ala Ile Ser Phe Ser Leu Thr Ala Glu His Ser Gly Asn Tyr Tyr Cys
        435                 440                 445
Thr Ala Asp Asn Gly Phe Gly Pro Gln Arg Ser Lys Ala Val Ser Leu
450                 455                 460
Ser Val Thr Val Pro Val Ser His Pro Val Leu Thr Leu Ser Ser Ala
465                 470                 475                 480
Glu Ala Leu Thr Phe Glu Gly Ala Thr Val Thr Leu His Cys Glu Val
                485                 490                 495
Gln Arg Gly Ser Pro Gln Ile Leu Tyr Gln Phe Tyr His Glu Asp Met
            500                 505                 510
Pro Leu Trp Ser Ser Ser Thr Pro Ser Val Gly Arg Val Ser Phe Ser
        515                 520                 525
Phe Ser Leu Thr Glu Gly His Ser Gly Asn Tyr Tyr Cys Thr Ala Asp
    530                 535                 540
Asn Gly Phe Gly Pro Gln Arg Ser Glu Val Val Ser Leu Phe Val Thr
545                 550                 555                 560
Val Pro Val Ser Arg Pro Ile Leu Thr Leu Arg Val Pro Arg Ala Gln
                565                 570                 575
Ala Val Val Gly Asp Leu Leu Glu Leu His Cys Glu Ala Pro Arg Gly
            580                 585                 590
Ser Pro Pro Ile Leu Tyr Trp Phe Tyr His Glu Asp Val Thr Leu Gly
        595                 600                 605
Ser Ser Ser Ala Pro Ser Gly Gly Glu Ala Ser Phe Asn Leu Ser Leu
    610                 615                 620
Thr Ala Glu His Ser Gly Asn Tyr Ser Cys Glu Ala Asn Asn Gly Leu
625                 630                 635                 640
Val Ala Gln His Ser Asp Thr Ile Ser Leu Ser Val Ile Val Pro Val
                645                 650                 655
Ser Arg Pro Ile Leu Thr Phe Arg Ala Pro Arg Ala Gln Ala Val Val
            660                 665                 670
Gly Asp Leu Leu Glu Leu His Cys Glu Ala Leu Arg Gly Ser Ser Pro
        675                 680                 685
```

-continued

```
Ile Leu Tyr Trp Phe Tyr His Glu Asp Val Thr Leu Gly Lys Ile Ser
        690                 695                 700
Ala Pro Ser Gly Gly Gly Ala Ser Phe Asn Leu Ser Leu Thr Thr Glu
705                 710                 715                 720
His Ser Gly Ile Tyr Ser Cys Glu Ala Asp Asn Gly Leu Glu Ala Gln
                725                 730                 735
Arg Ser Glu Met Val Thr Leu Lys Val Ala Val Pro Val Ser Arg Pro
            740                 745                 750
Val Leu Thr Leu Arg Ala Pro Gly Thr His Ala Ala Val Gly Asp Leu
        755                 760                 765
Leu Glu Leu His Cys Glu Ala Leu Arg Gly Ser Pro Leu Ile Leu Tyr
770                 775                 780
Arg Phe Phe His Glu Asp Val Thr Leu Gly Asn Arg Ser Ser Pro Ser
785                 790                 795                 800
Gly Gly Ala Ser Leu Asn Leu Ser Leu Thr Ala Glu His Ser Gly Asn
                805                 810                 815
Tyr Ser Cys Glu Ala Asp Asn Gly Leu Gly Ala Gln Arg Ser Glu Thr
            820                 825                 830
Val Thr Leu Tyr Ile Thr Gly Leu Thr Ala Asn Arg Ser Gly Pro Phe
        835                 840                 845
Ala Thr Gly Val Ala Gly Gly Leu Leu Ser Ile Ala Gly Leu Ala Ala
850                 855                 860
Gly Ala Leu Leu Leu Tyr Cys Trp Leu Ser Arg Lys Ala Gly Arg Lys
865                 870                 875                 880
Pro Ala Ser Asp Pro Ala Arg Ser Pro Ser Asp Ser Asp Ser Gln Glu
                885                 890                 895
Pro Thr Tyr His Asn Val Pro Ala Trp Glu Glu Leu Gln Pro Val Tyr
            900                 905                 910
Thr Asn Ala Asn Pro Arg Gly Glu Asn Val Val Tyr Ser Glu Val Arg
        915                 920                 925
Ile Ile Gln Glu Lys Lys Lys His Ala Val Ala Ser Asp Pro Arg His
930                 935                 940
Leu Arg Asn Lys Gly Ser Pro Ile Ile Tyr Ser Glu Val Lys Val Ala
945                 950                 955                 960
Ser Thr Pro Val Ser Gly Ser Leu Phe Leu Ala Ser Ser Ala Pro His
                965                 970                 975
Arg
```

<210> SEQ ID NO 115
<211> LENGTH: 5
<212> TYPE: PRT
<213> ORGANISM: Artificial Sequence
<220> FEATURE:
<223> OTHER INFORMATION: Synthetic construct

<400> SEQUENCE: 115

```
Ser Tyr Tyr Ile His
1               5
```

<210> SEQ ID NO 116
<211> LENGTH: 17
<212> TYPE: PRT
<213> ORGANISM: Artificial Sequence
<220> FEATURE:
<223> OTHER INFORMATION: Synthetic construct

<400> SEQUENCE: 116

```
Trp Ile Tyr Pro Glu Asn Asp Asn Thr Lys Tyr Asn Glu Lys Phe Lys
1               5                   10                  15

Asp

<210> SEQ ID NO 117
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa is Tyr or Ala

<400> SEQUENCE: 117

Asp Gly Tyr Ser Arg Xaa Tyr Phe Asp Tyr
1               5                   10

<210> SEQ ID NO 118
<211> LENGTH: 17
<212> TYPE: PRT
<213> ORGANISM: Artificial Sequence
<220> FEATURE:
<223> OTHER INFORMATION: Synthetic construct

<400> SEQUENCE: 118

Lys Ser Ser Gln Ser Leu Leu Asn Ser Arg Thr Arg Lys Asn Tyr Leu
1               5                   10                  15

Ala

<210> SEQ ID NO 119
<211> LENGTH: 7
<212> TYPE: PRT
<213> ORGANISM: Artificial Sequence
<220> FEATURE:
<223> OTHER INFORMATION: Synthetic construct

<400> SEQUENCE: 119

Trp Thr Ser Thr Arg Lys Ser
1               5

<210> SEQ ID NO 120
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Lys or Thr

<400> SEQUENCE: 120

Xaa Gln Ser Phe Ile Leu Arg Thr
1               5

<210> SEQ ID NO 121
<211> LENGTH: 10
<212> TYPE: PRT
<213> ORGANISM: Artificial Sequence
<220> FEATURE:
<223> OTHER INFORMATION: Synthetic construct

<400> SEQUENCE: 121

Asp Gly Tyr Ser Arg Tyr Tyr Phe Asp Tyr
1               5                   10
```

<210> SEQ ID NO 122
<211> LENGTH: 10
<212> TYPE: PRT
<213> ORGANISM: Artificial Sequence
<220> FEATURE:
<223> OTHER INFORMATION: Synthetic construct

<400> SEQUENCE: 122

Asp Gly Tyr Ser Arg Ala Tyr Phe Asp Tyr
1               5                   10

<210> SEQ ID NO 123
<211> LENGTH: 8
<212> TYPE: PRT
<213> ORGANISM: Artificial Sequence
<220> FEATURE:
<223> OTHER INFORMATION: Synthetic construct

<400> SEQUENCE: 123

Lys Gln Ser Phe Ile Leu Arg Thr
1               5

<210> SEQ ID NO 124
<211> LENGTH: 8
<212> TYPE: PRT
<213> ORGANISM: Artificial Sequence
<220> FEATURE:
<223> OTHER INFORMATION: Synthetic construct

<400> SEQUENCE: 124

Thr Gln Ser Phe Ile Leu Arg Thr
1               5

<210> SEQ ID NO 125
<211> LENGTH: 30
<212> TYPE: PRT
<213> ORGANISM: Artificial Sequence
<220> FEATURE:
<223> OTHER INFORMATION: Synthetic construct

<400> SEQUENCE: 125

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr
            20                  25                  30

<210> SEQ ID NO 126
<211> LENGTH: 14
<212> TYPE: PRT
<213> ORGANISM: Artificial Sequence
<220> FEATURE:
<223> OTHER INFORMATION: Synthetic construct

<400> SEQUENCE: 126

Trp Val Arg Gln Ala Pro Gly Gln Gly Leu Glu Trp Ile Gly
1               5                   10

<210> SEQ ID NO 127
<211> LENGTH: 32
<212> TYPE: PRT
<213> ORGANISM: Artificial Sequence
<220> FEATURE:
<223> OTHER INFORMATION: Synthetic construct

<400> SEQUENCE: 127

Arg Val Thr Ile Thr Ala Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 128
<211> LENGTH: 11
<212> TYPE: PRT
<213> ORGANISM: Artificial Sequence
<220> FEATURE:
<223> OTHER INFORMATION: Synthetic construct

<400> SEQUENCE: 128

Trp Gly Gln Gly Thr Leu Val Thr Val Ser Ser
1               5                   10

<210> SEQ ID NO 129
<211> LENGTH: 23
<212> TYPE: PRT
<213> ORGANISM: Artificial Sequence
<220> FEATURE:
<223> OTHER INFORMATION: Synthetic construct

<400> SEQUENCE: 129

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 130
<211> LENGTH: 15
<212> TYPE: PRT
<213> ORGANISM: Artificial Sequence
<220> FEATURE:
<223> OTHER INFORMATION: Synthetic construct

<400> SEQUENCE: 130

Trp Tyr Gln Gln Lys Pro Gly Gln Ser Pro Lys Leu Leu Ile Tyr
1               5                   10                  15

<210> SEQ ID NO 131
<211> LENGTH: 32
<212> TYPE: PRT
<213> ORGANISM: Artificial Sequence
<220> FEATURE:
<223> OTHER INFORMATION: Synthetic construct

<400> SEQUENCE: 131

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 132
<211> LENGTH: 10
<212> TYPE: PRT
<213> ORGANISM: Artificial Sequence
<220> FEATURE:
<223> OTHER INFORMATION: Synthetic construct

<400> SEQUENCE: 132

Phe Gly Gln Gly Thr Lys Val Glu Ile Lys
1               5                   10

<210> SEQ ID NO 133

<211> LENGTH: 119
<212> TYPE: PRT
<213> ORGANISM: Artificial Sequence
<220> FEATURE:
<223> OTHER INFORMATION: Synthetic construct

<400> SEQUENCE: 133

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Leu Val Thr Val Ser Ser
        115

<210> SEQ ID NO 134
<211> LENGTH: 112
<212> TYPE: PRT
<213> ORGANISM: Artificial Sequence
<220> FEATURE:
<223> OTHER INFORMATION: Synthetic construct

<400> SEQUENCE: 134

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110

<210> SEQ ID NO 135
<211> LENGTH: 119
<212> TYPE: PRT
<213> ORGANISM: Artificial Sequence
<220> FEATURE:
<223> OTHER INFORMATION: Synthetic construct

<400> SEQUENCE: 135

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

```
Tyr Ile His Trp Val Arg Gln Ala Pro Gly Gln Gly Leu Glu Trp Ile
            35                  40                  45

Gly Trp Ile Tyr Pro Glu Asn Asp Asn Thr Lys Tyr Asn Glu Lys Phe
 50                  55                  60

Lys Asp Arg Val Thr Ile Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Gly Tyr Ser Arg Ala Tyr Phe Asp Tyr Trp Gly Gln Gly
                100                 105                 110

Thr Leu Val Thr Val Ser Ser
            115

<210> SEQ ID NO 136
<211> LENGTH: 112
<212> TYPE: PRT
<213> ORGANISM: Artificial Sequence
<220> FEATURE:
<223> OTHER INFORMATION: Synthetic construct

<400> SEQUENCE: 136

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
                 20                  25                  30

Arg Thr Arg Lys Asn Tyr Leu Ala Trp Tyr Gln Gln Lys Pro Gly Gln
             35                  40                  45

Ser Pro Lys Leu Leu Ile Tyr Trp Thr Ser Thr Arg Lys Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95

Ser Phe Ile Leu Arg Thr Phe Gly Gln Gly Thr Lys Val Glu Ile Lys
                100                 105                 110

<210> SEQ ID NO 137
<211> LENGTH: 119
<212> TYPE: PRT
<213> ORGANISM: Artificial Sequence
<220> FEATURE:
<223> OTHER INFORMATION: Synthetic construct

<400> SEQUENCE: 137

Glu Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Ser Tyr
             20                  25                  30

Tyr Ile His Trp Val Arg Gln Ala Pro Gly Gln Gly Leu Glu Trp Ile
            35                  40                  45

Gly Trp Ile Tyr Pro Glu Asn Asp Asn Thr Lys Tyr Asn Glu Lys Phe
 50                  55                  60

Lys Asp Arg Val Thr Ile Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Gly Tyr Ser Arg Tyr Tyr Phe Asp Tyr Trp Gly Gln Gly
                100                 105                 110
```

```
Thr Leu Val Thr Val Ser Ser
        115

<210> SEQ ID NO 138
<211> LENGTH: 112
<212> TYPE: PRT
<213> ORGANISM: Artificial Sequence
<220> FEATURE:
<223> OTHER INFORMATION: Synthetic construct

<400> SEQUENCE: 138

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Leu Leu Asn Ser
            20                  25                  30

Arg Thr Arg Lys Asn Tyr Leu Ala Trp Tyr Gln Lys Pro Gly Gln
        35                  40                  45

Ser Pro Lys Leu Leu Ile Tyr Trp Thr Ser Arg Lys Ser Gly Val
    50                  55                  60

Pro Asp Arg Phe Ser Gly Ser Gly Ser Gly Thr Asp Phe Thr Leu Thr
65              70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

<210> SEQ ID NO 139
<211> LENGTH: 5
<212> TYPE: PRT
<213> ORGANISM: Artificial Sequence
<220> FEATURE:
<223> OTHER INFORMATION: Synthetic construct

<400> SEQUENCE: 139

Asn Tyr Tyr Ile His
1               5

<210> SEQ ID NO 140
<211> LENGTH: 17
<212> TYPE: PRT
<213> ORGANISM: Artificial Sequence
<220> FEATURE:
<223> OTHER INFORMATION: Synthetic construct

<400> SEQUENCE: 140

Trp Ile Tyr Pro Gly Asp Gly Asn Thr Lys Tyr Asn Glu Lys Phe Lys
1               5                   10                  15

Gly

<210> SEQ ID NO 141
<211> LENGTH: 10
<212> TYPE: PRT
<213> ORGANISM: Artificial Sequence
<220> FEATURE:
<223> OTHER INFORMATION: Synthetic construct

<400> SEQUENCE: 141

Asp Ser Tyr Ser Asn Tyr Tyr Phe Asp Tyr
1               5                   10

<210> SEQ ID NO 142
<211> LENGTH: 17
```

```
<212> TYPE: PRT
<213> ORGANISM: Artificial Sequence
<220> FEATURE:
<223> OTHER INFORMATION: Synthetic construct

<400> SEQUENCE: 142

Lys Ser Ser Gln Ser Leu Leu Asn Ser Arg Thr Arg Lys Asn Tyr Leu
1               5                   10                  15

Ala

<210> SEQ ID NO 143
<211> LENGTH: 7
<212> TYPE: PRT
<213> ORGANISM: Artificial Sequence
<220> FEATURE:
<223> OTHER INFORMATION: Synthetic construct

<400> SEQUENCE: 143

Trp Ala Ser Thr Arg Glu Ser
1               5

<210> SEQ ID NO 144
<211> LENGTH: 8
<212> TYPE: PRT
<213> ORGANISM: Artificial Sequence
<220> FEATURE:
<223> OTHER INFORMATION: Synthetic construct

<400> SEQUENCE: 144

Thr Gln Ser Phe Ile Leu Arg Thr
1               5

<210> SEQ ID NO 145
<211> LENGTH: 30
<212> TYPE: PRT
<213> ORGANISM: Artificial Sequence
<220> FEATURE:
<223> OTHER INFORMATION: Synthetic construct

<400> SEQUENCE: 145

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 146
<211> LENGTH: 14
<212> TYPE: PRT
<213> ORGANISM: Artificial Sequence
<220> FEATURE:
<223> OTHER INFORMATION: Synthetic construct

<400> SEQUENCE: 146

Trp Val Arg Gln Ala Pro Gly Gln Gly Leu Glu Trp Ile Gly
1               5                   10

<210> SEQ ID NO 147
<211> LENGTH: 32
<212> TYPE: PRT
<213> ORGANISM: Artificial Sequence
<220> FEATURE:
<223> OTHER INFORMATION: Synthetic construct

<400> SEQUENCE: 147

Arg Ala Thr Leu Thr Ala Asp Thr Ser Thr Ser Thr Ala Tyr Leu Glu
1               5                   10                  15
```

```
Leu Ser Ser Leu Arg Ser Glu Asp Thr Ala Val Tyr Tyr Cys Ala Arg
            20                  25                  30
```

<210> SEQ ID NO 148
<211> LENGTH: 11
<212> TYPE: PRT
<213> ORGANISM: Artificial Sequence
<220> FEATURE:
<223> OTHER INFORMATION: Synthetic construct

<400> SEQUENCE: 148

```
Trp Gly Gln Gly Thr Leu Val Thr Val Ser Ser
1               5                   10
```

<210> SEQ ID NO 149
<211> LENGTH: 23
<212> TYPE: PRT
<213> ORGANISM: Artificial Sequence
<220> FEATURE:
<223> OTHER INFORMATION: Synthetic construct

<400> SEQUENCE: 149

```
Asp Ile Val Met Thr Gln Ser Pro Asp Ser Leu Ala Val Ser Leu Gly
1               5                   10                  15

Glu Arg Ala Thr Ile Asn Cys
            20
```

<210> SEQ ID NO 150
<211> LENGTH: 15
<212> TYPE: PRT
<213> ORGANISM: Artificial Sequence
<220> FEATURE:
<223> OTHER INFORMATION: Synthetic construct

<400> SEQUENCE: 150

```
Trp Tyr Gln Gln Lys Pro Gly Gln Pro Pro Lys Leu Leu Ile Tyr
1               5                   10                  15
```

<210> SEQ ID NO 151
<211> LENGTH: 32
<212> TYPE: PRT
<213> ORGANISM: Artificial Sequence
<220> FEATURE:
<223> OTHER INFORMATION: Synthetic construct

<400> SEQUENCE: 151

```
Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30
```

<210> SEQ ID NO 152
<211> LENGTH: 10
<212> TYPE: PRT
<213> ORGANISM: Artificial Sequence
<220> FEATURE:
<223> OTHER INFORMATION: Synthetic construct

<400> SEQUENCE: 152

```
Phe Gly Gln Gly Thr Lys Val Glu Ile Lys
1               5                   10
```

<210> SEQ ID NO 153
<211> LENGTH: 119
<212> TYPE: PRT

<213> ORGANISM: Artificial Sequence
<220> FEATURE:
<223> OTHER INFORMATION: Synthetic construct

<400> SEQUENCE: 153

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115
```

<210> SEQ ID NO 154
<211> LENGTH: 112
<212> TYPE: PRT
<213> ORGANISM: Artificial Sequence
<220> FEATURE:
<223> OTHER INFORMATION: Synthetic construct

<400> SEQUENCE: 154

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110
```

<210> SEQ ID NO 155
<211> LENGTH: 5
<212> TYPE: PRT
<213> ORGANISM: Artificial Sequence
<220> FEATURE:
<223> OTHER INFORMATION: Synthetic construct

<400> SEQUENCE: 155

```
Gly Tyr Thr Met Asn
1               5
```

<210> SEQ ID NO 156
<211> LENGTH: 17
<212> TYPE: PRT
<213> ORGANISM: Artificial Sequence

```
<220> FEATURE:
<223> OTHER INFORMATION: Synthetic construct
<220> FEATURE:
<221> NAME/KEY: MISC_FEATURE
<222> LOCATION: (9)..(9)
<223> OTHER INFORMATION: Xaa is Ser or Thr
<220> FEATURE:
<221> NAME/KEY: MISC_FEATURE
<222> LOCATION: (12)..(12)
<223> OTHER INFORMATION: Xaa is Asn or Ala
<220> FEATURE:
<221> NAME/KEY: MISC_FEATURE
<222> LOCATION: (13)..(13)
<223> OTHER INFORMATION: Xaa is Gln or Asp
<220> FEATURE:
<221> NAME/KEY: MISC_FEATURE
<222> LOCATION: (14)..(14)
<223> OTHER INFORMATION: Xaa is Lys or Ser
<220> FEATURE:
<221> NAME/KEY: MISC_FEATURE
<222> LOCATION: (15)..(15)
<223> OTHER INFORMATION: Xaa is Val or Phe
<220> FEATURE:
<221> NAME/KEY: MISC_FEATURE
<222> LOCATION: (17)..(17)
<223> OTHER INFORMATION: Xaa is Gly or Asp

<400> SEQUENCE: 156

Leu Ile Asn Pro Tyr Lys Gly Val Xaa Thr Tyr Xaa Xaa Xaa Xaa Lys
1               5                   10                  15

Xaa

<210> SEQ ID NO 157
<211> LENGTH: 13
<212> TYPE: PRT
<213> ORGANISM: Artificial Sequence
<220> FEATURE:
<223> OTHER INFORMATION: Synthetic construct

<400> SEQUENCE: 157

Ser Gly Tyr Tyr Gly Asp Ser Asp Trp Tyr Phe Asp Val
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Synthetic construct

<400> SEQUENCE: 158

Arg Ala Ser Gln Asp Ile Arg Asn Tyr Leu Asn
1               5                   10

<210> SEQ ID NO 159
<211> LENGTH: 7
<212> TYPE: PRT
<213> ORGANISM: Artificial Sequence
<220> FEATURE:
<223> OTHER INFORMATION: Synthetic construct

<400> SEQUENCE: 159

Tyr Thr Ser Arg Leu Glu Ser
1               5

<210> SEQ ID NO 160
<211> LENGTH: 9
<212> TYPE: PRT
<213> ORGANISM: Artificial Sequence
<220> FEATURE:
```

<223> OTHER INFORMATION: Synthetic construct

<400> SEQUENCE: 160

Gln Gln Gly Asn Thr Leu Pro Trp Thr
1               5

<210> SEQ ID NO 161
<211> LENGTH: 17
<212> TYPE: PRT
<213> ORGANISM: Artificial Sequence
<220> FEATURE:
<223> OTHER INFORMATION: Synthetic construct

<400> SEQUENCE: 161

Leu Ile Asn Pro Tyr Lys Gly Val Thr Thr Tyr Ala Asp Ser Val Lys
1               5                   10                  15
Gly

<210> SEQ ID NO 162
<211> LENGTH: 17
<212> TYPE: PRT
<213> ORGANISM: Artificial Sequence
<220> FEATURE:
<223> OTHER INFORMATION: Synthetic construct

<400> SEQUENCE: 162

Leu Ile Asn Pro Tyr Lys Gly Val Ser Thr Tyr Asn Gln Lys Phe Lys
1               5                   10                  15
Asp

<210> SEQ ID NO 163
<211> LENGTH: 17
<212> TYPE: PRT
<213> ORGANISM: Artificial Sequence
<220> FEATURE:
<223> OTHER INFORMATION: Synthetic construct

<400> SEQUENCE: 163

Leu Ile Asn Pro Tyr Lys Gly Val Ser Thr Tyr Ala Asp Ser Val Lys
1               5                   10                  15
Gly

<210> SEQ ID NO 164
<211> LENGTH: 30
<212> TYPE: PRT
<213> ORGANISM: Artificial Sequence
<220> FEATURE:
<223> OTHER INFORMATION: Synthetic construct

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr
            20                  25                  30

<210> SEQ ID NO 165
<211> LENGTH: 14
<212> TYPE: PRT
<213> ORGANISM: Artificial Sequence
<220> FEATURE:
<223> OTHER INFORMATION: Synthetic construct

<400> SEQUENCE: 165

Trp Val Arg Gln Ala Pro Gly Lys Asp Leu Glu Trp Val Ala

<210> SEQ ID NO 166
<211> LENGTH: 32
<212> TYPE: PRT
<213> ORGANISM: Artificial Sequence
<220> FEATURE:
<223> OTHER INFORMATION: Synthetic construct

<400> SEQUENCE: 166

Arg Phe Thr Ile Ser Val Asp Lys Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 167
<211> LENGTH: 11
<212> TYPE: PRT
<213> ORGANISM: Artificial Sequence
<220> FEATURE:
<223> OTHER INFORMATION: Synthetic construct

<400> SEQUENCE: 167

Trp Gly Gln Gly Thr Leu Val Thr Val Ser Ser
1               5                   10

<210> SEQ ID NO 168
<211> LENGTH: 23
<212> TYPE: PRT
<213> ORGANISM: Artificial Sequence
<220> FEATURE:
<223> OTHER INFORMATION: Synthetic construct

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 169
<211> LENGTH: 15
<212> TYPE: PRT
<213> ORGANISM: Artificial Sequence
<220> FEATURE:
<223> OTHER INFORMATION: Synthetic construct

<400> SEQUENCE: 169

Trp Tyr Gln Gln Lys Pro Gly Lys Ala Pro Lys Leu Leu Ile Tyr
1               5                   10                  15

<210> SEQ ID NO 170
<211> LENGTH: 32
<212> TYPE: PRT
<213> ORGANISM: Artificial Sequence
<220> FEATURE:
<223> OTHER INFORMATION: Synthetic construct

<400> SEQUENCE: 170

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 171
<211> LENGTH: 10

<212> TYPE: PRT
<213> ORGANISM: Artificial Sequence
<220> FEATURE:
<223> OTHER INFORMATION: Synthetic construct

<400> SEQUENCE: 171

Phe Gly Gln Gly Thr Lys Leu Glu Leu Lys
1               5                   10

<210> SEQ ID NO 172
<211> LENGTH: 122
<212> TYPE: PRT
<213> ORGANISM: Artificial Sequence
<220> FEATURE:
<223> OTHER INFORMATION: Synthetic construct

<400> SEQUENCE: 172

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Asp Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
            115                 120

<210> SEQ ID NO 173
<211> LENGTH: 107
<212> TYPE: PRT
<213> ORGANISM: Artificial Sequence
<220> FEATURE:
<223> OTHER INFORMATION: Synthetic construct

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Leu Glu Leu Lys
            100                 105

<210> SEQ ID NO 174
<211> LENGTH: 28
<212> TYPE: PRT

```
<213> ORGANISM: Artificial Sequence
<220> FEATURE:
<223> OTHER INFORMATION: Synthetic construct

<400> SEQUENCE: 174

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys
            20                  25

<210> SEQ ID NO 175
<211> LENGTH: 16
<212> TYPE: PRT
<213> ORGANISM: Artificial Sequence
<220> FEATURE:
<223> OTHER INFORMATION: Synthetic construct

<400> SEQUENCE: 175

Val Ile Trp Arg Gly Gly Ser Thr Asp Tyr Asn Pro Ala Phe Met Ser
1               5                   10                  15

<210> SEQ ID NO 176
<211> LENGTH: 16
<212> TYPE: PRT
<213> ORGANISM: Artificial Sequence
<220> FEATURE:
<223> OTHER INFORMATION: Synthetic construct

<400> SEQUENCE: 176

Val Ile Trp Arg Gly Gly Ser Thr Asp Tyr Asn Ala Ala Phe Gly Ser
1               5                   10                  15

<210> SEQ ID NO 177
<211> LENGTH: 16
<212> TYPE: PRT
<213> ORGANISM: Artificial Sequence
<220> FEATURE:
<223> OTHER INFORMATION: Synthetic construct

<400> SEQUENCE: 177

Val Ile Trp Arg Gly Gly Ser Thr Asp Tyr Asn Ala Ala Phe Met Asp
1               5                   10                  15

<210> SEQ ID NO 178
<211> LENGTH: 16
<212> TYPE: PRT
<213> ORGANISM: Artificial Sequence
<220> FEATURE:
<223> OTHER INFORMATION: Synthetic construct

<400> SEQUENCE: 178

Val Ile Trp Arg Gly Gly Ser Thr Asp Tyr Asn Ala Ala Phe Met Pro
1               5                   10                  15

<210> SEQ ID NO 179
<211> LENGTH: 30
<212> TYPE: PRT
<213> ORGANISM: Artificial Sequence
<220> FEATURE:
<223> OTHER INFORMATION: Synthetic construct

<400> SEQUENCE: 179

Ser Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr
            20                  25                  30
```

<210> SEQ ID NO 180
<211> LENGTH: 30
<212> TYPE: PRT
<213> ORGANISM: Artificial Sequence
<220> FEATURE:
<223> OTHER INFORMATION: Synthetic construct

<400> SEQUENCE: 180

Phe Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr
            20                  25                  30

<210> SEQ ID NO 181
<211> LENGTH: 30
<212> TYPE: PRT
<213> ORGANISM: Artificial Sequence
<220> FEATURE:
<223> OTHER INFORMATION: Synthetic construct

<400> SEQUENCE: 181

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Pro Leu Thr
            20                  25                  30

<210> SEQ ID NO 182
<211> LENGTH: 14
<212> TYPE: PRT
<213> ORGANISM: Artificial Sequence
<220> FEATURE:
<223> OTHER INFORMATION: Synthetic construct

<400> SEQUENCE: 182

Trp Tyr Arg Gln Pro Pro Gly Lys Gly Leu Glu Trp Leu Gly
1               5                   10

<210> SEQ ID NO 183
<211> LENGTH: 32
<212> TYPE: PRT
<213> ORGANISM: Artificial Sequence
<220> FEATURE:
<223> OTHER INFORMATION: Synthetic construct

<400> SEQUENCE: 183

Arg Leu Thr Ile Ser Lys Asp Asn Ser Lys Asn Gln Val Ser Leu Met
1               5                   10                  15

Leu Ser Ser Val Thr Ala Ala Asp Thr Ala Val Tyr Tyr Cys Ser Asn
            20                  25                  30

<210> SEQ ID NO 184
<211> LENGTH: 32
<212> TYPE: PRT
<213> ORGANISM: Artificial Sequence
<220> FEATURE:
<223> OTHER INFORMATION: Synthetic construct

<400> SEQUENCE: 184

Arg Leu Thr Ile Ser Lys Asp Asn Ser Lys Asn Gln Val Ser Leu Lys
1               5                   10                  15

Leu Ser Asp Val Thr Ala Ala Asp Thr Ala Val Tyr Tyr Cys Ser Asn
            20                  25                  30

```
<210> SEQ ID NO 185
<211> LENGTH: 120
<212> TYPE: PRT
<213> ORGANISM: Artificial Sequence
<220> FEATURE:
<223> OTHER INFORMATION: Synthetic construct

<400> SEQUENCE: 185
```

Ser Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
            100                 105                 110

Gly Thr Leu Val Thr Val Ser Ser
        115                 120

```
<210> SEQ ID NO 186
<211> LENGTH: 107
<212> TYPE: PRT
<213> ORGANISM: Artificial Sequence
<220> FEATURE:
<223> OTHER INFORMATION: Synthetic construct

<400> SEQUENCE: 186
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Ile
            20                  25                  30

Val Val Trp Phe Gln Gln Lys Pro Gly Lys Ser Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ser Pro Tyr
                85                  90                  95

Thr Phe Gly Gln Gly Thr Lys Val Glu Ile Lys
            100                 105

```
<210> SEQ ID NO 187
<211> LENGTH: 120
<212> TYPE: PRT
<213> ORGANISM: Artificial Sequence
<220> FEATURE:
<223> OTHER INFORMATION: Synthetic construct

<400> SEQUENCE: 187
```

Phe Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Gly Lys Gly Leu Glu Trp Leu
            35                  40                  45

Gly Val Ile Trp Arg Gly Gly Ser Thr Asp Tyr Asn Ala Ala Phe Met
            50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                    85                  90                  95

Asn His Tyr Tyr Gly Ser Ser Asp Tyr Ala Leu Asp Asn Trp Gly Gln
                100                 105                 110

Gly Thr Leu Val Thr Val Ser Ser
            115                 120

<210> SEQ ID NO 188
<211> LENGTH: 107
<212> TYPE: PRT
<213> ORGANISM: Artificial Sequence
<220> FEATURE:
<223> OTHER INFORMATION: Synthetic construct

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Ile
                20                  25                  30

Val Val Trp Phe Gln Gln Lys Pro Gly Lys Ser Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ser Pro Tyr
                85                  90                  95

Thr Phe Gly Gln Gly Thr Lys Val Glu Ile Lys
                100                 105

<210> SEQ ID NO 189
<211> LENGTH: 120
<212> TYPE: PRT
<213> ORGANISM: Artificial Sequence
<220> FEATURE:
<223> OTHER INFORMATION: Synthetic construct

<400> SEQUENCE: 189

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Pro Leu Thr Arg Phe
                20                  25                  30

Gly Val His Trp Val Arg Gln Pro Pro Gly Lys Gly Leu Glu Trp Leu
            35                  40                  45

Gly Val Ile Trp Arg Gly Gly Ser Thr Asp Tyr Asn Ala Ala Phe Met
            50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                    85                  90                  95

Asn His Tyr Tyr Gly Ser Ser Asp Tyr Ala Leu Asp Asn Trp Gly Gln

```
                    100                 105                 110

Gly Thr Leu Val Thr Val Ser Ser
            115                 120

<210> SEQ ID NO 190
<211> LENGTH: 107
<212> TYPE: PRT
<213> ORGANISM: Artificial Sequence
<220> FEATURE:
<223> OTHER INFORMATION: Synthetic construct

<400> SEQUENCE: 190

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Ile
            20                  25                  30

Val Val Trp Phe Gln Gln Lys Pro Gly Lys Ser Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ser Pro Tyr
                85                  90                  95

Thr Phe Gly Gln Gly Thr Lys Val Glu Ile Lys
            100                 105

<210> SEQ ID NO 191
<211> LENGTH: 120
<212> TYPE: PRT
<213> ORGANISM: Artificial Sequence
<220> FEATURE:
<223> OTHER INFORMATION: Synthetic construct

<400> SEQUENCE: 191

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Thr Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Met
50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
            100                 105                 110

Gly Thr Leu Val Thr Val Ser Ser
            115                 120

<210> SEQ ID NO 192
<211> LENGTH: 107
<212> TYPE: PRT
<213> ORGANISM: Artificial Sequence
<220> FEATURE:
<223> OTHER INFORMATION: Synthetic construct

<400> SEQUENCE: 192
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Ile
            20                  25                  30

Val Val Trp Phe Gln Lys Pro Gly Lys Ser Pro Lys Leu Leu Ile
            35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln His Tyr Ser Ser Pro Tyr
                85                  90                  95

Thr Phe Gly Gln Gly Thr Lys Val Glu Ile Lys
            100                 105

<210> SEQ ID NO 193
<211> LENGTH: 120
<212> TYPE: PRT
<213> ORGANISM: Artificial Sequence
<220> FEATURE:
<223> OTHER INFORMATION: Synthetic construct

<400> SEQUENCE: 193

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Tyr Arg Gln Pro Pro Gly Lys Gly Leu Glu Trp Leu
            35                  40                  45

Gly Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Gln Val Ser Leu
65              70                  75                  80

Lys Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
            100                 105                 110

Gly Thr Leu Val Thr Val Ser Ser
            115                 120

<210> SEQ ID NO 194
<211> LENGTH: 107
<212> TYPE: PRT
<213> ORGANISM: Artificial Sequence
<220> FEATURE:
<223> OTHER INFORMATION: Synthetic construct

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Ile
            20                  25                  30

Val Val Trp Phe Gln Lys Pro Gly Lys Ser Pro Lys Leu Leu Ile
            35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln His Tyr Ser Ser Pro Tyr
                    85                  90                  95

Thr Phe Gly Gln Gly Thr Lys Val Glu Ile Lys
                100                 105
```

<210> SEQ ID NO 195
<211> LENGTH: 120
<212> TYPE: PRT
<213> ORGANISM: Artificial Sequence
<220> FEATURE:
<223> OTHER INFORMATION: Synthetic construct

<400> SEQUENCE: 195

```
Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
                20                  25                  30

Gly Val His Trp Val Arg Gln Pro Pro Gly Lys Gly Leu Glu Trp Leu
            35                  40                  45

Gly Val Ile Trp Arg Gly Gly Ser Thr Asp Tyr Asn Pro Ala Phe Met
        50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
                100                 105                 110

Gly Thr Leu Val Thr Val Ser Ser
            115                 120
```

<210> SEQ ID NO 196
<211> LENGTH: 107
<212> TYPE: PRT
<213> ORGANISM: Artificial Sequence
<220> FEATURE:
<223> OTHER INFORMATION: Synthetic construct

<400> SEQUENCE: 196

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Ile
                20                  25                  30

Val Val Trp Phe Gln Gln Lys Pro Gly Lys Ser Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ser Pro Tyr
                85                  90                  95

Thr Phe Gly Gln Gly Thr Lys Val Glu Ile Lys
                100                 105
```

<210> SEQ ID NO 197
<211> LENGTH: 120
<212> TYPE: PRT
<213> ORGANISM: Artificial Sequence
<220> FEATURE:

<223> OTHER INFORMATION: Synthetic construct

<400> SEQUENCE: 197

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Gly
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
            100                 105                 110

Gly Thr Leu Val Thr Val Ser Ser
        115                 120

<210> SEQ ID NO 198
<211> LENGTH: 107
<212> TYPE: PRT
<213> ORGANISM: Artificial Sequence
<220> FEATURE:
<223> OTHER INFORMATION: Synthetic construct

<400> SEQUENCE: 198

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Ile
            20                  25                  30

Val Val Trp Phe Gln Gln Lys Pro Gly Lys Ser Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ser Pro Tyr
                85                  90                  95

Thr Phe Gly Gln Gly Thr Lys Val Glu Ile Lys
            100                 105

<210> SEQ ID NO 199
<211> LENGTH: 120
<212> TYPE: PRT
<213> ORGANISM: Artificial Sequence
<220> FEATURE:
<223> OTHER INFORMATION: Synthetic construct

<400> SEQUENCE: 199

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Met

```
                    50                  55                  60

Asp Arg Leu Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ser
                     85                  90                  95

Asn His Tyr Tyr Gly Ser Ser Asp Tyr Ala Leu Asp Asn Trp Gly Gln
                    100                 105                 110

Gly Thr Leu Val Thr Val Ser Ser
            115                 120

<210> SEQ ID NO 200
<211> LENGTH: 107
<212> TYPE: PRT
<213> ORGANISM: Artificial Sequence
<220> FEATURE:
<223> OTHER INFORMATION: Synthetic construct

<400> SEQUENCE: 200

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Ser Asn Ile
                20                  25                  30

Val Val Trp Phe Gln Gln Lys Pro Gly Lys Ser Pro Lys Leu Leu Ile
             35                  40                  45

Tyr Ser Ala Ser Tyr Arg Tyr Thr Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Ser Ser Pro Tyr
                 85                  90                  95

Thr Phe Gly Gln Gly Thr Lys Val Glu Ile Lys
                100                 105

<210> SEQ ID NO 201
<211> LENGTH: 120
<212> TYPE: PRT
<213> ORGANISM: Artificial Sequence
<220> FEATURE:
<223> OTHER INFORMATION: Synthetic construct

<400> SEQUENCE: 201

Glu Val Gln Leu Val Glu Ser Gly Pro Gly Leu Val Lys Pro Ser Glu
 1               5                  10                  15

Thr Leu Ser Leu Thr Cys Thr Val Ser Gly Phe Ser Leu Thr Arg Phe
                20                  25                  30

Gly Val His Trp Val Arg Gln Pro Pro Gly Lys Gly Leu Glu Trp Leu
             35                  40                  45

Gly Val Ile Trp Arg Gly Gly Ser Thr Asp Tyr Asn Ala Ala Phe Met
         50                  55                  60

Pro Arg Leu Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ser
                 85                  90                  95

Asn His Tyr Tyr Gly Ser Ser Asp Tyr Ala Leu Asp Asn Trp Gly Gln
                100                 105                 110

Gly Thr Leu Val Thr Val Ser Ser
            115                 120
```

<210> SEQ ID NO 202
<211> LENGTH: 107
<212> TYPE: PRT
<213> ORGANISM: Artificial Sequence
<220> FEATURE:
<223> OTHER INFORMATION: Synthetic construct

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Ile
            20                  25                  30

Val Val Trp Phe Gln Gln Lys Pro Gly Lys Ser Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ser Pro Tyr
                85                  90                  95

Thr Phe Gly Gln Gly Thr Lys Val Glu Ile Lys
            100                 105

<210> SEQ ID NO 203
<211> LENGTH: 120
<212> TYPE: PRT
<213> ORGANISM: Artificial Sequence
<220> FEATURE:
<223> OTHER INFORMATION: Synthetic construct

<400> SEQUENCE: 203

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Gln Val Ser Leu
65                  70                  75                  80

Met Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
            100                 105                 110

Gly Thr Leu Val Thr Val Ser Ser
        115                 120

<210> SEQ ID NO 204
<211> LENGTH: 107
<212> TYPE: PRT
<213> ORGANISM: Artificial Sequence
<220> FEATURE:
<223> OTHER INFORMATION: Synthetic construct

<400> SEQUENCE: 204

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Ile

```
                    20                  25                  30

Val Val Trp Phe Gln Gln Lys Pro Gly Lys Ser Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ser Pro Tyr
                85                  90                  95

Thr Phe Gly Gln Gly Thr Lys Val Glu Ile Lys
                100                 105

<210> SEQ ID NO 205
<211> LENGTH: 120
<212> TYPE: PRT
<213> ORGANISM: Artificial Sequence
<220> FEATURE:
<223> OTHER INFORMATION: Synthetic construct

<400> SEQUENCE: 205

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Gln Val Ser Leu
65                  70                  75                  80

Lys Leu Ser Asp Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
                100                 105                 110

Gly Thr Leu Val Thr Val Ser Ser
        115                 120

<210> SEQ ID NO 206
<211> LENGTH: 107
<212> TYPE: PRT
<213> ORGANISM: Artificial Sequence
<220> FEATURE:
<223> OTHER INFORMATION: Synthetic construct

<400> SEQUENCE: 206

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Ile
            20                  25                  30

Val Val Trp Phe Gln Gln Lys Pro Gly Lys Ser Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ser Pro Tyr
                85                  90                  95
```

Thr Phe Gly Gln Gly Thr Lys Val Glu Ile Lys
            100                 105

<210> SEQ ID NO 207
<211> LENGTH: 120
<212> TYPE: PRT
<213> ORGANISM: Artificial Sequence
<220> FEATURE:
<223> OTHER INFORMATION: Synthetic construct

<400> SEQUENCE: 207

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                85                  90                  95

Asn His Tyr Tyr Gly Ser Pro Asp Tyr Ala Leu Asp Asn Trp Gly Gln
            100                 105                 110

Gly Thr Leu Val Thr Val Ser Ser
        115                 120

<210> SEQ ID NO 208
<211> LENGTH: 107
<212> TYPE: PRT
<213> ORGANISM: Artificial Sequence
<220> FEATURE:
<223> OTHER INFORMATION: Synthetic construct

<400> SEQUENCE: 208

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Ile
            20                  25                  30

Val Val Trp Phe Gln Gln Lys Pro Gly Lys Ser Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ser Pro Tyr
                85                  90                  95

Thr Phe Gly Gln Gly Thr Lys Val Glu Ile Lys
            100                 105

<210> SEQ ID NO 209
<211> LENGTH: 120
<212> TYPE: PRT
<213> ORGANISM: Artificial Sequence
<220> FEATURE:
<223> OTHER INFORMATION: Synthetic construct

<400> SEQUENCE: 209

Glu Val Gln Leu Val Glu Ser Gly Pro Gly Leu Val Lys Pro Ser Glu

```
                1               5                  10                    15
            Thr Leu Ser Leu Thr Cys Thr Val Ser Gly Phe Ser Leu Thr Arg Phe
                        20                   25                  30

Gly Val His Trp Val Arg Gln Pro Pro Gly Lys Gly Leu Glu Trp Leu
                        35                   40                  45

Gly Val Ile Trp Arg Gly Gly Ser Thr Asp Tyr Asn Ala Ala Phe Val
                        50                   55                  60

Ser Arg Leu Thr Ile Ser Lys Asp Asn Ser Lys Asn Gln Val Ser Leu
            65                  70                   75                  80

Lys Leu Ser Ser Val Thr Ala Ala Asp Thr Ala Val Tyr Tyr Cys Ser
                                85                   90                  95

Asn His Tyr Tyr Gly Ser Ser Asp Tyr Ala Leu Asp Asn Trp Gly Gln
                            100                  105                 110

Gly Thr Leu Val Thr Val Ser Ser
                        115                  120
```

<210> SEQ ID NO 210
<211> LENGTH: 107
<212> TYPE: PRT
<213> ORGANISM: Artificial Sequence
<220> FEATURE:
<223> OTHER INFORMATION: Synthetic construct

<400> SEQUENCE: 210

```
            Asp Ile Gln Met Thr Gln Ser Pro Ser Ser Leu Ser Ala Ser Val Gly
            1               5                   10                  15

Asp Arg Val Thr Ile Thr Cys Lys Ala Ser Gln Asp Val Ser Asn Leu
                        20                  25                  30

Val Val Trp Phe Gln Gln Lys Pro Gly Lys Ser Pro Lys Leu Leu Ile
                        35                  40                  45

Tyr Ser Gly Ser Tyr Arg Tyr Ser Gly Val Pro Ser Arg Phe Ser Gly
                        50                  55                  60

Ser Gly Ser Gly Thr Asp Phe Thr Leu Thr Ile Ser Ser Leu Gln Pro
            65                  70                  75                  80

Glu Asp Phe Ala Thr Tyr Tyr Cys Gln Gln His Tyr Ser Pro Pro Tyr
                                85                  90                  95

Thr Phe Gly Gln Gly Thr Lys Val Glu Ile Lys
                            100                 105
```

<210> SEQ ID NO 211
<211> LENGTH: 120
<212> TYPE: PRT
<213> ORGANISM: Artificial Sequence
<220> FEATURE:
<223> OTHER INFORMATION: Synthetic construct

<400> SEQUENCE: 211

```
            Glu Val Gln Leu Val Glu Ser Gly Pro Gly Leu Val Lys Pro Ser Glu
            1               5                   10                  15

Thr Leu Ser Leu Thr Cys Thr Val Ser Gly Phe Ser Leu Thr Arg Phe
                        20                  25                  30

Gly Val His Trp Val Arg Gln Pro Pro Gly Lys Gly Leu Glu Trp Leu
                        35                  40                  45

Gly Val Ile Trp Arg Gly Gly Ser Thr Asp Tyr Asn Ala Ala Phe Val
                        50                  55                  60

Ser Arg Leu Thr Ile Ser Lys Asp Asn Ser Lys Asn Gln Val Ser Leu
            65                  70                  75                  80
```

Lys Leu Ser Ser Val Thr Ala Ala Asp Thr Ala Val Tyr Tyr Cys Ser
            85                  90                  95

Asn His Tyr Tyr Gly Ser Ser Asp Tyr Ala Leu Asp Asn Trp Gly Gln
                100                 105                 110

Gly Thr Leu Val Thr Val Ser Ser
        115                 120

<210> SEQ ID NO 212
<211> LENGTH: 107
<212> TYPE: PRT
<213> ORGANISM: Artificial Sequence
<220> FEATURE:
<223> OTHER INFORMATION: Synthetic construct

<400> SEQUENCE: 212

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Leu
            20                  25                  30

Val Val Trp Phe Gln Gln Lys Pro Gly Lys Ser Pro Lys Leu Leu Ile
        35                  40                  45

Tyr Ser Gly Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Pro Pro Tyr
                85                  90                  95

Thr Phe Gly Gln Gly Thr Lys Val Glu Ile Lys
            100                 105

<210> SEQ ID NO 213
<211> LENGTH: 120
<212> TYPE: PRT
<213> ORGANISM: Artificial Sequence
<220> FEATURE:
<223> OTHER INFORMATION: Synthetic construct

<400> SEQUENCE: 213

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Val
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
            85                  90                  95

Asn His Tyr Tyr Gly Ser Pro Asp Tyr Ala Leu Asp Asn Trp Gly Gln
                100                 105                 110

Gly Thr Leu Val Thr Val Ser Ser
        115                 120

<210> SEQ ID NO 214
<211> LENGTH: 107
<212> TYPE: PRT
<213> ORGANISM: Artificial Sequence
<220> FEATURE:
<223> OTHER INFORMATION: Synthetic construct

<400> SEQUENCE: 214

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Leu
            20                  25                  30

Val Val Trp Phe Gln Gln Lys Pro Gly Lys Ser Pro Lys Leu Leu Ile
        35                  40                  45

Tyr Ser Gly Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Pro Pro Tyr
                85                  90                  95

Thr Phe Gly Gln Gly Thr Lys Val Glu Ile Lys
            100                 105

<210> SEQ ID NO 215
<211> LENGTH: 975
<212> TYPE: PRT
<213> ORGANISM: Macaca fascicularis

<400> SEQUENCE: 215

Met Leu Leu Trp Val Ile Leu Val Leu Ala Pro Val Ser Gly Gln
1               5                   10                  15

Phe Val Arg Thr Tyr Lys Ser His Phe Leu Gln Pro Pro Trp Thr Thr
            20                  25                  30

Val Phe Arg Gly Glu Arg Val Asn Leu Thr Cys Lys Gly Phe Gly Phe
        35                  40                  45

Tyr Ser Ser Gln Lys Thr Lys Trp Tyr Tyr Arg His Leu Gly Lys Glu
    50                  55                  60

Ile Ser Arg Glu Thr Gln Lys Asn Thr Leu Glu Val Gln Glu Ser Gly
65                  70                  75                  80

Glu Tyr Arg Cys Gln Ala Gln Gly Ser Pro Leu Ser Ser Pro Val Ser
                85                  90                  95

Leu Asp Phe Ser Ser Ala Ser Leu Ile Leu Gln Ala Pro Leu Ser Val
            100                 105                 110

Phe Glu Gly Asp Ser Val Val Leu Arg Cys Arg Ala Lys Ala Glu Val
            115                 120                 125

Thr Leu Lys Thr Thr Ile Tyr Lys Asn Glu Asn Val Leu Ala Phe Leu
        130                 135                 140

Asn Lys Ser Thr Asp Phe His Ile Ser His Ala Ser Leu Lys Asp Asn
145                 150                 155                 160

Gly Ala Tyr Arg Cys Thr Gly Tyr Lys Glu Thr Cys Cys Leu Val Ser
                165                 170                 175

Ser Asn Thr Val Lys Ile Gln Val Gln Glu Ser Phe Thr Arg Pro Val
            180                 185                 190

Leu Arg Val Ser Ser Phe Gln Pro Ile Ser Gly Ser Pro Val Thr Leu
        195                 200                 205

Thr Cys Glu Thr Gln Leu Ser Leu Glu Arg Ser Asp Val Pro Leu Gln
    210                 215                 220

Phe Cys Phe Phe Arg Asn Asp Gln Met Leu Gly Ser Gly Cys Ser Leu
225                 230                 235                 240

-continued

```
Ser Pro Lys Phe Arg Ile Thr Ala Met Trp Ser Lys Asp Ser Gly Ser
                245                 250                 255

Tyr Trp Cys Lys Ala Ala Thr Met Cys Tyr Asp Thr Thr Ser Asn Ser
            260                 265                 270

Leu Arg Ser Trp Ile Gln Val Leu Ile Pro Ala Ser His Pro Val Leu
        275                 280                 285

Thr Leu Ser Pro Glu Lys Ala Leu Asn Phe Glu Gly Thr Lys Val Lys
    290                 295                 300

Leu His Cys Glu Thr Gln Glu Asp Ser Leu Arg Thr Leu Tyr Lys Phe
305                 310                 315                 320

Tyr His Asp Gly Val Pro Leu Arg Tyr Lys Ser Val Arg Cys Glu Lys
                325                 330                 335

Gly Ala Ser Ile Ser Phe Ser Leu Thr Thr Glu His Ser Gly Asn Tyr
            340                 345                 350

Tyr Cys Thr Ala Asp Asn Gly His Gly Ala Lys Pro Ser Glu Ala Val
        355                 360                 365

Ser Leu Ser Val Thr Val Pro Val Ser Arg Pro Val Leu Thr Leu Ser
    370                 375                 380

Ser Ala Glu Asp Leu Ile Ser Glu Gly Ala Lys Leu Thr Leu His Cys
385                 390                 395                 400

Glu Ala Gln Arg Gly Ser Leu Pro Ile Val Tyr Gln Phe His His Glu
                405                 410                 415

Asn Ala Ser Leu Gly Asn Arg Ser Ala His Ser Ala Gly Gly Val Ala
            420                 425                 430

Ile Ser Phe Ser Leu Thr Ala Asp His Ser Gly Asn Tyr Tyr Cys Thr
        435                 440                 445

Ala Asn Asn Gly Phe Gly Pro Gln Arg Ser Glu Ala Val Ser Leu Ser
    450                 455                 460

Ile Thr Val Pro Val Ser Arg Pro Val Leu Thr Leu Ser Ser Ala Glu
465                 470                 475                 480

Ala Leu Thr Phe Glu Gly Ala Thr Val Thr Leu Tyr Cys Glu Val Gln
                485                 490                 495

Arg Gly Ser Pro Arg Ile Leu Tyr Gln Phe Tyr His Glu Asp Val Pro
            500                 505                 510

Leu Gly Ser Asn Ser Thr Pro Ser Val Gly Lys Val Ser Phe Ser Phe
        515                 520                 525

Ser Leu Thr Ala Ala His Ser Gly Asn Tyr Tyr Cys Thr Ala Asp Asn
    530                 535                 540

Gly Phe Gly Pro Gln Arg Ser Glu Ala Val Ser Leu Phe Val Thr Val
545                 550                 555                 560

Pro Val Ser Arg Pro Ile Leu Thr Leu Arg Val Pro Arg Ala Gln Ala
                565                 570                 575

Val Val Gly Asp Leu Leu Glu Leu Arg Cys Glu Ala Leu Arg Gly Ser
            580                 585                 590

Pro Pro Ile Met Tyr Trp Phe Tyr His Glu Asp Val Thr Leu Gly Ser
        595                 600                 605

Ser Ser Val Pro Ser Gly Gly Glu Ala Ser Phe Asn Leu Ser Leu Thr
    610                 615                 620

Ala Glu His Ser Gly Asn Tyr Ser Cys Glu Ala Asn Asn Gly Leu Val
625                 630                 635                 640

Ala Gln His Ser Asp Thr Ile Ser Leu Ser Val Ile Val Pro Val Ser
                645                 650                 655

Arg Pro Ile Leu Thr Phe Arg Ala Pro Arg Ala Gln Ala Val Val Gly
```

-continued

```
                660             665             670
Asp Leu Leu Glu Leu His Cys Glu Ala Leu Arg Gly Ser Ser Pro Ile
            675             680             685
Leu Tyr Trp Phe Tyr His Glu Asp Val Thr Leu Gly Lys Ile Ser Ala
            690             695             700
Pro Ser Gly Gly Gly Ala Tyr Phe Asn Leu Ser Leu Thr Thr Glu His
705             710             715             720
Ser Gly Ile Tyr Ser Cys Glu Ala Asp Asn Gly Leu Glu Ala Gln Arg
            725             730             735
Ser Glu Met Val Thr Leu Lys Val Ala Val Pro Val Ser Arg Pro Val
            740             745             750
Leu Thr Leu Arg Ala Pro Arg Ala Gln Val Ala Val Gly Asp Leu Leu
            755             760             765
Glu Leu His Cys Glu Ala Leu Arg Gly Ser Pro Leu Ile Leu Tyr Gln
            770             775             780
Phe Tyr His Glu Asp Val Thr Leu Gly Asn Ser Ser Ala Leu Ser Gly
785             790             795             800
Gly Ala Phe Phe Asn Leu Ser Leu Thr Ala Glu His Gly Asn Tyr Ser
            805             810             815
Cys Glu Ala Asp Asn Gly Leu Gly Ala Gln Arg Ser Glu Thr Val Thr
            820             825             830
Leu Tyr Leu Thr Gly Leu Thr Glu Asn Arg Ser Gly Pro Val Ala Thr
            835             840             845
Gly Val Thr Gly Gly Leu Leu Ser Leu Ala Gly Leu Ala Ala Val Ala
            850             855             860
Leu Leu Leu Tyr Cys Trp Leu Ser Arg Lys Ala Gly Arg Glu Pro Ala
865             870             875             880
Ser Asp Pro Cys Arg Ser Pro Ser Asp Leu Asp Ser Gln Glu Pro Thr
            885             890             895
Tyr His Asn Val Pro Ala Trp Glu Glu Leu Gln Pro Val Tyr Ser Asn
            900             905             910
Val Asn Pro Arg Gly Glu Asn Val Val Tyr Ser Glu Val Arg Ile Ile
            915             920             925
Arg Glu Lys Lys Lys His Ala Val Ala Ser Asn Pro Arg His Leu Arg
            930             935             940
Asn Lys Gly Ser Cys Ile Ile Tyr Ser Glu Val Lys Val Ala Ser Thr
945             950             955             960
Pro Ala Ser Arg Cys Leu Phe Leu Ala Ser Ser Ala Pro His Arg
            965             970             975
```